(12) United States Patent
Scheiner et al.

(10) Patent No.: US 10,543,332 B2
(45) Date of Patent: Jan. 28, 2020

(54) PATIENT INTERFACE

(71) Applicant: ResMed Pty Ltd, Bella Vista, New South Wales (AU)

(72) Inventors: Rupert Christian Scheiner, Sydney (AU); William Laurence Hitchcock, Sydney (AU); Anthony Paul Barbara, Sydney (AU); Adam Francis Barlow, Sydney (AU); Craig David Edwards, Sydney (AU); Lachlan Richard Goldspink, Sydney (AU); Kirrily Michele Haskard, Sydney (AU); Murray William Lee, Sydney (AU); Frederick Arlet May, Sydney (AU); Gerard Michael Rummery, Woodford (AU); Shiva Kumar Shanmuga Sundara, Sydney (AU); Chia Ik Tan, Sydney (AU); Stewart Joseph Wagner, Hawkesbury (AU); Alicia Kristianne Wells, Sydney (AU); Martin Forrester, Trenton (CA); Ralph Jourdan, Morfelden (DE)

(73) Assignee: ResMed Pty Ltd, Bella Vista (AU)

( * ) Notice: Subject to any disclaimer, the term of this patent is extended or adjusted under 35 U.S.C. 154(b) by 931 days.

(21) Appl. No.: 14/760,808

(22) PCT Filed: Jan. 16, 2014

(86) PCT No.: PCT/AU2014/000026
§ 371 (c)(1),
(2) Date: Jul. 14, 2015

(87) PCT Pub. No.: WO2014/110626
PCT Pub. Date: Jul. 24, 2014

(65) Prior Publication Data
US 2015/0352306 A1    Dec. 10, 2015

Related U.S. Application Data

(60) Provisional application No. 61/817,674, filed on Apr. 30, 2013, provisional application No. 61/823,192, (Continued)

(30) Foreign Application Priority Data

Jan. 16, 2013   (AU) ................................ 2013900132
Jan. 16, 2013   (NZ) ....................................... 605907
Jan. 18, 2013   (AU) ................................ 2013900168

(51) Int. Cl.
*A61M 16/06*         (2006.01)

(52) U.S. Cl.
CPC .... *A61M 16/0622* (2014.02); *A61M 16/0683* (2013.01)

(58) Field of Classification Search
CPC ........... A61M 2016/0015–0042; A61M 16/00; A61M 16/0003–0012;
(Continued)

(56) References Cited

U.S. PATENT DOCUMENTS 4,686,354 A    8/1987   Makin
4,782,832 A   11/1988   Trimble et al.
(Continued)

FOREIGN PATENT DOCUMENTS

AU    2010256351 B2   12/2010
CN     101242866 A     8/2008
(Continued)

OTHER PUBLICATIONS

"Respiratory Physiology", by John B. West, Lippincott Williams & Wilkins, 9th edition published 2011 (8 pages).
(Continued)

*Primary Examiner* — Tan-Uyen T Ho
*Assistant Examiner* — Ned T Heffner
(74) *Attorney, Agent, or Firm* — Nixon & Vanderhye P.C.

(57) ABSTRACT

A patient interface for delivery of a supply of pressurised air or breathable gas to an entrance of a patient's airways
(Continued)

comprising: a cushion member that includes a retaining structure and a seal-forming structure permanently connected to the retaining structure; a frame member attachable to the retaining structure; and a positioning and stabilising structure attachable to the frame member.

34 Claims, 230 Drawing Sheets

Related U.S. Application Data filed on May 14, 2013, provisional application No. 61/823,353, filed on May 14, 2013, provisional application No. 61/837,521, filed on Jun. 20, 2013, provisional application No. 61/839,916, filed on Jun. 27, 2013, provisional application No. 61/904,974, filed on Nov. 15, 2013.

(58) Field of Classification Search
CPC ........... A61M 16/20–209; A61M 16/06–0694; A62B 7/00; A62B 7/04; A62B 7/14; A62B 18/00; A62B 18/10; B63C 11/12; B63C 11/18
See application file for complete search history.

(56) References Cited

U.S. PATENT DOCUMENTS

| | | | |
|---|---|---|---|
| 4,907,584 A | 3/1990 | McGinnis | |
| 4,944,310 A | 7/1990 | Sullivan | |
| 5,181,507 A | 1/1993 | Michel et al. | |
| 5,357,948 A | 10/1994 | Eilentropp | |
| 5,704,345 A * | 1/1998 | Berthon-Jones | A61B 5/087 128/204.21 |
| 5,724,965 A * | 3/1998 | Handke | A61M 16/06 128/205.25 |
| 5,896,857 A | 4/1999 | Hely et al. | |
| 6,119,694 A | 9/2000 | Correa et al. | |
| 6,152,186 A | 11/2000 | Arney et al. | |
| 6,418,929 B1 | 7/2002 | Norfleet | |
| 6,467,483 B1 | 10/2002 | Kopacko et al. | |
| 6,532,959 B1 | 3/2003 | Berthon-Jones | |
| 6,581,594 B1 | 6/2003 | Drew et al. | |
| 6,823,869 B2 | 11/2004 | Raje et al. | |
| 7,210,481 B1 | 5/2007 | Lovell et al. | |
| 7,219,669 B1 | 5/2007 | Lovell et al. | |
| 7,296,575 B1 | 11/2007 | Radney | |
| 7,370,652 B2 | 5/2008 | Matula, Jr. et al. | |
| 7,562,658 B2 | 7/2009 | Madaus et al. | |
| 7,743,767 B2 | 6/2010 | Ging et al. | |
| 7,856,982 B2 | 12/2010 | Matula, Jr. et al. | |
| 7,866,944 B2 | 1/2011 | Kenyon et al. | |
| 7,900,628 B2 | 3/2011 | Matula, Jr. et al. | |
| 8,136,525 B2 | 3/2012 | Lubke et al. | |
| 8,297,285 B2 | 10/2012 | Henry et al. | |
| 8,636,479 B2 | 1/2014 | Kenyon et al. | |
| 8,638,014 B2 | 1/2014 | Sears et al. | |
| 8,851,074 B2 | 10/2014 | Chien | |
| 2002/0053347 A1 | 5/2002 | Ziaee | |
| 2002/0195107 A1 | 12/2002 | Smaldone | |
| 2003/0075180 A1 | 4/2003 | Raje et al. | |
| 2003/0196655 A1 | 10/2003 | Ging et al. | |
| 2003/0196656 A1 | 10/2003 | Moore et al. | |
| 2004/0149280 A1 | 8/2004 | Semeniuk | |
| 2004/0182398 A1 | 9/2004 | Sprinkle et al. | |
| 2004/0221850 A1 | 11/2004 | Ging et al. | |
| 2005/0011524 A1 | 1/2005 | Thomlinson et al. | |
| 2005/0109343 A1 | 5/2005 | Flannigan et al. | |
| 2005/0155604 A1 | 7/2005 | Ging et al. | |
| 2005/0228822 A1 | 10/2005 | Wason | |
| 2005/0241644 A1 | 11/2005 | Gunaratnam et al. | |
| 2006/0060200 A1 | 3/2006 | Ho et al. | |
| 2006/0081256 A1 | 4/2006 | Palmer | |
| 2006/0096598 A1 | 5/2006 | Ho et al. | |
| 2006/0124131 A1 | 6/2006 | Chandran et al. | |
| 2007/0272249 A1 | 11/2007 | Chandran et al. | |
| 2008/0006277 A1 | 1/2008 | Worboys et al. | |
| 2009/0044808 A1 | 2/2009 | Guney et al. | |
| 2009/0050156 A1 | 2/2009 | Ng et al. | |
| 2009/0078259 A1 | 3/2009 | Kooij et al. | |
| 2009/0107508 A1 | 4/2009 | Brambilla et al. | |
| 2009/0120442 A1 | 5/2009 | Ho | |
| 2009/0250065 A1 | 10/2009 | Omura et al. | |
| 2009/0277525 A1 | 11/2009 | Jourdan | |
| 2010/0000534 A1 | 1/2010 | Kooij et al. | |
| 2010/0000542 A1 | 1/2010 | Chu et al. | |
| 2010/0000543 A1 | 1/2010 | Berthon-Jones et al. | |
| 2010/0108072 A1 * | 5/2010 | D'Souza | A61M 16/06 128/206.24 |
| 2010/0132716 A1 | 6/2010 | Selvarajan et al. | |
| 2010/0224276 A1 | 9/2010 | Forrester et al. | |
| 2011/0023874 A1 | 2/2011 | Bath et al. | |
| 2011/0056497 A1 | 3/2011 | Scheiner et al. | |
| 2011/0088699 A1 * | 4/2011 | Skipper | A61M 16/06 128/206.26 |
| 2011/0146685 A1 | 6/2011 | Allan et al. | |
| 2011/0220114 A1 | 9/2011 | Lithgow et al. | |
| 2011/0247619 A1 | 10/2011 | Formica et al. | |
| 2011/0308526 A1 | 12/2011 | Ho et al. | |
| 2012/0067349 A1 | 3/2012 | Barlow et al. | |
| 2012/0080035 A1 | 4/2012 | Guney et al. | |
| 2012/0138063 A1 | 6/2012 | Eves et al. | |
| 2012/0234326 A1 | 9/2012 | Mazzone et al. | |
| 2012/0318270 A1 | 12/2012 | McAuley et al. | |
| 2012/0325218 A1 | 12/2012 | Brambilla et al. | |
| 2013/0074845 A1 | 3/2013 | Smith et al. | |
| 2013/0133660 A1 | 5/2013 | Ng et al. | |
| 2013/0213400 A1 | 8/2013 | Barlow et al. | |
| 2014/0283842 A1 | 9/2014 | Bearne et al. | |
| 2015/0182719 A1 | 7/2015 | Grashow et al. | |
| 2016/0296720 A1 | 10/2016 | Henry et al. | |

FOREIGN PATENT DOCUMENTS

| | | |
|---|---|---|
| CN | 101378810 A | 3/2009 |
| CN | 101455871 A | 6/2009 |
| CN | 101523104 A | 9/2009 |
| CN | 103153379 A | 6/2013 |
| EP | 0 747 078 | 12/1996 |
| EP | 2 027 880 | 2/2009 |
| EP | 2 042 209 A1 | 4/2009 |
| EP | 2 140 902 | 1/2010 |
| GB | 2 385 533 | 8/2003 |
| JP | H09-10311 | 1/1997 |
| JP | 2004-573 | 1/2004 |
| JP | 2007-527271 | 9/2007 |
| JP | 2008-532659 | 8/2008 |
| JP | 2009-39528 | 2/2009 |
| JP | 2009-504354 | 2/2009 |
| JP | 2009-72596 | 4/2009 |
| JP | 2011-500229 | 1/2011 |
| JP | 2012-526592 | 11/2012 |
| JP | 2012-527908 | 11/2012 |
| JP | 2012-528608 | 11/2012 |
| NZ | 553756 | 6/2007 |
| NZ | 553824 | 6/2007 |
| NZ | 553825 | 6/2007 |
| NZ | 562418 | 11/2007 |
| RU | 2 214 295 C1 | 9/2002 |
| RU | 2 379 075 C2 | 1/2008 |
| WO | WO 1998/004310 | 2/1998 |
| WO | WO1998004310 | 2/1998 |
| WO | WO 1998/034665 | 8/1998 |
| WO | WO1998034665 | 8/1998 |
| WO | WO 00/69521 | 11/2000 |
| WO | WO 2000/078381 | 12/2000 |
| WO | WO2000078381 | 12/2000 |
| WO | WO 2001/097892 | 12/2001 |
| WO | WO 2002/011804 | 2/2002 |
| WO | WO 2002/047749 | 6/2002 |
| WO | WO 03/090827 | 11/2003 |
| WO | WO 2004/022147 | 3/2004 |

(56) References Cited

FOREIGN PATENT DOCUMENTS

| WO | WO 2004/041342 | 5/2004 |
|---|---|---|
| WO | WO 2004/073778 | 9/2004 |
| WO | WO 2005/063328 | 7/2005 |
| WO | WO2005063328 | 7/2005 |
| WO | WO 2005/076874 A2 | 8/2005 |
| WO | WO 2006/069415 | 7/2006 |
| WO | WO 2006/074513 | 7/2006 |
| WO | WO2006074513 | 7/2006 |
| WO | WO 2006/130903 | 12/2006 |
| WO | WO2006130903 | 12/2006 |
| WO | WO 2007/012140 | 2/2007 |
| WO | WO 2007/022562 | 3/2007 |
| WO | WO 2007/022562 A1 | 3/2007 |
| WO | WO 2007/041751 | 4/2007 |
| WO | WO 2007/041786 | 4/2007 |
| WO | WO 2007/133332 A2 | 11/2007 |
| WO | WO 2008/007985 | 1/2008 |
| WO | WO 2008/011682 | 1/2008 |
| WO | WO 2008/011683 | 1/2008 |
| WO | WO 2009/022250 A2 | 2/2009 |
| WO | WO 2009/052560 | 4/2009 |
| WO | WO 2009/139647 A1 | 11/2009 |
| WO | WO 2010/073142 | 1/2010 |
| WO | WO 2010/073142 | 7/2010 |
| WO | WO 2010/131189 A1 | 11/2010 |
| WO | 2010/0139014 A1 | 12/2010 |
| WO | WO 2010/135785 | 12/2010 |
| WO | WO 2010/135785 A1 | 12/2010 |
| WO | WO 2010/139014 A1 | 12/2010 |
| WO | WO2010135785 | 12/2010 |
| WO | WO 2011/022751 | 3/2011 |
| WO | WO 2011/048510 | 4/2011 |
| WO | WO 2011/048519 | 4/2011 |
| WO | WO 2011/059346 A1 | 5/2011 |
| WO | WO 2011/060479 A1 | 5/2011 |
| WO | WO 2011/110961 | 9/2011 |
| WO | WO 2011/121466 | 10/2011 |
| WO | WO 2011/142678 | 11/2011 |
| WO | 2012/040791 | 4/2012 |
| WO | WO 2012/040792 A1 | 4/2012 |
| WO | WO 2012/047121 A1 | 4/2012 |
| WO | WO 2012/055886 A1 | 5/2012 |
| WO | WO 2012/061783 A1 | 5/2012 |
| WO | WO 2012/171072 | 12/2012 |
| WO | WO2012171072 | 12/2012 |
| WO | WO 2013/020167 | 2/2013 |
| WO | WO 2013/026091 | 2/2013 |
| WO | WO2013020167 | 2/2013 |
| WO | 2013/042003 | 3/2013 |
| WO | WO 2013/057647 | 4/2013 |
| WO | WO 2013/006065 | 10/2013 |
| WO | 2014/015382 | 1/2014 |
| WO | WO 2014/077708 A1 | 5/2014 |

OTHER PUBLICATIONS

First Examination Report issued in related New Zealand Application No. 630702 dated Sep. 1, 2015, 3 pages.
Patent Examination Report No. 1 issued in related Australian Patent Application No. 2014207247, dated Mar. 17, 2016, (3 pages).
Notification of Transmittal of International Preliminary Report on Patentability issued in related Australian Patent Application No. PCT/AU2014/050352, dated Mar. 15, 2016, (301 pages).
European Search Report issued in related European Application No. 14740791, dated Sep. 7, 2016, 14 pages.
First Office Action issued in related Chinese Patent Application No. 201480019556.3 dated Nov. 10, 2016, 19 pages.
Non-Final Office Action issued in U.S. Appl. No. 14/417,610, dated Mar. 24, 2017, 45 pages.
Office Action issued in related Russian Application No. 2015105510 with English translation, dated Mar. 24, 2017, (9 pages).
European Search Report issued in related European Application No. 14862678.1, dated May 3, 2017, (16 pages).
Office Action issued in related Russian Application No. 2015105510 with English translation, dated Jun. 1, 2017, (7 pages).
Office Action issued in related Chinese Application No. 201480072903.9 with English translation, dated Jun. 28, 2017, (15 pages).
First Office Action issued in related Taiwan Application No. 103101682 with English translation, dated Jul. 27, 2017, (17 pages).
Second Office Action issued in related Chinese Application No. 201480019556.3 with English translation, dated Jul. 12, 2017, (18 pages).
Examination Report No. 1 issued in Australian Application No. 2017201346 dated Oct. 31, 2017 (3 pages).
First Office Action issued in related Japanese Application No. 2015-552955 with English Translation, dated Nov. 2, 2017, 10 pages.
Third Office Action issued in related Chinese Application No. 201480019556.3 with English Translation, dated Jan. 24, 2018, 18 pages.
Decision of Rejection issued in related Japanese Application No. 2015-523344 with English Translation, dated Feb. 5, 2018, 8 pages.
First Examination Report issued in related New Zealand Application No. 724289, dated Apr. 19, 2017, (2 pages).
First Office Action issued in related Japanese Application No. 2015-523344 with English translation, dated May 29, 2017, (13 pages).
Communication pursuant to Article 94(3) EPC issued in European Application No. 14 740 791.0, dated Feb. 16, 2018, 9 pages.
Second Office Action issued in related Japanese Application No. 2015-552955 with English Translation, dated Apr. 9, 2018, 5 pages.
First Office Action issued in Taiwanese Application No. 106116271 dated Jul. 10, 2018, with English translation, (21 pages).
International Search Report for PCT/AU2014/050352 dated Mar. 10, 2015, 9 pages.
Written Opinion for PCT/AU2014/050352 dated Mar. 10, 2015, 12 pages.
Further Examination Report issued in New Zealand Application No. 724289 dated Nov. 16, 2018, (2 pages).
First Office Action issued in Chinese Application No. 201380050915.7 dated Nov. 30, 2018, with English translation, (14 pages).
Notice of Opposition issued in New Zealand Application No. 728967 dated Dec. 21, 2018, (2 pages).
Non-Final Office Action issued in U.S. Appl. No. 15/036,570 dated Jan. 30, 2019, (54 pages).
International Search Report for PCT/AU2014/000026 dated May 20, 2014, 7 pages.
Written Opinion of the ISA for PCT/AU2014/000026 dated May 20, 2014, 13 pages.
Written Opinion of the IPEA for PCT/AU2014/000026 dated Feb. 5, 2015, 10 pages.
International Preliminary Report for PCT/AU2014/000026 dated May 15, 2015, 270 pages.
International Search Report and Written Opinion for PCT/AU2013/000830 dated Nov. 22, 2013, 27 pages.
Further Examination Report issued in New Zealand Application No. 724289 dated Jun. 20, 2018, (2 pages).
First Examination Report issued in related New Zealand Application No. 744244 dated Aug. 6, 2018, (4 pages).
First Office Action issued in Taiwanese Application No. 103139474 dated Aug. 15, 2018, with English translation, (9 pages).
First Examination Report issued in related Australian Application No. 2017203609 dated Sep. 7, 2018, (5 pages).
Pre-Appeal Examination Report issued in Japanese Application No. JP 2015-523344, dated Sep. 10, 2018, with English translation (9 pages).
First Office Action issued in Japanese Application No. JP 2016-530878, dated Sep. 14, 2018, with English translation (17 pages).
Cover Letter for SE Adverse Report and Examiner's Report to the Registrar issued in Malaysian Application No. PI201570023, dated Sep. 28, 2018 (3 pages).
Third Office Action issued in related Japanese Application No. 2015-552955, dated Oct. 15, 2018, with English translation (26 pages).

(56) References Cited

OTHER PUBLICATIONS

Final Rejection dated May 27, 2019 issued in Japanese Application No. 2015-552955 with English translation (16 pages).

* cited by examiner

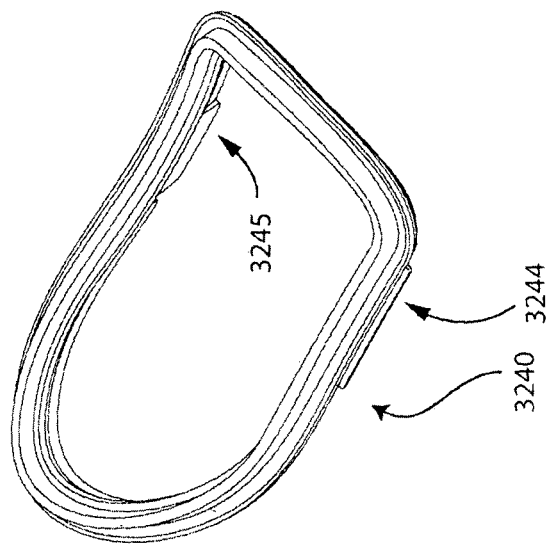
FIG. 24
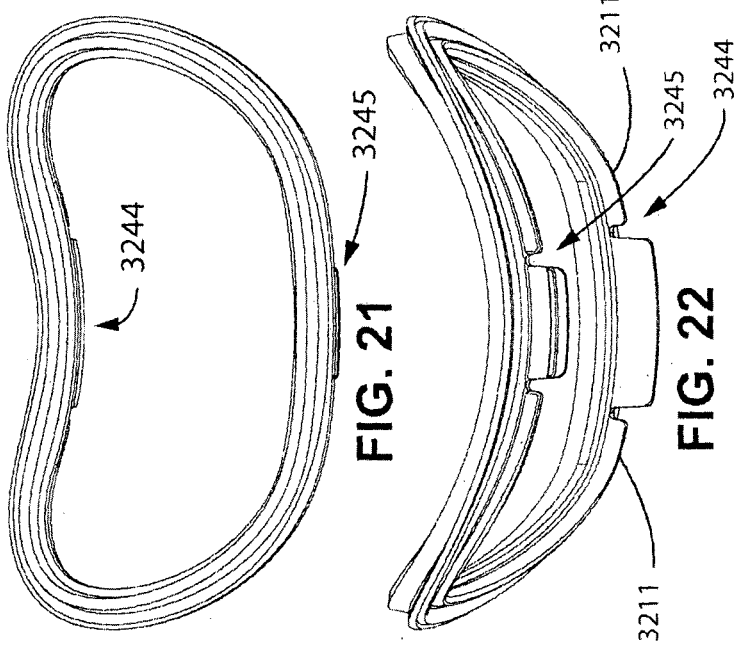
FIG. 21
FIG. 22
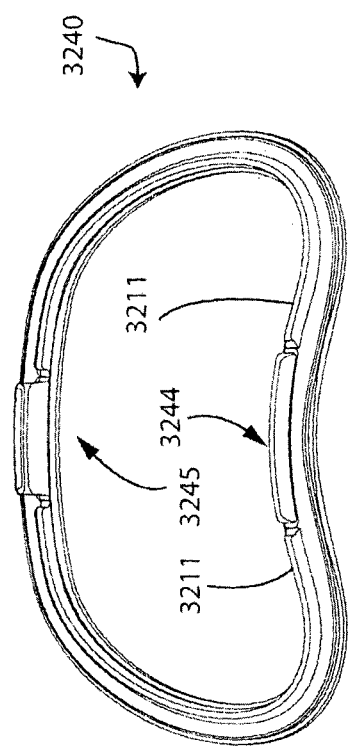
FIG. 23
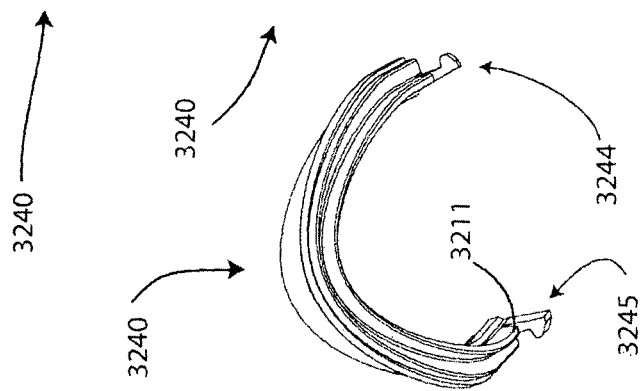
FIG. 20

FIG. 65
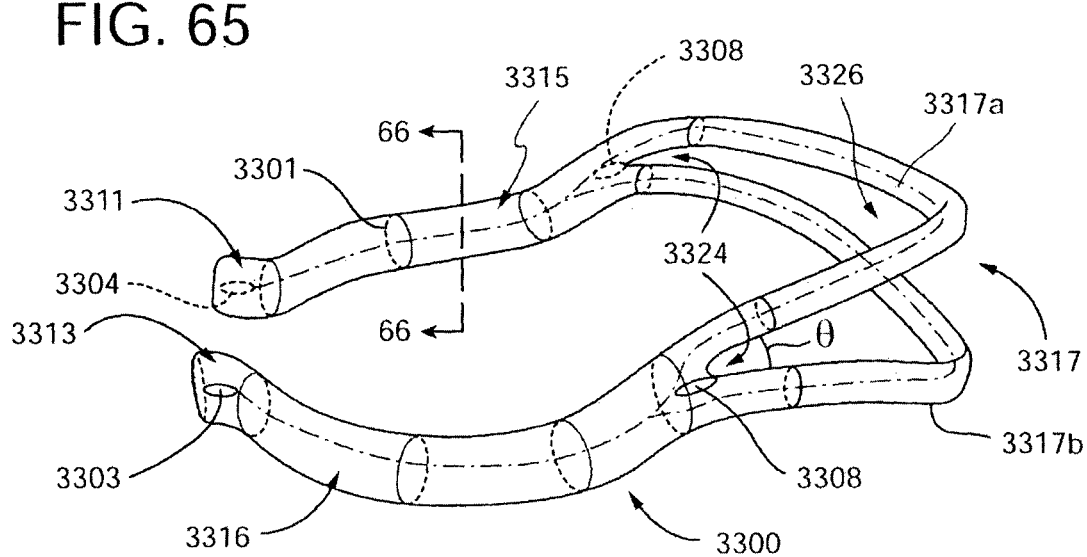
FIG. 66
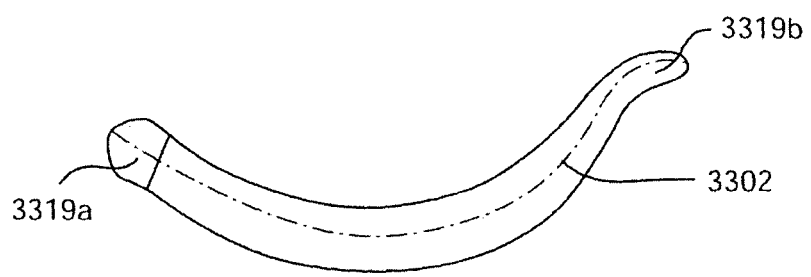
FIG. 67

Swift FX
0mm

Respironics
0mm

Respironics 60mm

Wisp
0mm

Wisp
30mm

Wisp
60mm

Wisp
120mm

PATIENT INTERFACE

CROSS-REFERENCE TO RELATED APPLICATIONS

This application is the U.S. national phase of International Application No. PCT/AU2014/000026 filed Jan. 16, 2014 which designated the U.S. and claims the benefit of U.S. Provisional Appln. No. 61/904,974, filed Nov. 15, 2013, 61/817,674, filed Apr. 30, 2013, 61/823,192, filed May 14, 2013, 61/823,353, filed May 14, 2013, 61/837,521, filed Jun. 20, 2013, and 61/839,916, filed Jun. 27, 2013. This application claims the benefit of Australian Provisional Appln. Nos. 2013900132, filed Jan. 16, 2013, and 2013900168, filed Jan. 18, 2013. This application claims the benefit of New Zealand Appln. Nos. 605907, filed Jan. 16, 2013. Each of the applications referenced above is incorporated herein by reference in its entirety.

BACKGROUND OF THE TECHNOLOGY

(1) Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lungs is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

Systems

One known product used for treating SDB is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to the entrance of the airways of a patient is facilitated by the use of a patient interface, such as a nasal mask, full-face mask, nasal pillows or a nasal cradle mask. A full-face mask includes a mask with one sealing-forming portion covering at least the nares and mouth, or more than one sealing-forming portion to individually cover at least the nares and mouth. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Seal-Forming Structure

Patient interfaces typically include a seal-forming structure.

One type of seal-forming structure extends around the periphery of the patient interface, and is intended to seal against the user's face when force is applied to the patient interface with the seal-forming structure in confronting engagement with the user's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material so positioned about the periphery of the mask so as to provide a self-sealing action against the face of the user when positive pressure is applied within the mask. Like the previous style of seal-forming structure, if the match between the face and the mask is not good, additional force may be required to effect a seal, or the mask may leak. Furthermore, if the shape of the seal-forming structure does not match that of the patient, it may crease or buckle in use, giving rise to leaks.

Another form of seal-forming structure may use adhesive to affect a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

Rigid elements, also known as "rigidisers", have been used with stretchable headgears previously. One known problem is associated with the fact that a rigidiser permanently attached (e.g. laminated or stitched) to a large area of the stretchable material limits the stretchable length of the material, thus affecting the elastic properties of the entire headgear. Another issue concerns cleaning the headgear which would require both the rigidiser and stretchable material to be washed together as they are permanently attached to each other.

Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner of the patient, e.g. through noise or focussed airflow. Some vents cannot be properly cleaned and must be discarded after they become blocked. Some vents are intended to be used for a short duration of time, i.e. less than three months, and therefore are manufactured from fragile material to prevent washing or frequent washing so as to encourage more frequent replacement of the vent. ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 m)

| Mask name | Mask type | A-weighted sound power level dbA (uncertainty) | A-weighted sound pressure dbA (uncertainty) | Year (approx.) |
|---|---|---|---|---|
| Glue-on(*) | nasal | 50.9 | 42.9 | 1981 |
| ResCare standard(*) | nasal | 31.5 | 23.5 | 1993 |
| ResMed Mirage(*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift(*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Swift FX | nasal pillows | 25 (3) | 17 (3) | 2011 |
| ResMed Mirage series I, II(*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(* one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT II™ nasal pillows mask, SWIFT LT™ nasal pillows mask, SWIFT FX™ nasal pillows mask and LIBERTY full-face mask. The following patent applications, assigned to ResMed Limited, describe nasal pillows masks: International Patent Application WO2004/073,778 (describing amongst other things aspects of ResMed SWIFT™ nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY™ full-face mask); International Patent Application WO 2009/052,560 (describing amongst other things aspects of ResMed SWIFT FX™ nasal pillows).

PAP Device

The air at positive pressure is typically supplied to the airway of a patient by a PAP device such as a motor-driven blower. The outlet of the blower is connected via a flexible delivery conduit to a patient interface as described above.

Mandibular Repositioning

A mandibular repositioning device (MRD) is one of the treatment options for sleep apnea. It is a custom made, adjustable oral appliance available from a dentist that holds the lower jaw in a forward position during sleep. This mechanical protrusion expands the space behind the tongue, puts tension on the pharyngeal walls to reduce collapse of the airway and diminishes palate vibration.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

One aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One aspect of one form of the present technology is a patient interface with a seal-forming structure that is removable for cleaning. It is the desire of the present technology to provide a patient interface that is light-weight compared to prior art patient interfaces, more unobtrusive compared to prior art patient interfaces and more quiet in use compared to prior art patient interfaces. It is also desirable to provide a patient interface that is intuitive to a patient when connecting mask components prior to commencement of therapy and is also simple to adjust and wear for therapy.

An aspect of one form of the present technology is a patient interface having a seal-forming structure that is locatable in position on the patient interface via a hard-to-hard connection. Another aspect of one form of the present technology is seal-forming structure of a patient interface that is removable for cleaning without requiring disconnection of a headgear portion of the patient interface.

An aspect of one form of the present technology is a patient interface comprising a seal-forming structure, a plenum chamber and a connection portion, wherein the seal-forming structure and the plenum chamber are formed from a relatively soft material, and the connection portion is formed from relatively rigid material. In one form the connection portion is removably connectable to a frame of the patient interface, e.g. via a snap-action, toggle or bi-stable mechanism. In one form the connection portion is insert moulded to the plenum chamber.

Another aspect of one form of the present technology is a patient interface that is moulded or otherwise constructed with a clearly defined perimeter shape which is intended to match that of an intended wearer (i.e. patient) and be intimate and conform with the face of the intended wearer.

An aspect of one form of the present technology is a method of manufacturing the patient interface described herein. It is a desire of the present technology to provide a method of manufacture that has less complexity than methods of manufacturing prior art patient interfaces to increase manufacturing efficiency, uses fewer raw materials and requires less assembly time by operators.

Another aspect of the present technology is directed to a patient interface for delivery of a supply of pressurised air or breathable gas to an entrance of a patient's airways. The patient interface may comprise: a cushion member that includes a retaining structure and a seal-forming structure permanently connected to the retaining structure; and a frame member, wherein the retaining structure and the frame member are repeatedly removably attachable to one another, wherein a gas chamber is formed at least in part by engagement of the cushion member and the frame member; and wherein an increase in air pressure within the cushion member causes a sealing force between the seal-forming structure and the frame member to increase.

An aspect of one form of the present technology is a method of manufacturing the patient interface.

Another aspect of the present technology is directed to a patient interface to deliver pressurized gas to a patient to treat sleep disordered breathing. The patient interface may comprise: a seal-forming structure having a nasal opening to provide pressurized gas to both nares of the patient and a plenum chamber formed in one piece, the plenum chamber including a plenum connection region, and the seal-forming structure is configured to seal around an inferior periphery of the patient's nose and below the bridge of the nose; a frame releasably attachable to the plenum connection region; a connection port formed in one piece with the frame; and a gas delivery tube permanently joined to the frame at the connection port, the gas delivery tube may comprise: a helical coil comprised of a plurality of adjacent coils, each coil separated by a width and having an outer surface defining a coil diameter; and a web of material coaxial to the helical coil attached to the helical coil between adjacent ones of the plurality of adjacent coils and having at least one fold extending radially outward between adjacent ones of the plurality of adjacent coils, said at least one fold defined by a predetermined fold line.

In examples, (a) a vertex of said at least one fold may define a fold diameter, (b) when the gas delivery tube is in a neutral state the coil diameter may be substantially equal to the fold diameter and the adjacent coils may be separated from each other in the neutral state, (c) the gas delivery tube may comprise one of three different states: a neutral state wherein the gas delivery tube comprises a neutral length, an extended state wherein the gas delivery tube is extended along its longitudinal axis to an extended length that is greater than the neutral length, and a compressed state wherein the gas delivery tube is compressed along its longitudinal axis to a compressed length that is less than the neutral length, (d) the web of material may comprise the at least one fold extending radially outward along at least one lengthwise portion of the gas delivery tube, (e) the web of material may have a slope angle that increases from the helical coil to the vertex of the at least one fold when the gas delivery tube is in the neutral state, (f) the web of material may have an asymmetrical cross-sectional profile about the predetermined fold line, (g) the predetermined fold line may be spaced evenly between adjacent ones of the plurality of adjacent coils, (h) the width separating adjacent ones of the plurality of adjacent coils may be substantially equal to a width of the helical coil when the gas delivery tube is in the neutral state, (i) the helical coil may comprise a greater proportion of a superficial surface area of the gas delivery tube than the at least one fold of the web of material, (j) an outer portion of the helical coil may have a rounded profile, (k) the helical coil may have a greater thickness than the web of material, (l) the web of material may have a substantially uniform thickness, (m) the helical coil may comprise a thermoplastic elastomer (TPE) or thermoplastic polyurethane (TPU) and/or the web of material may comprise a thermoplastic elastomer (TPE) or thermoplastic polyurethane (TPU), (n) the gas delivery tube may be permanently joined to the frame at the connection port by insert molding the frame to the gas delivery tube, (o) the web of material and the helical coil may be bonded to form a uniform and continuous inner surface of the gas delivery tube, (p) the at least one fold may extend radially outward between alternating ones of the plurality of adjacent coils, (q) said seal-forming structure may include a recessed portion to receive the tip of the nose of the patient, (r) a compliant region may be located above the recessed portion, said compliant region being thin and flexible relative to the remainder of the seal-forming structure, (s) said seal-forming structure may comprise foam, gel, and/or low durometer silicone, (t) said seal-forming structure may have a varied thickness around said nasal opening at predetermined positions, (u) said seal-forming structure may comprise a pair of protruding ends extending symmetrically about the nasal opening, each protruding end may be configured to seal against a region of the patient's face where the ala of the nose joins to the patient's face, (v) said seal-forming structure may comprise a pair of protruding end support sections corresponding to each protruding end and structured to support each protruding end and said pair of protruding end support sections may extend into a gas chamber defined at least in part by the seal-forming structure, (w) a lower portion of said seal-forming structure may be concave in a relaxed state to seal against the upper lip of the patient and to follow a curvature of the upper lip of the patient, and/or (x) the seal-forming structure may comprise a dual wall cushion to prevent collapse of the seal-forming structure when the seal-forming structure is engaged with the nose of the patient to form a pneumatic seal.

Another aspect of the present technology is directed to a patient interface to deliver pressurized gas to a patient to treat sleep disordered breathing. The patient interface may comprise: a seal-forming structure having a nasal opening to provide pressurized gas to both nares of the patient and a plenum chamber formed in one piece, the plenum chamber including a plenum connection region, and the seal-forming structure is configured to seal around an inferior periphery of the patient's nose and below the bridge of the nose; a frame releasably attachable to the plenum connection region, said frame comprising a first material; and a pair of rigidiser arms comprising a second material, said second material being different from said first material, wherein said frame and said pair of rigidiser arms are permanently connected.

In examples, (a) the first material may be relatively more resiliently flexible than the second material, (b) the frame may be overmolded to the pair of rigidiser arms to form a mechanical interlock, (c) the mechanical interlock may comprise an enclosable section extending from each of the pair of rigidiser arms that is overmolded by the material of the frame, (d) the enclosable section may have a hook and a portion of a bend, (e) the first material may be unable to be integrally bonded with the second material, (f) the first material may be a thermoplastic polyester elastomer and the second material may be a thermoplastic polymer, (g) the thermoplastic polymer may be polypropylene (PP), (h) the first material may be a fiber reinforced composite polypropylene material and the second material may be polypropylene, (i) each of the pair of rigidiser arms may include a protruding end configured to retain a pocketed end of a strap of a positioning and stabilising structure, and the protruding end may be proximal to the frame, (j) the first material may not be stretchable, and each of the pair of rigidiser arms may be structured such that it is more flexible in a plane substantially parallel to a patient's Frankfort horizontal compared to other planes, (k) each of the rigidiser arms may comprise: a main body having a curvature to substantially follow a cheek shape of a patient; and a connection portion configured to connect to the frame, the connection portion located at a distal end of the rigidiser arm, (l) the connection portion may comprise at least one protrusion and at least one void configured to be overmolded to connect to the frame, (m) said seal-forming structure may include a recessed portion to receive the tip of the nose of the patient, (n) a compliant region may be located above the recessed portion, said compliant region being thin and flexible relative to the remainder of the seal-forming structure, (o) said seal-forming structure may comprise foam, gel, and/or low durometer silicone, (p) said seal-forming structure may have a varied thickness around said nasal opening at predetermined positions, (q) said seal-forming structure may comprise a pair of protruding ends extending symmetrically about the nasal opening, each protruding end may be configured to seal against a region of the patient's face where the ala of the nose joins to the patient's face, (r) said seal-forming structure may comprise a pair of protruding end support sections corresponding to each protruding end and structured to support each protruding end and said pair of protruding end support sections may extend into a gas chamber defined at least in part by the seal-forming structure, (s) a lower portion of said seal-forming structure may be concave in a relaxed state to seal against the upper lip of the patient and to follow a curvature of the upper lip of the patient, and/or (t) the seal-forming structure may comprise a dual wall cushion to prevent collapse of the seal-forming structure when the seal-forming structure is engaged with the nose of the patient to form a pneumatic seal.

Another aspect of the present technology is directed to a patient interface to deliver pressurized gas to a patient to treat sleep disordered breathing. The patient interface may comprise: a seal-forming structure having a nasal opening to provide pressurized gas to both nares of the patient and a plenum chamber formed in one piece, the plenum chamber including a plenum connection region, and the seal-forming structure is configured to seal around an inferior periphery of the patient's nose and below the bridge of the nose; a frame releasably attachable to the plenum connection region; a connection port formed in one piece with the frame; and at least one vent to washout exhaled air, the vent permanently connected to the frame, wherein the at least one vent is made from a textile formed by interlacing plastic fibers, the textile having a predetermined amount of porosity.

In examples, (a) the at least one vent may comprise two vents permanently connected to the frame on opposite sides of the connection port, (b) the two vents may comprise a first vent having a first airflow rate and a second vent having a second airflow rate different from the first airflow rate, (c) the first airflow rate and the second airflow rate may be selected such that an average airflow rate of the first airflow rate and the second airflow rate is within a predetermined range, (d) the first airflow rate and/or the second airflow rate may be obtained by heat staking a portion of the first vent and/or the second vent, respectively, to the predetermined amount of porosity, (e) the plastic fibers may be made from a thermoplastic polymer from any one of the group consisting of: polypropylene, a woven polypropylene material, polycarbonate, nylon and polyethylene, (f) the at least one vent may be permanently connected to the frame by molecular adhesion using any one of the group consisting of: overmolding, co-injection molding and two shot (2K) injection molding, (g) the at least one vent may comprise a semi-circle shape or D-shape, (h) said seal-forming structure may include a recessed portion to receive the tip of the nose of the patient, (i) a compliant region may be located above the recessed portion, said compliant region being thin and flexible relative to the remainder of the seal-forming structure, (j) said seal-forming structure may comprise foam, gel, and/or low durometer silicone, (k) said seal-forming structure may have a varied thickness around said nasal opening at predetermined positions, (l) said seal-forming structure may comprise a pair of protruding ends extending symmetrically about the nasal opening, each protruding end may be configured to seal against a region of the patient's face where the ala of the nose joins to the patient's face, (m) said seal-forming structure may comprise a pair of protruding end support sections corresponding to each protruding end and structured to support each protruding end and said pair of protruding end support sections may extend into a gas chamber defined at least in part by the seal-forming structure, (n) a lower portion of said seal-forming structure may be concave in a relaxed state to seal against the upper lip of the patient and to follow a curvature of the upper lip of the patient, and/or (o) the seal-forming structure may comprise a dual wall cushion to prevent collapse of the seal-forming structure when the seal-forming structure is engaged with the nose of the patient to form a pneumatic seal.

Another aspect of the present technology is directed to a positioning and stabilising structure for a patient interface device. The positioning and stabilising structure may comprise: at least one strap; and at least one rigidiser arm, the at least one rigidiser arm including a main body and an extension to connect the main body to a mask frame, wherein the positioning and stabilising structure is arranged to position the at least one strap and the at least one rigidiser arm with regard to one another such that the at least one rigidiser arm imparts a predetermined shape to the at least one strap at a rigidised portion of the at least one strap and allowing at least the rigidised portion of the at least one strap to move relative to the at least one rigidiser arm, and said extension may be configured to prevent movement of the at least one rigidiser arm relative to the mask frame in a plane parallel with the patient's sagittal plane.

In examples, (a) the at least one rigidiser arm may be affixed to the at least one strap at one localized point or area only, (b) the at least one rigidiser arm may be affixed to the at least one strap in a limited area of the at least one strap, (c) the limited area may be adjacent a pocket or a sleeve opening of the at least one strap, (d) the at least one rigidiser arm may be multi-axially deformable to conform to a patient's facial profile, (e) the at least one rigidiser arm may be shaped to extend from a mask frame to a position proximally on or below the patient's cheekbone, (f) the at least one rigidiser arm may have a side profile that is crescent shaped, (g) an end portion of the at least one rigidiser arm may be affixed to the at least one strap, (h) the at least one rigidiser arm may be affixed to the at least one strap by sewing, welding, gluing, heat staking, clamping, buttoning, snapping a cover over an end, and/or snapping on an external part, (i) the imparted predetermined shape may direct pressure of the positioning and stabilising structure to predetermined portions of a wearers' face, (j) the at least one rigidiser arm may be incapable of stretching and is relatively more rigid than the at least one strap, (k) the positioning and stabilising structure may comprise two or more rigidiser arms symmetrically disposed on opposite sides of a patient's face, (l) the at least one rigidiser arm may be completely removable from the at least one strap, (m) the at least one strap may comprise two pockets, each receiving a rigidiser arm to releasably secure the at least one strap to the rigidiser arms, (n) the at least one strap may comprise at least one retaining means, said retaining means may comprise a loop, a sleeve and/or a pocket, for receiving the at least one rigidiser arm and holding the at least one rigidiser arm in place, (o) the at least one rigidiser arm may comprise at least one retaining means, said retaining means may comprise a loop, a sleeve and/or a pocket, for receiving the at least one strap and holding the at least one strap in place, (p) the at least one rigidiser arm may be affixed to a guiding element provided to the at least one strap, (q) the guiding element may be a loop- or sheath-like portion or passage or a pocket into which or through which the at least one rigidiser arm extends, (r) the guiding element may allow longitudinal expansion or retraction of the at least one strap relative to the at least one rigidiser arm and/or may allow substantially free movement or floating of the at least one rigidiser arm relative to the at least one strap, (s) said extension may be configured to allow flexing of the at least one rigidiser arm in a plane parallel with the patient's Frankfort horizontal, (t) said extension may be substantially equal in width to the main body, (u) the at least one strap may be substantially inelastic such that the positioning and stabilising structure is length-adjustable by at least one of flexing of the at least one rigidiser arm, ladder lock clips, buckle connections, and hook and loop connections, (v) a patient interface system for sealed delivery of a flow of breathable gas at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O, e.g., typically about 10 cmH2O, above ambient air pressure in use, throughout the patient's respiratory cycle, while the patient is sleeping, to ameliorate sleep disordered breathing, e.g., sleep apnea, the patient interface system may comprise: a positioning and stabilising structure according to any one or more of the above examples; and a patient interface comprising: a seal-forming structure to provide pressurized gas at least to both nares of the patient and a plenum chamber pressurised at a pressure above ambient pressure in use, the seal-forming structure and the plenum chamber formed in one piece, the plenum chamber including a plenum connection region, and the seal-forming structure is configured to seal around an inferior periphery of the patient's nose and below the bridge of the nose; a gas washout vent configured to allow a flow of patient exhaled CO2 to an exterior of the patient interface to minimise rebreathing of exhaled CO2 by the patient and a frame releasably attachable to the plenum connection region, (w) the extension may be permanently fixed to the mask frame and the main body, is detachable from the extension, and/or (x) the extension and the main body may comprise one piece and the extension is detachable from the mask frame.

Another aspect of the present technology is directed to a cushion member for a patient interface for delivery of a supply of pressurised air or breathable gas to an entrance of a patient's airways. The cushion member may comprise: a retaining structure for repeatable engagement with and disengagement from a frame member; and a seal-forming structure having a nasal opening to provide pressurized gas to both nares of the patient and a plenum chamber formed in one piece, the seal-forming structure configured to seal around an inferior periphery of the patient's nose and below the bridge of the nose, and the seal-forming structure and plenum chamber permanently connected to the retaining structure; wherein the seal-forming structure is made from a first material and the retaining structure is made from a second material with different mechanical characteristics from the first material and the second material is more rigid than the first material; and wherein an increase in air pressure within the cushion member causes a sealing force between the seal-forming structure and the frame member to increase.

In examples, (a) the first material may be silicone and the second material may be silicone with a higher durometer than the first material, (b) the cushion member may comprise a plenum chamber located between the retaining structure and the seal-forming structure, (c) the cushion member may comprise a frame member made from the second material, (d) the first material may permit the seal-forming structure to readily conform to finger pressure and the second material may prevent the retaining structure from readily conforming to finger pressure, (e) said seal-forming structure may include a recessed portion to receive the tip of the nose of the patient, (f) a compliant region may be located above the recessed portion, said compliant region being thin and flexible relative to the remainder of the seal-forming structure, (g) said seal-forming structure may comprise foam, gel, and/or low durometer silicone, (h) said seal-forming structure may have a varied thickness around said nasal opening at predetermined positions, (i) said seal-forming structure may comprise a pair of protruding ends extending symmetrically about the nasal opening, each protruding end may be configured to seal against a region of the patient's face where the ala of the nose joins to the patient's face, (j) said seal-forming structure may comprise a pair of protruding end support sections corresponding to each protruding end and structured to support each protruding end and said pair of protruding end support sections may extend into a gas chamber defined at least in part by the seal-forming structure, (k) a lower portion of said seal-forming structure may be concave in a relaxed state to seal against the upper lip of the patient and to follow a curvature of the upper lip of the patient, (l) the seal-forming structure may comprise a dual wall cushion to prevent collapse of the seal-forming structure when the seal-forming structure is engaged with the nose of the patient to form a pneumatic seal, and/or (m) a patient interface for sealed delivery of a flow of breathable gas at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, said patient interface may comprise: the cushion member of any one of the above examples; a positioning and stabilising structure to maintain the cushion member in sealing contact with an area surrounding an entrance to at least the patient's nasal airways while maintaining a therapeutic pressure at the entrance to at least the patient's nasal airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

Another aspect of the present technology is directed to a patient interface to provide breathable gas to a patient. The patient interface may comprise: a seal-forming structure having a nasal opening to provide pressurized gas to both nares of the patient and a plenum chamber formed in one piece, the plenum chamber including a plenum connection region, and the seal-forming structure is configured to seal around an inferior periphery of the patient's nose and below the bridge of the nose; and a frame comprising a frame connection region and a headgear connection region; wherein the frame connection region is configured for attachment to the plenum chamber at the plenum connection region, and wherein a sealing lip is adapted to form a pneumatic seal between the plenum connection region and the frame connection region.

In examples, (a) the frame connection region may comprise at least one retention feature to facilitate connection with the plenum connection region, and the plenum connection region may comprise at least one complementary connection region to receive the at least one retention feature corresponding thereto, (b) the at least one retention feature may be a barb, said barb may have a leading surface and a trailing surface and the at least one complementary connection region may comprise a lead-in surface and a retaining surface, (c) said seal-forming structure may include a recessed portion to receive the tip of the nose of the patient, (d) a compliant region may be located above the recessed portion, said compliant region being thin and flexible relative to the remainder of the seal-forming structure, (e) said seal-forming structure may comprise foam, gel, and/or low durometer silicone, (f) said seal-forming structure may have a varied thickness around said nasal opening at predetermined positions, (g) said seal-forming structure may comprise a pair of protruding ends extending symmetrically about the nasal opening, each protruding end may be configured to seal against a region of the patient's face where the ala of the nose joins to the patient's face, (h) said seal-forming structure may comprise a pair of protruding end support sections corresponding to each protruding end and structured to support each protruding end and said pair of protruding end support sections may extend into a gas chamber defined at least in part by the seal-forming structure, (i) a lower portion of said seal-forming structure may be concave in a relaxed state to seal against the upper lip of the patient and to follow a curvature of the upper lip of the patient, and/or (j) the seal-forming structure may comprise a dual wall cushion to prevent collapse of the seal-forming structure when the seal-forming structure is engaged with the nose of the patient to form a pneumatic seal.

Another aspect of the present technology is directed to a cushion member for a nasal cradle mask for delivery of a supply of pressurised air or breathable gas to an entrance of a patient's airways. The cushion member may comprise: a retaining structure for repeatable engagement with and disengagement from a frame member; and a seal-forming structure having a nasal opening to provide pressurized gas to both nares of the patient and a plenum chamber formed in one piece, the seal-forming structure configured to seal around an inferior periphery of the patient's nose and below the bridge of the nose, and the seal-forming structure and plenum chamber permanently connected to the retaining structure; wherein an increase in air pressure within the cushion member causes a sealing force between the seal-forming structure and the frame member to increase; and wherein a retention force between the retaining structure and the frame member is higher than a disengagement force to disengage the retaining structure from the frame member.

In examples, (a) said seal-forming structure may include a recessed portion to receive the tip of the nose of the patient, (b) a compliant region may be located above the recessed portion, said compliant region being thin and flexible relative to the remainder of the seal-forming structure, (c) said seal-forming structure may comprise foam, gel, and/or low durometer silicone, (d) said seal-forming structure may have a varied thickness around said nasal opening at predetermined positions, (e) said seal-forming structure may comprise a pair of protruding ends extending symmetrically about the nasal opening, each protruding end may be configured to seal against a region of the patient's face where the ala of the nose joins to the patient's face, (f) said seal-forming structure may comprise a pair of protruding end support sections corresponding to each protruding end and structured to support each protruding end and said pair of protruding end support sections may extend into a gas chamber defined at least in part by the seal-forming structure, (g) a lower portion of said seal-forming structure may be concave in a relaxed state to seal against the upper lip of the patient and to follow a curvature of the upper lip of the patient, (h) the seal-forming structure may comprise a dual wall cushion to prevent collapse of the seal-forming structure when the seal-forming structure is engaged with the nose of the patient to form a pneumatic seal, and/or (i) a patient interface for sealed delivery of a flow of breathable gas at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, said patient interface may comprise: the cushion member of any one of the above examples; a positioning and stabilising structure to maintain the cushion member in sealing contact with an area surrounding an entrance to at least the patient's nasal airways while maintaining a therapeutic pressure at the entrance to at least the patient's nasal airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

Another aspect of the present technology is directed to a cushion member for a patient interface for delivery of a supply of pressurised air or breathable gas to an entrance of a patient's airways. The cushion member may comprise: a retaining structure for repeatable engagement with and disengagement from a frame member; and a seal-forming structure having a nasal opening to provide pressurized gas to both nares of the patient and a plenum chamber formed in one piece, the seal-forming structure configured to seal around an inferior periphery of the patient's nose and below the bridge of the nose, and the seal-forming structure and plenum chamber permanently connected to the retaining structure, wherein said seal-forming structure includes a recessed portion to receive the tip of the nose of the patient, and wherein said seal-forming structure comprises a pair of protruding ends extending symmetrically about the nasal opening, each protruding end configured to seal against a region of the patient's face where the ala of the nose joins to the patient's face.

In examples, (a) the seal-forming structure may comprise a dual wall cushion to prevent collapse of the seal-forming structure when the seal-forming structure is engaged with the nose of the patient to form a pneumatic seal, (b) a compliant region may be located above the recessed portion, said compliant region being thin and flexible relative to the remainder of the seal-forming structure, (c) said seal-forming structure may comprise foam, gel, and/or low durometer silicone, (d) said seal-forming structure may have a varied thickness around said nasal opening at predetermined positions, (e) the seal-forming structure may include an overhang at the nasal opening of the seal-forming structure, said overhang located proximal to the recessed portion, (d) said seal-forming structure may comprise a pair of protruding end support sections corresponding to each protruding end and structured to support each protruding end and said pair of protruding end support sections may extend into a gas chamber defined at least in part by the seal-forming structure, (e) a lower portion of said seal-forming structure may be concave in a relaxed state to seal against the upper lip of the patient and to follow a curvature of the upper lip of the patient, (f) said lower portion may have a reduced material thickness relative to the rest of the seal-forming structure, and/or (g) a patient interface for sealed delivery of a flow of breathable gas at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, said patient interface may comprise: the cushion member of any one of the above examples; a positioning and stabilising structure to maintain the cushion member in sealing contact with an area surrounding an entrance to at least the patient's nasal airways while maintaining a therapeutic pressure at the entrance to at least the patient's nasal airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

Another aspect of the present technology is directed to a patient interface system to provide breathable gas to a patient. The patient interface may comprise: a patient interface including a seal-forming structure to provide a pneumatic connection to a patient's airways; and a positioning and stabilising structure including at least one strap and at least one rigidiser arm and configured to releasably retain the patient interface on the patient, wherein the at least one strap may be permanently attached to the at least one rigidiser arm at an attachment point.

In examples, (a) the attachment point may comprise an ultrasonic weld, (b) the attachment point may comprise a heat stake, (c) the attachment point may comprise stitching, (d) the attachment point may comprise a hinged mechanism, and/or (e) the attachment point may comprise barbs on the at least one rigidiser arm.

Another aspect of the present technology is directed to a patient interface system to provide breathable gas to a patient. The patient interface may comprise: a patient interface including a seal-forming structure to provide a pneumatic connection to a patient's airways; and a positioning and stabilising structure including at least one strap and at least one rigidiser arm and configured to releasably retain the patient interface on the patient, wherein the at least one strap may be releasably attached to the at least one rigidiser arm.

In examples, (a) the at least one strap may comprise an elastic tube and the at least one rigidiser arm may comprise a raised stop, (b) the at least rigidiser arm may comprise a tab to releasably attach the at least one strap with a hook and loop connection, (c) the at least one strap may comprise at least one lock and the at least one rigidiser arm may comprise at least one notch that corresponds with said at least one lock, and/or (d) the at least one strap may comprise an end having hook material to form a hook and loop connection with a loop material on the at least one strap by looping the at least one strap through a first slot and a second slot of the at least one rigidiser arm.

Another aspect of the present technology is directed to a patient interface system to provide breathable gas to a patient. The patient interface may comprise: a patient interface including a seal-forming structure to provide a pneumatic connection to a patient's airways; and a positioning and stabilising structure including at least one strap and at least one rigidiser arm and configured to releasably retain the patient interface on the patient, wherein the at least one rigidiser arm may be releasably attachable to a frame of the patient interface, the frame supporting the seal-forming structure against the patient's face.

In examples, (a) the at least one rigidiser arm may be releasably attachable to a corresponding extension of the frame in a rotate and lock arrangement, (b) the patient interface may further comprise pins and corresponding sockets to releasably attach the at least one rigidiser arm to an extension of the frame, (c) the at least one rigidiser may further comprise a projection and an arm supported on a shaft to releasably attach the at least one rigidiser arm to an extension of the frame at a shaft receiver and an arm receiver, (d) the at least one rigidiser arm may comprise an extension to releasably attach to a receiver of the frame with a snap-fit, (e) the at least one rigidiser arm may comprise an extension to releasably attach to a receiver of the frame with a press-fit, (f) the at least one rigidiser arm may comprise an extension having a column to releasably attach to a receiver of the frame with a snap-fit, the extension may further comprise an end to prevent rotation about a longitudinal axis of the column, (g) the frame may comprise at least one slot through which a corresponding at least one rigidiser arm may be threaded for releasable attachment, the at least one rigidiser arm may comprise a locking end, (h) the at least one rigidiser arm may comprise an extension with a pin to releasably attach to a socket of the frame with a snap-fit, (i) the at least one rigidiser arm may comprise a first magnet and the frame may comprise a second magnet to releasably attach the at least one rigidiser arm to the frame, (j) the at least one rigidiser arm may comprise a first L-shaped section having at least one post and the frame may comprise a second L-shaped section having at least one hole and the at least one rigidiser arm may be releasably attached to the frame by engagement between the at least one post and the at least one hole, (k) the frame may comprise a boss and the at least one rigidiser arm may comprise a cavity to releasably attach to said boss, and/or (l) the at least one rigidiser arm may comprise prongs and a hole and an extension of the frame may comprise slots corresponding with said prongs and a post corresponding with said hole for releasable attachment between the at least one rigidiser arm and the frame.

Another aspect of the present technology is directed to a patient interface system to provide breathable gas to a patient. The patient interface may comprise: a patient interface including a seal-forming structure to provide a pneumatic connection to a patient's airways; and a positioning and stabilising structure including at least one strap and at least one rigidiser arm and configured to releasably retain the patient interface on the patient, wherein an extension joins each at least one rigidiser arm to a frame of the patient interface, the frame supporting the seal-forming structure against the patient's face.

In examples, (a) the at least one rigidiser arm may comprise ribs at a bend to resist deformation at the bend, (b) the extension may comprise ribs at a bend to resist deformation at the bend, and/or (c) the extension may comprise a longitudinal rib along a bend and straight section of the extension to resist deformation.

Another aspect of the present technology is directed to a patient interface for sealed delivery of a flow of breathable gas at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O, e.g., typically about 10 cmH2O, above ambient air pressure in use, throughout the patient's respiratory cycle, while the patient is sleeping, to ameliorate sleep disordered breathing, e.g., sleep apnea, said patient interface may comprise: a sealing structure to form seal with at least nasal airways of the patient; a positioning and stabilising structure to maintain the sealing structure in sealing contact with an area surrounding an entrance to at least the patient's nasal airways while maintaining a therapeutic pressure at the entrance to at least the patient's nasal airways; a plenum chamber pressurised at a pressure above ambient pressure in use; a gas washout vent configured to allow a flow of patient exhaled CO2 to an exterior of the patient interface to minimise rebreathing of exhaled CO2 by the patient.

Of course, portions of the aspects may form sub-aspects of the present technology. Also, various ones of the, examples, sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Therapy

Respiratory System

Figure 2A:
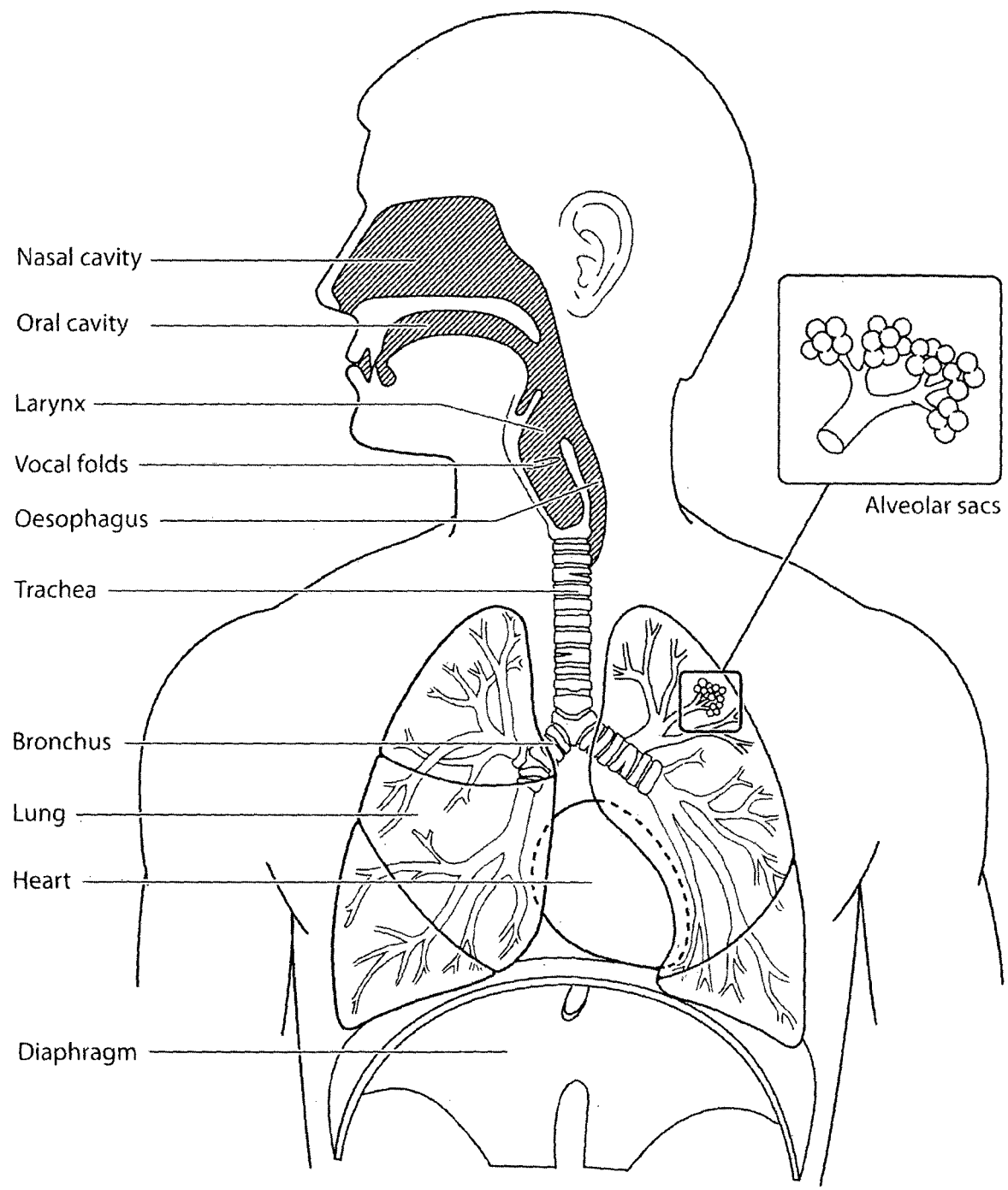

FIG. 2a shows an overview of a human respiratory system including the nasal and oral cavities, the larynx, vocal folds, oesophagus, trachea, bronchus, lung, alveolar sacs, heart and diaphragm.

Figure 2B:
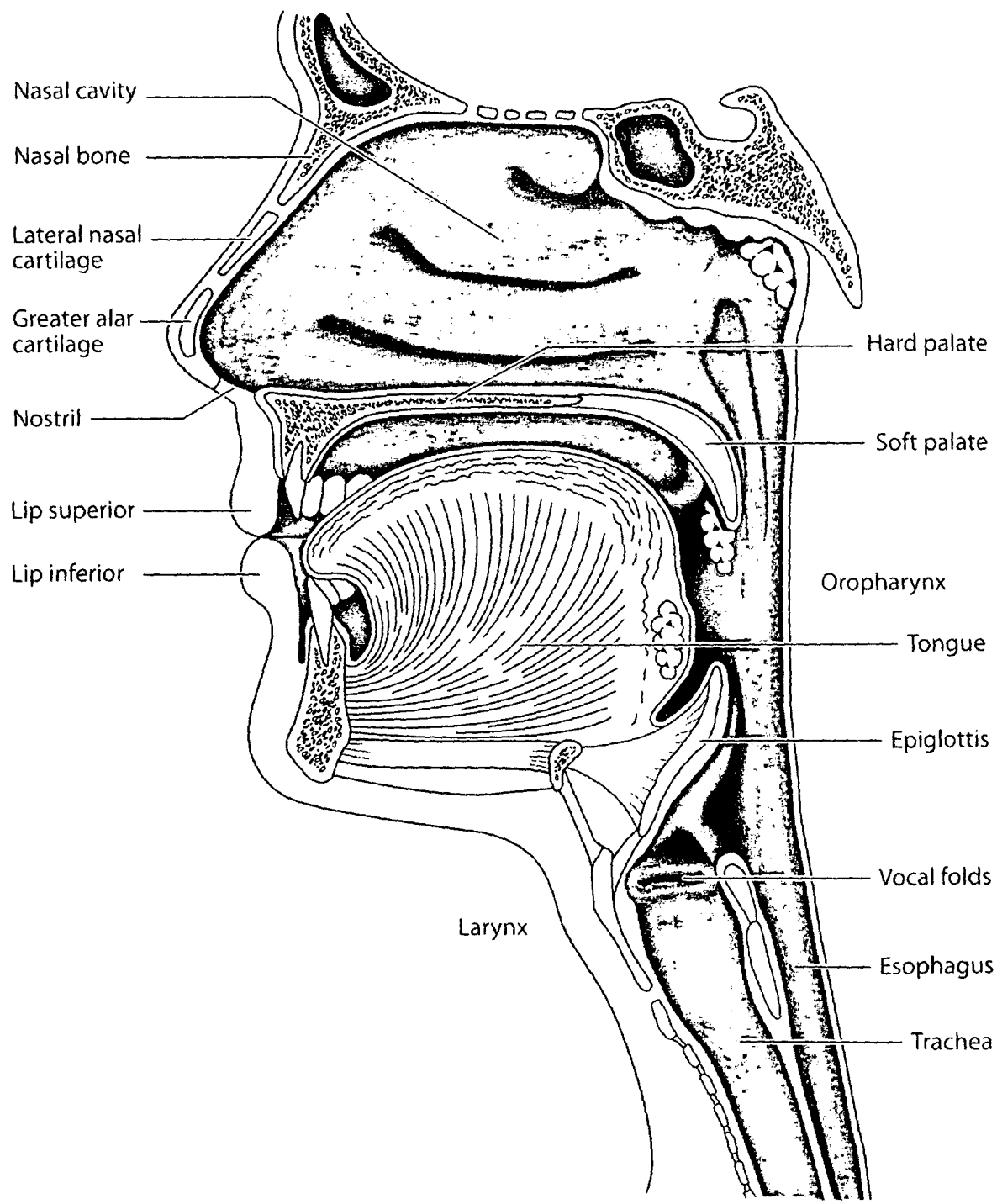

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Facial Anatomy

Figure 2C:
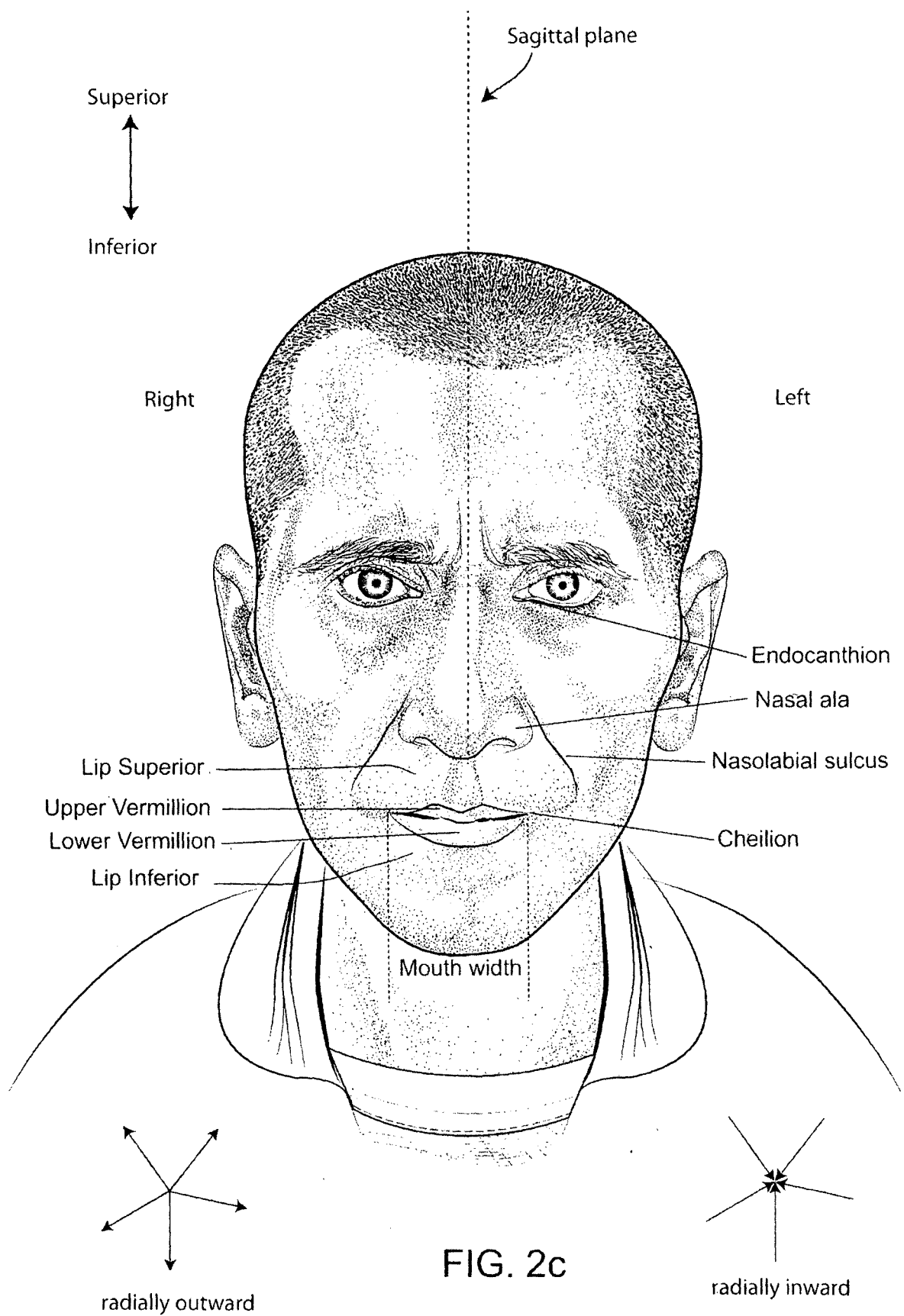

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
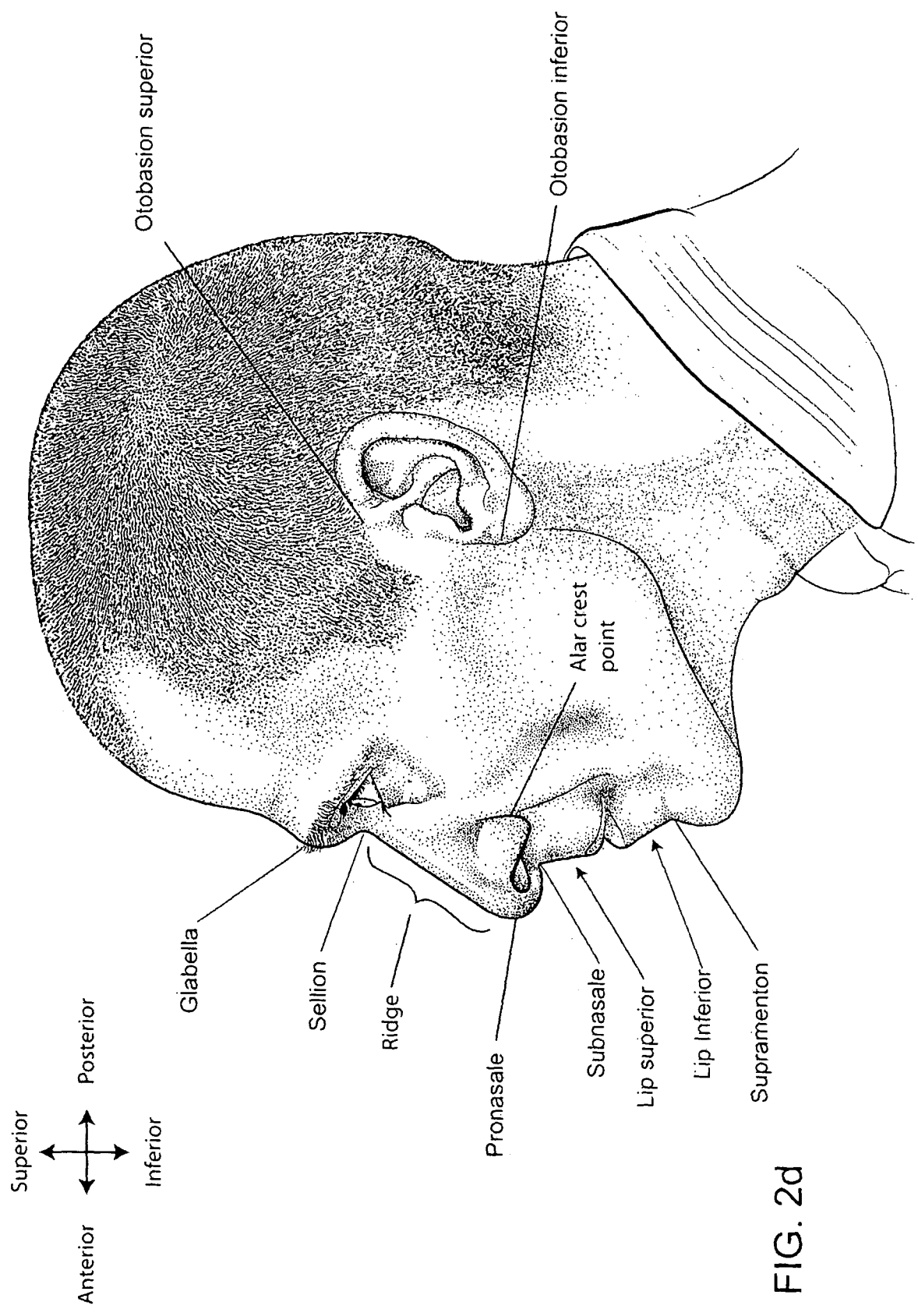

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
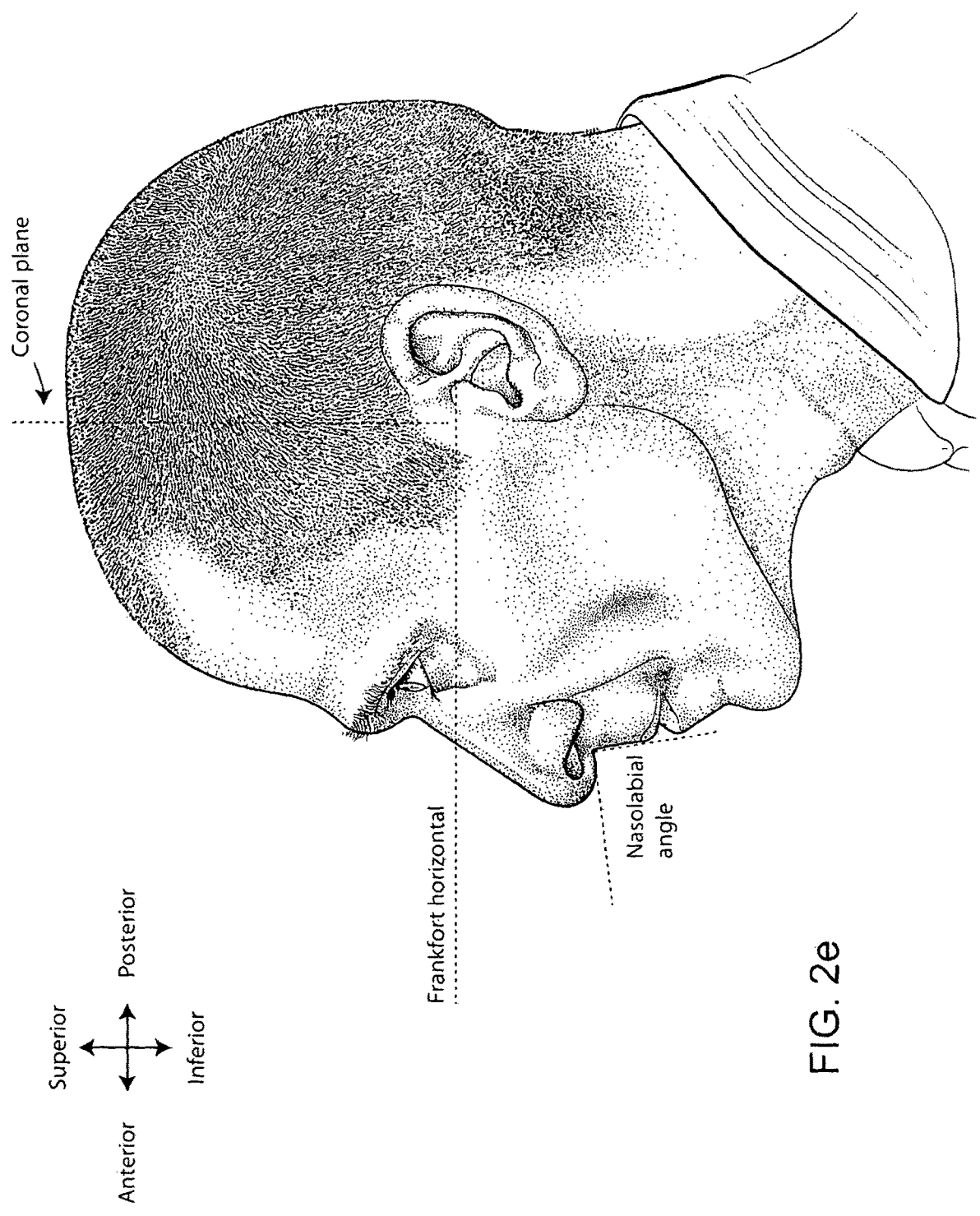

FIG. 2e is a further side view of a head. The approximate locations of the Frankfort horizontal and nasolabial angle are indicated.

Figure 2F:
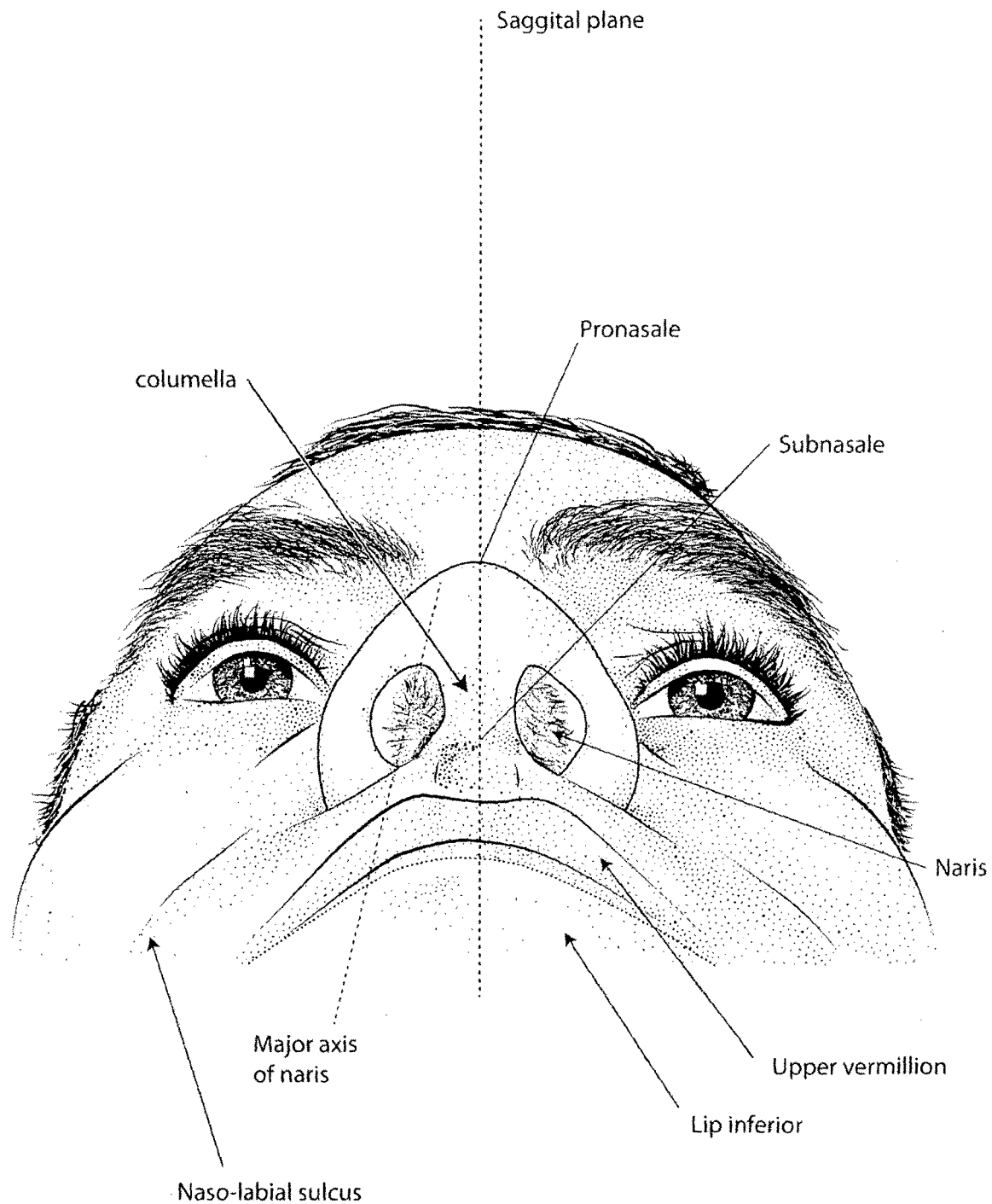

FIG. 2f shows a base view of a nose.

Figure 2I:
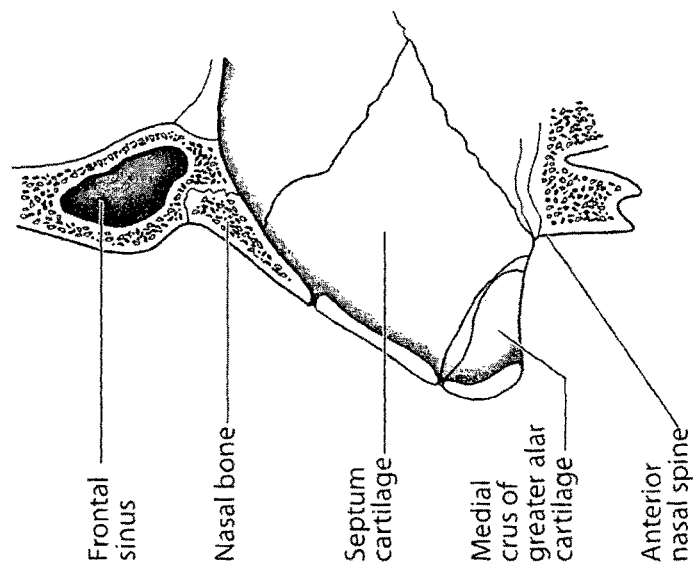
Figure 2H:
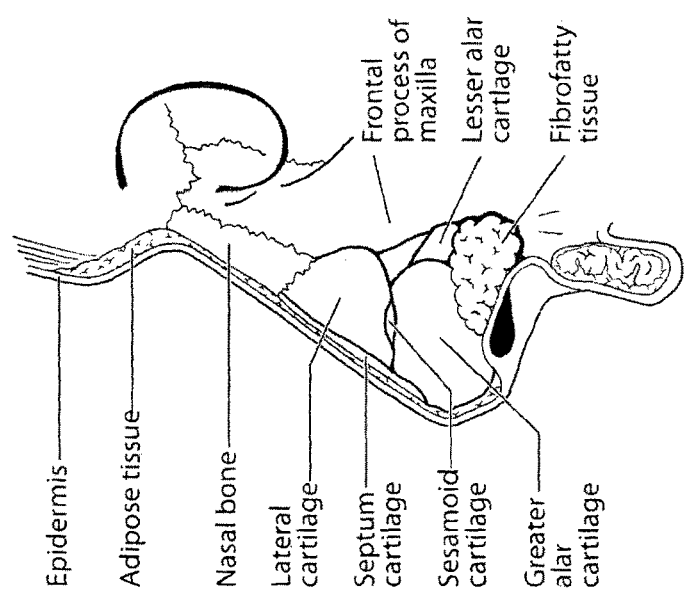
Figure 2G:

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
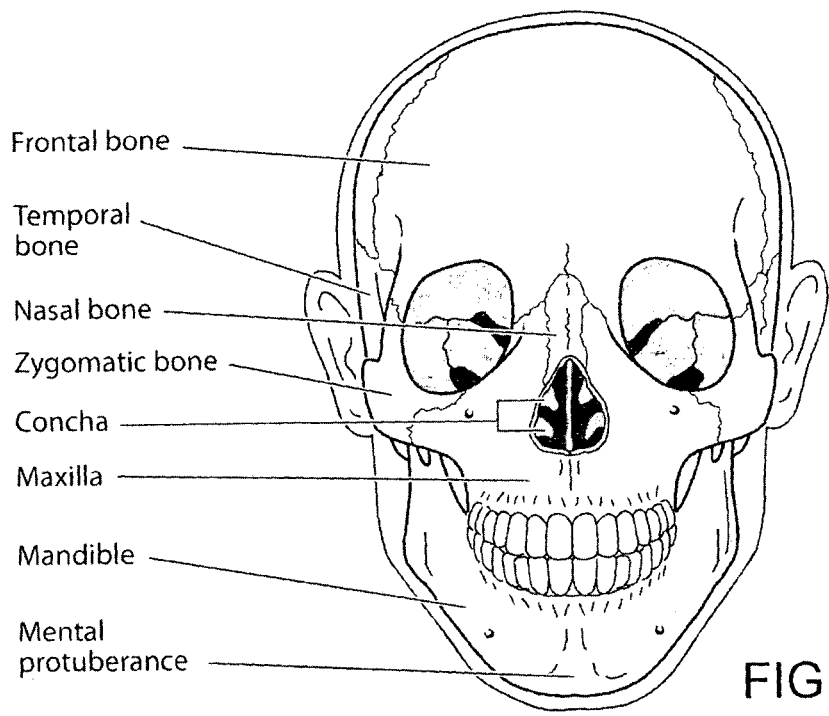

FIG. 2j shows a front view of the bones of a skull including the frontal, temporal, nasal and zygomatic bones. Nasal concha are indicated, as are the maxilla, mandible and mental protuberance.

Figure 2K:
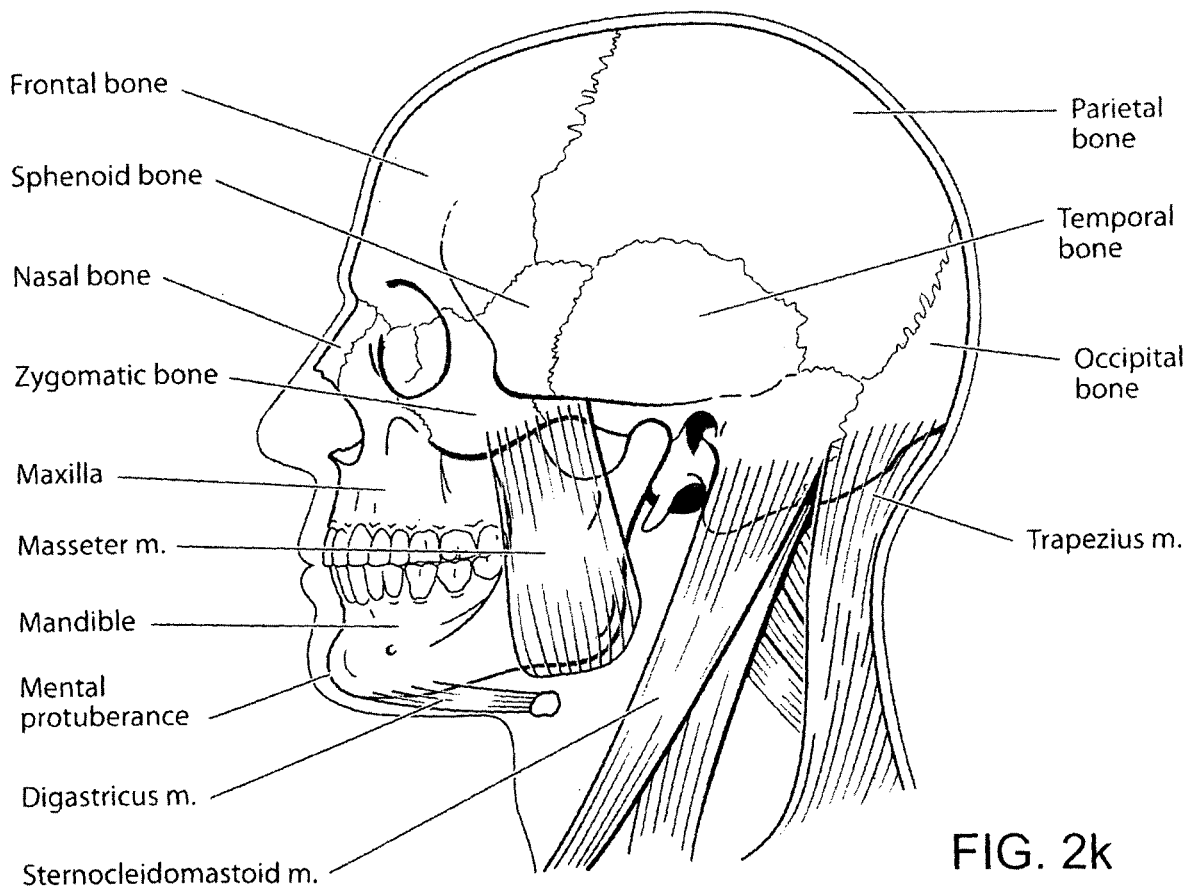

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of a nose.

PAP Device and Humidifier

Figure 3A:
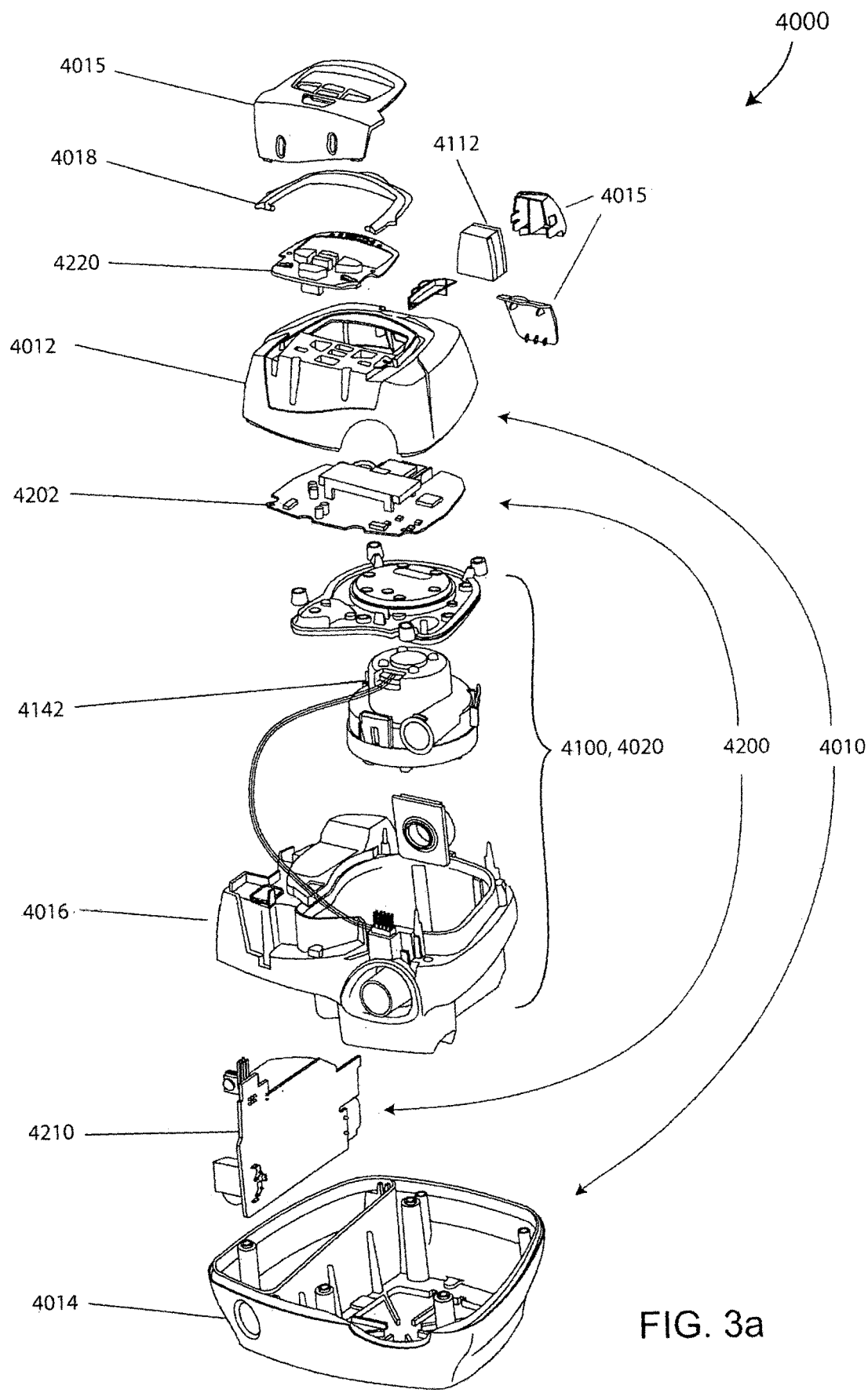

FIG. 3a shows an exploded view of a PAP device according to an example of the present technology.

Figure 3B:
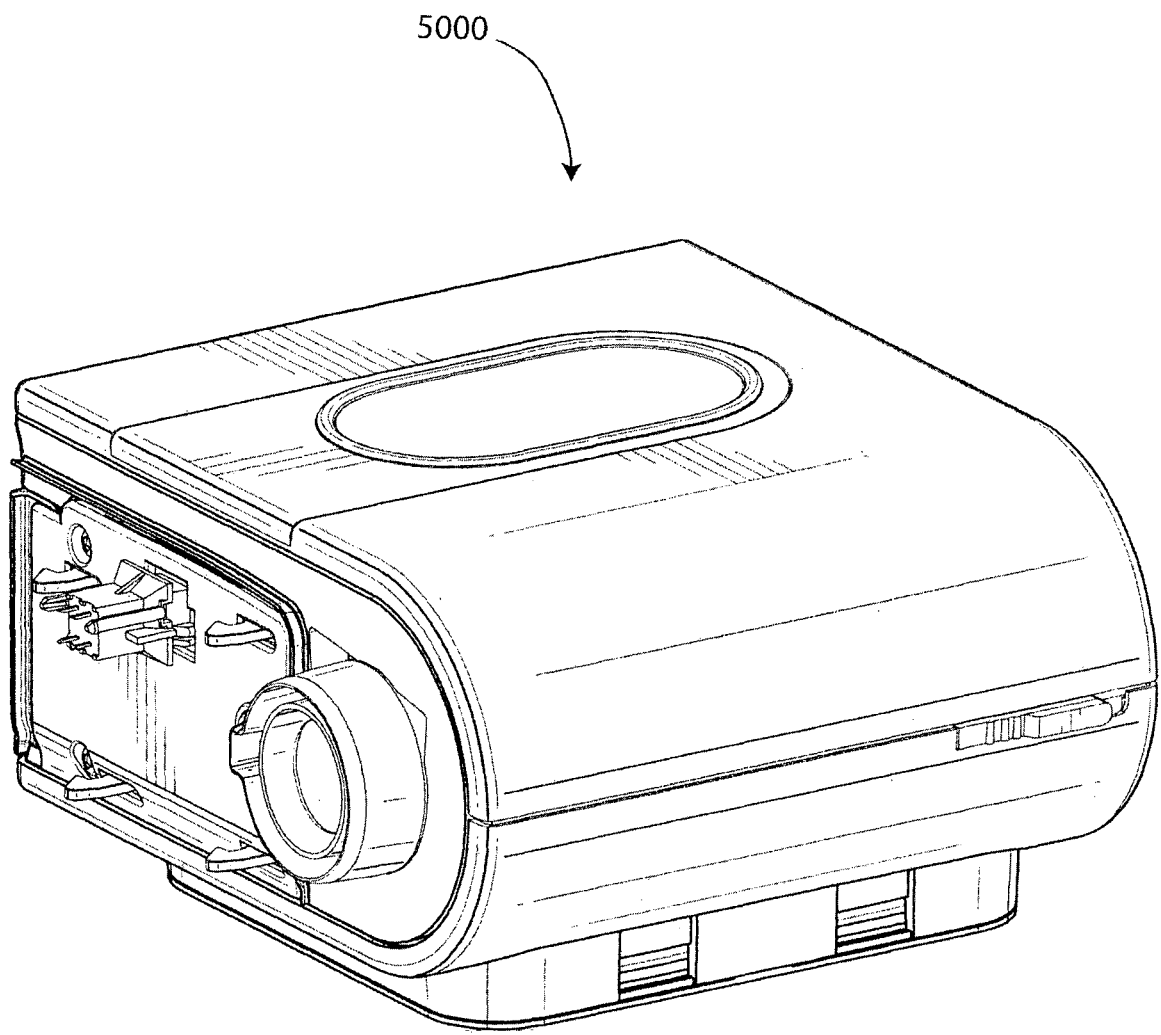

FIG. 3b shows a perspective view of a humidifier in accordance with one form of the present technology.

Figure 3C:
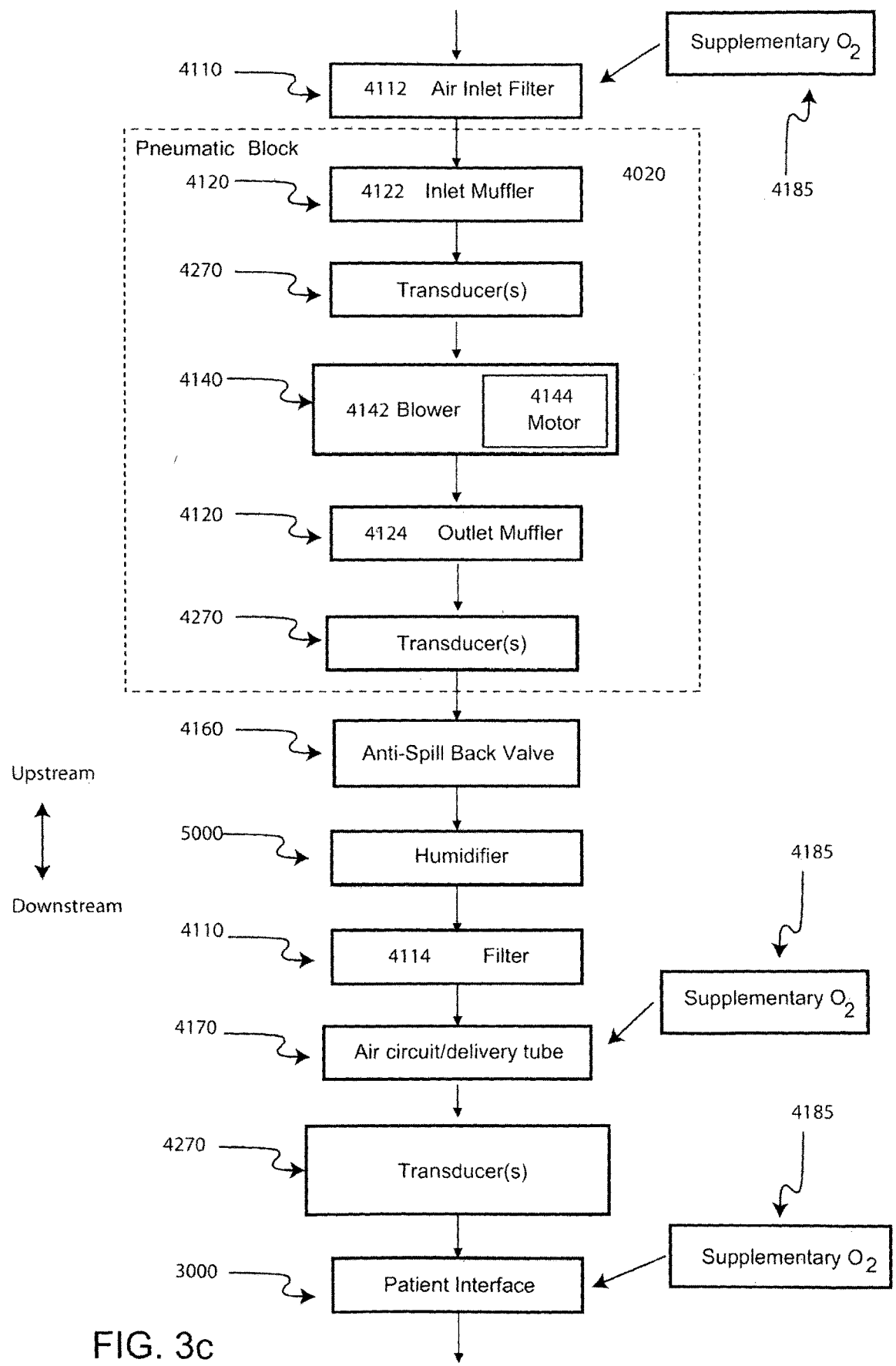

FIG. 3c shows a schematic diagram of the pneumatic circuit of a PAP device in accordance with one form of the present technology. The directions of upstream and downstream are indicated.

Patient Interface

Figure 4:
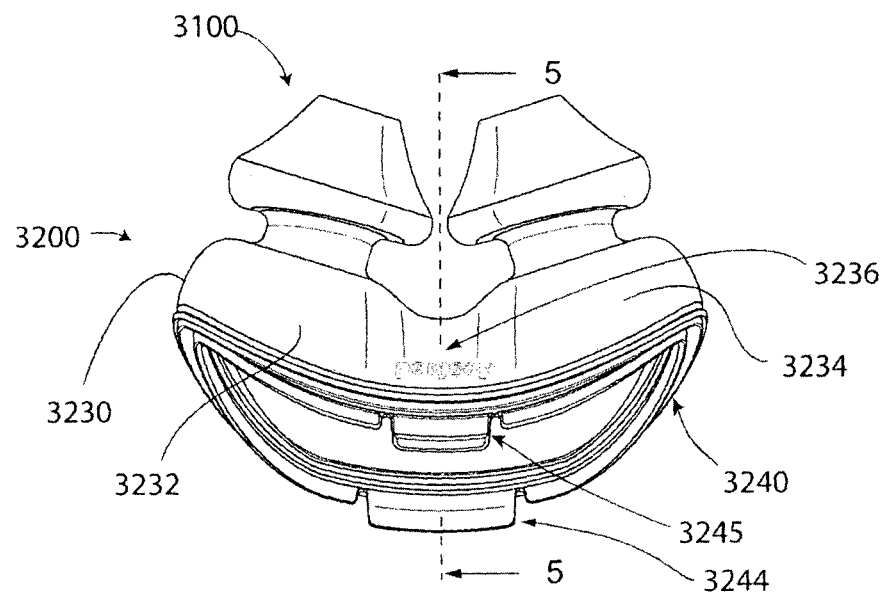

FIG. 4 is an anterior view of a plenum chamber in accordance with one form of the present technology.

Figure 5:
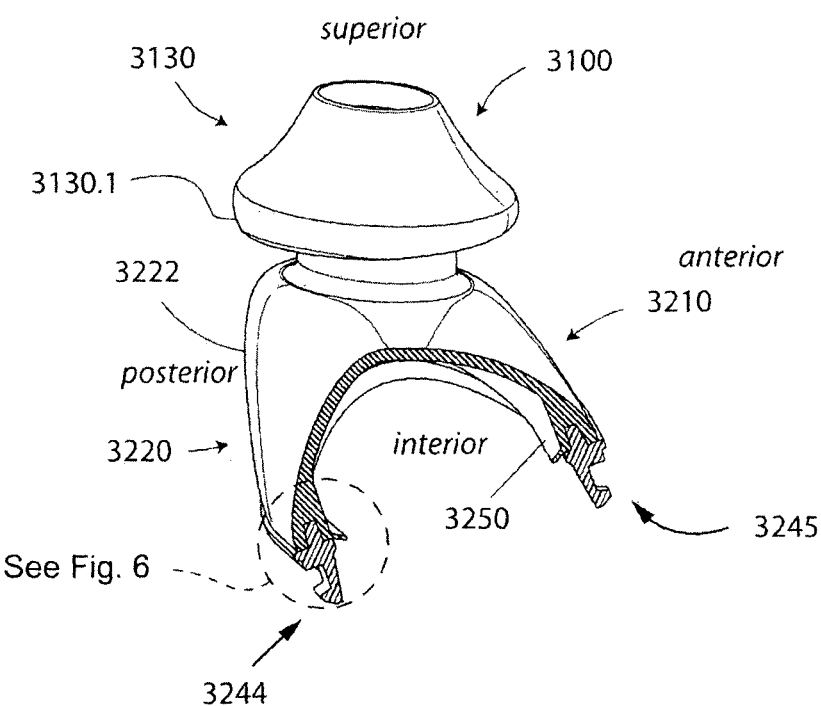

FIG. 5 is a cross section along line 5-5 of FIG. 4.

Figure 6:
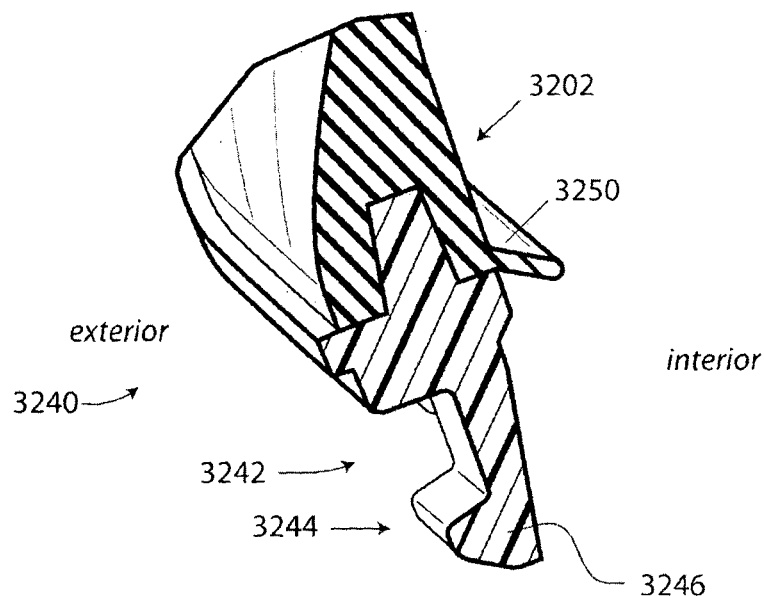

FIG. 6 is an enlarged detail view taken from FIG. 5.

Figure 7:
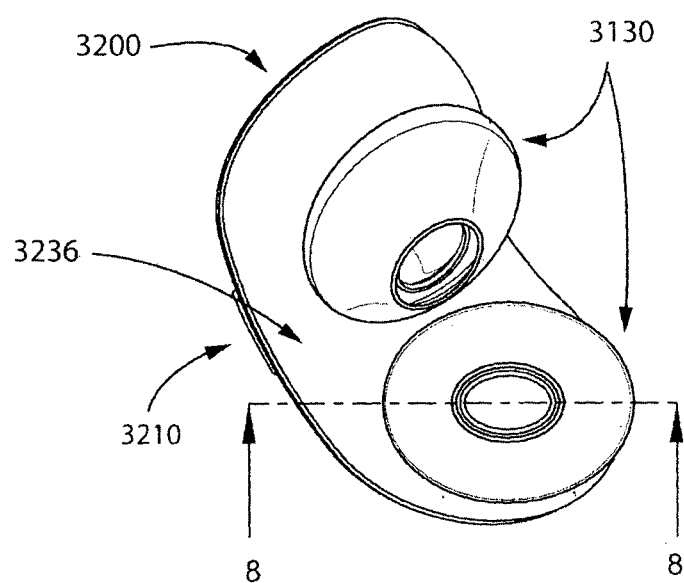

FIG. 7 is a perspective view from the top of the plenum chamber shown in FIG. 4.

Figure 8:
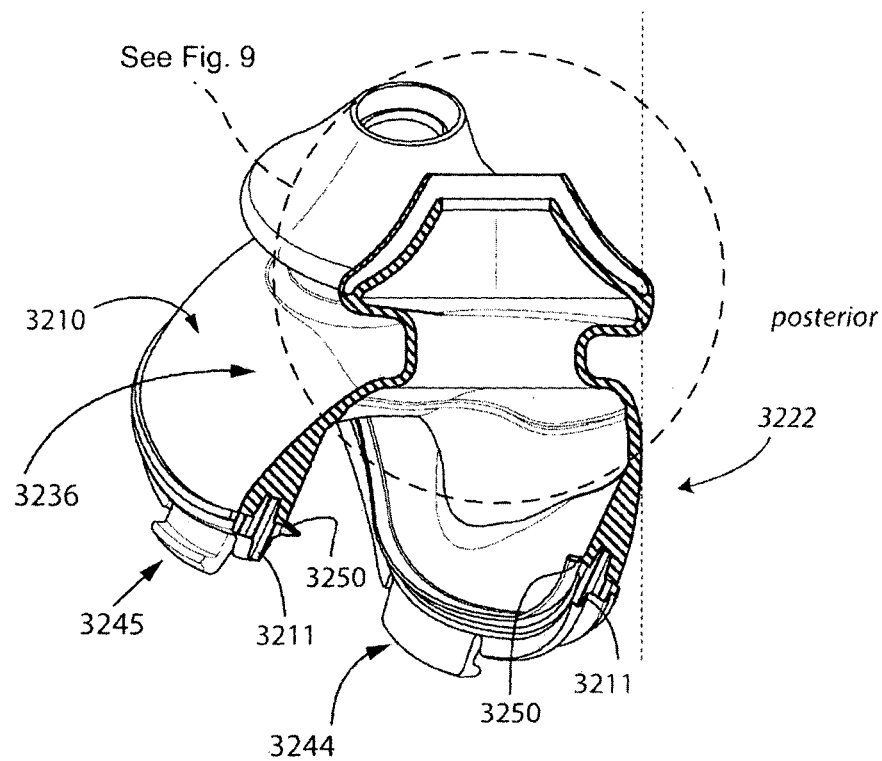

FIG. 8 is a cross-section along line 8-8 of FIG. 7.

Figure 9:
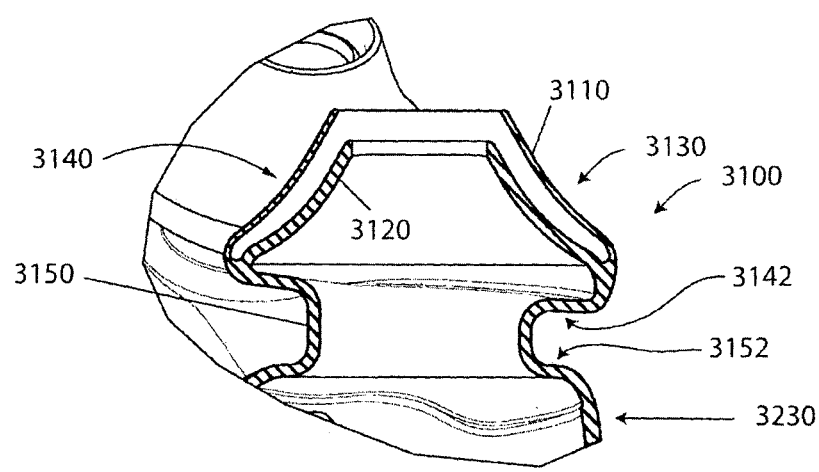

FIG. 9 is an enlarged detail view taken from FIG. 8.

Figure 10:
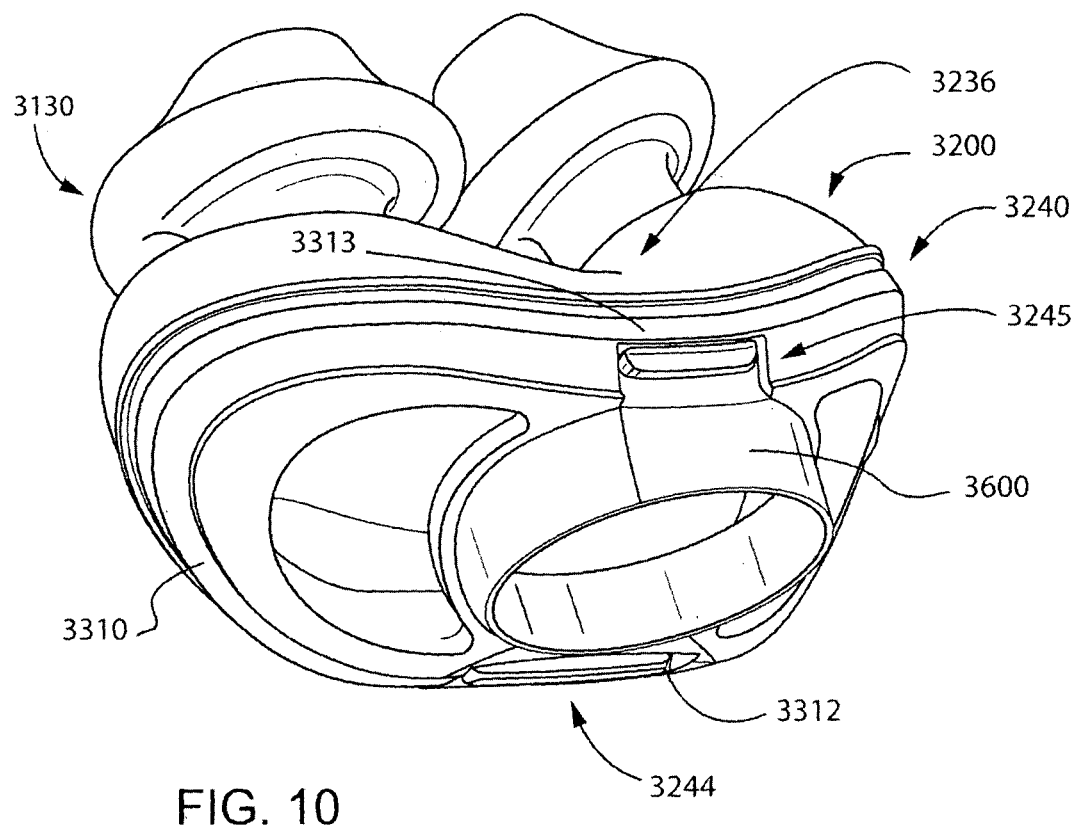

FIG. 10 is a perspective view from the front side of a plenum chamber according to one example of the present technology.

Figure 11:
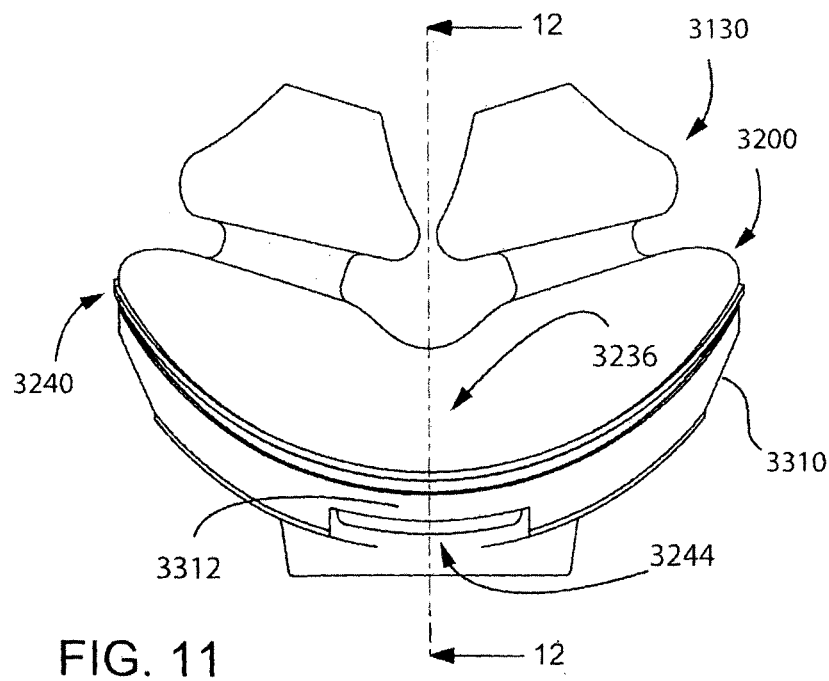

FIG. 11 is a view of the plenum chamber shown in FIG. 4.

Figure 12:
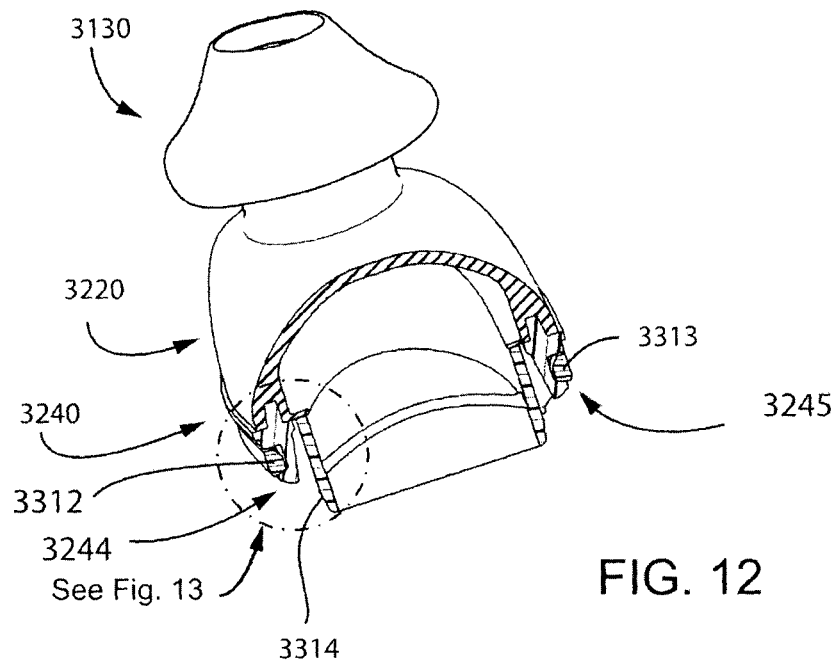

FIG. 12 is a cross-section taken along line 12-12 of FIG. 11.

Figure 13:
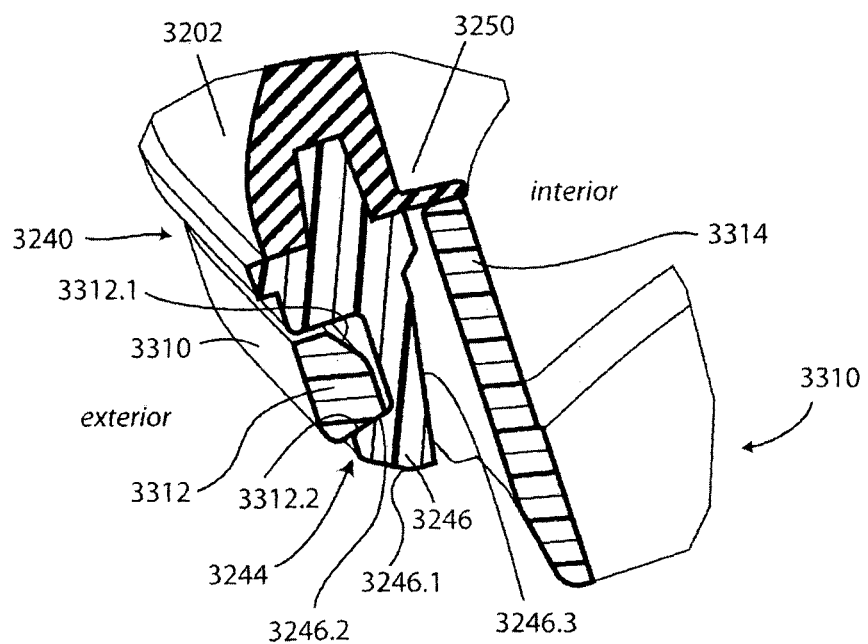

FIG. 13 is an enlarged detail view taken from FIG. 12.

Figure 14:
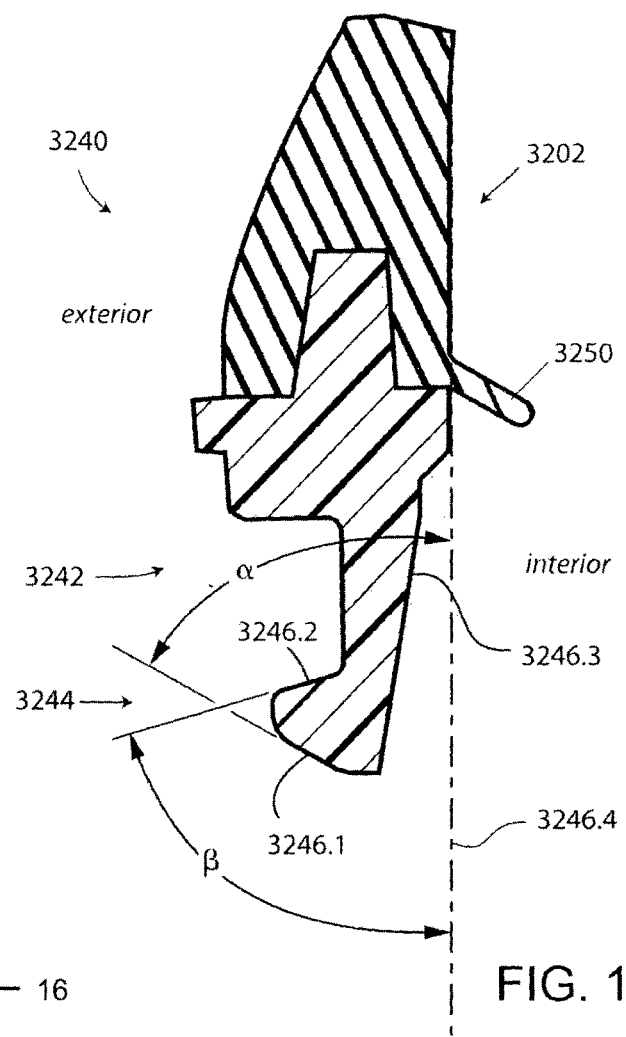

FIG. 14 is an enlarged cross-sectional view of the plenum connection region.

Figure 15:
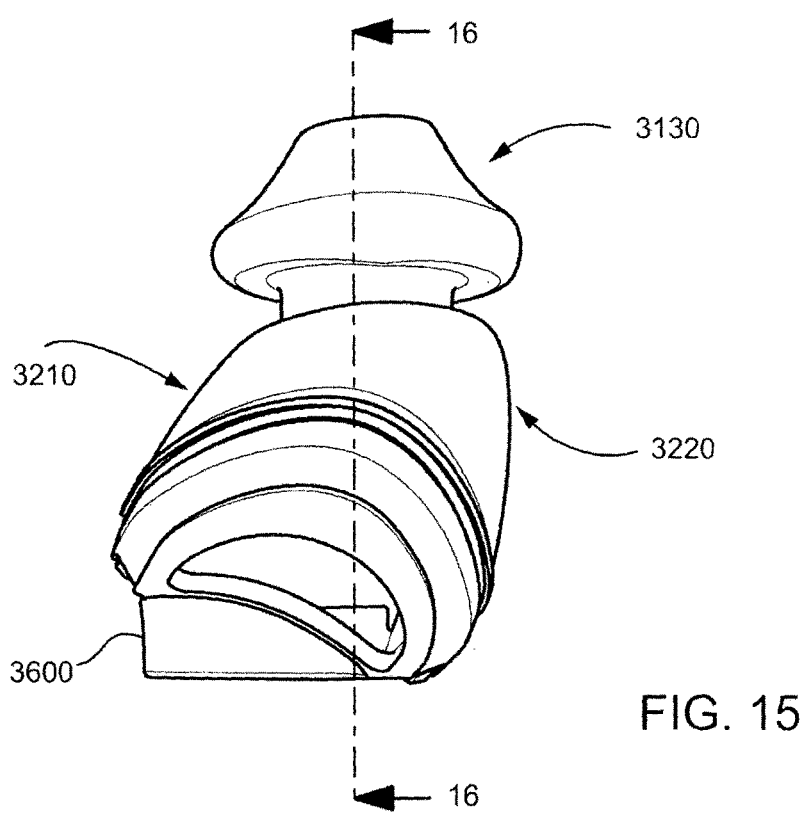

FIG. 15 is a side view of the patient interface shown in FIG. 11.

Figure 16:
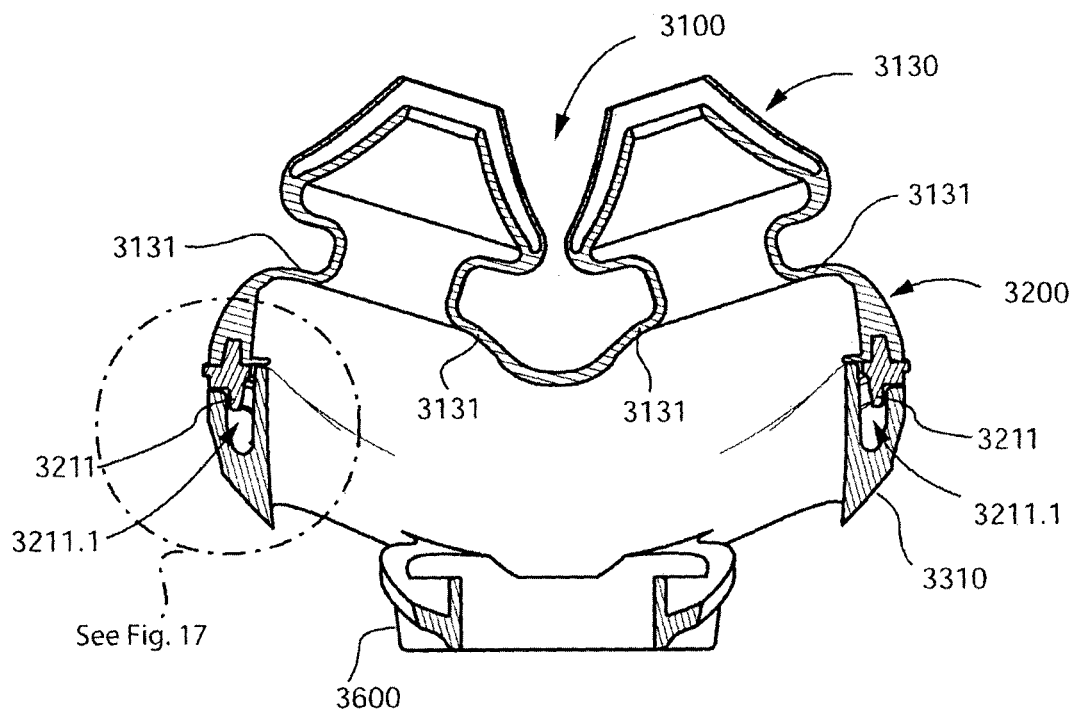

FIG. 16 is a cross-section taken along line 16-16 of FIG. 15.

Figure 17:
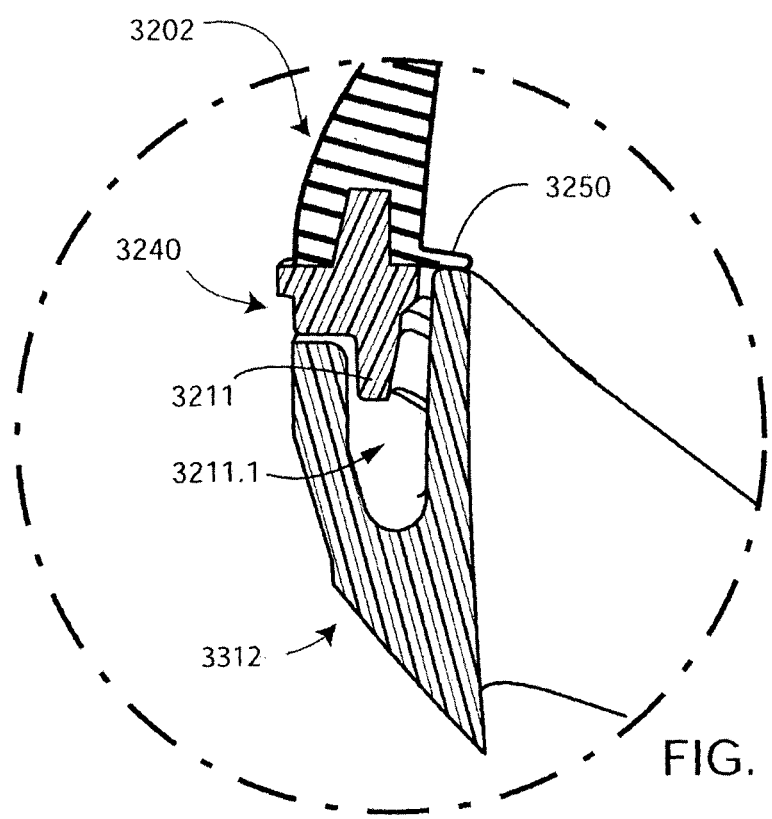

FIG. 17 is an enlarged detail view taken from FIG. 16.

Figure 18:
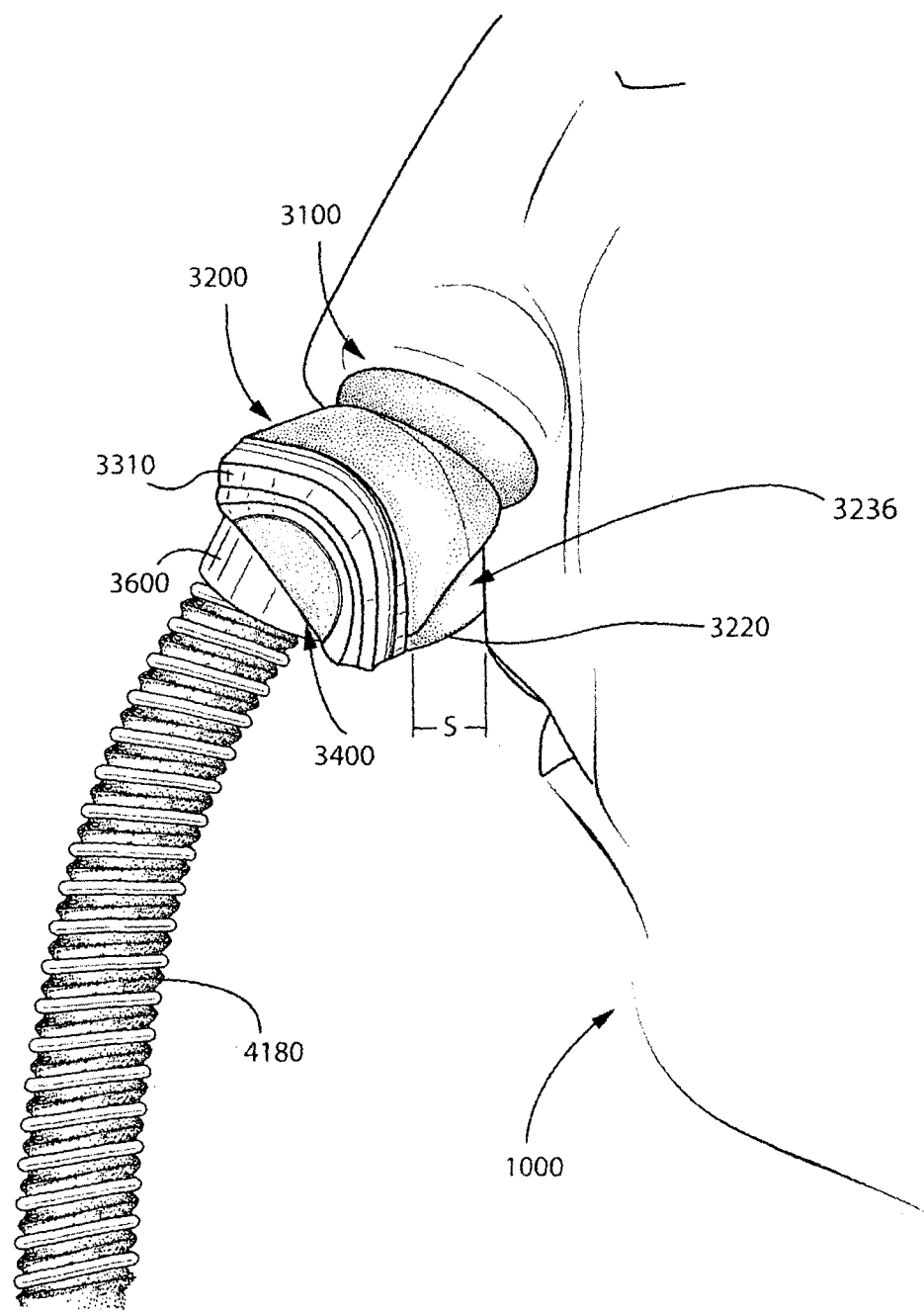

FIG. 18 is a side view of a patient interface in position on a model patient's head without any positioning and stabilising structure shown.

Figure 19:
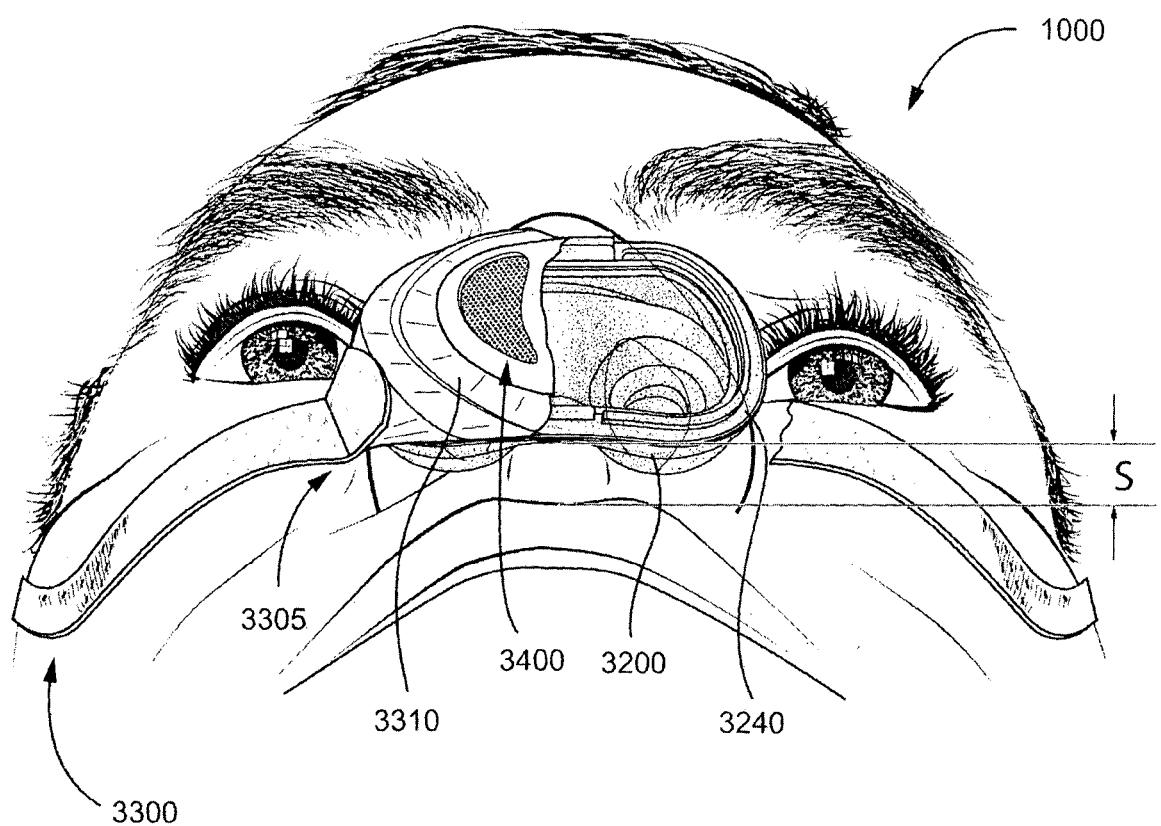

FIG. 19 is a partial, inferior view of a portion of a patient interface in position on a model patient's head accordance with one form of the present technology. Note that only a portion of the positioning and stabilising structure connecting to the frame is shown for clarity.

FIG. 20 is a side view of a plenum connection region of a plenum chamber in accordance with one form of the present technology.

Figure 21:
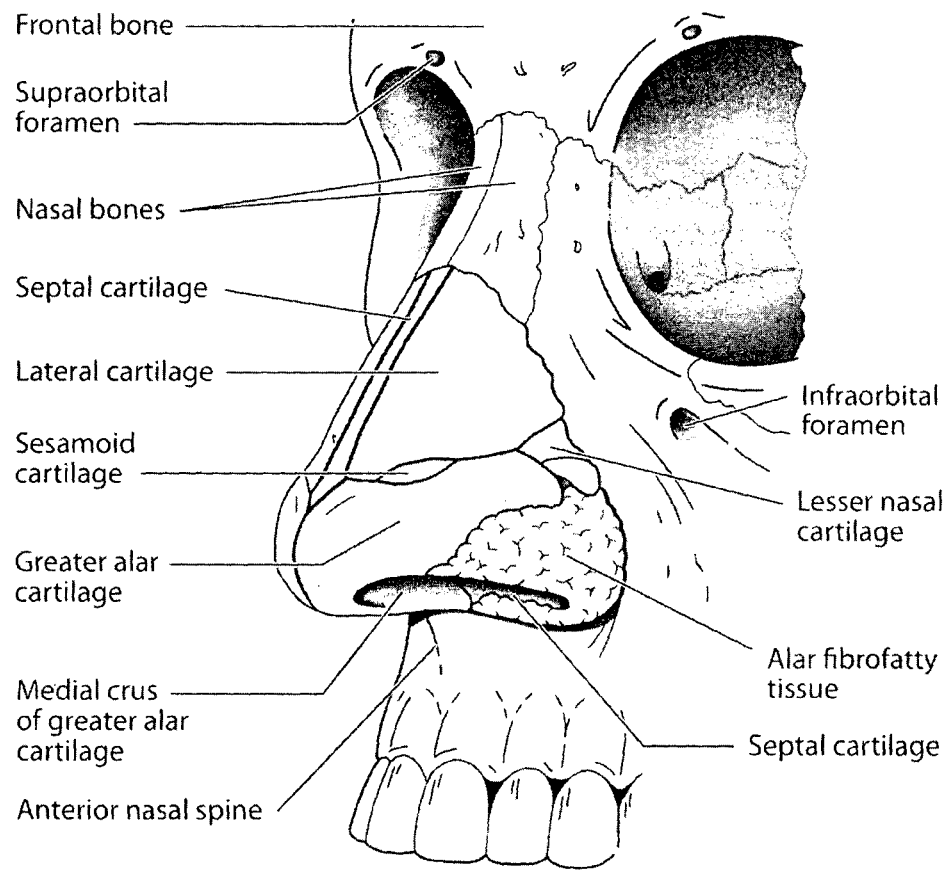

FIG. 21 is a view of a superior portion thereof.

FIG. 22 is an anterior view thereof.

FIG. 23 is an inferior view thereof.

FIG. 24 is a perspective view thereof.

Figure 25:
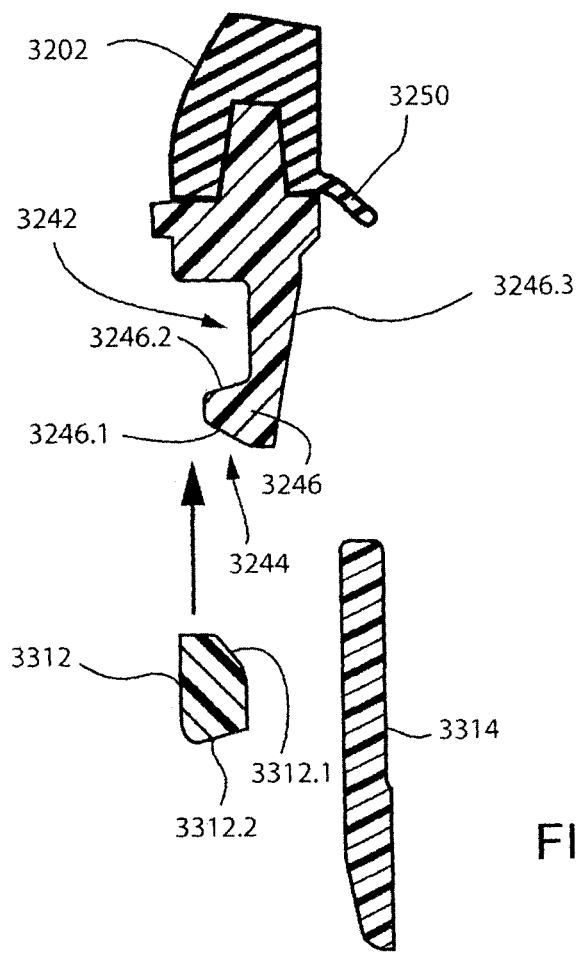

FIG. 25 is a cross-sectional view of the connection portion and the frame connection region, wherein the plenum chamber and the frame are not engaged.

Figure 26:
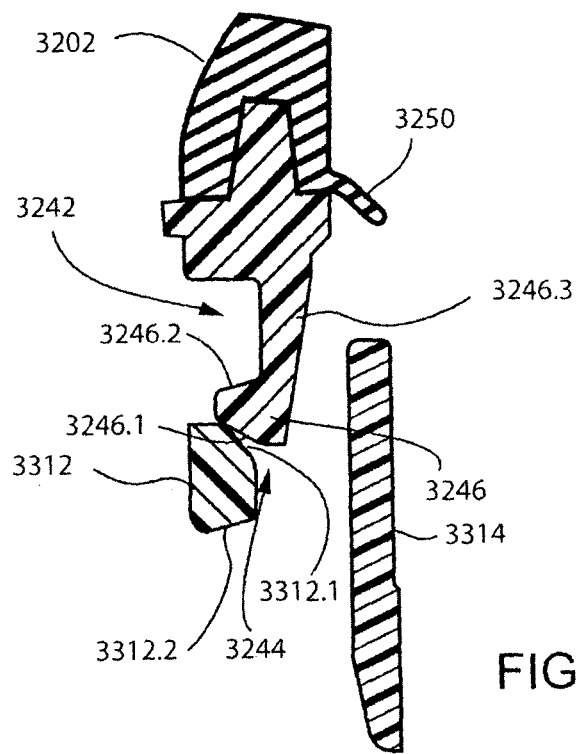

FIG. 26 is a cross-sectional view of the connection portion and the frame connection region, wherein the plenum chamber and the frame are in contact but not fully engaged.

Figure 27:
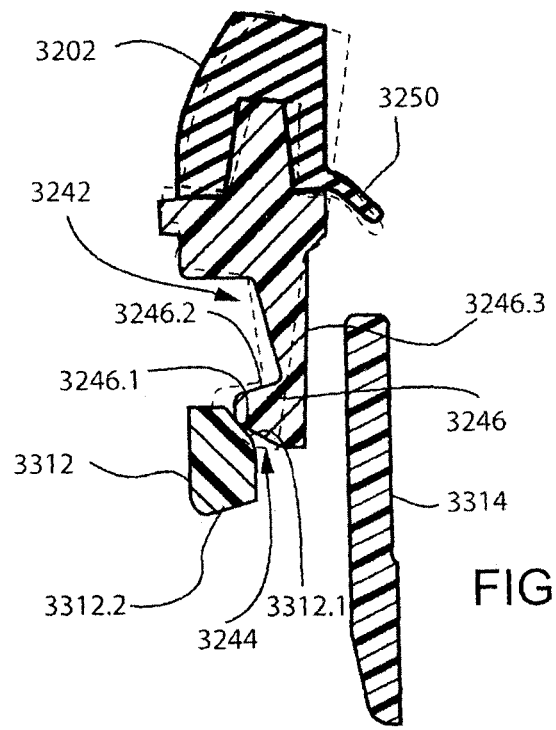

FIG. 27 is a cross-sectional view of the connection portion and the frame connection region, wherein the plenum chamber and the frame are nearly in full engagement with another such that the retention feature is deflected.

Figure 28:
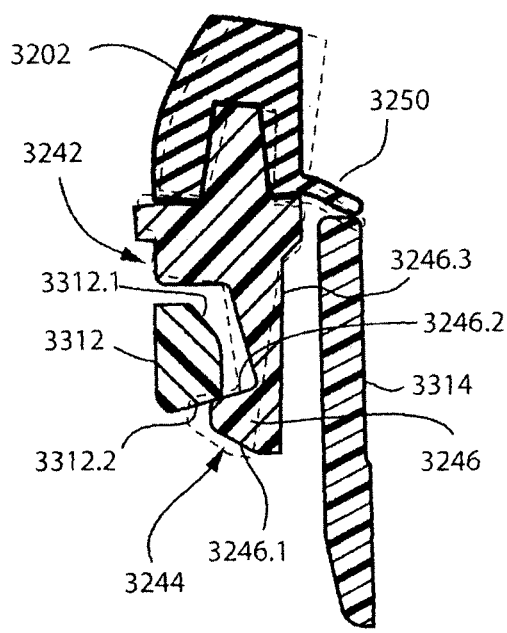

FIG. 28 is a cross-sectional view of the connection portion and the frame connection region, wherein the plenum chamber and the frame are engaged but separated such that the retention feature is deflected.

Figure 29:
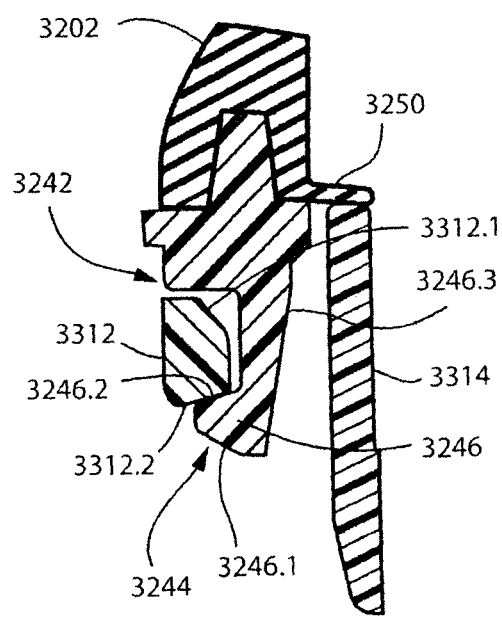

FIG. 29 is a cross-sectional view of the connection portion and the frame connection region, wherein the plenum chamber and the frame are fully engaged.

Figure 30:
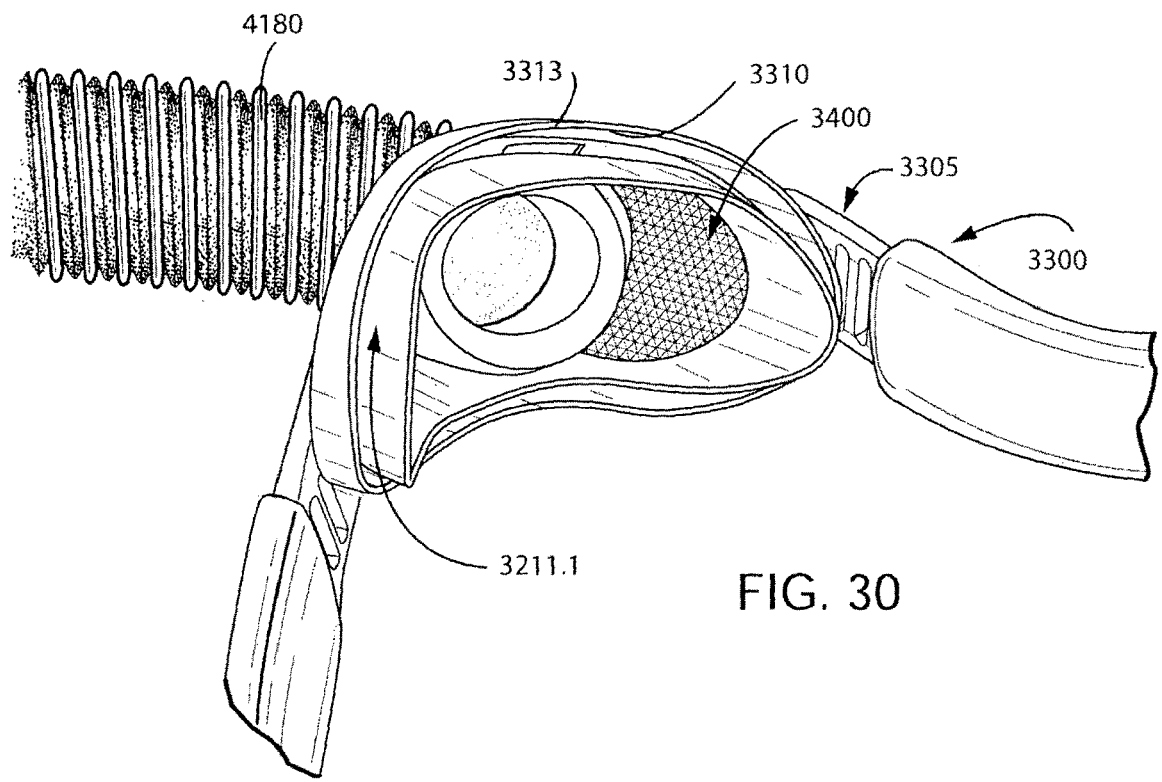

FIG. 30 is a rear perspective view of a patient interface according to an example of the present technology with the plenum chamber and seal-forming structure detached.

Figure 31:
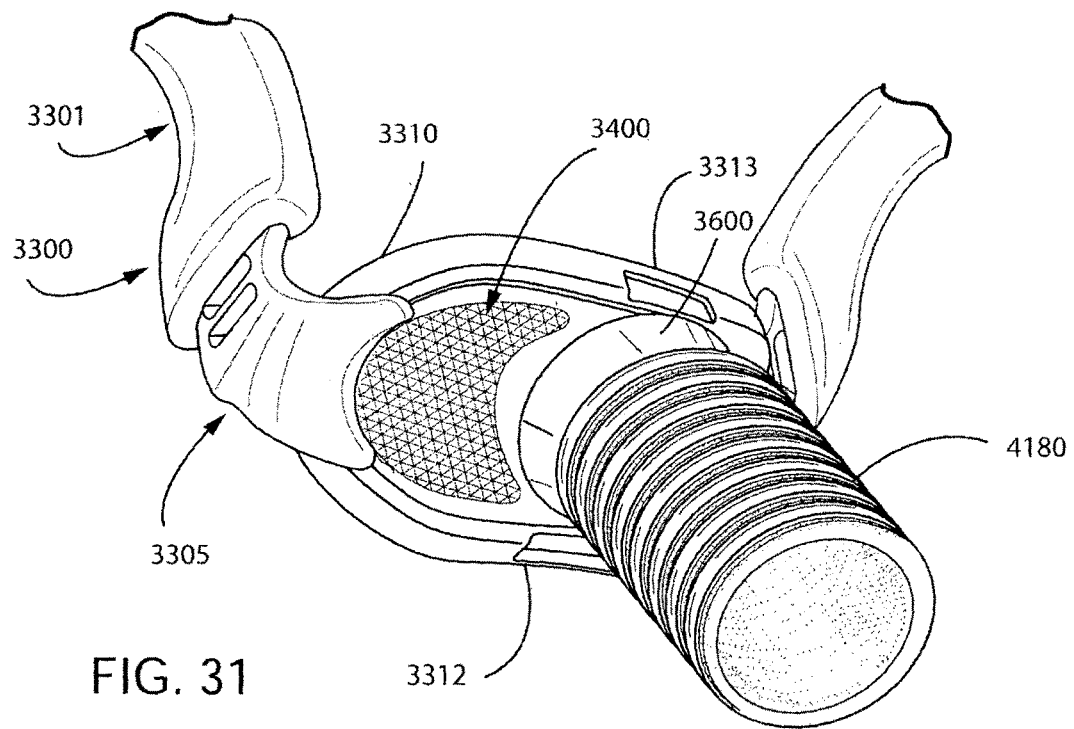

FIG. 31 is a front perspective view of a patient interface according to an example of the present technology with the plenum chamber and seal-forming structure detached.

Figure 32:
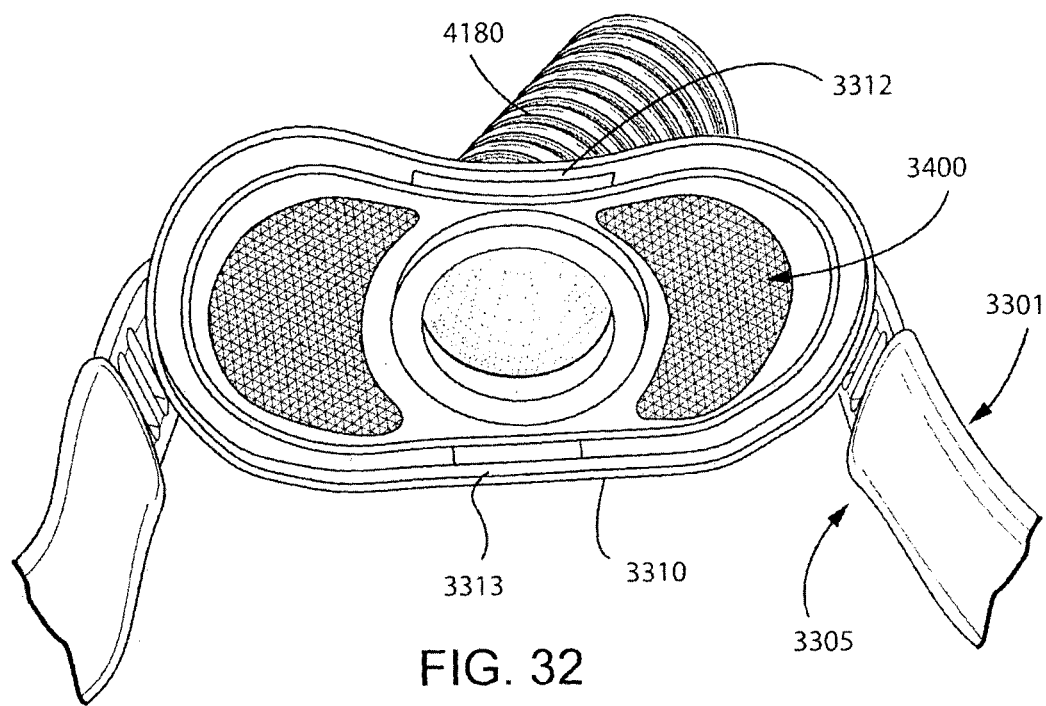

FIG. 32 is a rear view of a patient interface according to an example of the present technology with the plenum chamber and seal-forming structure detached.

Figure 33:
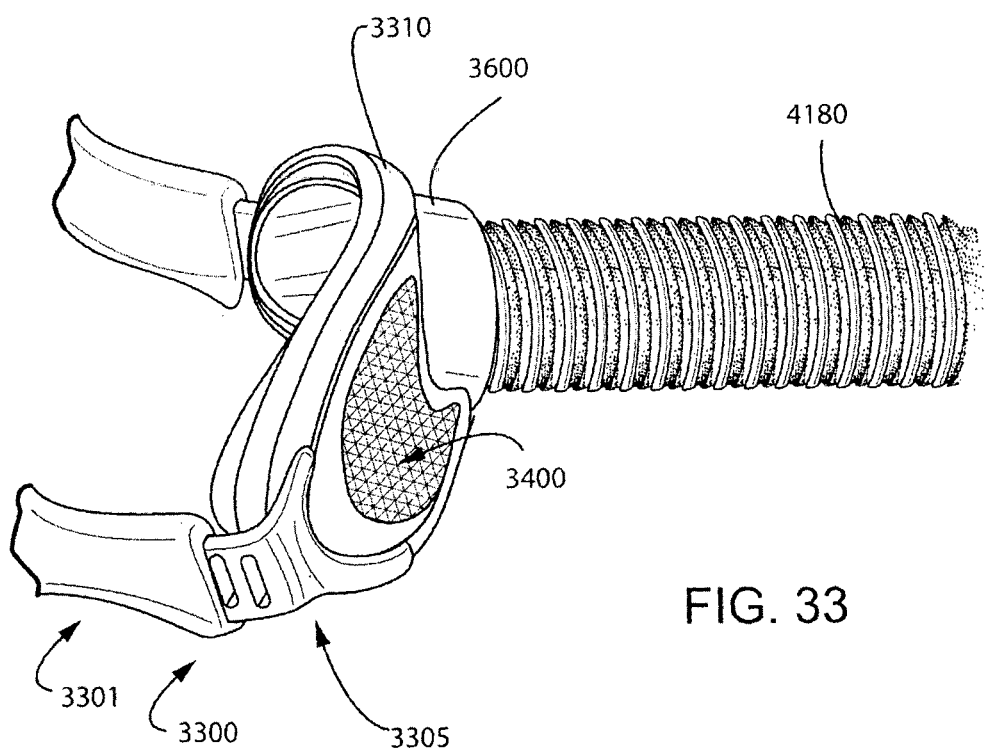

FIG. 33 is a side view of a patient interface according to an example of the present technology with the plenum chamber and seal-forming structure detached.

Figure 34:
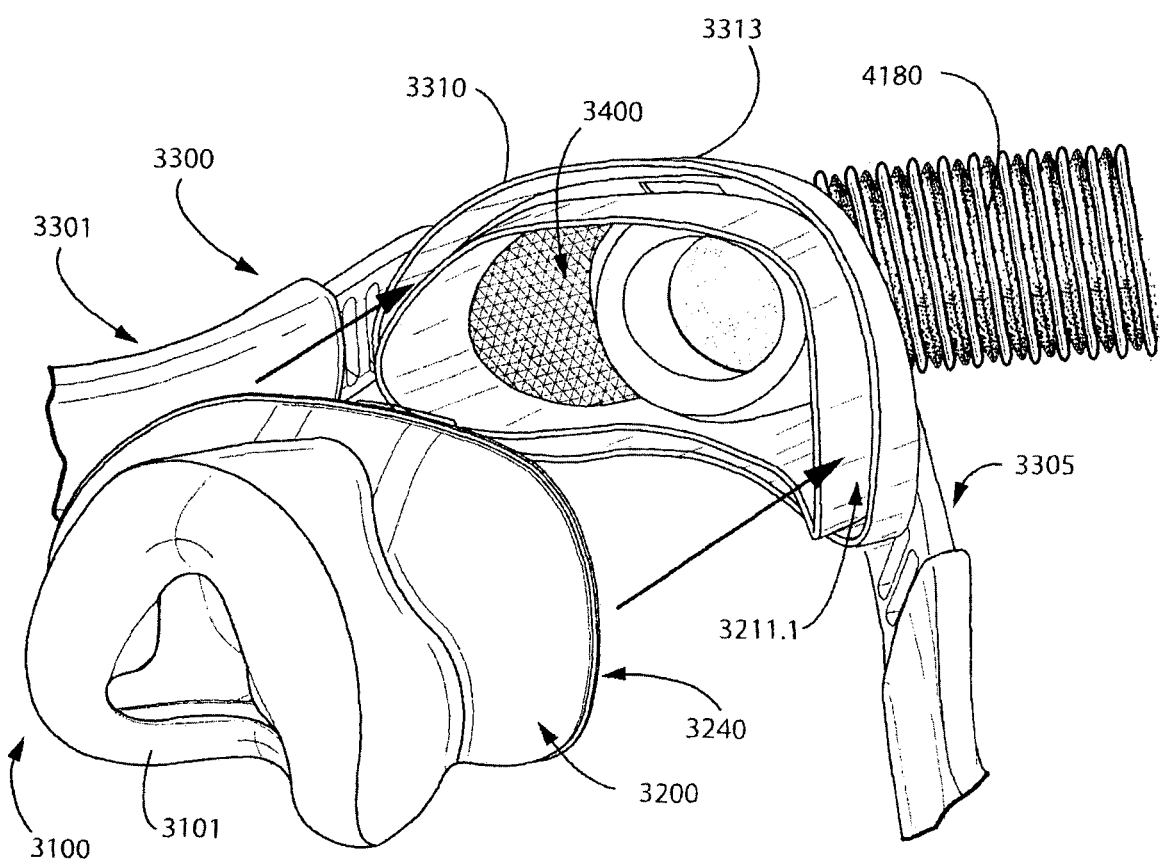

FIG. 34 shows a perspective view of a patient interface according to another example of the present technology indicating the attachment of an exemplary seal-forming structure and plenum chamber to a frame of the patient interface.

Figure 35:
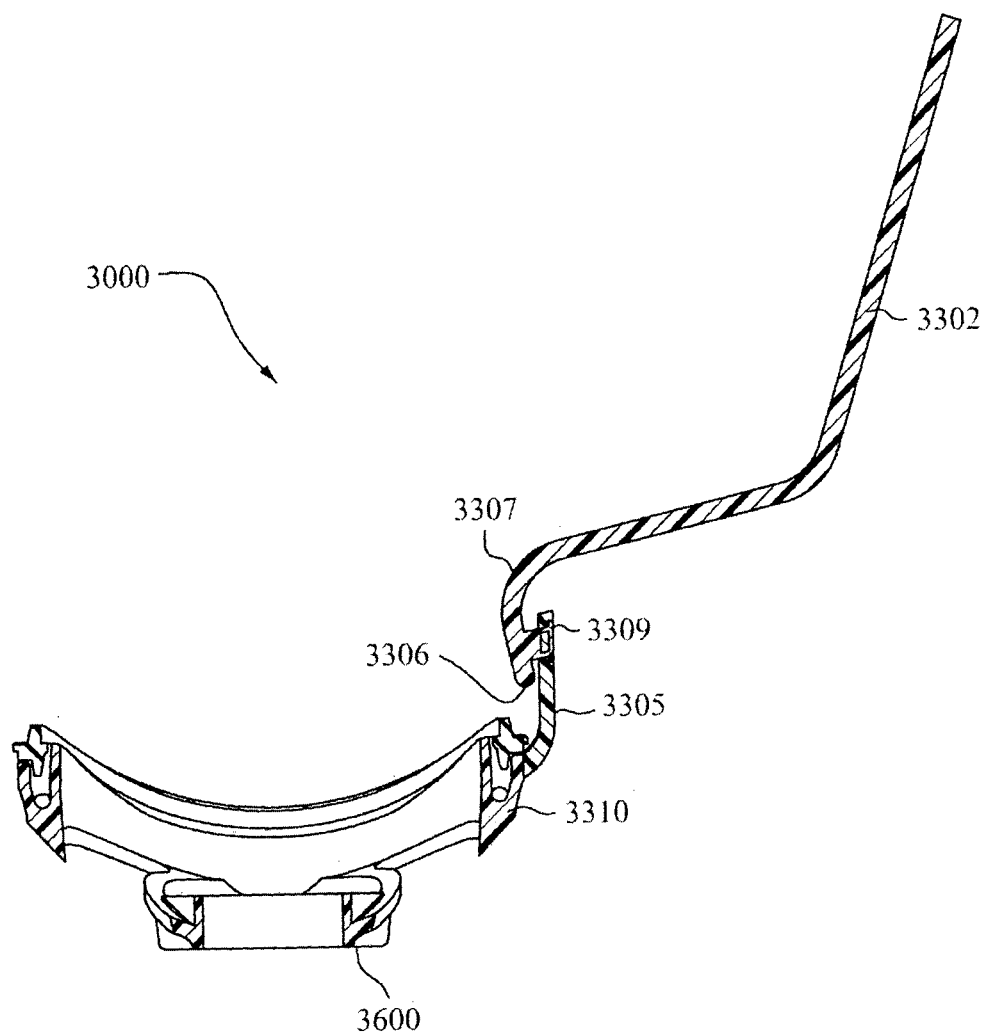

FIG. 35 shows a cross-sectional view of a patient interface including a mask frame, a flexible joint, and a rigidiser arm according to an example of the present technology.

Figure 36:
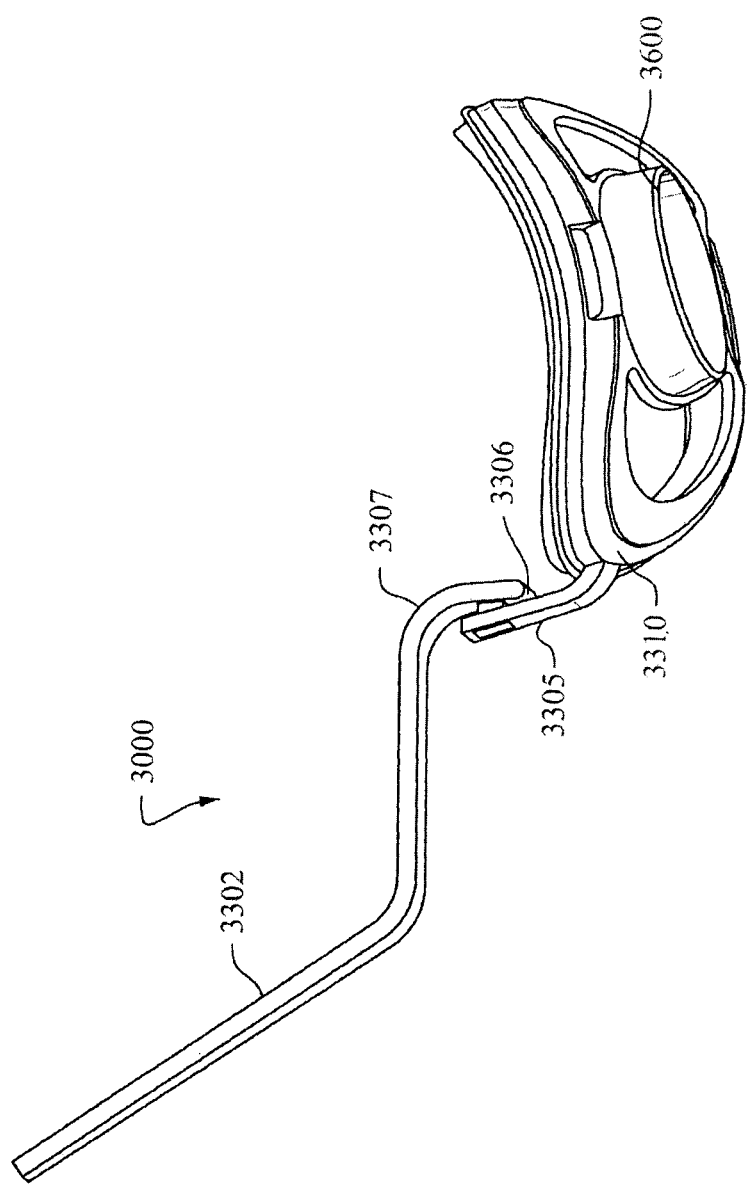

FIG. 36 shows a perspective view of a patient interface including a mask frame, a flexible joint, and a rigidiser arm according to an example of the present technology.

Figure 37:
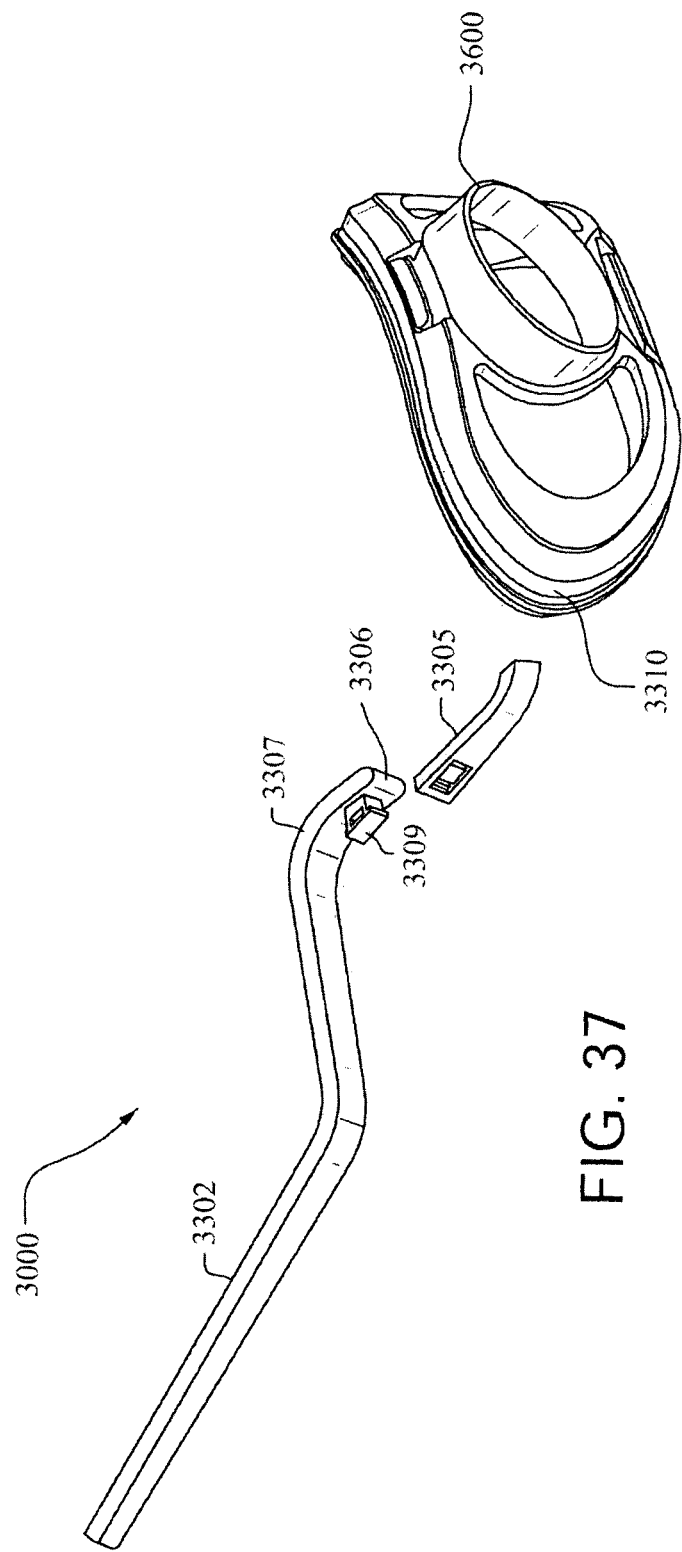

FIG. 37 shows an exploded view of a patient interface including a mask frame, a flexible joint, and a rigidiser arm according to an example of the present technology.

Figure 38:
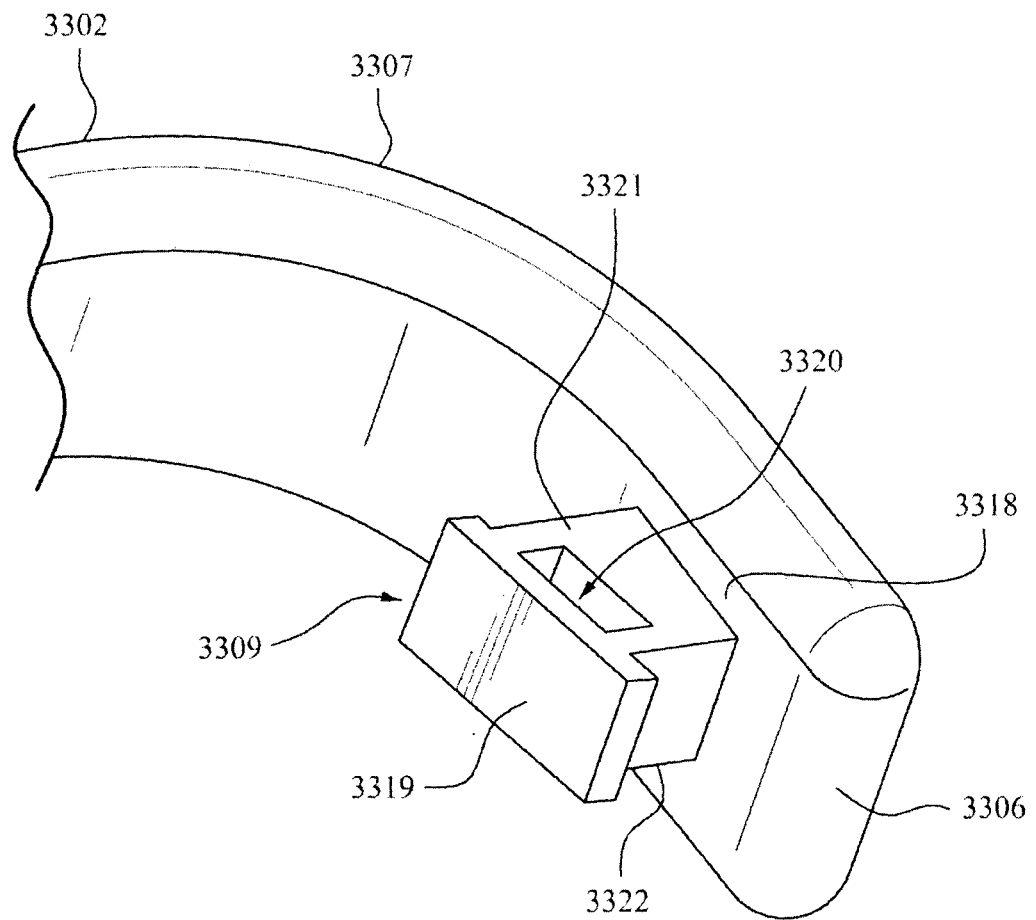

FIG. 38 shows a detailed view of an end of a rigidiser arm according to an example of the present technology.

Figure 39:
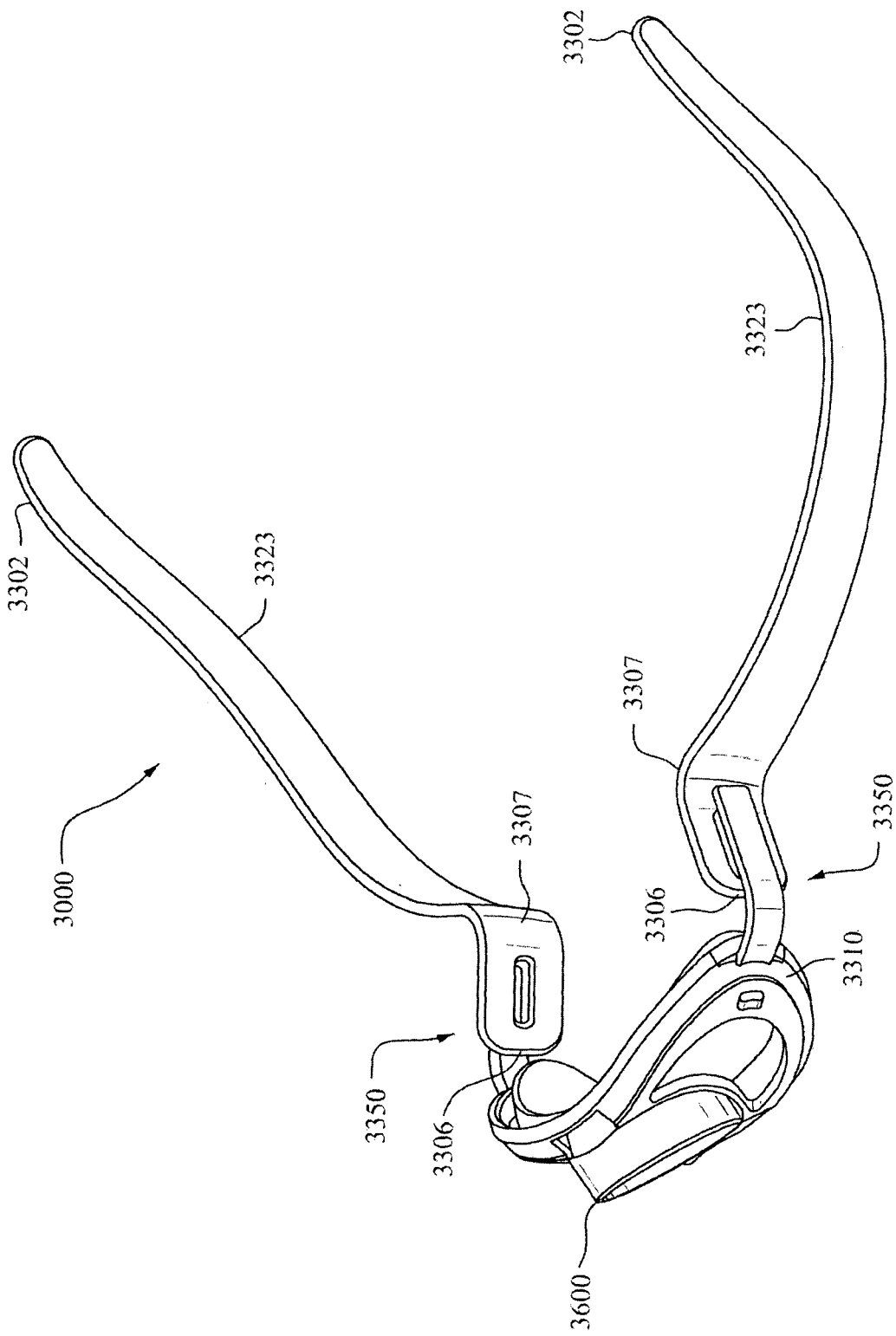

FIG. 39 shows a perspective view of a patient interface including a mask frame, flexible joints, and rigidiser arms according to an example of the present technology.

Figure 40:
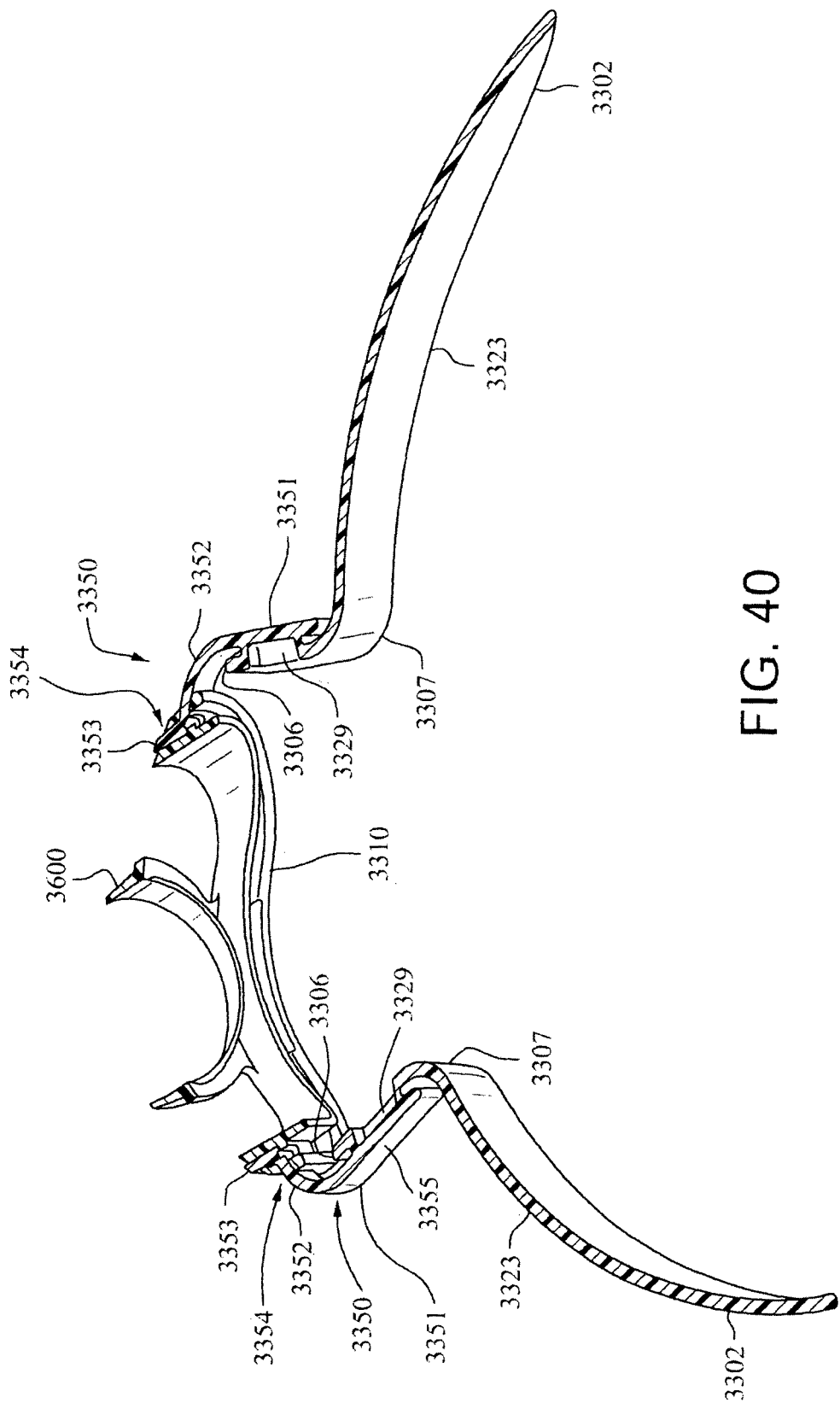

FIG. 40 shows a cross-sectional view of a patient interface including a mask frame, flexible joints, and rigidiser arms according to an example of the present technology.

Figure 41:
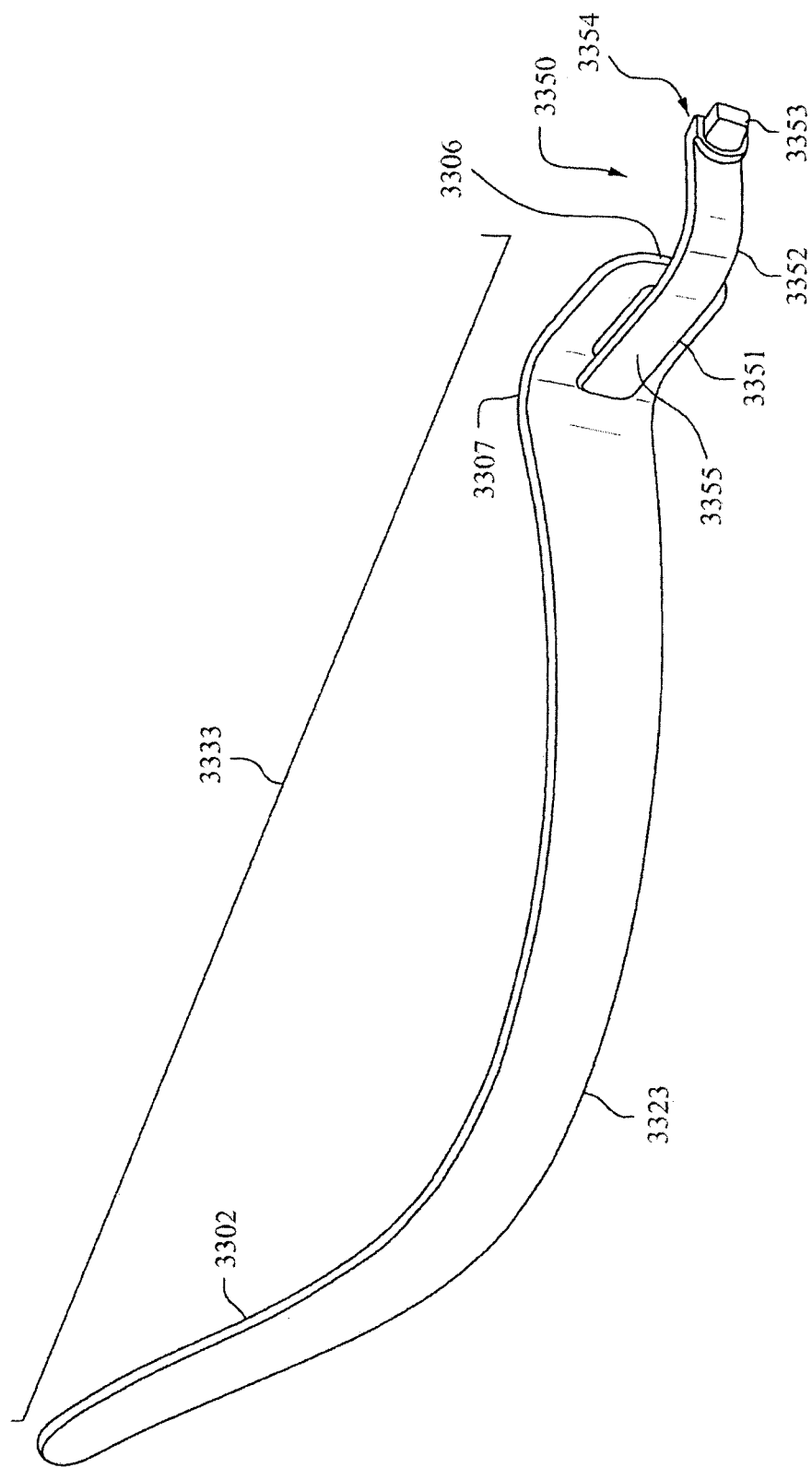

FIG. 41 shows a perspective view of a rigidiser arm according to an example of the present technology.

Figure 42:
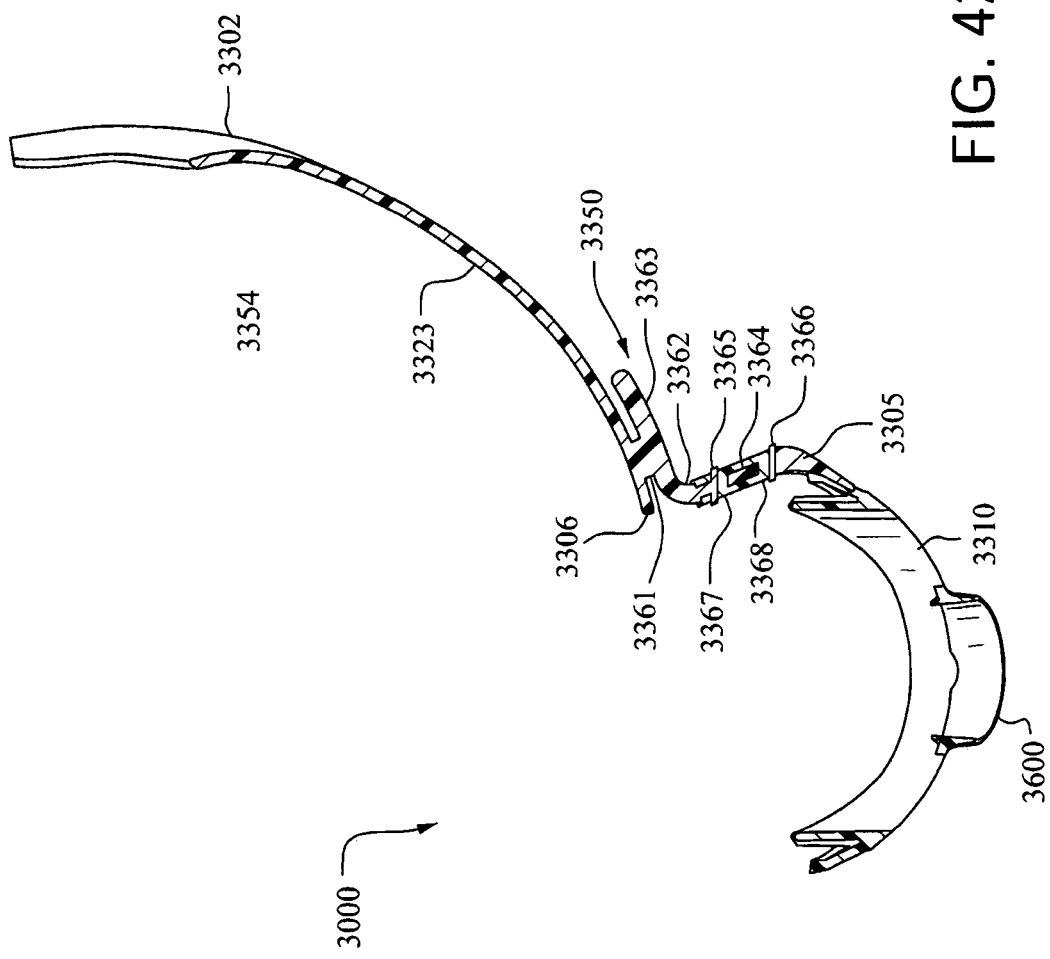

FIG. 42 shows a cross-sectional view of a patient interface including a mask frame, a flexible joint, and a rigidiser arm according to an example of the present technology.

Figure 43:
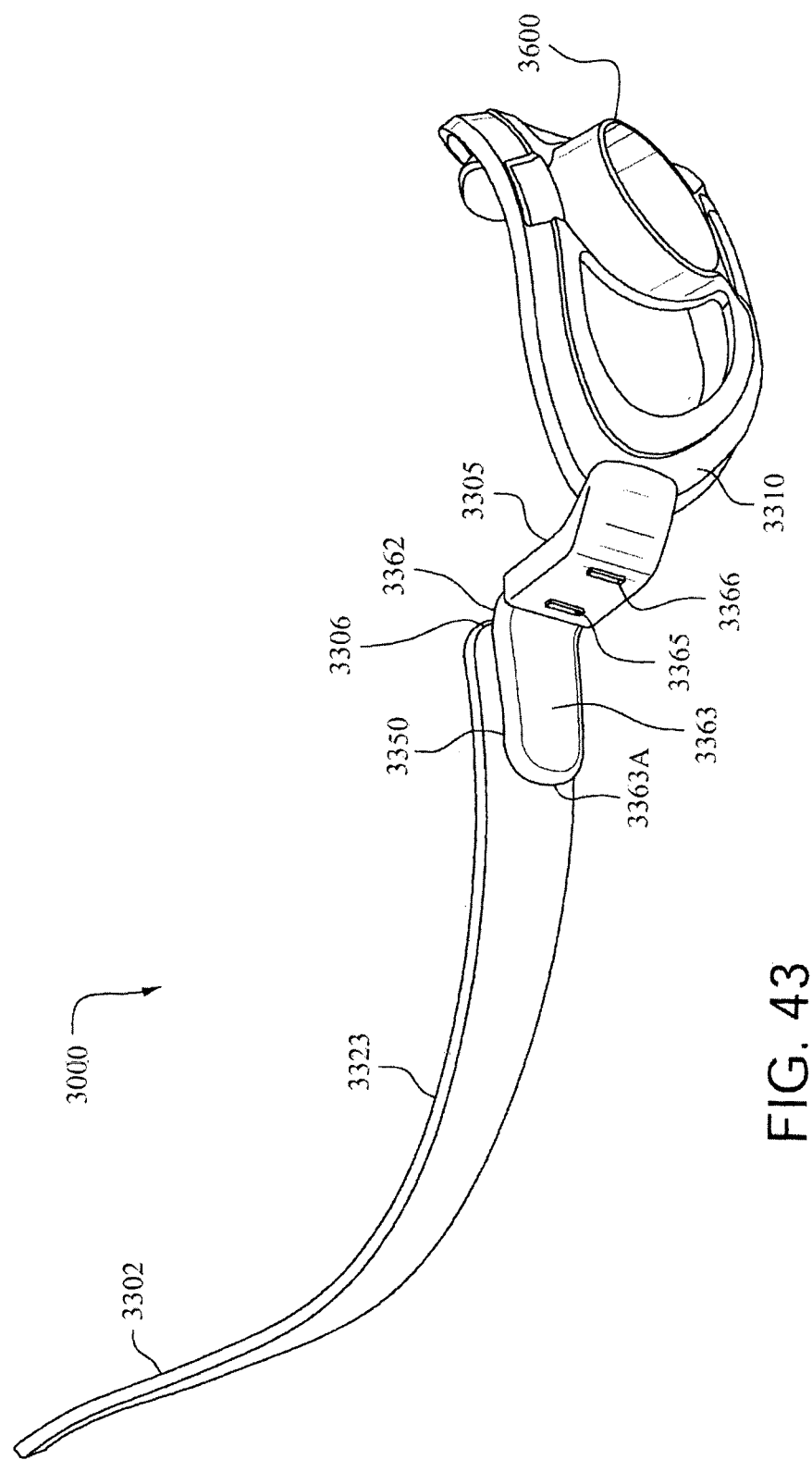

FIG. 43 shows a perspective view of a patient interface including a mask frame, a flexible joint, and a rigidiser arm according to an example of the present technology.

Figure 44:
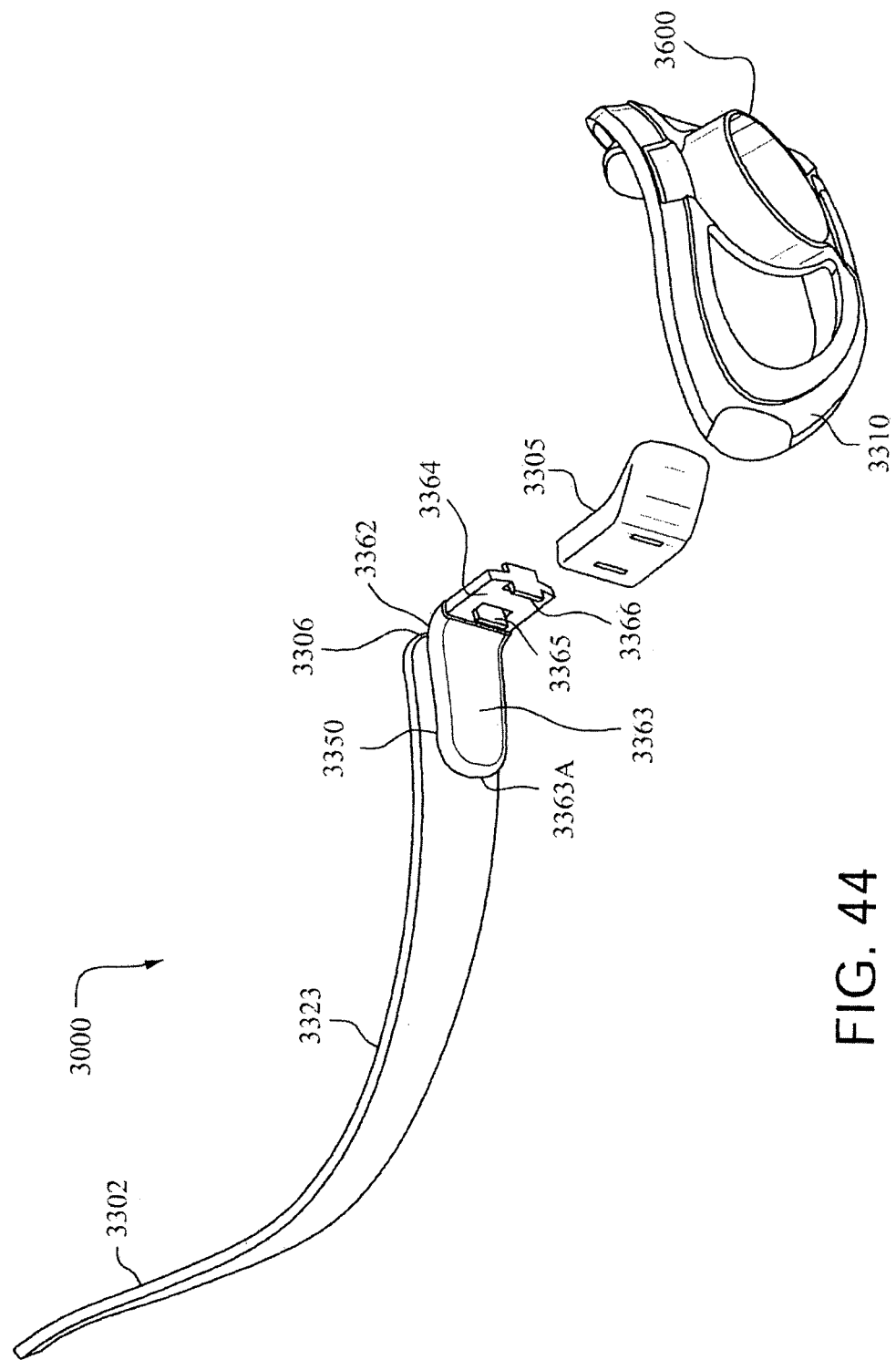

FIG. 44 shows an exploded view of a patient interface including a mask frame, a flexible joint, and a rigidiser arm according to an example of the present technology.

Figure 45:
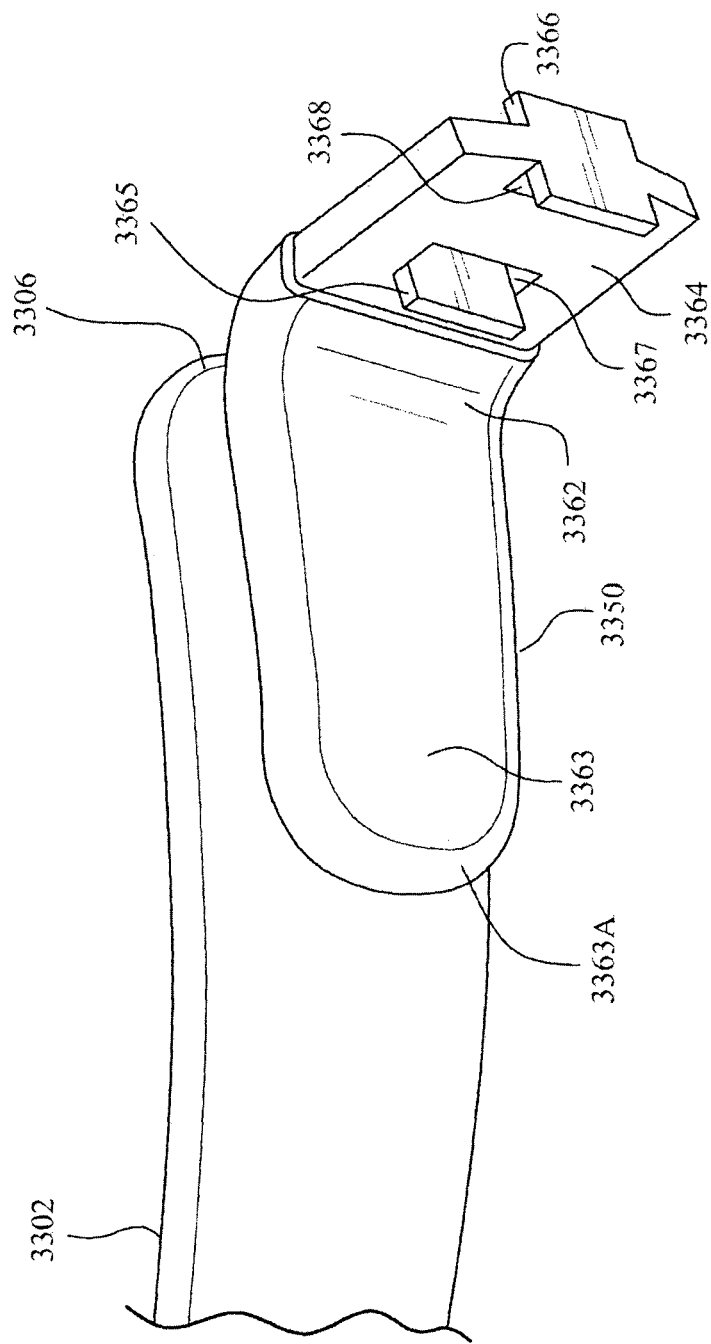

FIG. 45 shows a detailed view of an end of a rigidiser arm according to an example of the present technology.

Figure 46:
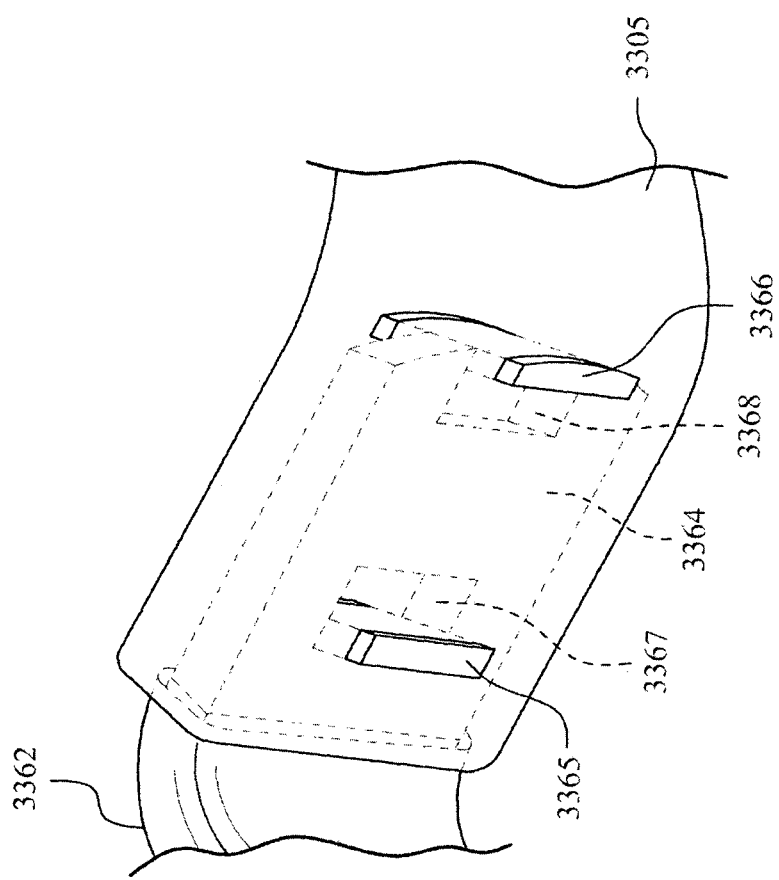

FIG. 46 shows a detailed view of an end of a rigidiser arm and a flexible joint according to an example of the present technology.

Figure 47:
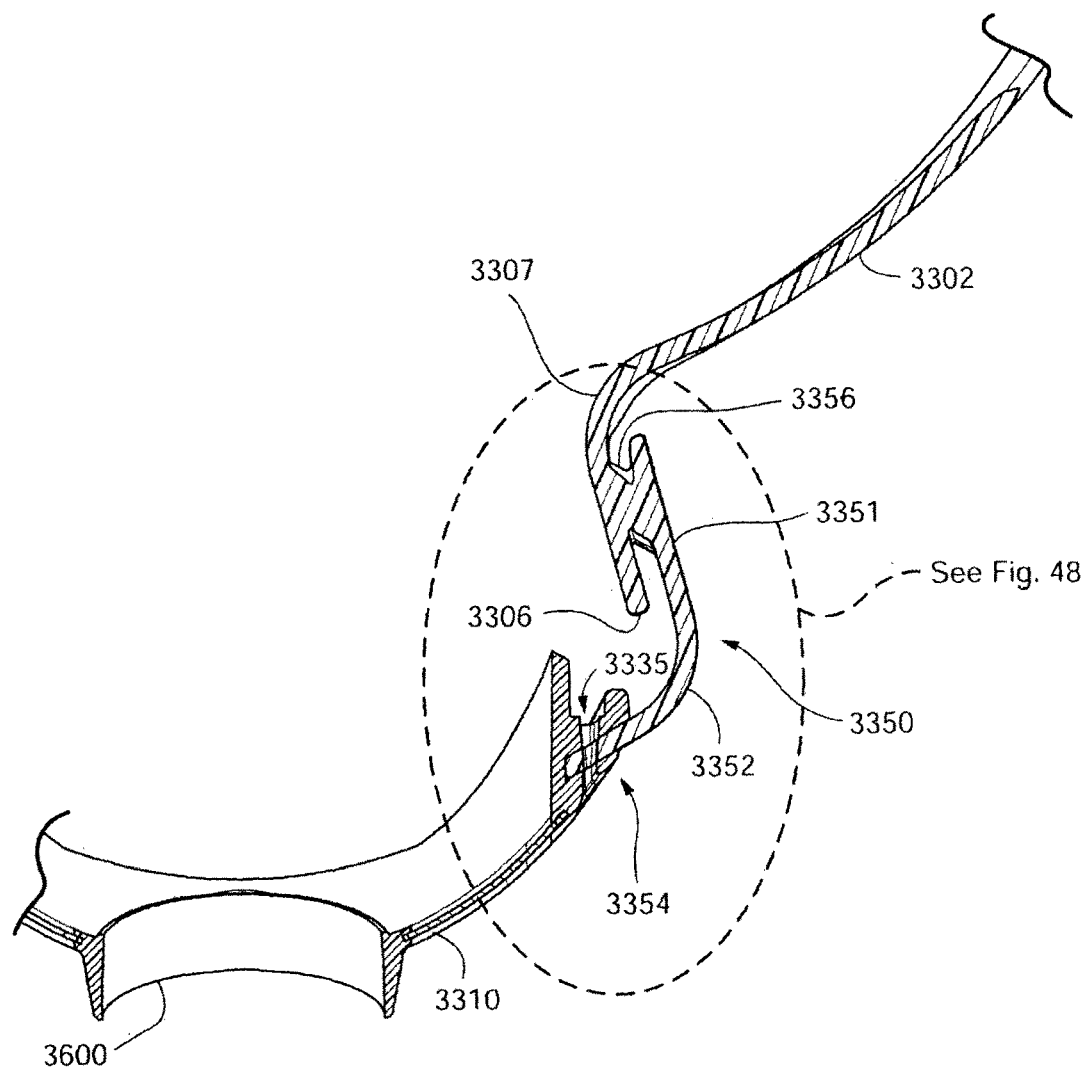

FIG. 47 shows a cross-sectional view of a rigidiser and a mask frame according to an example of the present technology.

Figure 48:
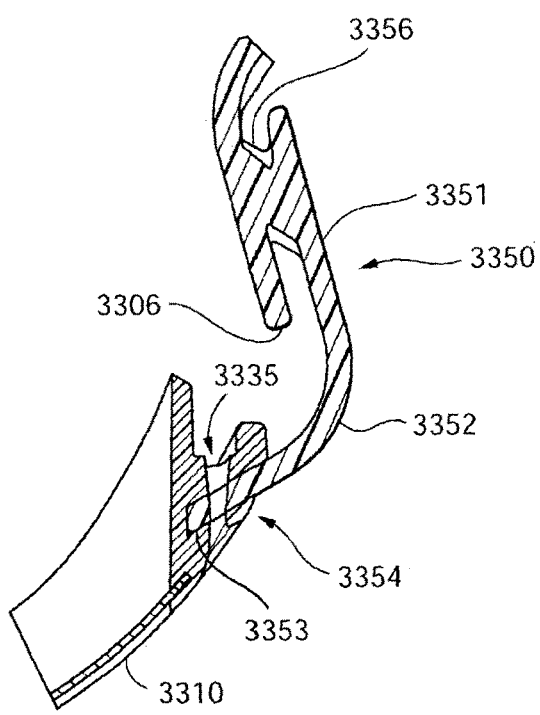

FIG. 48 shows a detailed cross-sectional view of a rigidiser arm and mask frame according to an example of the present technology.

Figure 49:
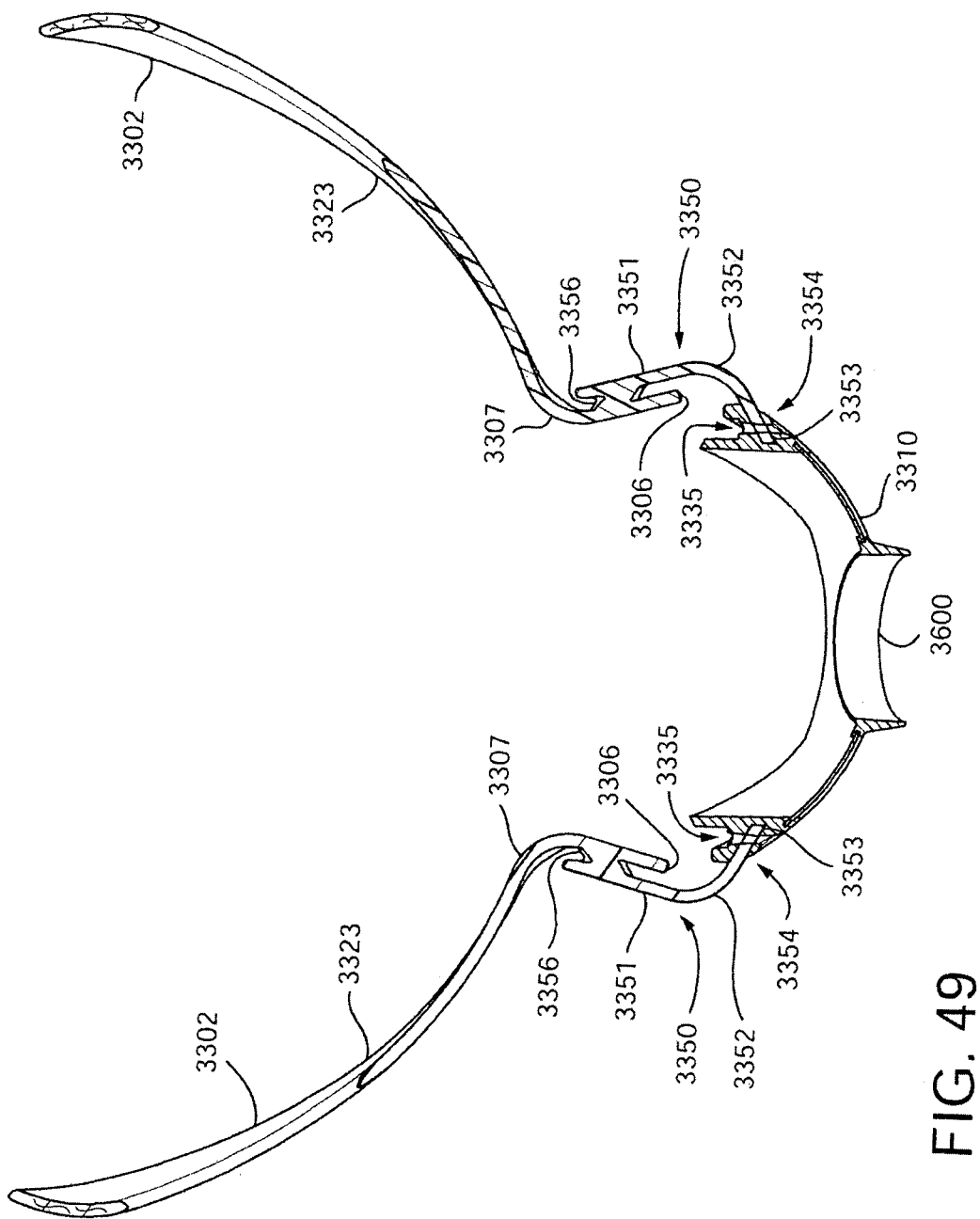

FIG. 49 shows a cross-sectional view of rigidiser arms and a mask frame according to an example of the present technology.

Figure 50:
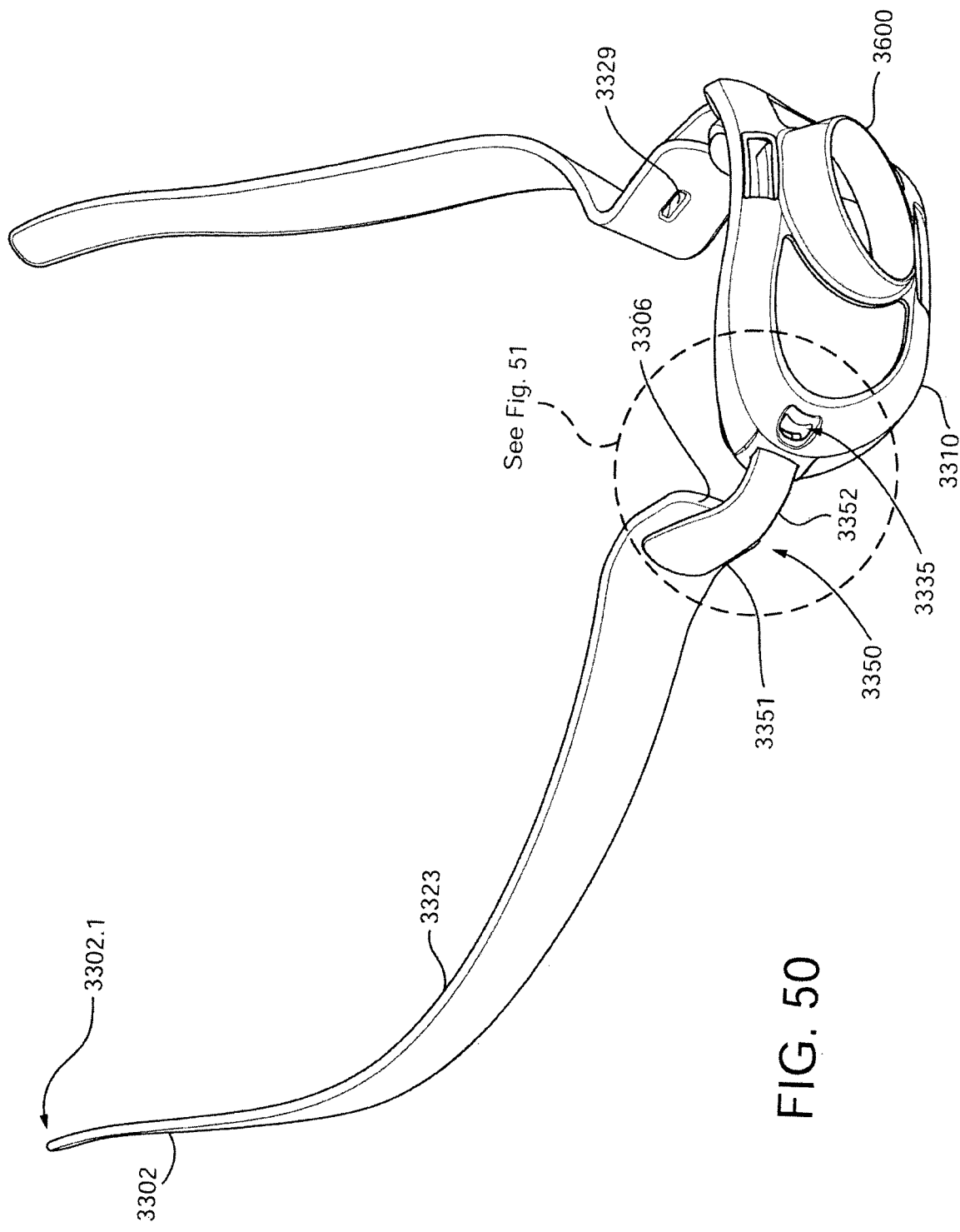

FIG. 50 shows a perspective view of rigidiser arms and a mask frame according to an example of the present technology.

Figure 51:
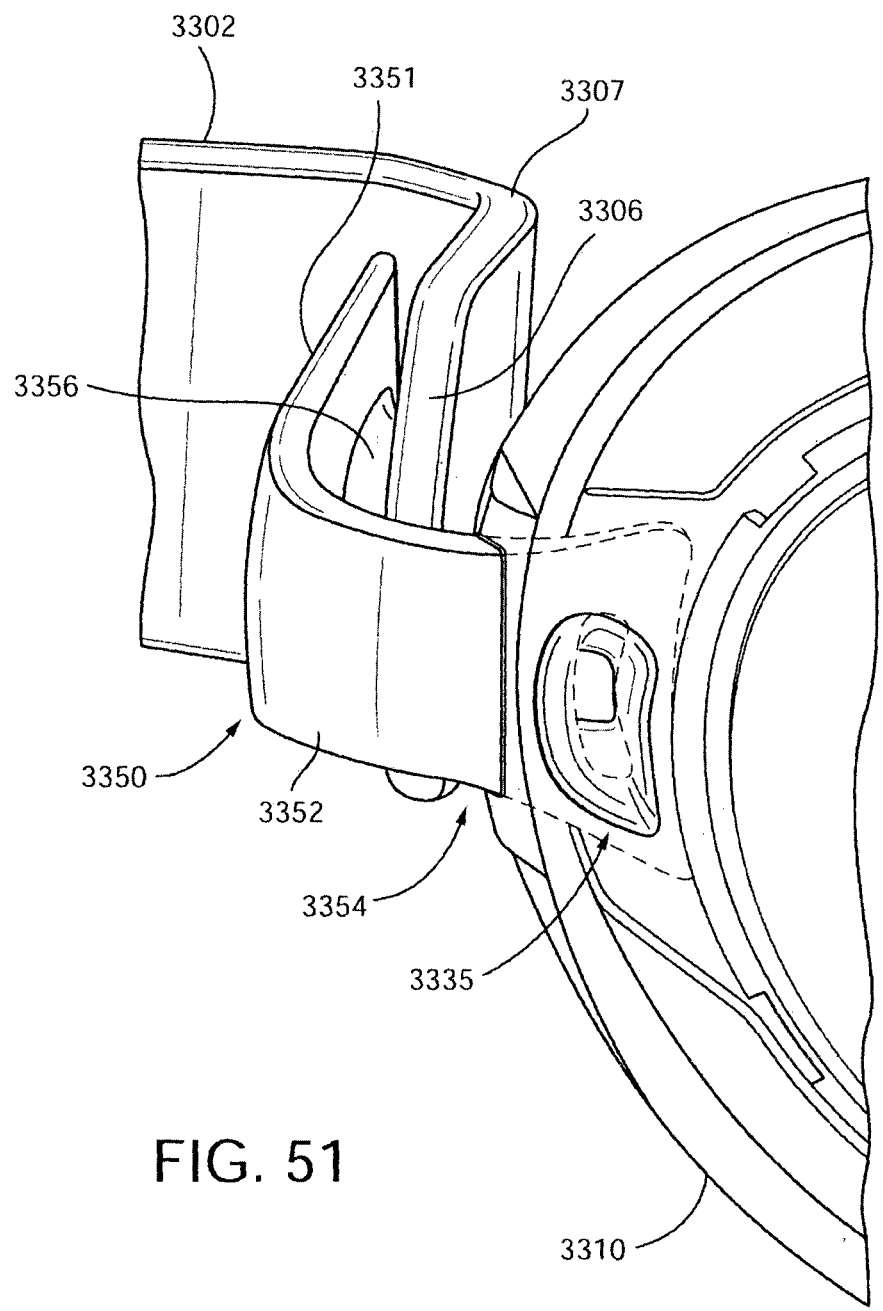

FIG. 51 shows a detailed perspective view of the connection between a rigidiser and a mask frame according to an example of the present technology.

Figure 52:
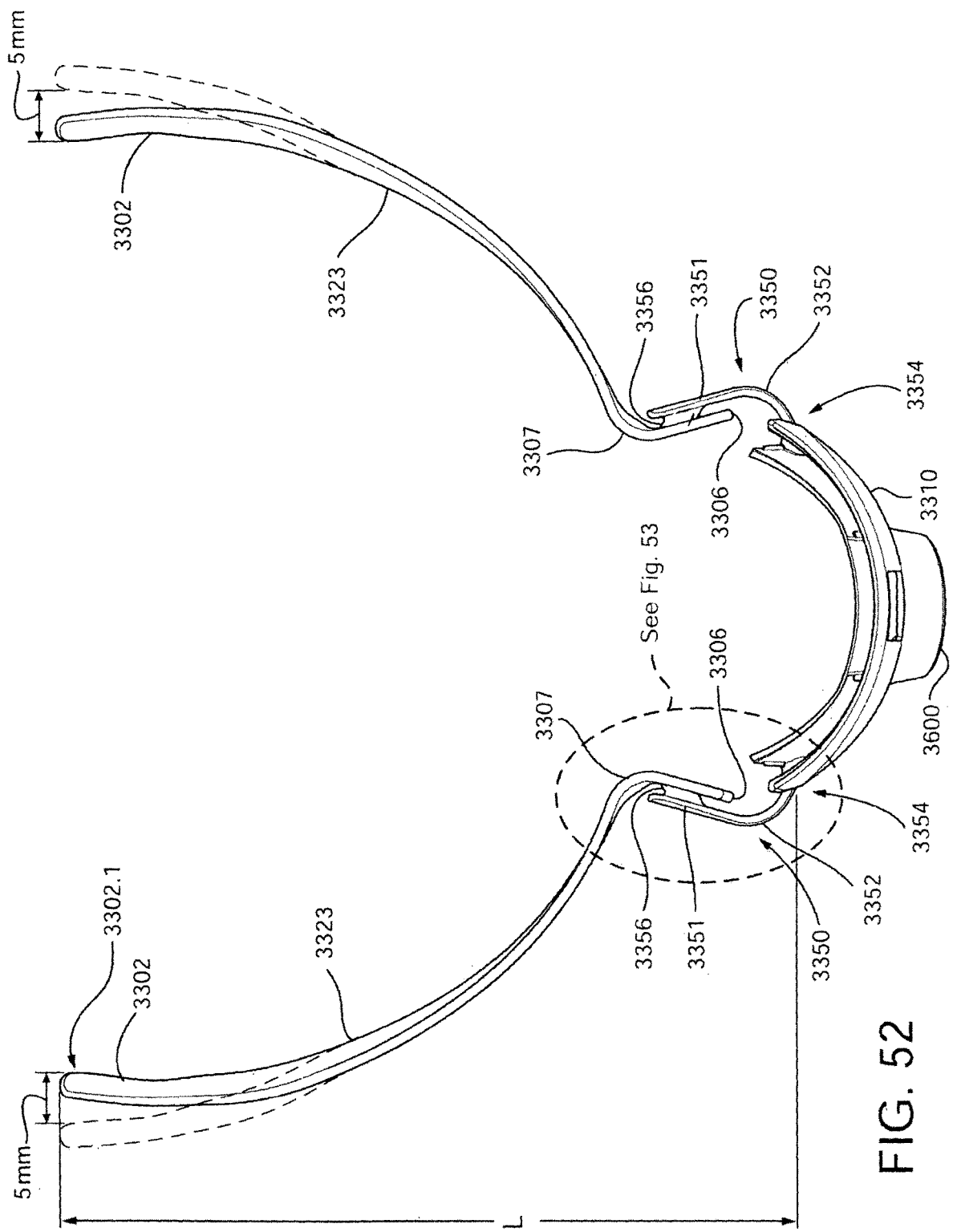

FIG. 52 shows a top view of rigidiser arms and a mask frame according to an example of the present technology, and in broken line indicates flexing of the rigidiser arm in a laterally outwards direction in the coronal plane.

Figure 53:
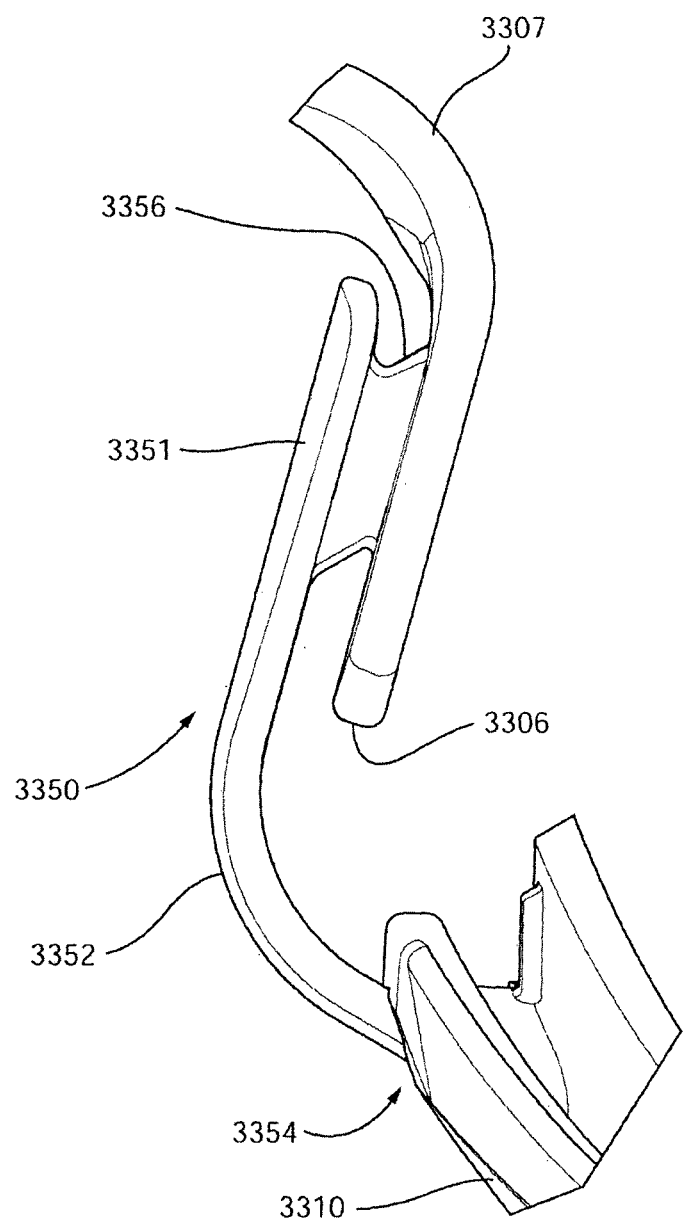

FIG. 53 shows a detailed top view of the connection between a rigidiser and a mask frame according to an example of the present technology.

Figure 54:
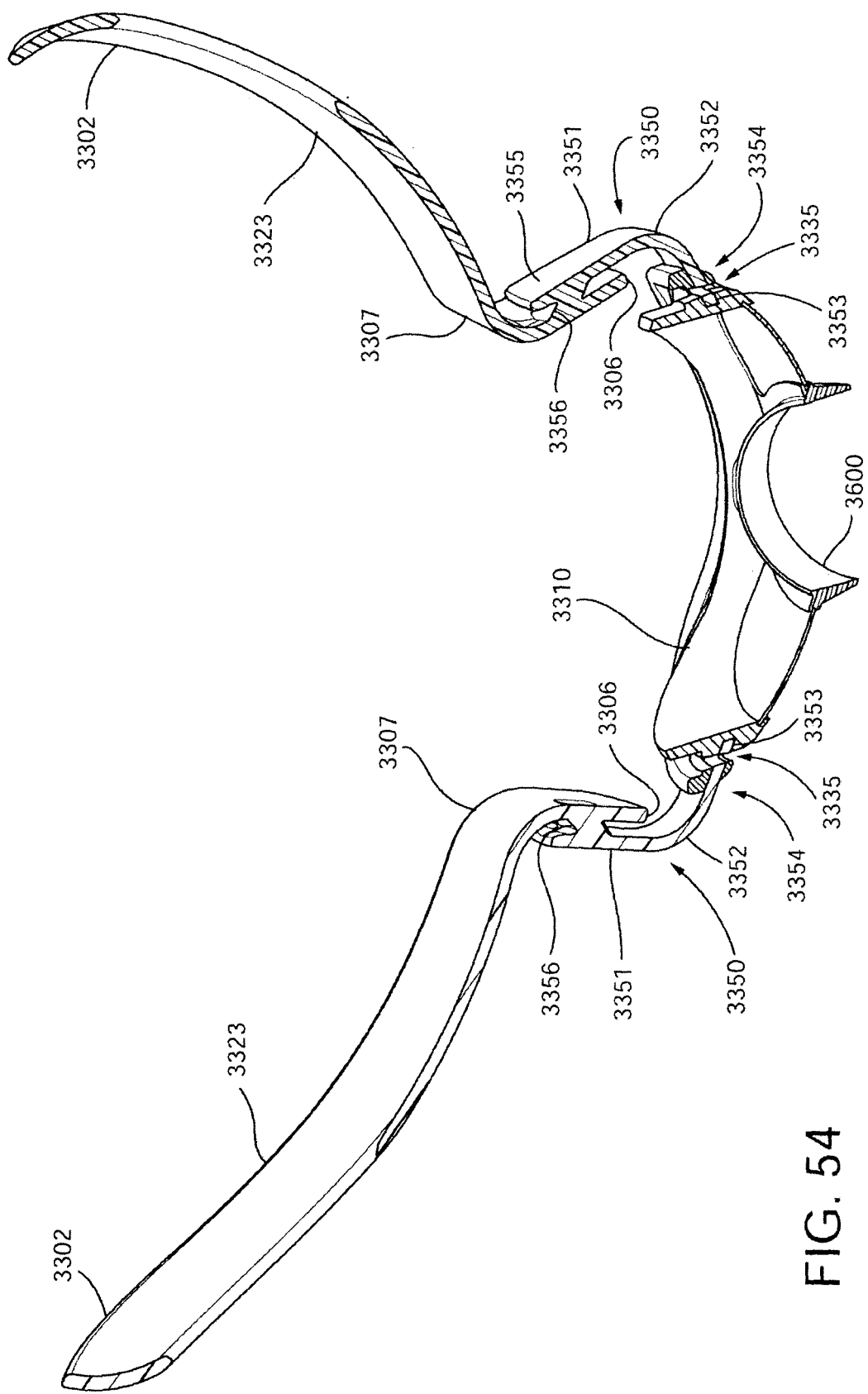

FIG. 54 shows a cross-sectional perspective view of rigidiser arms and a mask frame according to an example of the present technology.

Figure 55:
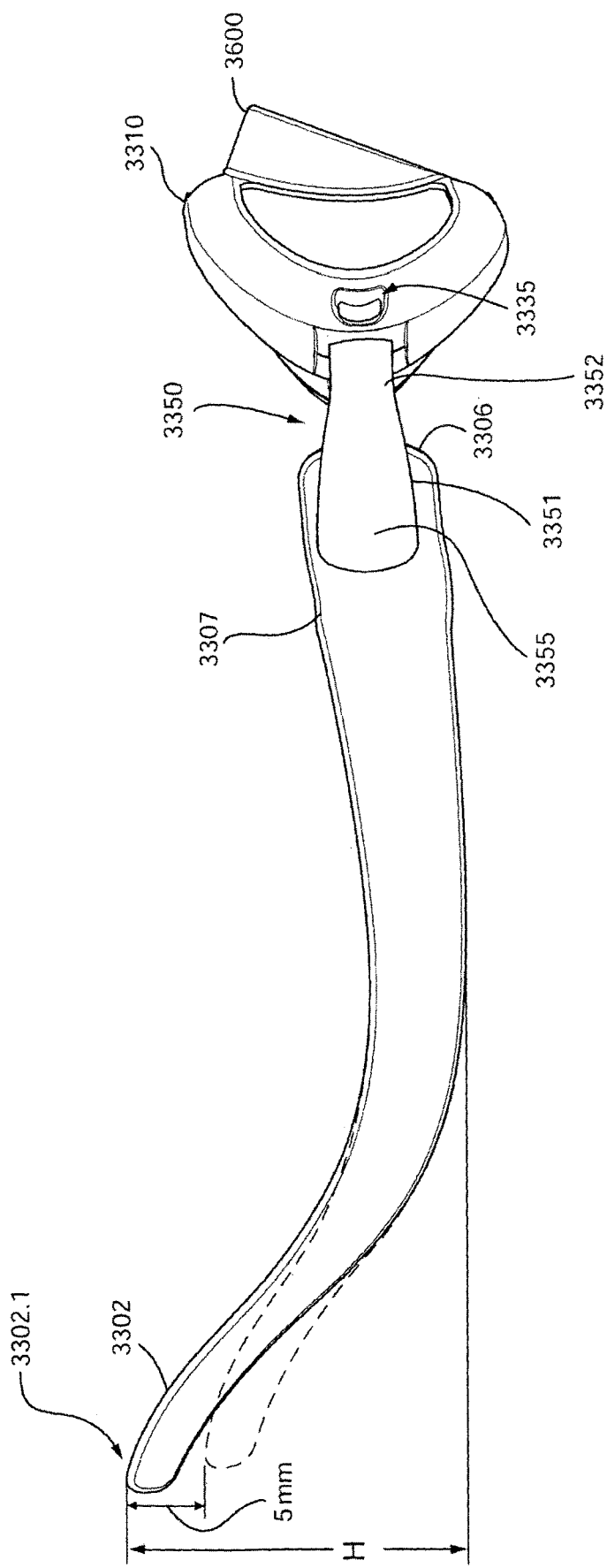

FIG. 55 shows a side view of a rigidiser and a mask frame according to an example of the present technology, and in broken line indicates flexing of the rigidiser arm in a vertically downward direction in the sagittal plane.

Figure 56:
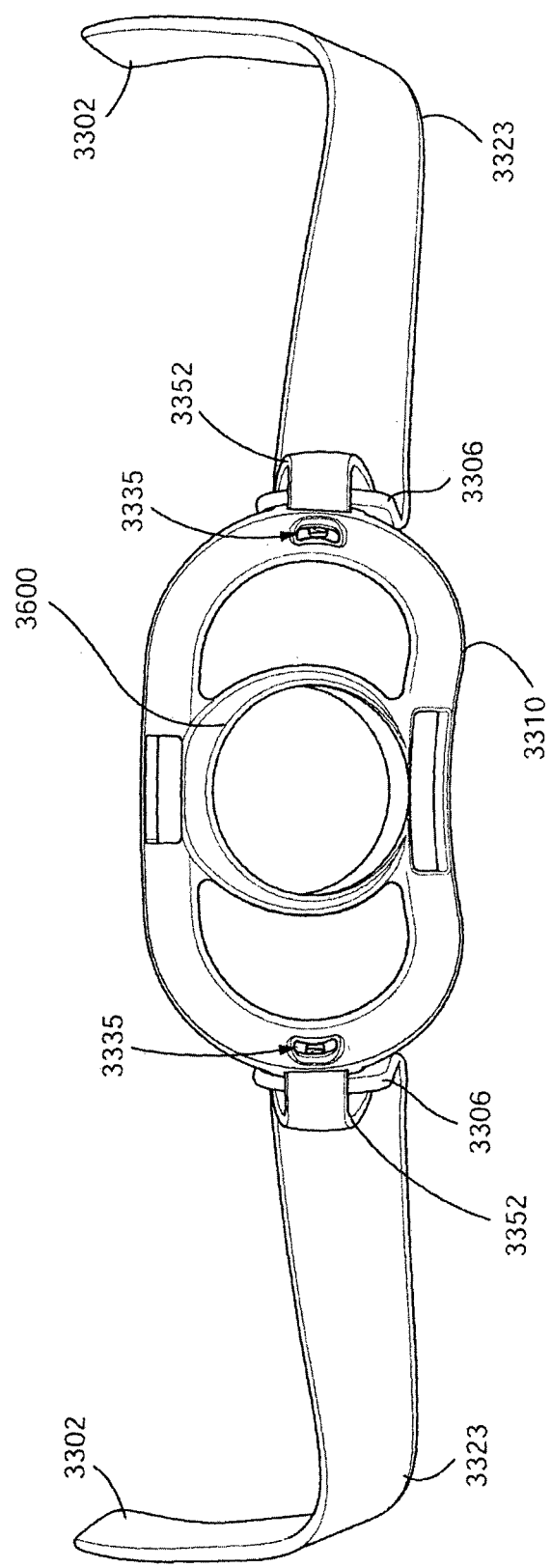

FIG. 56 shows a front view of a rigidiser and a mask frame according to an example of the present technology.

Figure 57:
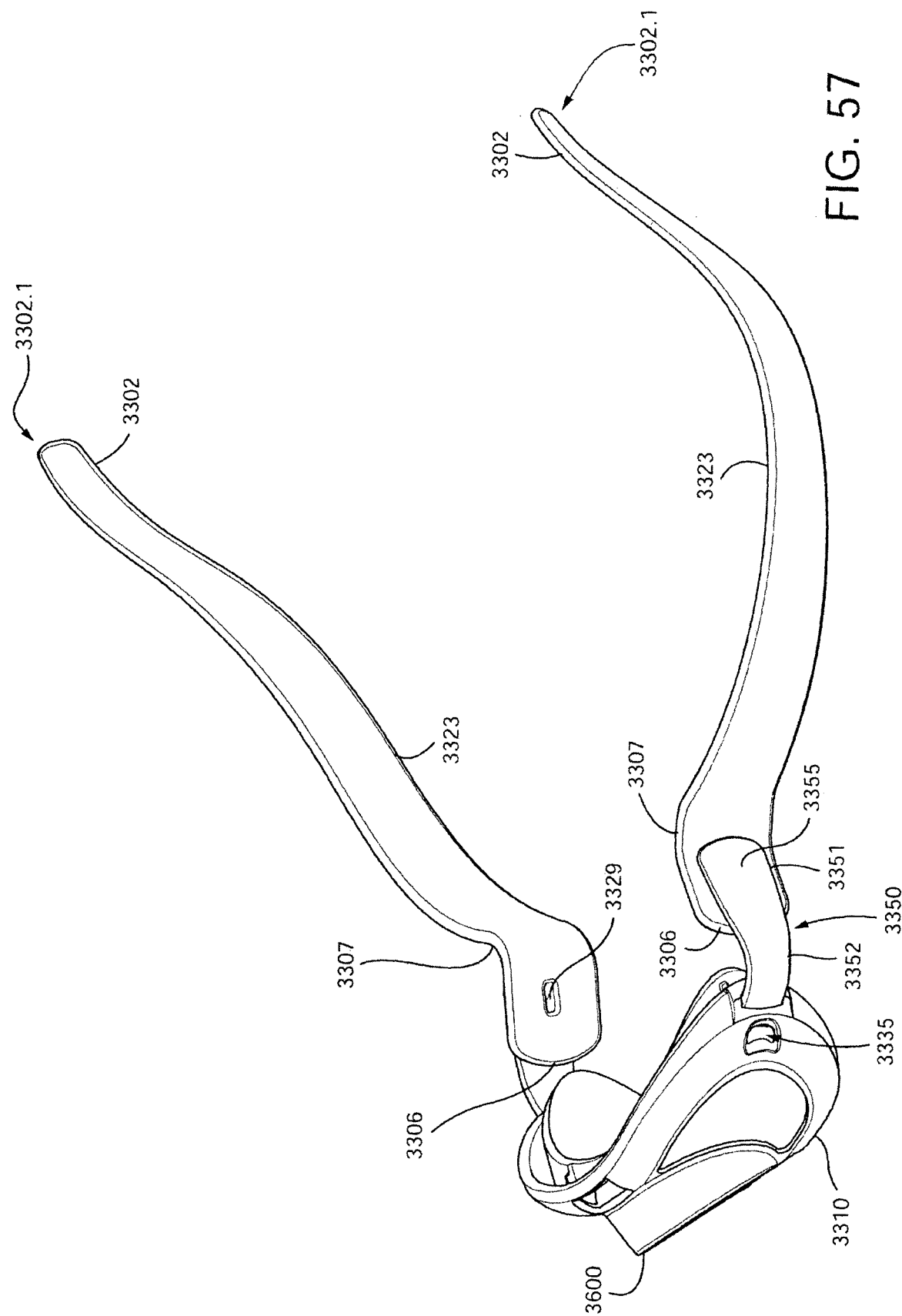

FIG. 57 shows a perspective view of rigidiser arms and a mask frame according to an example of the present technology.

Figure 58:
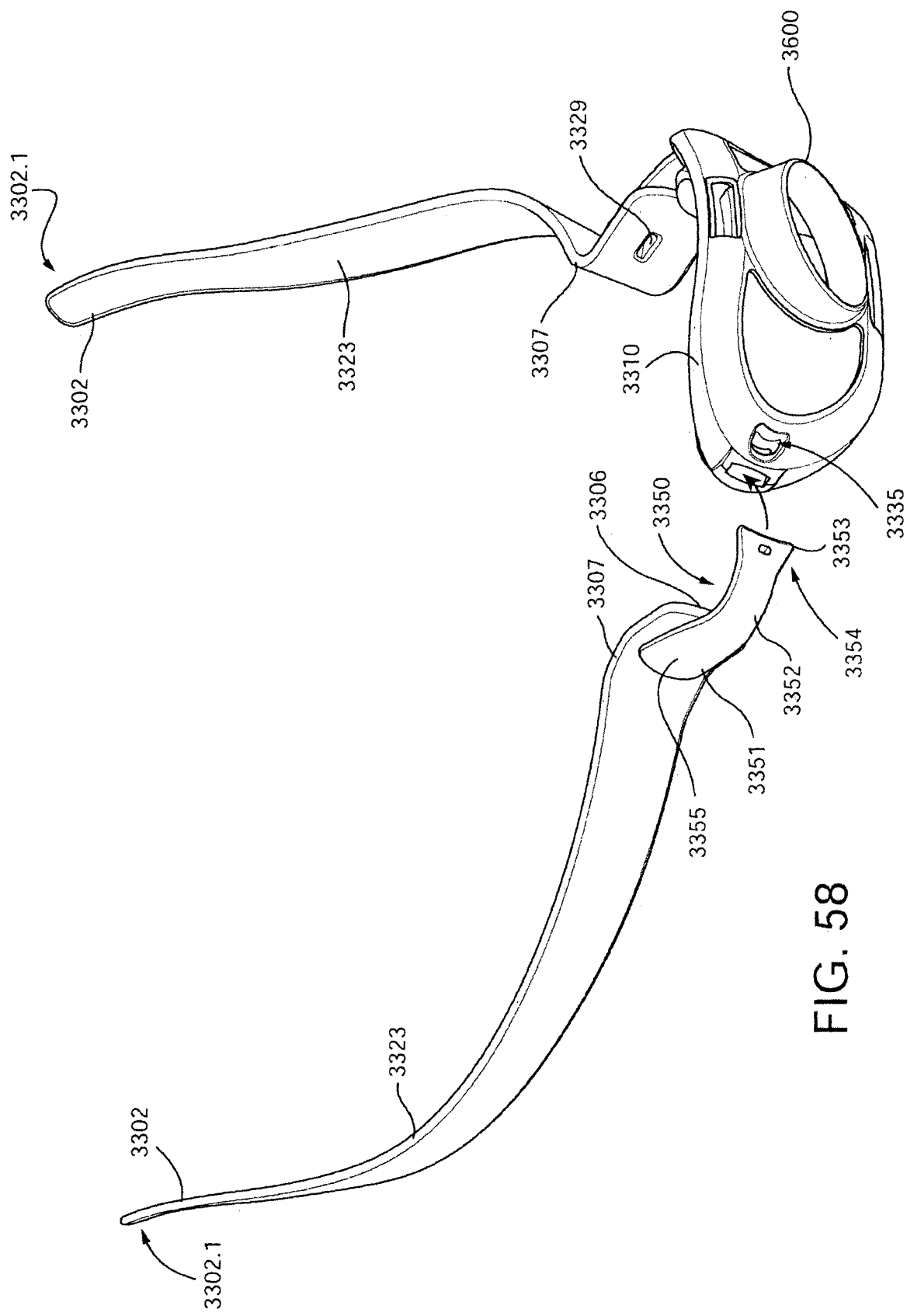

FIG. 58 shows a partially exploded perspective view of rigidiser arms and a mask frame according to an example of the present technology.

Figure 59:
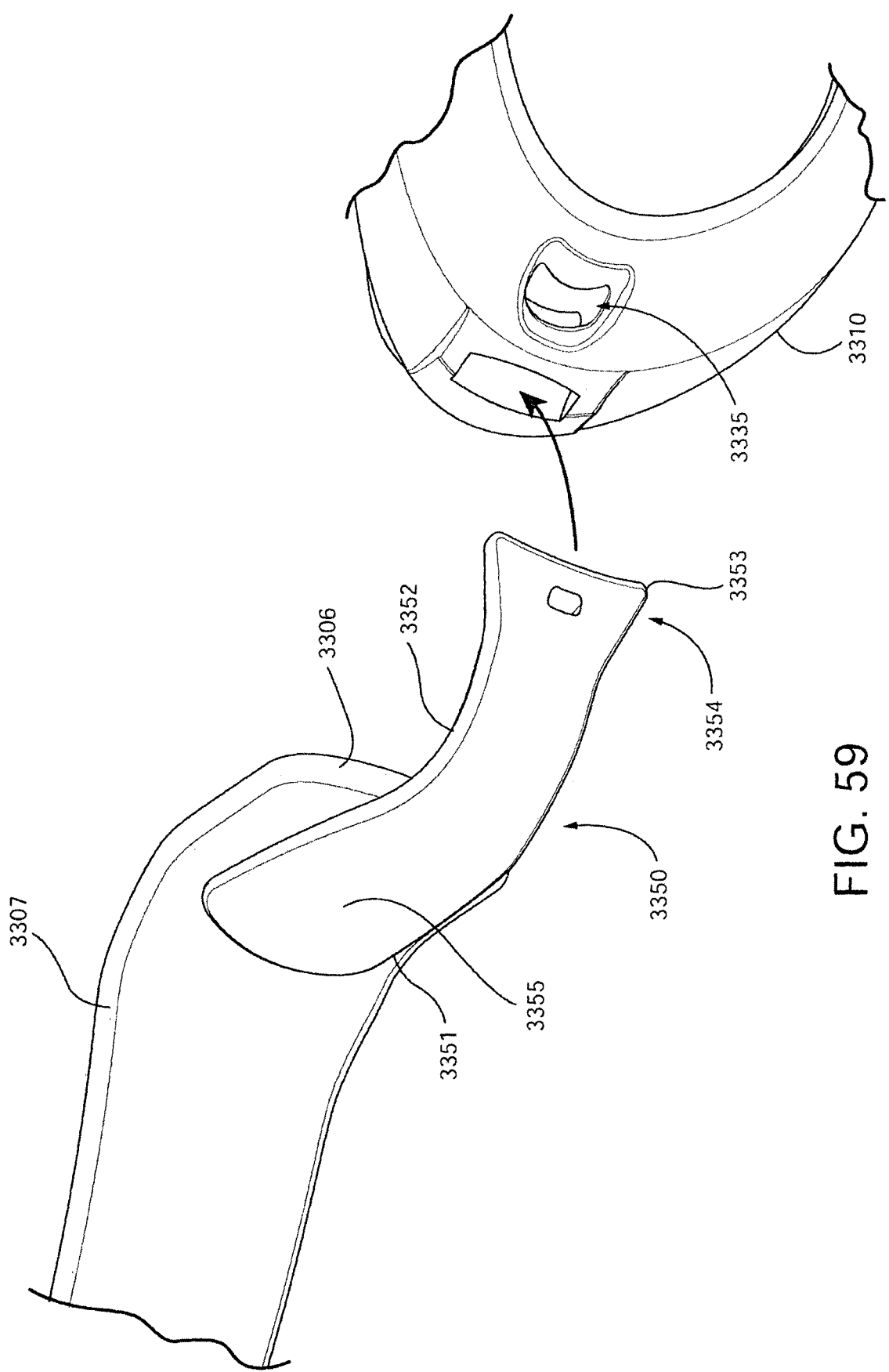

FIG. 59 shows a detailed and partially exploded perspective view of a rigidiser and a mask frame according to an example of the present technology.

Figure 60:
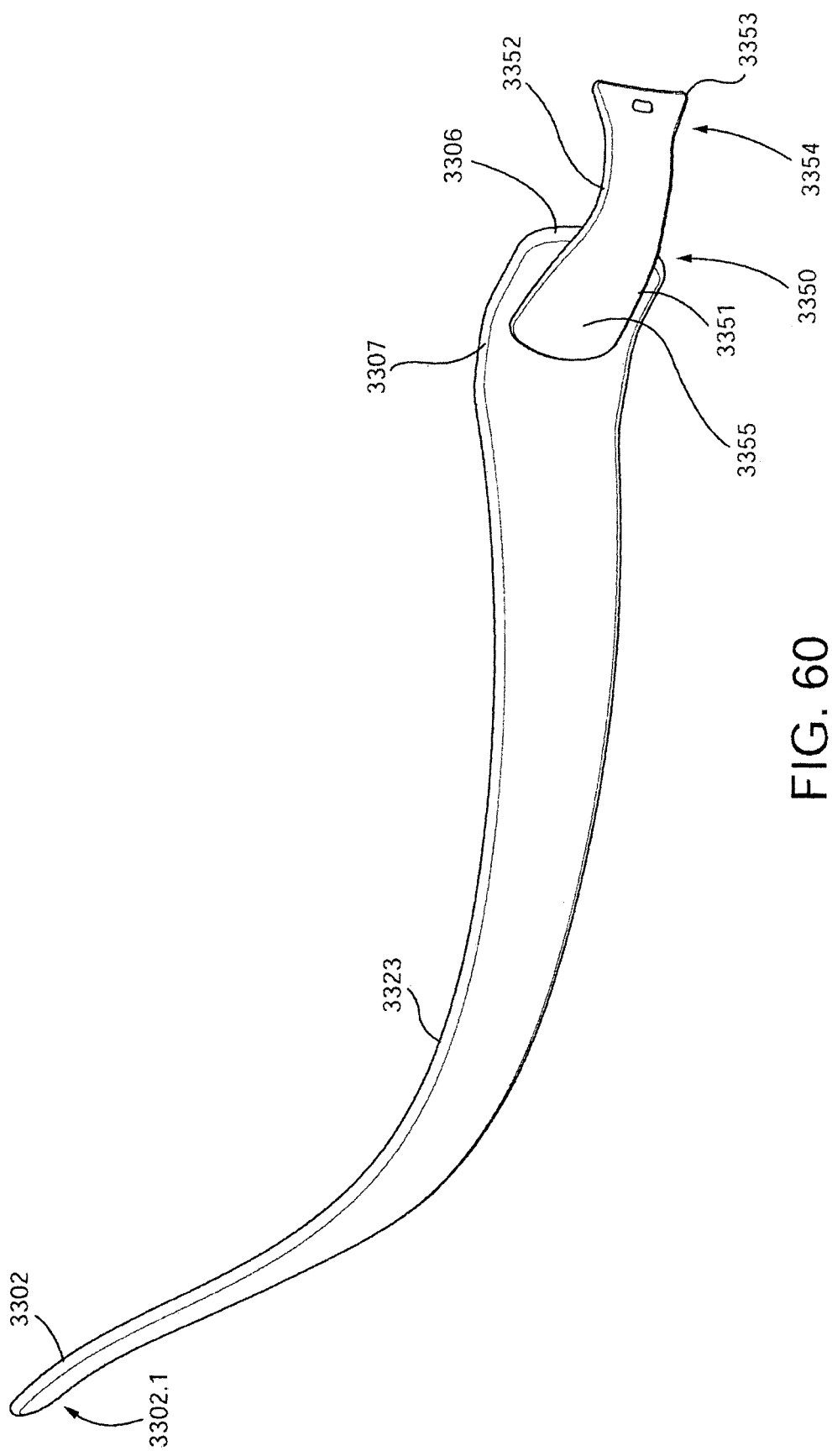

FIG. 60 shows a perspective view of a rigidiser according to an example of the present technology.

Figure 61:
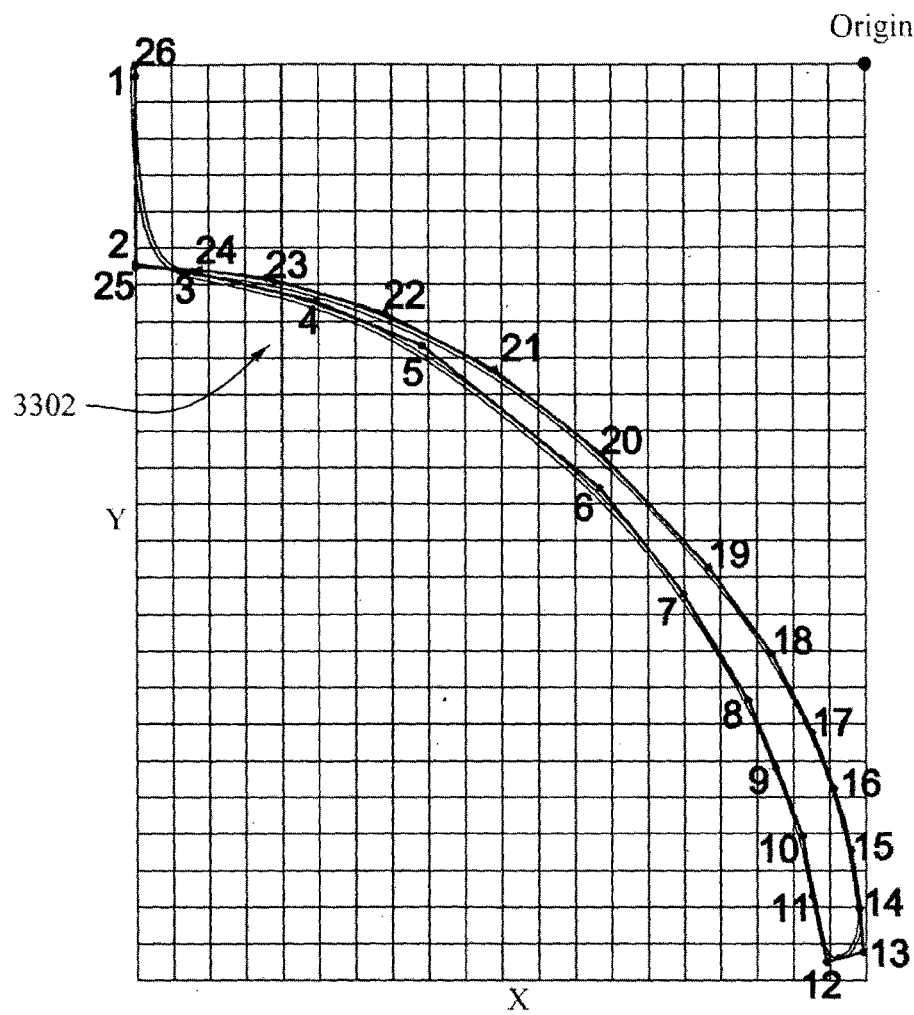

FIG. 61 shows a view of a rigidiser arm according to an example of the present technology plotted on a grid in an X-Y plane.

Figure 62:
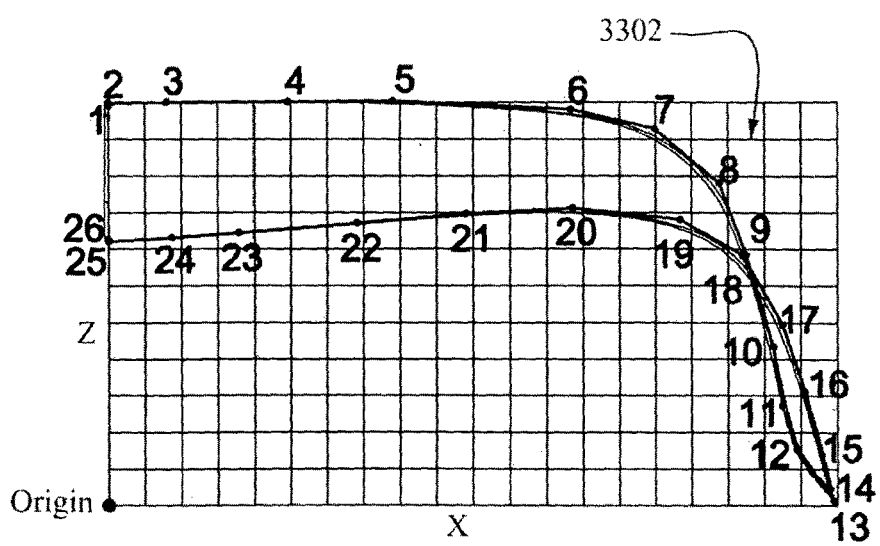

FIG. 62 shows a view of a rigidiser arm according to an example of the present technology plotted on a grid in an X-Z plane.

Figure 63:
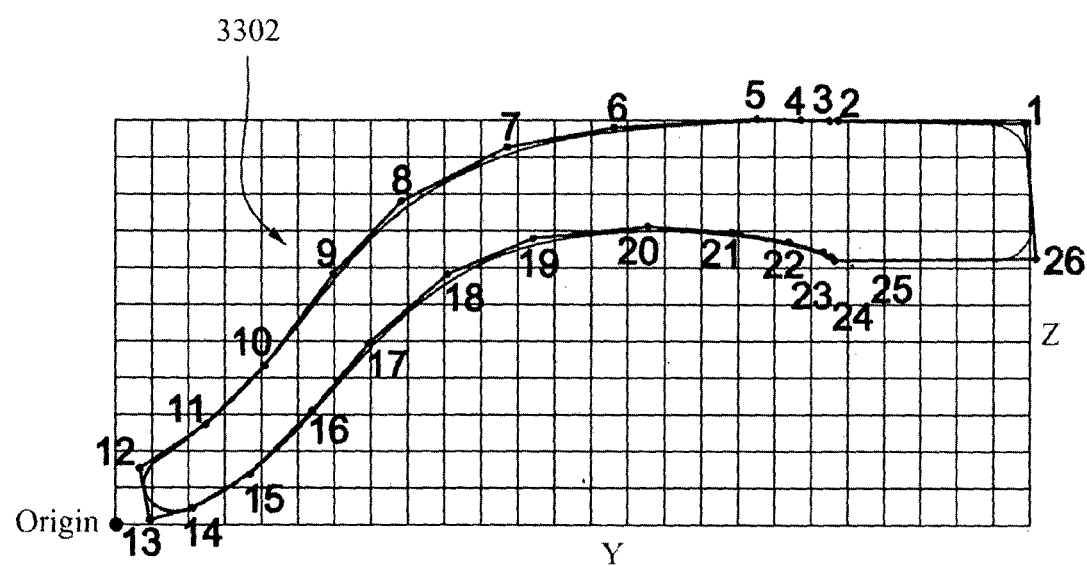

FIG. 63 shows a view of a rigidiser arm according to an example of the present technology plotted on a grid in a Y-Z plane.

Figure 64:
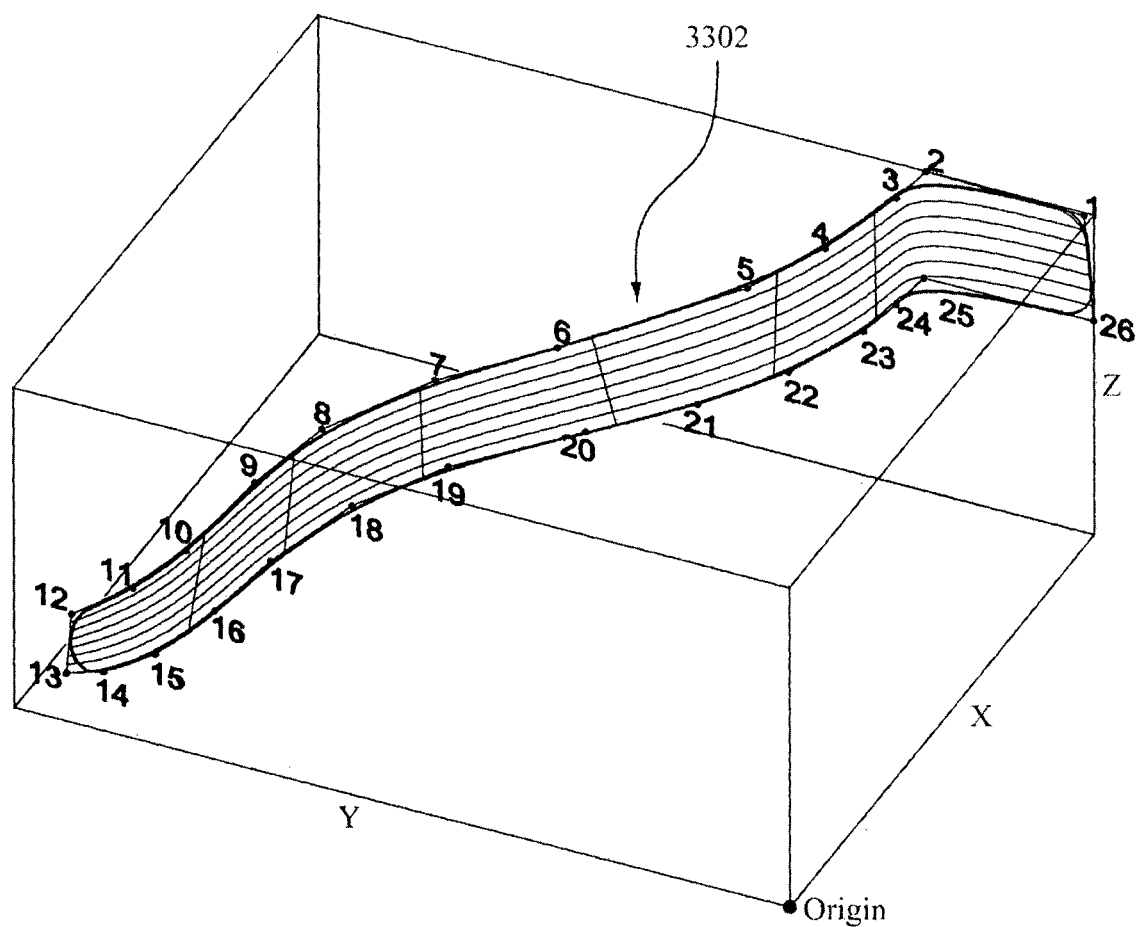

FIG. 64 shows a view of a rigidiser arm according to an example of the present technology plotted in three dimensions.

FIG. 65 shows a schematic perspective view of a positioning and stabilising structure in accordance with an example of the present technology.

FIG. 66 shows a cross-sectional view of a positioning and stabilising structure taken along line 66-66 in FIG. 65.

FIG. 67 shows a schematic side view of an exemplary rigidiser arm for a positioning and stabilising structure in accordance with the present technology.

Figure 68:
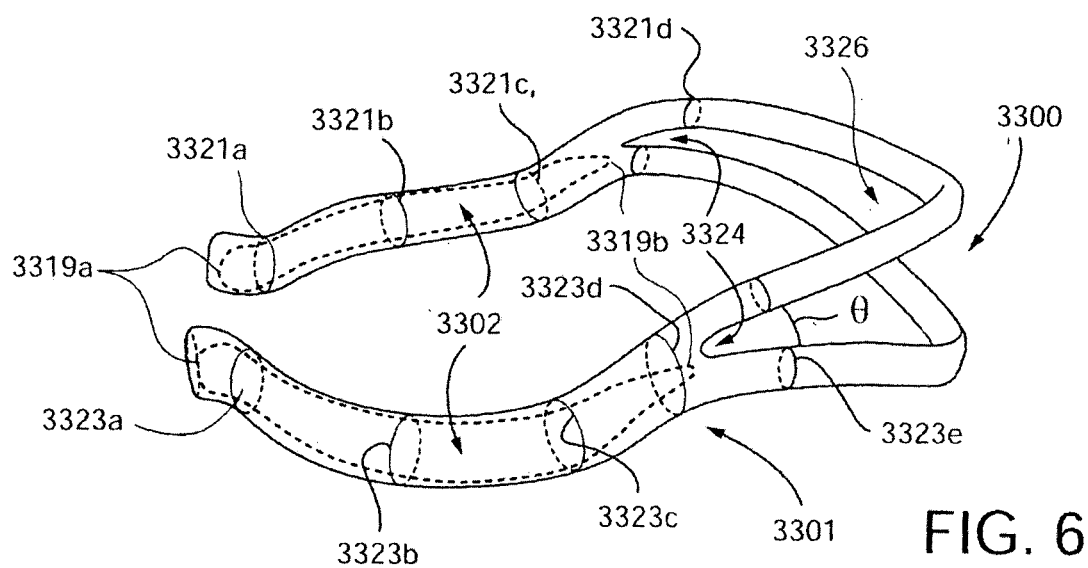

FIG. 68 shows a schematic perspective view of an exemplary positioning and stabilising structure containing a rigidiser arm in accordance with the present technology in a first state.

Figure 69:
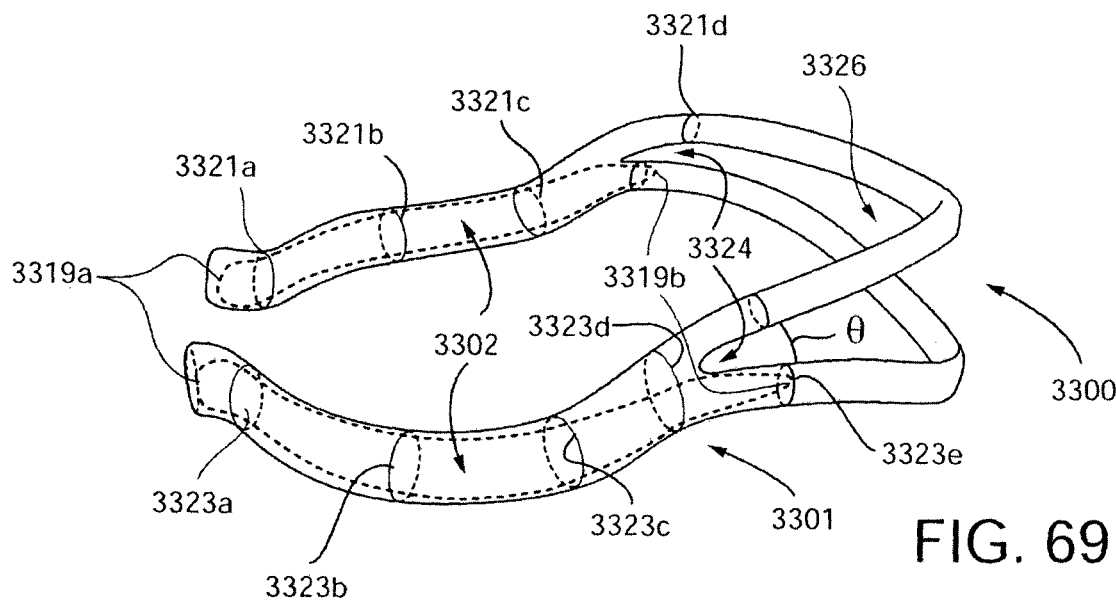

FIG. 69 shows a schematic perspective view of an exemplary positioning and stabilising structure containing a rigidiser arm in accordance with the present technology in a second state.

Figure 70:
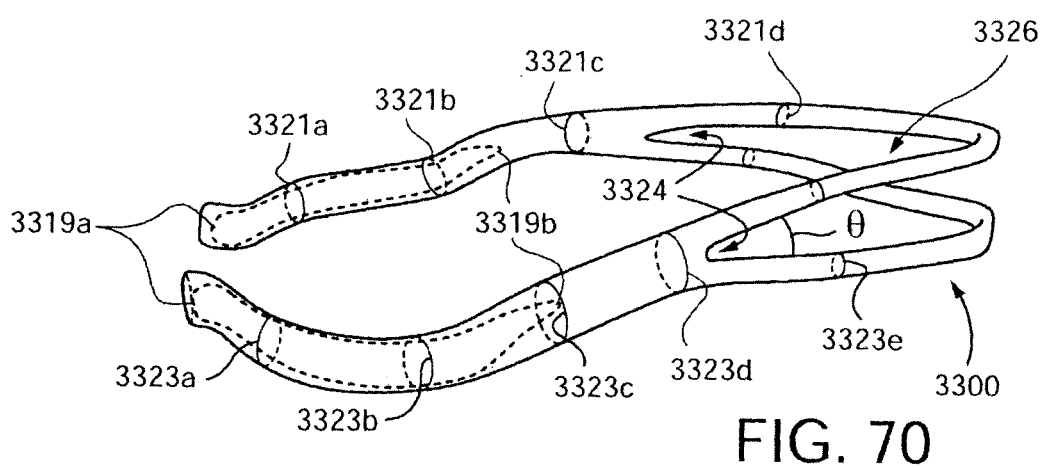

FIG. 70 shows a schematic perspective view of an exemplary positioning and stabilising structure containing a rigidiser arm in accordance with the present technology in a third state.

Figure 71:
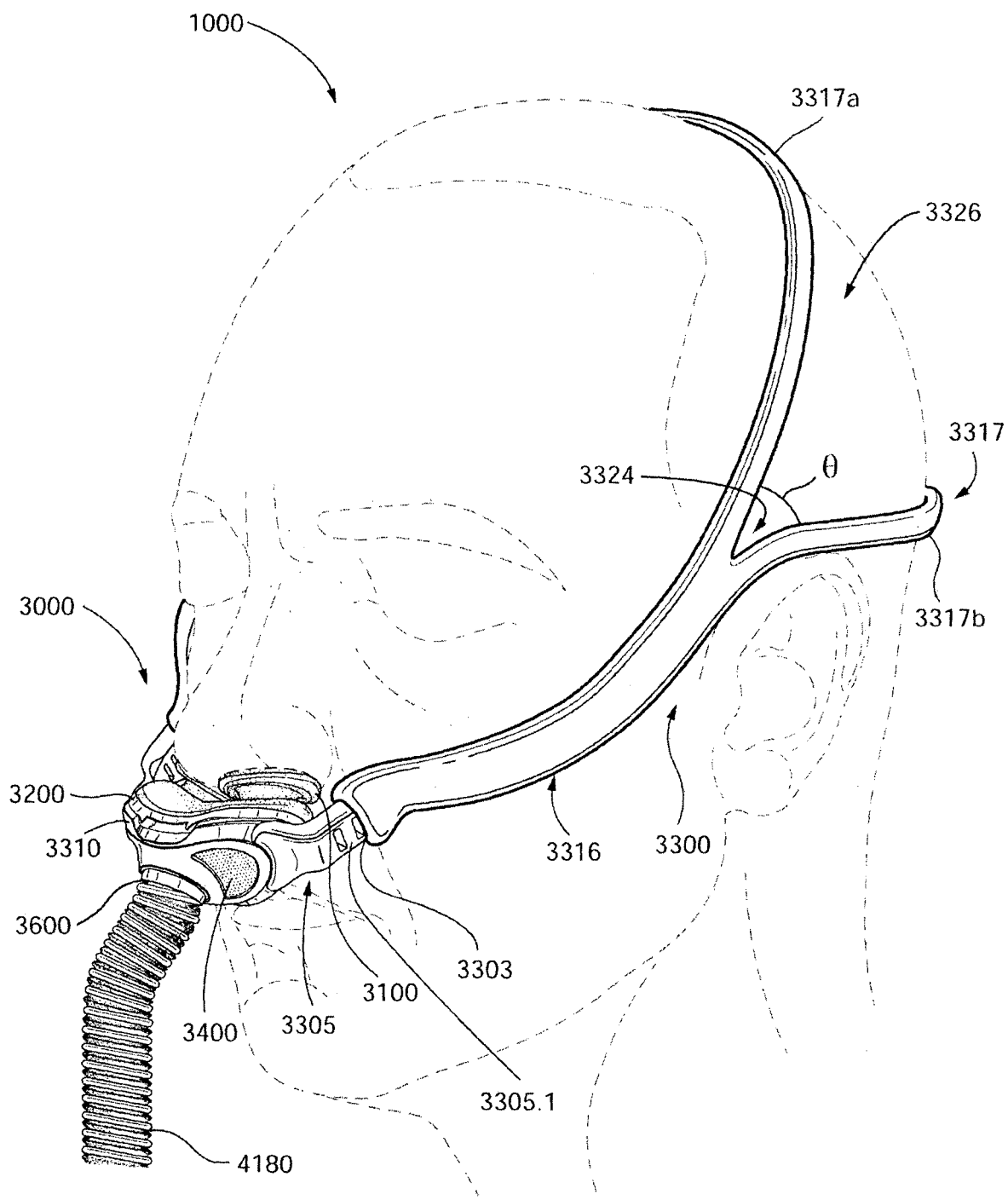

FIG. 71 shows a perspective view of an exemplary positioning and stabilising structure in accordance with the present technology donned on a patient.

Figure 72:
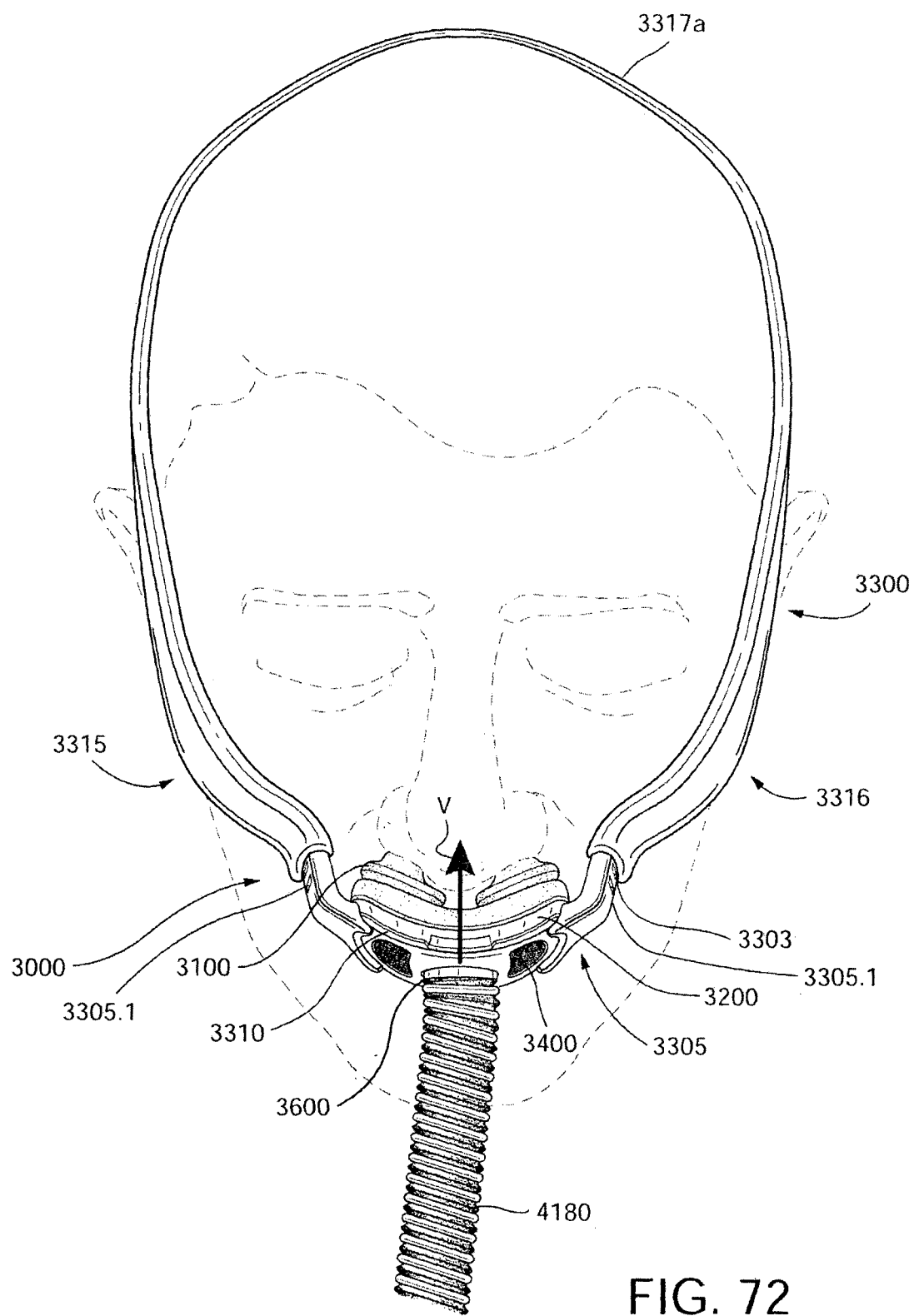

FIG. 72 shows a front view of an exemplary positioning and stabilising structure in accordance with the present technology donned on a patient.

Figure 73:
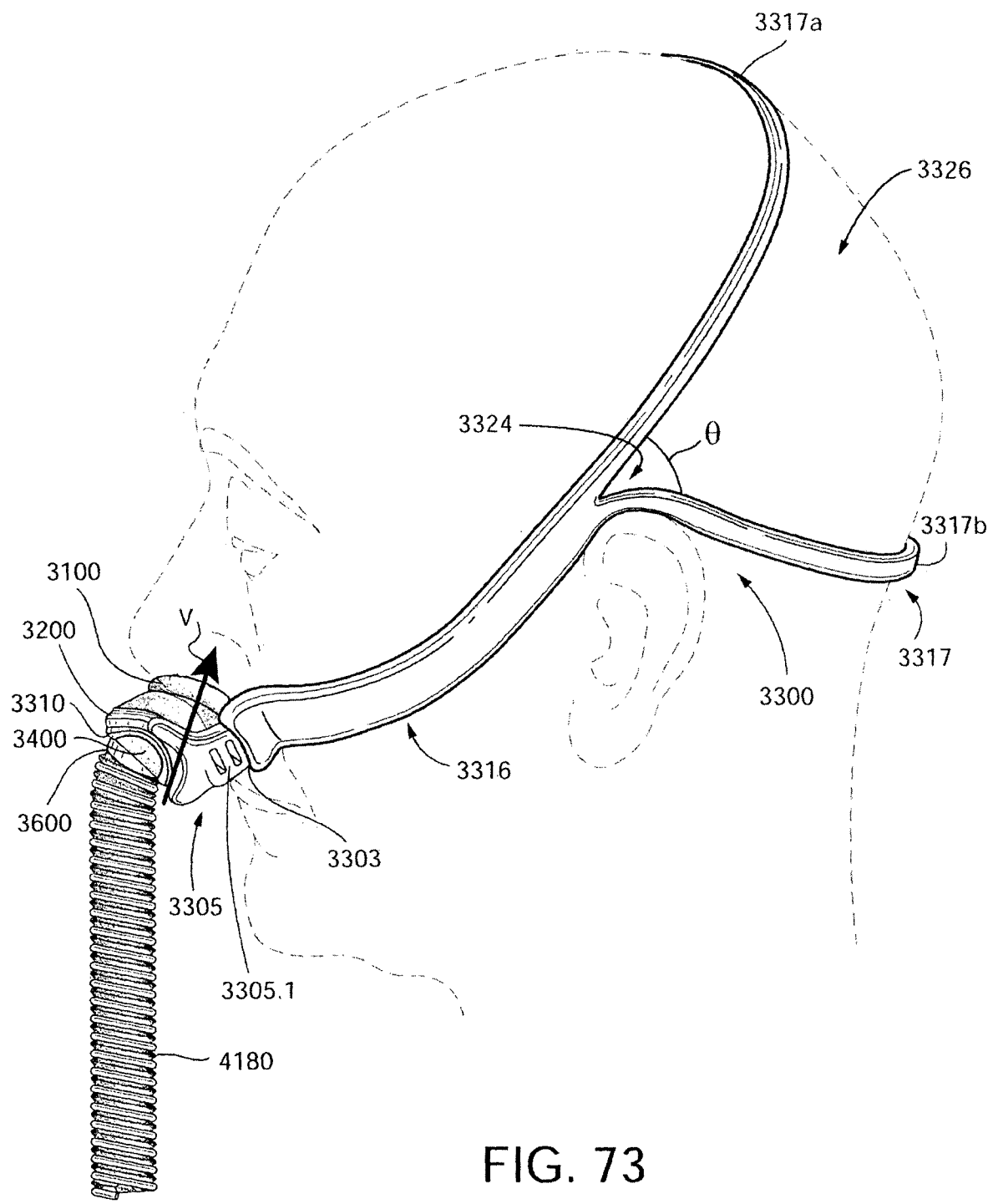

FIG. 73 shows a side view of an exemplary positioning and stabilising structure in accordance with the present technology donned on a patient.

Figure 74:
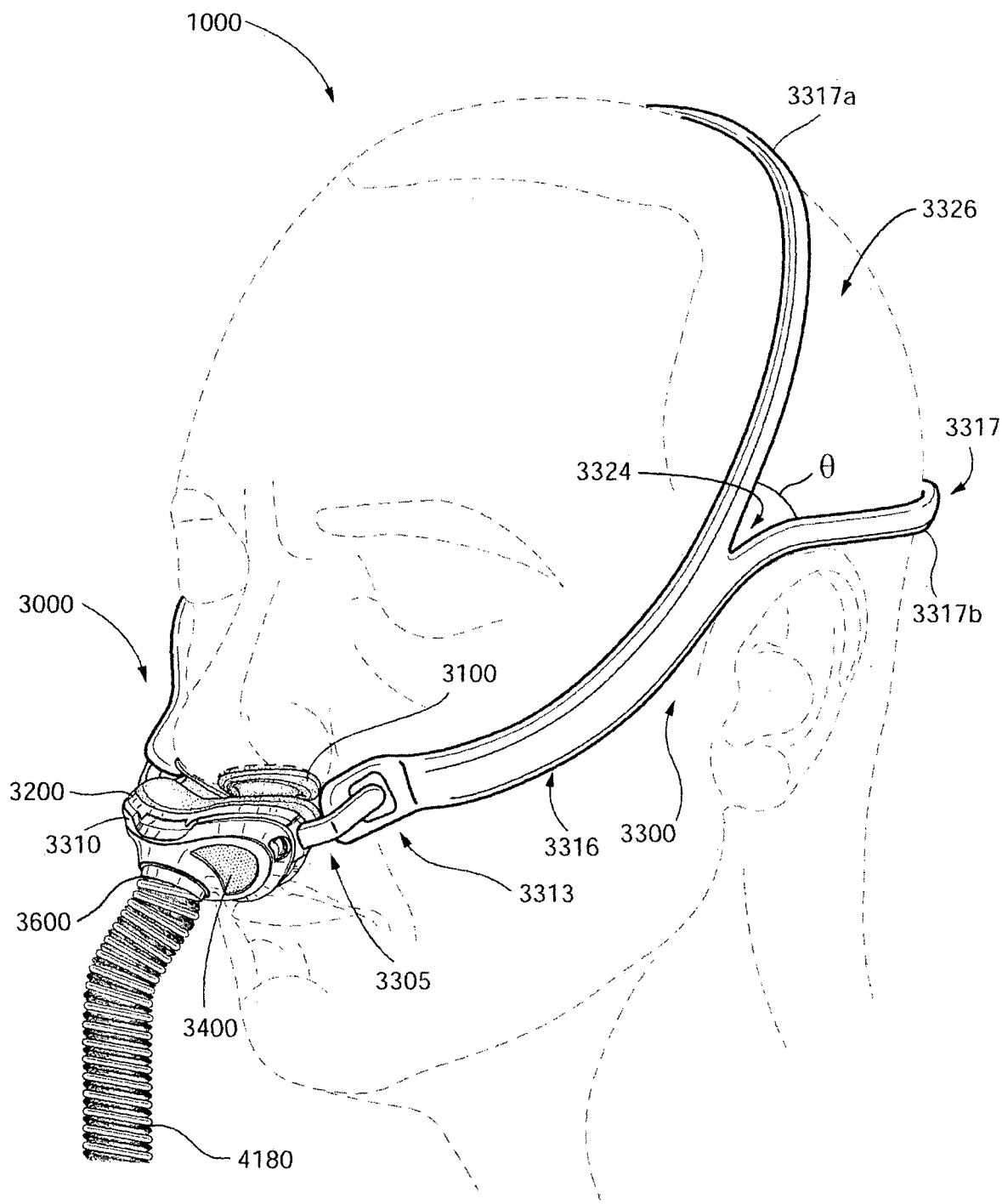

FIG. 74 shows a perspective view of an exemplary positioning and stabilising structure in accordance with the present technology donned on a patient.

Figure 75:
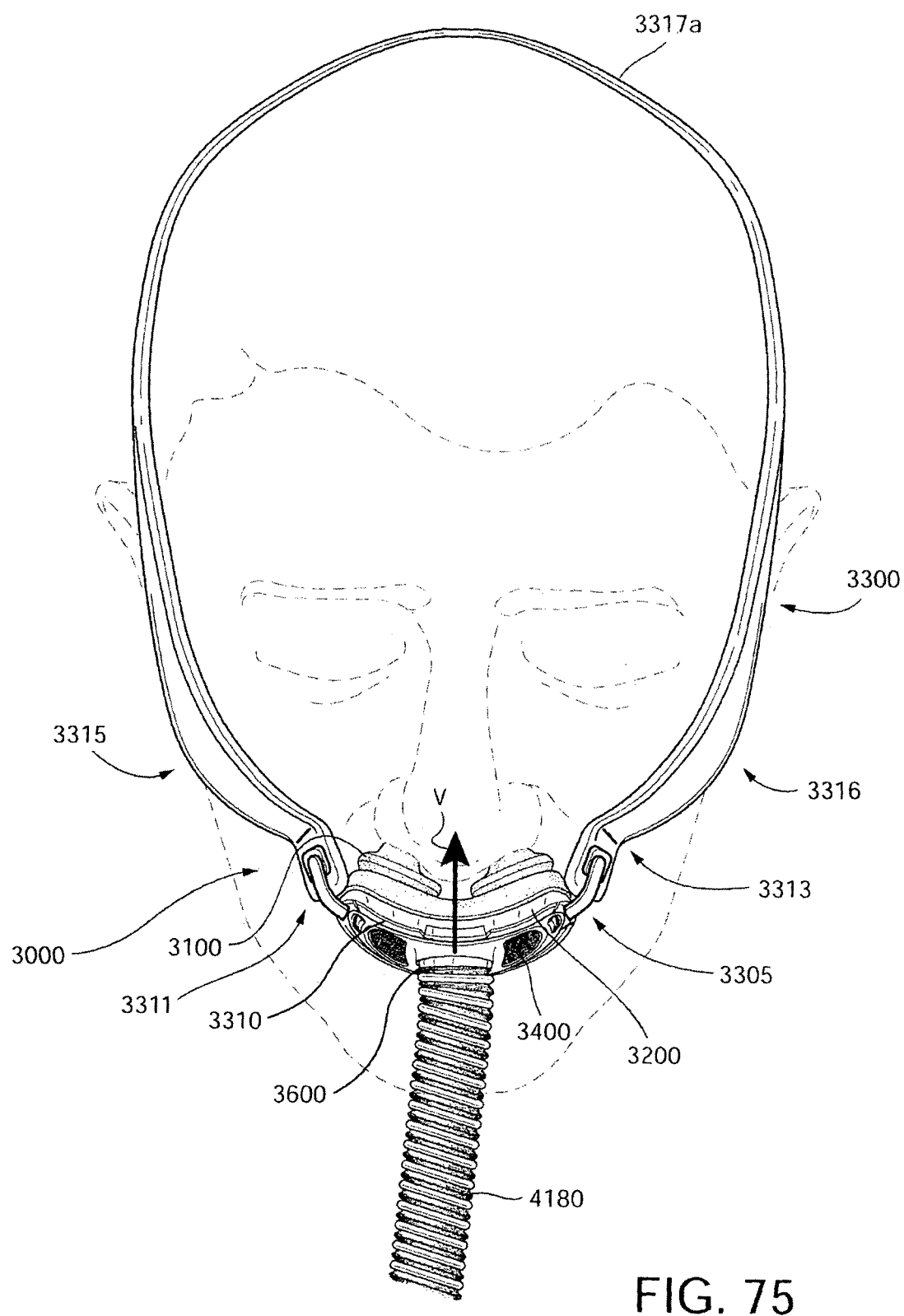

FIG. 75 shows a front view of an exemplary positioning and stabilising structure in accordance with the present technology donned on a patient.

Figure 76:
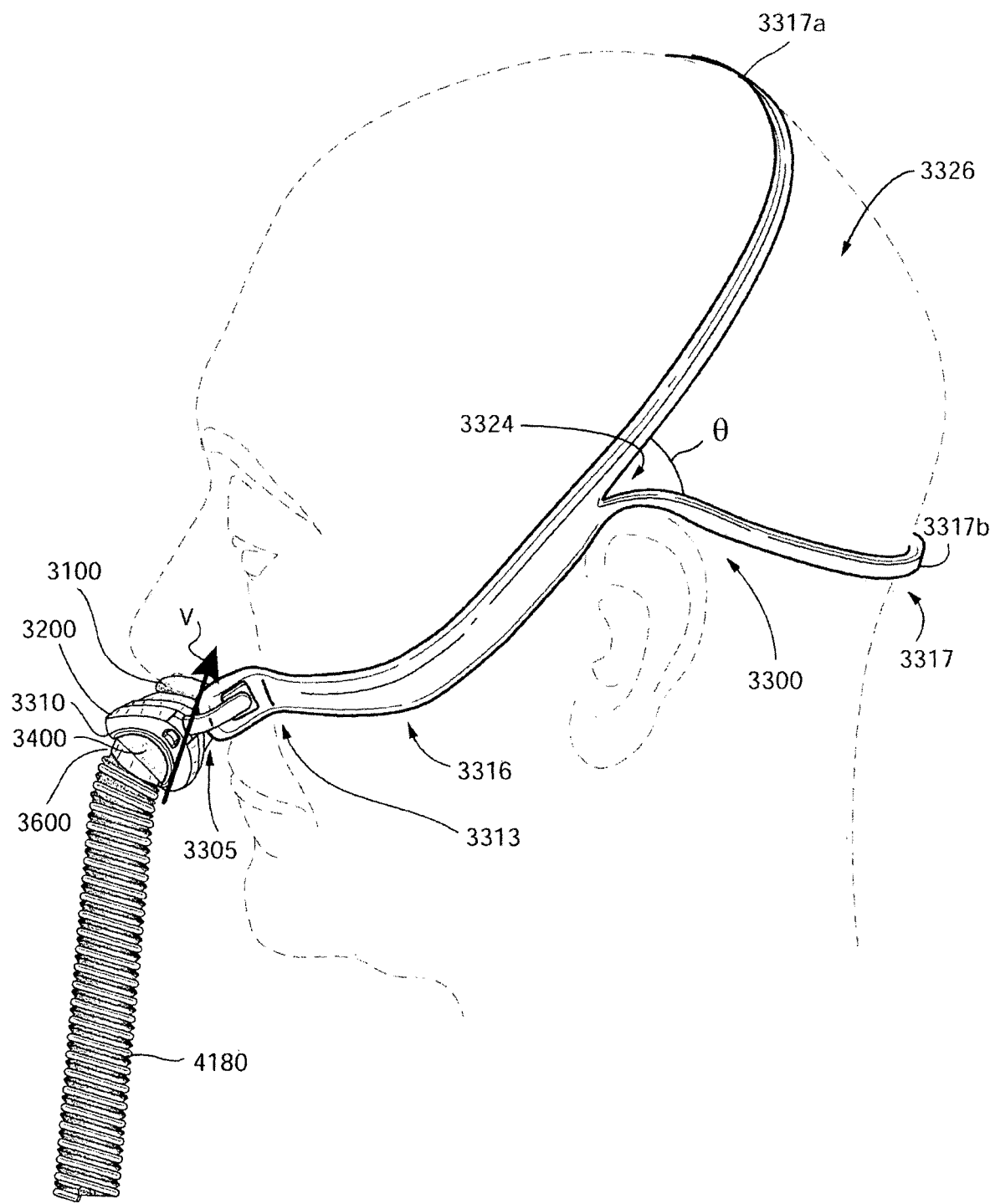

FIG. 76 shows a side view of an exemplary positioning and stabilising structure in accordance with the present technology donned on a patient.

Figure 77:
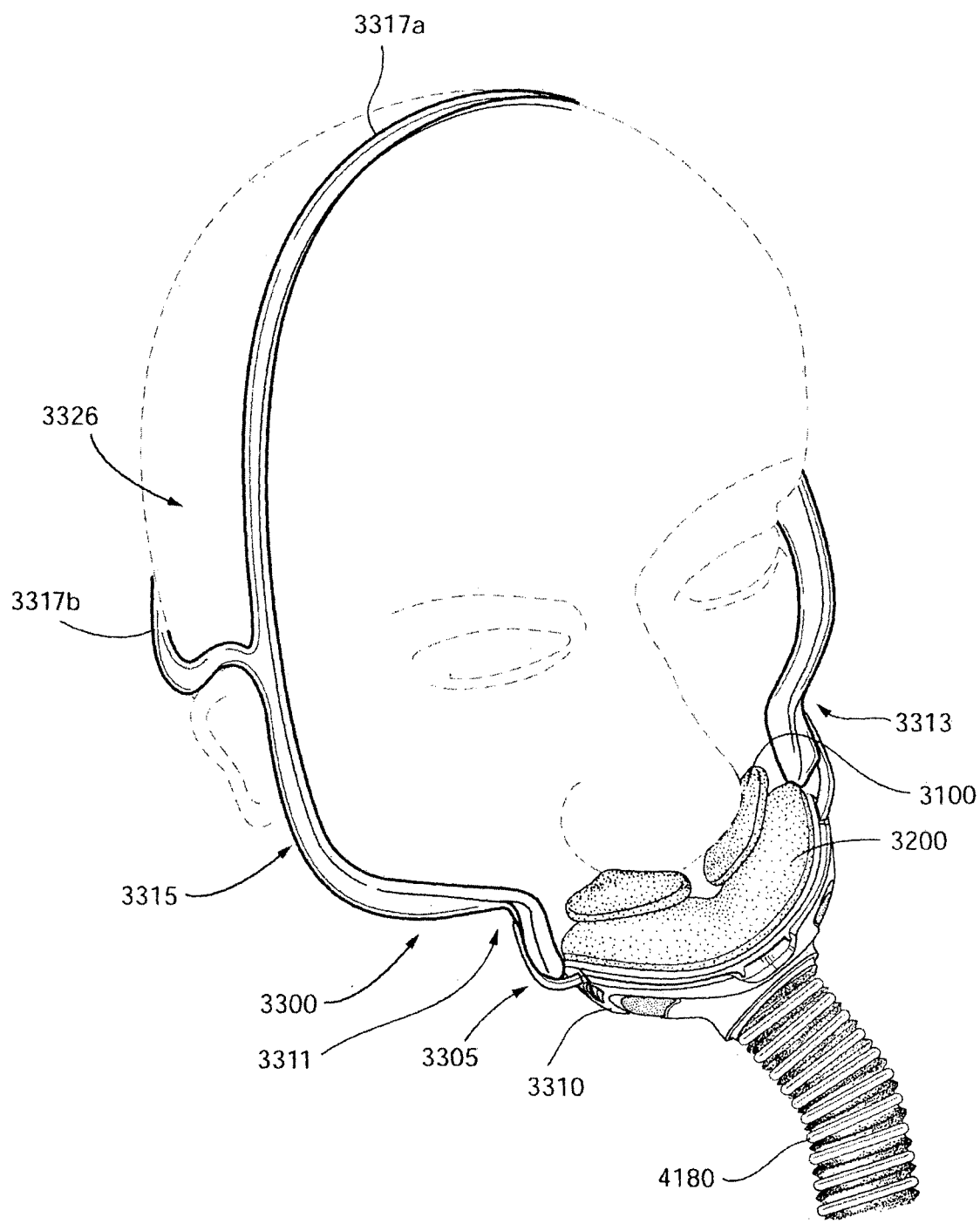

FIG. 77 shows a downward perspective view of an exemplary positioning and stabilising structure in accordance with the present technology donned on a patient.

Figure 78:
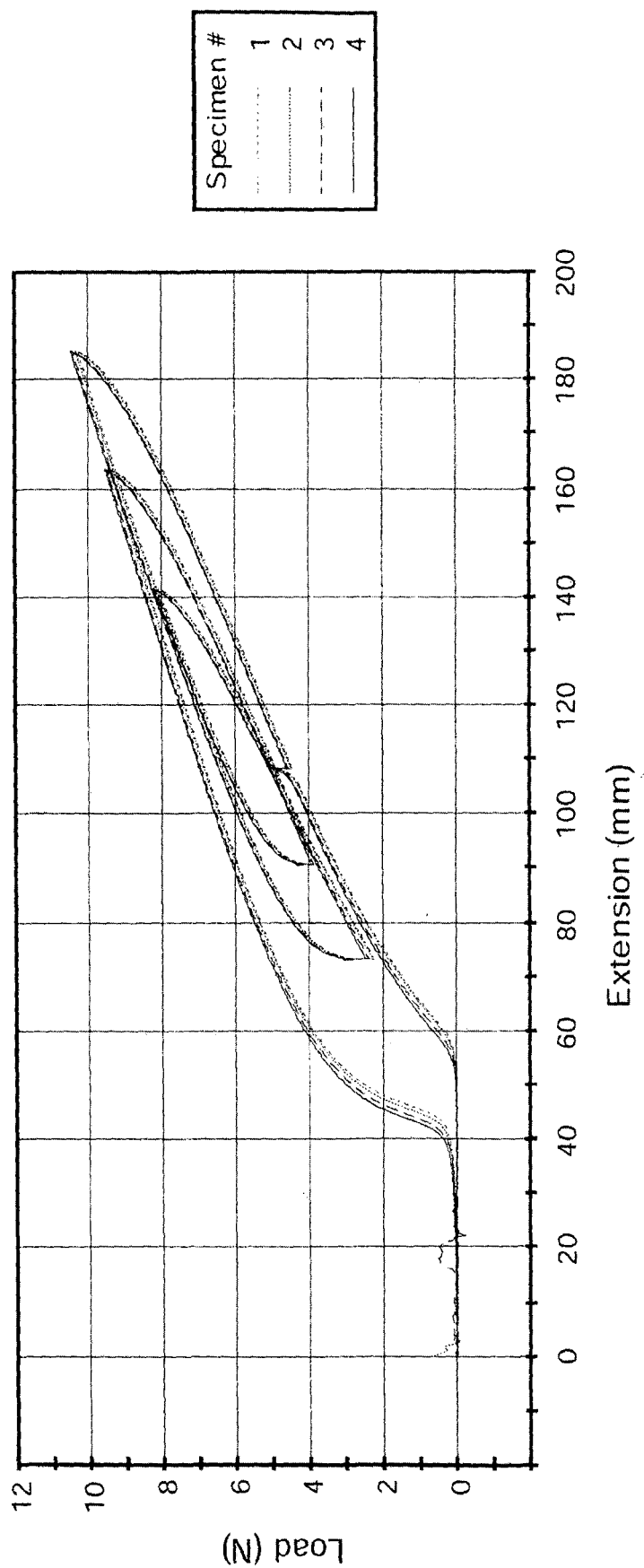

FIG. 78 shows a graph of the extension (in mm) of a strap of a positioning and stabilising structure according to an example of the present technology subjected to a range of loads (in Newtons).

Figure 79:
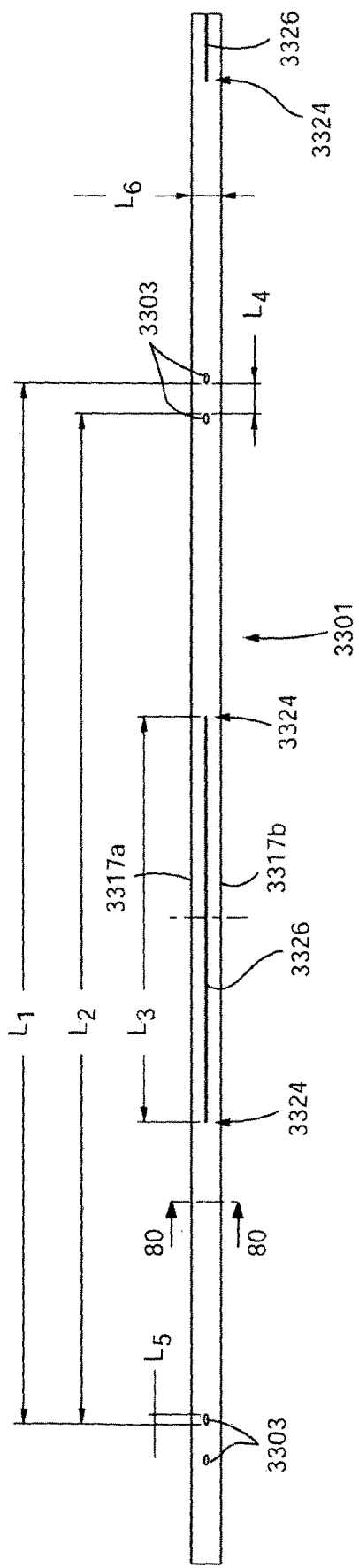

FIG. 79 shows a top view of a strap of a positioning and stabilising structure according to an example of the present technology during an intermediate stage of production.

Figure 80:
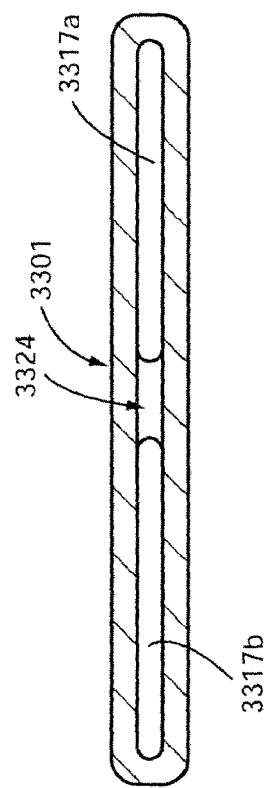

FIG. 80 shows a cross-sectional view taken through line 80-80 of FIG. 79 of a strap of a positioning and stabilising structure according to an example of the present technology during an intermediate stage of production.

Figure 81:
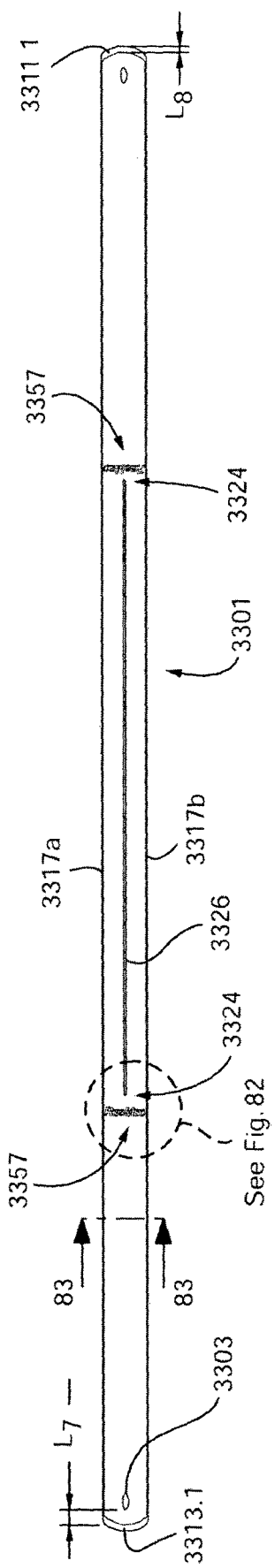

FIG. 81 shows a top view of a strap of a positioning and stabilising structure according to an example of the present technology.

Figure 82:
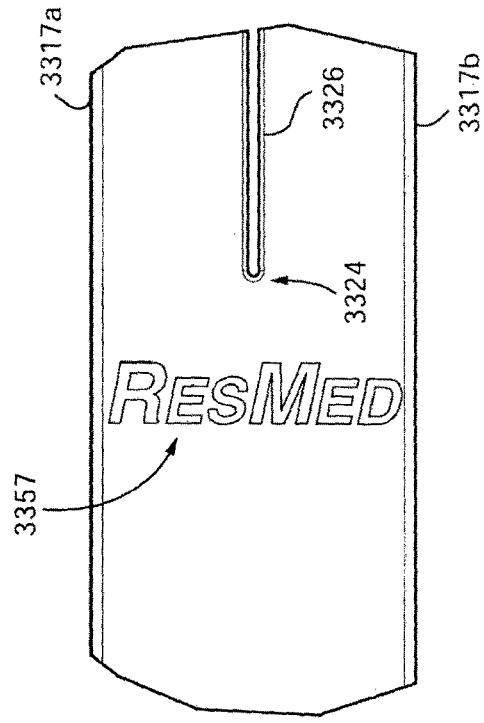

FIG. 82 shows a top detailed view of a strap of a positioning and stabilising structure according to an example of the present technology.

Figure 83:
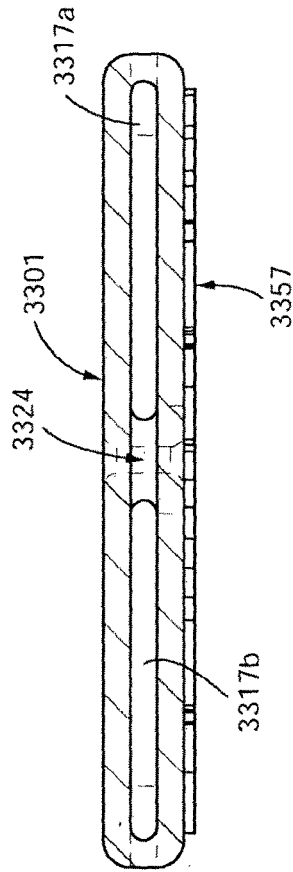

FIG. 83 shows a cross-sectional view taken through line 83-83 of FIG. 81 of a strap of a positioning and stabilising structure according to an example of the present technology.

FIGS. 84 to 88 show a sequence of perspective views of a patient donning a positioning and stabilising structure according to an example of the present technology.

FIGS. 89 to 93 show a sequence of side views of a patient donning a positioning and stabilising structure according to an example of the present technology.

FIGS. 94 to 98 show a sequence of front views of a patient donning a positioning and stabilising structure according to an example of the present technology.

FIGS. 99 to 104 show a sequence of side views of a patient donning a positioning and stabilising structure according to an example of the present technology.

Figure 105:
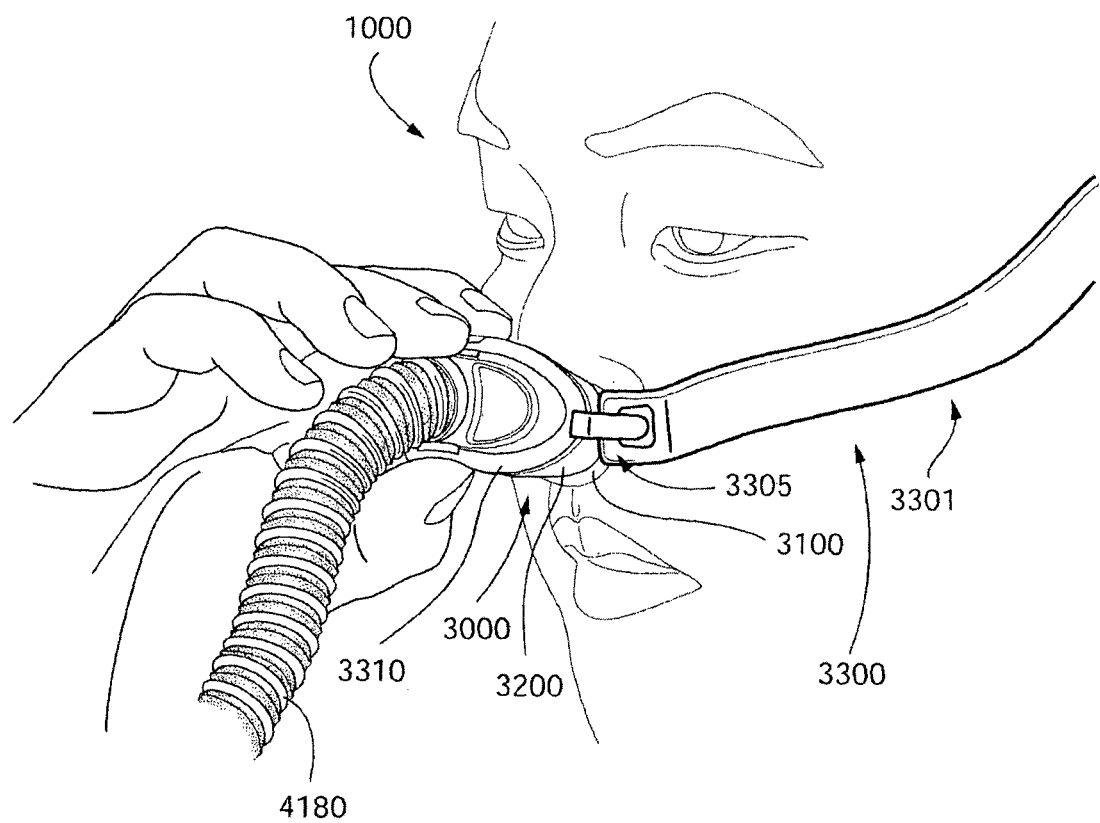
Figure 106:
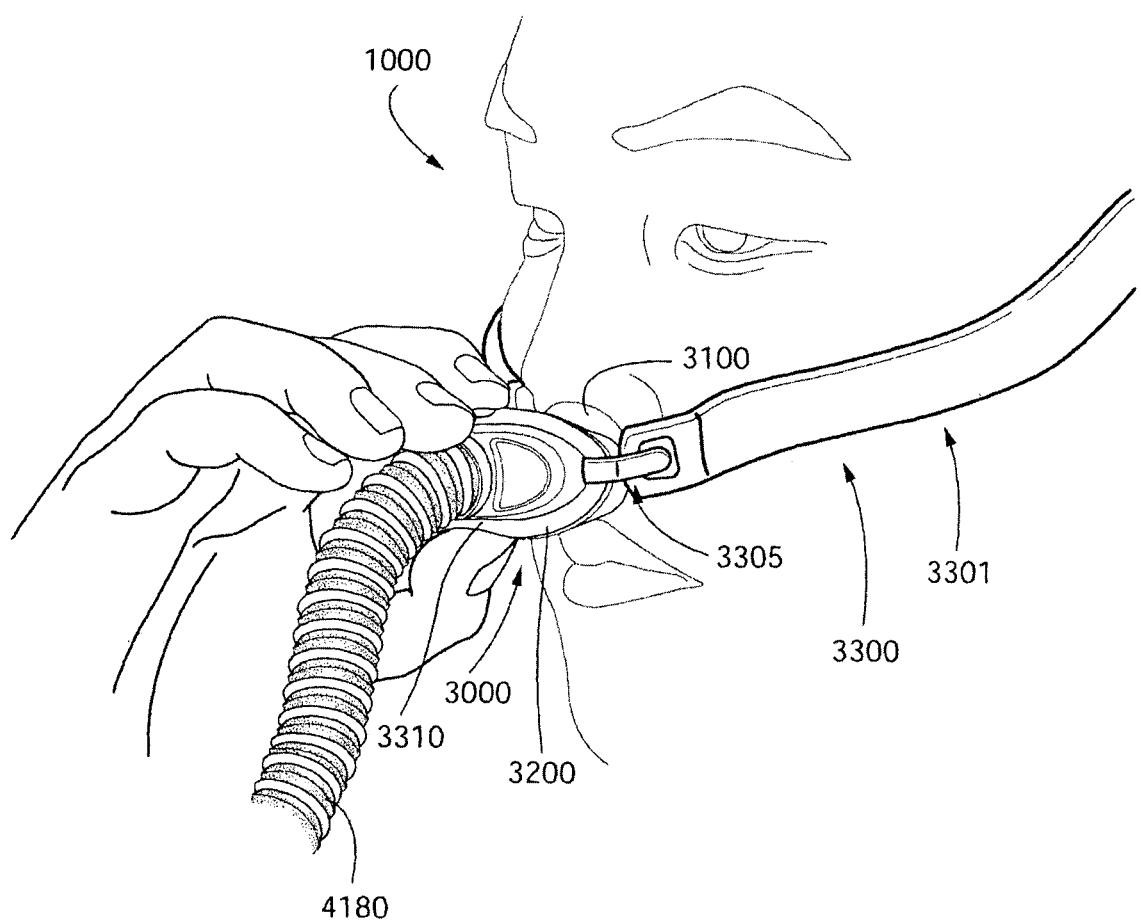
Figure 107:
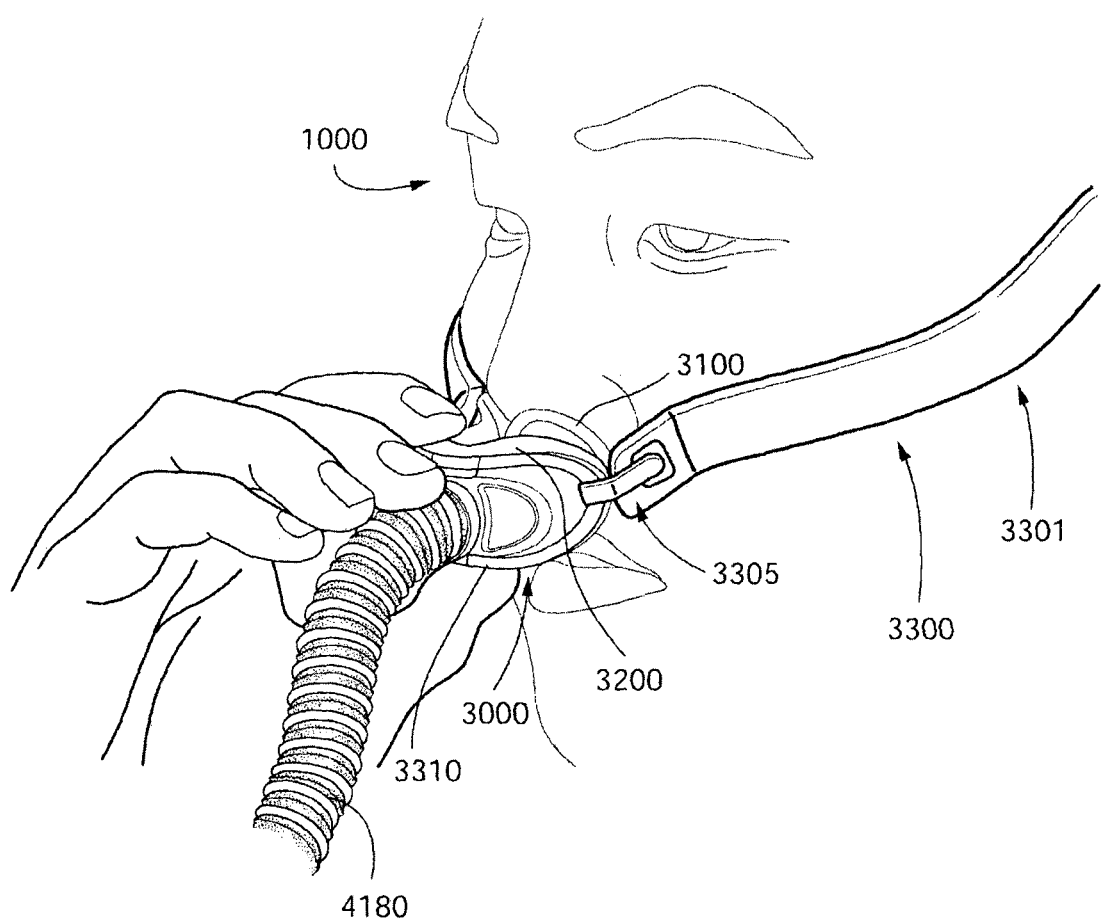

FIGS. 105 to 107 show a sequence of perspective views of a patient adjusting a patient interface according to an example of the present technology.

FIGS. 108 to 112 show a sequence of rear views of a patient adjusting a positioning and stabilising structure according to an example of the present technology.

Figure 113:
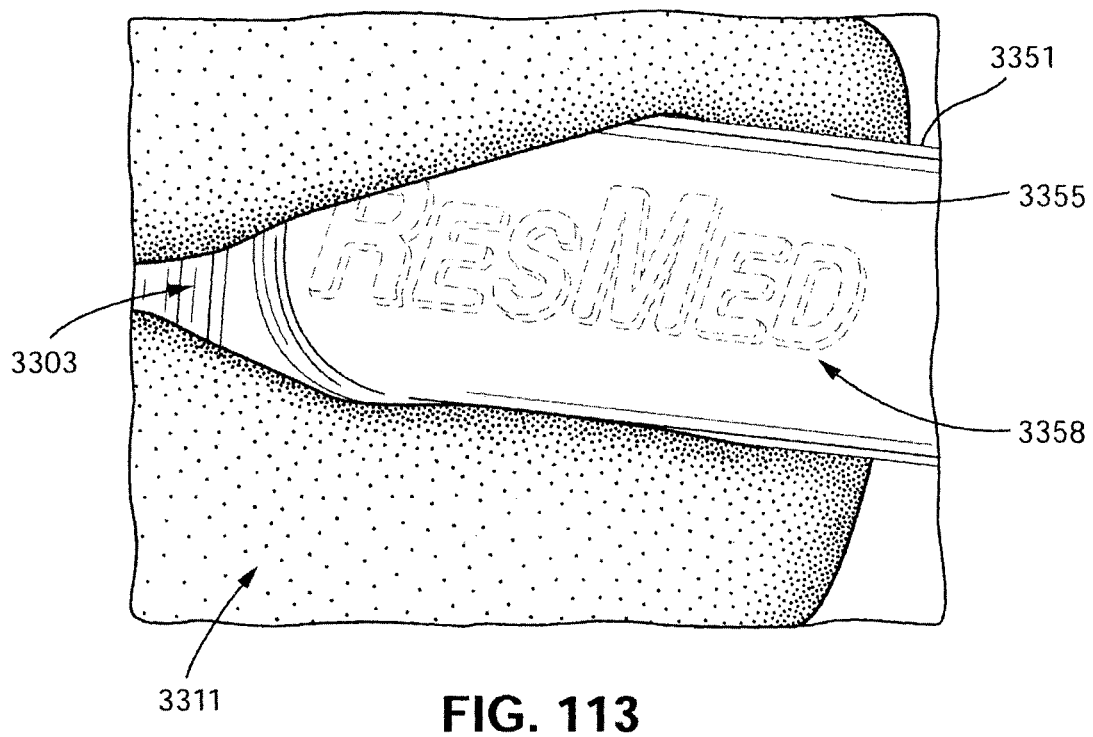

FIG. 113 shows a detailed view of the connection between a strap and a rigidiser arm of a positioning and stabilising structure according to an example of the present technology.

Figure 114:
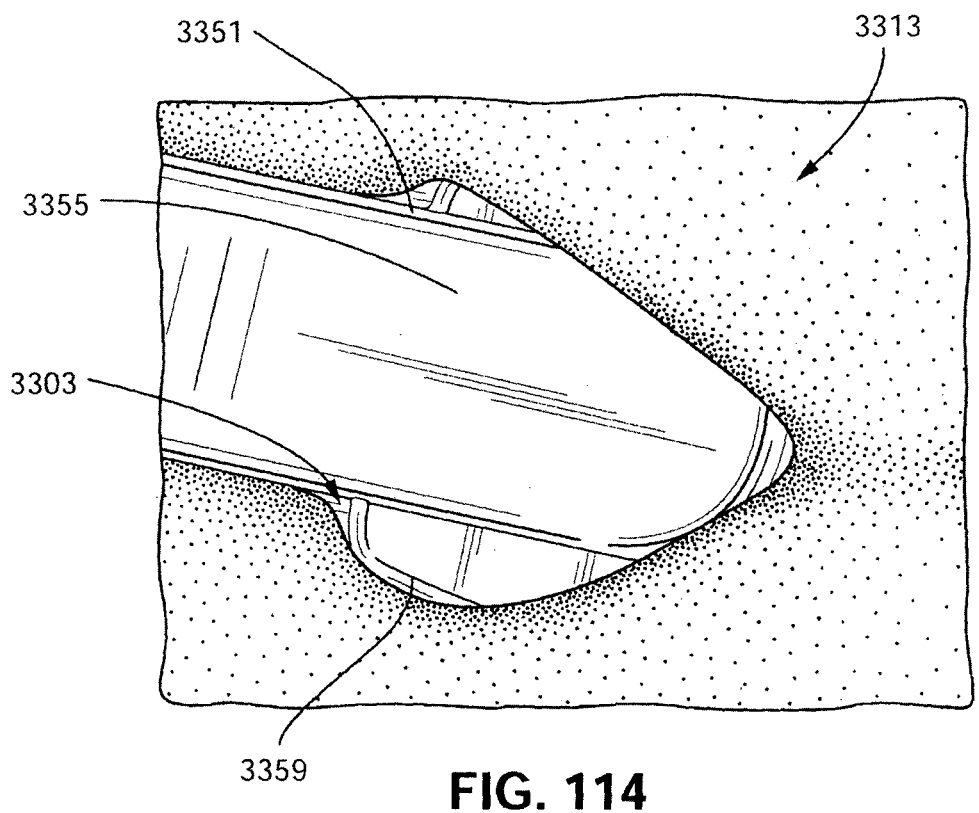

FIG. 114 shows another detailed view of the connection between a strap and a rigidiser arm of a positioning and stabilising structure according to an example of the present technology.

Figure 115:
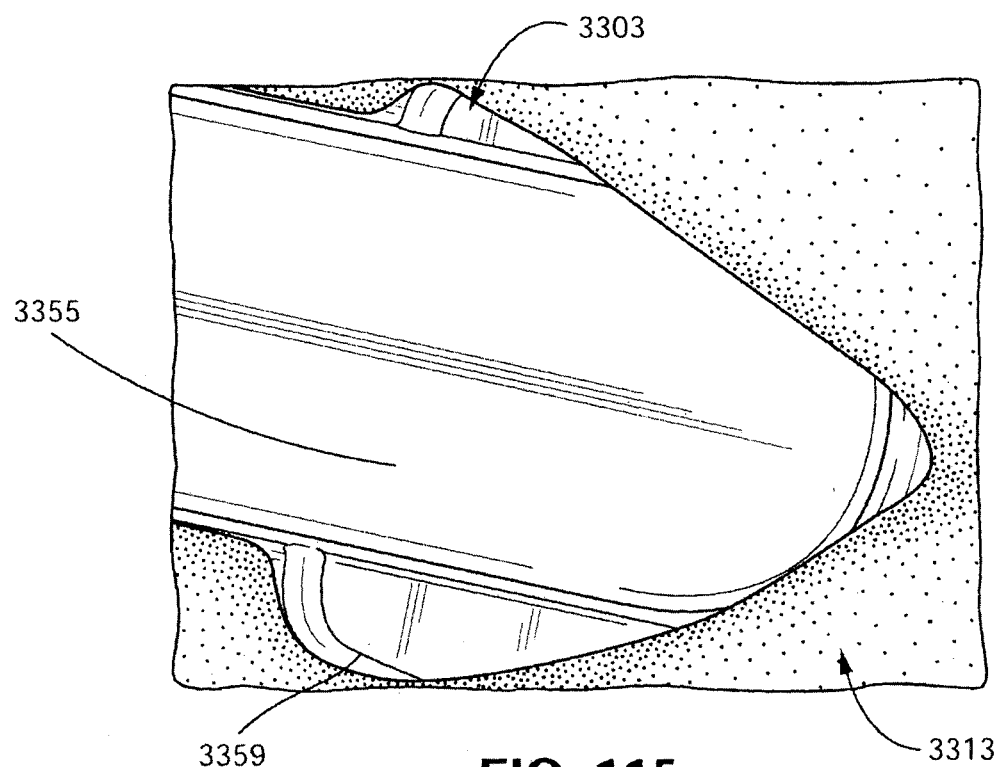

FIG. 115 shows another detailed view of the connection between a strap and a rigidiser arm of a positioning and stabilising structure according to an example of the present technology.

Figure 116:
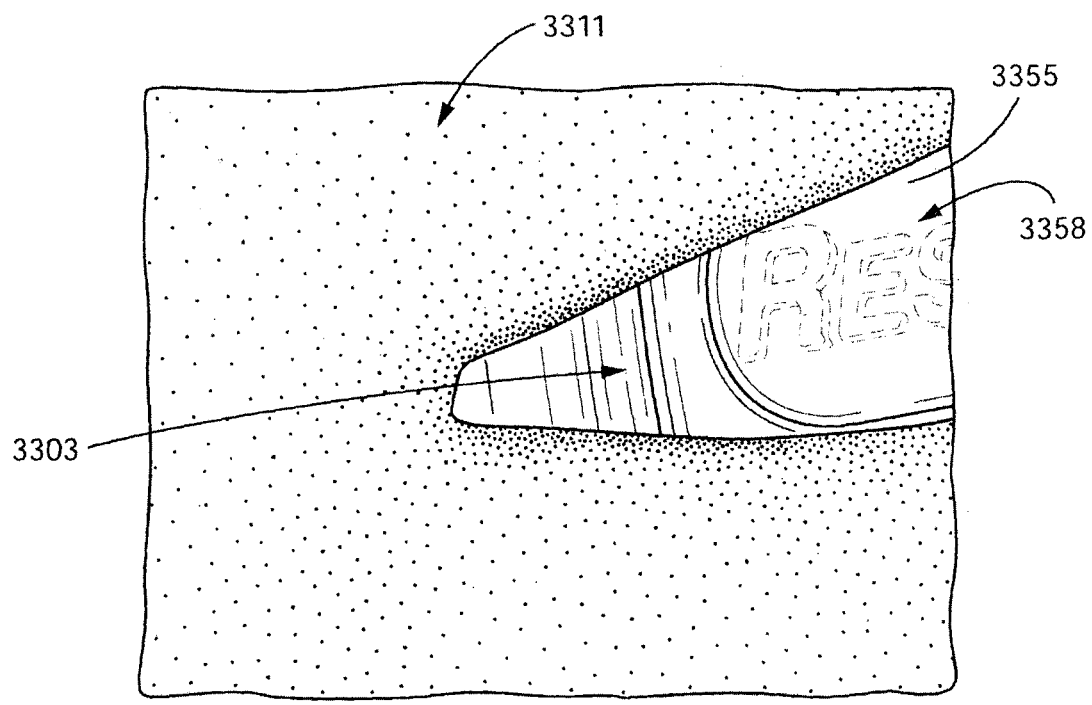

FIG. 116 shows another detailed view of the connection between a strap and a rigidiser arm of a positioning and stabilising structure according to an example of the present technology.

Figure 117:
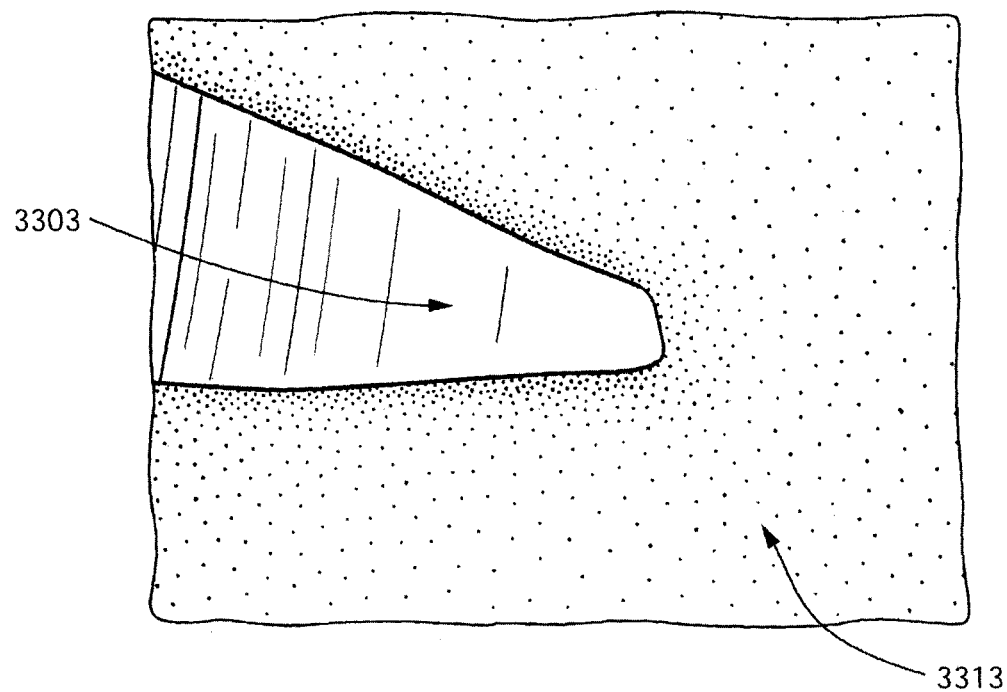

FIG. 117 shows another detailed view of the connection between a strap and a rigidiser arm of a positioning and stabilising structure according to an example of the present technology.

Figure 118:
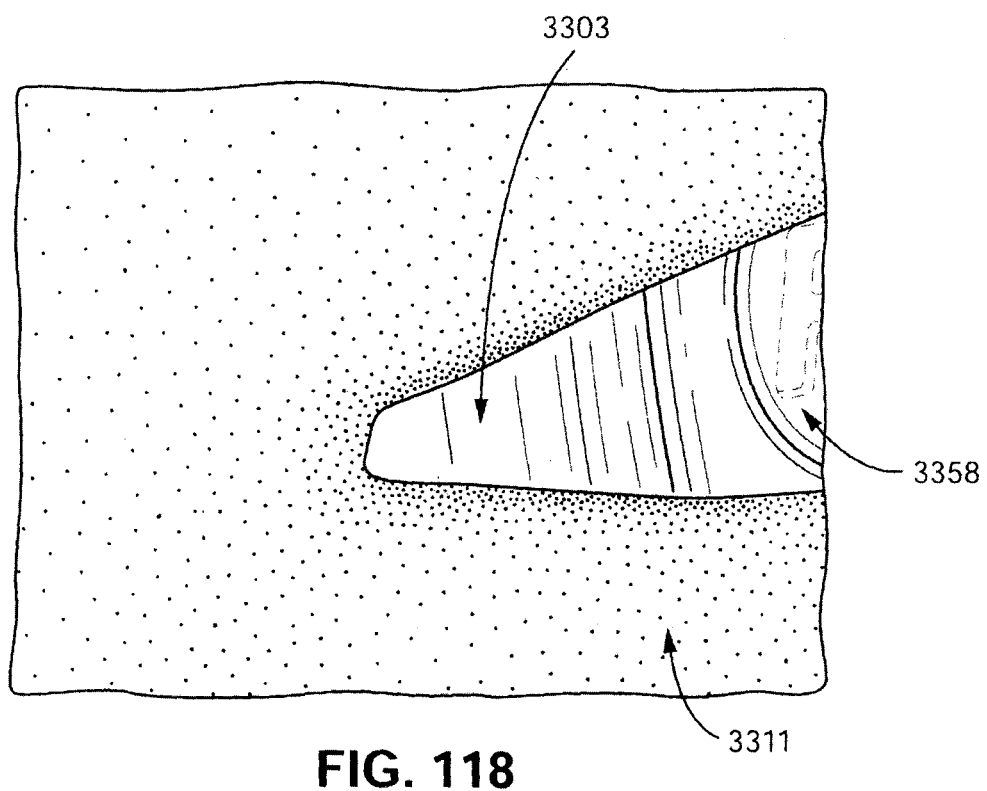

FIG. 118 shows another detailed view of the connection between a strap and a rigidiser arm of a positioning and stabilising structure according to an example of the present technology.

Figure 119:
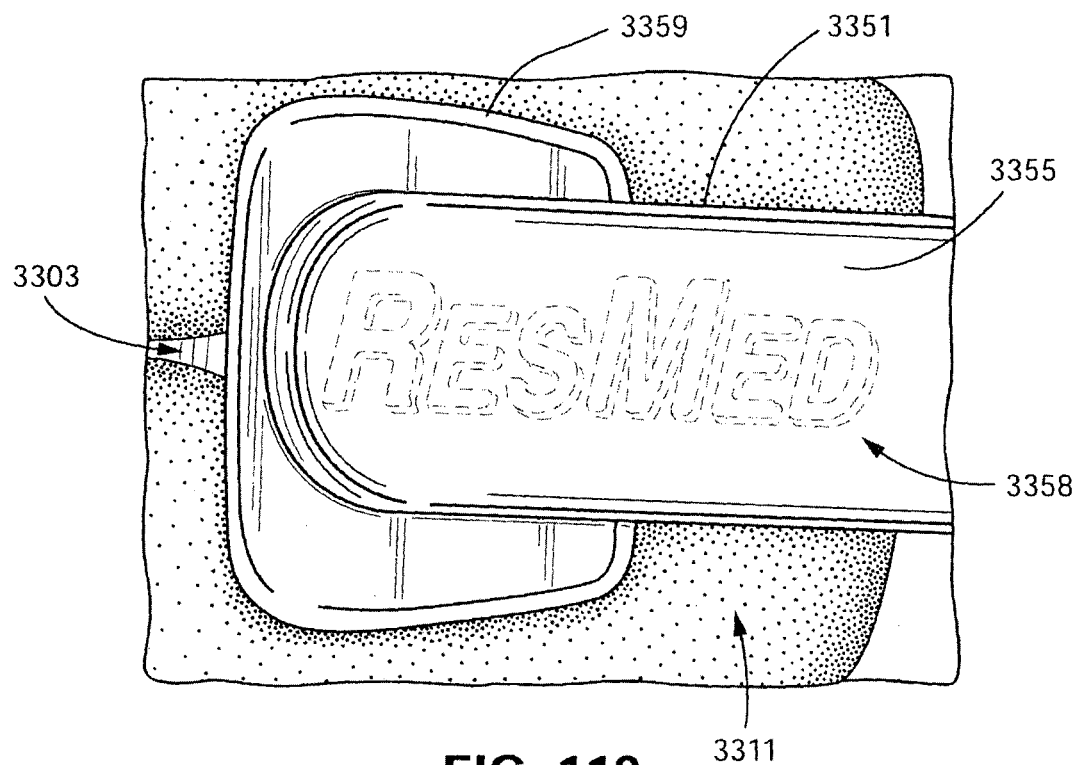

FIG. 119 shows a detailed view of the connection between a strap and a rigidiser arm of a positioning and stabilising structure according to an example of the present technology.

Figure 120:
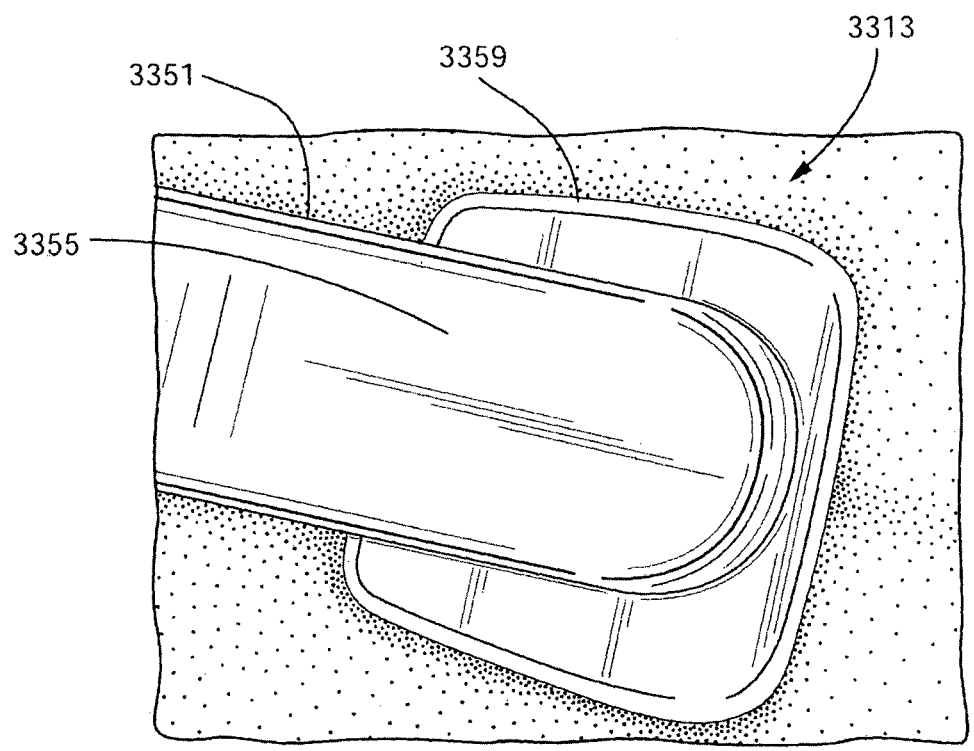

FIG. 120 shows another detailed view of the connection between a strap and a rigidiser arm of a positioning and stabilising structure according to an example of the present technology.

Figure 121:
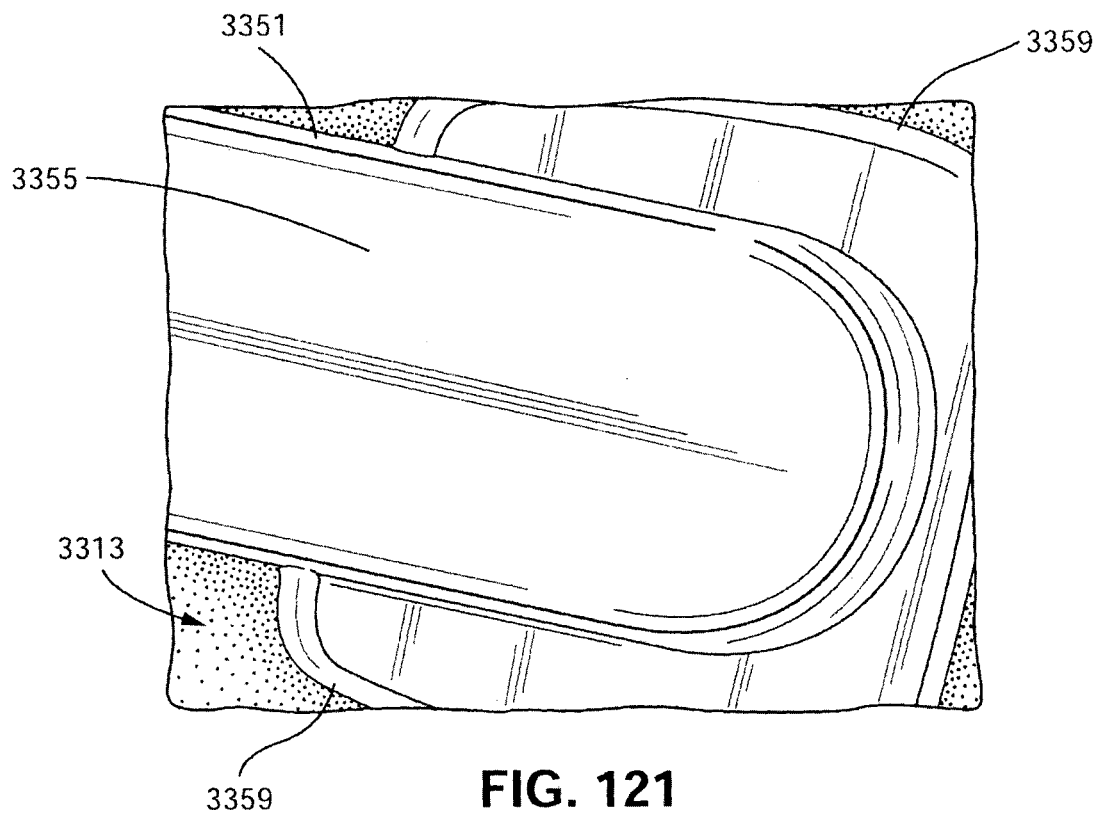

FIG. 121 shows another detailed view of the connection between a strap and a rigidiser arm of a positioning and stabilising structure according to an example of the present technology.

Figure 122:
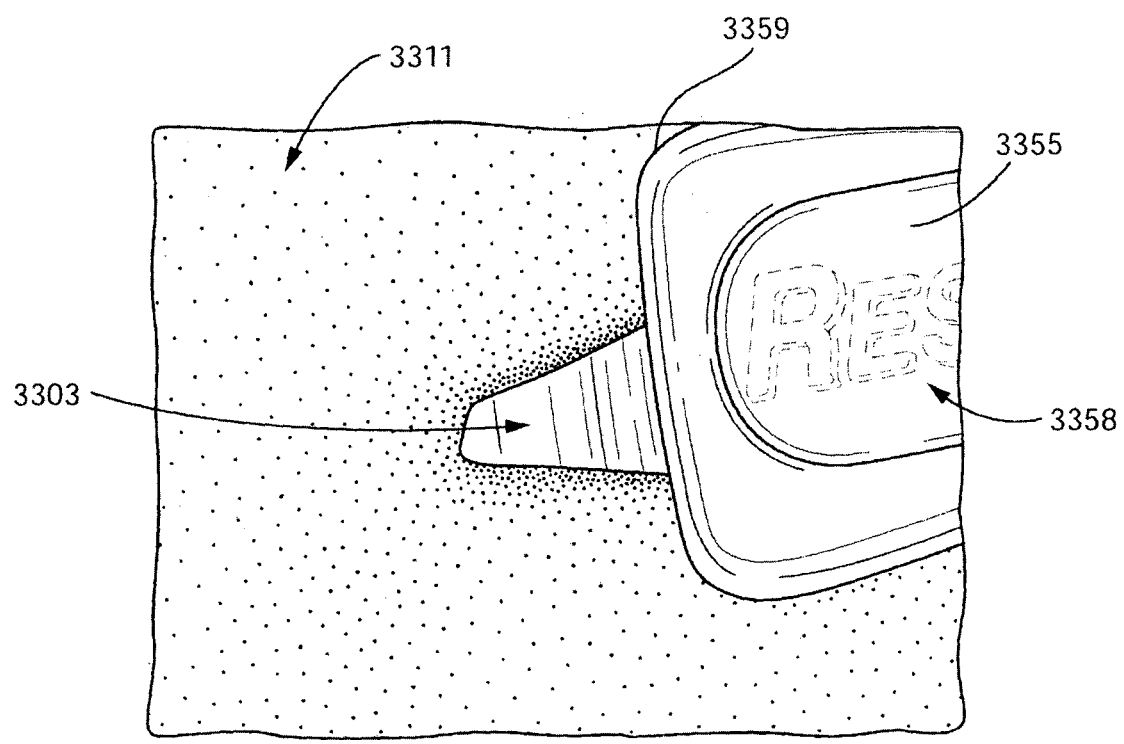

FIG. 122 shows another detailed view of the connection between a strap and a rigidiser arm of a positioning and stabilising structure according to an example of the present technology.

Figure 123:
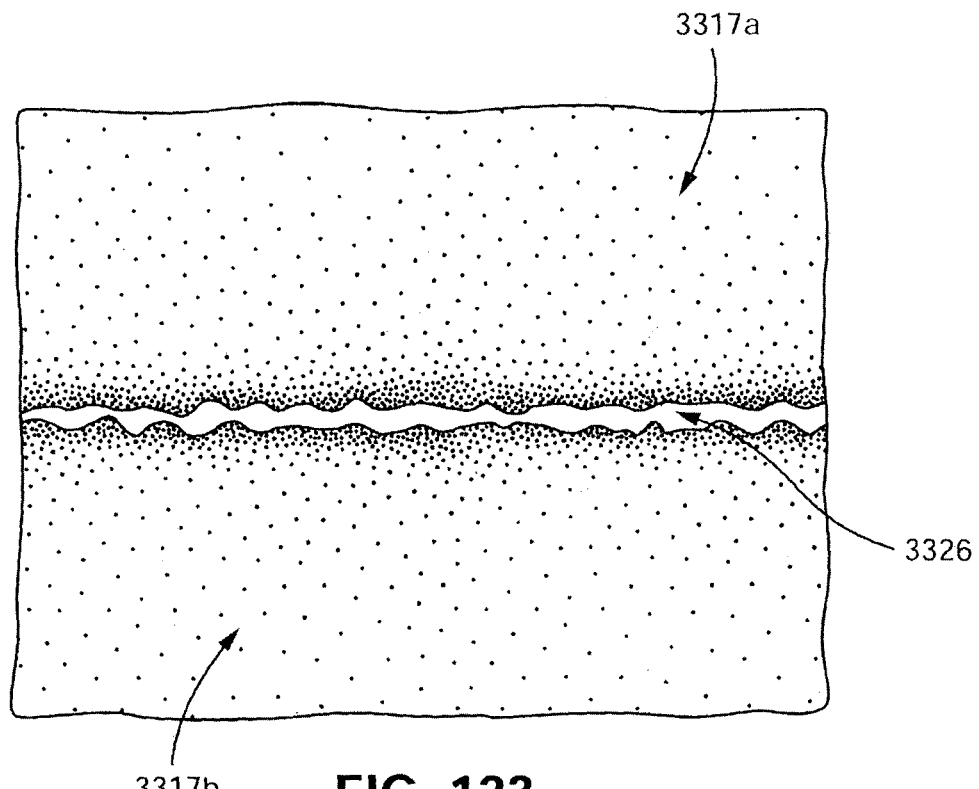

FIG. 123 shows a detailed view of a split region of a strap of a positioning and stabilising structure according to an example of the present technology.

Figure 124:
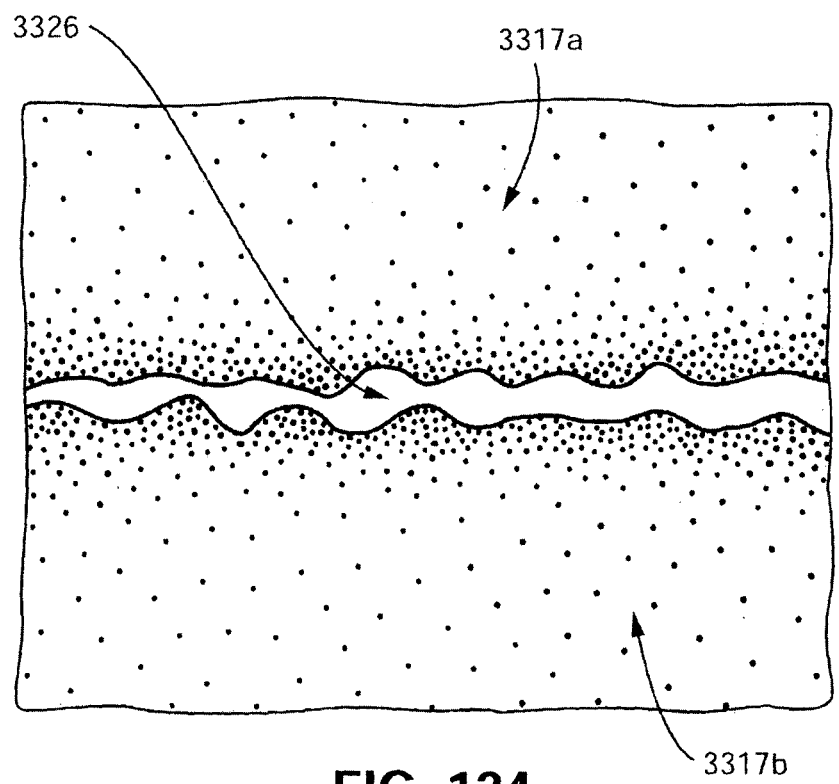

FIG. 124 shows another detailed view of a split region of a strap of a positioning and stabilising structure according to an example of the present technology.

Figure 125:
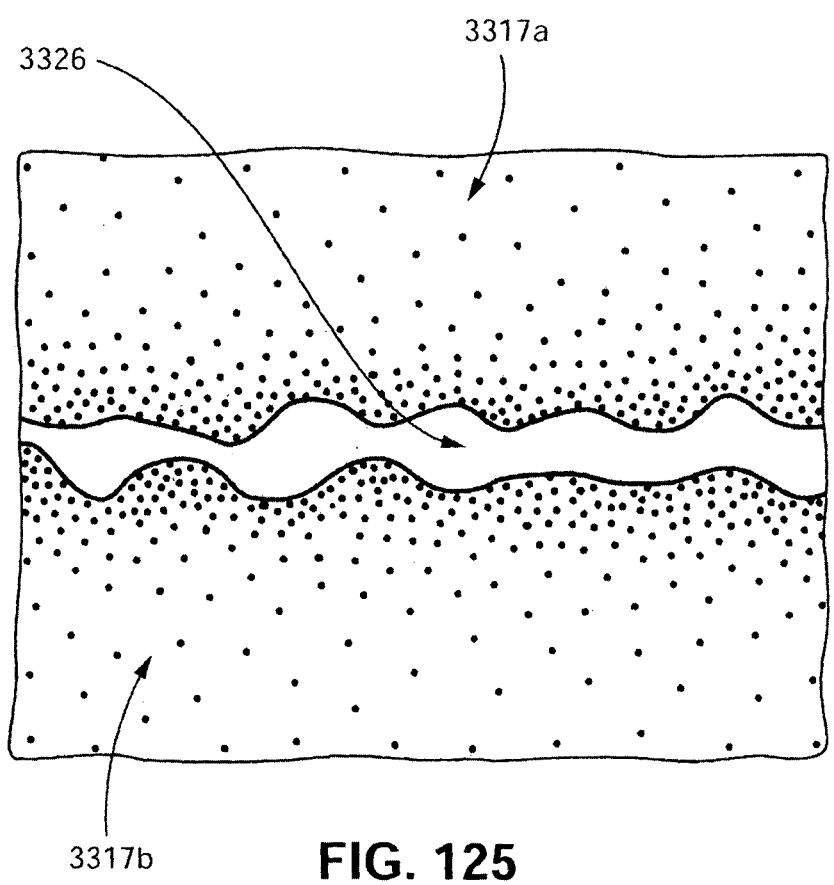

FIG. 125 shows another detailed view of a split region of a strap of a positioning and stabilising structure according to an example of the present technology.

Figure 126:
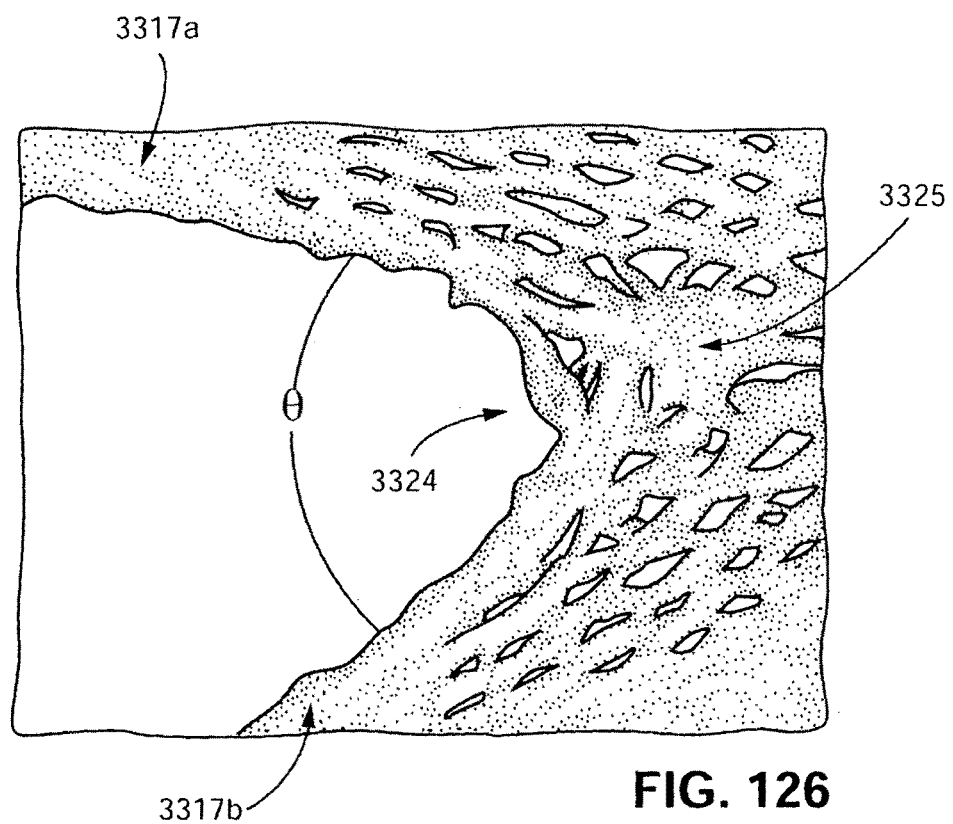

FIG. 126 shows a detailed view of a bifurcation of a strap of a positioning and stabilising structure according to an example of the present technology.

Figure 127:
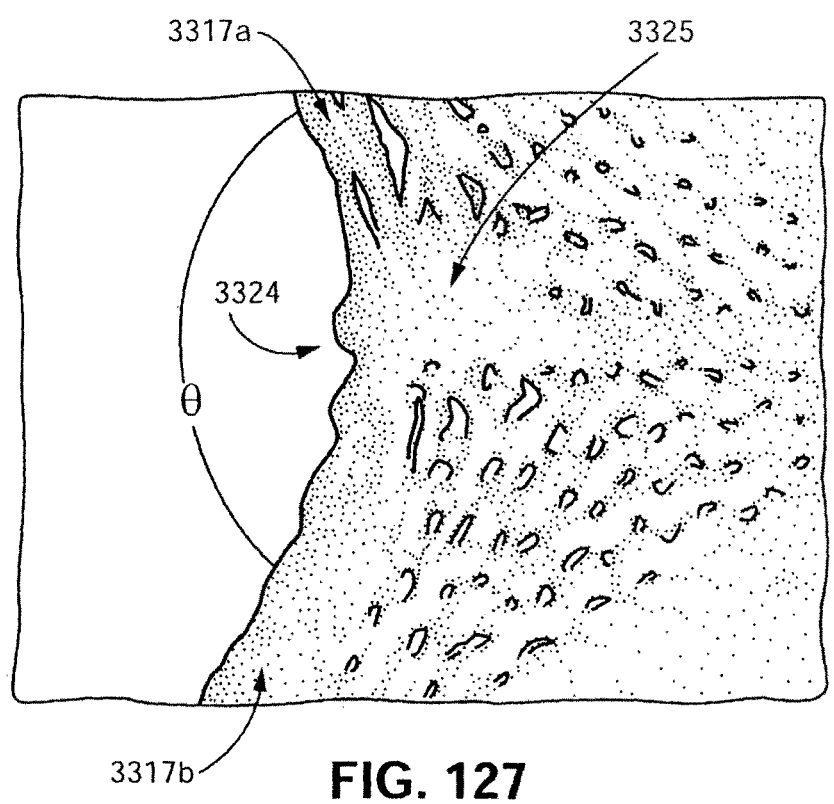

FIG. 127 shows another detailed view of a bifurcation of a strap of a positioning and stabilising structure according to an example of the present technology.

Figure 128:
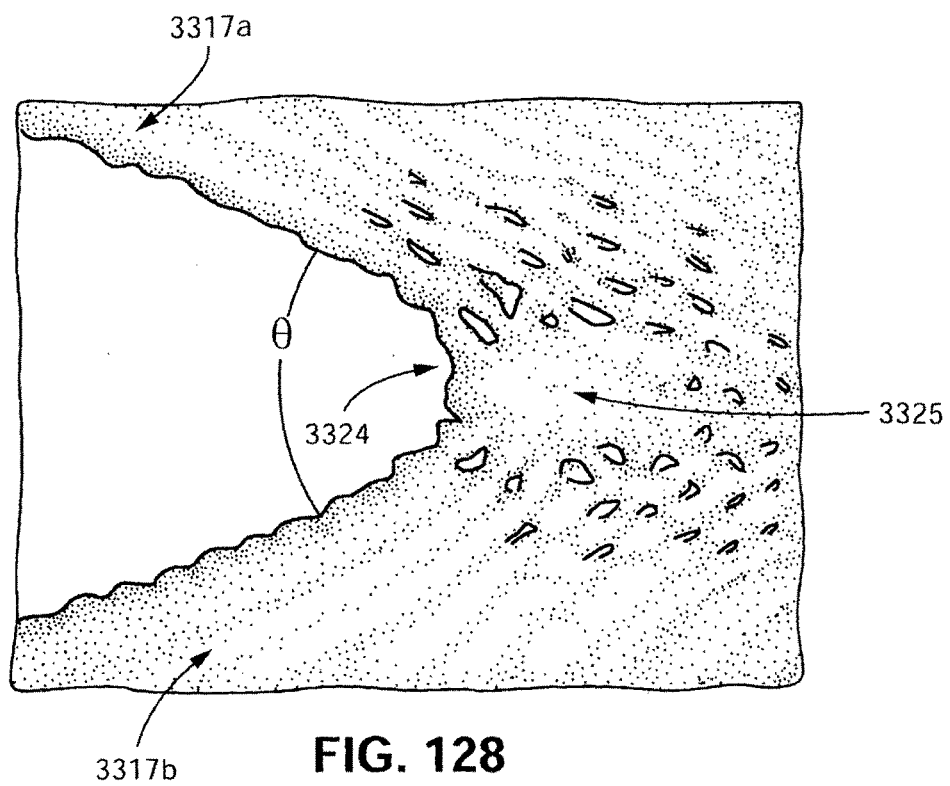

FIG. 128 shows another detailed view of a bifurcation of a strap of a positioning and stabilising structure according to an example of the present technology.

Figure 129:
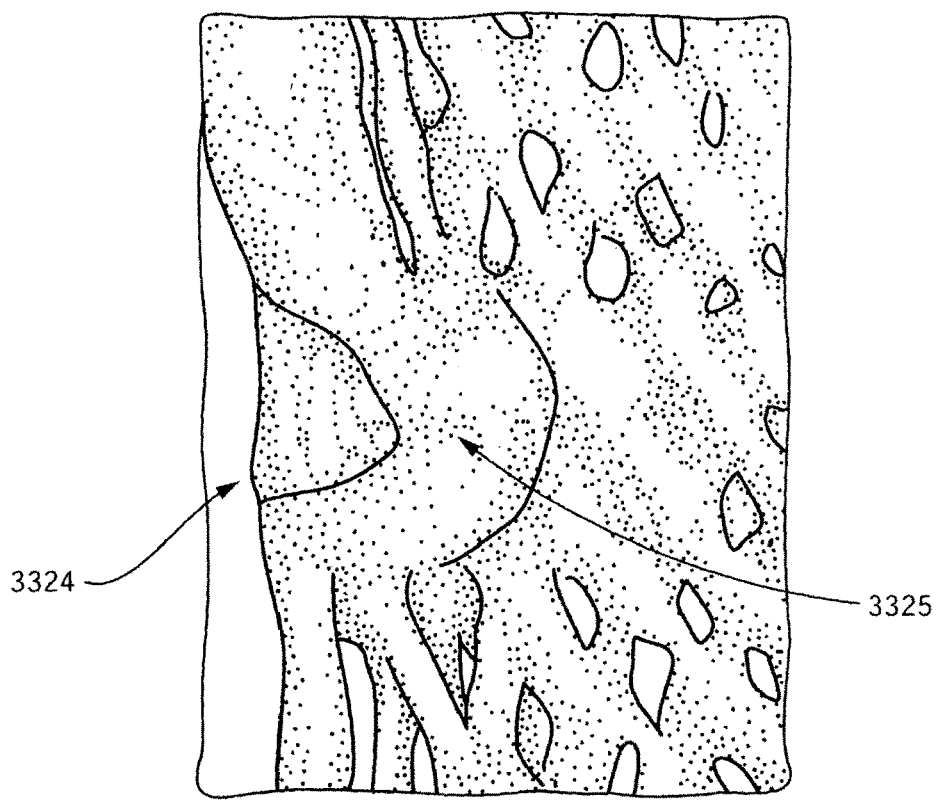

FIG. 129 shows another detailed view of a bifurcation of a strap of a positioning and stabilising structure according to an example of the present technology.

Figure 130:
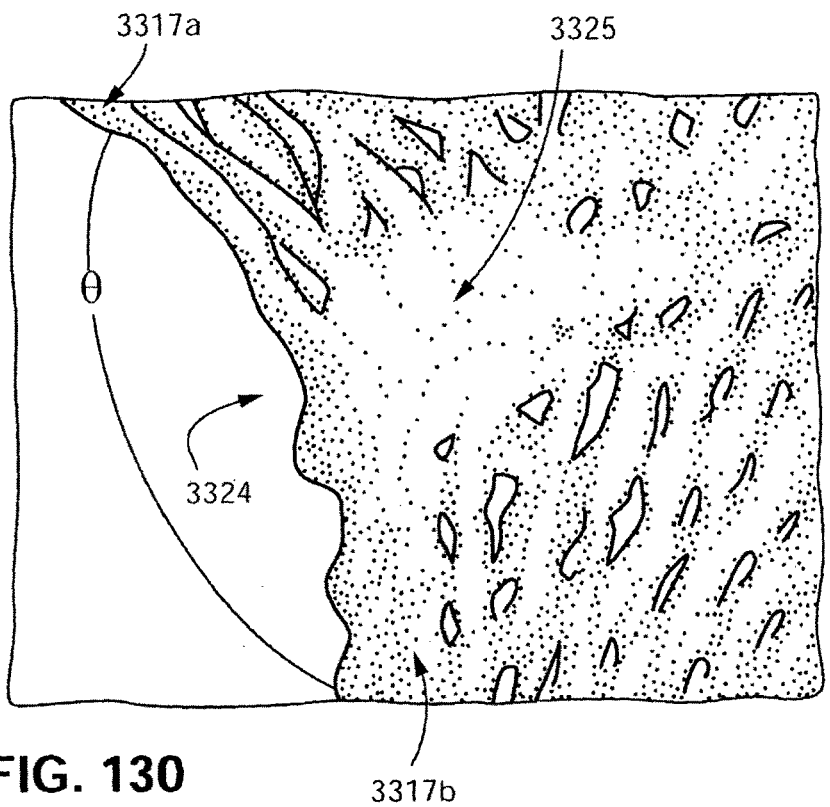

FIG. 130 shows another detailed view of a bifurcation of a strap of a positioning and stabilising structure according to an example of the present technology.

Figure 131:
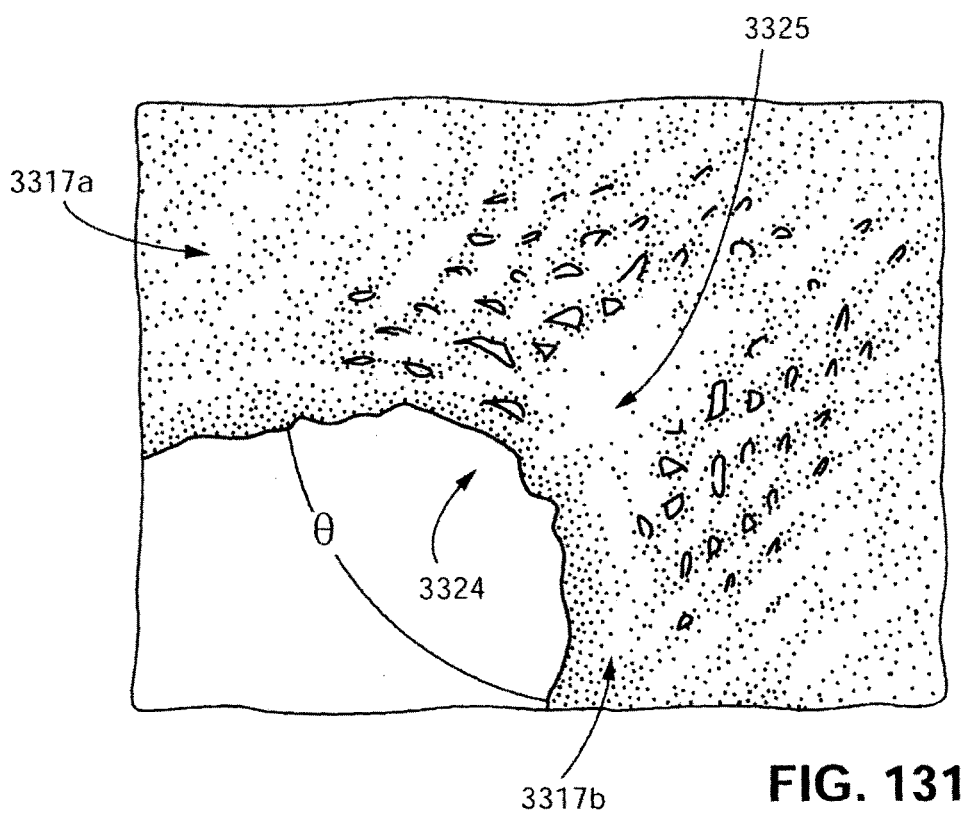

FIG. 131 shows another detailed view of a bifurcation of a strap of a positioning and stabilising structure according to an example of the present technology.

Figure 132:
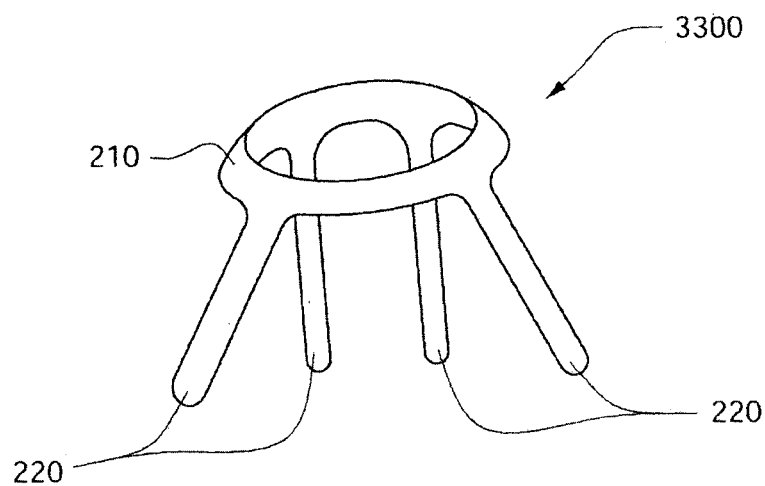

FIG. 132 shows a perspective view of a positioning and stabilising structure manufactured according to an example of the present technology.

Figure 133:
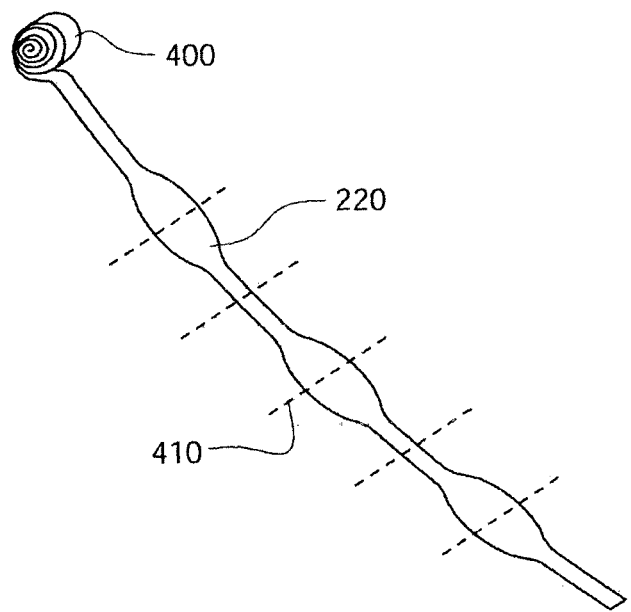

FIG. 133 shows a process of forming a positioning and stabilising structure straps from a continuous roll according to an example of the present technology.

Figure 134:
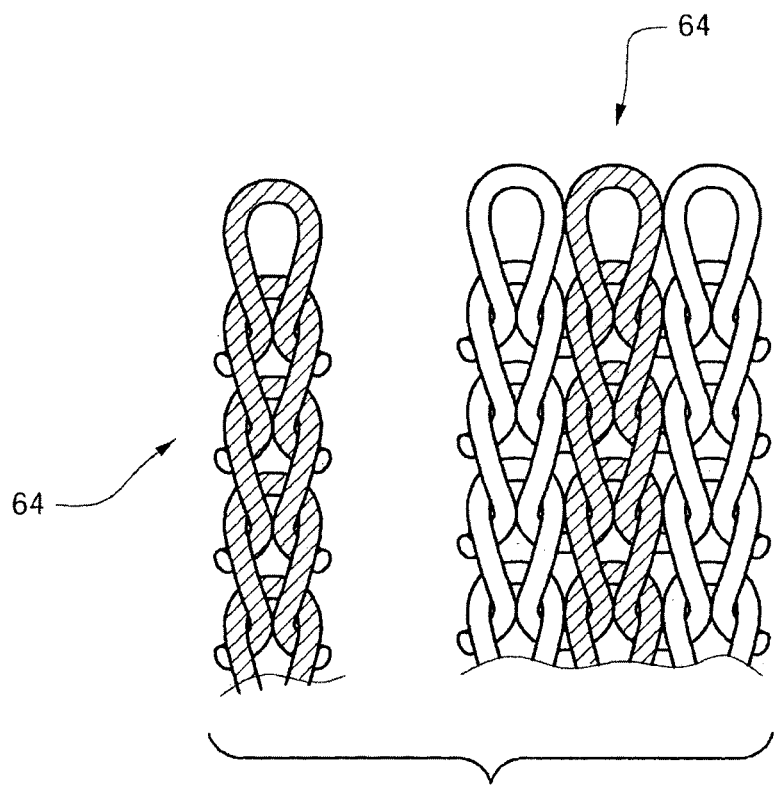

FIG. 134 shows a conventional example depicting a knitting process according to an example of the present technology.

Figure 135:
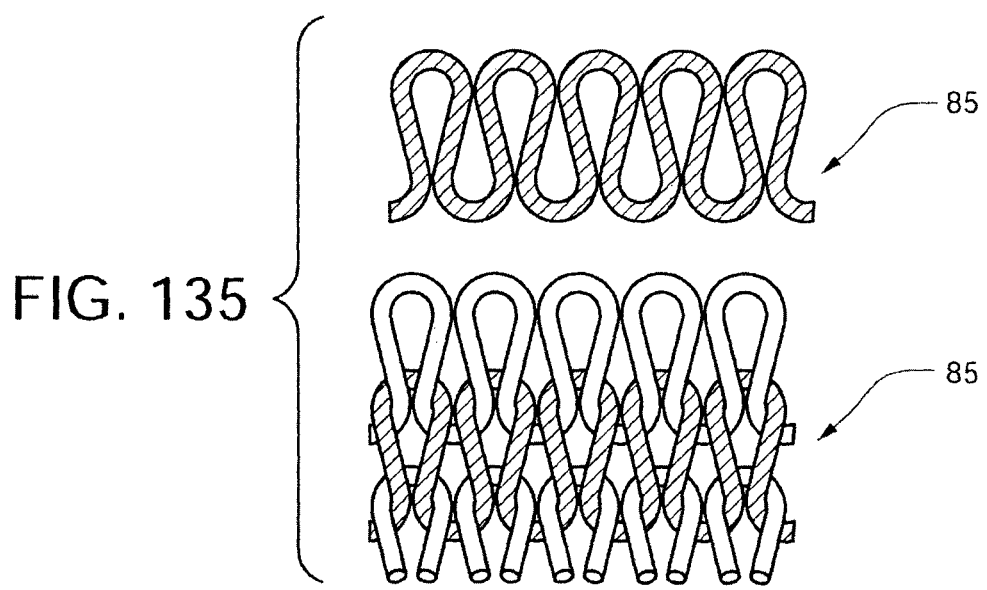

FIG. 135 shows a conventional example depicting a knitting process according to an example of the present technology.

Figure 136:
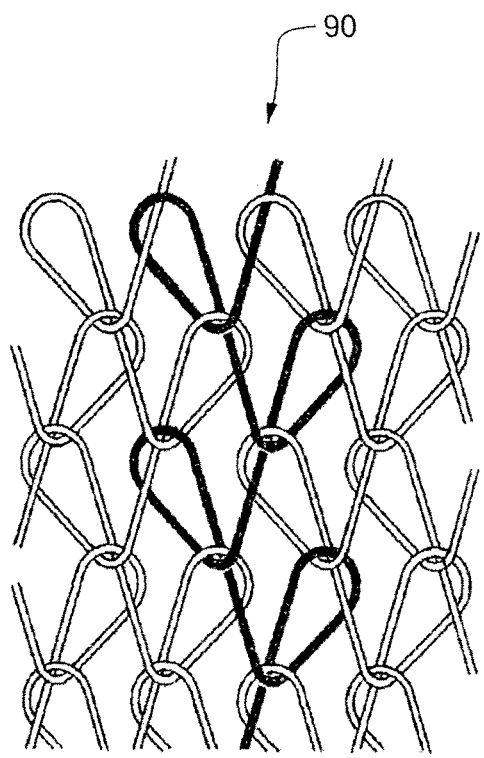

FIG. 136 illustrates a basic warp knitted fabric according to an example of the present technology.

Figure 137:
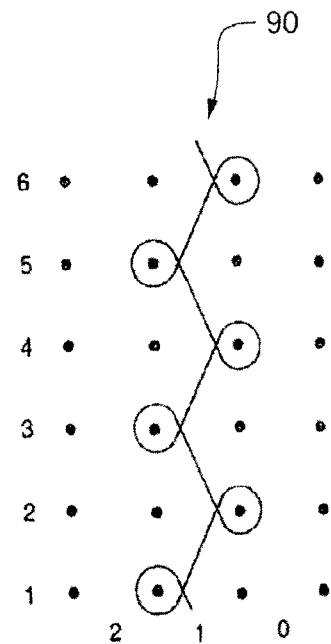

FIG. 137 is a schematic representation of the basic warp knitted fabric of FIG. 136.

Figure 138:
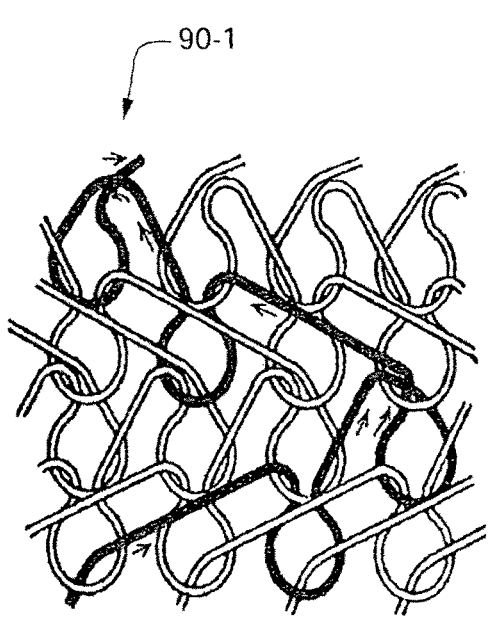

FIG. 138 illustrates a basic warp knitted fabric according to an example of the present technology.

Figure 139:
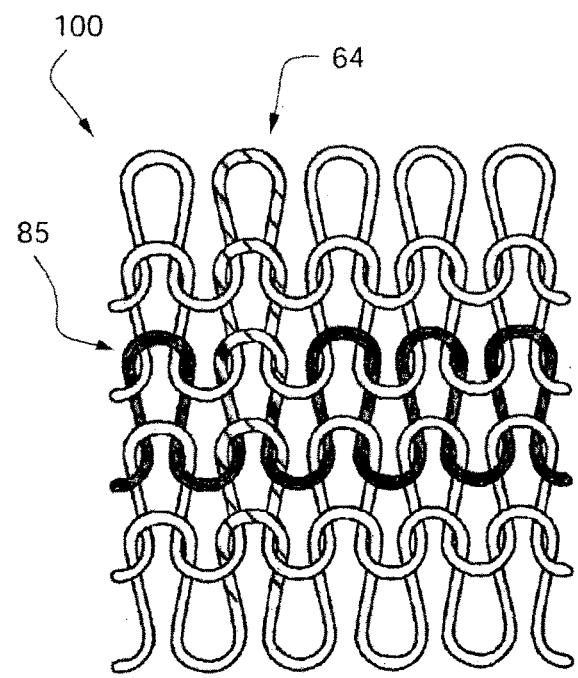

FIG. 139 illustrates a basic weft knitted fabric according to an example of the present technology.

Figure 140:
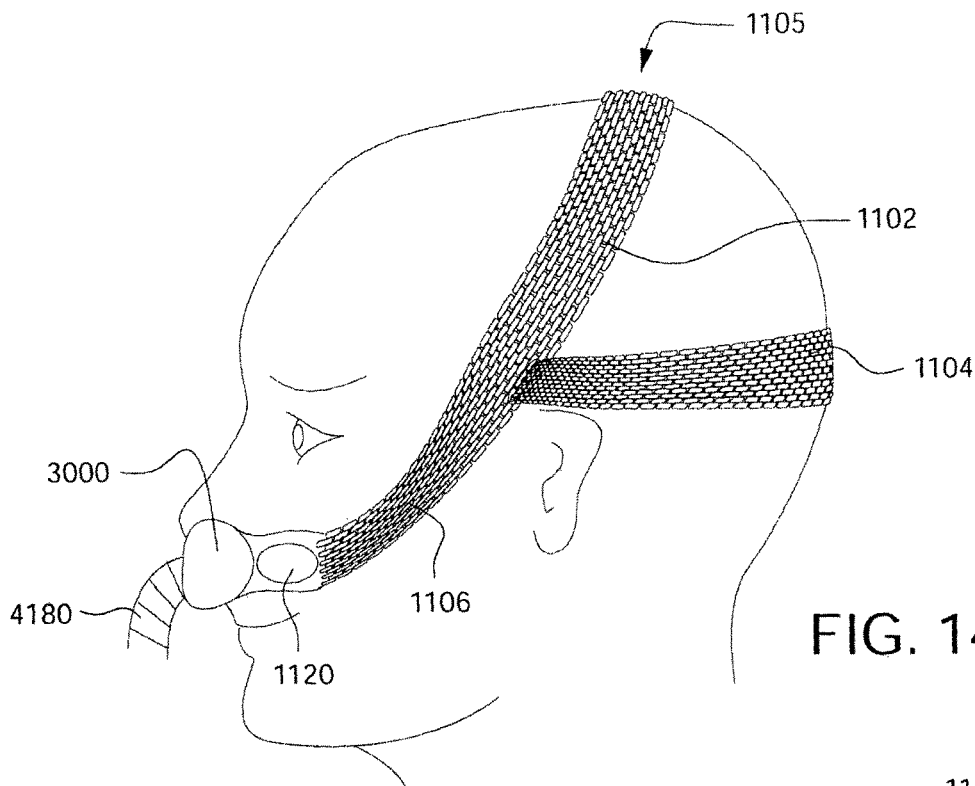

FIG. 140 is a side view of a positioning and stabilising structure positioned on a patient's head in accordance with an example of the present technology.

Figure 141:
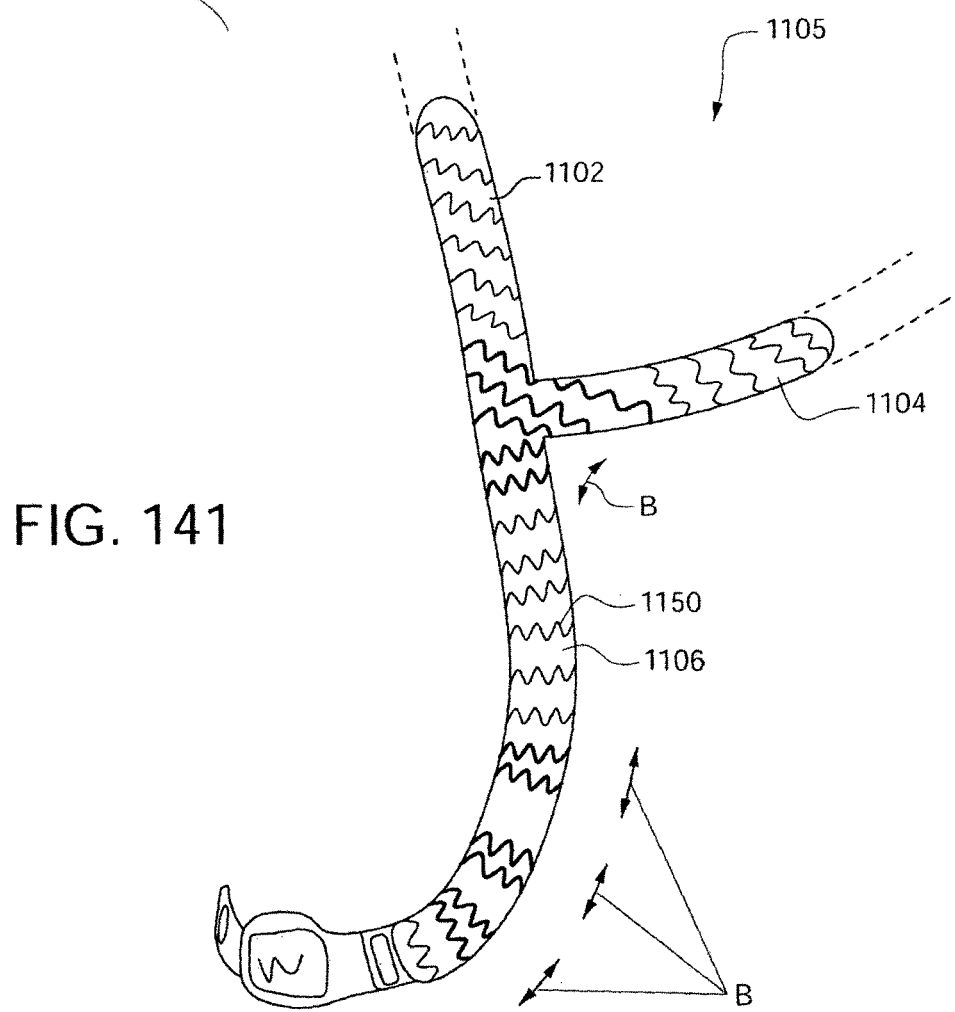

FIG. 141 shows the changing direction of the course or grain of the positioning and stabilising structure of FIG. 140 according to an example of the present technology.

Figure 142:
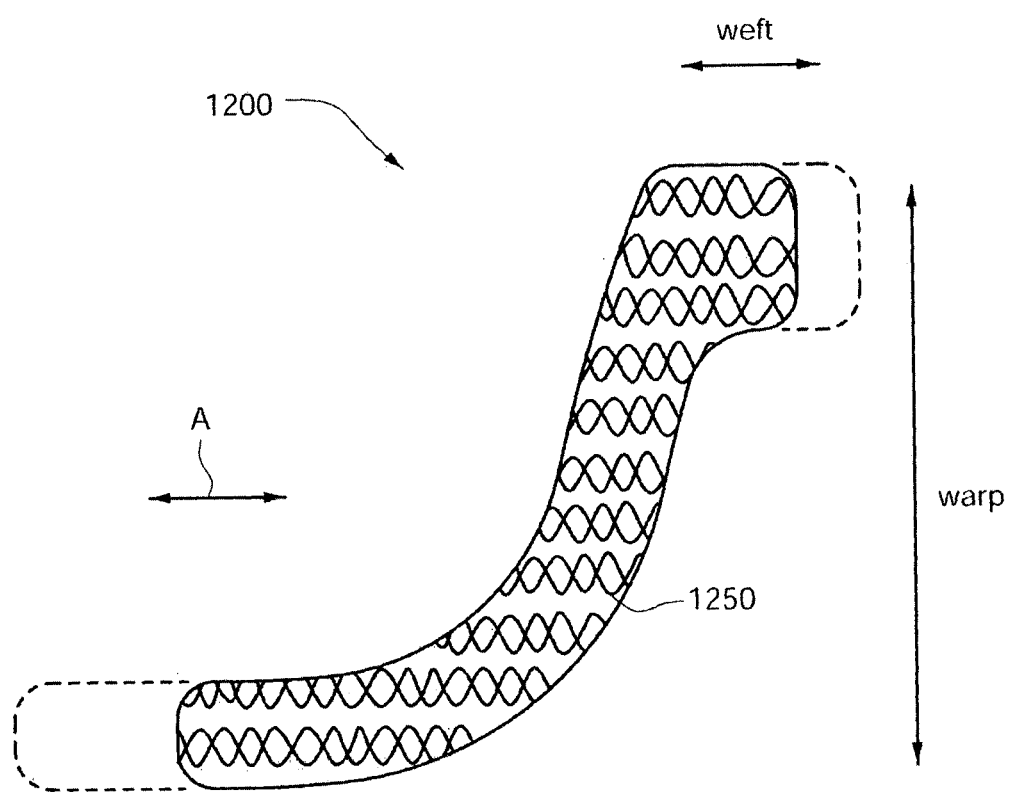

FIG. 142 illustrates an increased stretch in the direction of the course of a knitted positioning and stabilising structure according to an example of the present technology.

Figure 143:
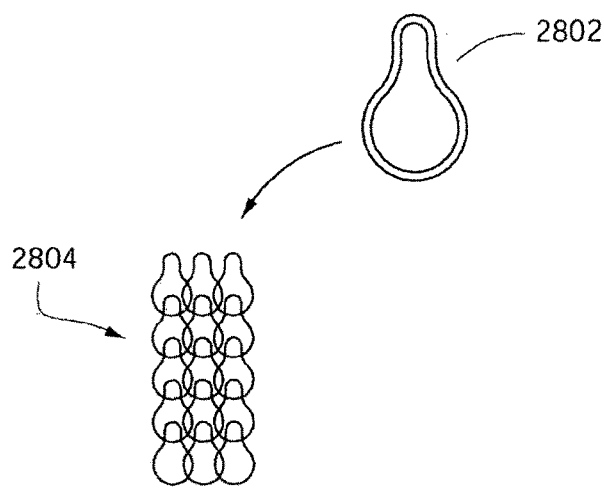
Figure 144:
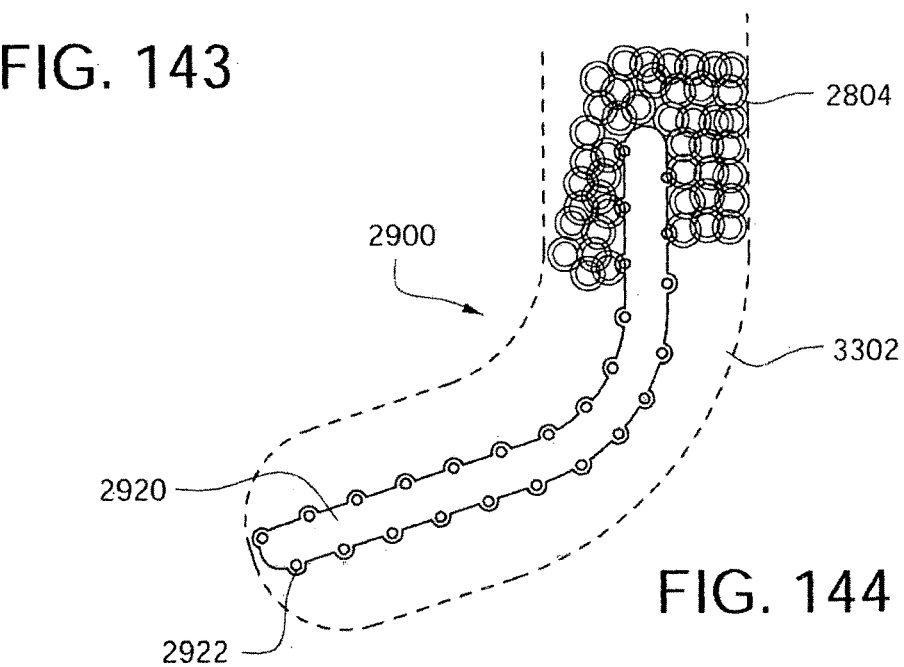

FIG. 143 shows 3D printed links used to form a positioning and stabilising structure according to an example of the present technology FIG. 144 shows a 3D printed positioning and stabilising structure piece including a rigidiser according to an example of the present technology.

Figure 145:
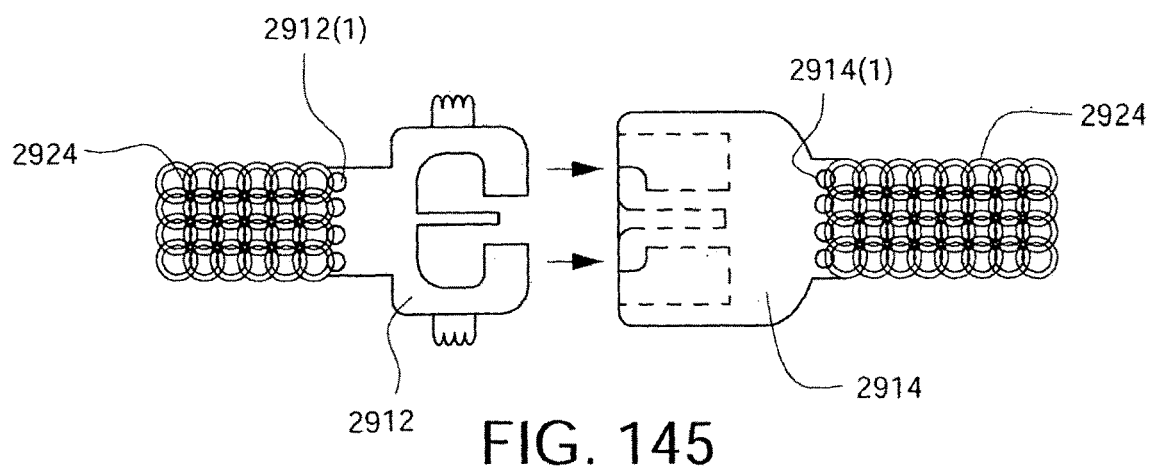

FIG. 145 shows a 3D printed positioning and stabilising structure straps and clips according to an example of the present technology.

Figure 146:
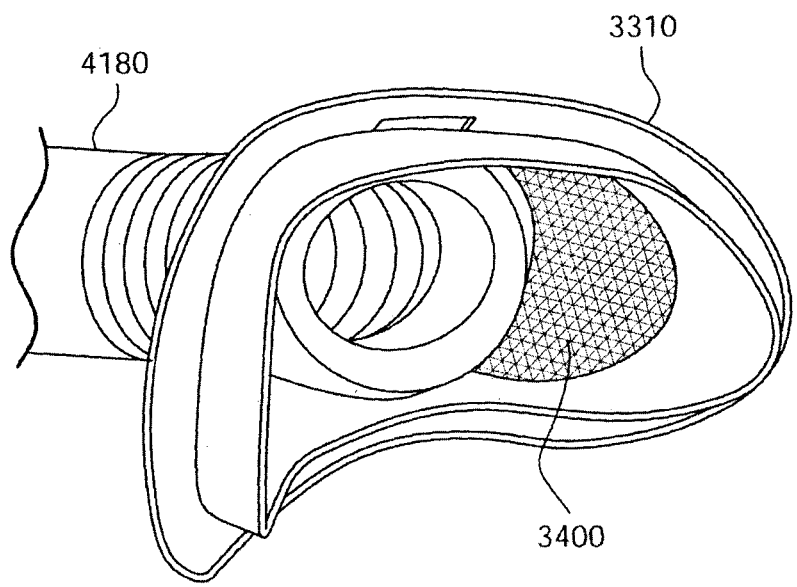

FIG. 146 shows a rear perspective view of a vent for a patient interface in accordance with one form of the present technology.

Figure 147:
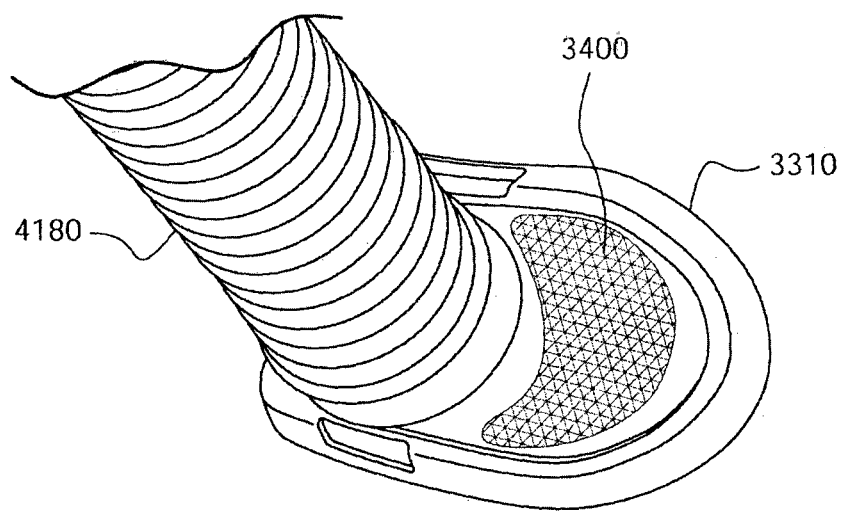

FIG. 147 shows a front perspective view of a vent for a patient interface in accordance with one form of the present technology.

Figure 148:
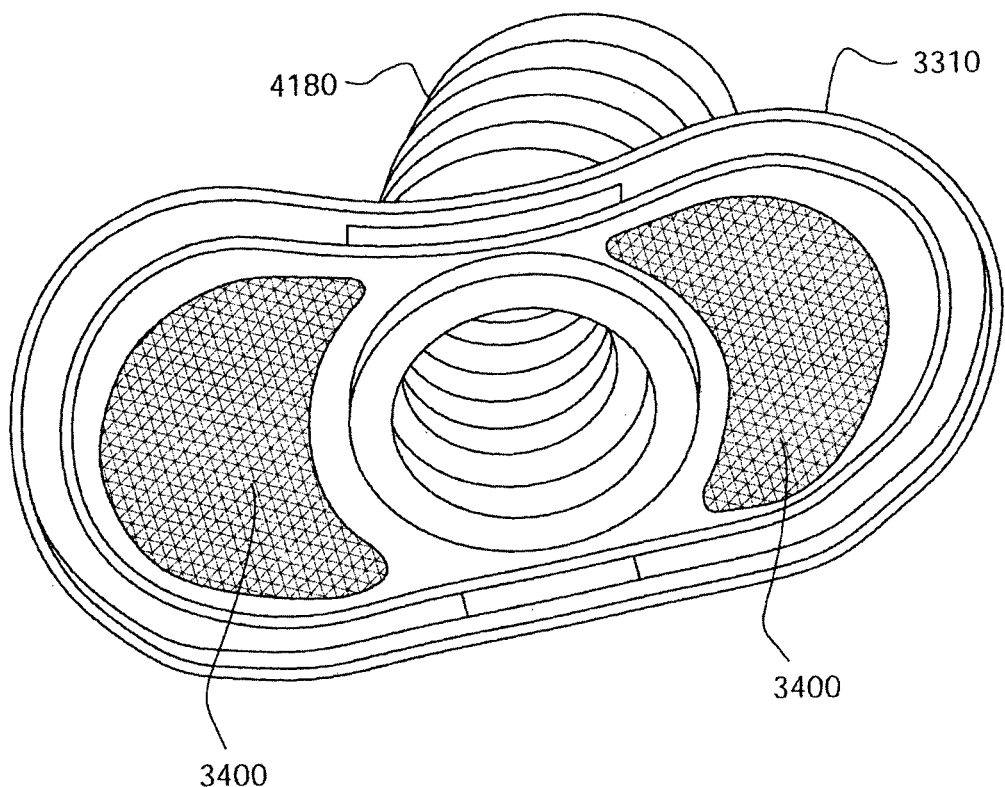

FIG. 148 shows a rear perspective view of a vent for a patient interface in accordance with one form of the present technology.

Figure 149:
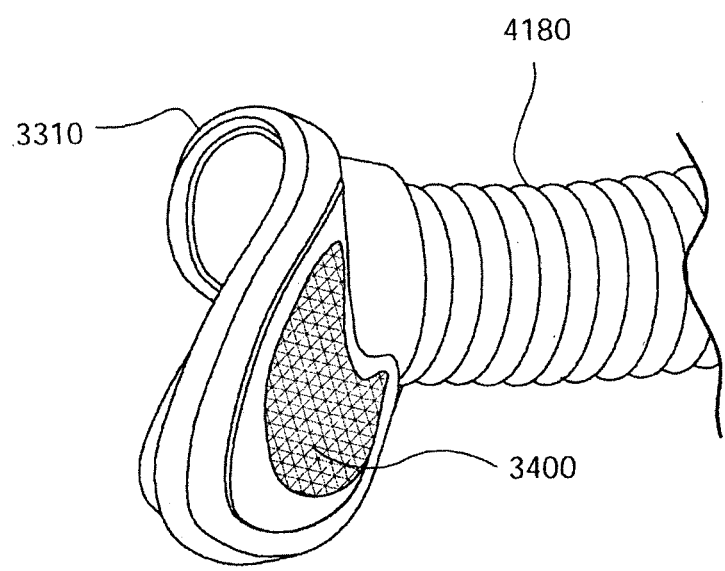

FIG. 149 shows a side perspective view of a vent for a patient interface in accordance with one form of the present technology.

Figure 150:
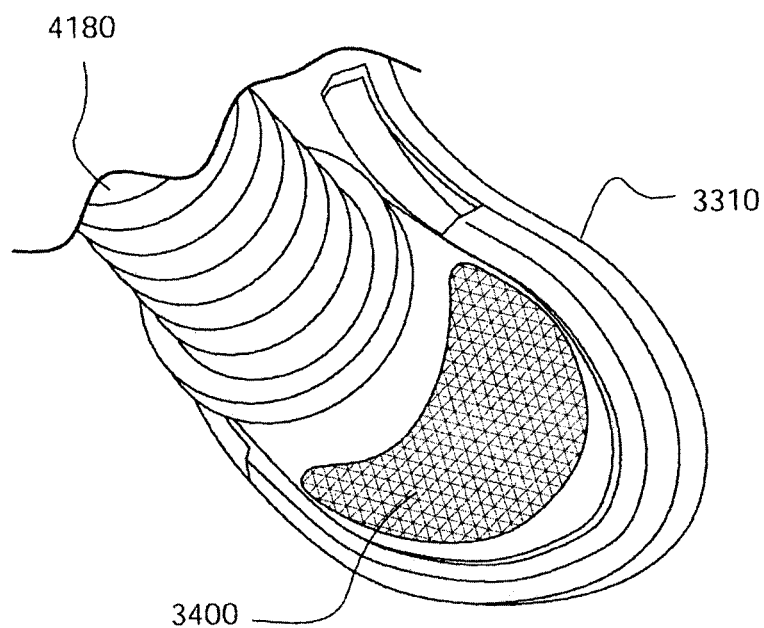

FIG. 150 shows a side perspective view of a vent for a patient interface in accordance with one form of the present technology.

Figure 151:
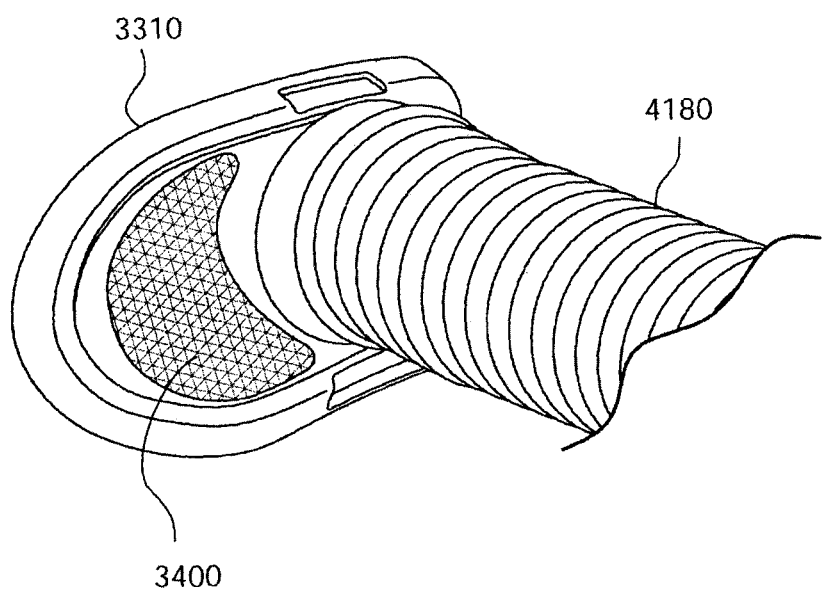

FIG. 151 shows a side perspective view of a vent for a patient interface in accordance with one form of the present technology.

Figure 152:
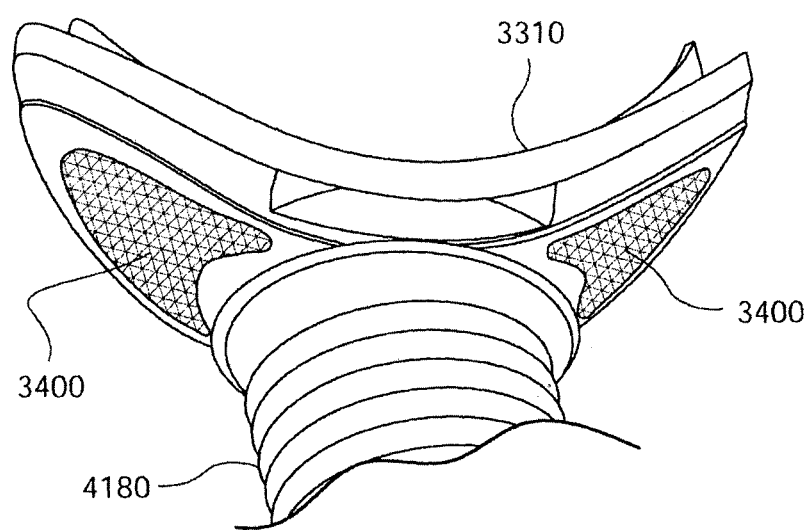

FIG. 152 shows a top perspective view of a vent for a patient interface in accordance with one form of the present technology.

Figure 153:
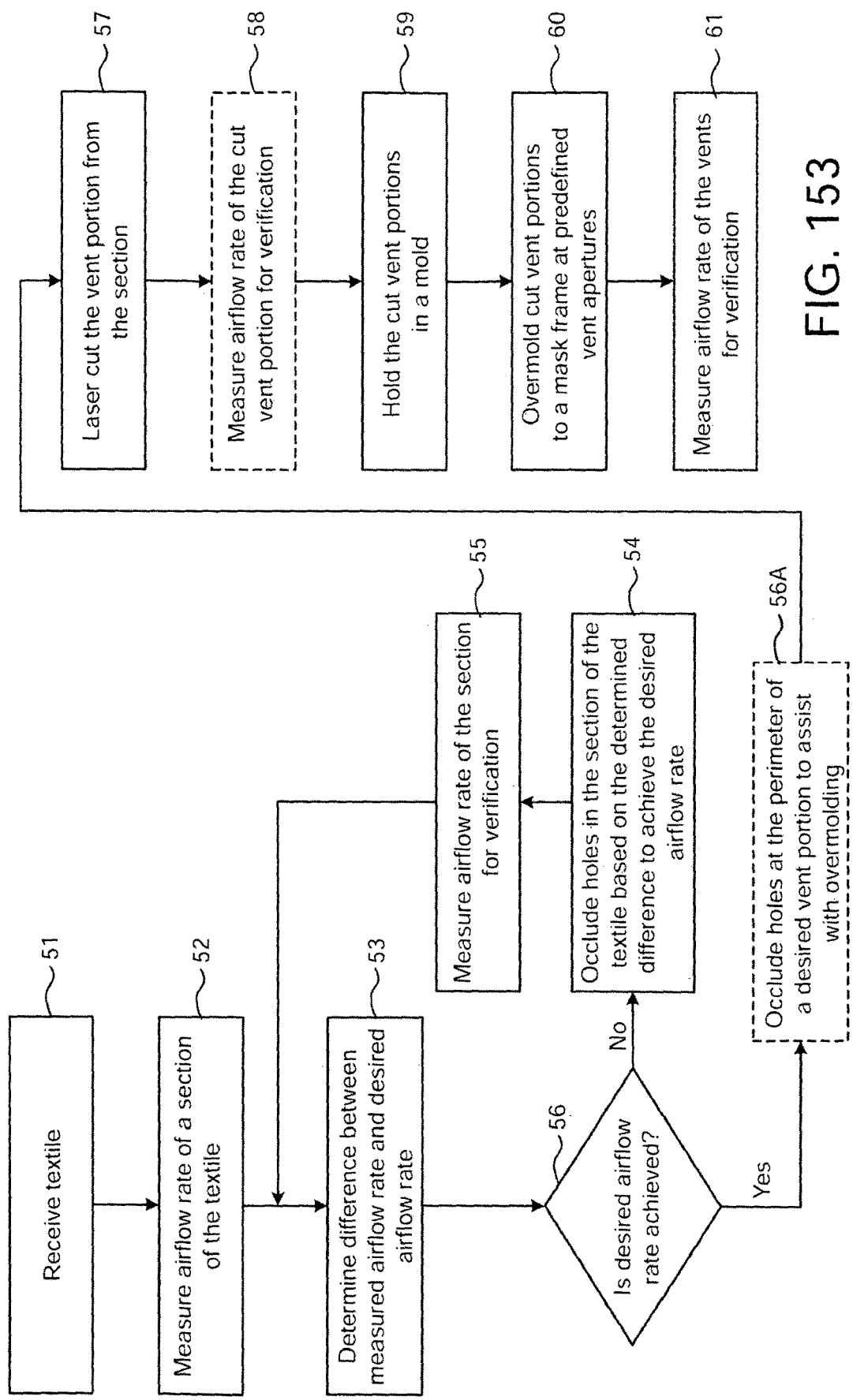

FIG. 153 is a process flow diagram depicting a method for manufacturing a patient interface for the treatment of respiratory disorders in accordance with an example of the present technology.

Figure 154:
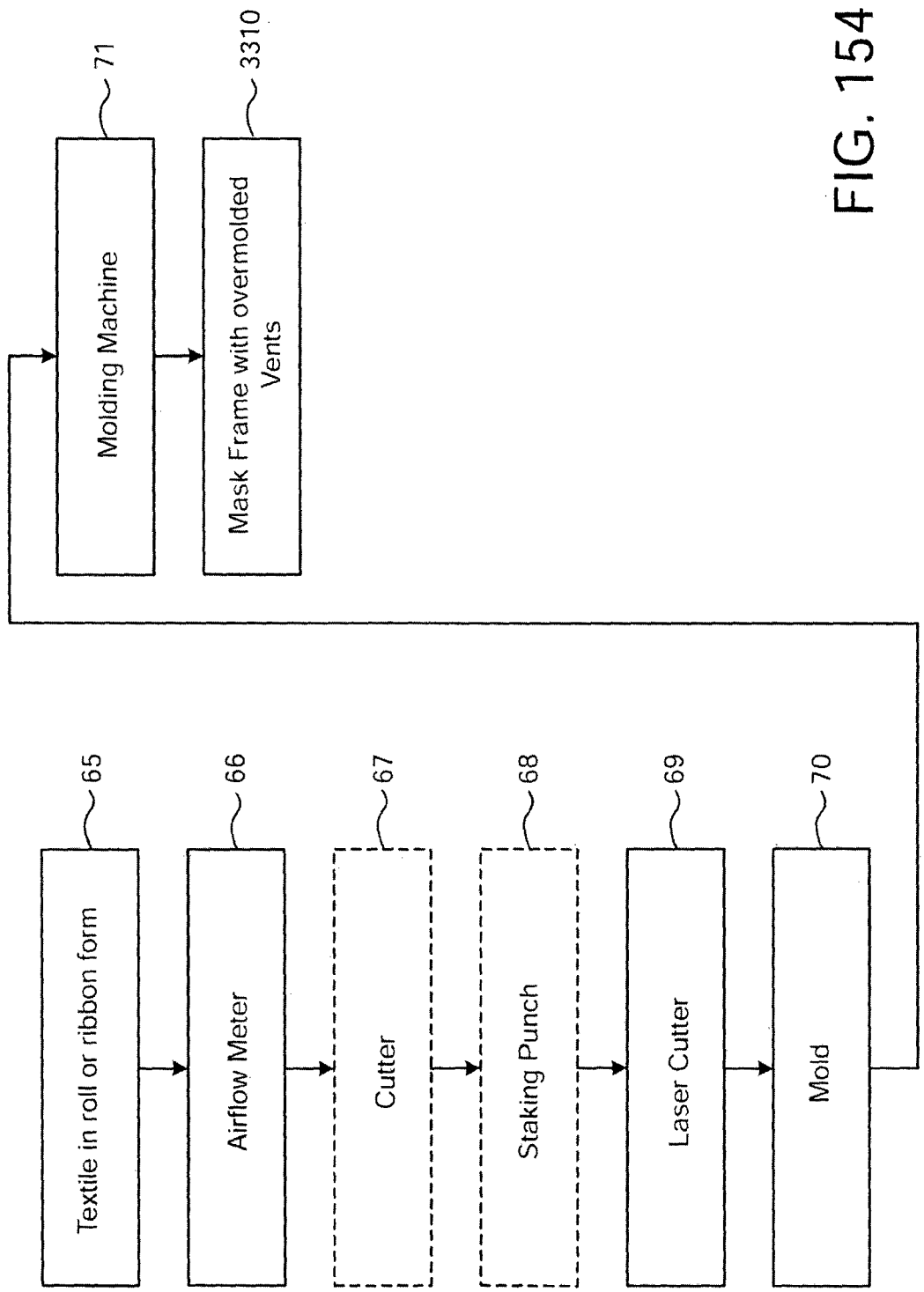

FIG. 154 is a system diagram generally depicting equipment used for carrying out the method of FIG. 153.

Figure 155:
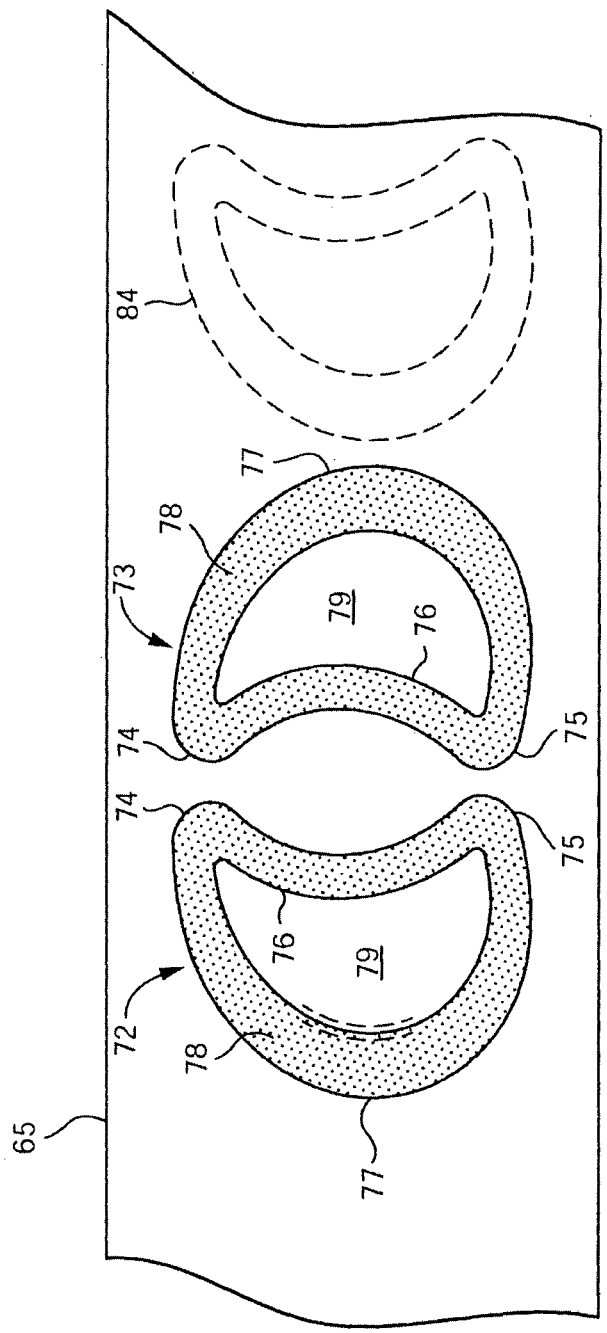

FIG. 155 is a top view of a textile depicting vent portions after heat staking in accordance with an example of the present technology.

Figure 156:
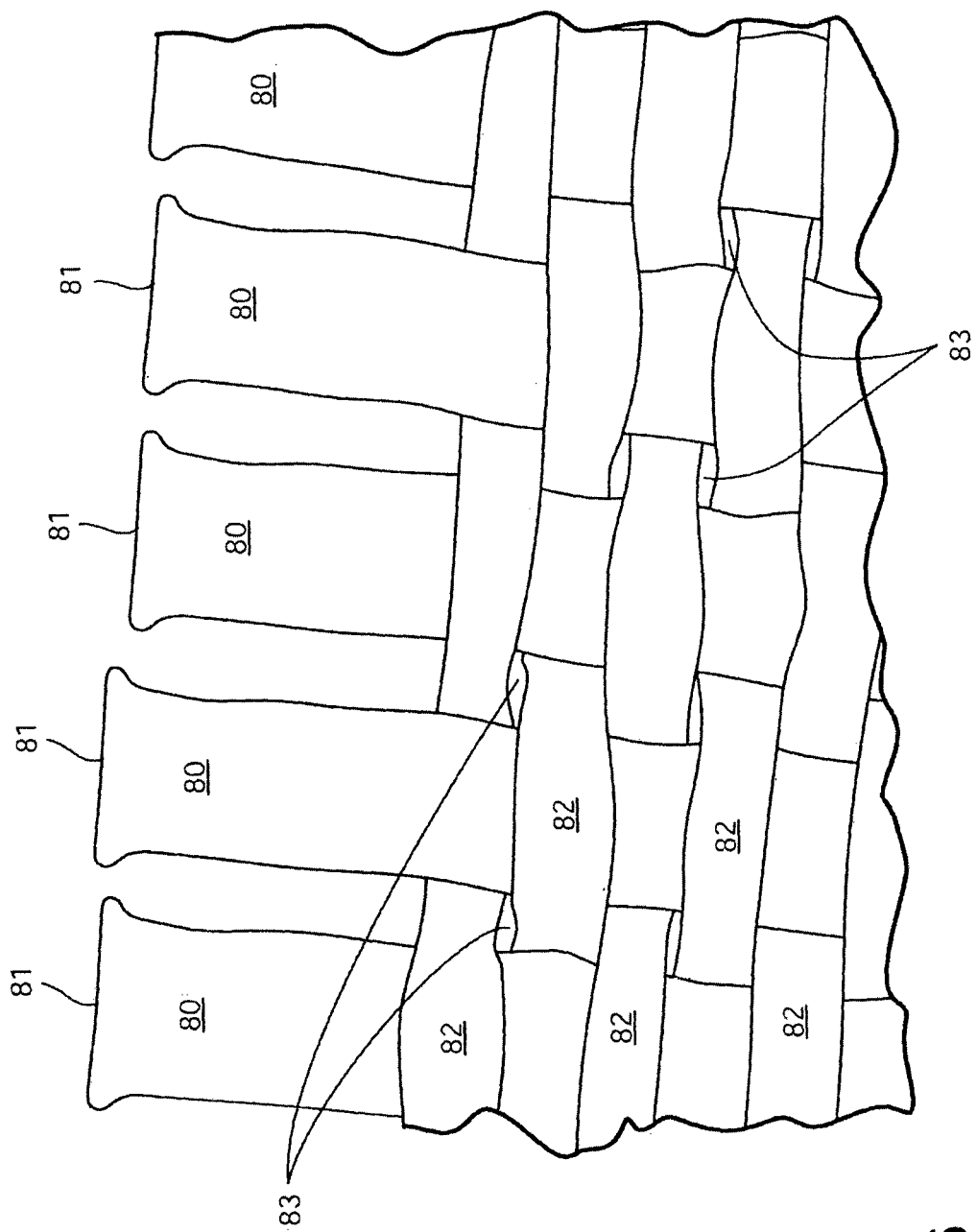

FIG. 156 is a magnified top view of a peripheral edge of a vent portion before heat staking in accordance with an example of the present technology.

Figure 157:
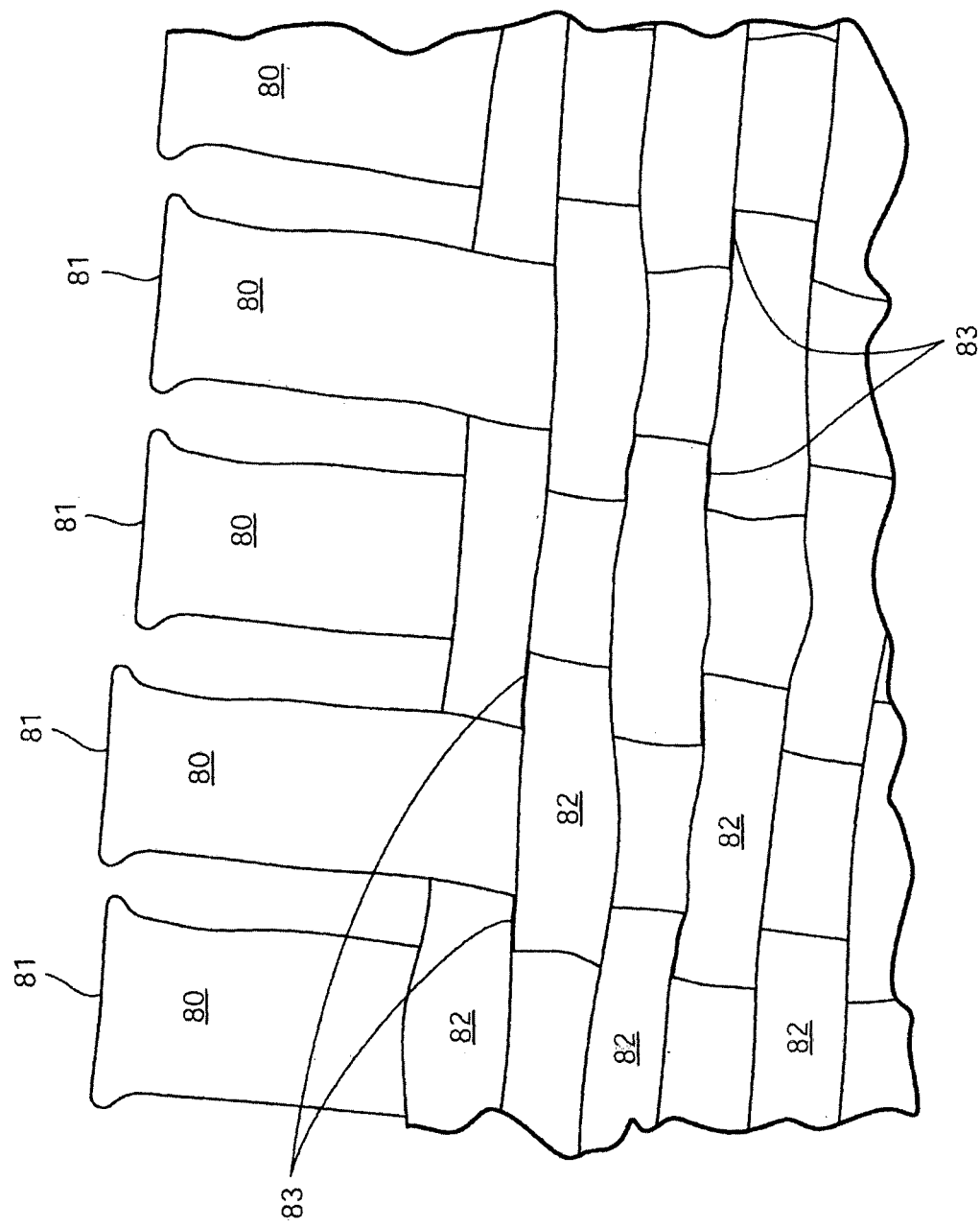

FIG. 157 is a magnified top view of a peripheral edge of a vent portion after heat staking in accordance with an example of the present technology.

Figure 158:
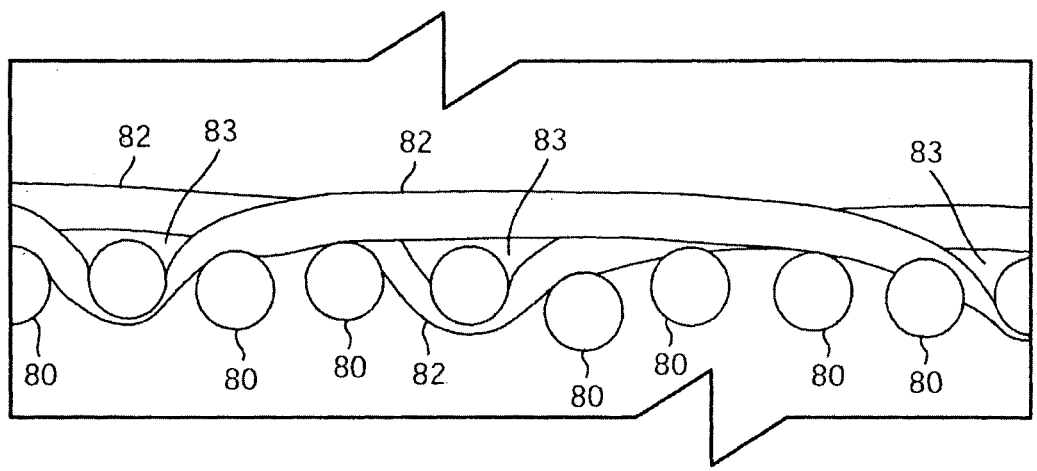

FIG. 158 is a magnified sectional side view of a peripheral edge of a vent portion before heat staking in accordance with an example of the present technology.

Figure 159:
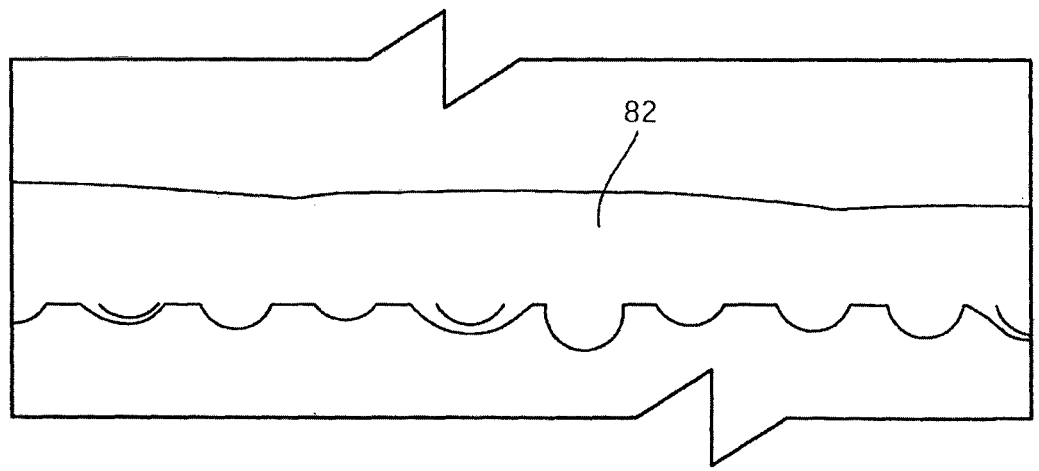

FIG. 159 is a magnified sectional side view of a peripheral edge of a vent portion after heat staking in accordance with an example of the present technology.

Figure 160:
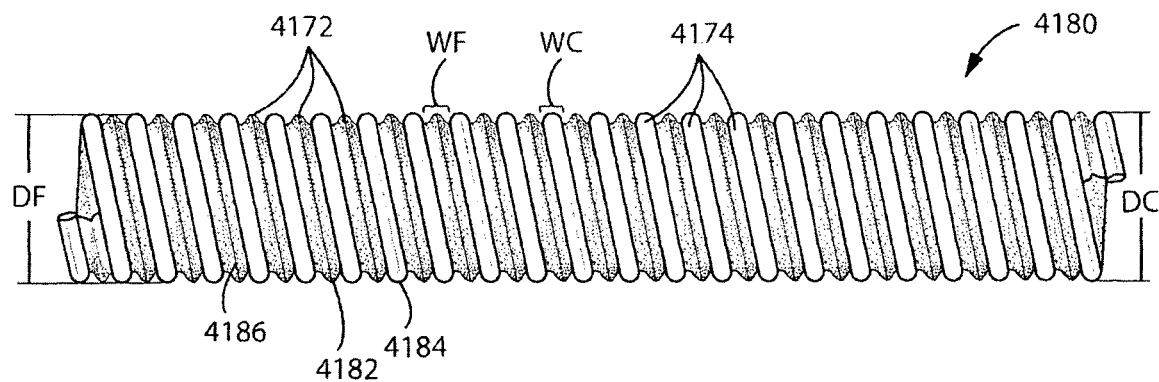

FIG. 160 shows a short tube in a neutral state according to an example of the present technology.

Figure 161:
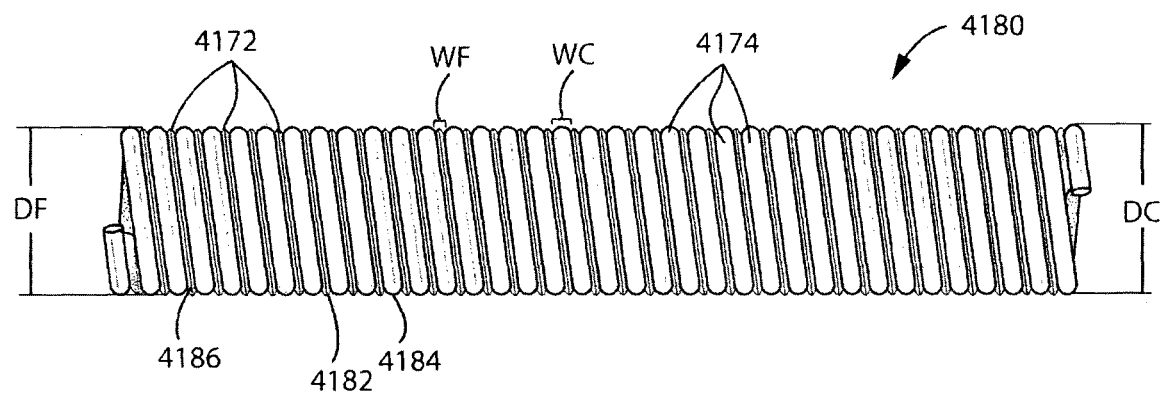

FIG. 161 shows a side view of a short tube in a compressed state according to an example of the present technology.

Figure 162:
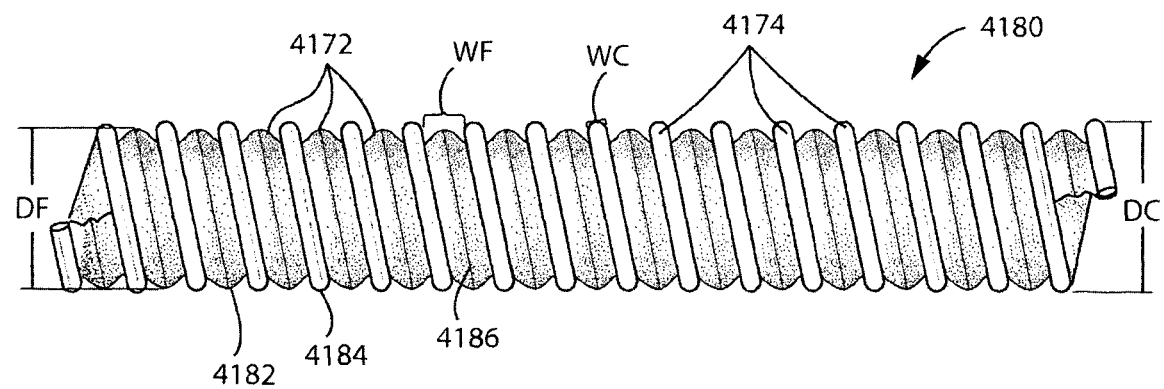

FIG. 162 shows a side view of a short tube in an elongated state according to an example of the present technology.

Figure 163:
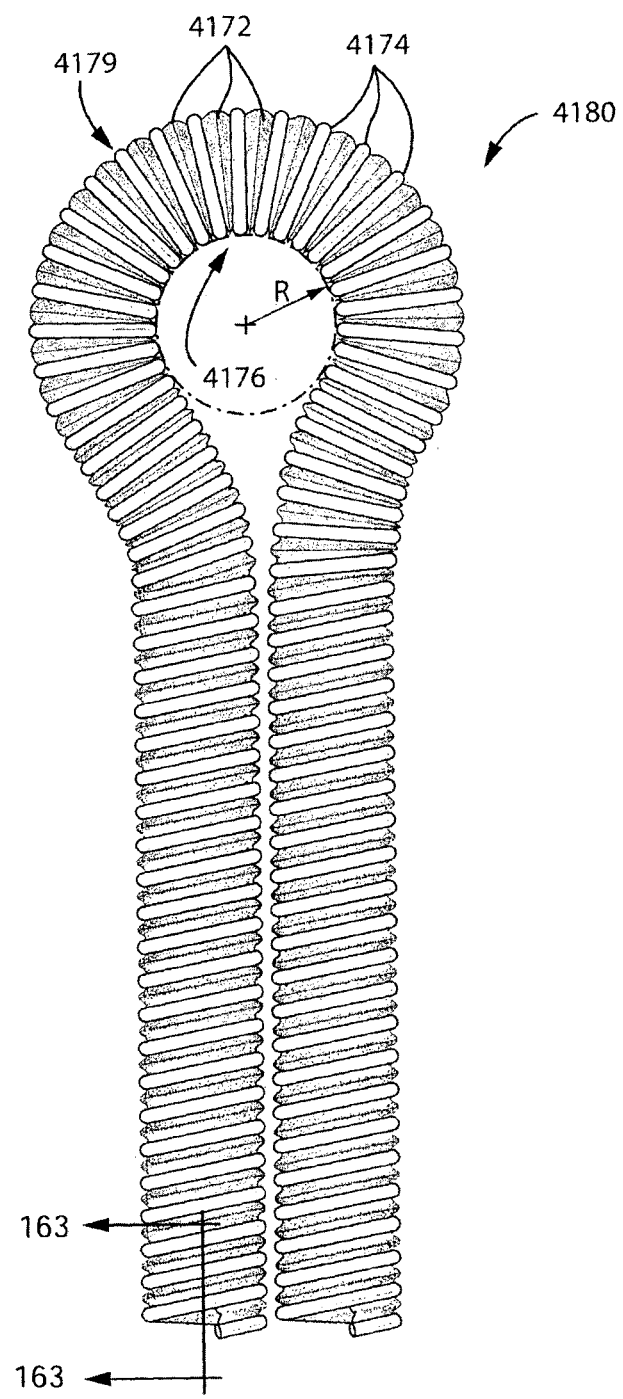

FIG. 163 shows a side view of a short tube in a curved state according to an example of the present technology.

Figure 164:
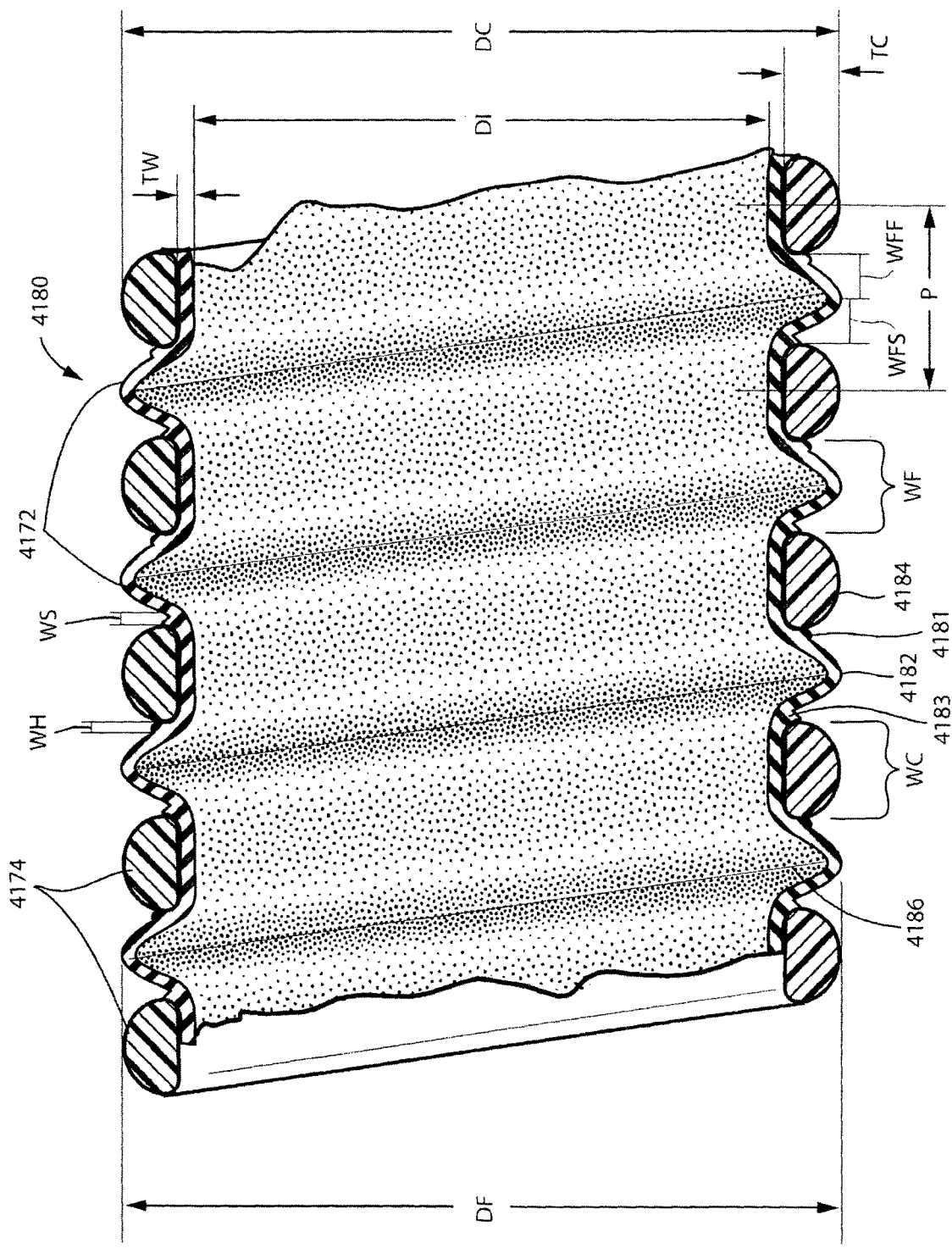

FIG. 164 shows a cross-sectional view of a short tube taken along line 163-163 as shown in FIG. 163 according to an example of the present technology.

Figure 165:
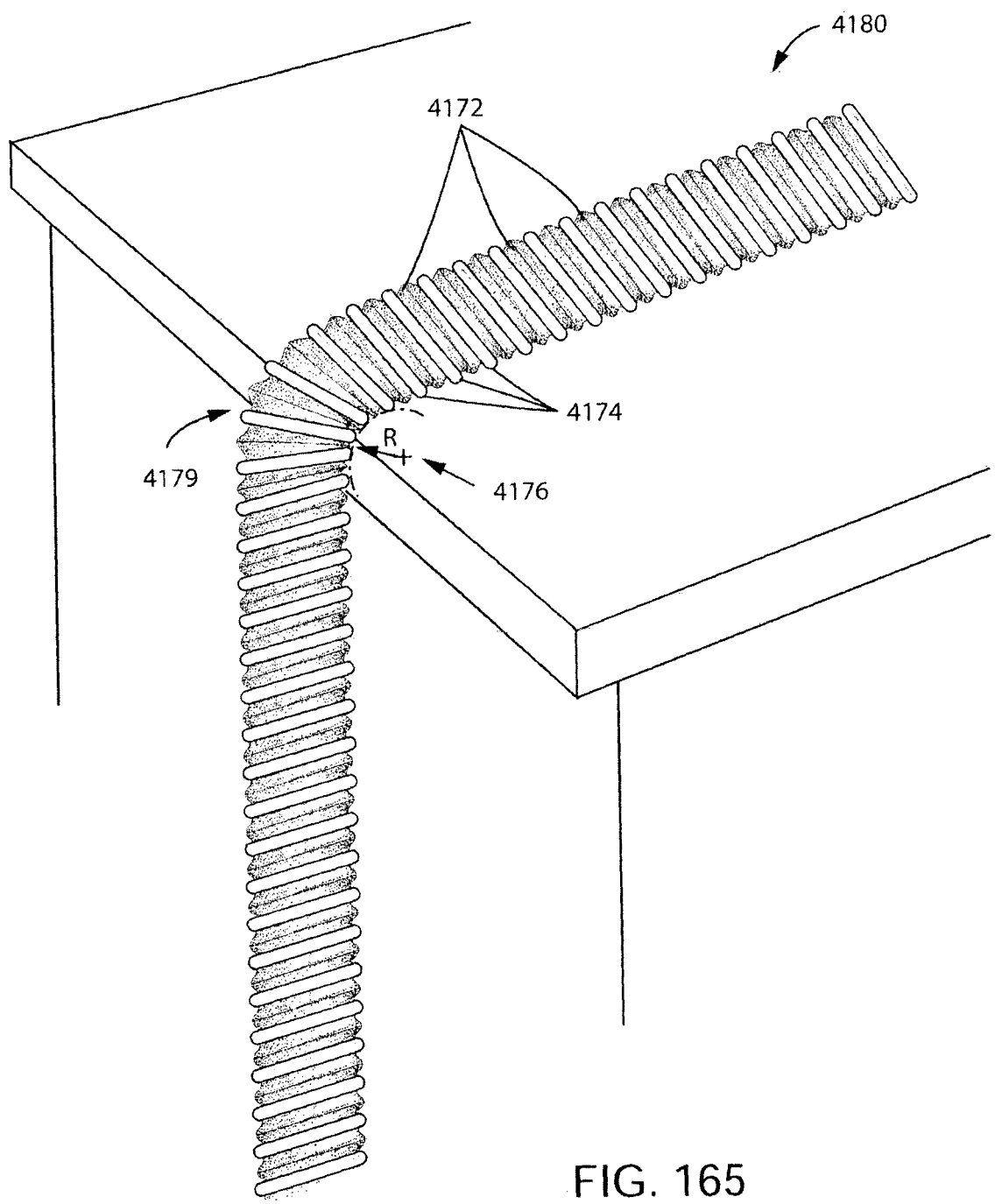

FIG. 165 shows a perspective view of a short tube in a curved and elongated state according to an example of the present technology.

Figure 166:
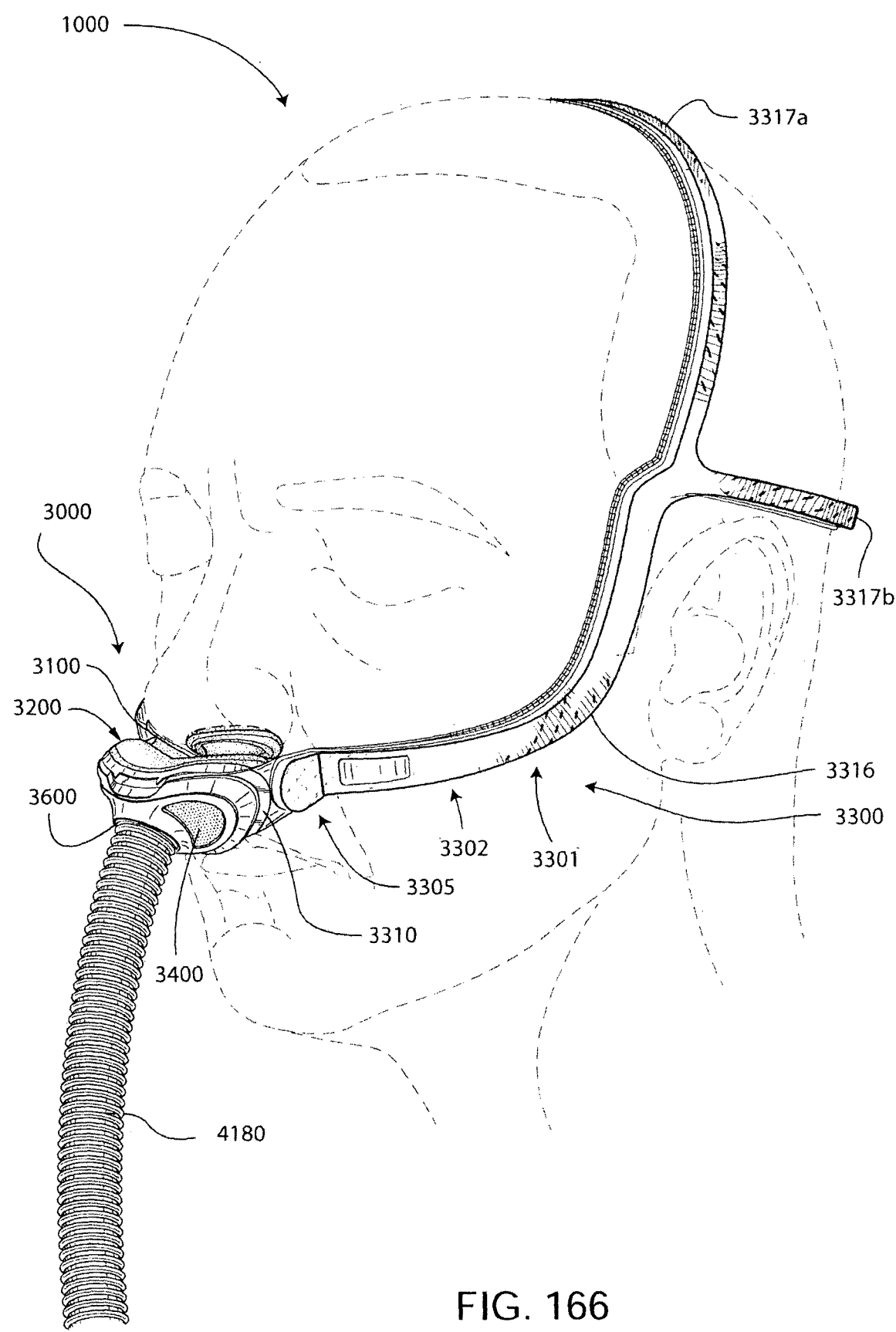

FIG. 166 is a perspective view showing a patient interface system in accordance with one form of the present technology in use on a patient.

Figure 167:
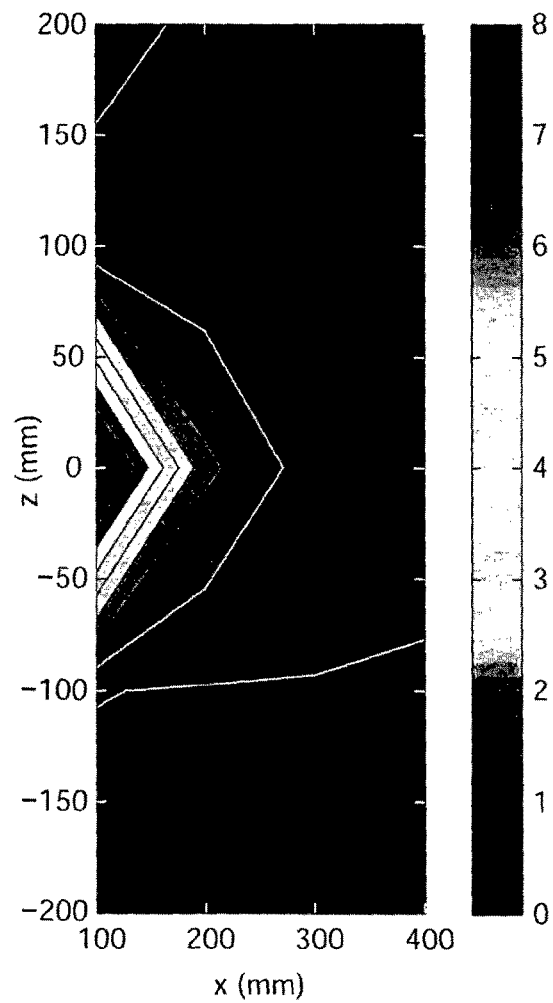

FIG. 167 is a chart depicting vertical plane air speed in m/s along the x and z axes from a vent of a SWIFT FX™ nasal pillows mask by ResMed Limited.

Figure 168:
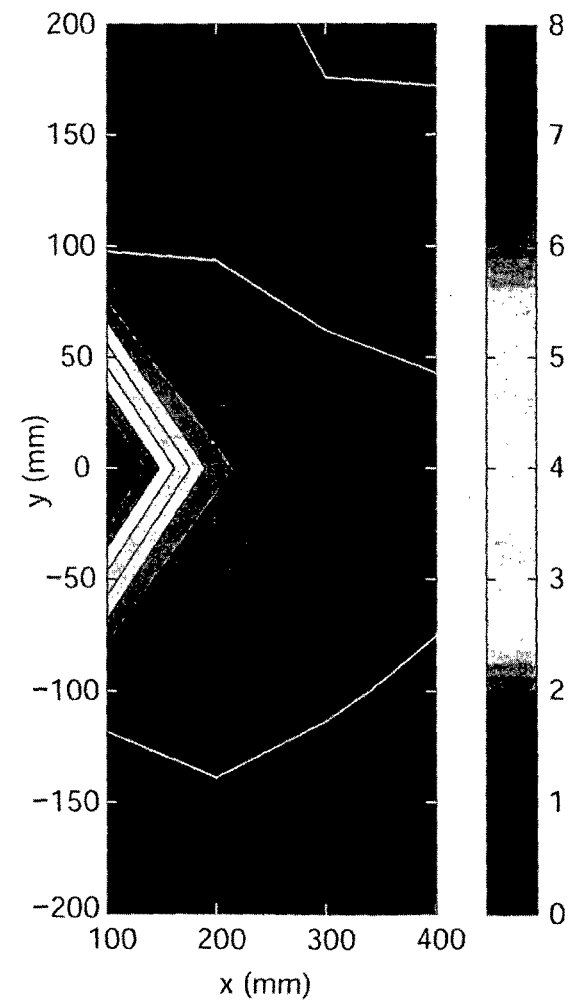

FIG. 168 is a chart depicting horizontal plane air speed in m/s along the x and y axes from a vent of a SWIFT FX™ nasal pillows mask by ResMed Limited.

Figure 169:
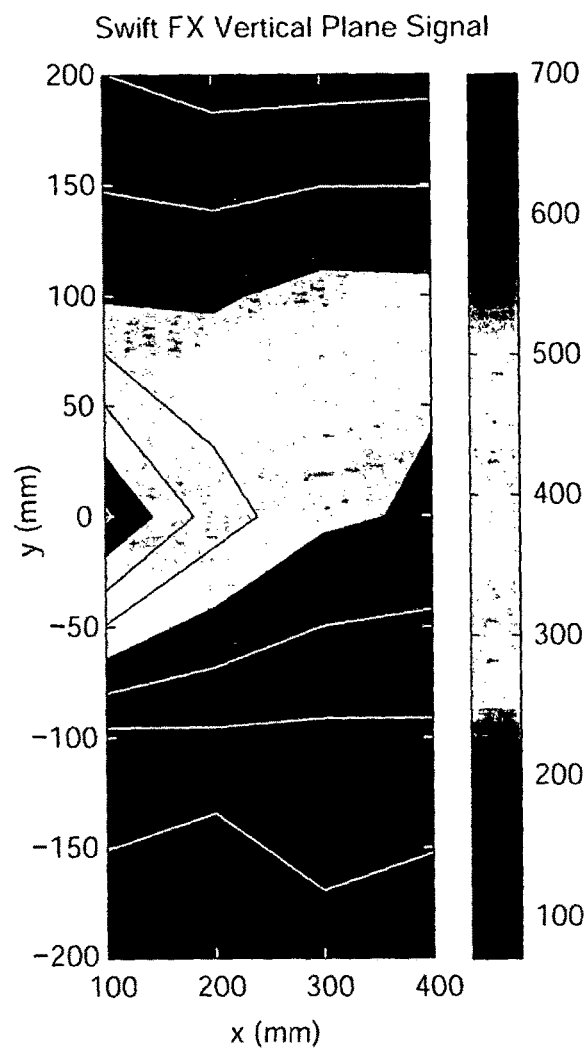

FIG. 169 is a chart depicting vertical plane signal along the x and y axes from a vent of a SWIFT FX™ nasal pillows mask by ResMed Limited.

Figure 170:
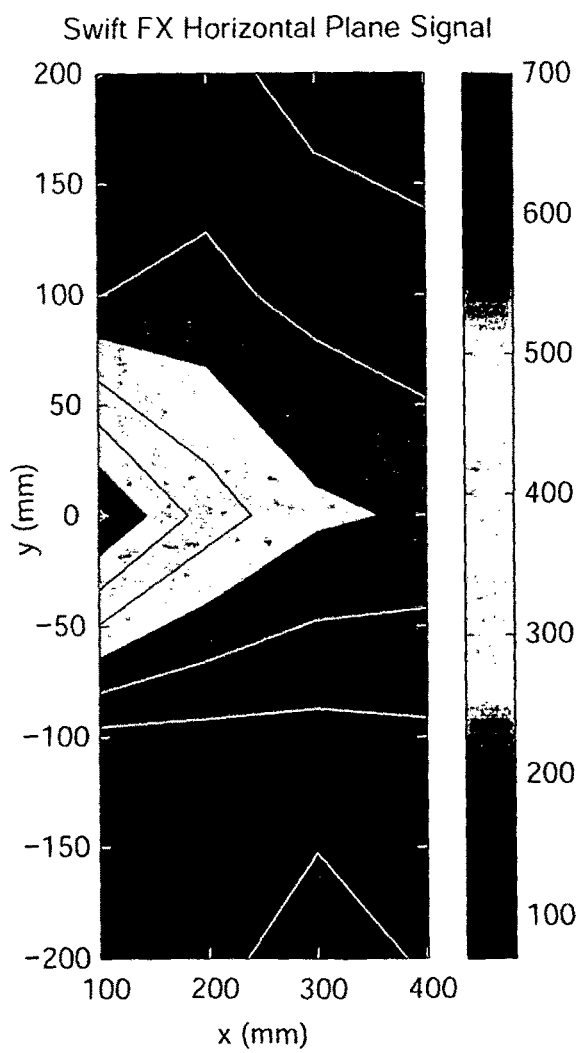

FIG. 170 is a chart depicting horizontal plane signal along the x and y axes from a vent of a SWIFT FX™ nasal pillows mask by ResMed Limited.

Figure 171:
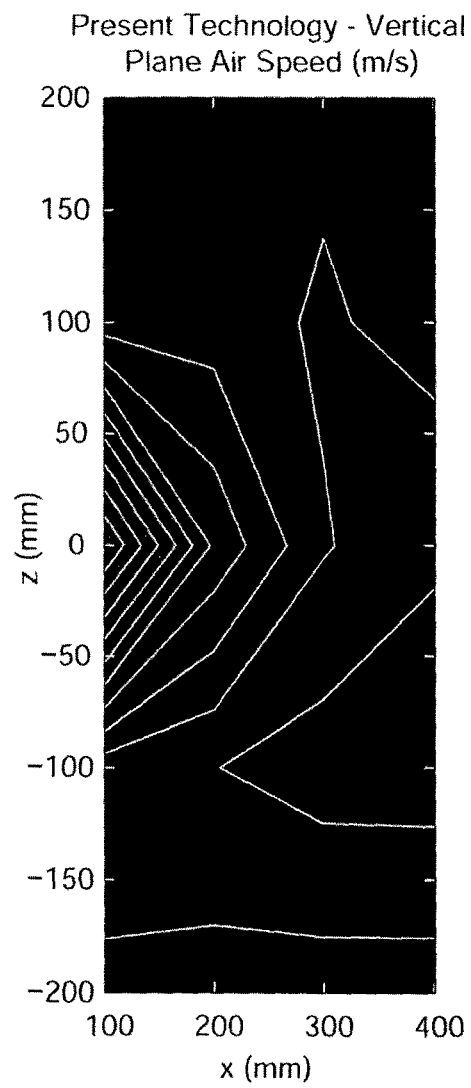

FIG. 171 is a chart depicting vertical plane air speed in m/s along the x and z axes from a vent of a patient interface system in accordance with one form of the present technology.

Figure 172:
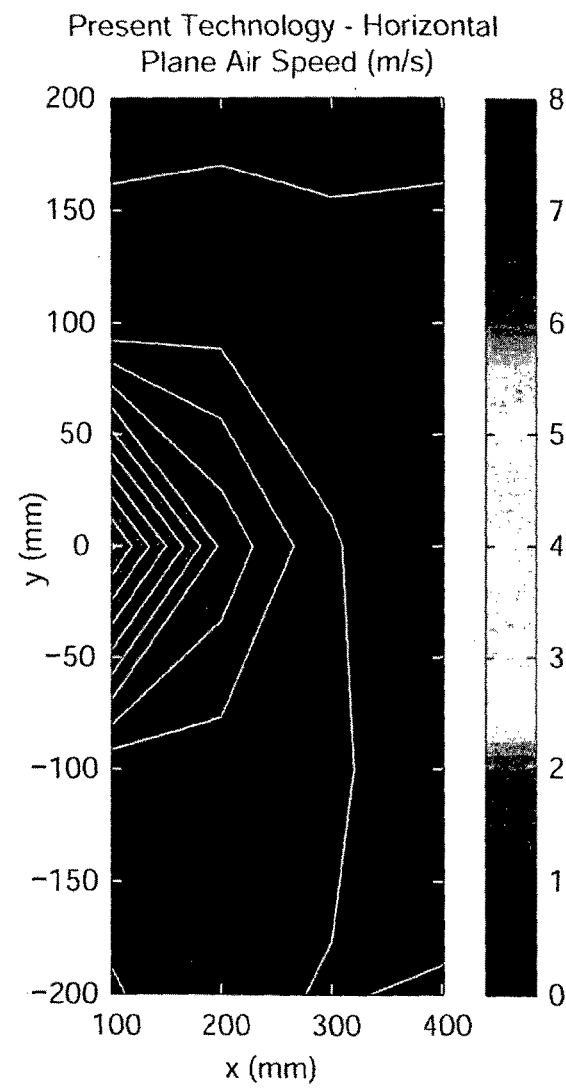

FIG. 172 is a chart depicting horizontal plane air speed in m/s along the x and y axes from a vent of a patient interface system in accordance with one form of the present technology.

Figure 173:
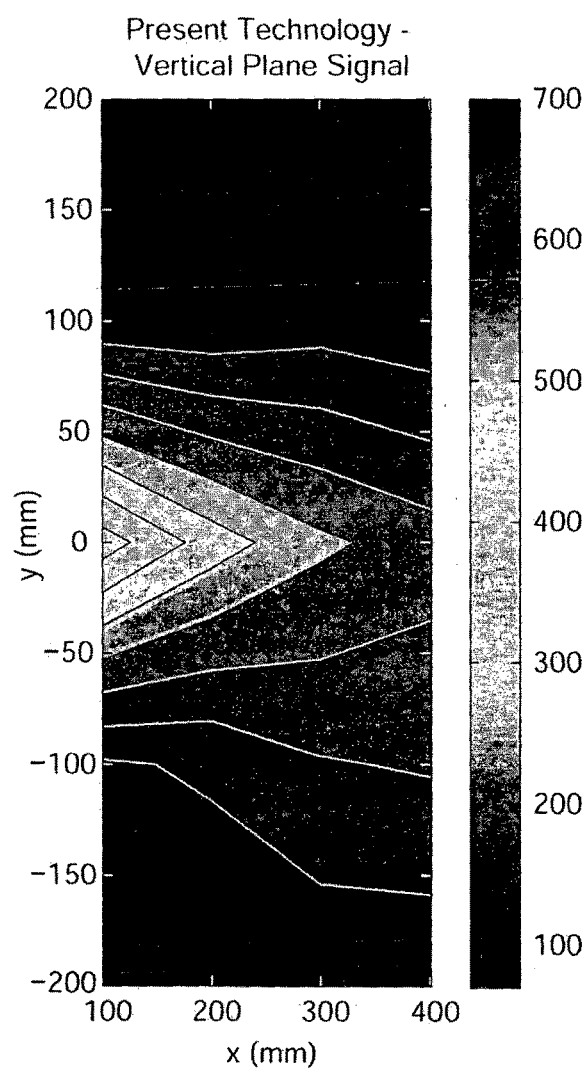

FIG. 173 is a chart depicting vertical plane signal along the x and y axes from a vent of a patient interface system in accordance with one form of the present technology.

Figure 174:
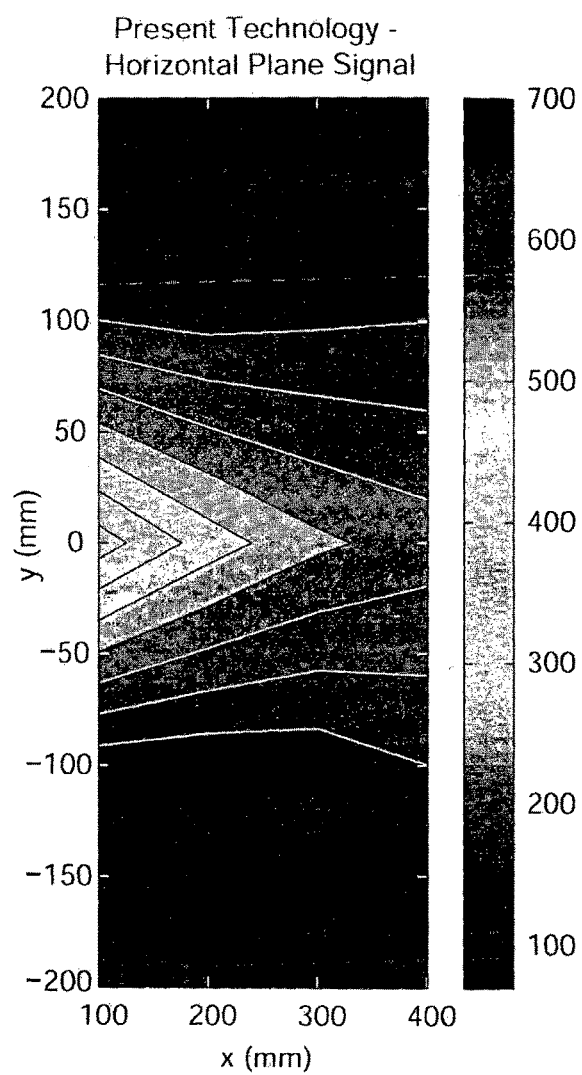

FIG. 174 is a chart depicting horizontal plane signal along the x and y axes from a vent of a patient interface system in accordance with one form of the present technology.

Figure 175:
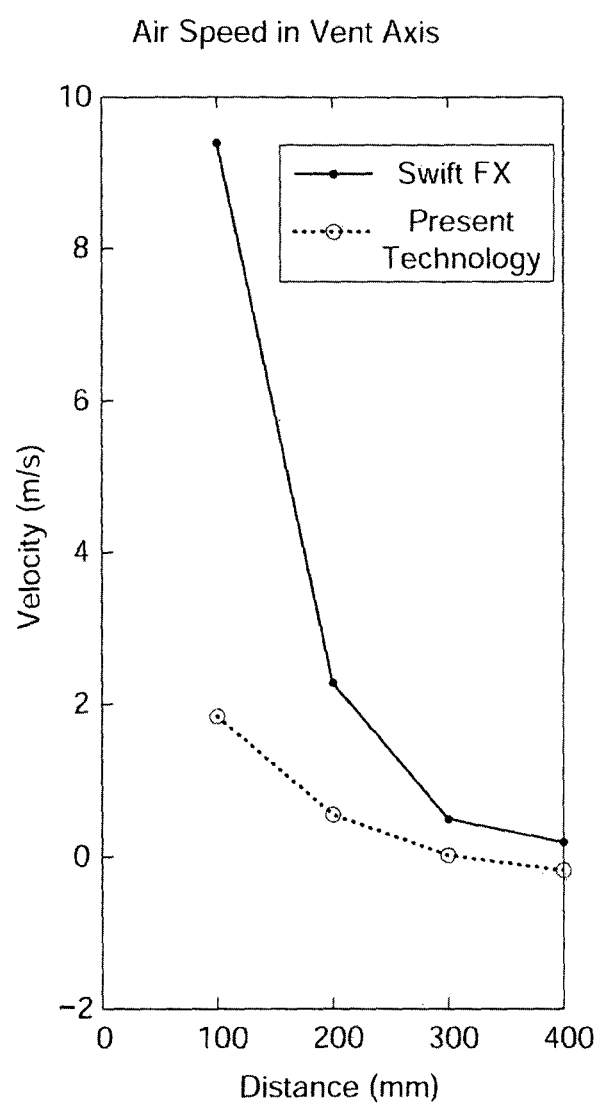

FIG. 175 is a chart comparing velocity (in m/s) along a vent axis according to distance (in mm) from a vent of a SWIFT FX™ nasal pillows mask by ResMed Limited and a vent of a patient interface system in accordance with one form of the present technology.

Figure 176:
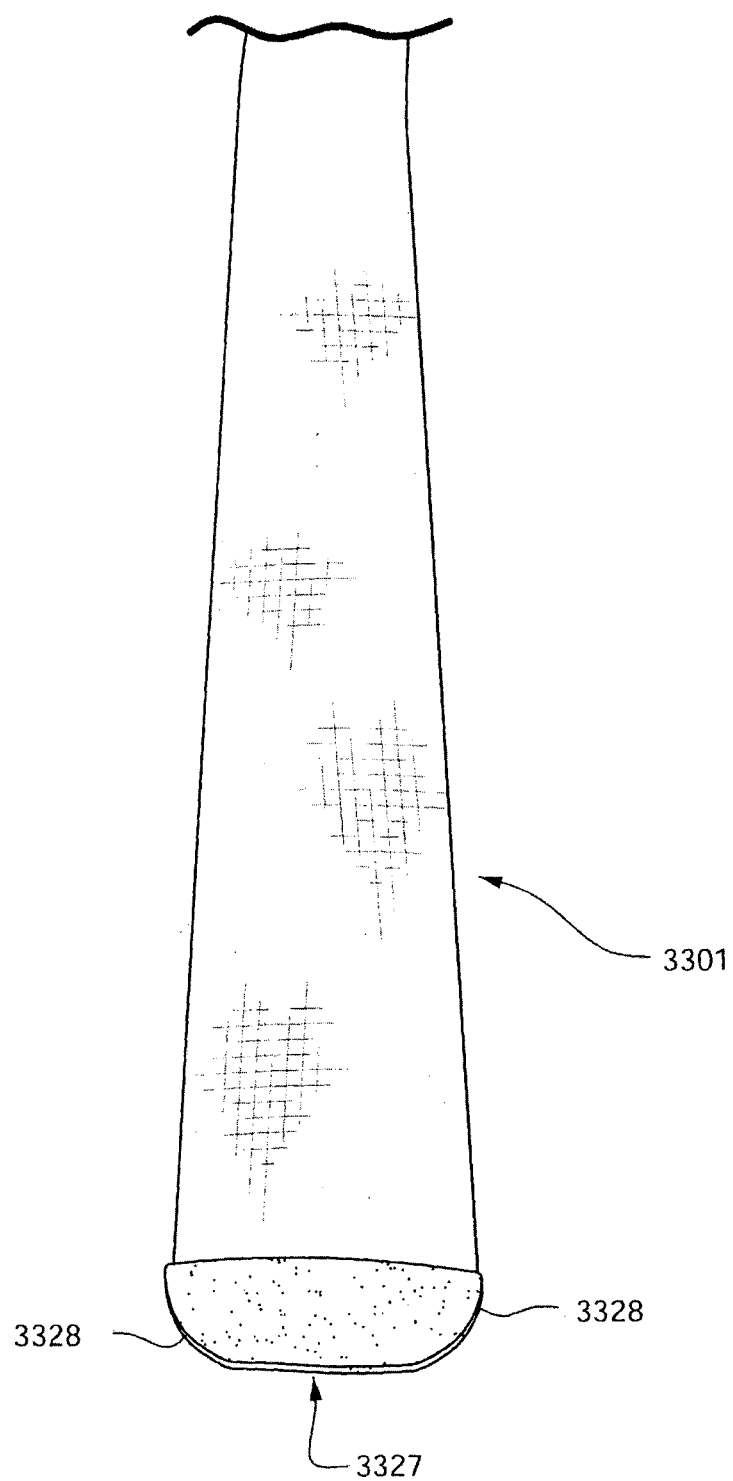
Figure 177:
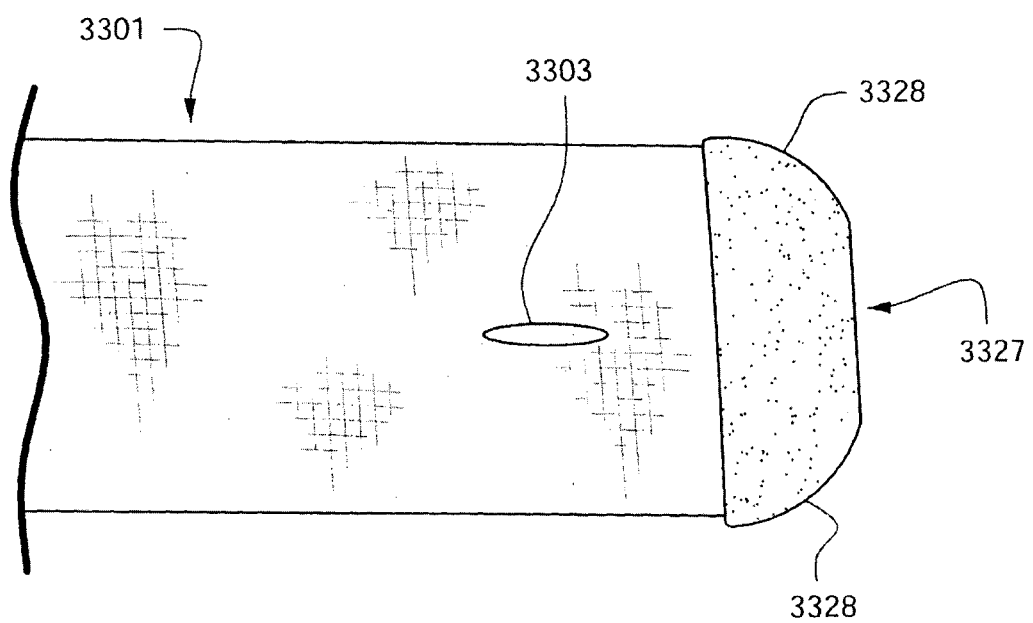

FIG. 176 is a bottom perspective view of a reinforcement portion folded over the end of a strap of a positioning and stabilising structure in accordance with one form of the present technology FIG. 177 is a top planar view of a reinforcement portion folded over the end of a strap of a positioning and stabilising structure in accordance with one form of the present technology.

Figure 178:
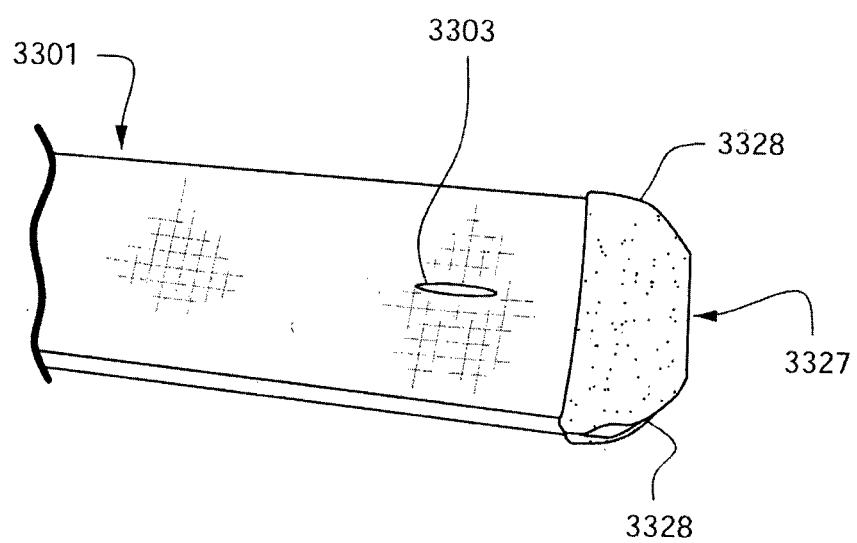

FIG. 178 is a side perspective view of a reinforcement portion folded over the end of a strap of a positioning and stabilising structure in accordance with one form of the present technology.

Figure 179:
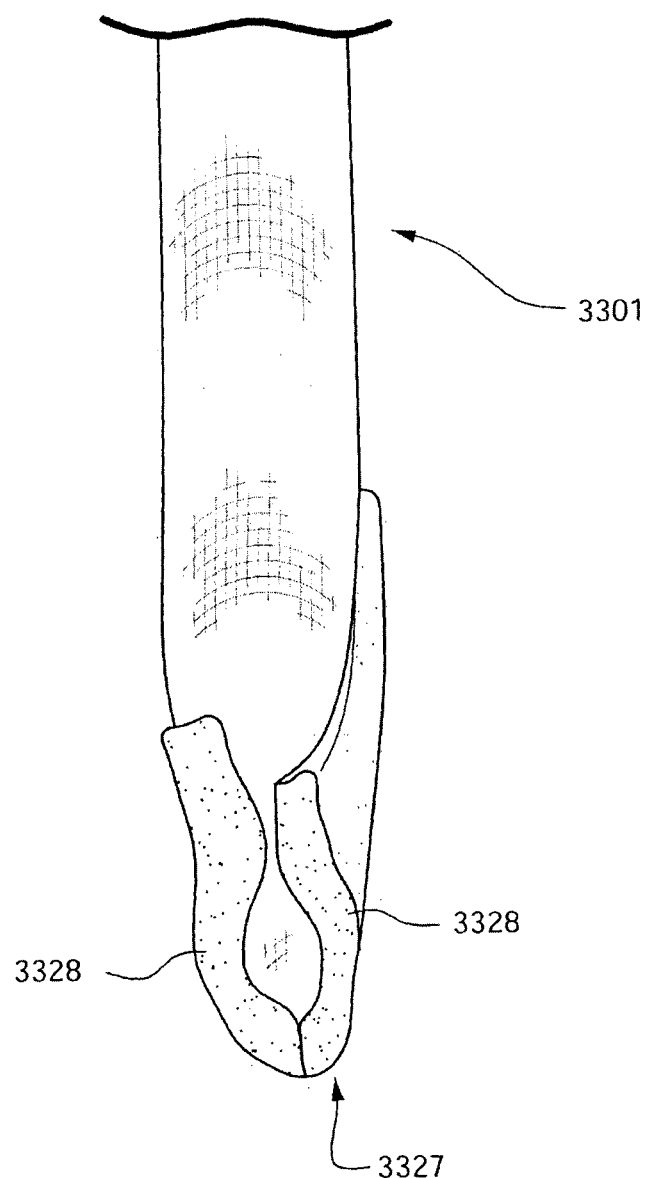

FIG. 179 is a side planar view of a reinforcement portion folded over the end of a strap of a positioning and stabilising structure in accordance with one form of the present technology.

Figure 180:
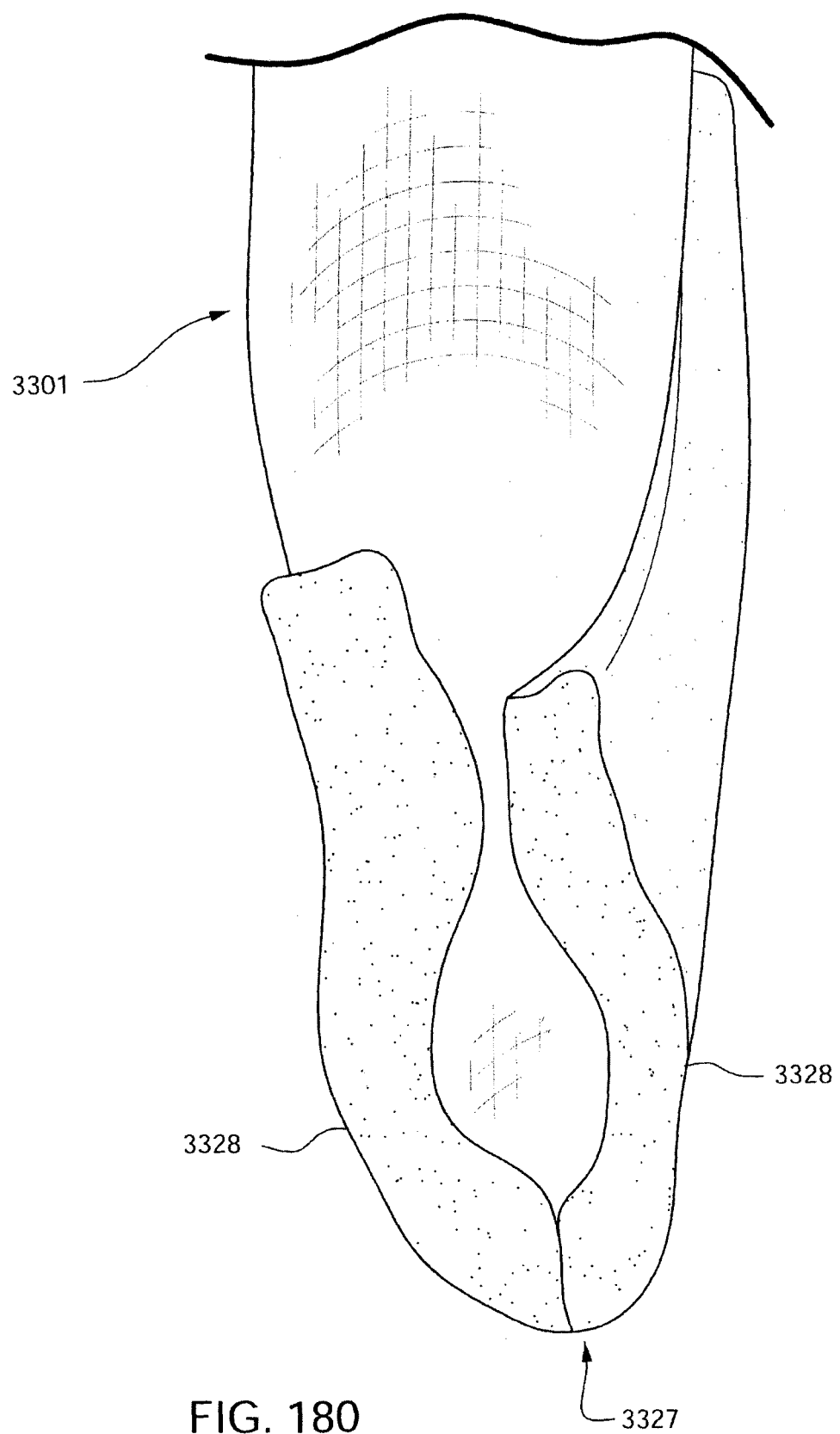

FIG. 180 is a magnified view of FIG. 179.

Figure 181:
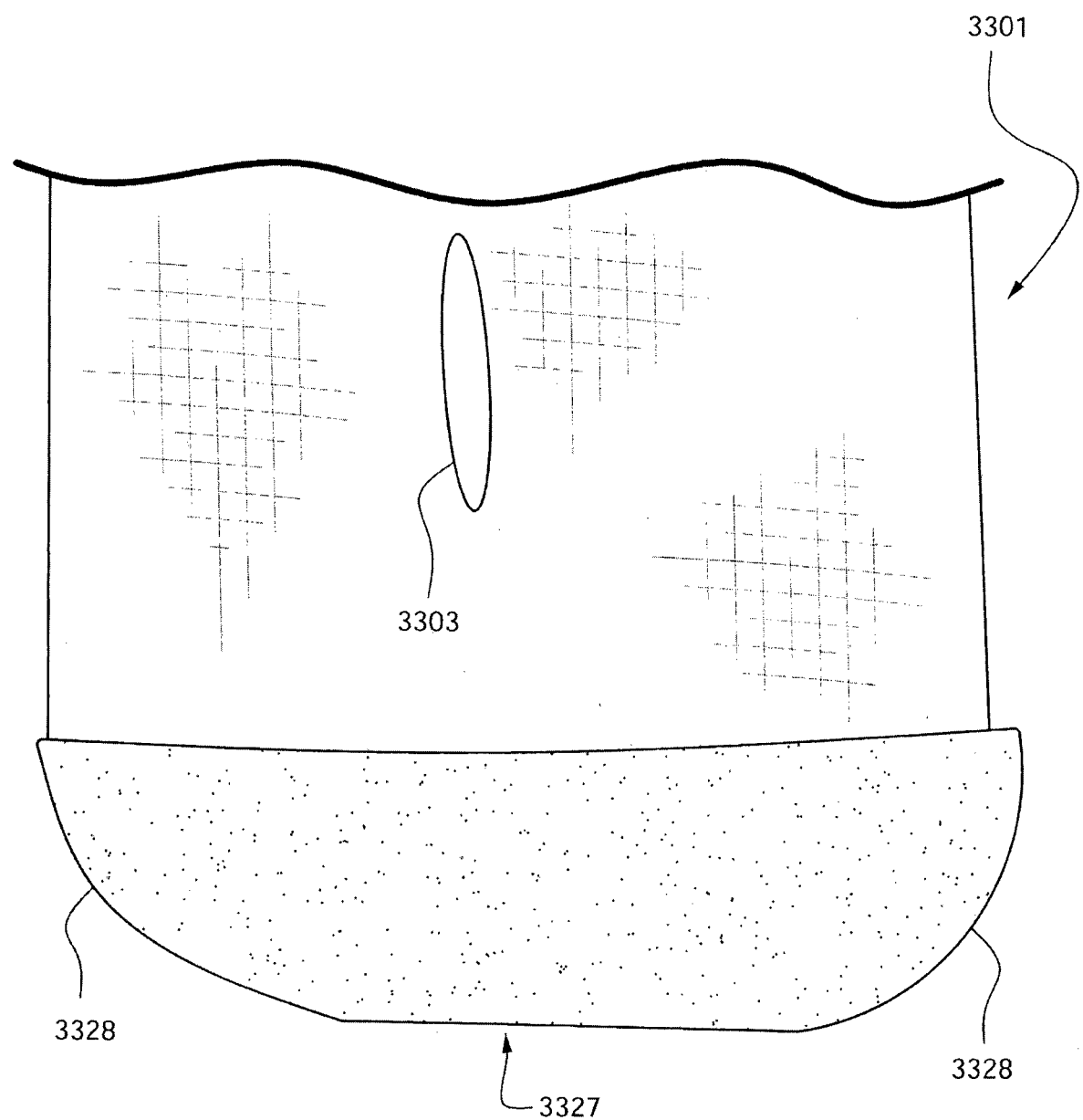

FIG. 181 is a magnified view of FIG. 177.

Figure 182:
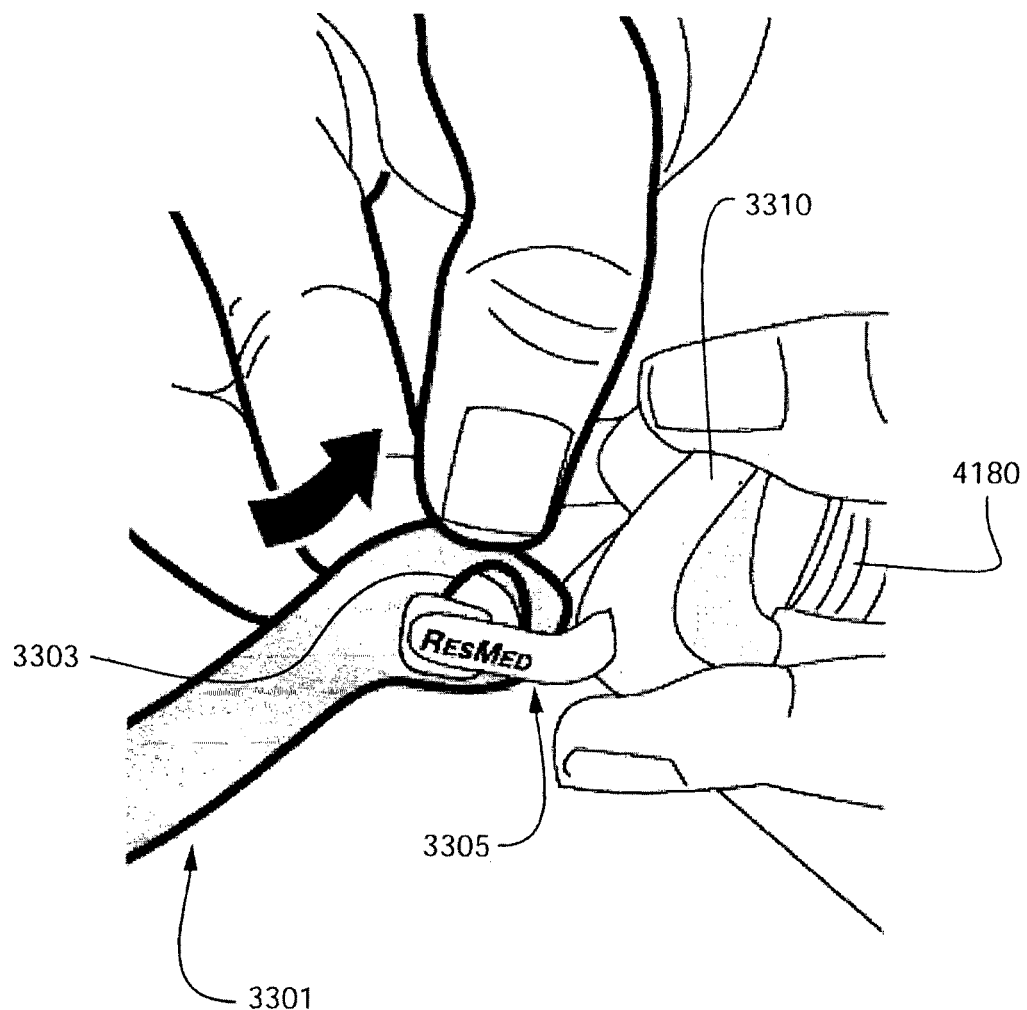
Figure 183:
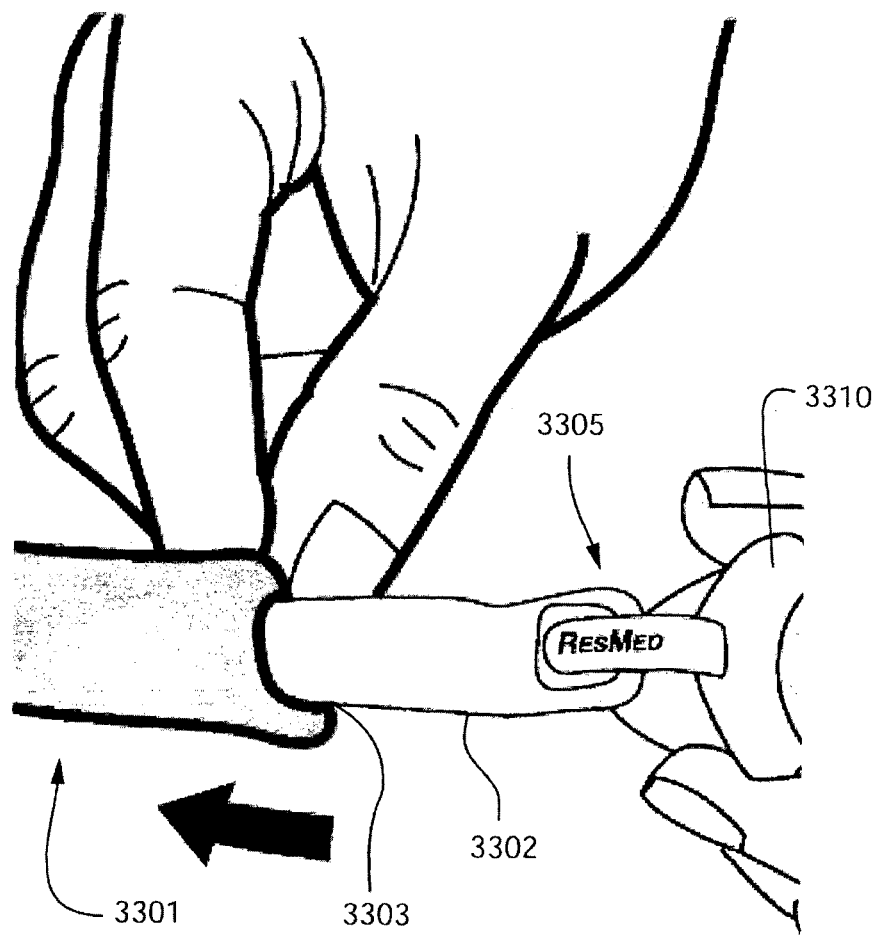
Figure 184:
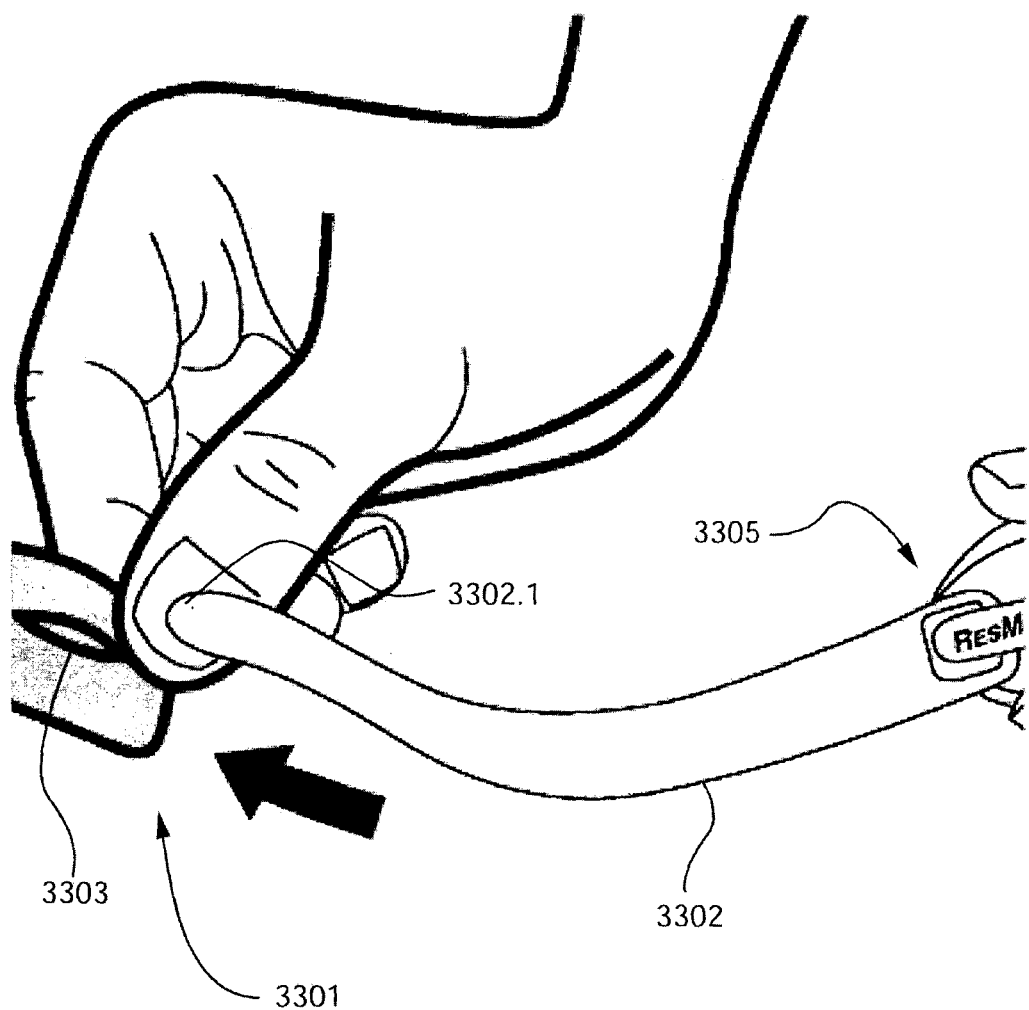

FIGS. 182 to 184 show a series of steps of removing a strap from a rigidiser arm of a positioning and stabilising structure in accordance with one form of the present technology.

Figure 185:
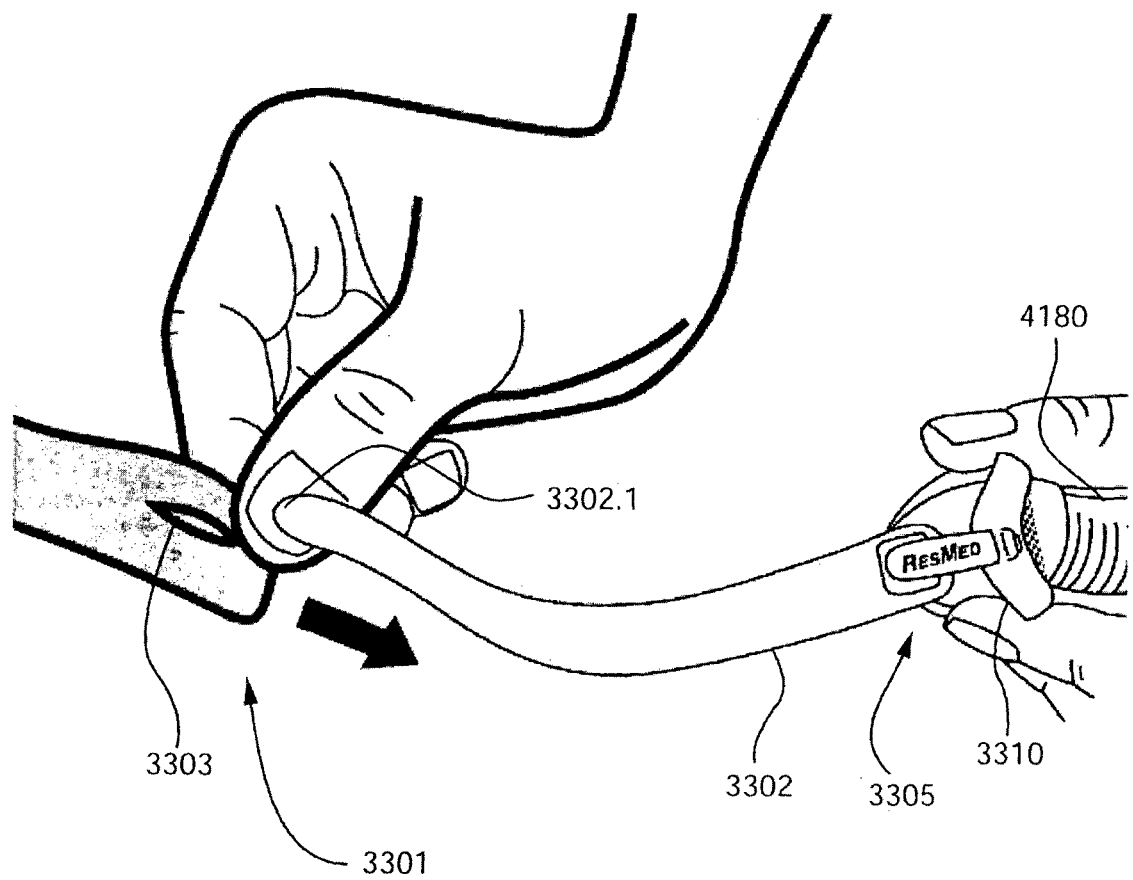
Figure 186:
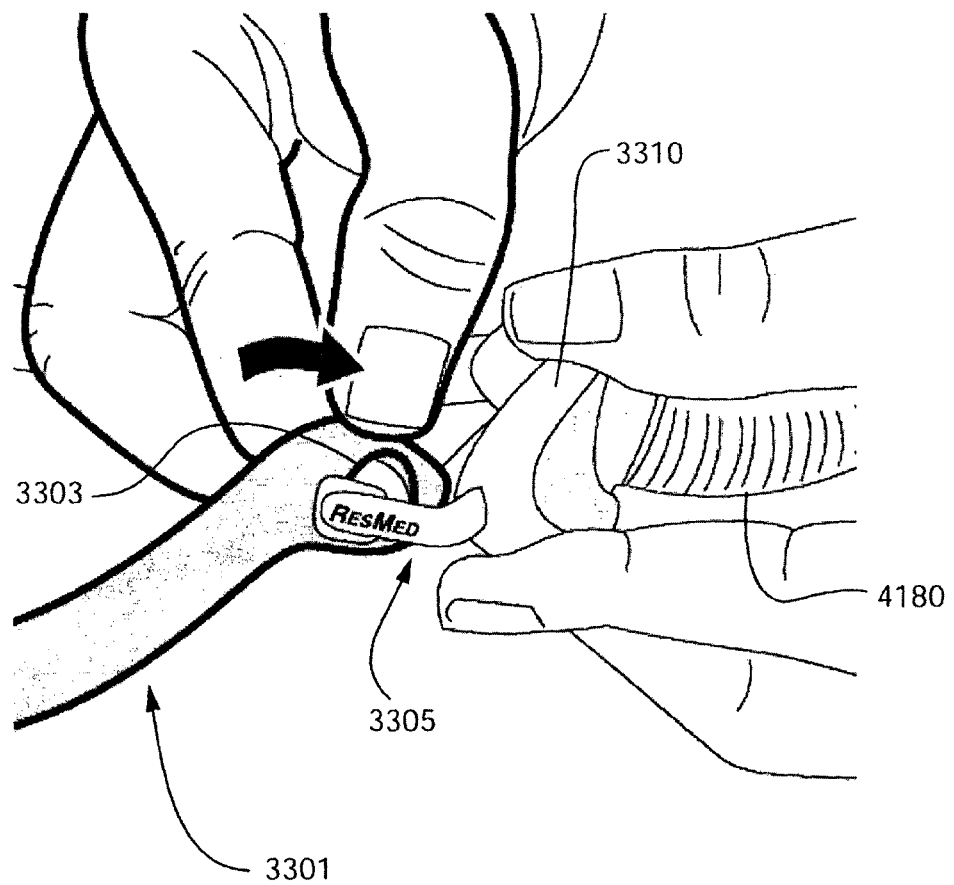

FIGS. 185 and 186 show a series of steps of attaching a strap to a rigidiser arm of a positioning and stabilising structure in accordance with one form of the present technology.

Figure 187:
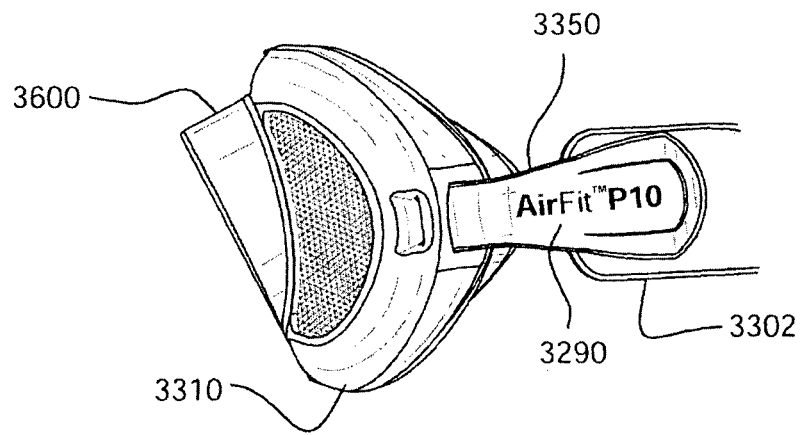

FIG. 187 is a side planar view of a rigidiser arm of a positioning and stabilising structure in accordance with one form of the present technology showing a visual indicator.

Figure 188:
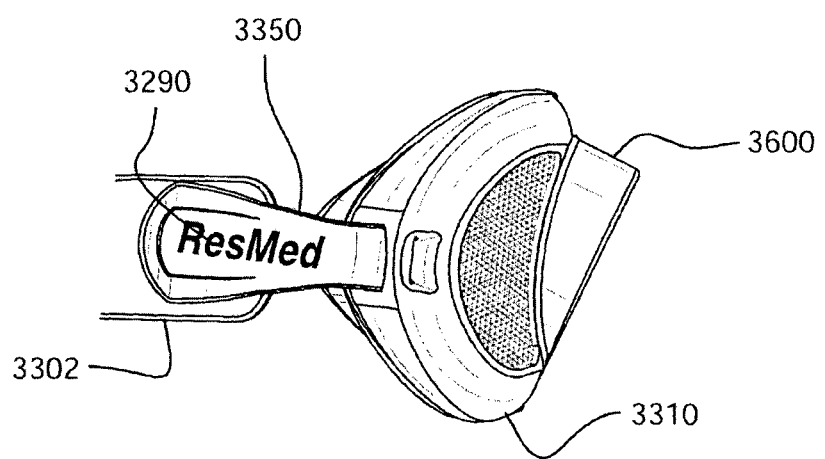

FIG. 188 is a side planar view of a rigidiser arm of a positioning and stabilising structure in accordance with one form of the present technology showing a visual indicator.

Figure 189:
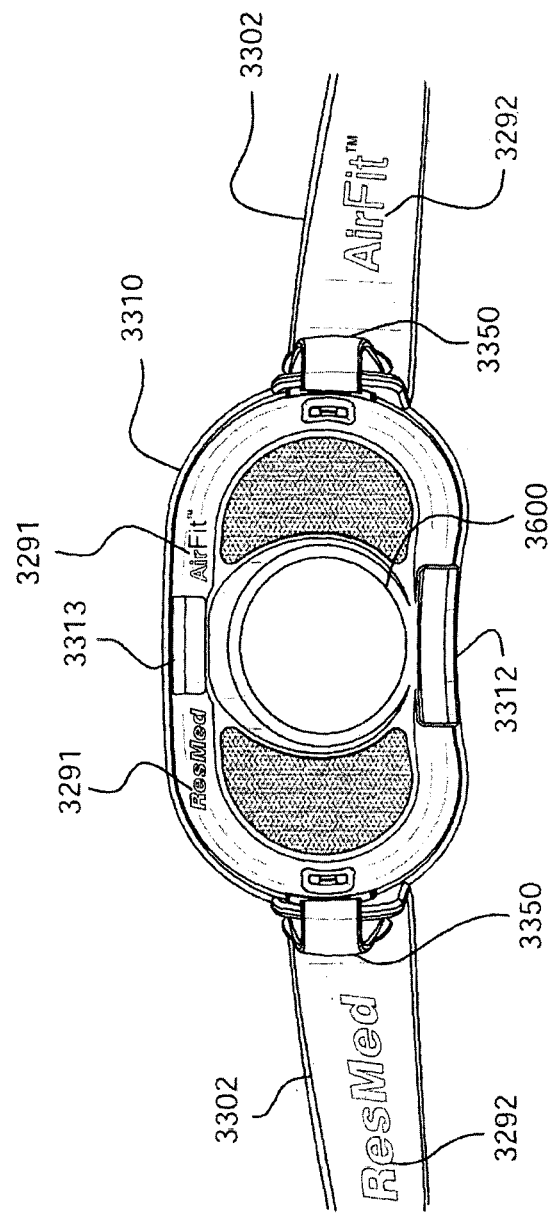

FIG. 189 is a front planar view of fame and rigidiser arms in accordance with one form of the present technology showing visual and tactile indicators.

Figure 190:
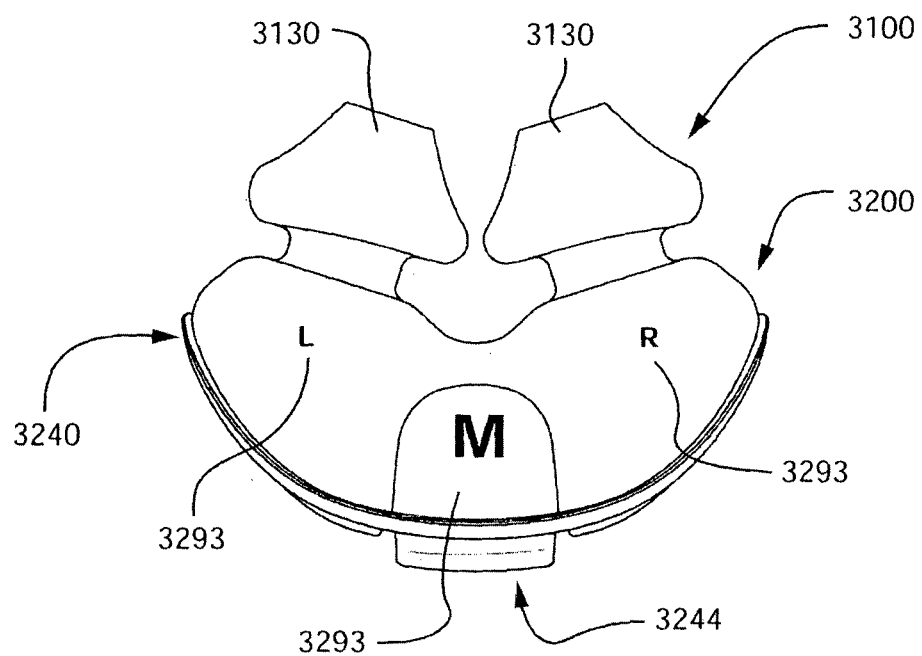

FIG. 190 is a top planar view of a seal-forming structure in accordance with one form of the present technology showing a visual indicator.

Figure 191:
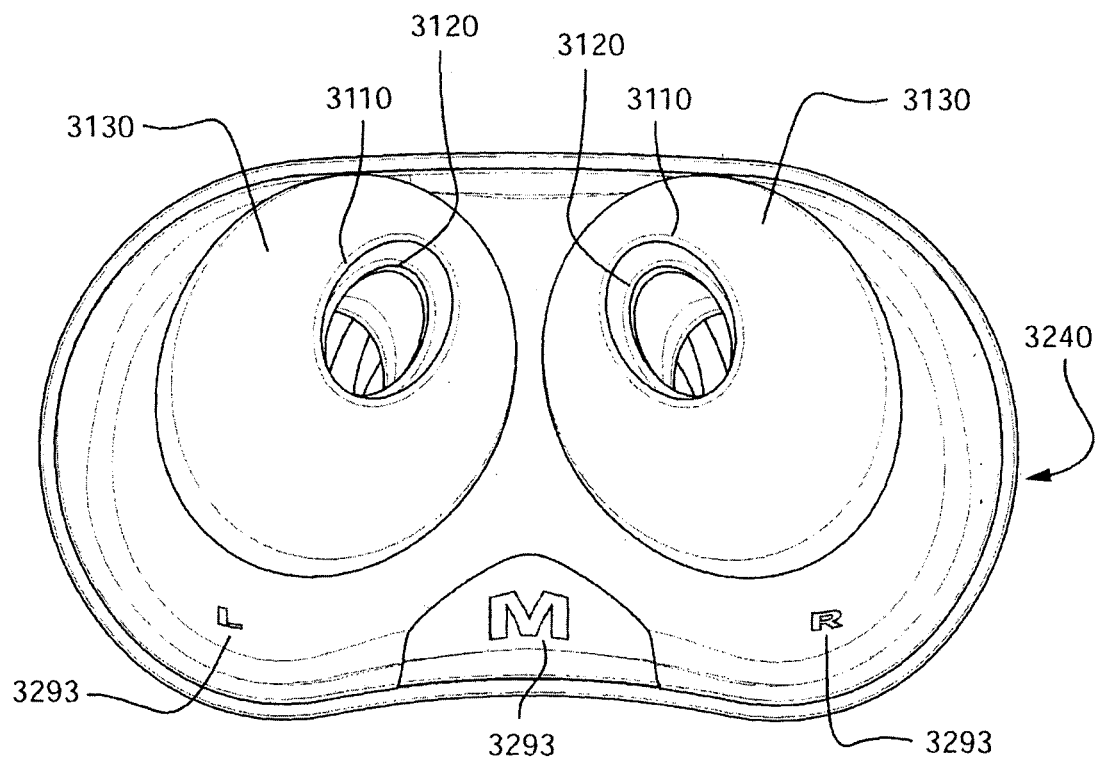

FIG. 191 is a rear planar view of a seal-forming structure in accordance with one form of the present technology showing a visual indicator.

Figure 192:
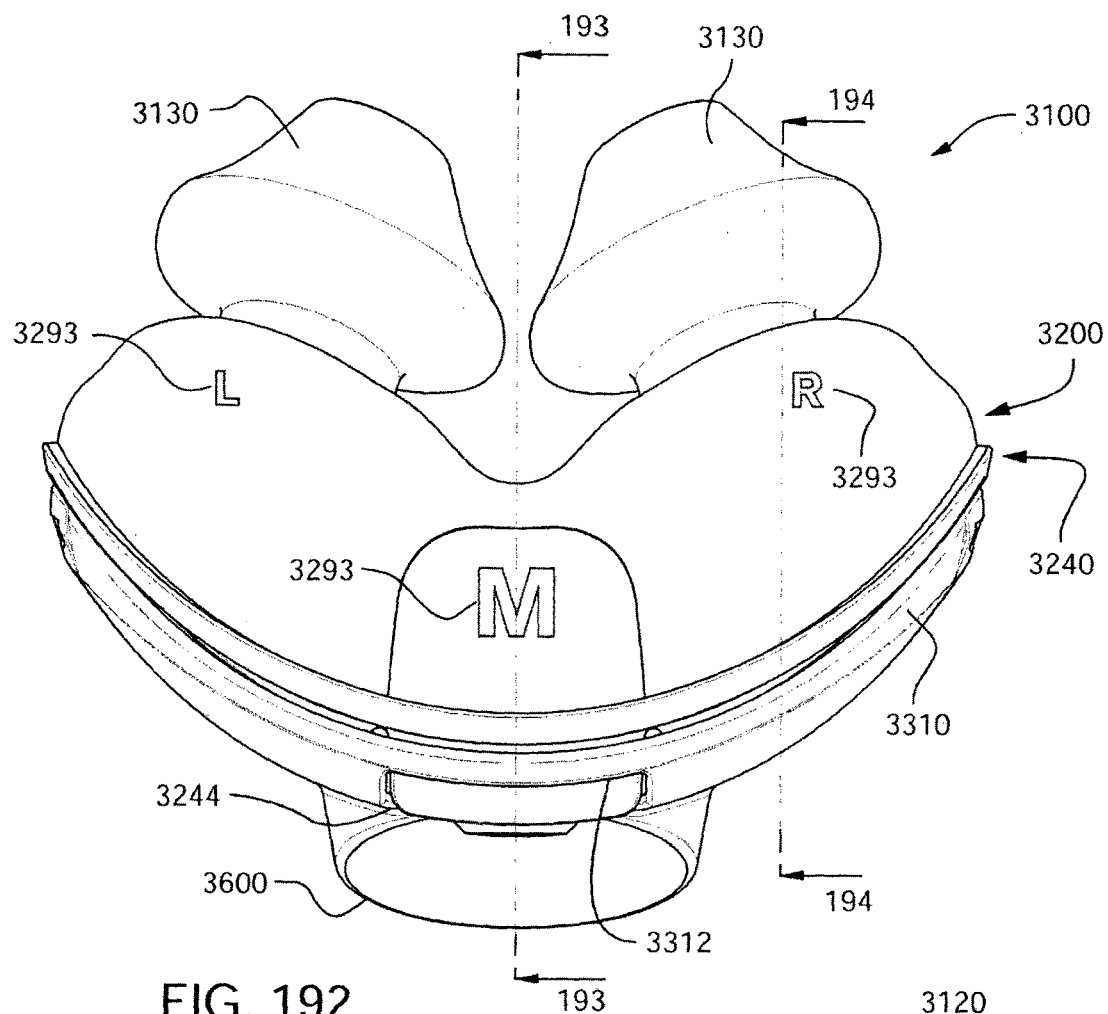

FIG. 192 is a top perspective view of a seal-forming structure in accordance with one form of the present technology showing a visual indicator.

Figures 193, 194:
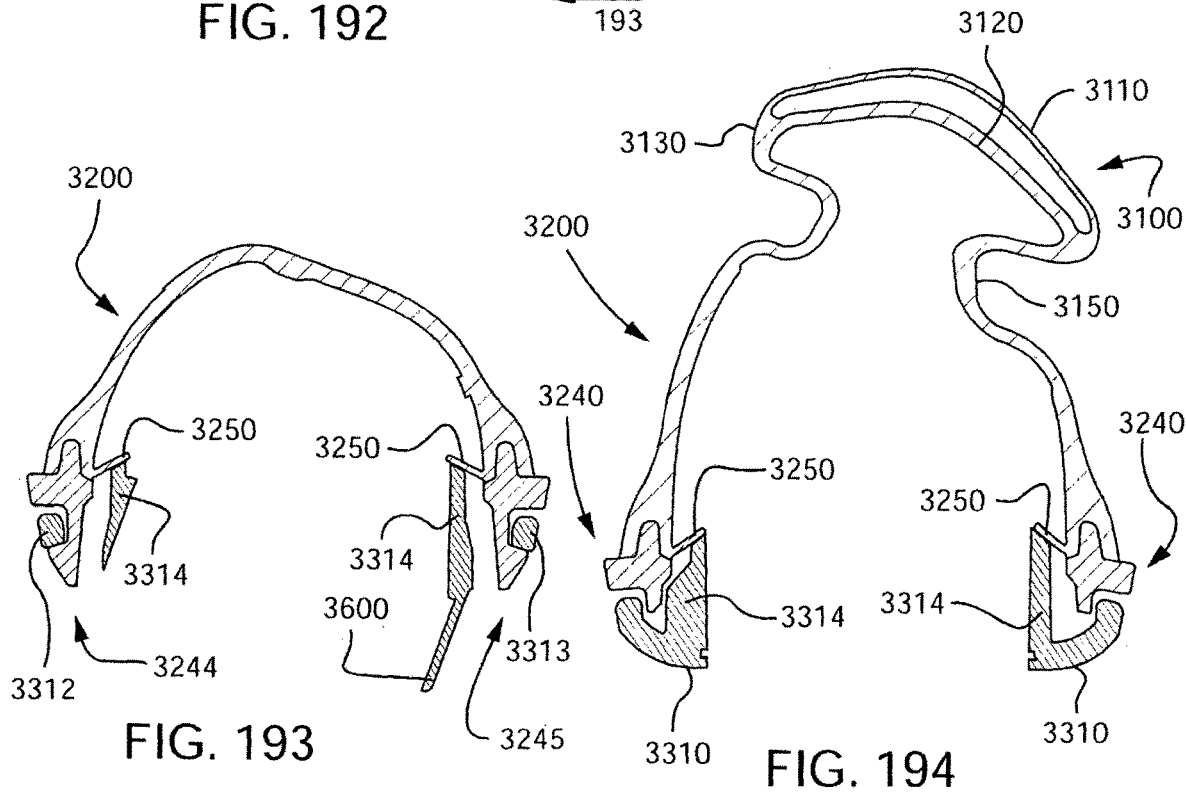

FIG. 193 is a cross-sectional view taken through line 193-193 of FIG. 192.

FIG. 194 is a cross-sectional view taken through line 194-194 of FIG. 192.

Figure 195:
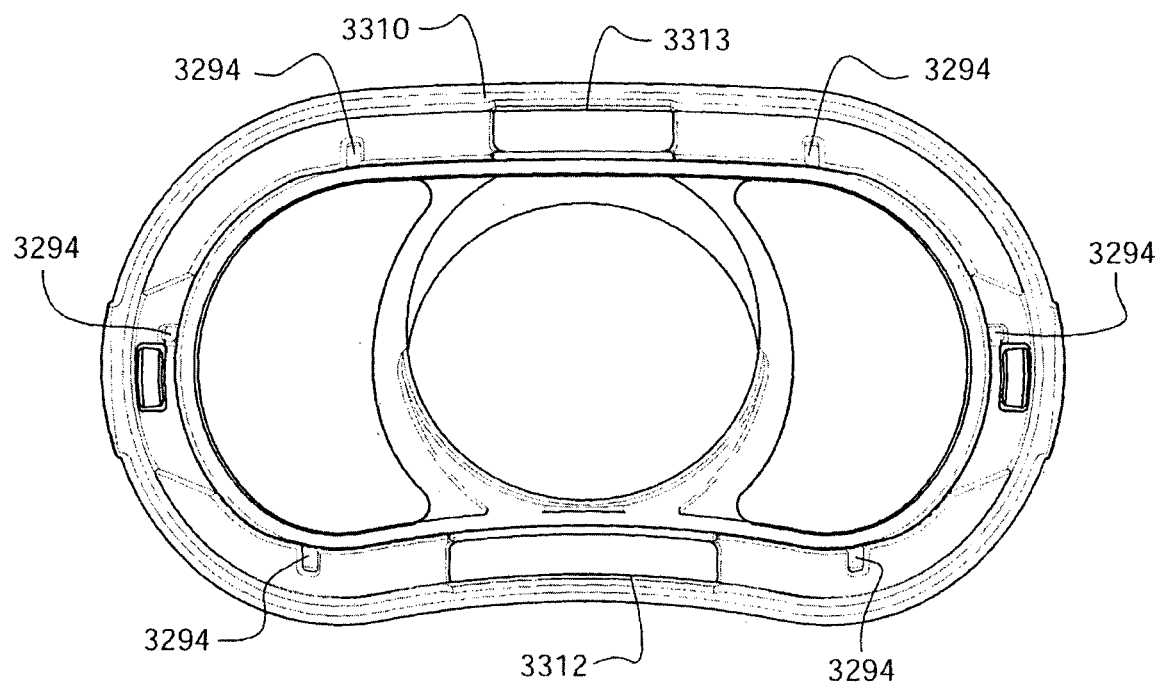

FIG. 195 is a rear planar view of a frame in accordance with one form of the present technology.

Figure 196:
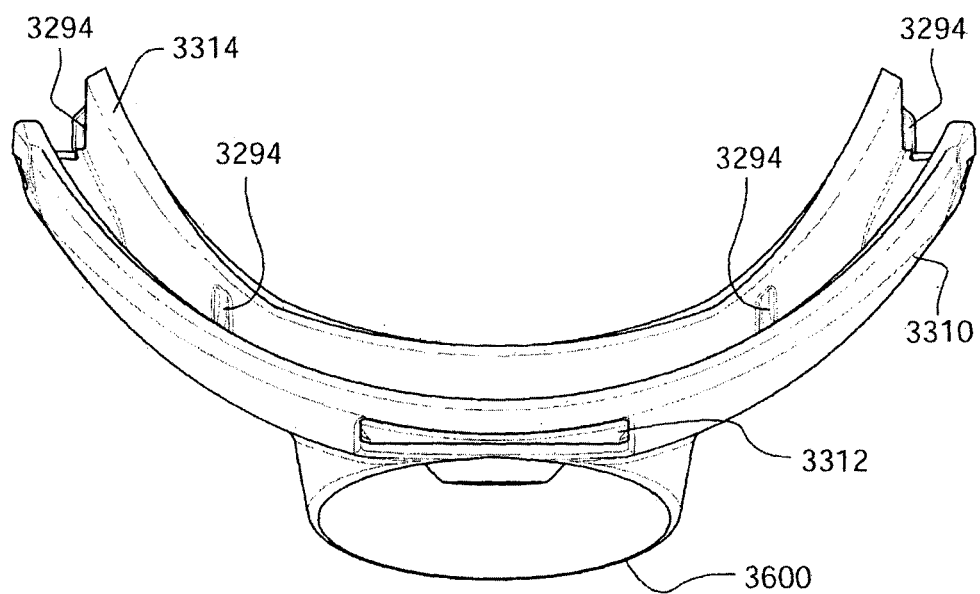

FIG. 196 is a top planar view of a frame in accordance with one form of the present technology.

Figure 197:
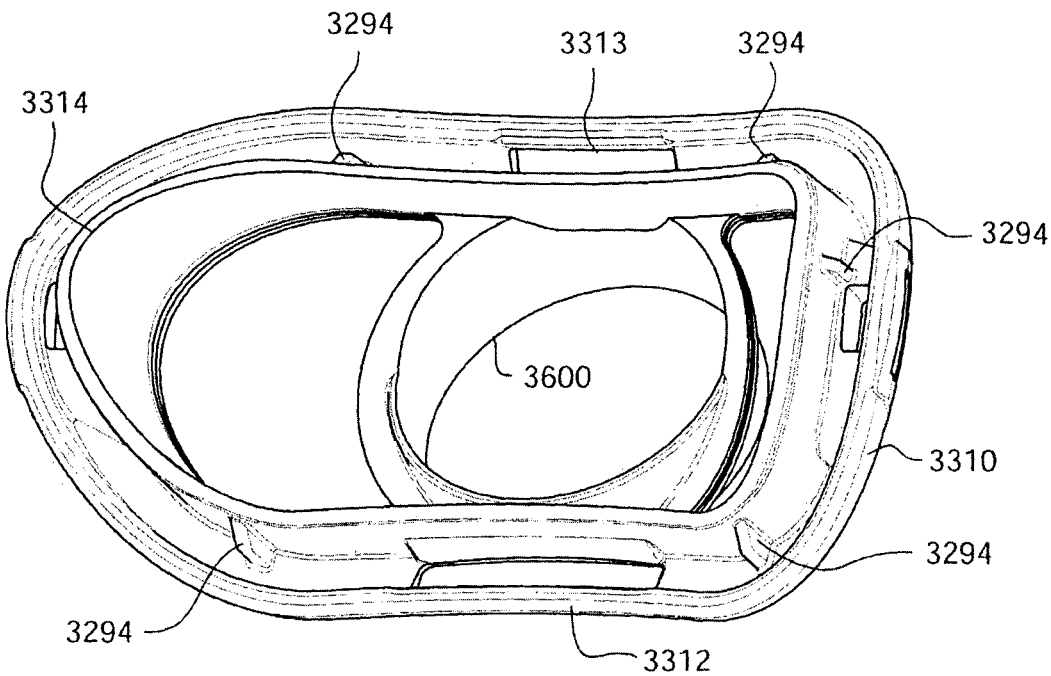

FIG. 197 is a rear perspective view of a frame in accordance with one form of the present technology.

Figure 198:
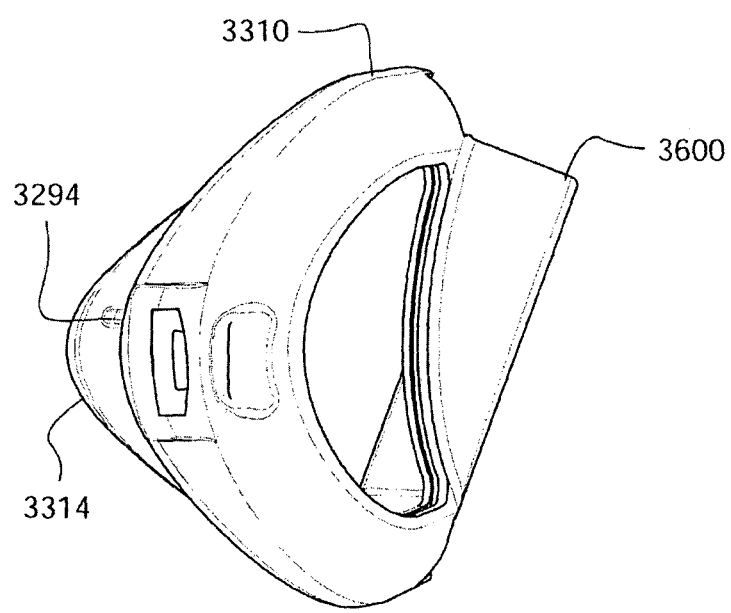

FIG. 198 is a side planar view of a frame in accordance with one form of the present technology.

Figure 199:
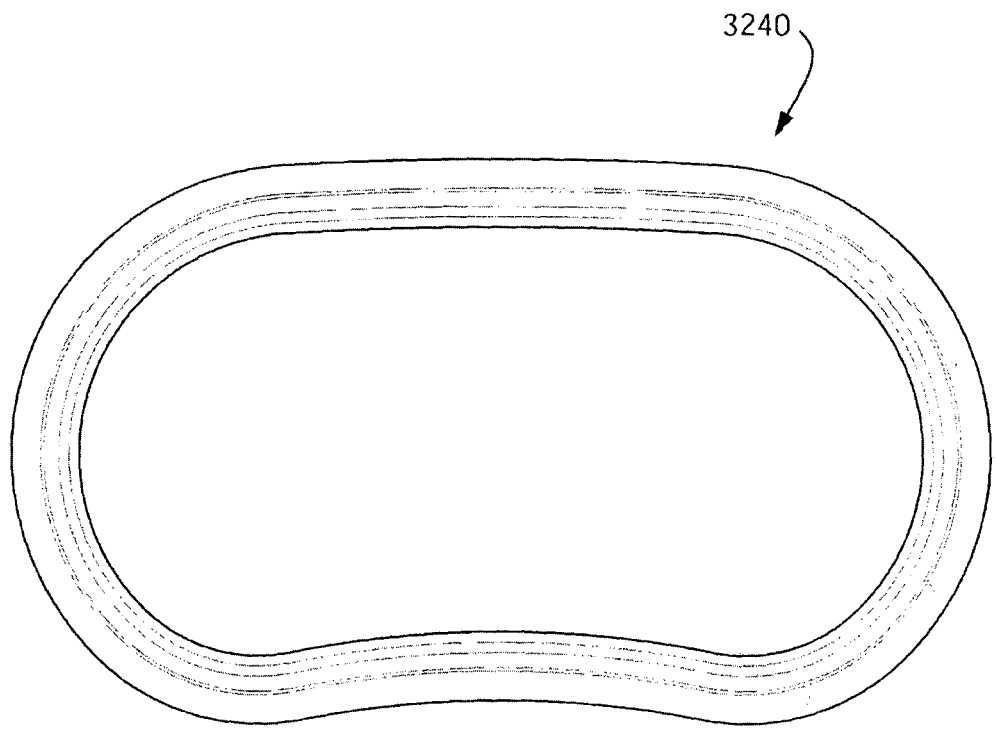

FIG. 199 is a rear planar view of a retaining structure of a plenum connection region in accordance with one form of the present technology.

Figure 200:
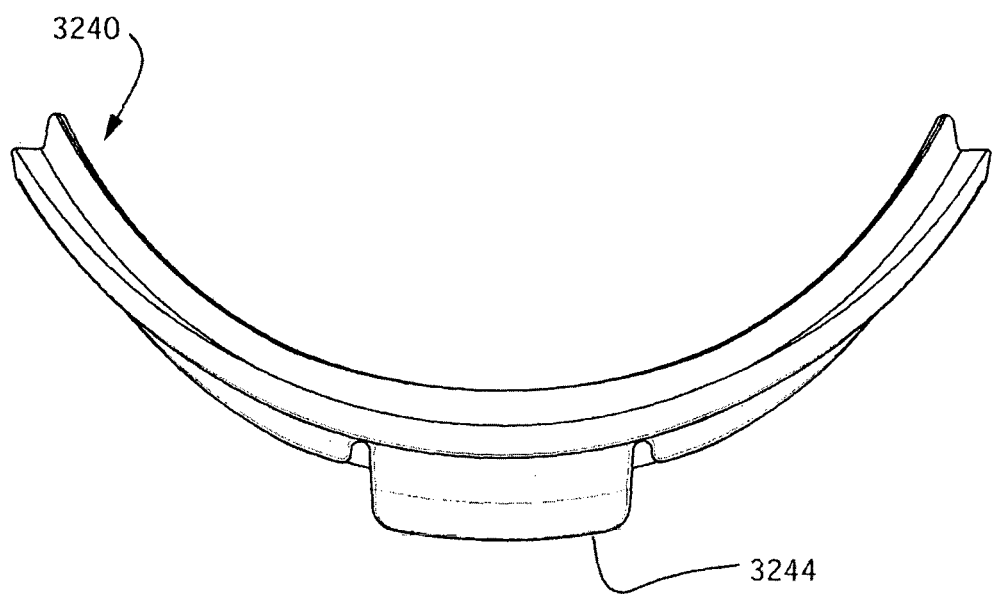

FIG. 200 is a bottom planar view of a retaining structure of a plenum connection region in accordance with one form of the present technology.

Figure 201:
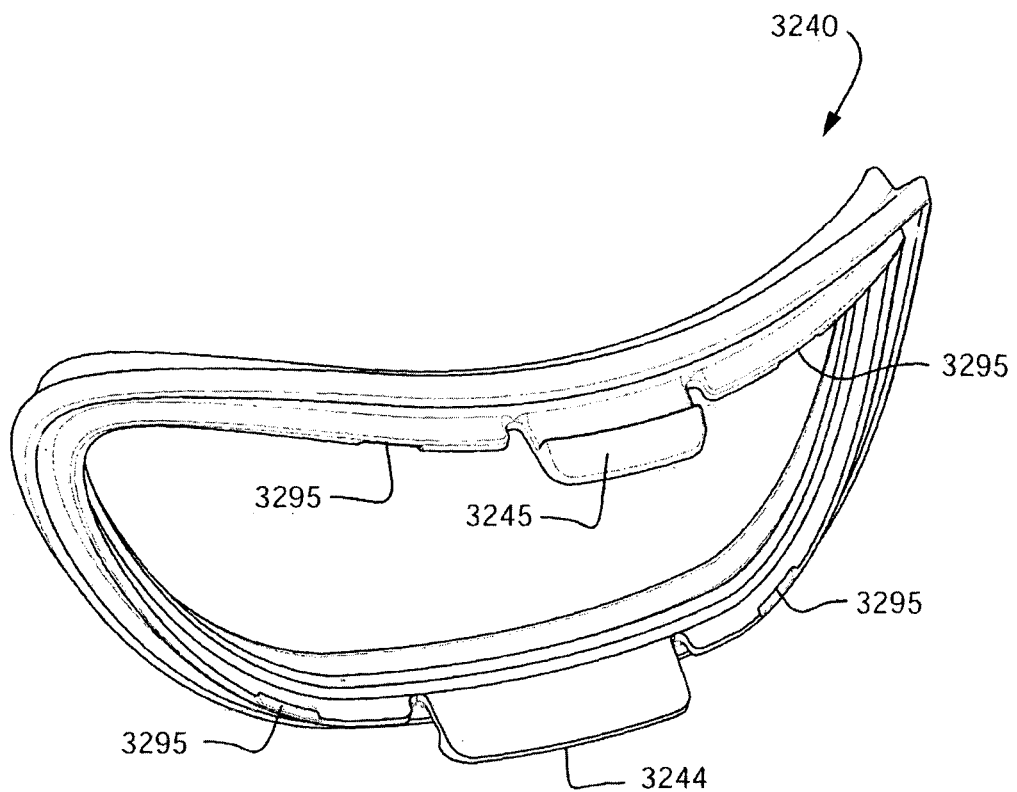

FIG. 201 is a rear perspective view of a retaining structure of a plenum connection region in accordance with one form of the present technology.

Figure 202:
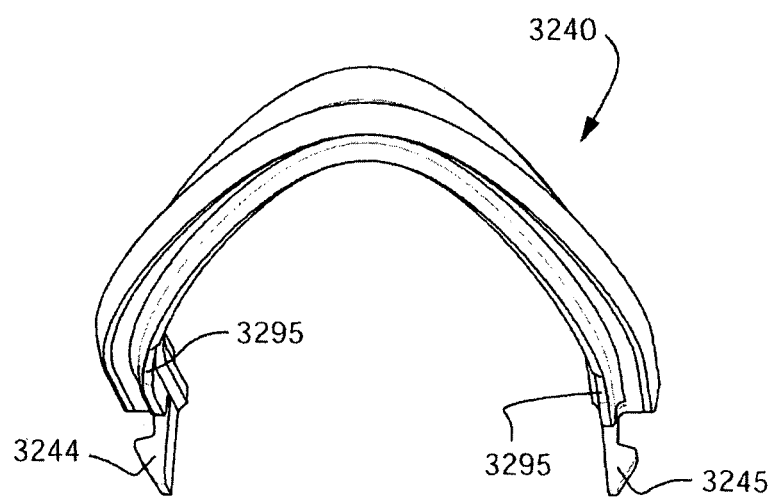
Figure 203:
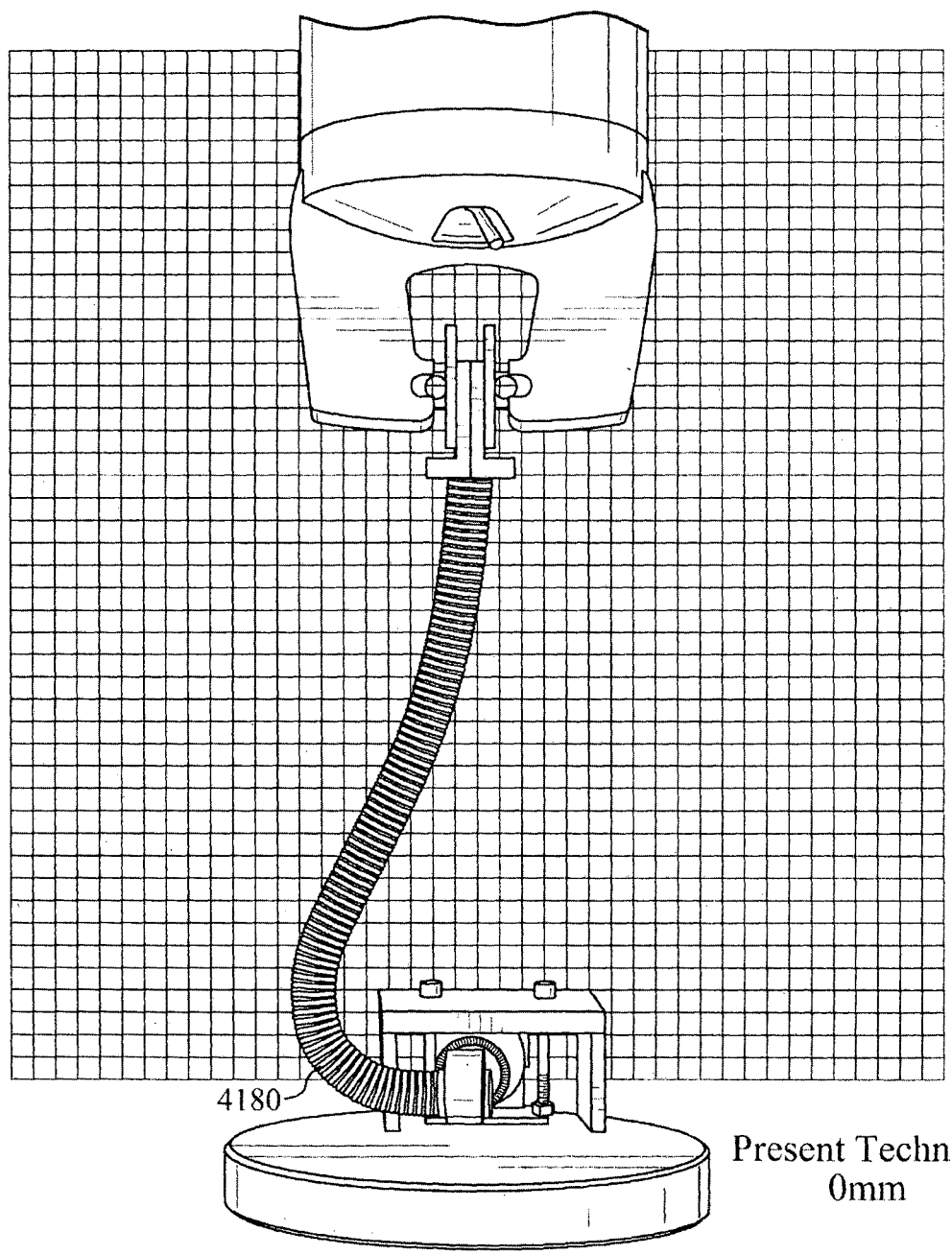
Figure 204:
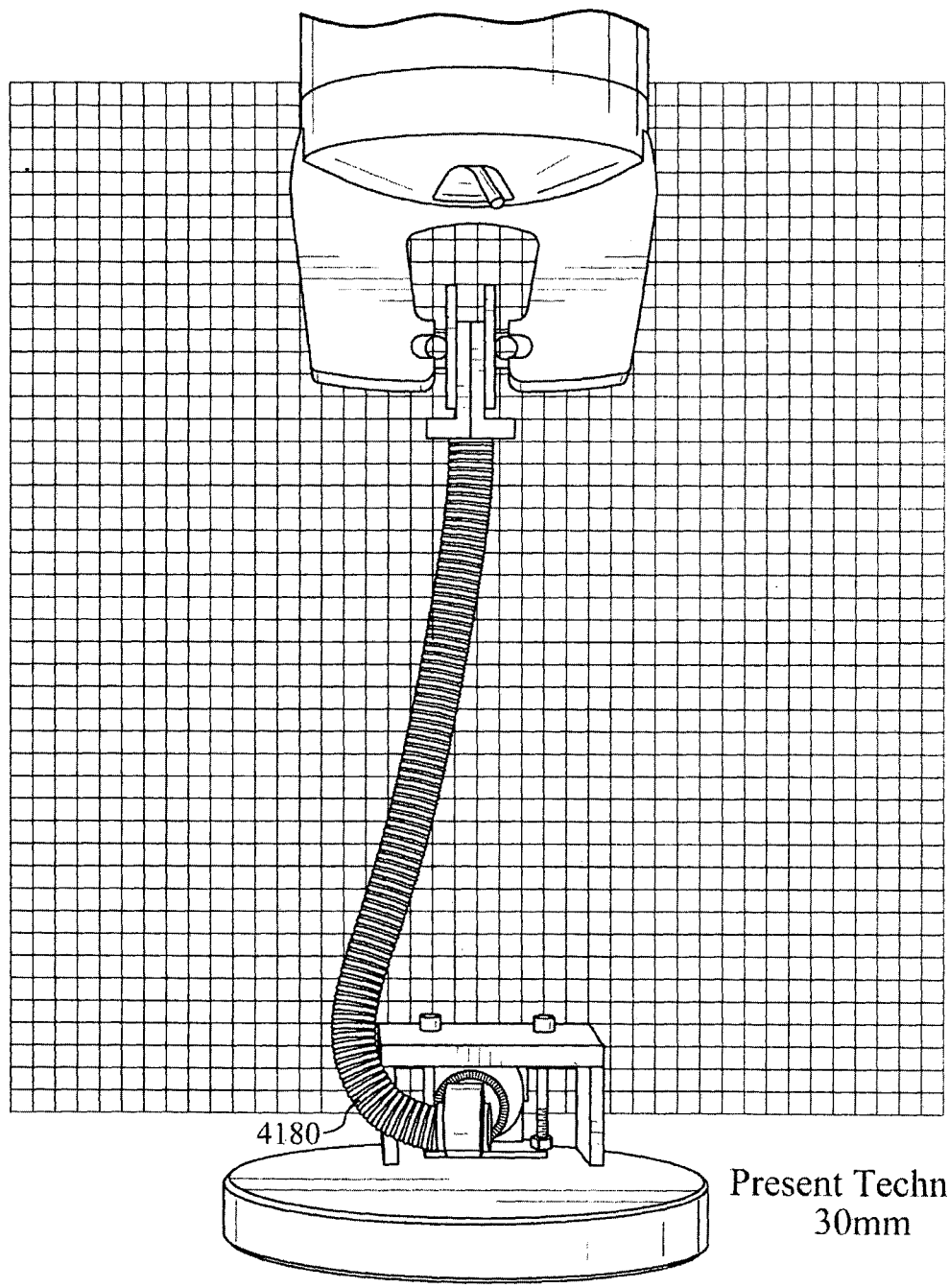
Figure 205:
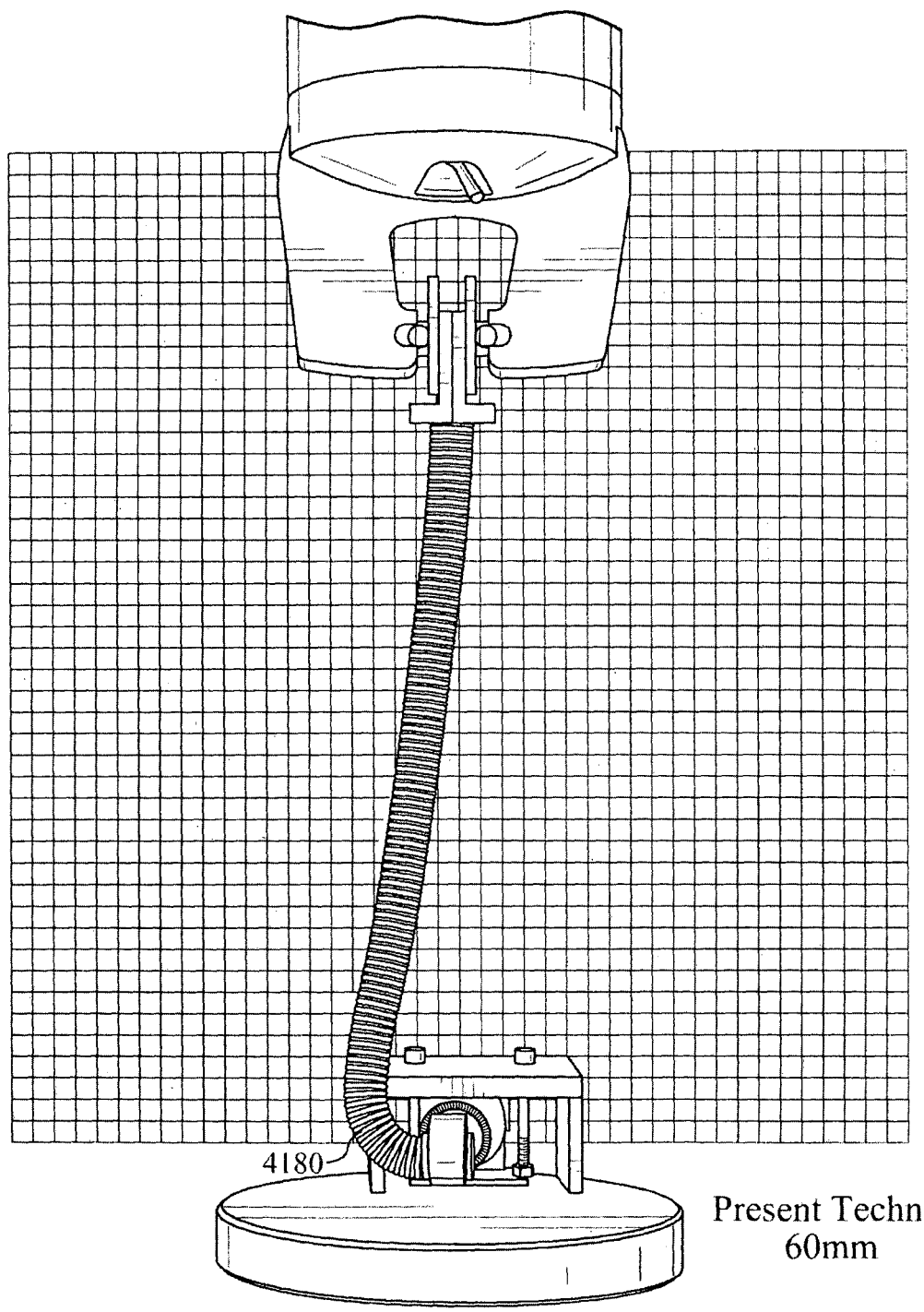
Figure 206:
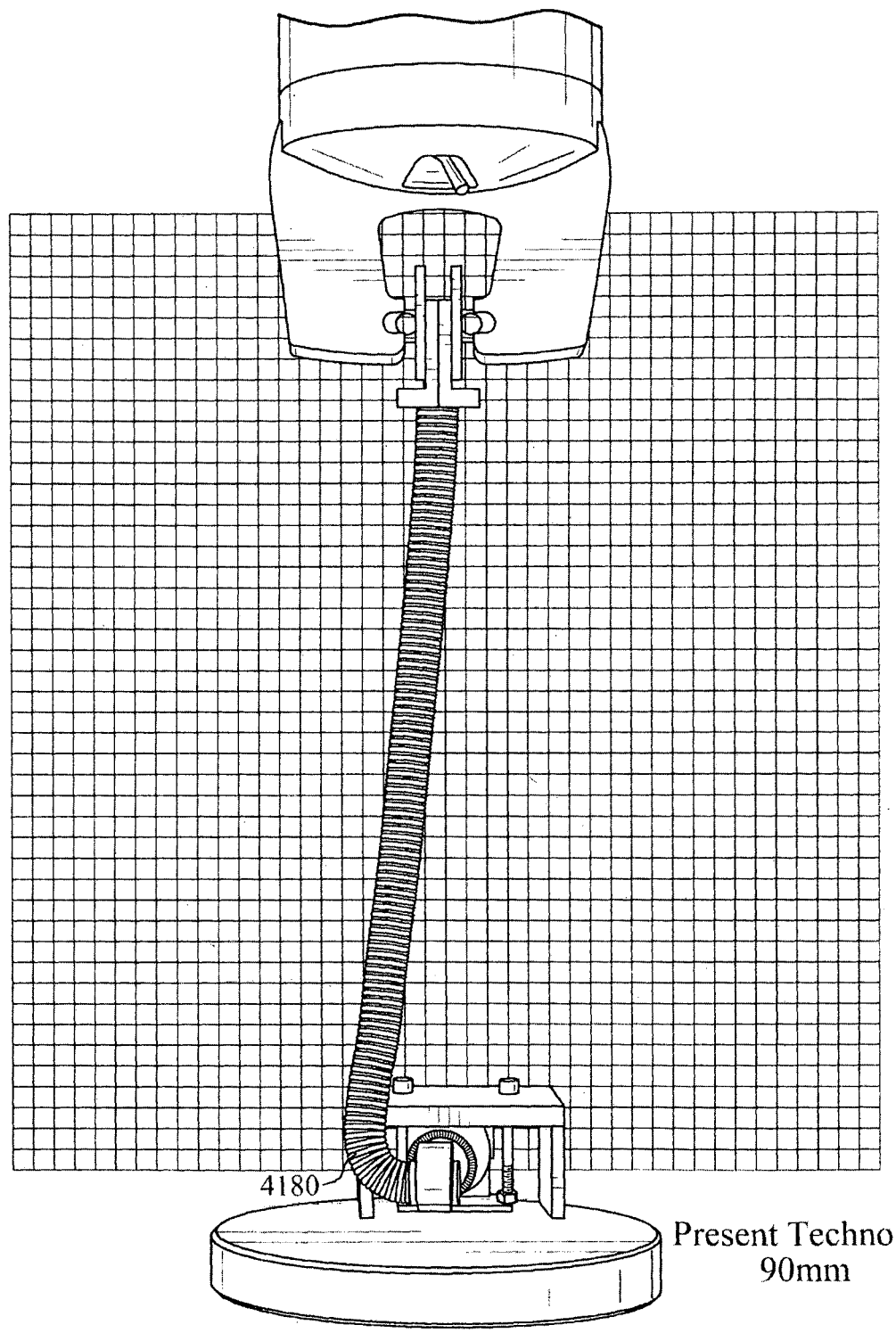
Figure 207:
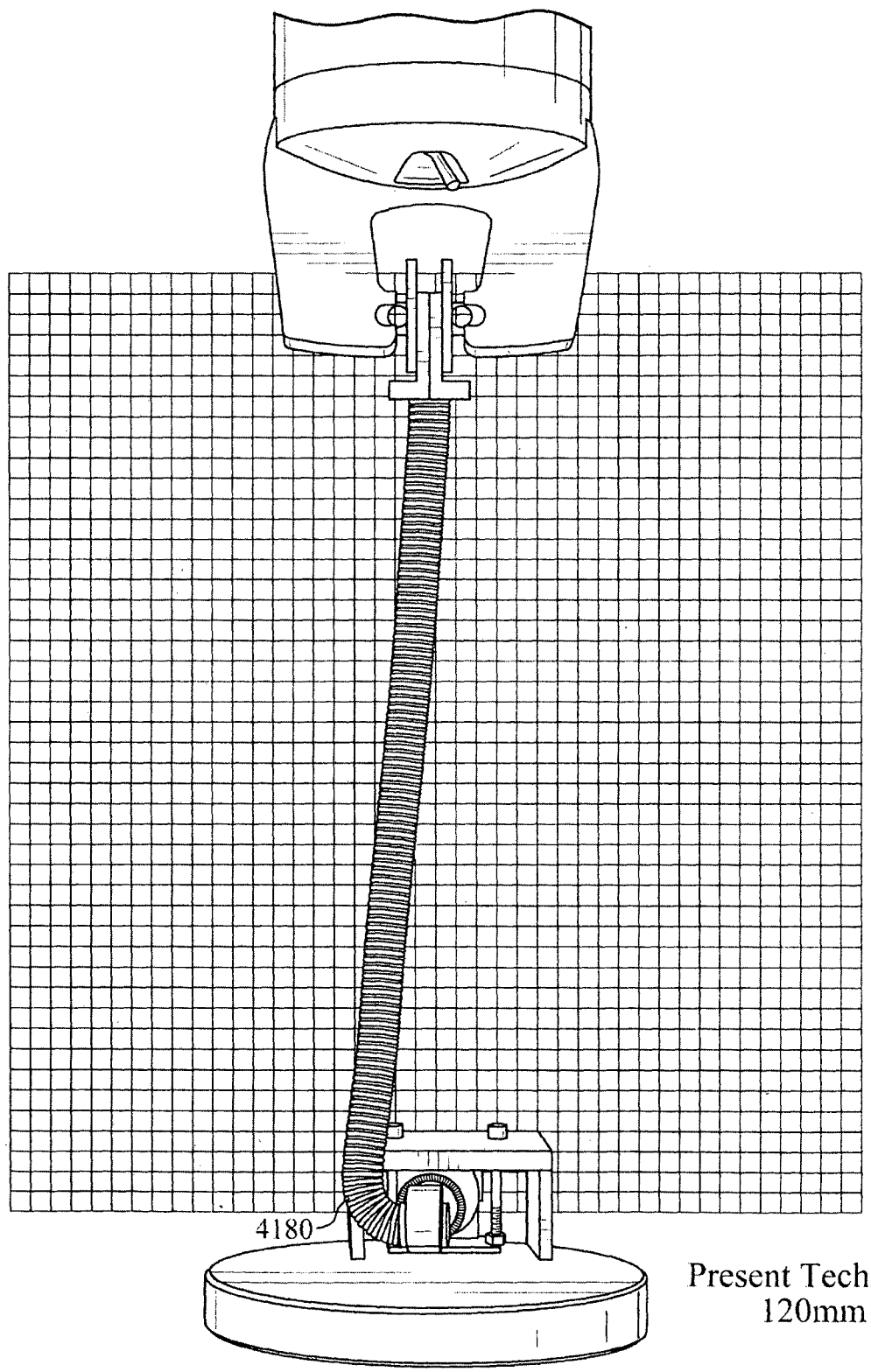
Figure 208:
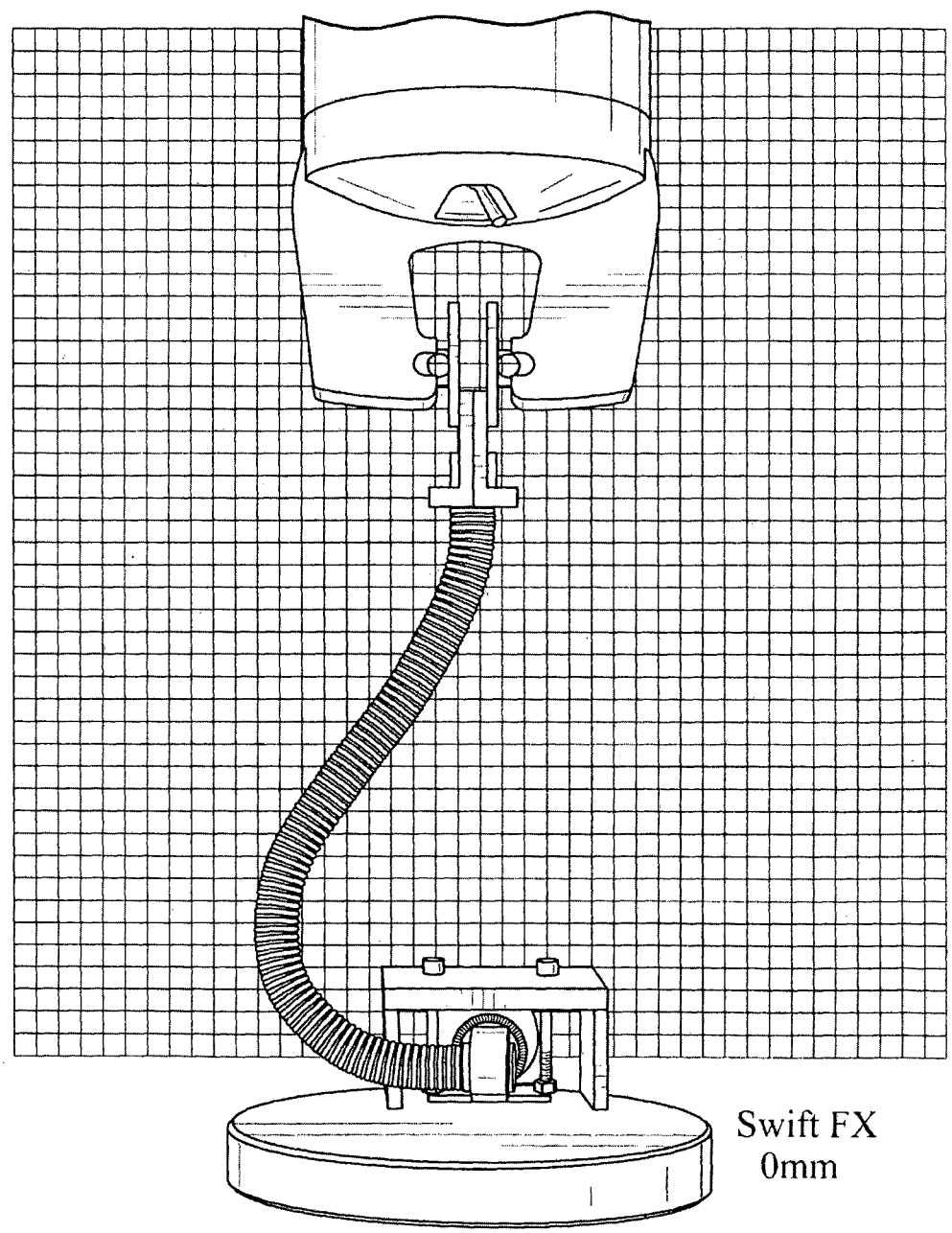
Figure 209:
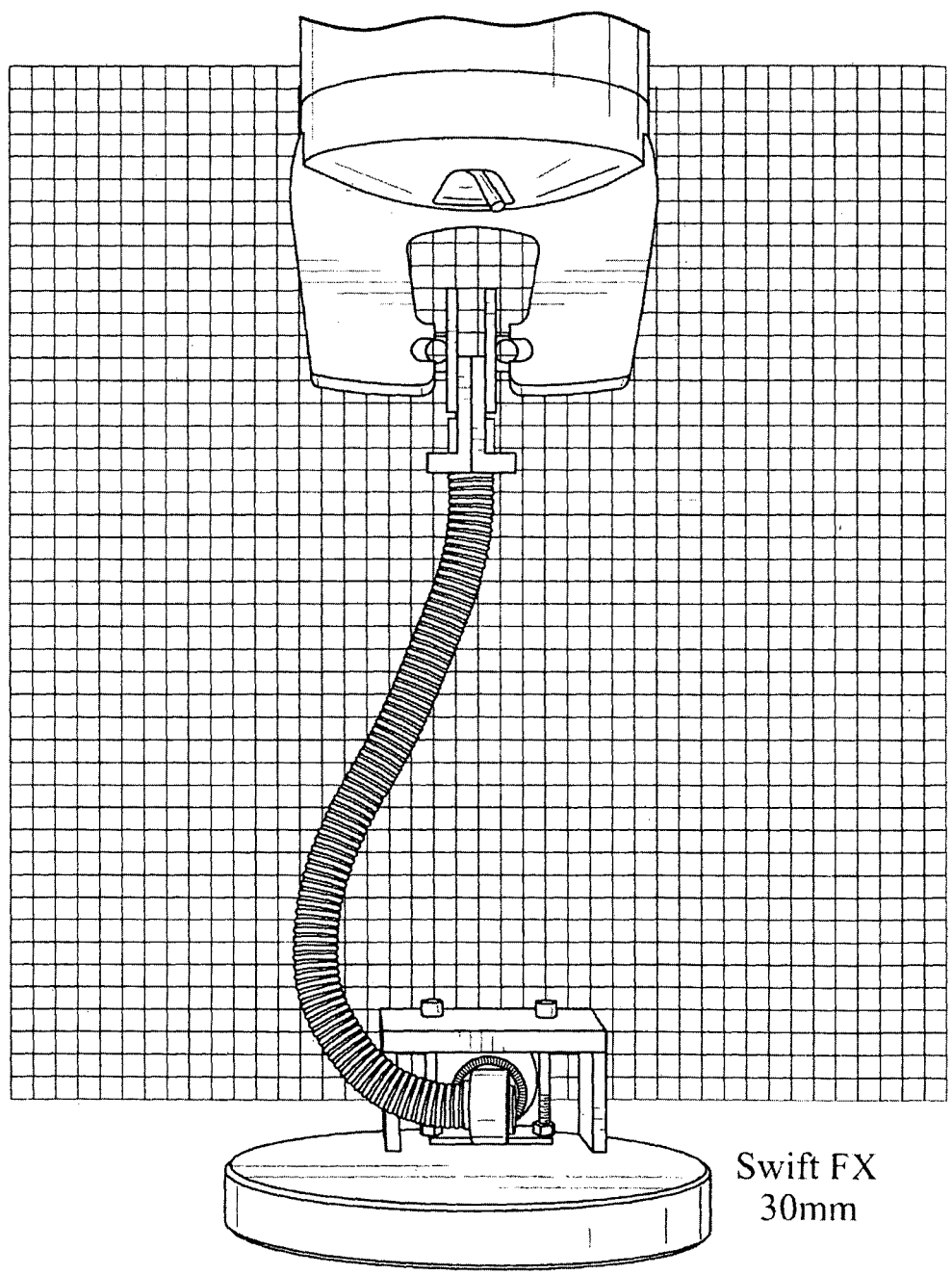
Figure 210:
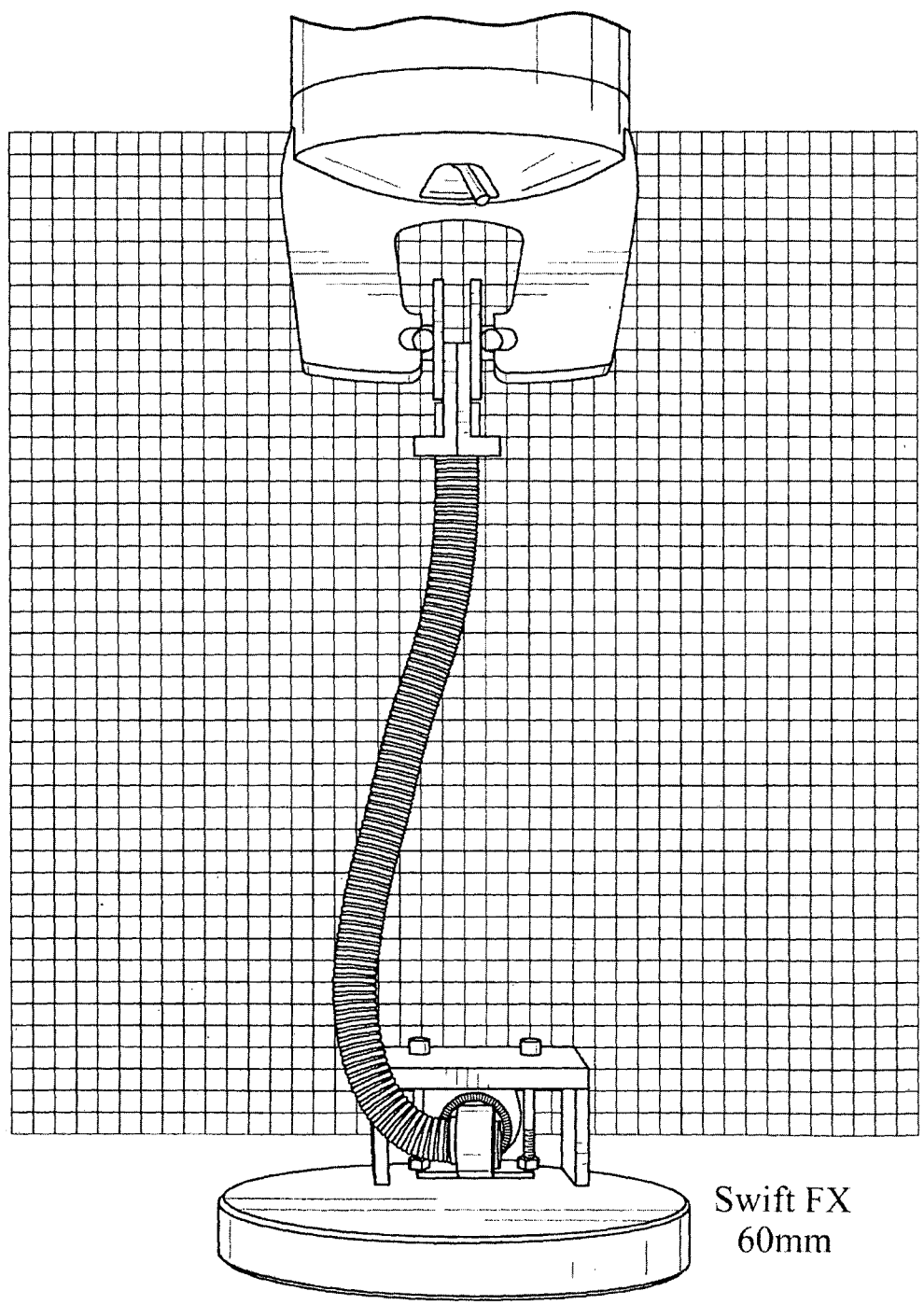
Figure 211:
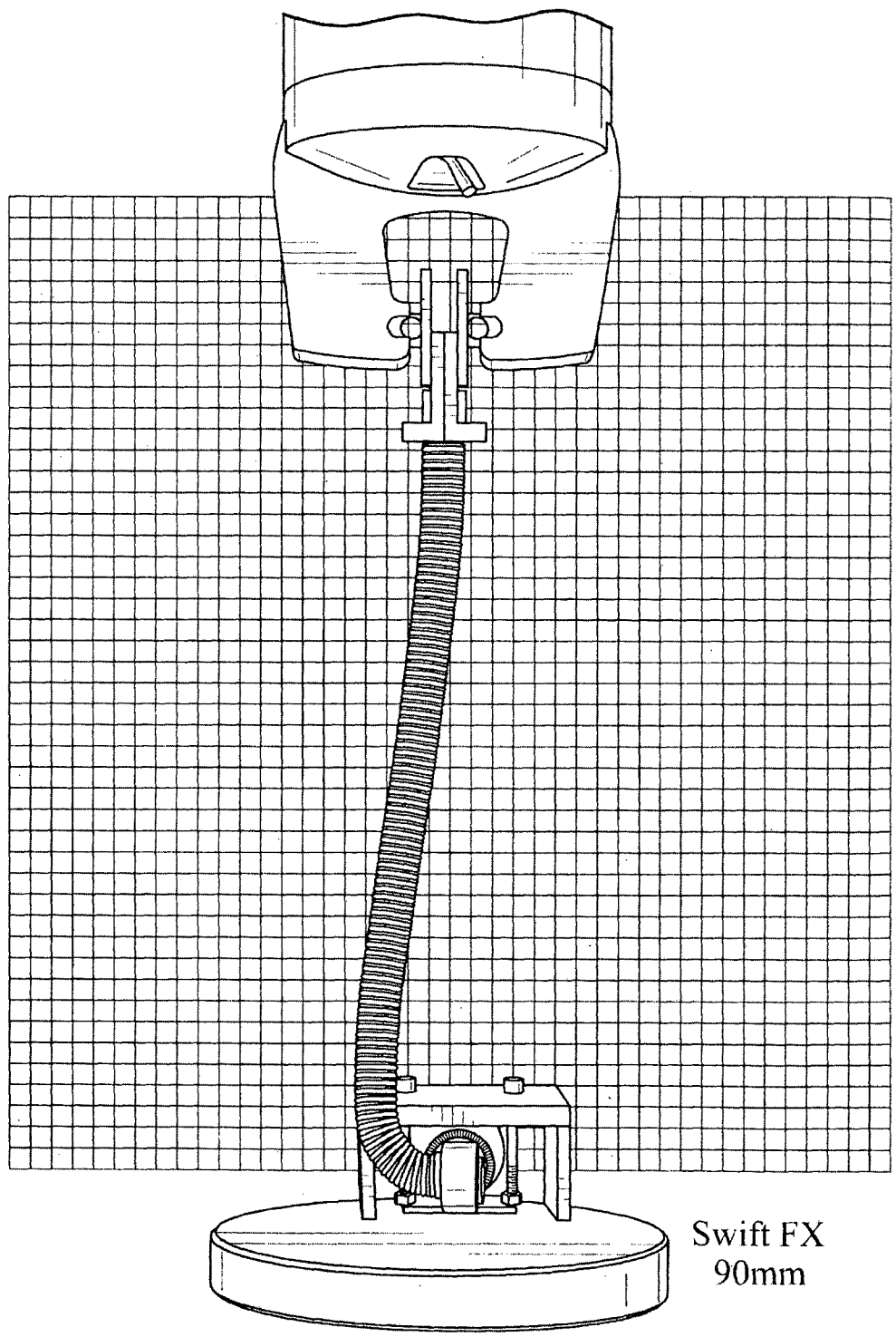
Figure 212:
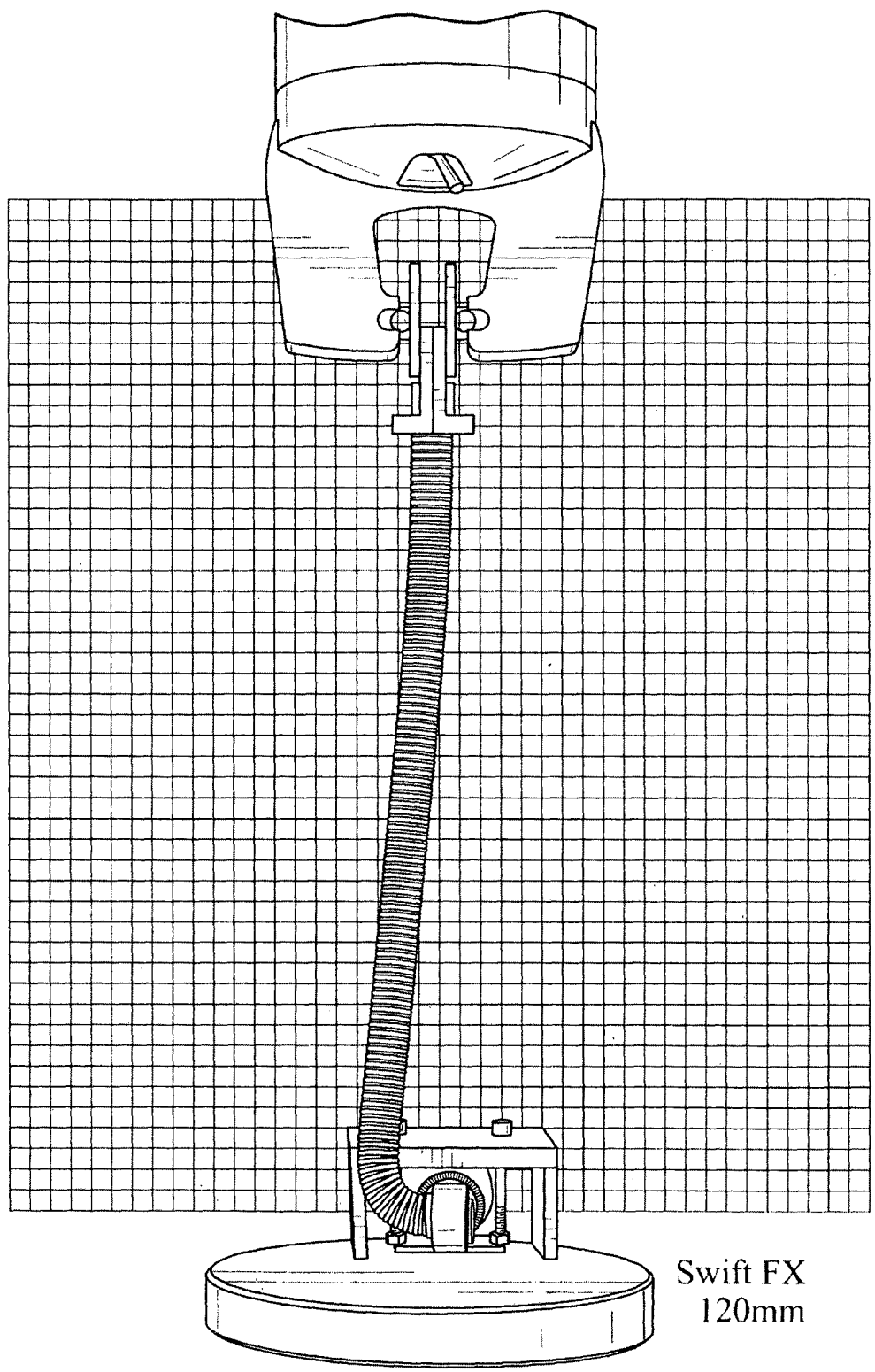
Figure 213:
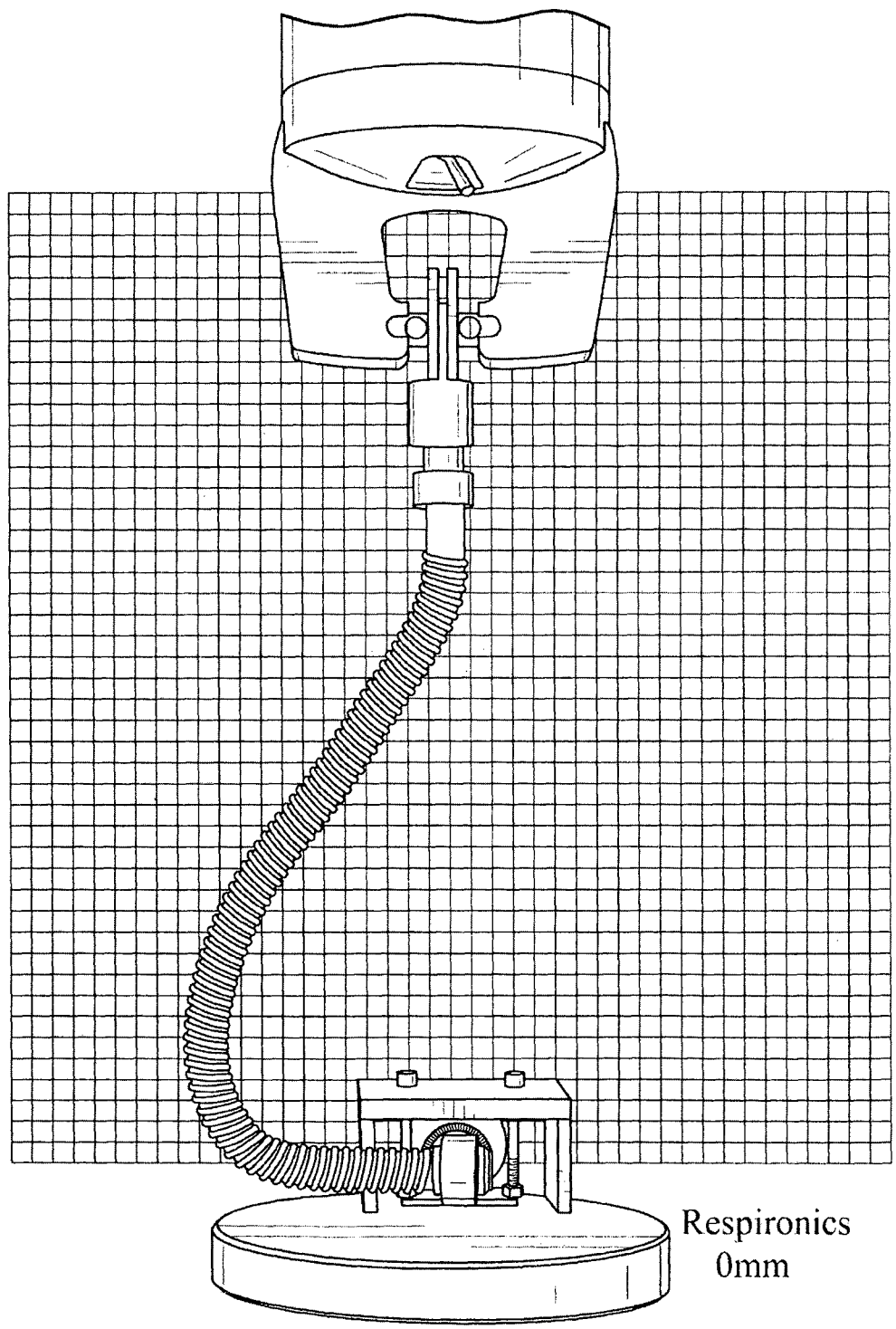
Figure 214:
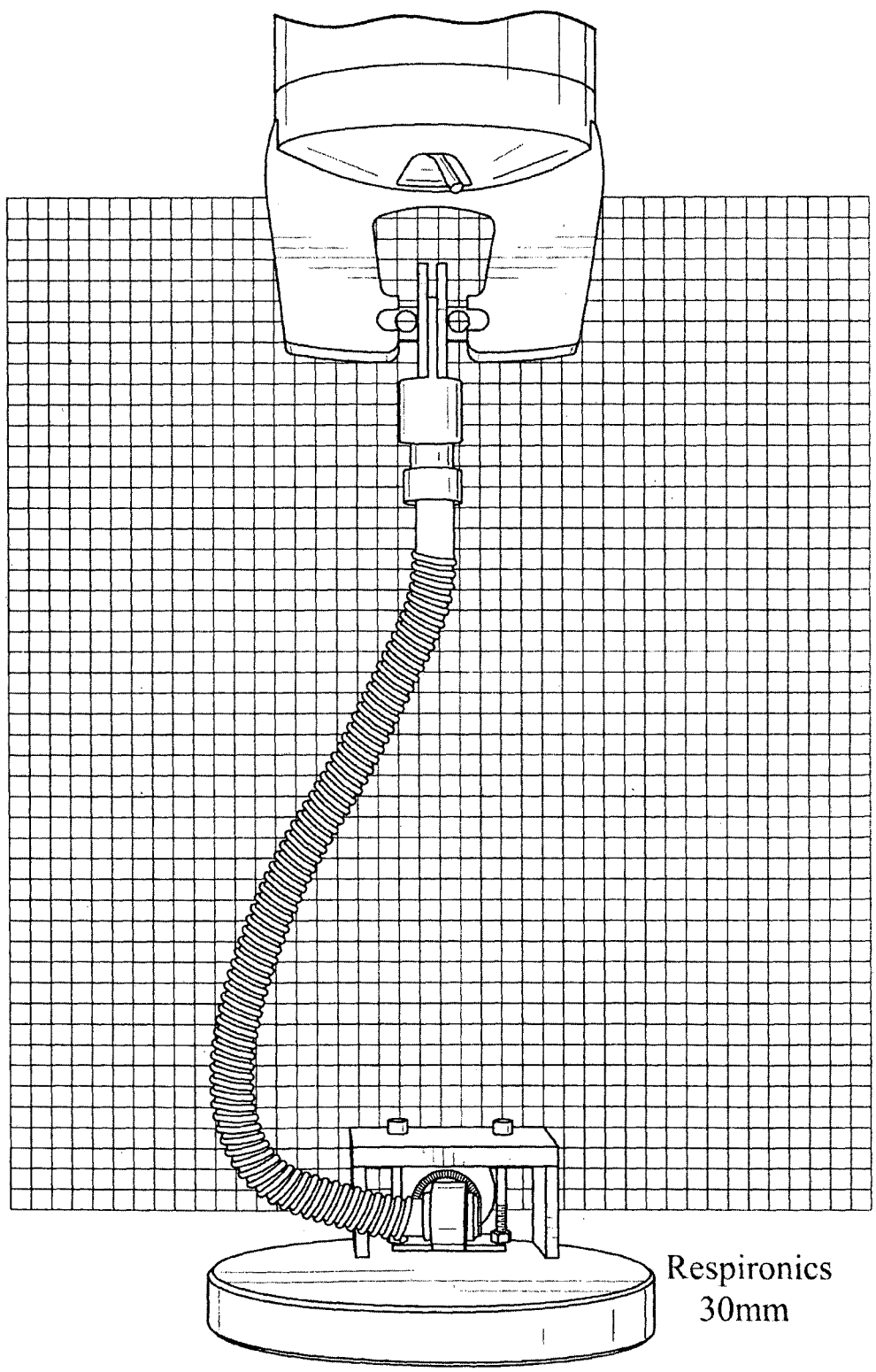
Figure 215:
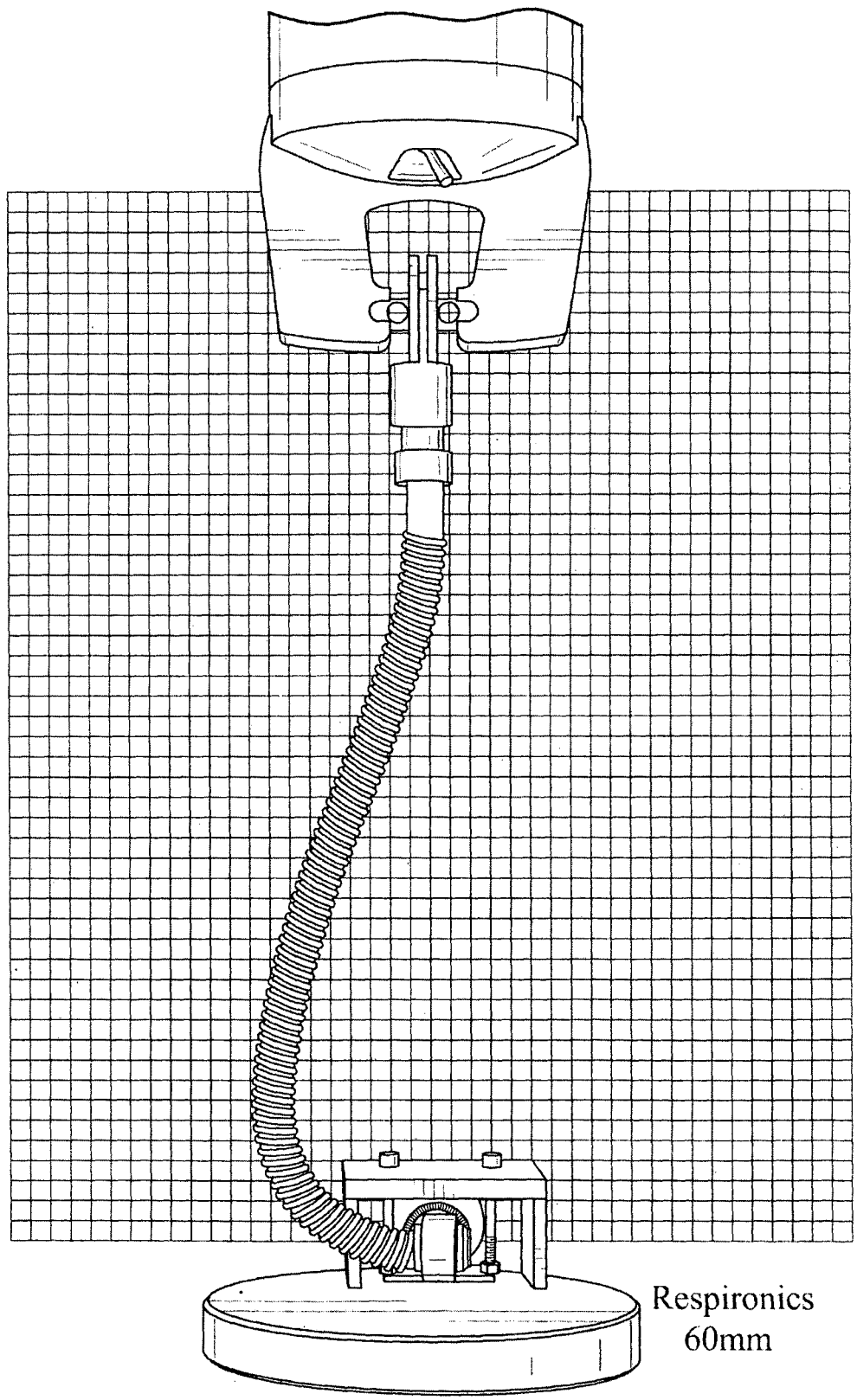
Figure 216:
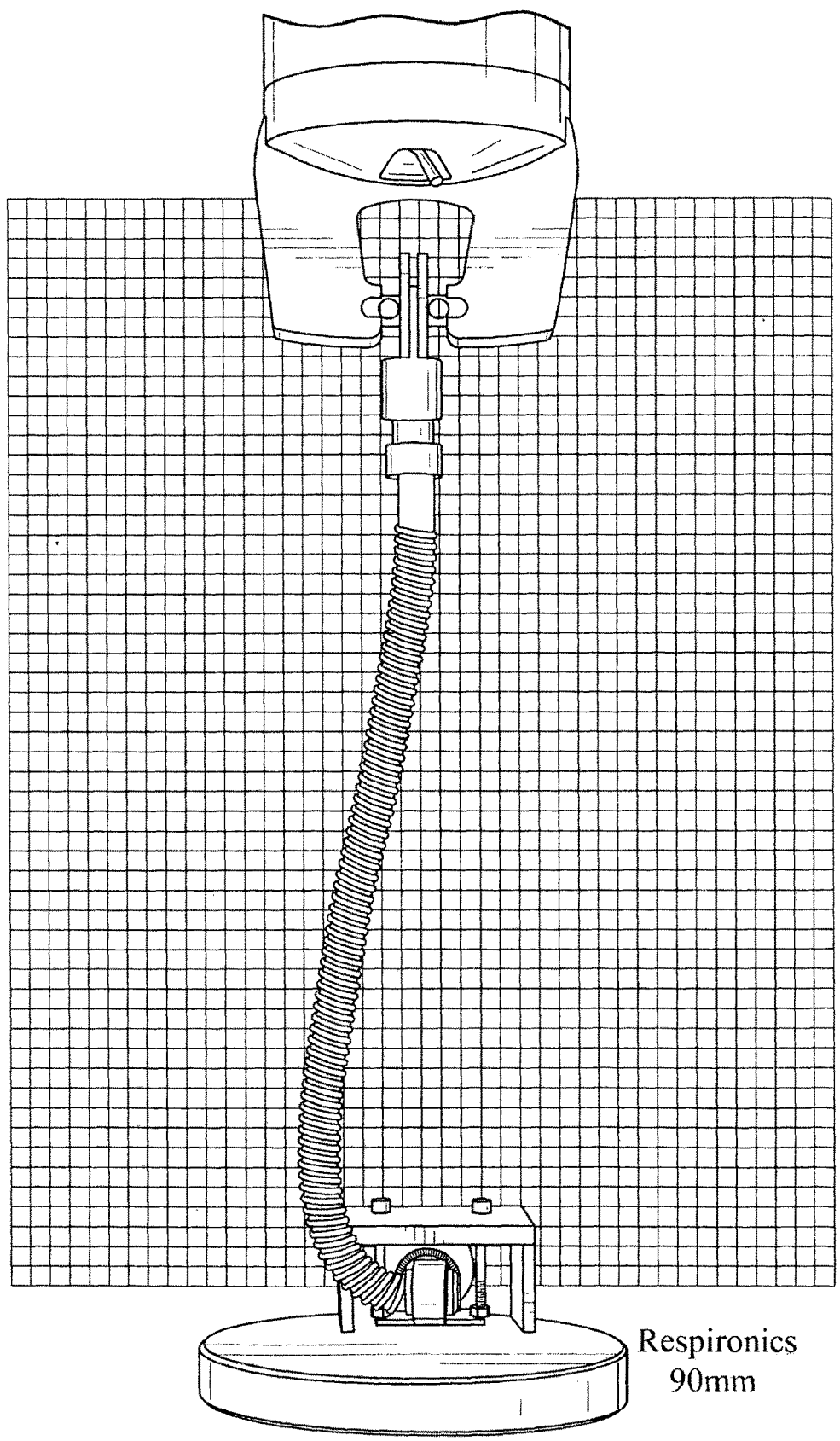
Figure 217:
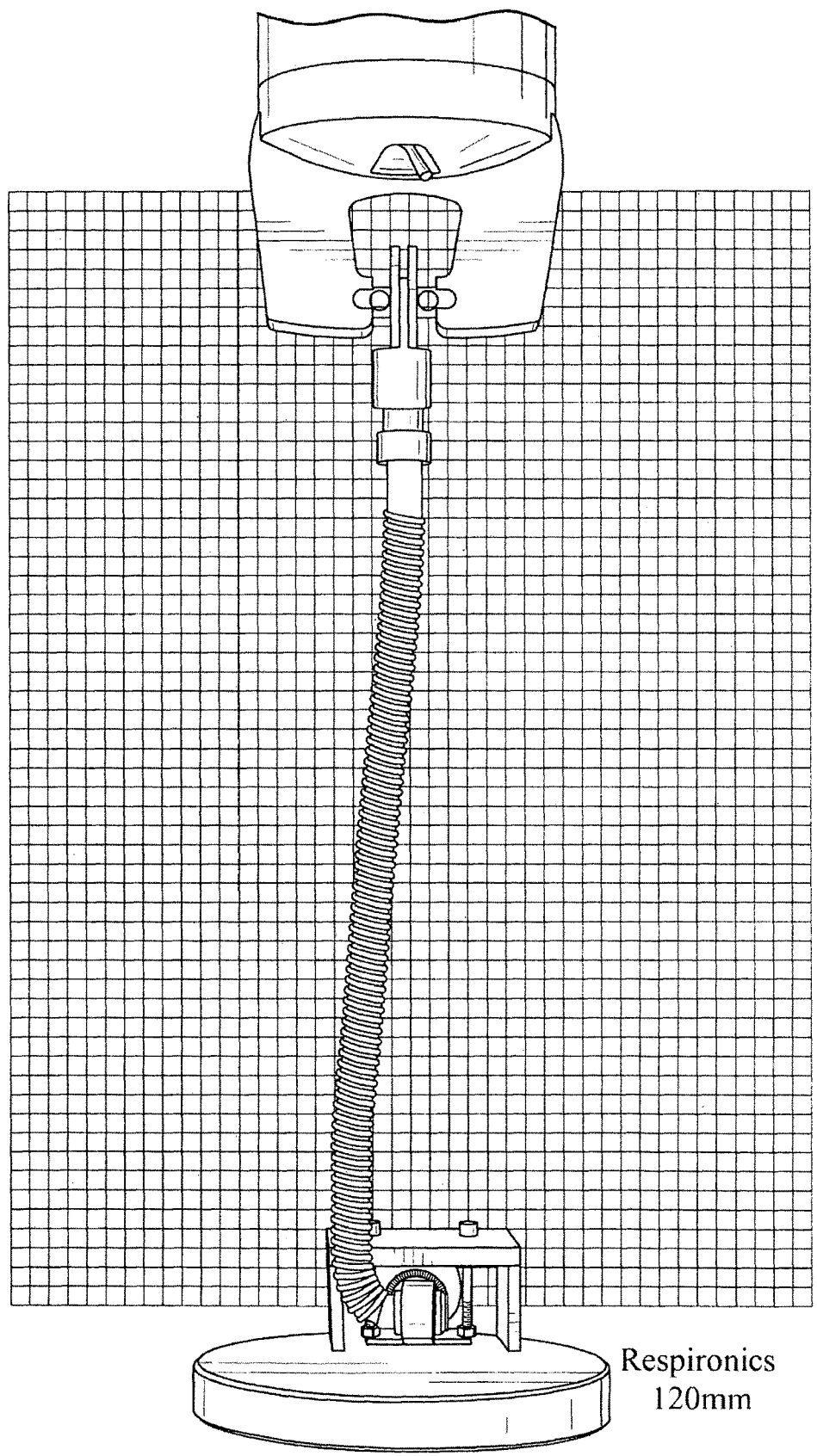
Figure 218:
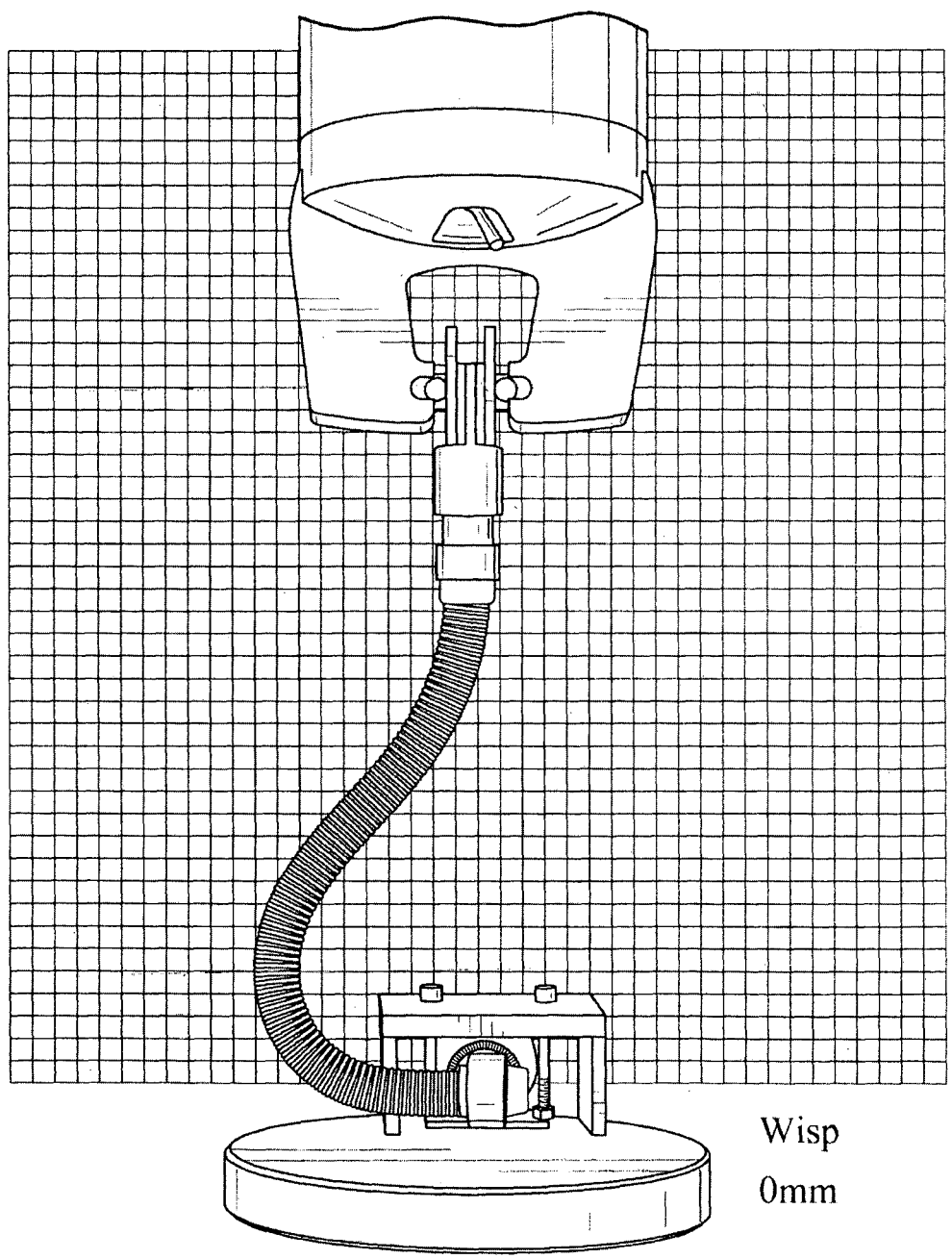
Figure 219:
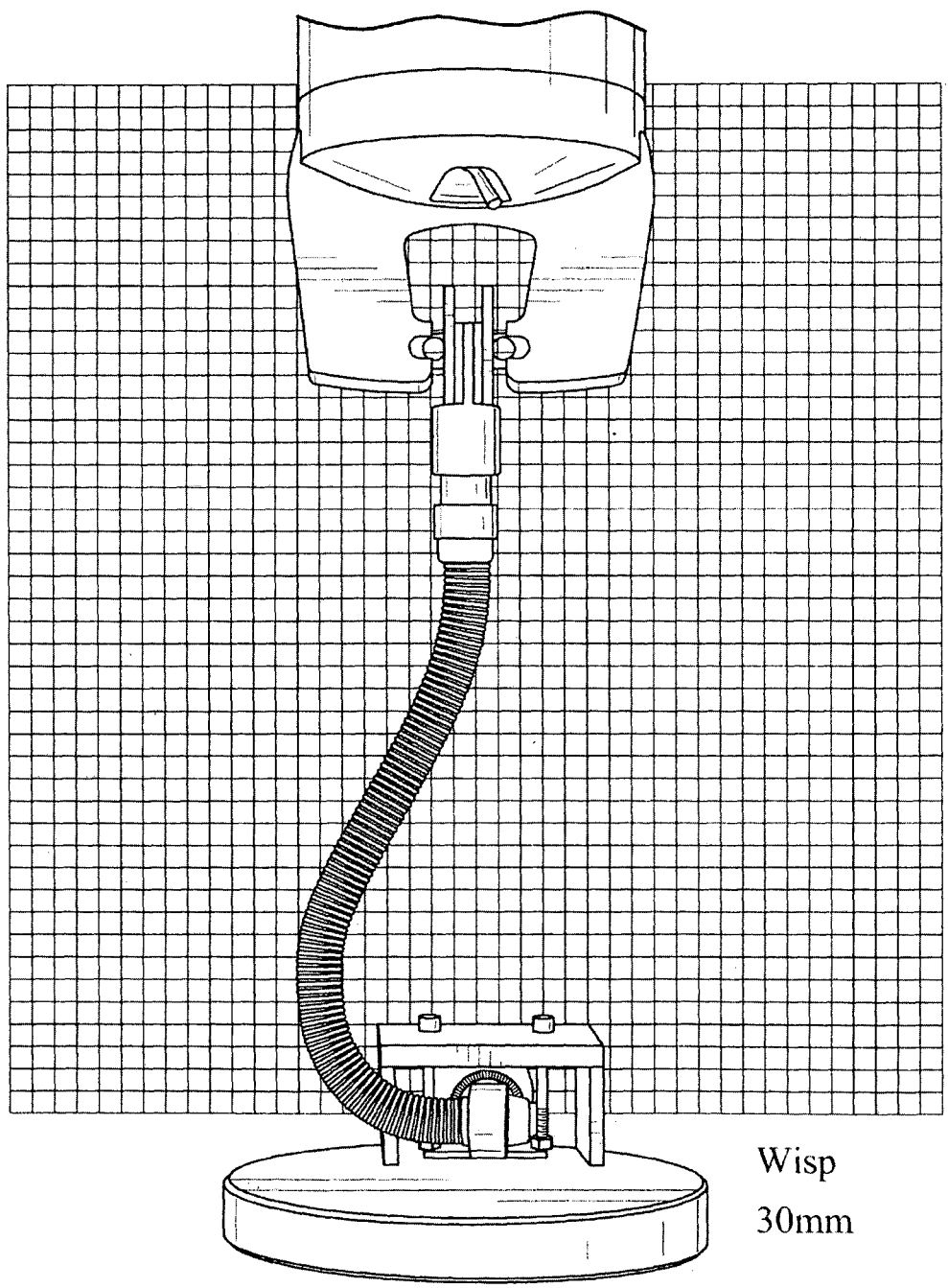
Figure 220:
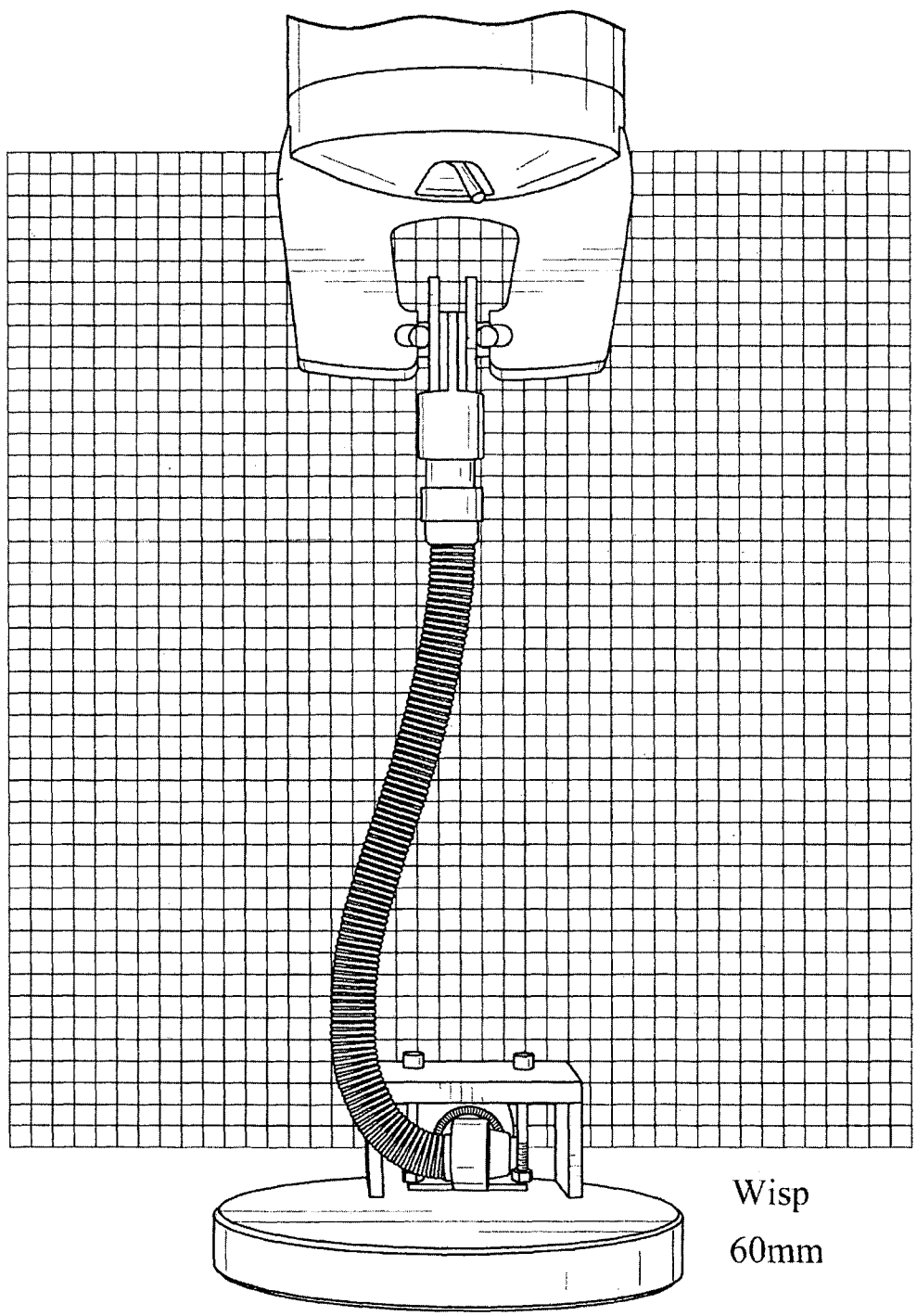
Figure 221:
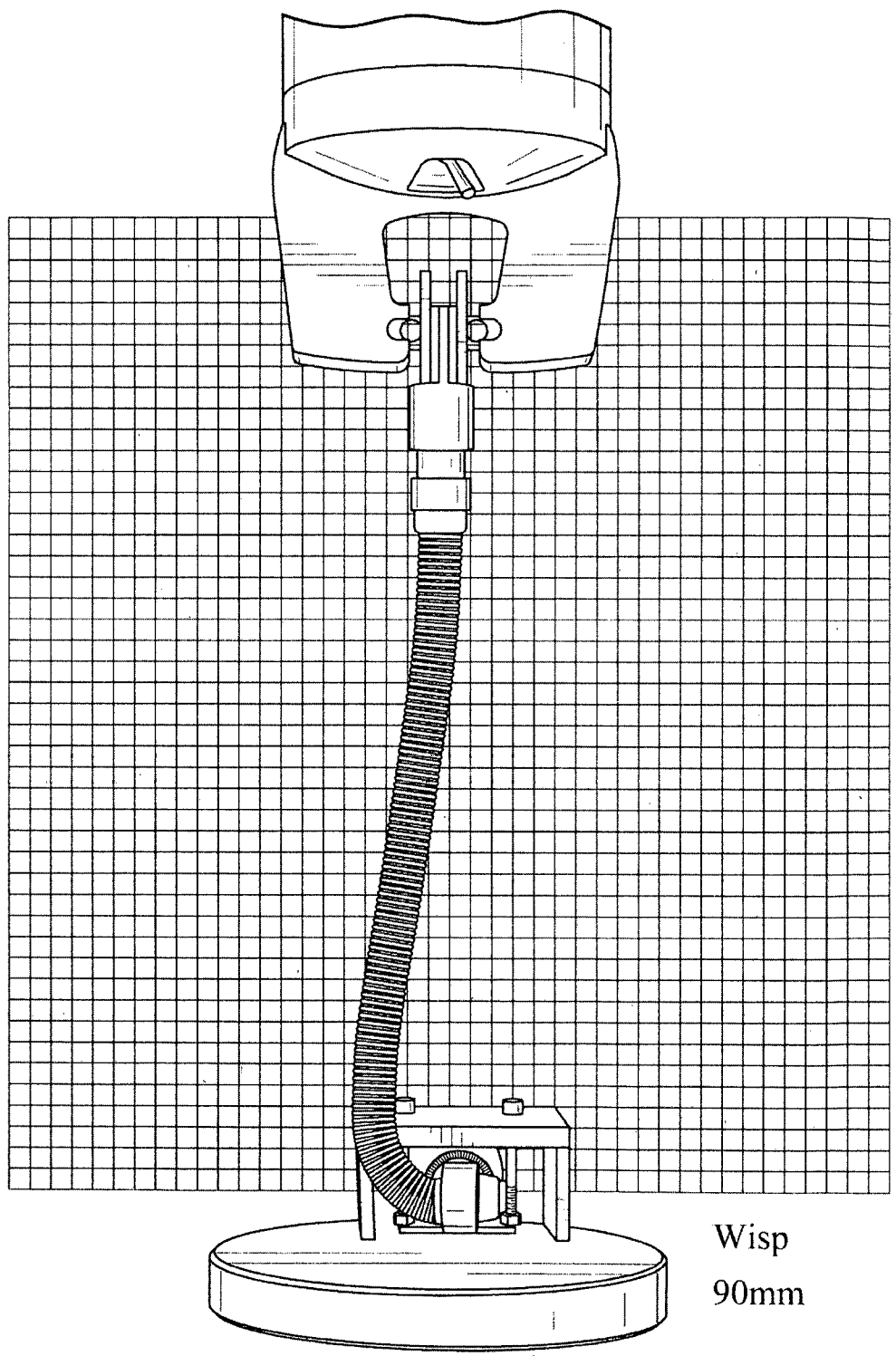
Figure 222:
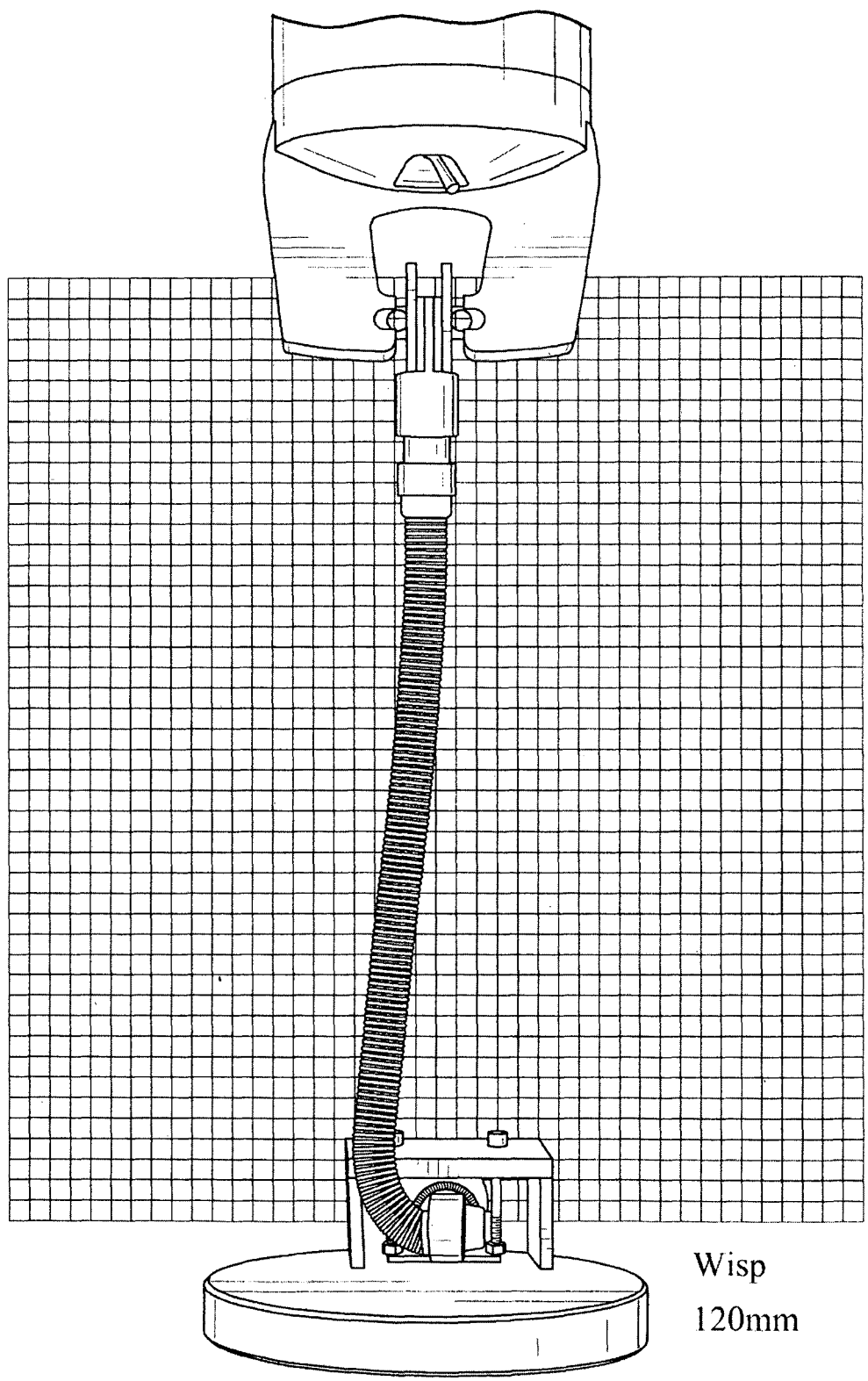

FIG. 202 is a side planar view of a retaining structure of a plenum connection region in accordance with one form of the present technology.

FIGS. 203 to 207 show a tube in accordance with one form of the present technology being elongated by a distance of 30 mm, 60 mm, 90 mm, and 120 mm with a lower end of the tube held in a fixed position with its longitudinal axis at its lower end being perpendicular to the direction of elongation before elongation commences.

FIGS. 208 to 212 show a ResMed™ Swift FX™ Nasal Pillows Mask tube being elongated by a distance of 30 mm, 60 mm, 90 mm, and 120 mm with a lower end of the tube held in a fixed position with its longitudinal axis at its lower end being perpendicular to the direction of elongation before elongation commences.

FIGS. 213 to 217 show a Philips™ Respironics™ GoLife™ Nasal Pillows Mask tube being elongated by a distance of 30 mm, 60 mm, 90 mm, and 120 mm with a lower end of the tube is held a fixed position with its longitudinal axis at its lower end being perpendicular to the direction of elongation before elongation commences.

FIGS. 218 to 222 show a Philips™ Respironics™ Wisp™ Nasal Mask tube being elongated by a distance of 30 mm, 60 mm, 90 mm, and 120 mm with a lower end of the tube held in a fixed position with its longitudinal axis at its lower end being perpendicular to the direction of elongation before elongation commences.

Figure 223:
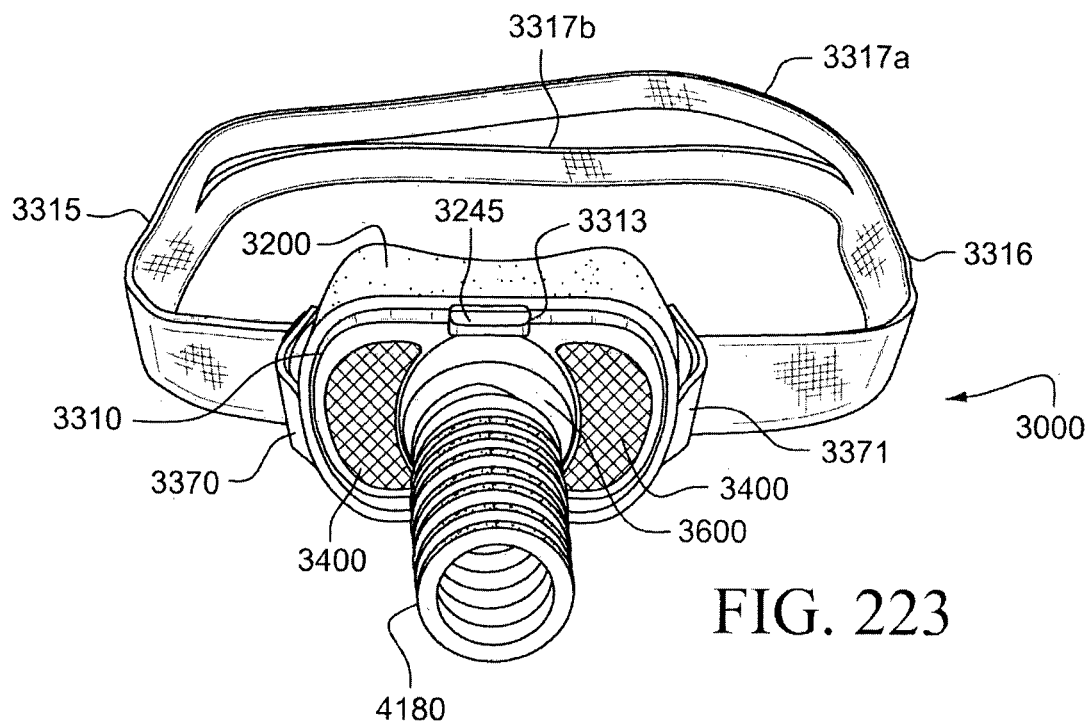

FIG. 223 shows a front view of a patient interface system according to an example of the present technology.

Figure 224:
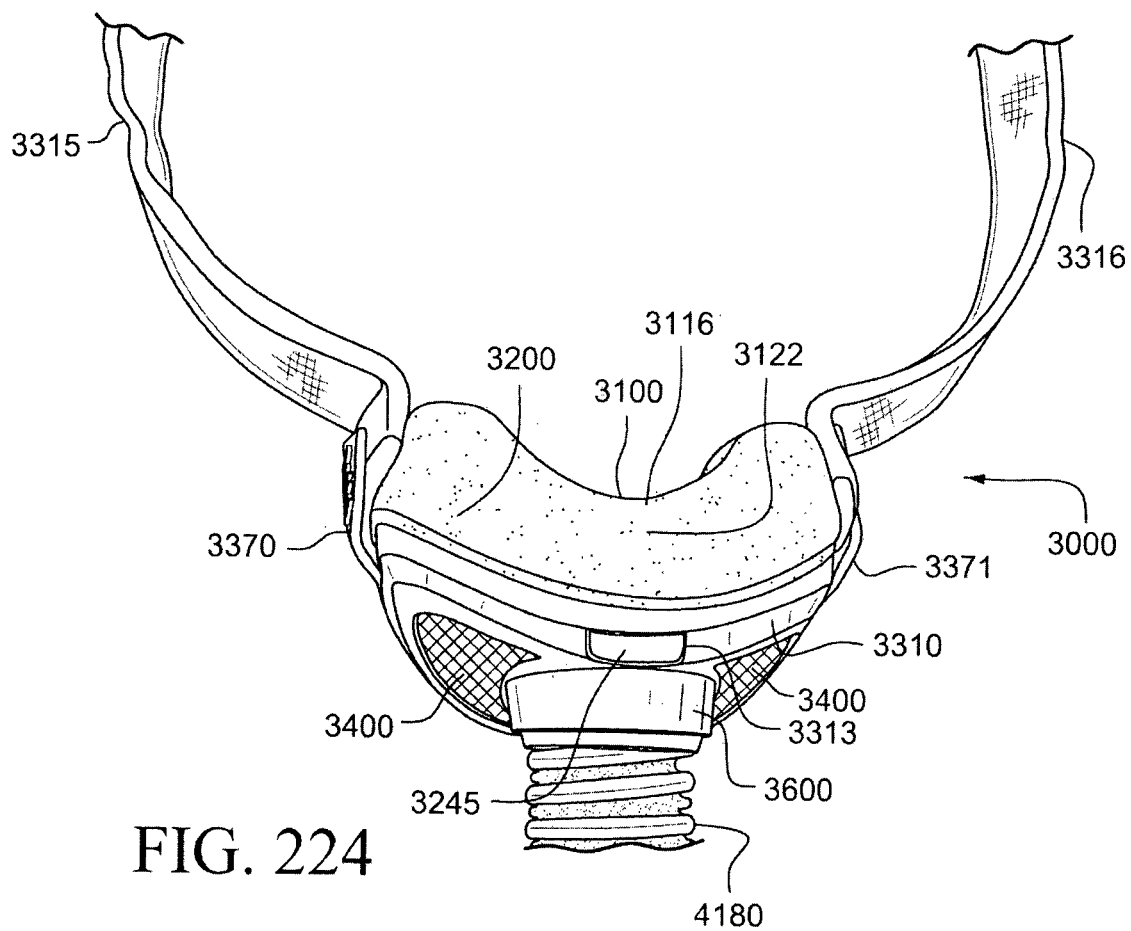

FIG. 224 shows a top view of a patient interface system according to an example of the present technology.

Figure 225:
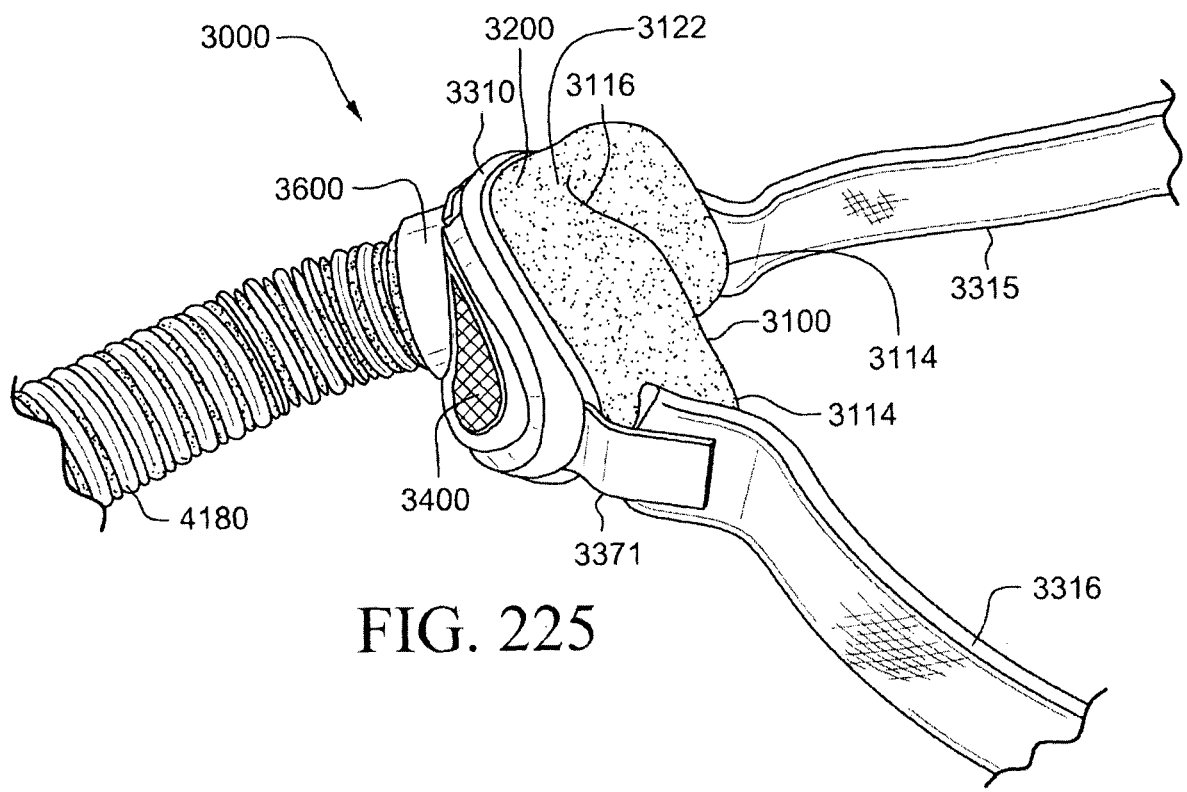

FIG. 225 shows a left side view of a patient interface system according to an example of the present technology.

Figure 226:
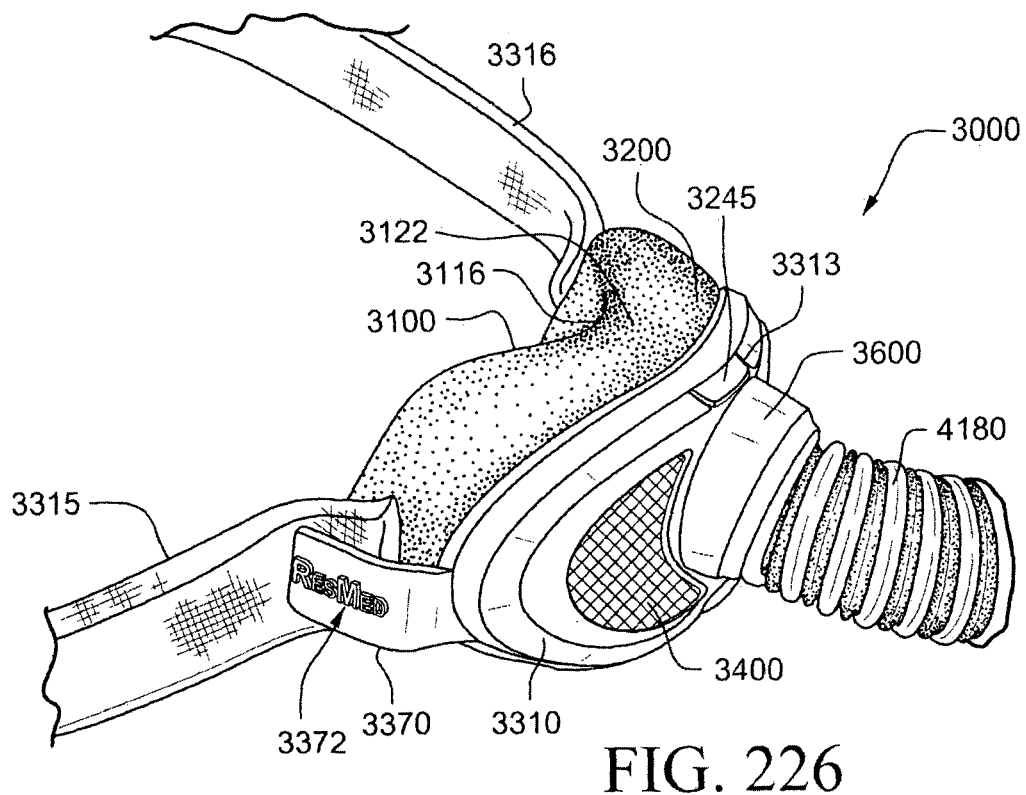

FIG. 226 shows a right side view of a patient interface system according to an example of the present technology.

Figure 227:
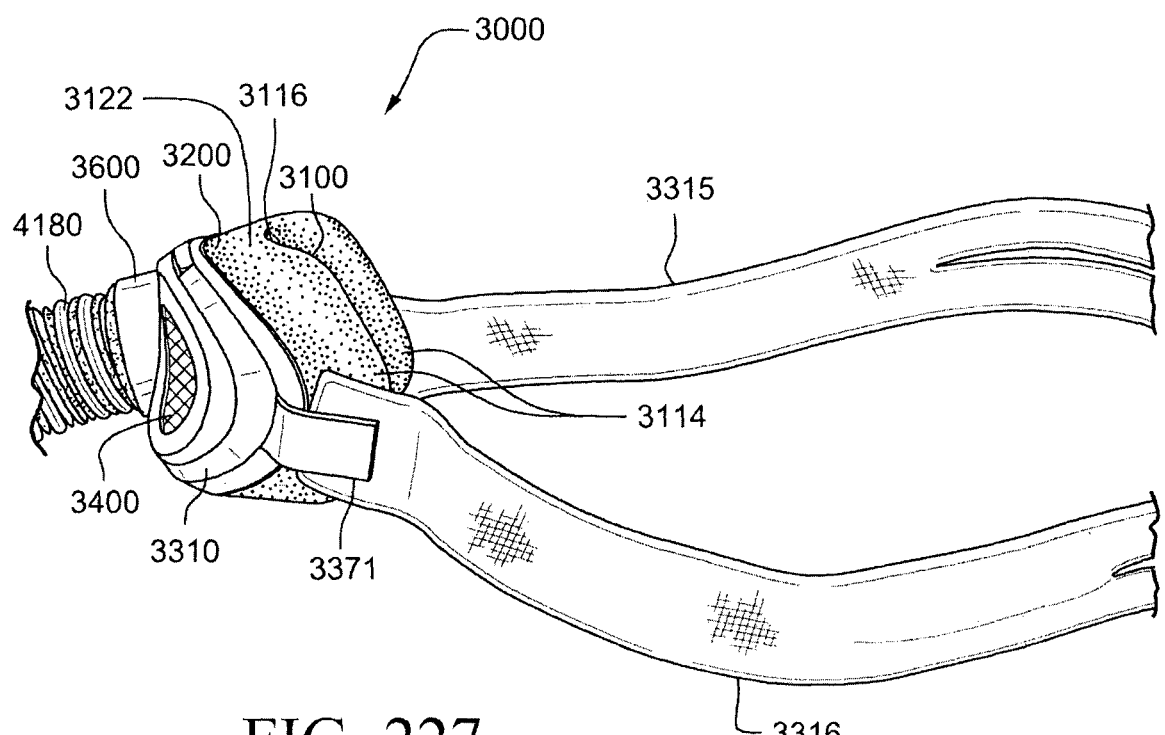

FIG. 227 shows another left side view of a patient interface system according to an example of the present technology.

Figure 228:
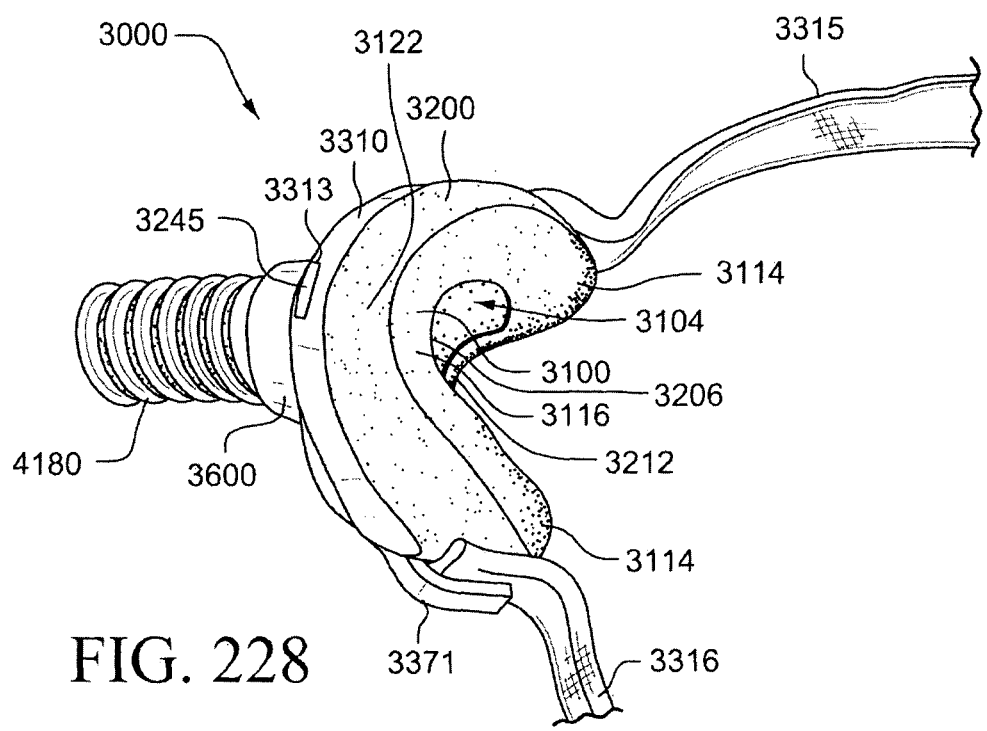

FIG. 228 shows another top view of a patient interface system according to an example of the present technology.

Figure 229:
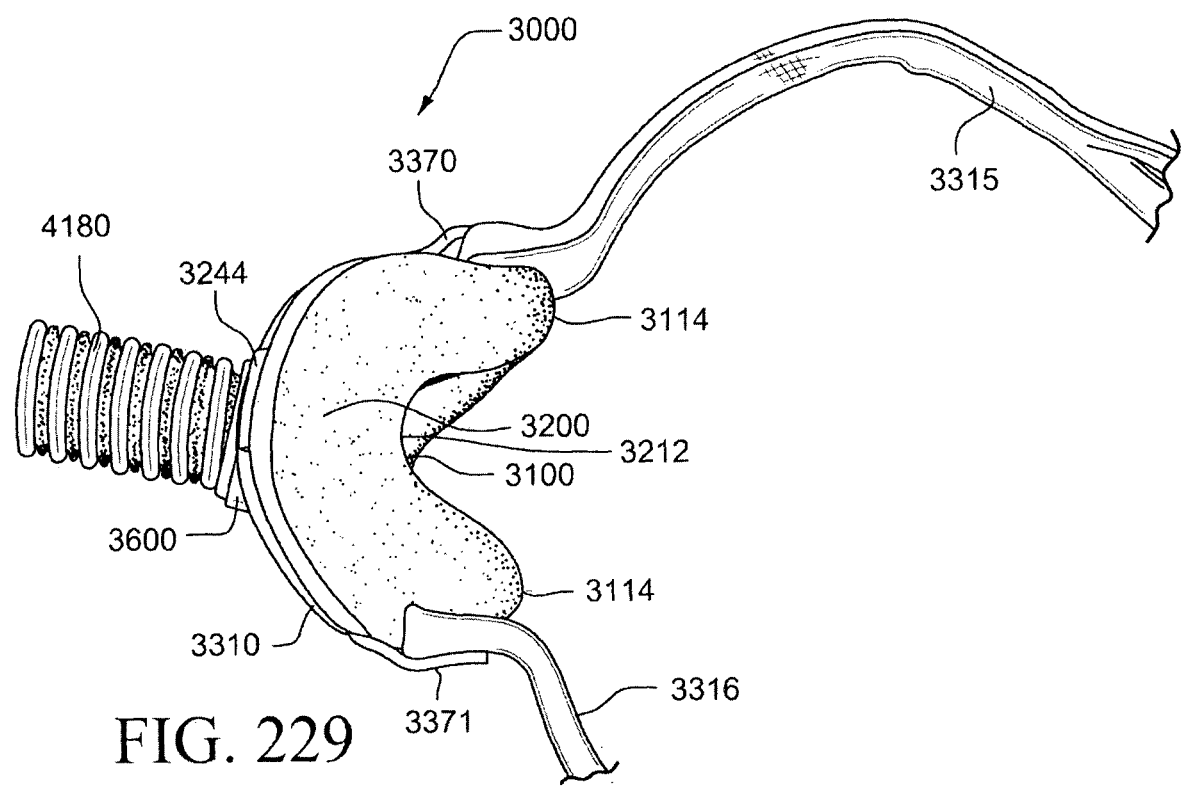

FIG. 229 shows another top view of a patient interface system according to an example of the present technology.

Figure 230:
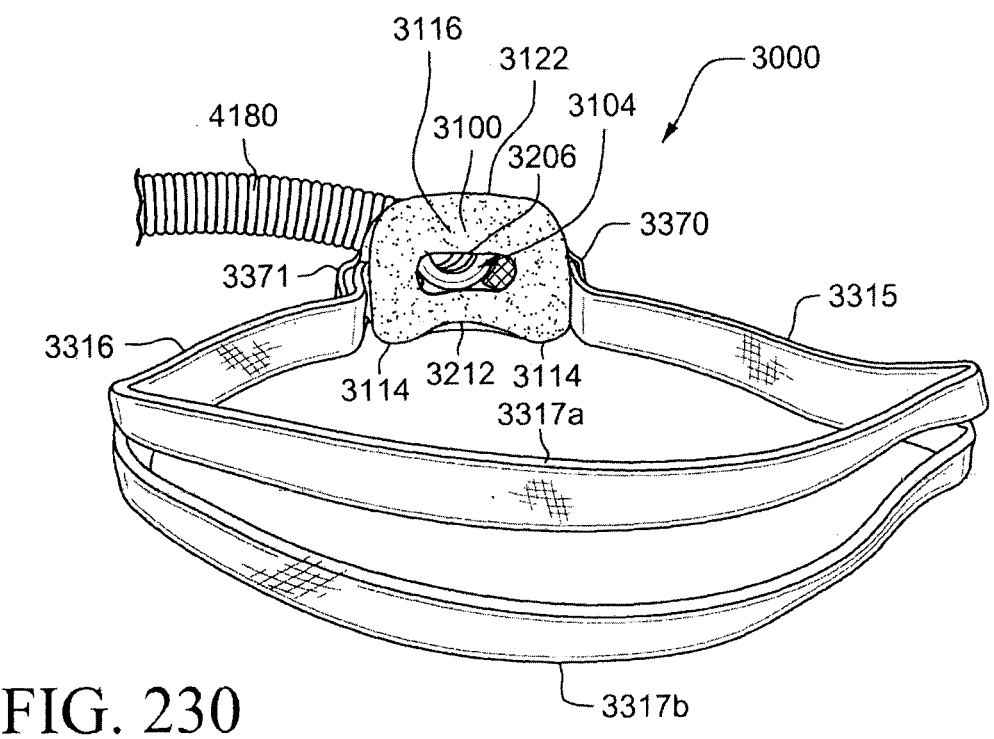

FIG. 230 shows a rear view of a patient interface system according to an example of the present technology.

Figure 231:
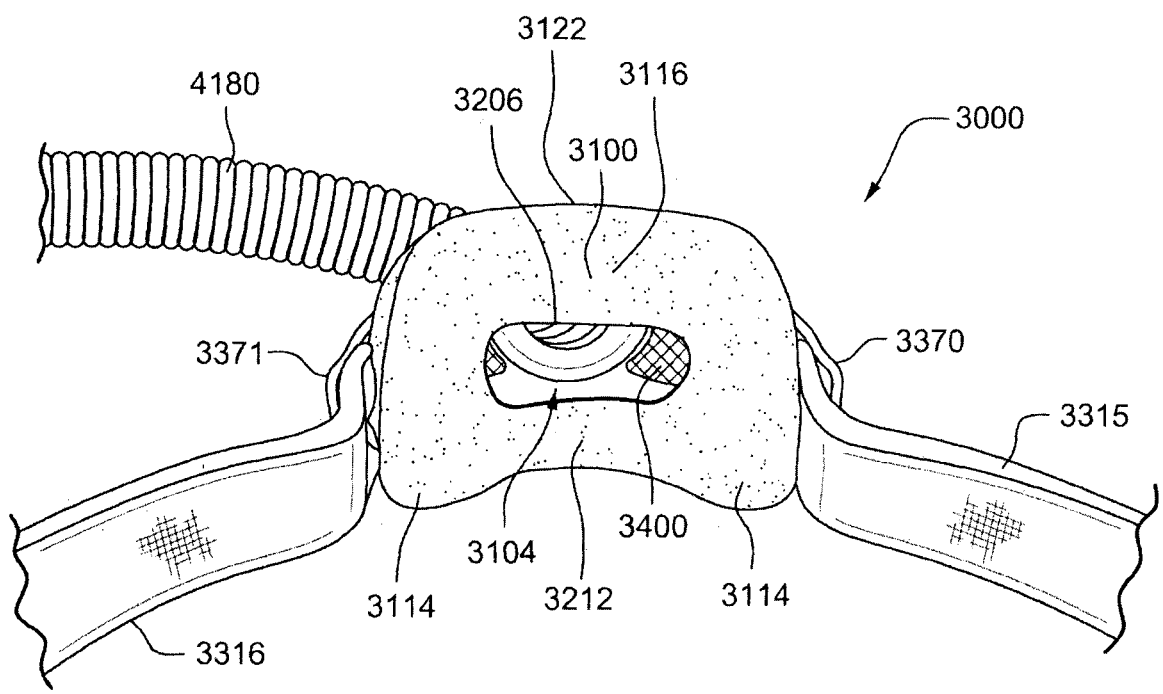

FIG. 231 shows another rear view of a patient interface system according to an example of the present technology.

Figure 232:
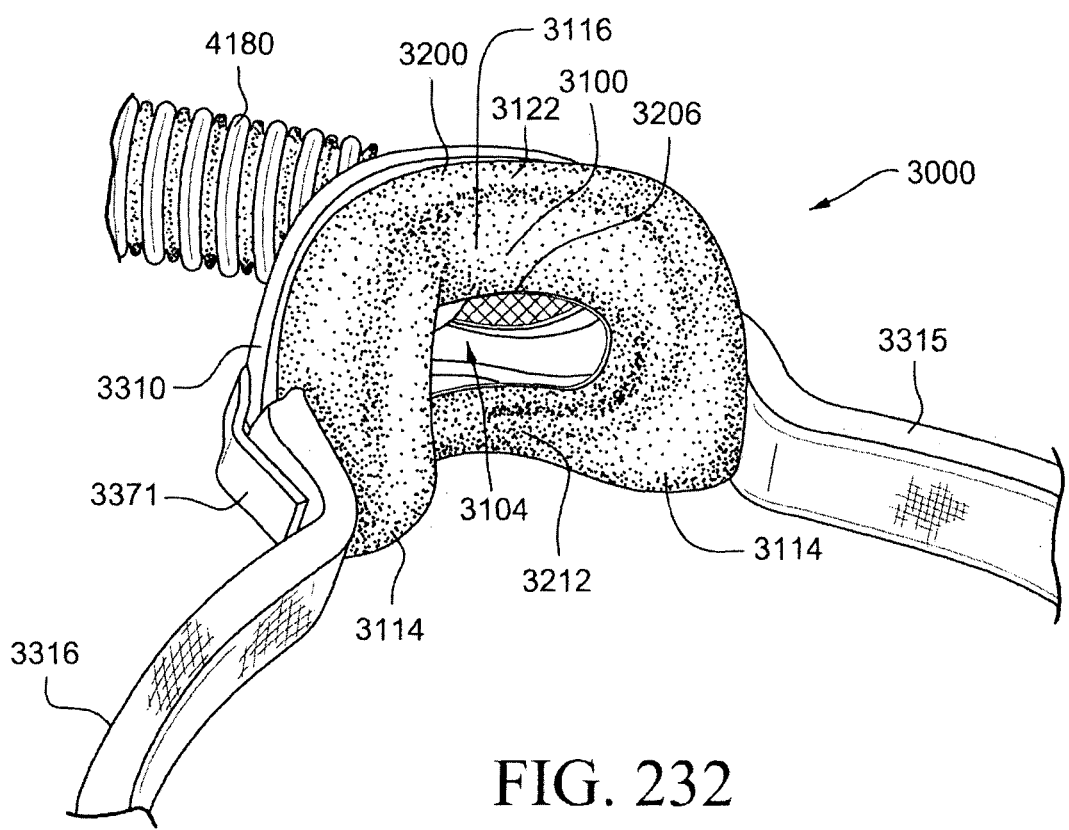

FIG. 232 shows a rear perspective view of a patient interface system according to an example of the present technology.

Figure 233A:
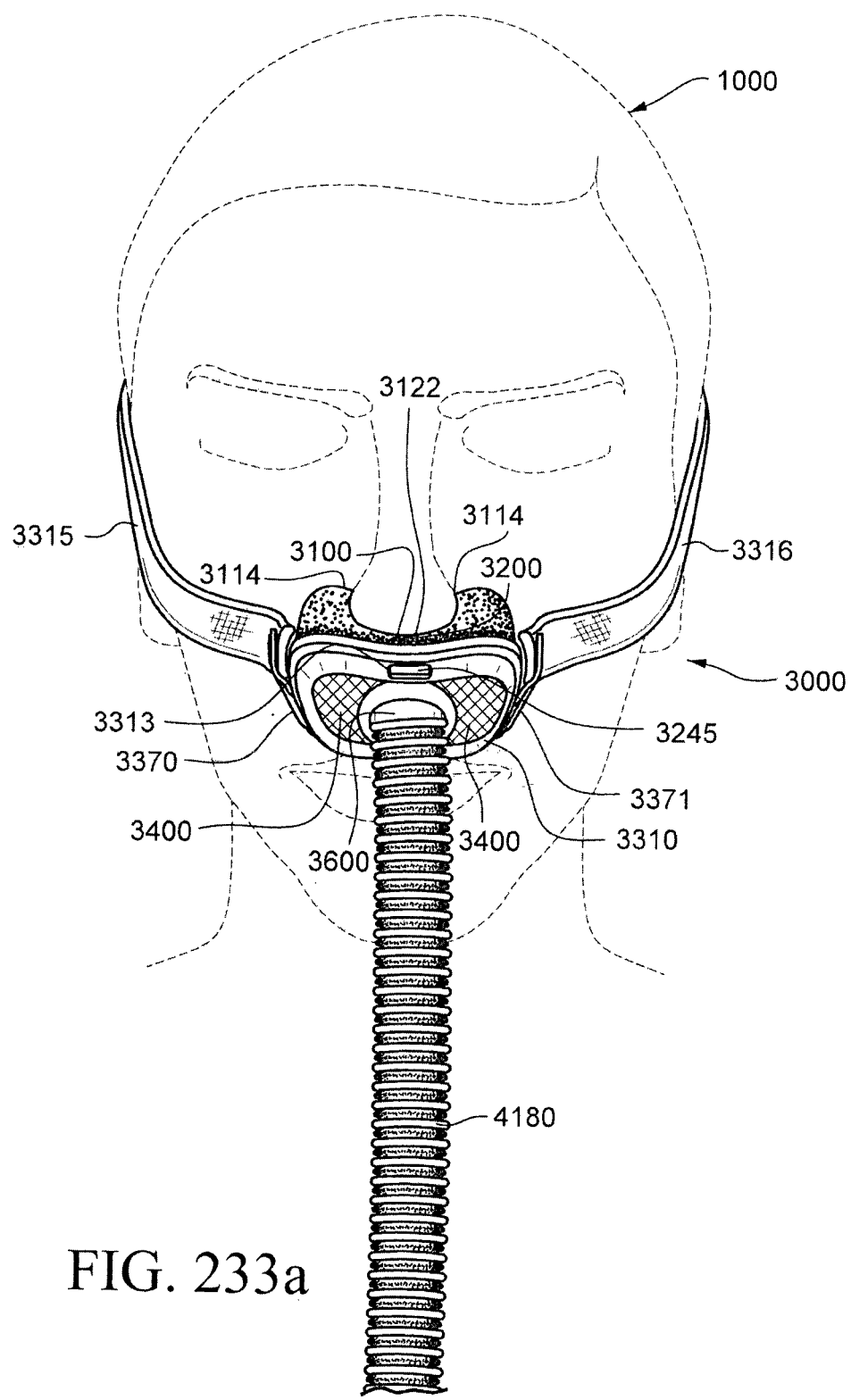

FIG. 233*a* shows a front view of a patient interface system according to an example of the present technology worn by a patient.

Figure 233B:
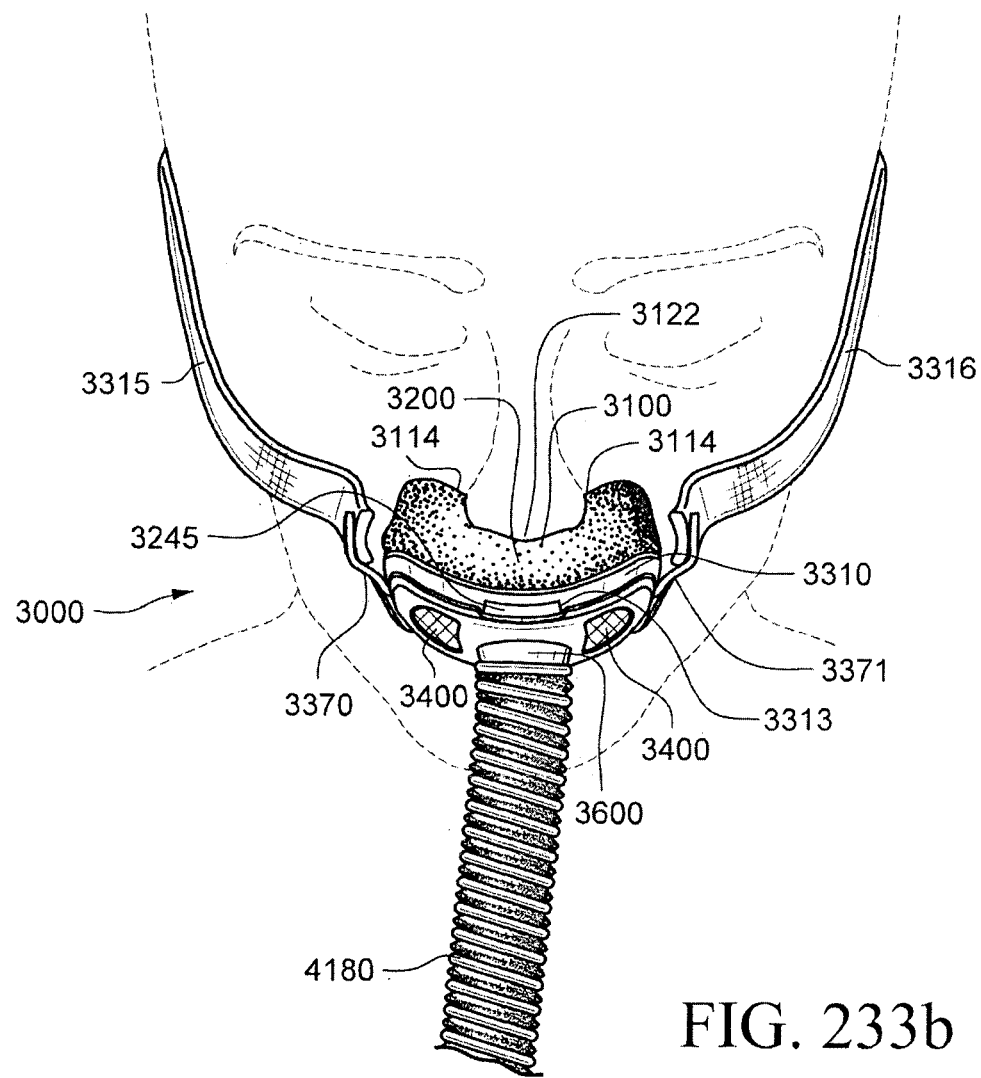

FIG. 233*b* shows a top view of a patient interface system according to an example of the present technology worn by a patient.

Figure 233C:
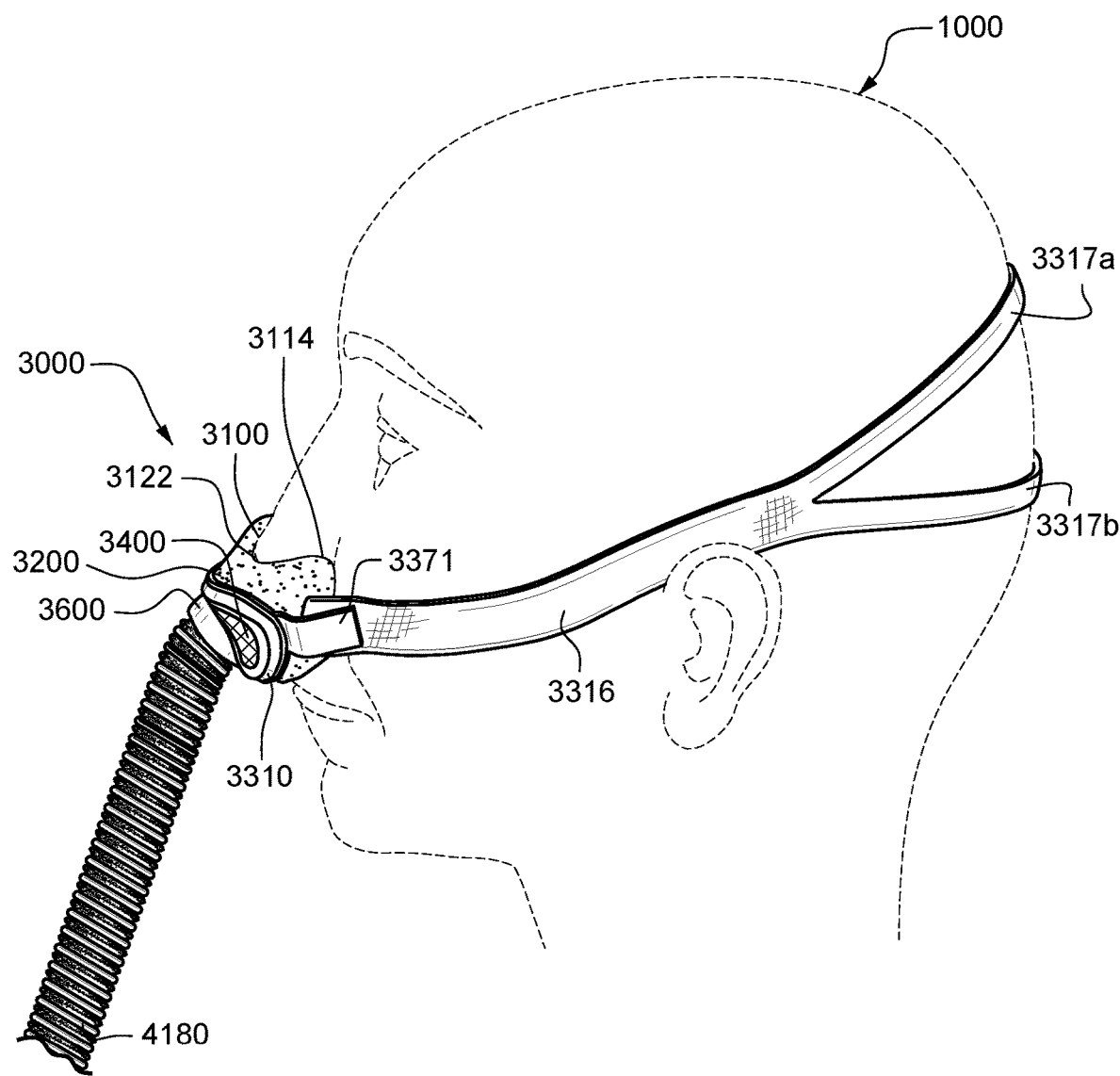

FIG. 233*c* shows a left side view of a patient interface system according to an example of the present technology worn by a patient.

Figure 233D:
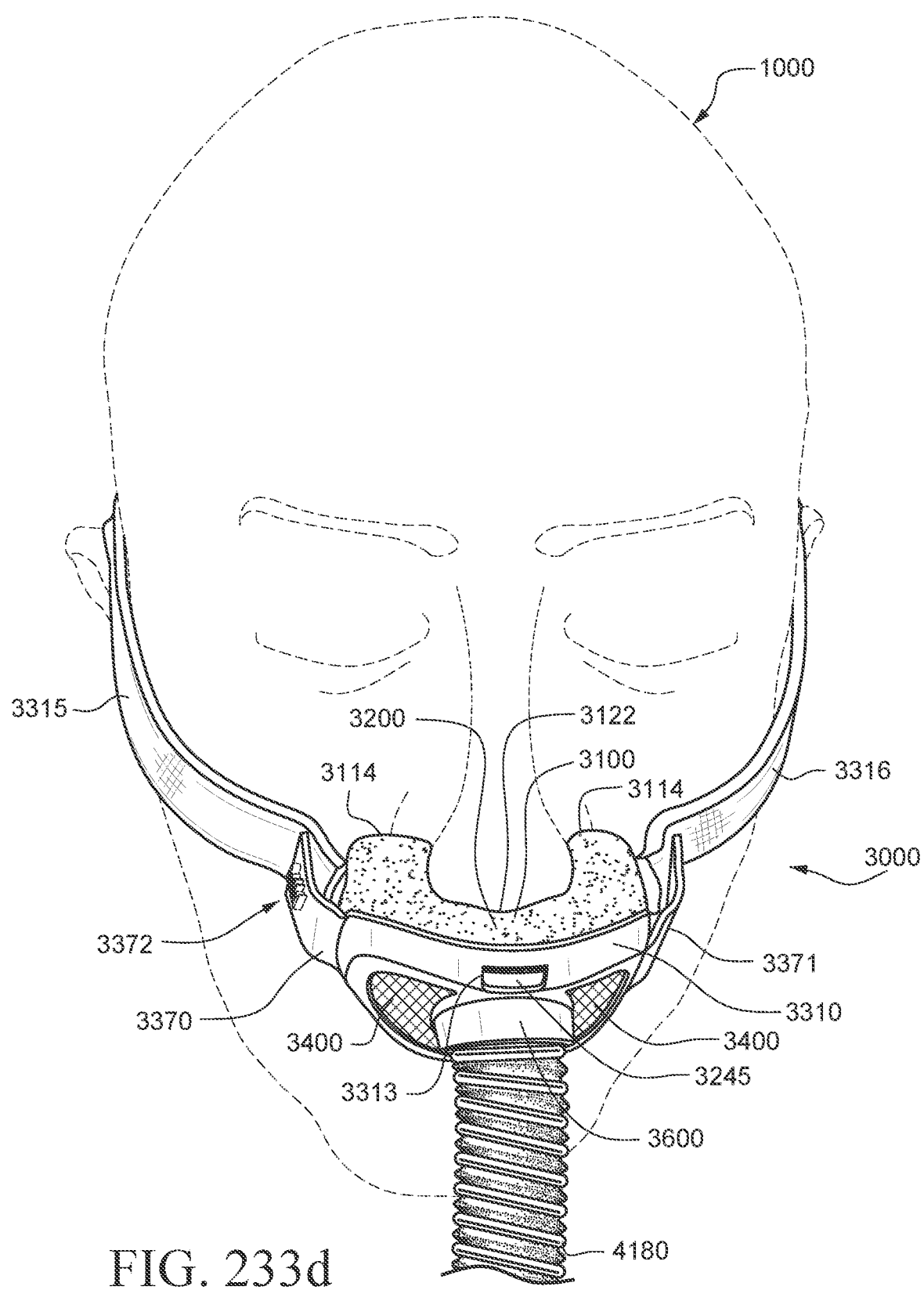

FIG. 233*d* shows a front perspective view of a patient interface system according to an example of the present technology worn by a patient.

Figure 233E:
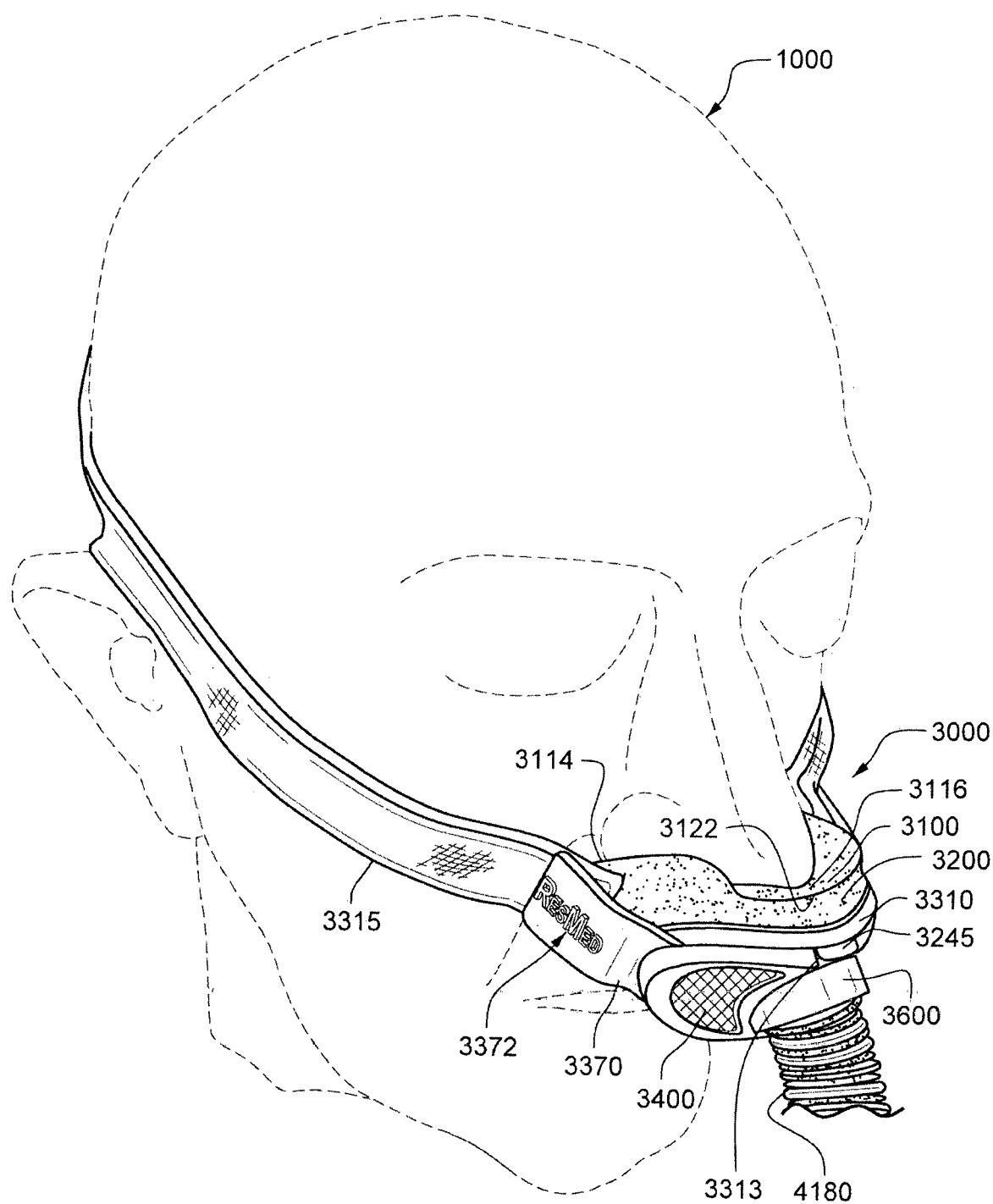

FIG. 233*e* shows a right side perspective view of a patient interface system according to an example of the present technology worn by a patient.

Figure 233F:
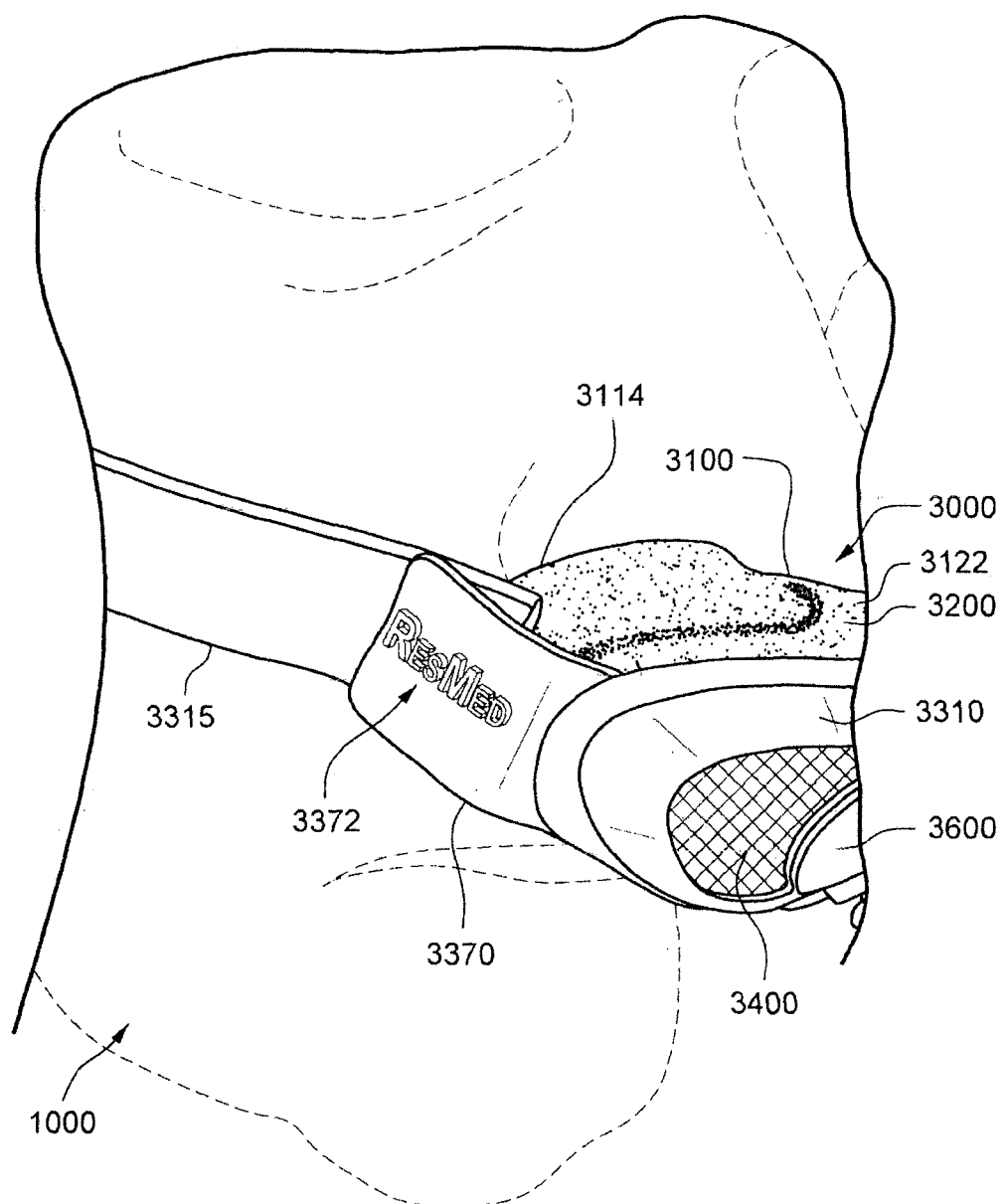

FIG. 233*f* shows a detailed right side perspective view of a patient interface system according to an example of the present technology worn by a patient.

Figure 233G:
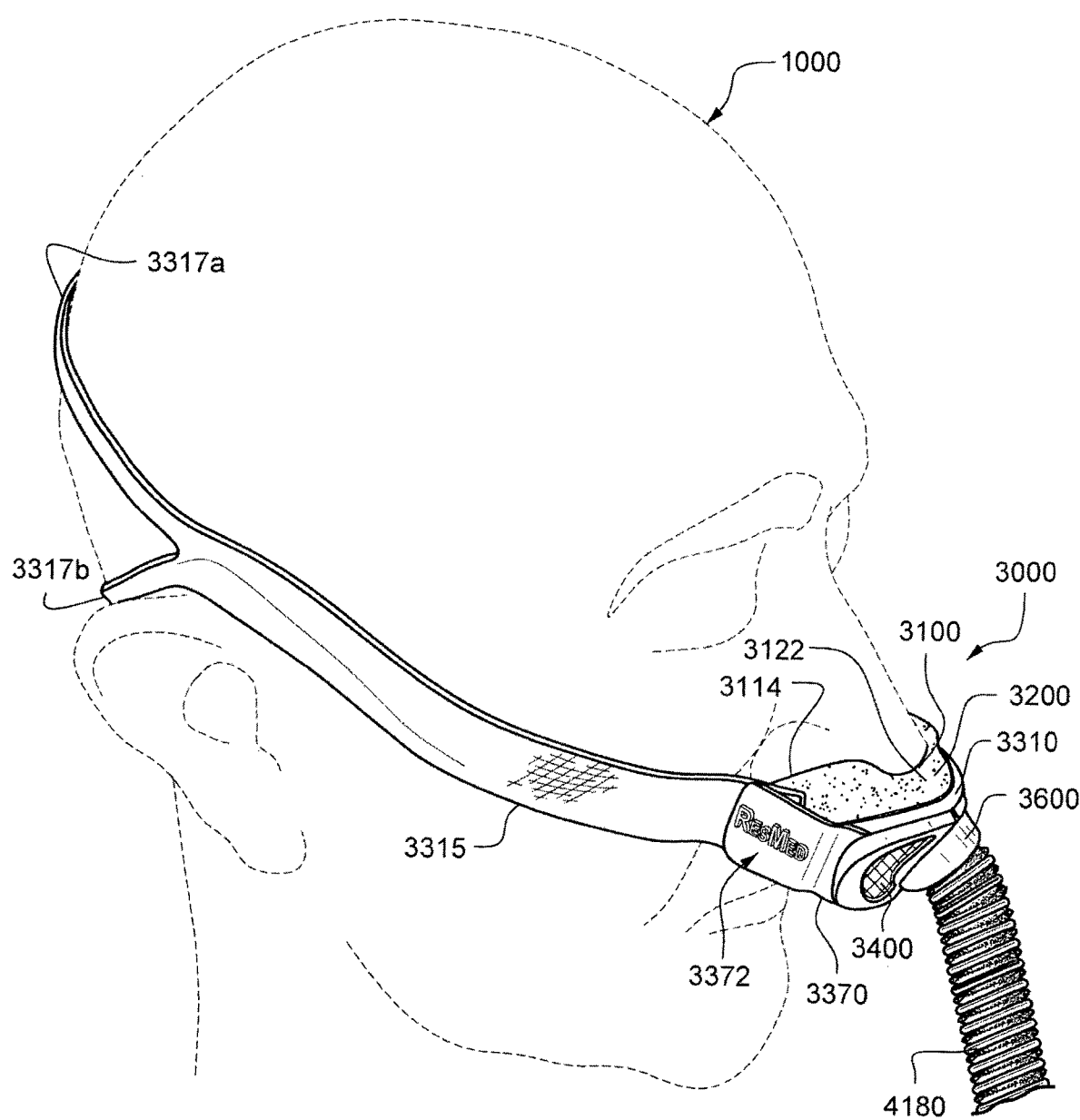

FIG. 233*g* shows another right side perspective view of a patient interface system according to an example of the present technology worn by a patient.

Figure 233H:
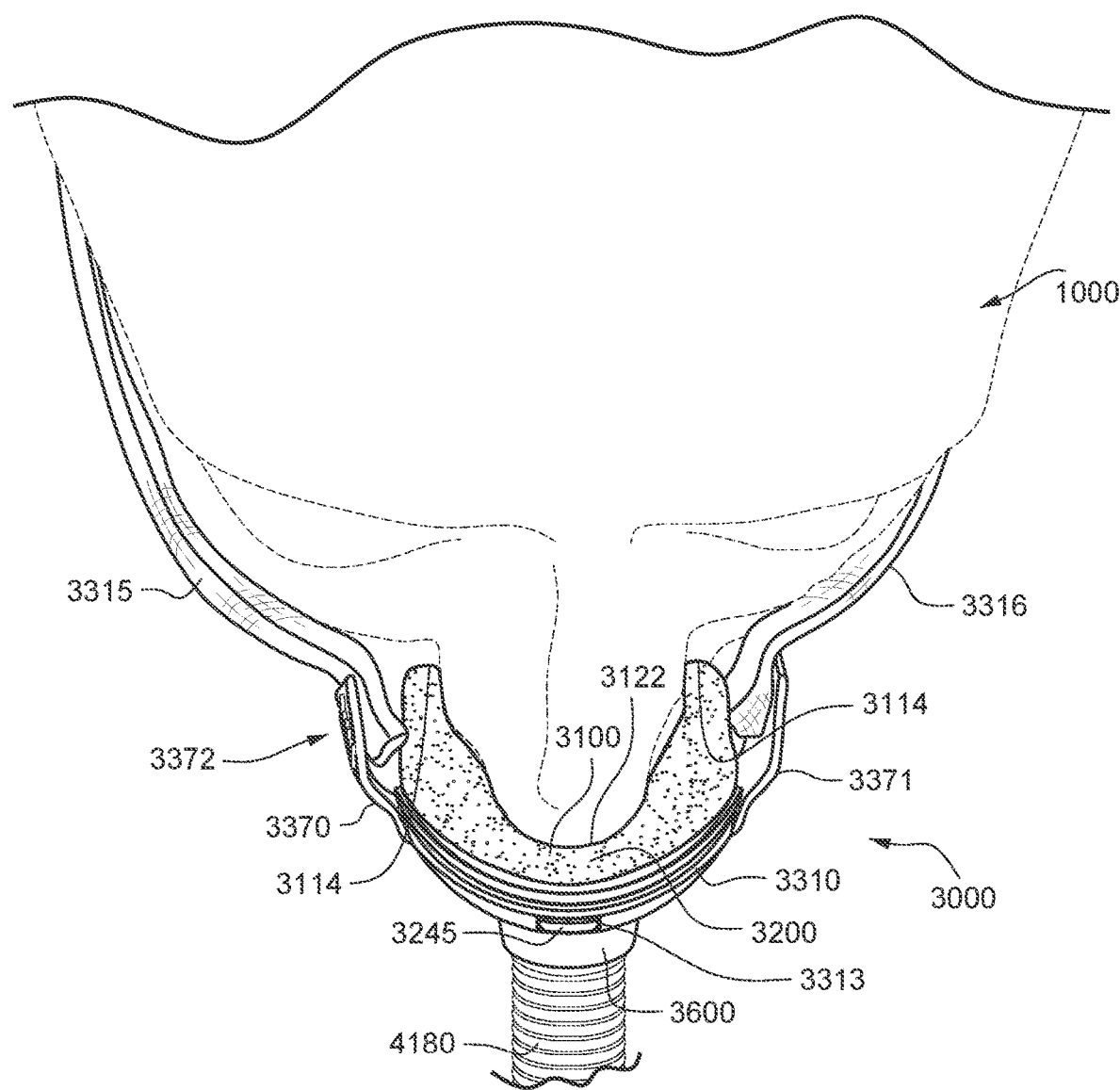

FIG. 233*h* shows a top view of a patient interface system according to an example of the present technology worn by a patient.

Figure 234A:
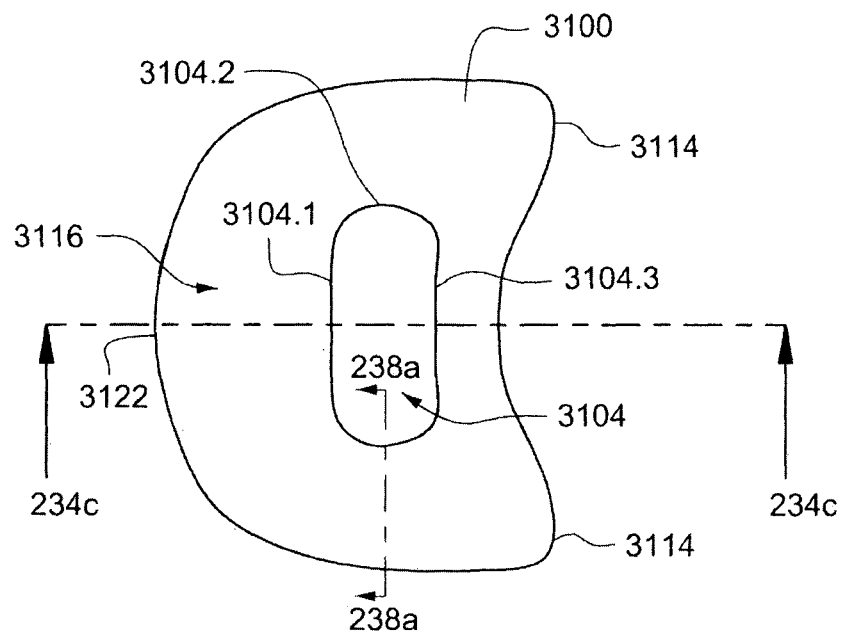

FIG. 234*a* shows a top view of a nasal cradle cushion of a patient interface in accordance with an example of the present technology.

Figure 234B:
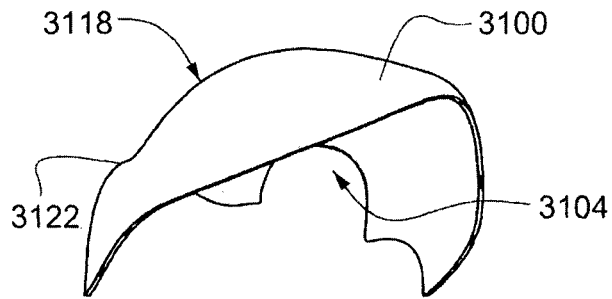

FIG. 234b shows a bottom cross-sectional view taken through line 234c-234c of FIG. 234a of a nasal cradle cushion of a patient interface in accordance with an example of the present technology.

Figure 234C:
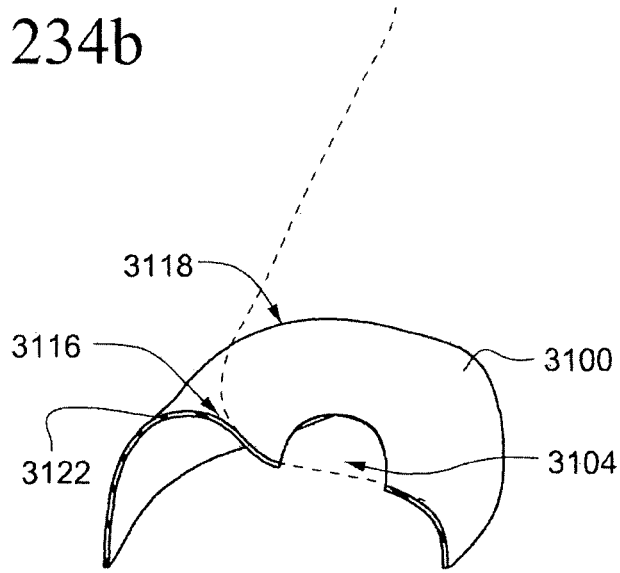

FIG. 234c shows a side cross-sectional view taken through line 234c-234c of FIG. 234a of a nasal cradle cushion of a patient interface in accordance with an example of the present technology. A patient's nose is shown in dashed lines.

Figure 235A:
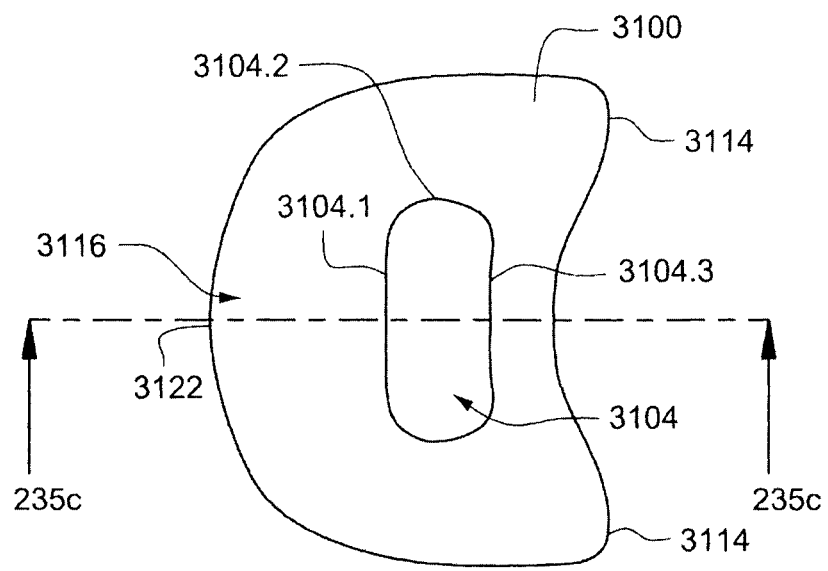

FIG. 235a shows a top view of another nasal cradle cushion of a patient interface in accordance with another example of the present technology.

Figure 235B:
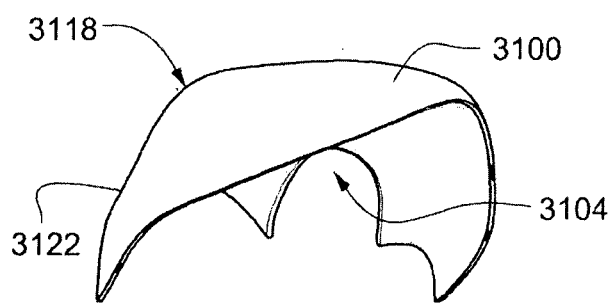

FIG. 235b shows a bottom cross-sectional view taken through line 235c-235c of FIG. 235a of another nasal cradle cushion of a patient interface in accordance with another example of the present technology.

Figure 235C:
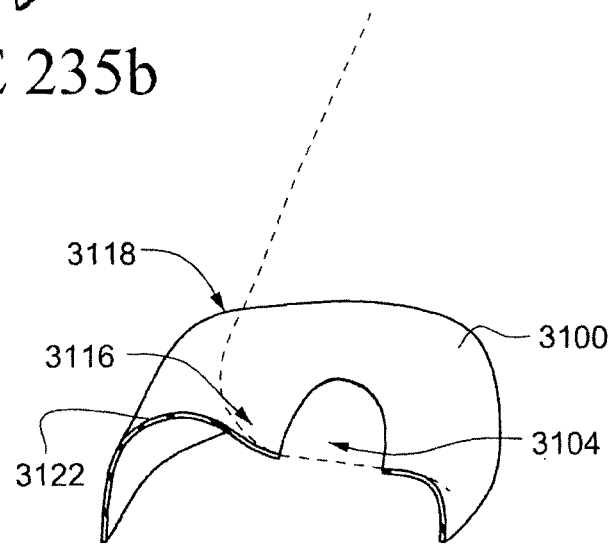

FIG. 235c shows a side cross-sectional view taken through line 235c-235c of FIG. 235a of another nasal cradle cushion of a patient interface in accordance with an example of the present technology. A patient's nose is shown in dashed lines.

Figure 236A:
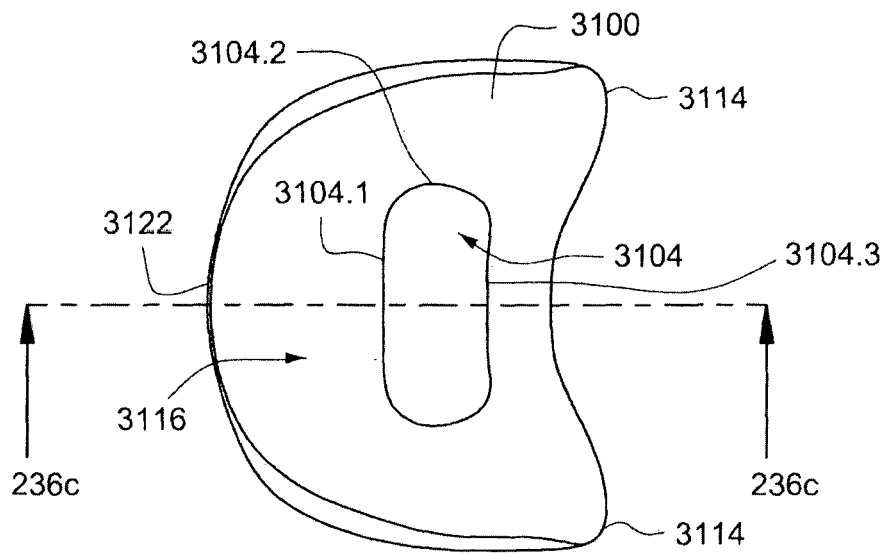

FIG. 236a shows a top view of another nasal cradle cushion of a patient interface in accordance with another example of the present technology.

Figure 236B:
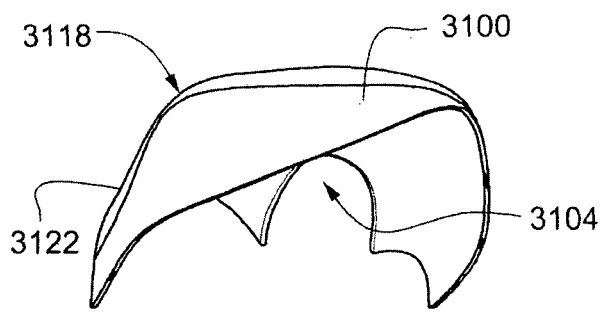

FIG. 236b shows a bottom cross-sectional view taken through line 236c-236c of FIG. 236a of another nasal cradle cushion of a patient interface in accordance with another example of the present technology.

Figure 236C:
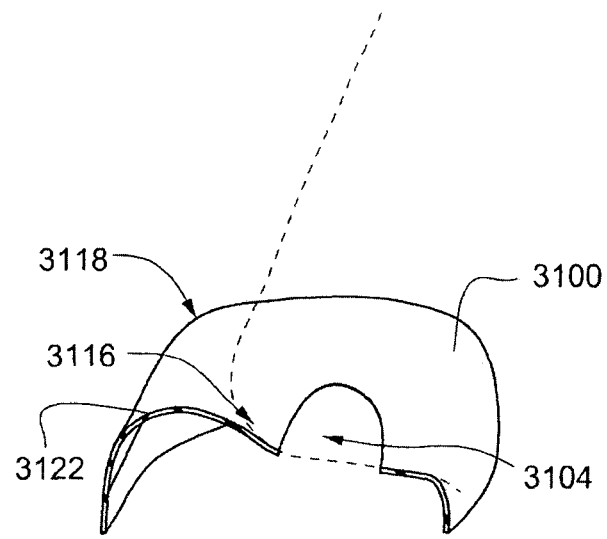

FIG. 236c shows a side cross-sectional view taken through line 236c-236c of FIG. 236a of another nasal cradle cushion of a patient interface in accordance with another example of the present technology. A patient's nose is shown in dashed lines.

Figure 237A:
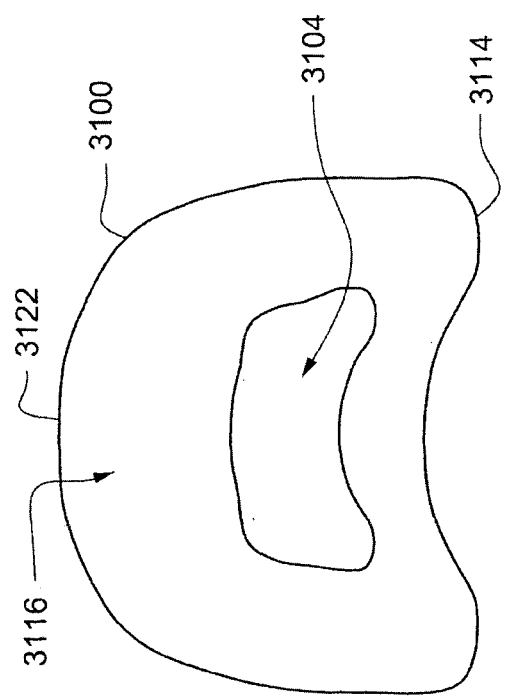

FIG. 237a shows a top view of a nasal cradle cushion of a patient interface in accordance with an example of the present technology.

Figure 237B:
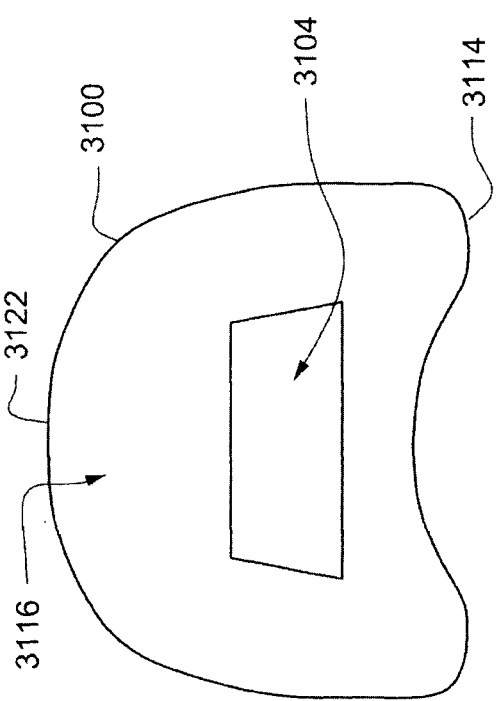

FIG. 237b shows a top view of a nasal cradle cushion of a patient interface in accordance with another example of the present technology.

Figure 237C:
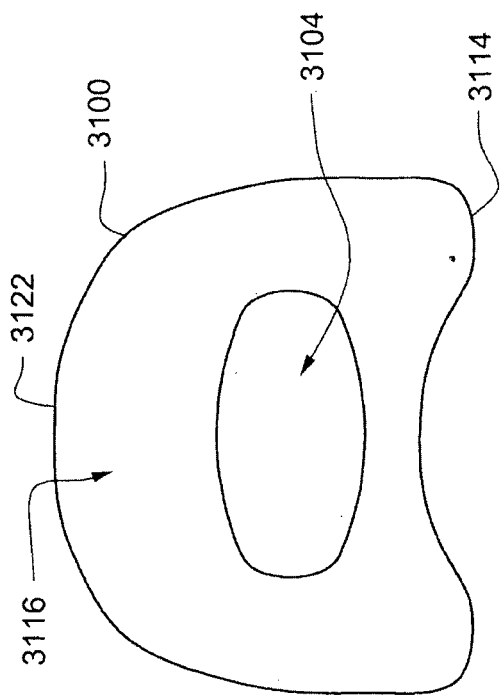

FIG. 237c shows a top view of a nasal cradle cushion of a patient interface in accordance with another example of the present technology.

Figure 237D:
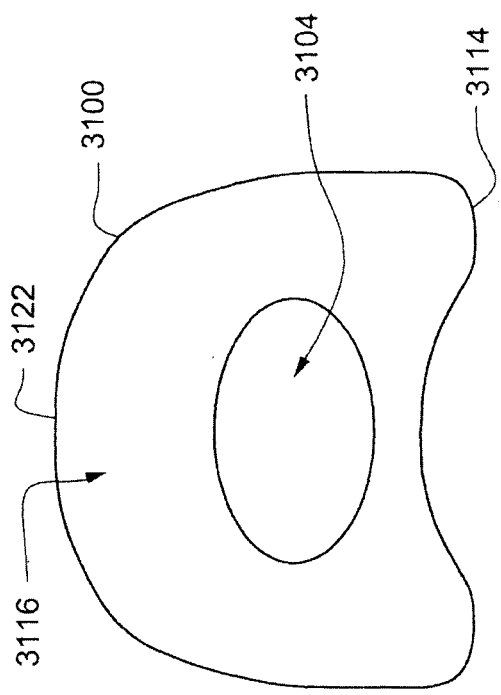

FIG. 237d shows a top view of a nasal cradle cushion of a patient interface in accordance with another example of the present technology.

Figure 238C:
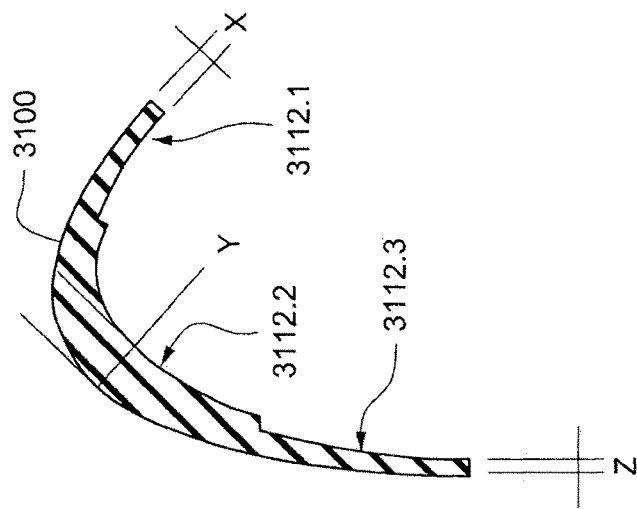
Figure 238B:
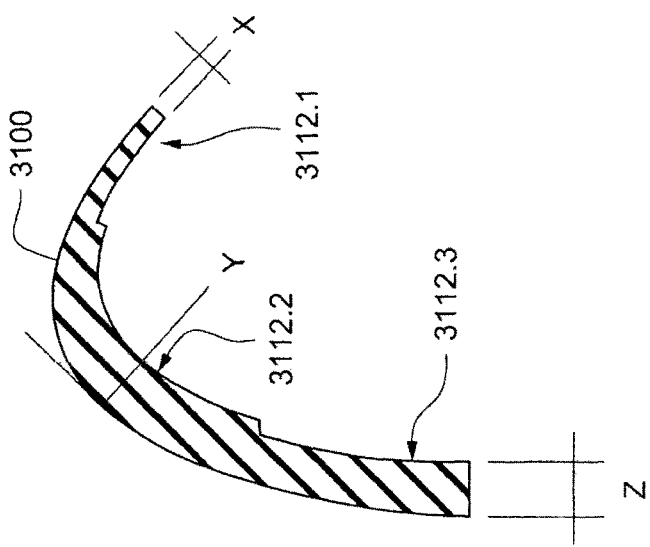
Figure 238A:
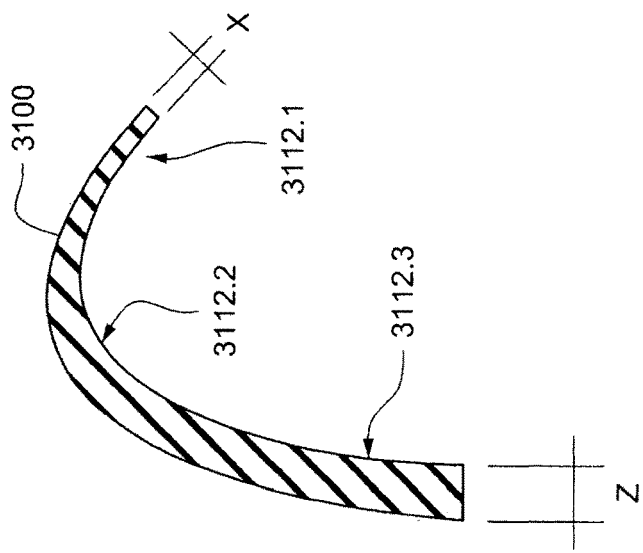

FIG. 238a shows a cross-section of a nasal cushion taken through line 238a-238a of FIG. 234a according to an example of the present technology.

Figure 239:
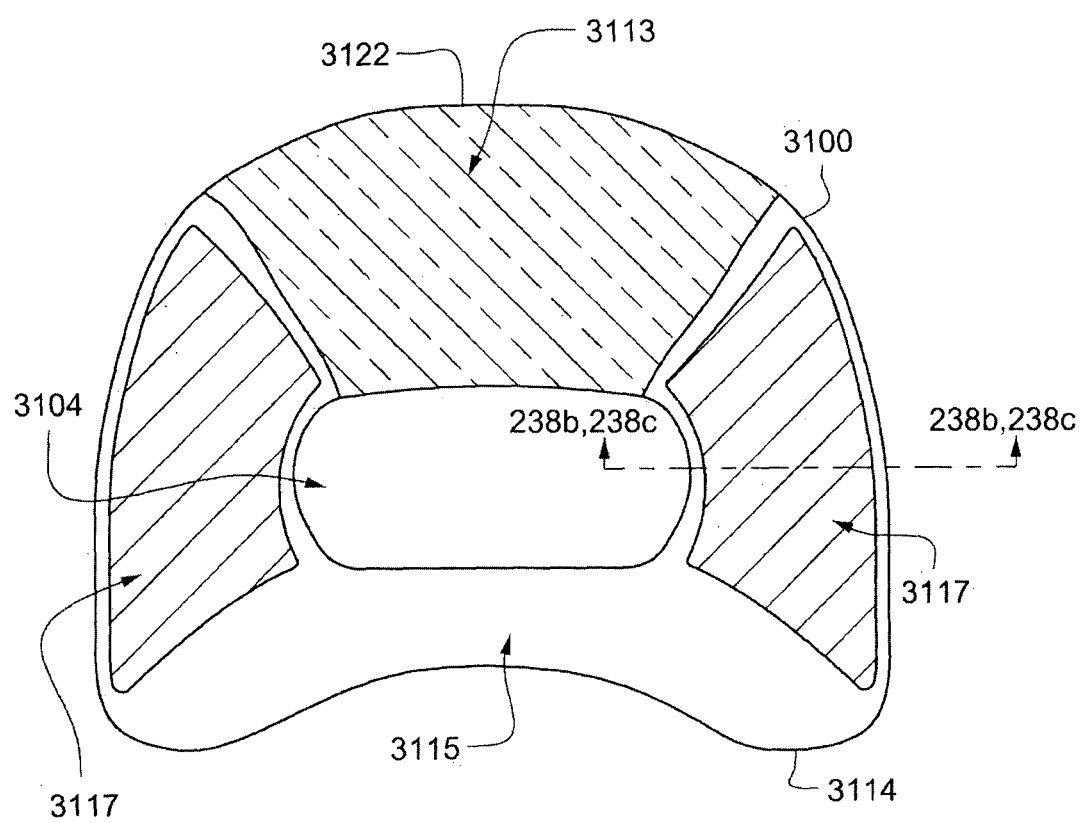

FIG. 238b shows a cross-section of a nasal cushion taken through line 238b, 238c-238b, 238c of FIG. 239 according to an example of the present technology.

FIG. 238c shows a cross-section of a nasal cushion taken through line 238b, 238c-238b, 238c of FIG. 239 according to an example of the present technology.

FIG. 239 shows a top view of a nasal cradle cushion of a patient interface in accordance with an example of the present technology.

Figure 240:
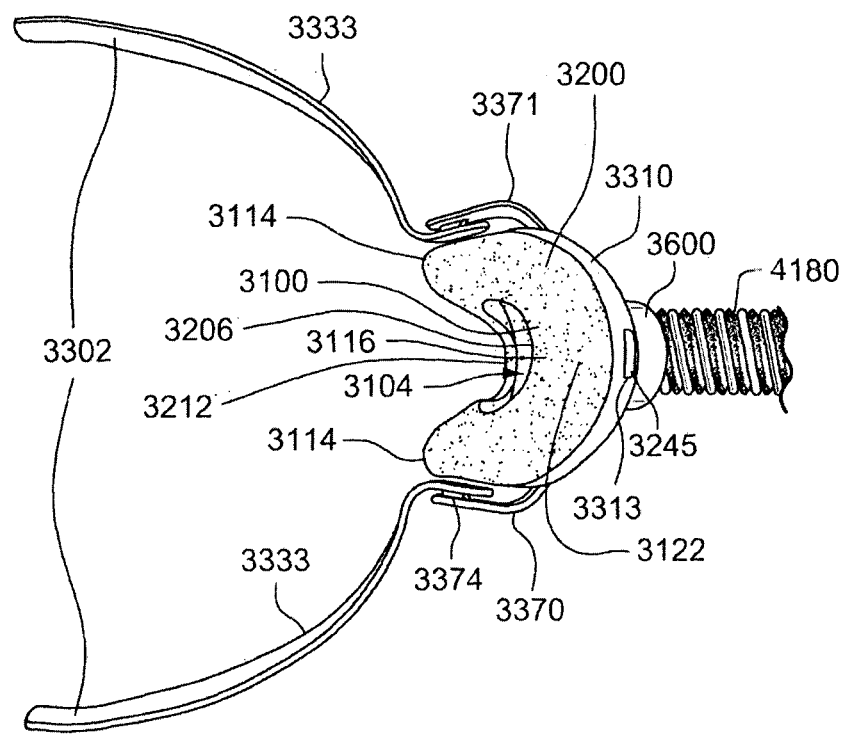

FIG. 240 shows a top view of a patient interface system according to an example of the present technology worn by a patient.

Figure 241:
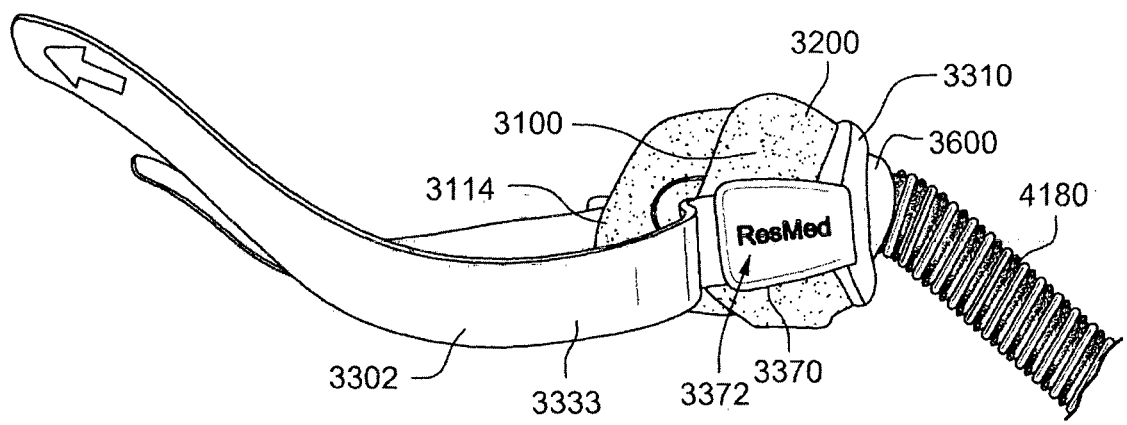

FIG. 241 shows a side view of a patient interface system according to an example of the present technology worn by a patient.

Figure 242:
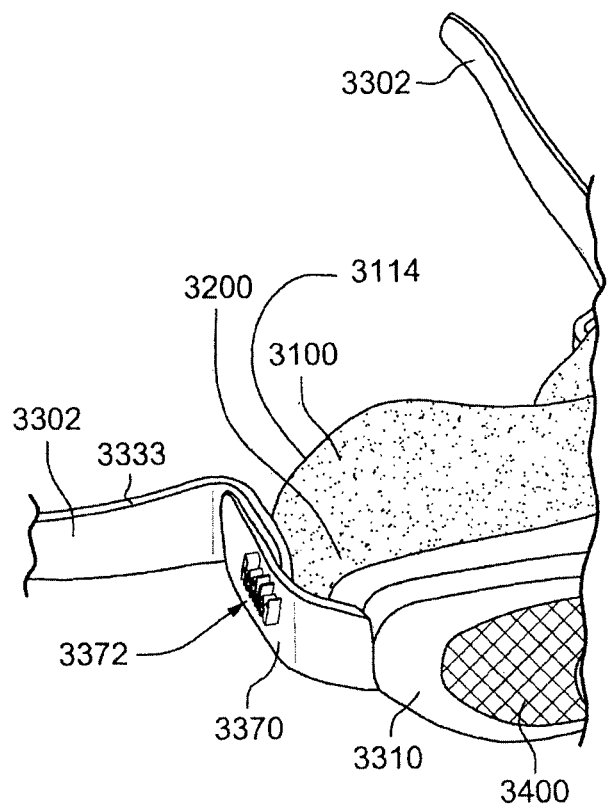

FIG. 242 shows an enlarged perspective view of a patient interface system according to an example of the present technology worn by a patient.

Figure 243:
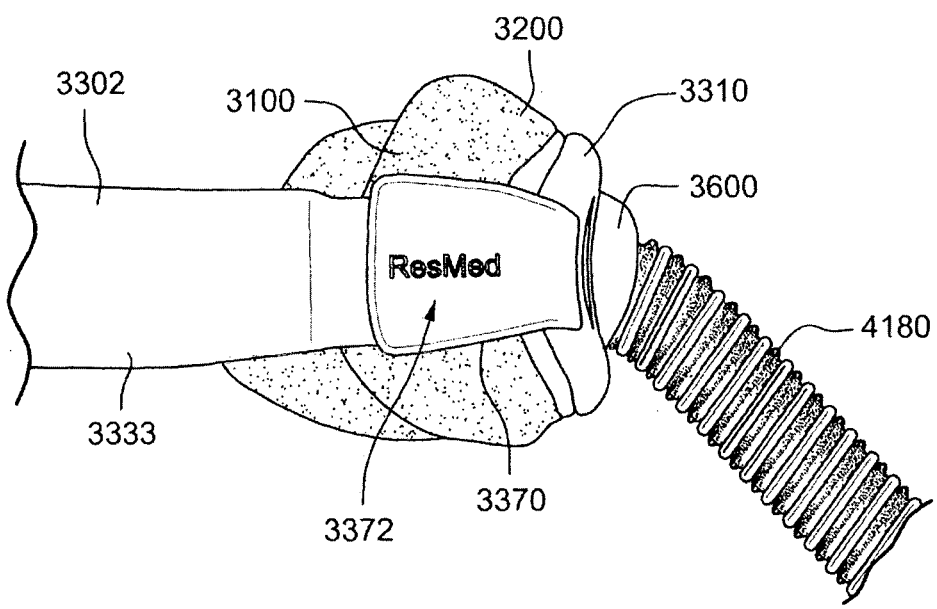

FIG. 243 shows an enlarged side view of a patient interface system according to an example of the present technology worn by a patient.

Figure 244:
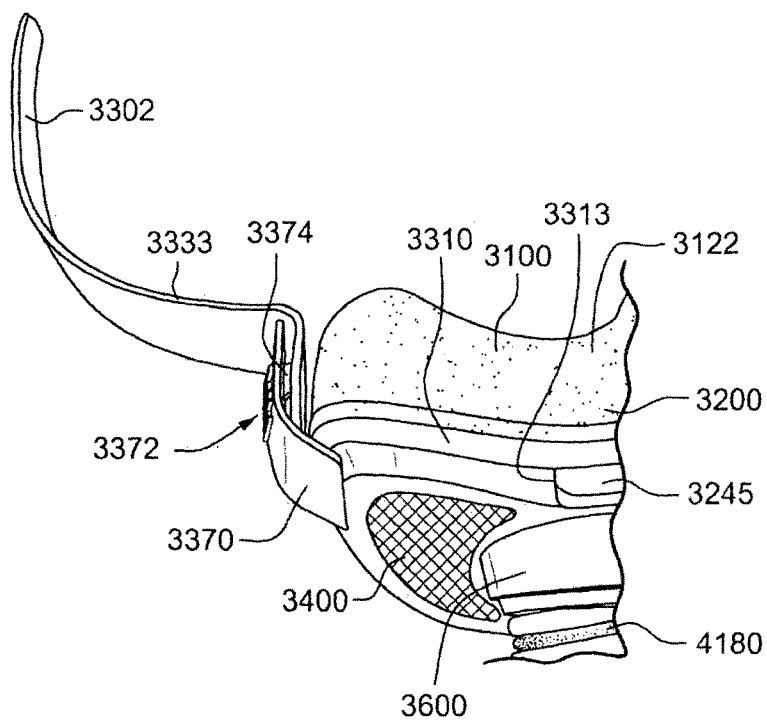

FIG. 244 shows an enlarged front view of a patient interface system according to an example of the present technology worn by a patient.

Figure 245A:
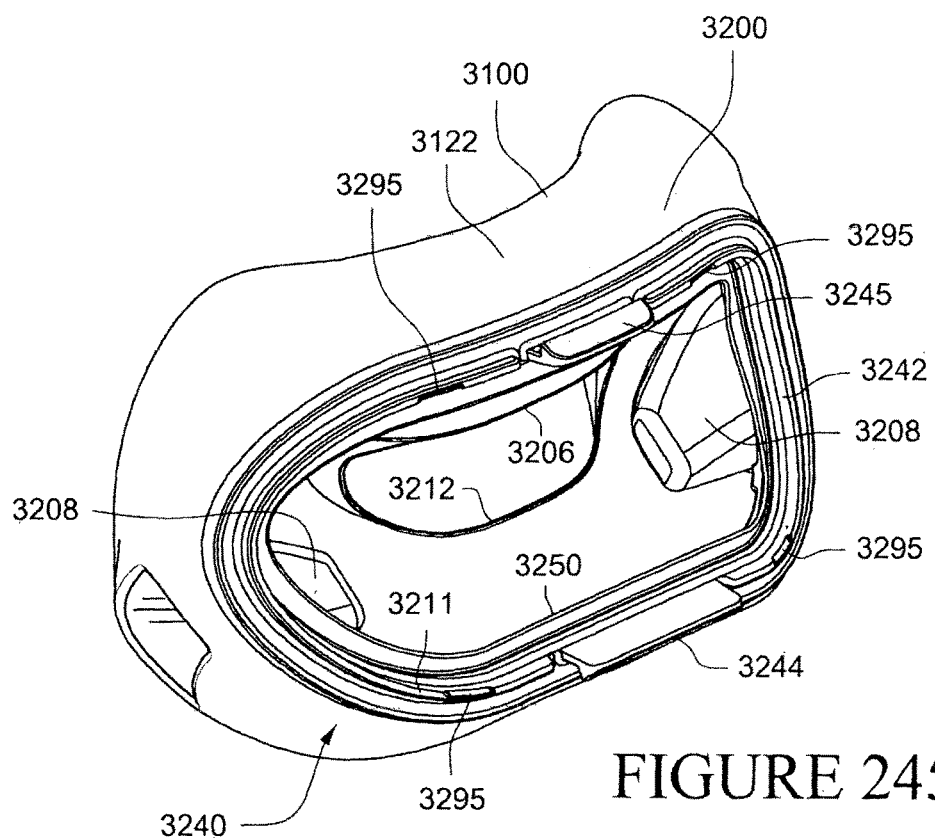

FIG. 245a shows a front perspective view of a seal-forming structure, plenum chamber, and retaining structure according to an example of the present technology.

Figure 245B:
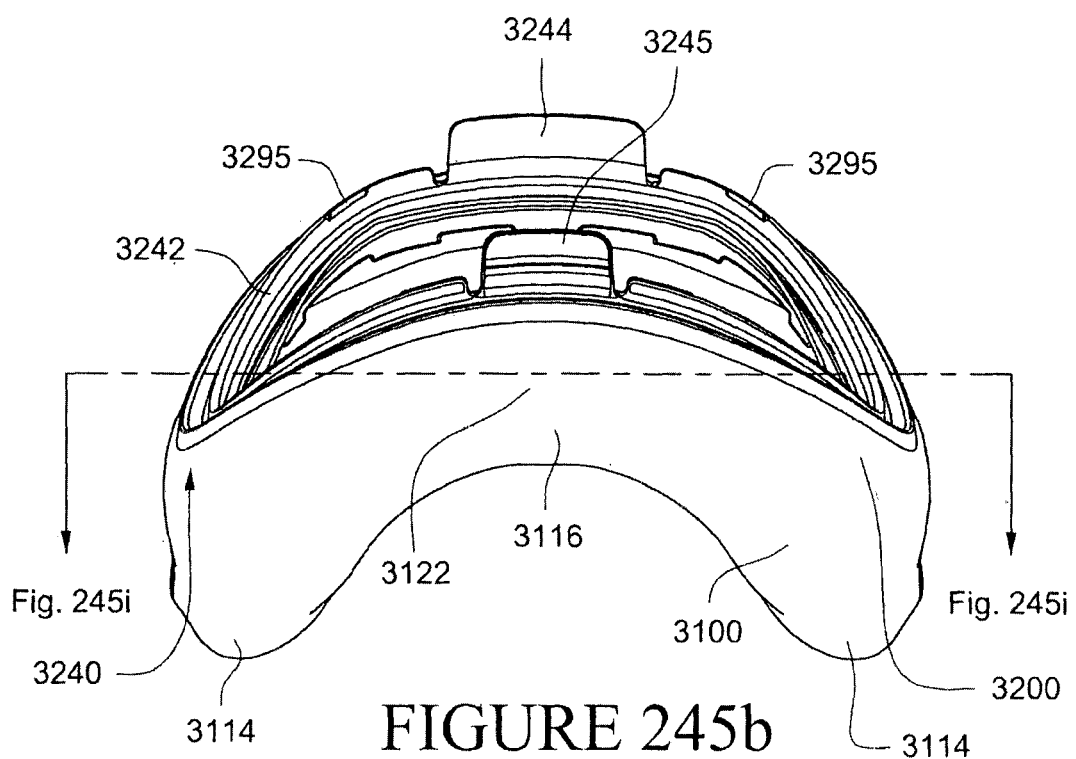

FIG. 245b shows a top view of a seal-forming structure, plenum chamber, and retaining structure according to an example of the present technology.

Figure 245C:
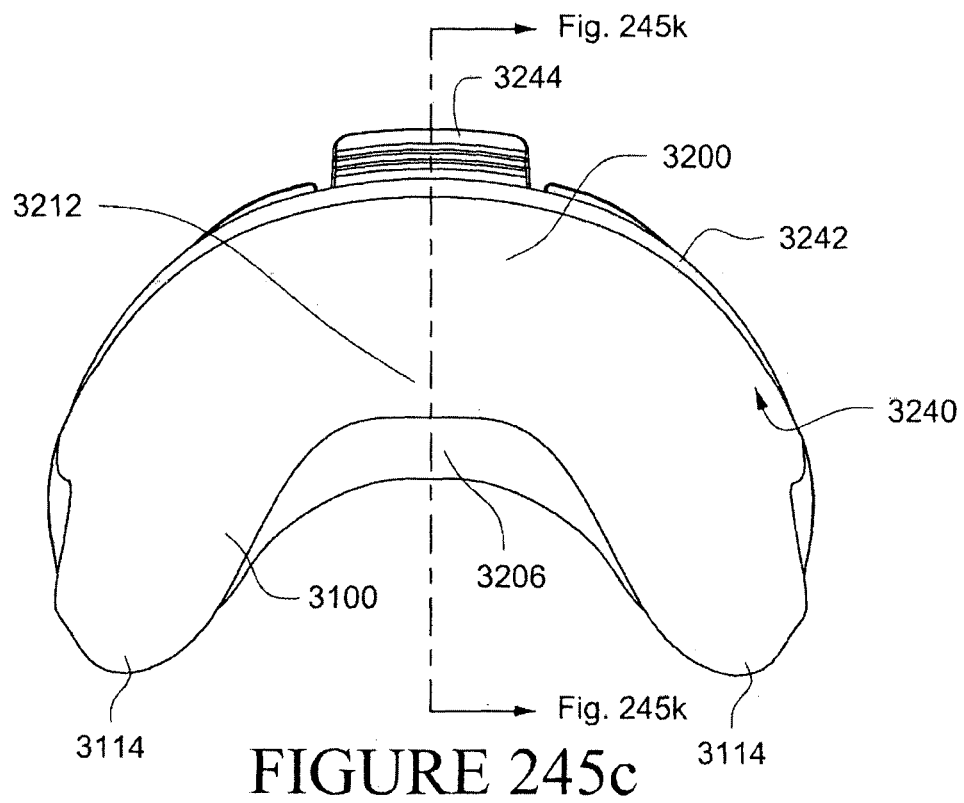

FIG. 245c shows a bottom view of a seal-forming structure, plenum chamber, and retaining structure according to an example of the present technology.

Figure 245D:
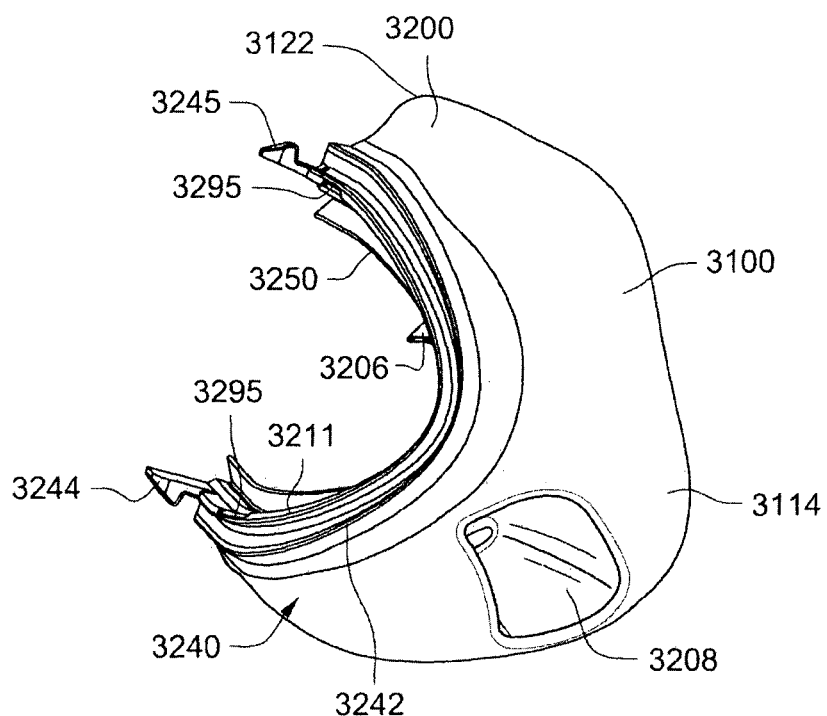

FIG. 245d shows a side view of a seal-forming structure, plenum chamber, and retaining structure according to an example of the present technology.

Figure 245E:
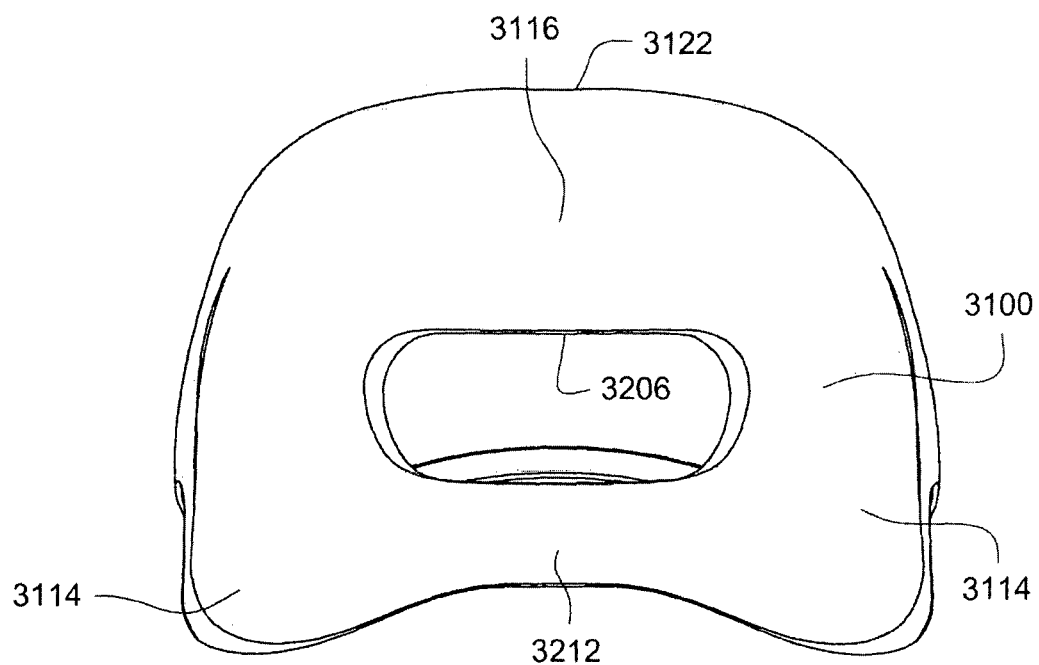

FIG. 245e shows a rear view of a seal-forming structure, plenum chamber, and retaining structure according to an example of the present technology.

Figure 245F:
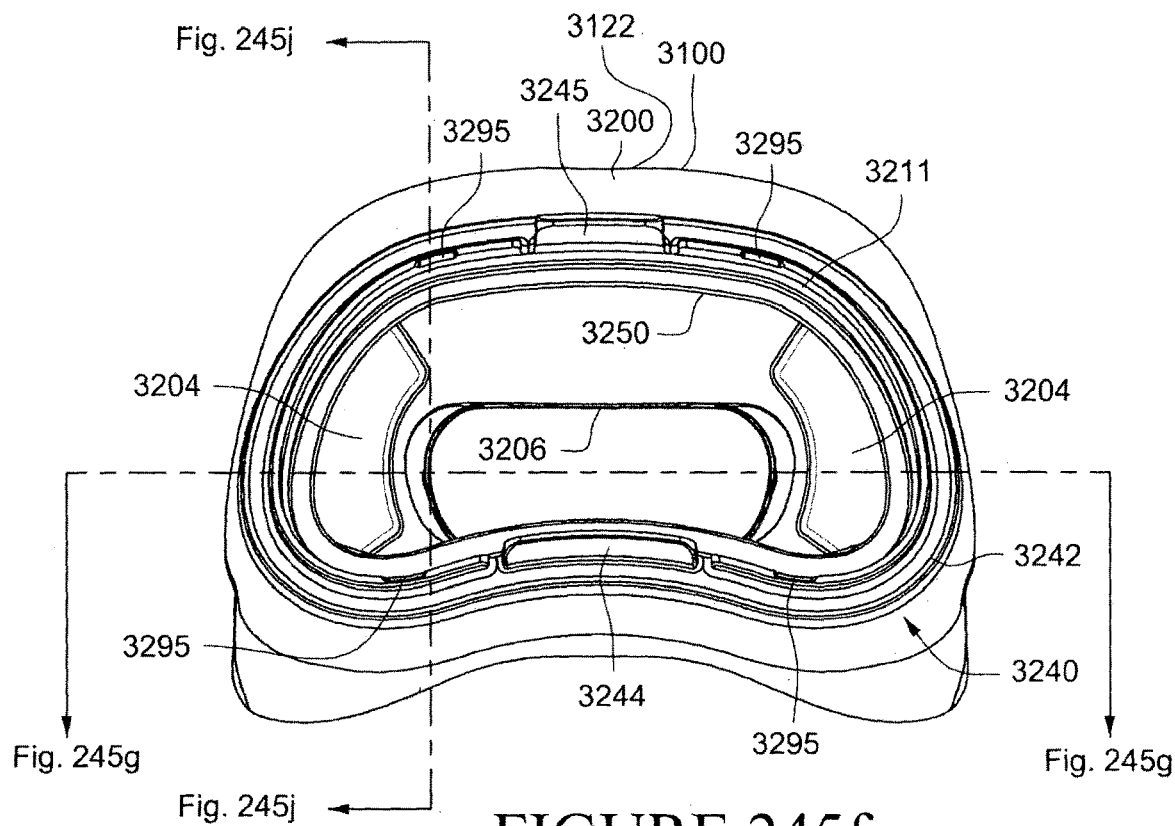

FIG. 245f shows a front view of a seal-forming structure, plenum chamber, and retaining structure according to an example of the present technology.

Figure 245G:
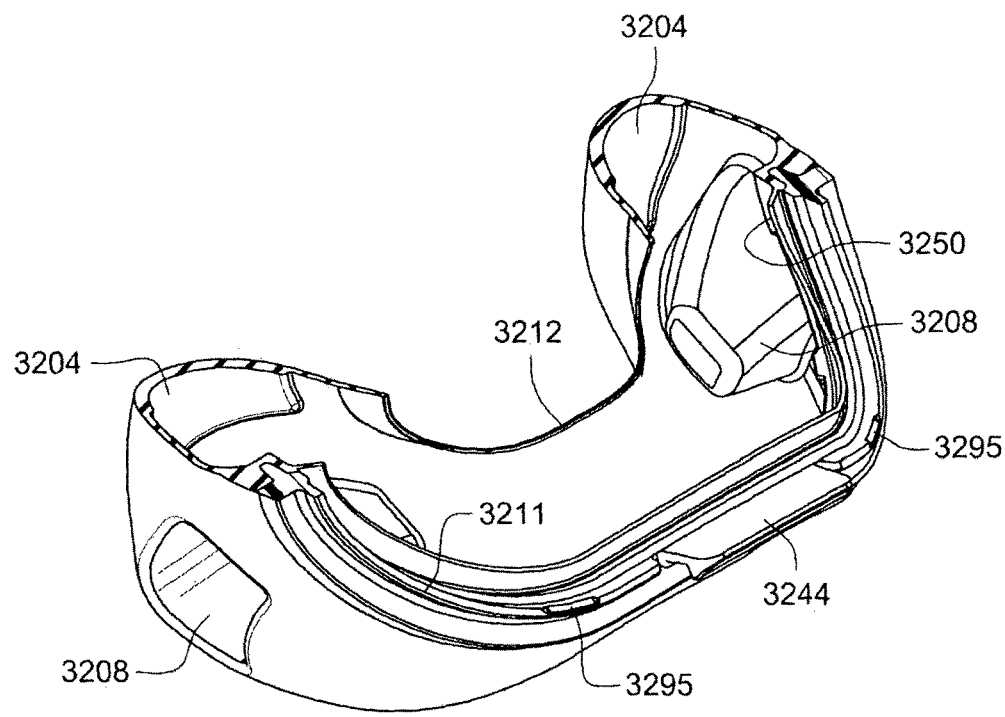

FIG. 245g shows a cross-sectional view of a seal-forming structure, plenum chamber, and retaining structure taken through line 245g-245g of FIG. 245f, according to an example of the present technology.

Figure 245H:
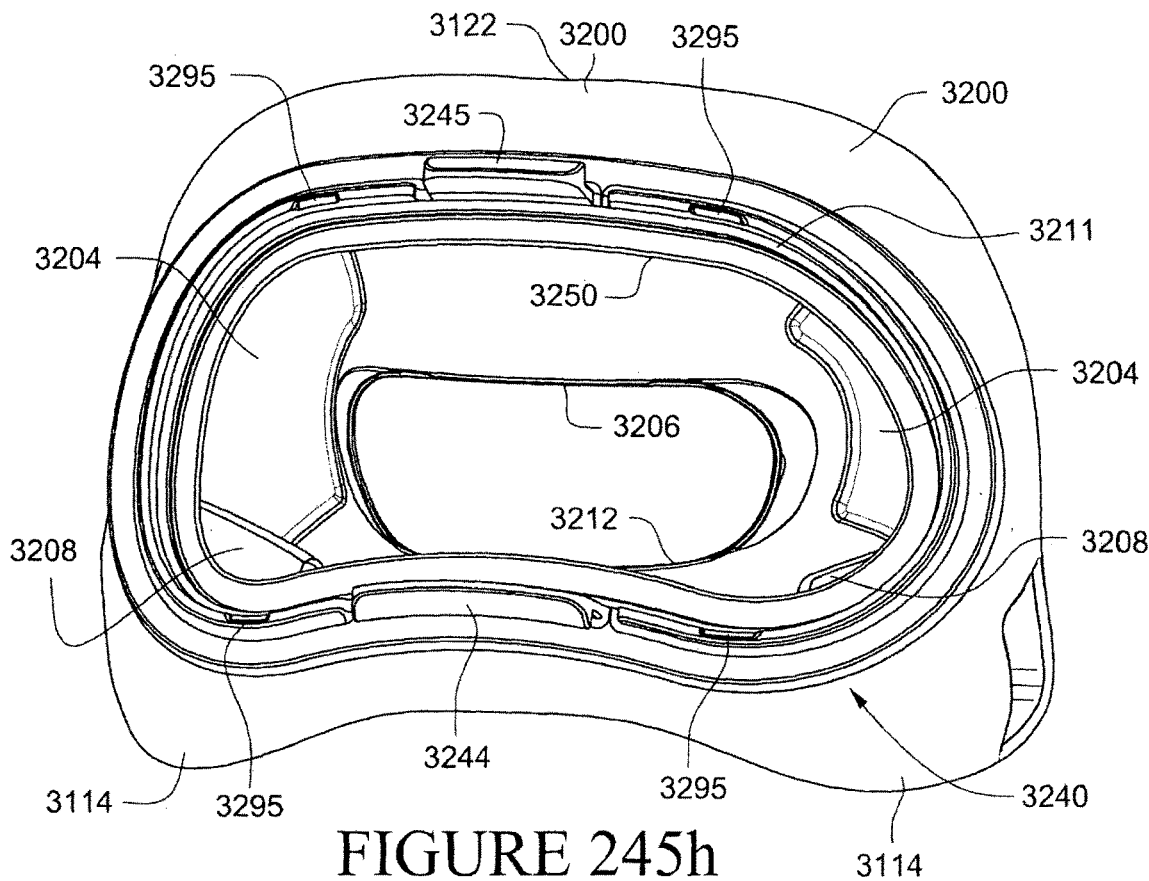

FIG. 245h shows another front perspective view of a seal-forming structure, plenum chamber, and retaining structure according to an example of the present technology.

Figure 245I:
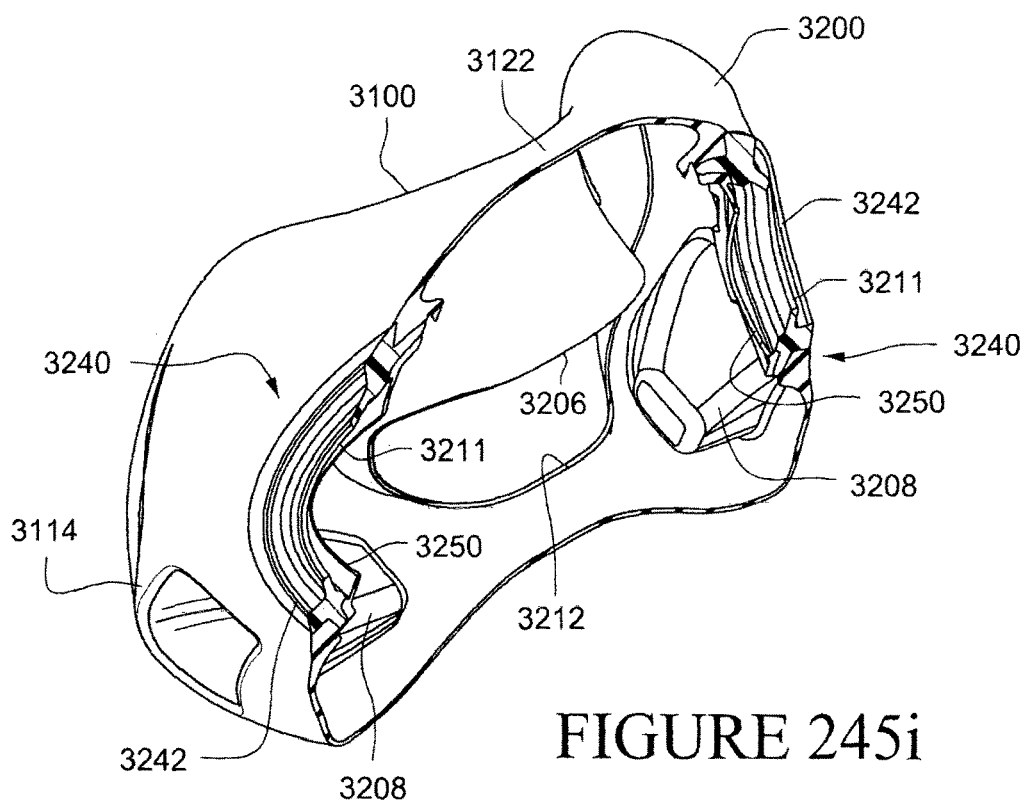

FIG. 245i shows a cross-sectional view of a seal-forming structure, plenum chamber, and retaining structure taken through line 245i-245i of FIG. 245b according to an example of the present technology.

Figure 245J:
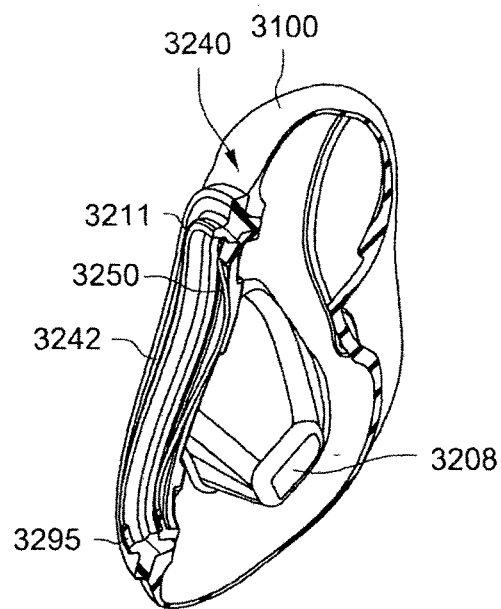

FIG. 245j shows a cross-sectional view of a seal-forming structure, plenum chamber, and retaining structure taken through line 245j-245j of FIG. 245f according to an example of the present technology.

Figure 245K:
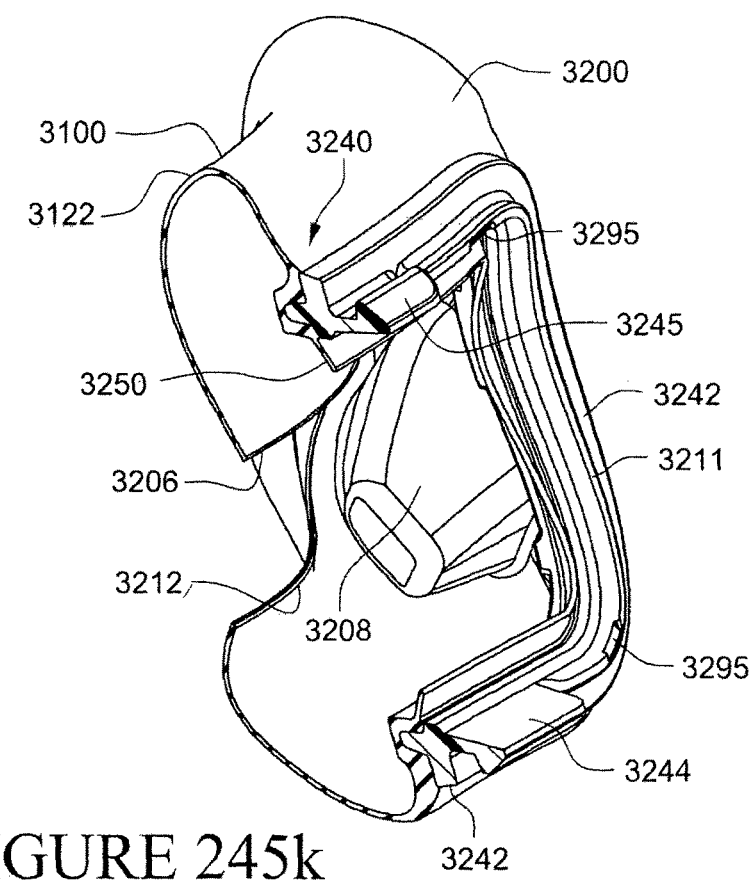

FIG. 245k shows a cross-sectional view of a seal-forming structure, plenum chamber, and retaining structure taken through line 245k-245k of FIG. 245c according to an example of the present technology.

Figure 246A:
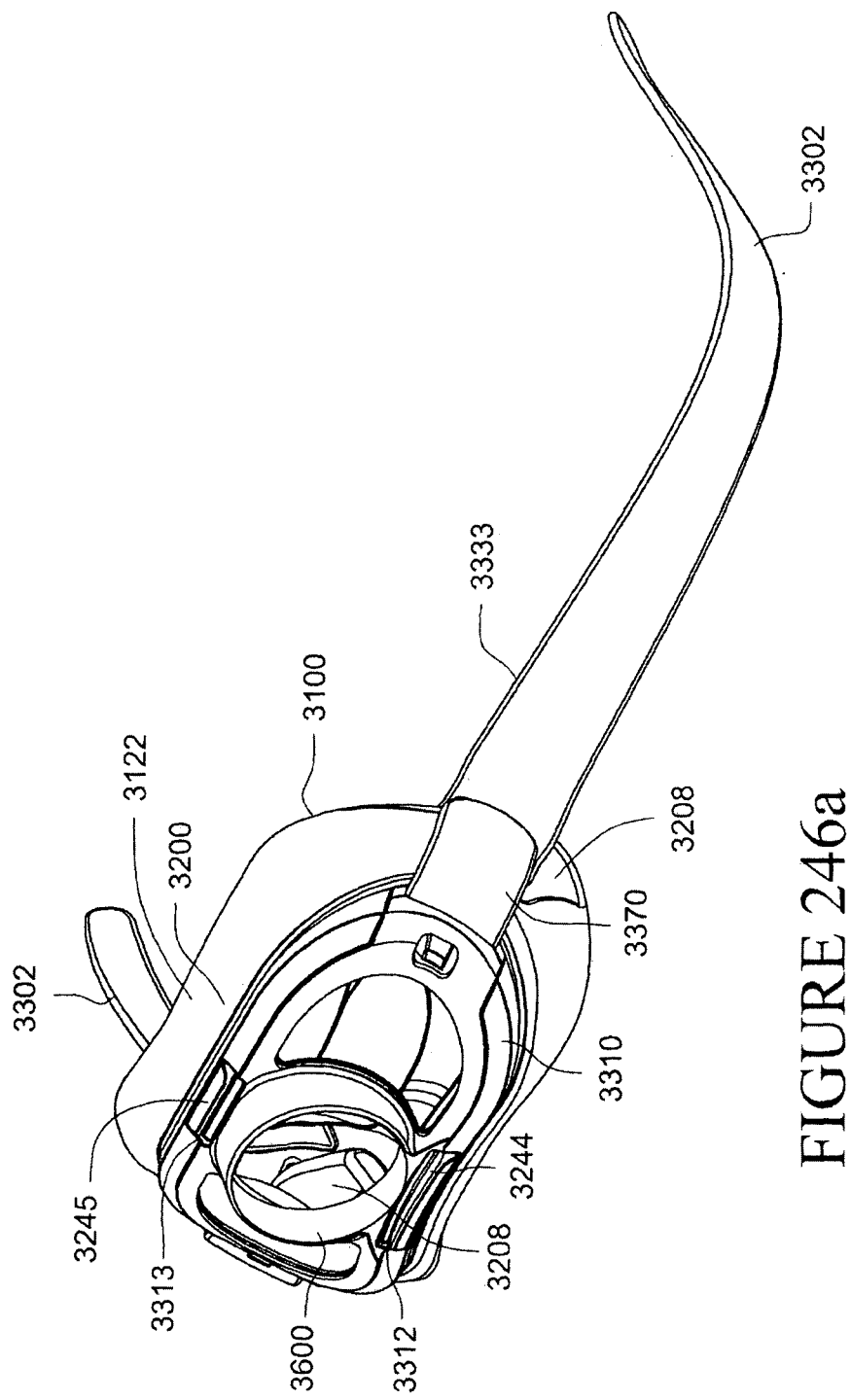

FIG. 246a shows a front perspective view of a patient interface system according to an example of the present technology.

Figure 246B:
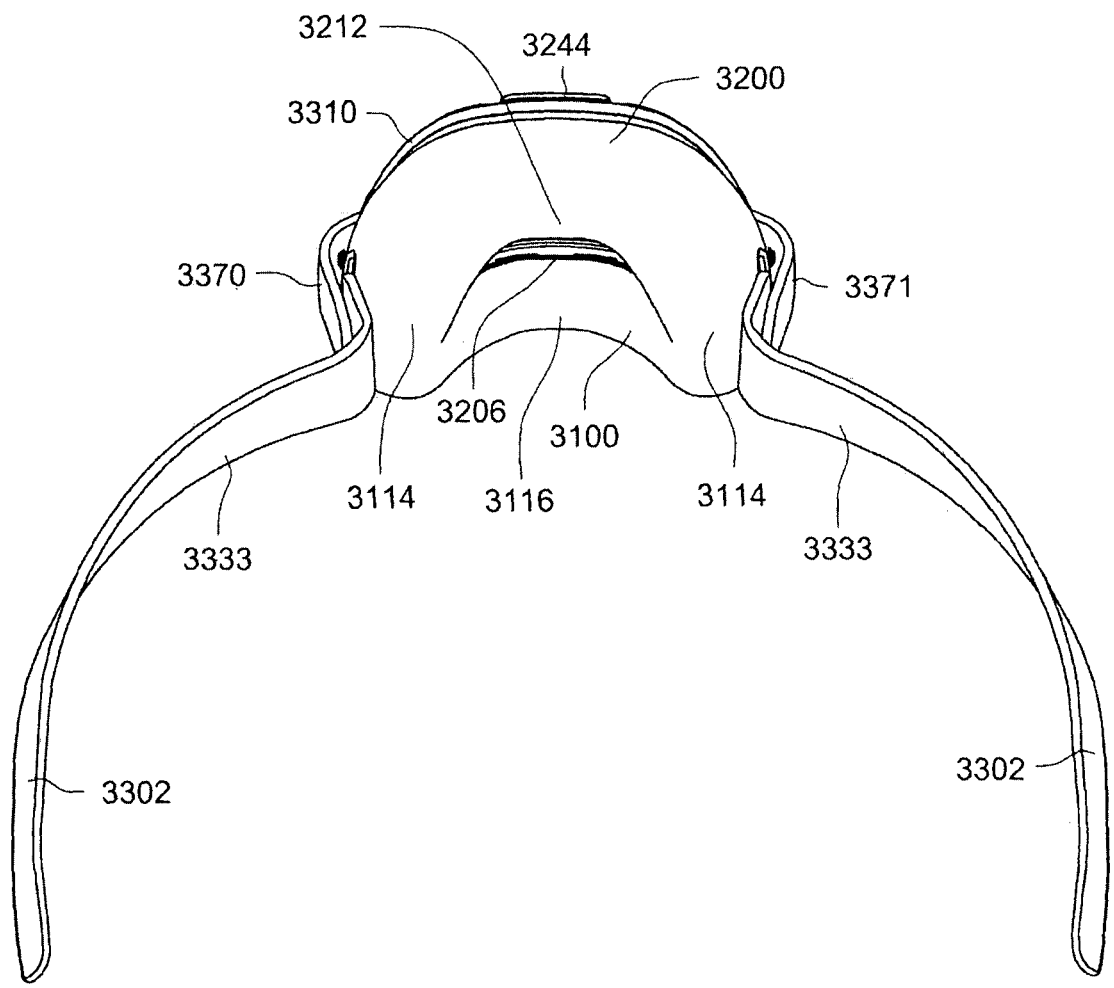

FIG. 246b shows a view of a patient interface system from an inferior and posterior perspective according to an example of the present technology.

Figure 246C:
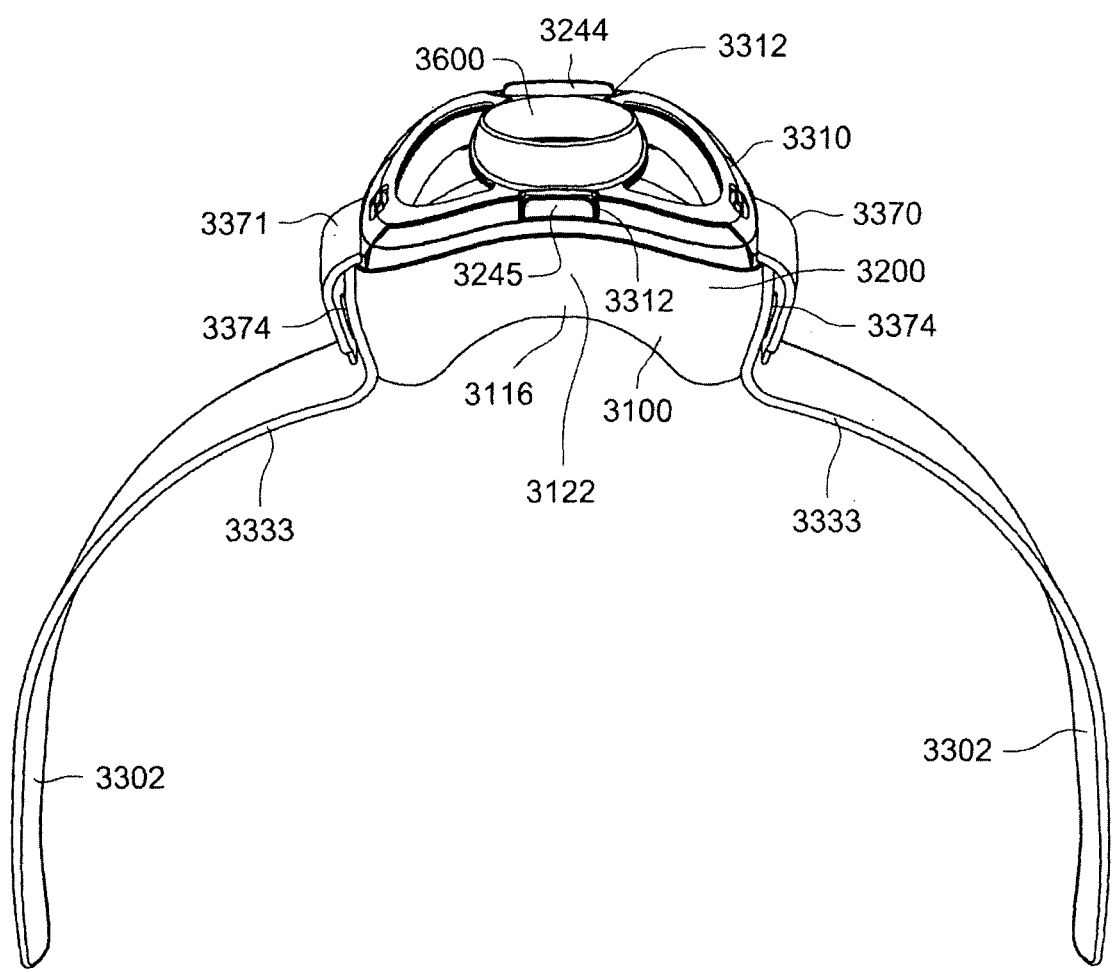

FIG. 246c shows a view of a patient interface system from a superior and anterior perspective according to an example of the present technology.

Figure 246D:
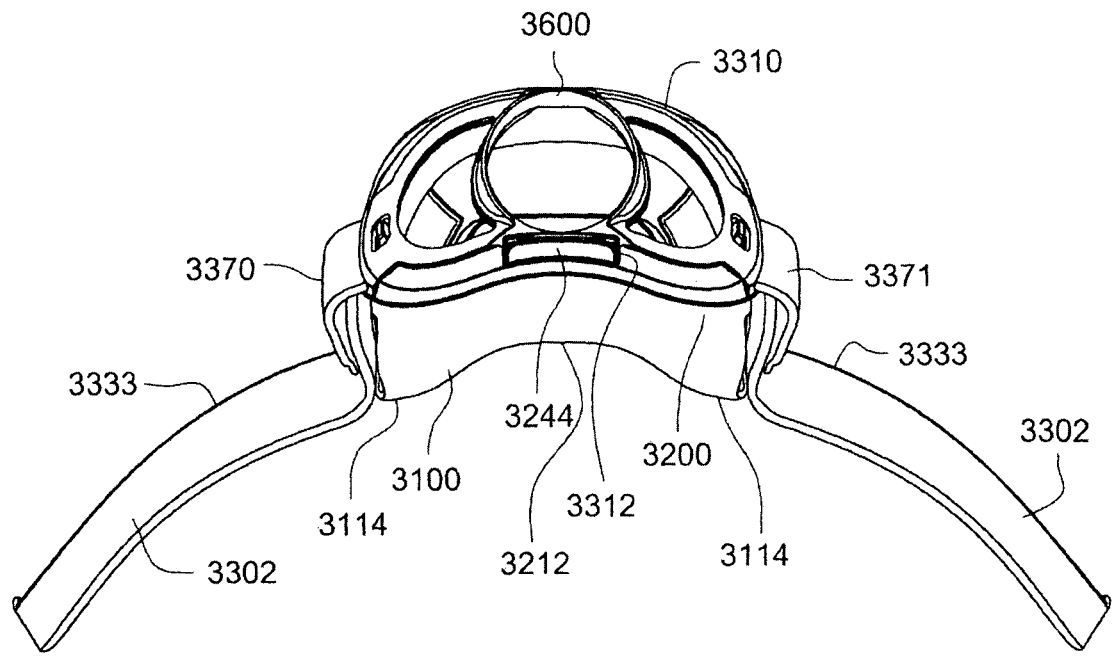

FIG. 246d shows a view of a patient interface system from an inferior and anterior perspective according to an example of the present technology.

Figure 246E:
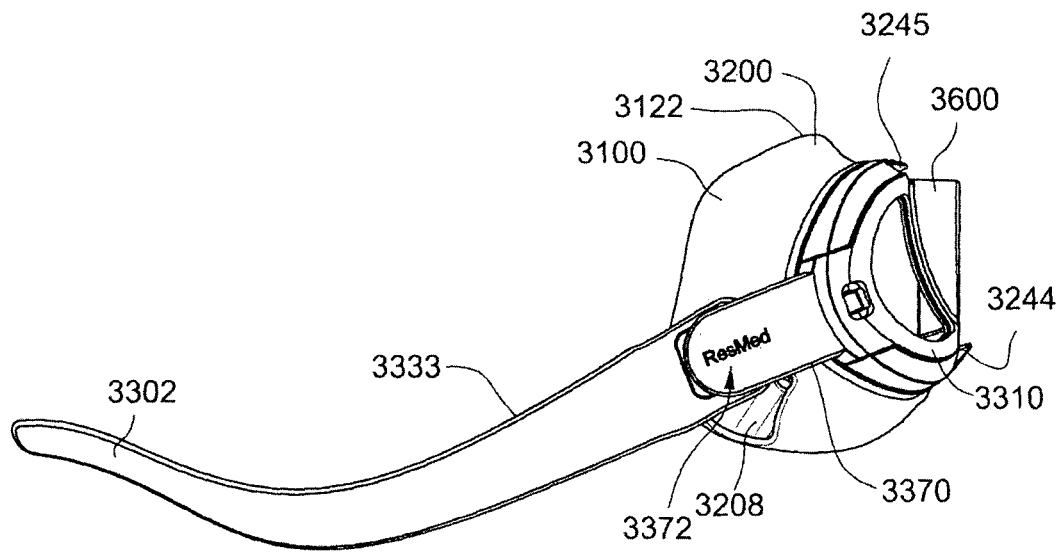

FIG. 246e shows a side view of a patient interface system according to an example of the present technology.

Figure 246F:
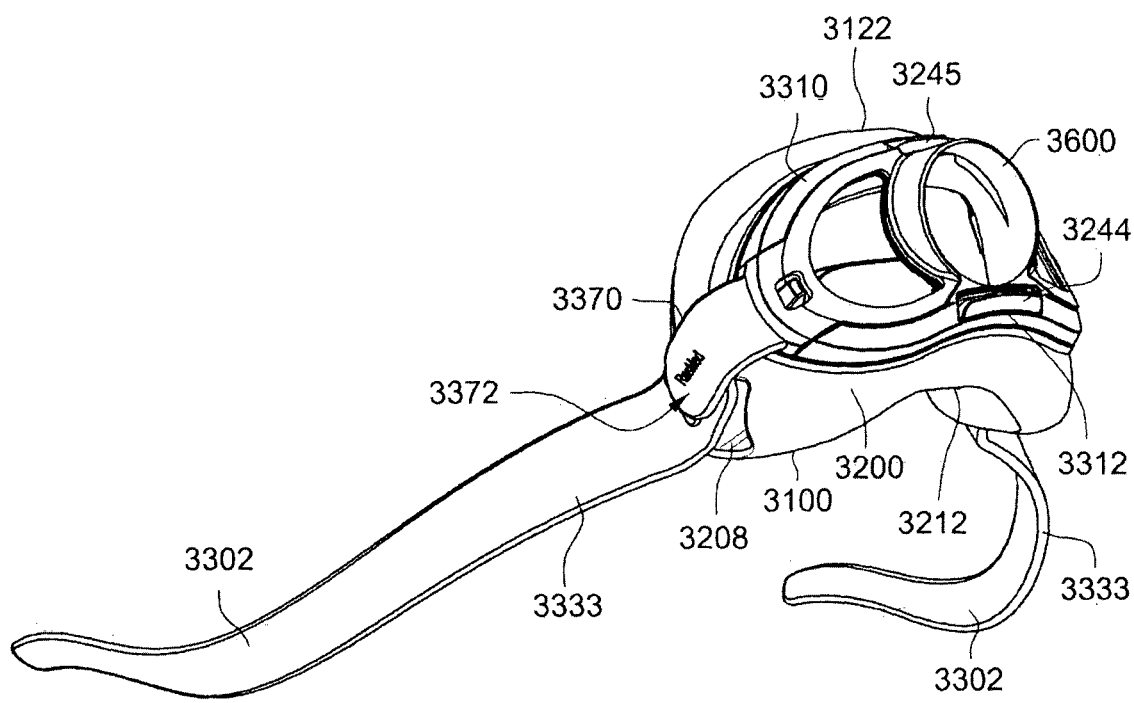

FIG. 246f shows a bottom perspective view of a patient interface system according to an example of the present technology.

Figure 246G:
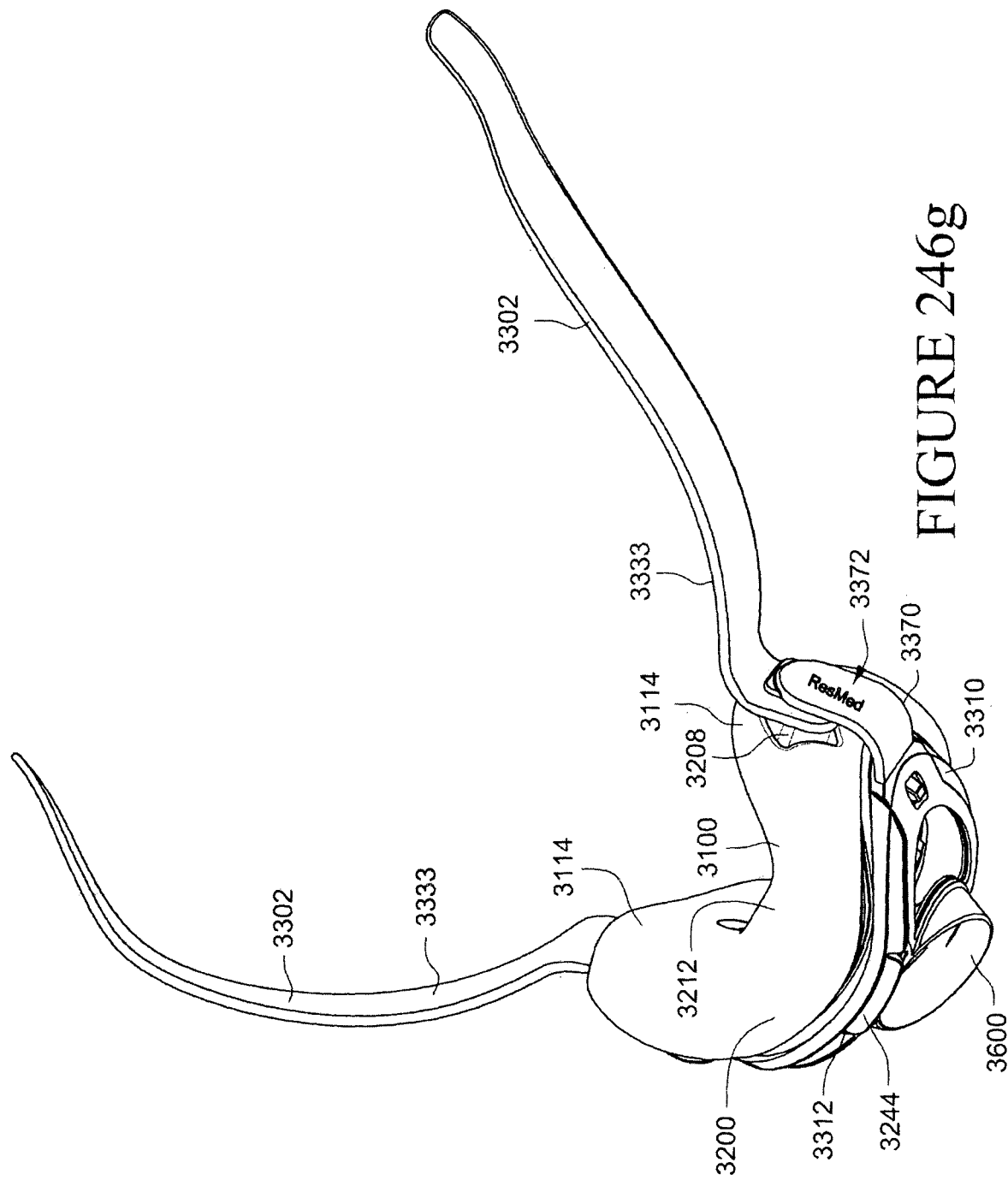

FIG. 246g shows another bottom perspective view of a patient interface system according to an example of the present technology.

Figure 247A:
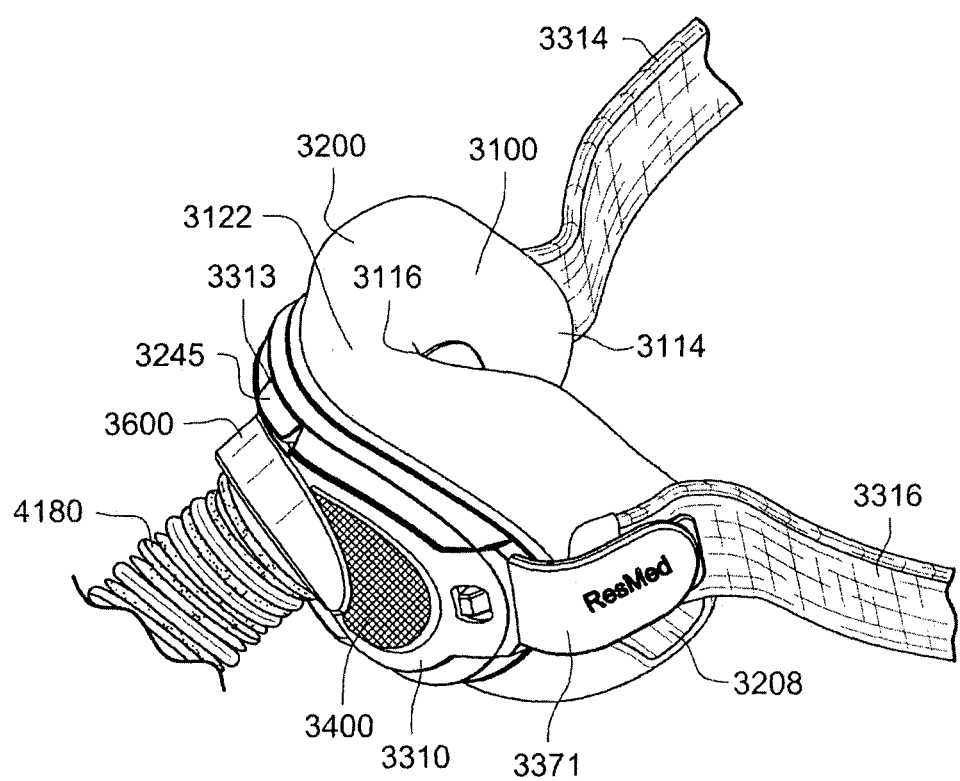

FIG. 247a shows a top perspective view of a patient interface system according to an example of the present technology.

Figure 247B:
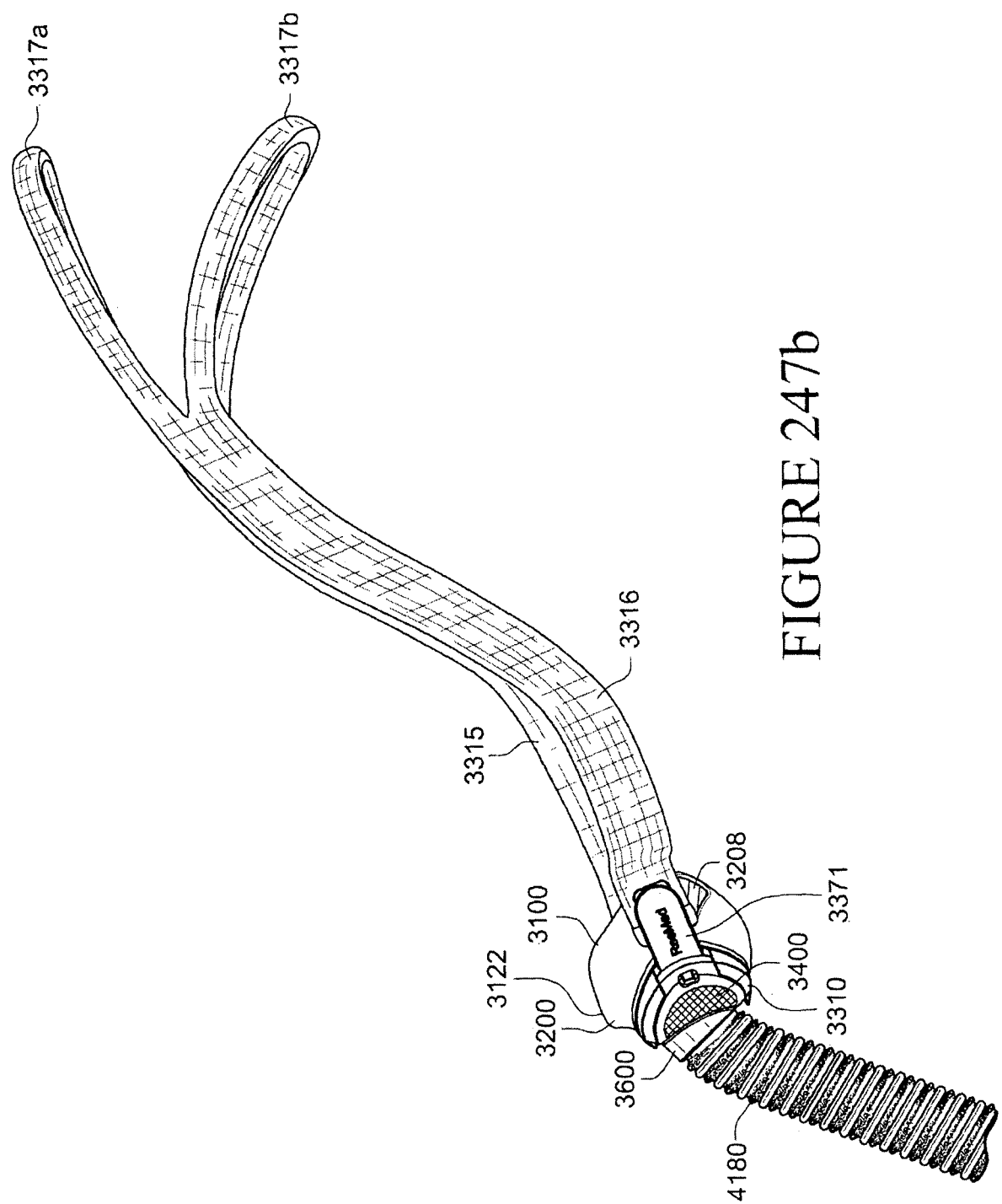

FIG. 247b shows a side view of a patient interface system according to an example of the present technology.

Figure 247C:
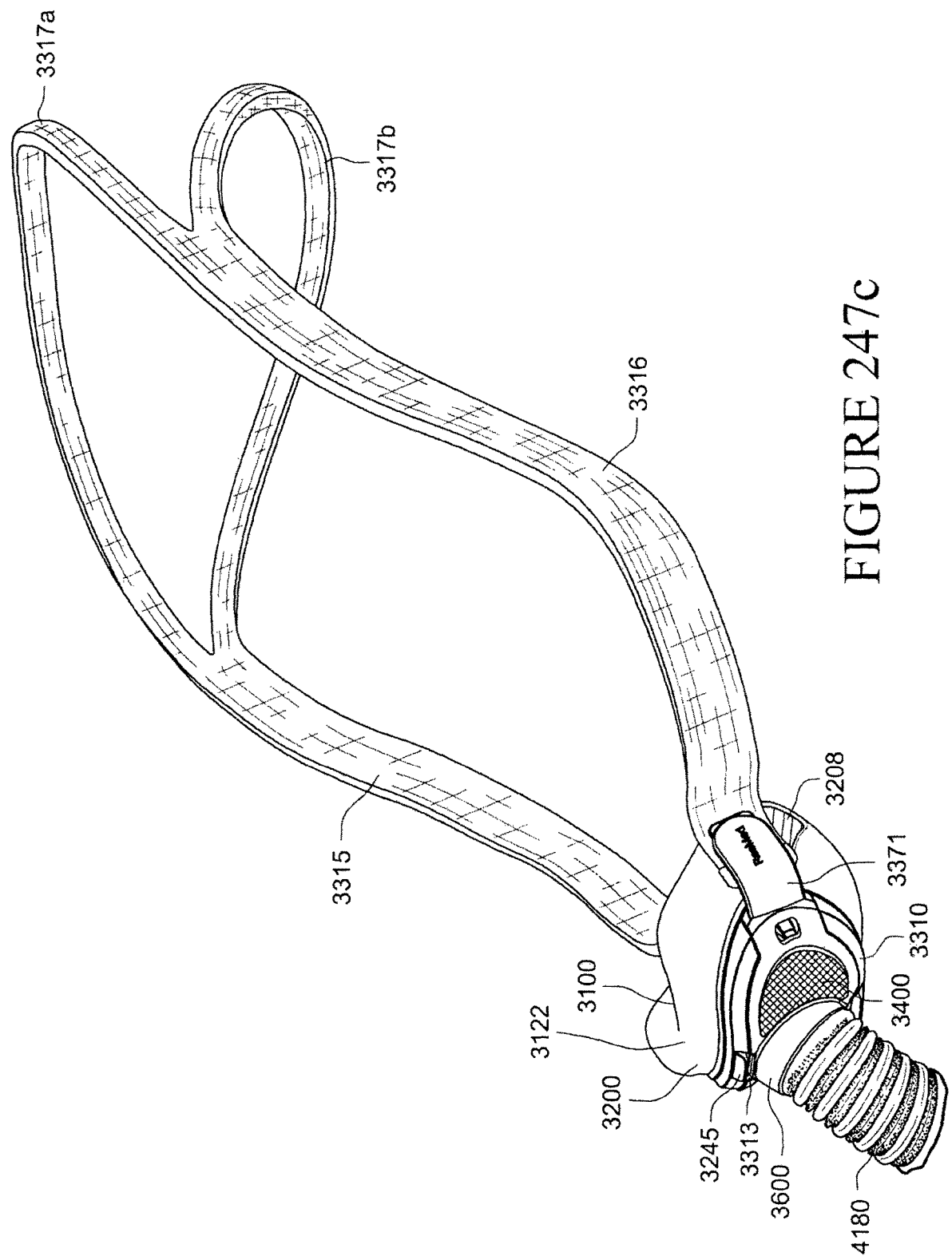

FIG. 247c shows a top perspective view of a patient interface system according to an example of the present technology.

Figure 248A:
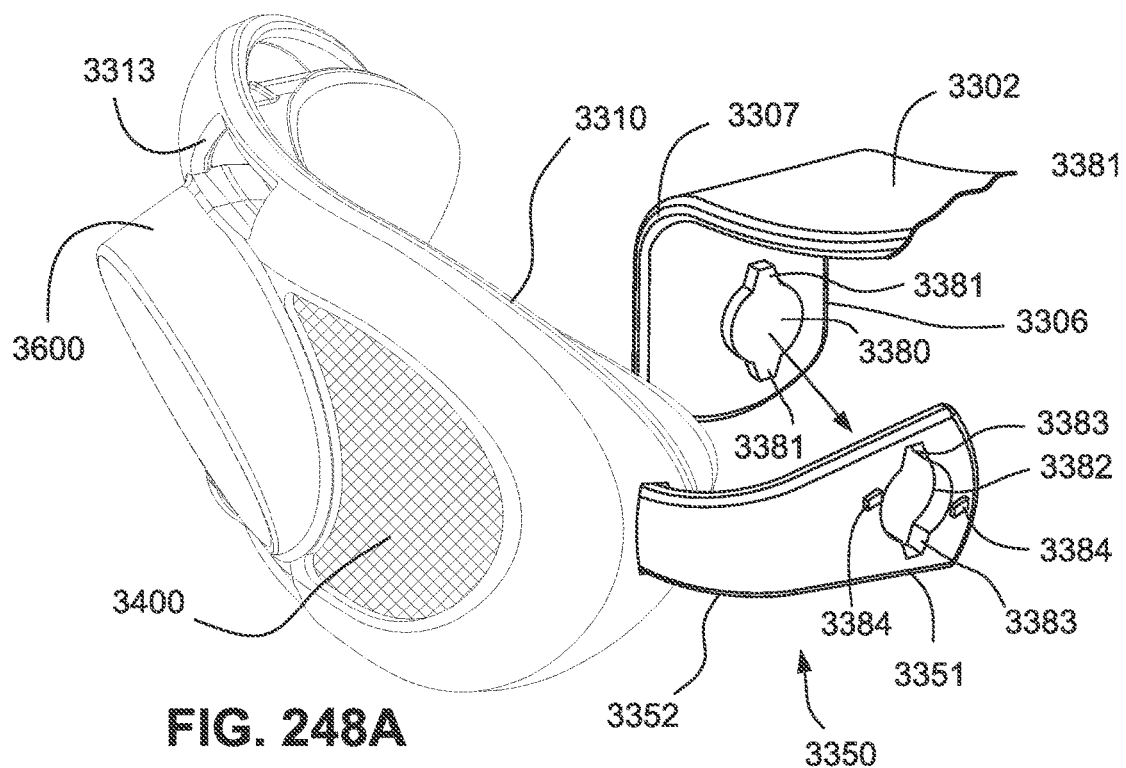

FIG. 248A shows a perspective view of a frame for a patient interface and a detachable rigidiser arm according to an example of the present technology.

Figure 248B:
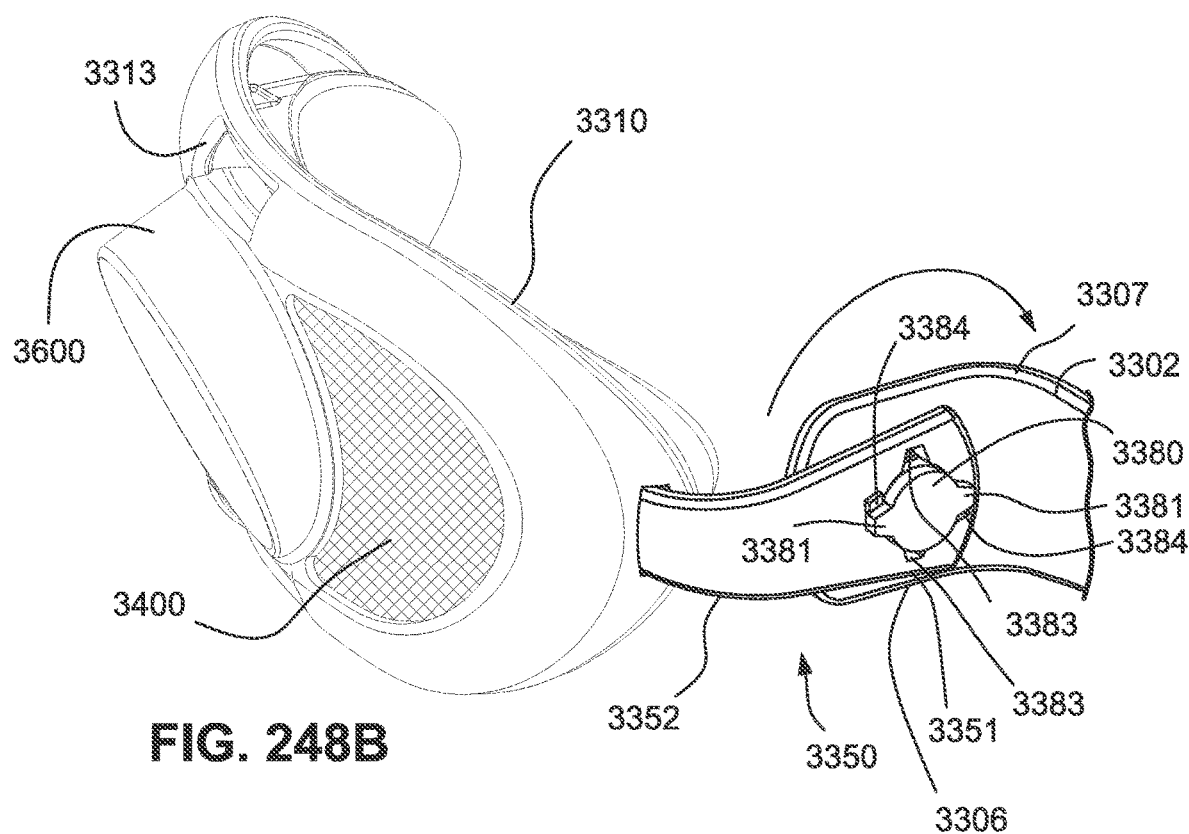

FIG. 248B shows a perspective view of a detachable rigidiser arm attached to a frame for a patient interface according to an example of the present technology.

Figure 249A:
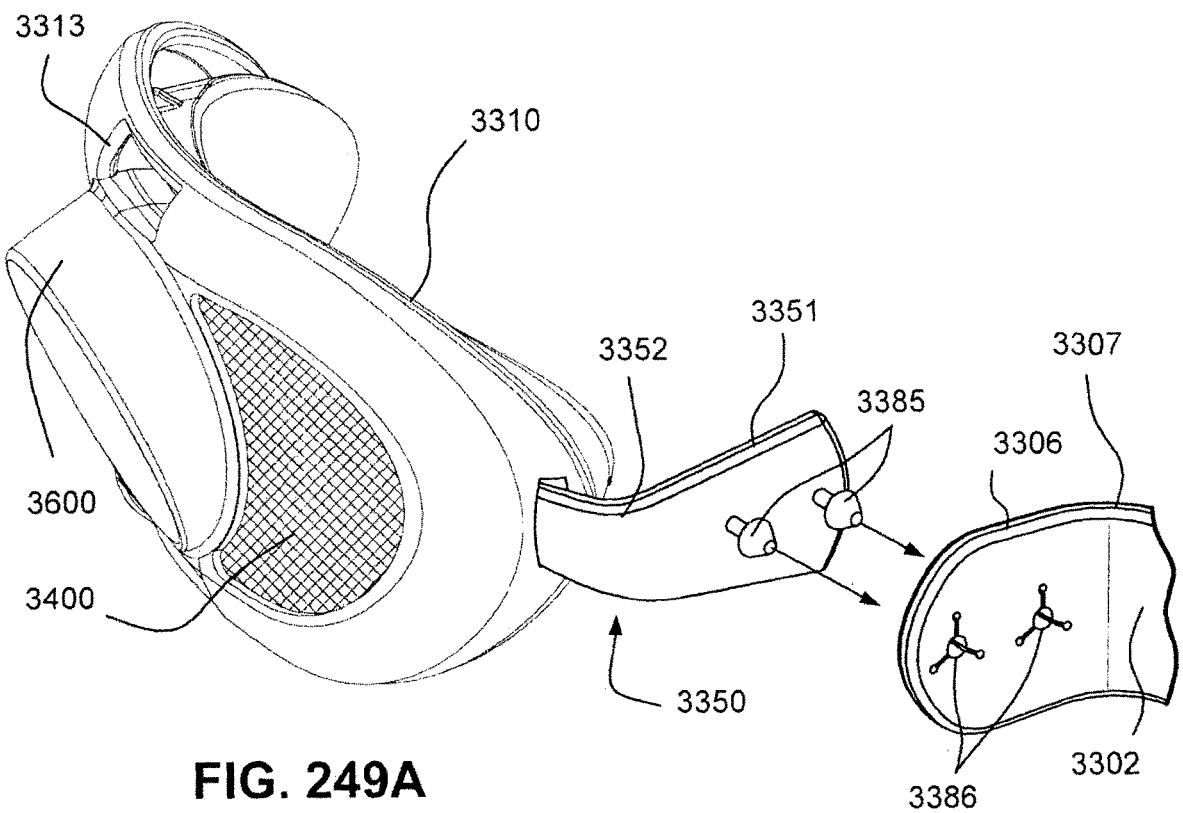

FIG. 249A shows a perspective view of a frame for a patient interface and a detachable rigidiser arm according to an example of the present technology.

Figure 249B:
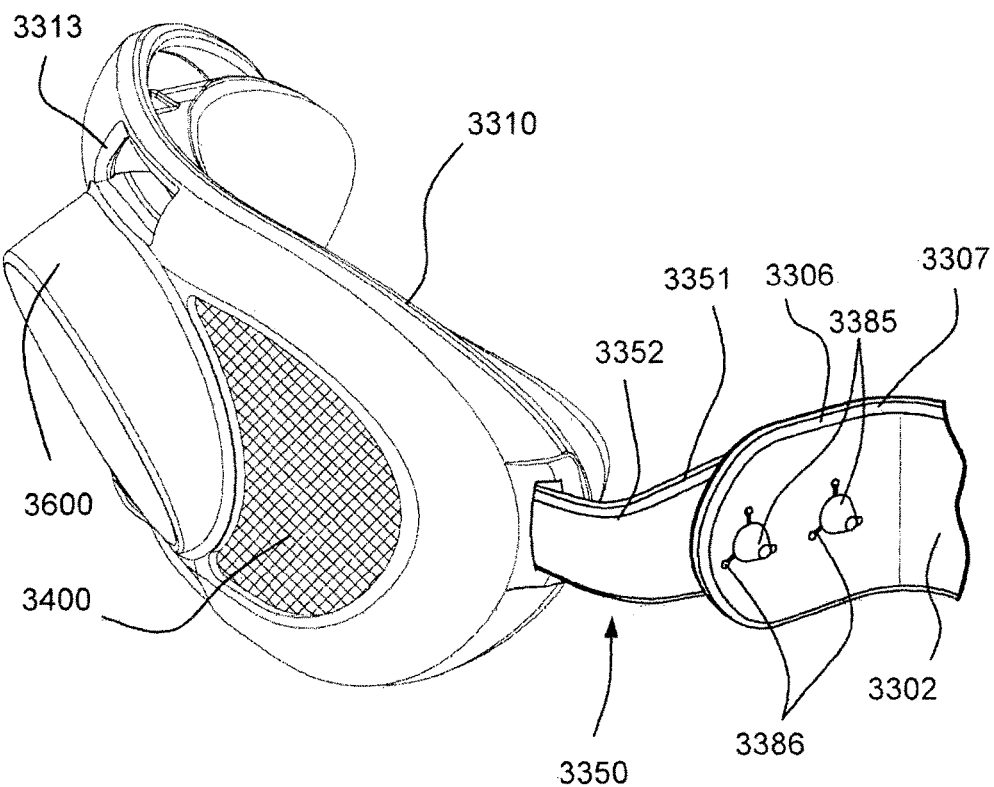

FIG. 249B shows a perspective view of a detachable rigidiser arm attached to a frame for a patient interface according to an example of the present technology.

Figure 250A:
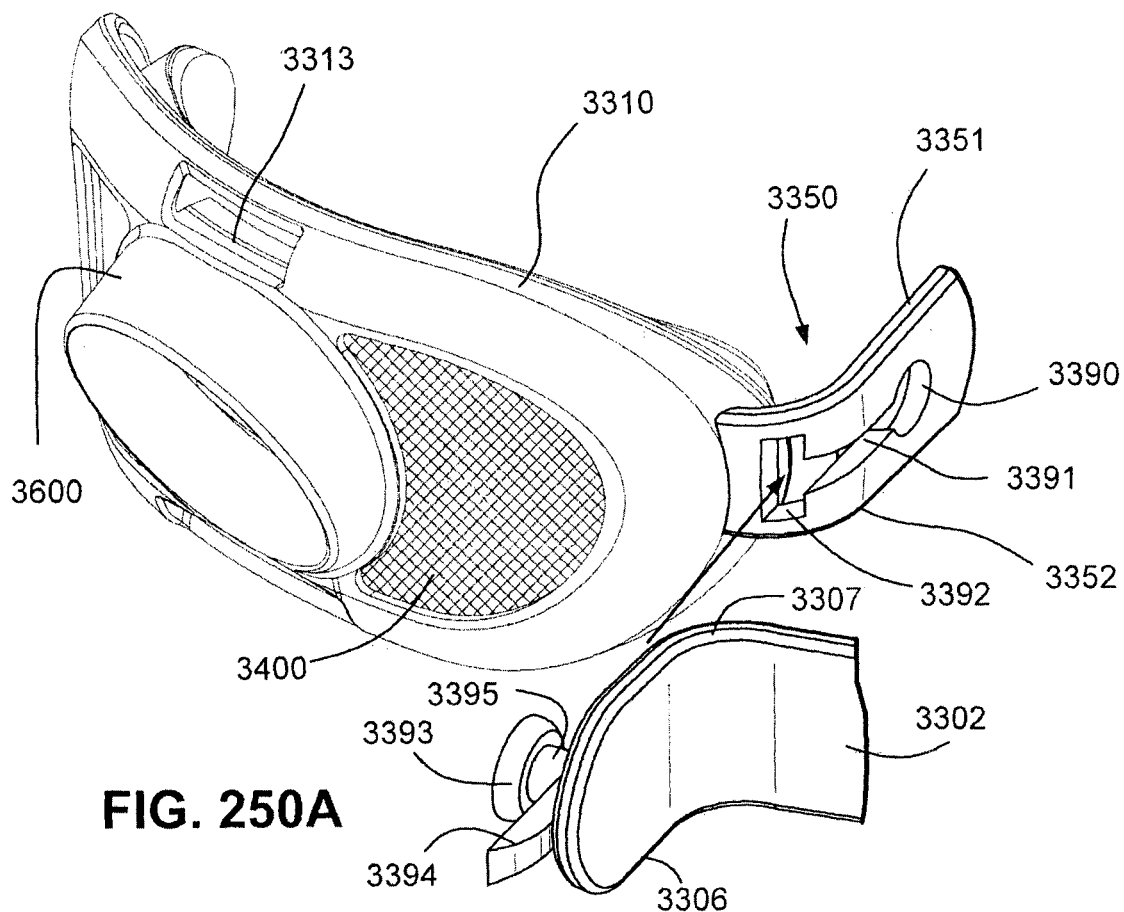

FIG. 250A shows a perspective view of a frame for a patient interface and a detachable rigidiser arm according to an example of the present technology.

Figure 250B:
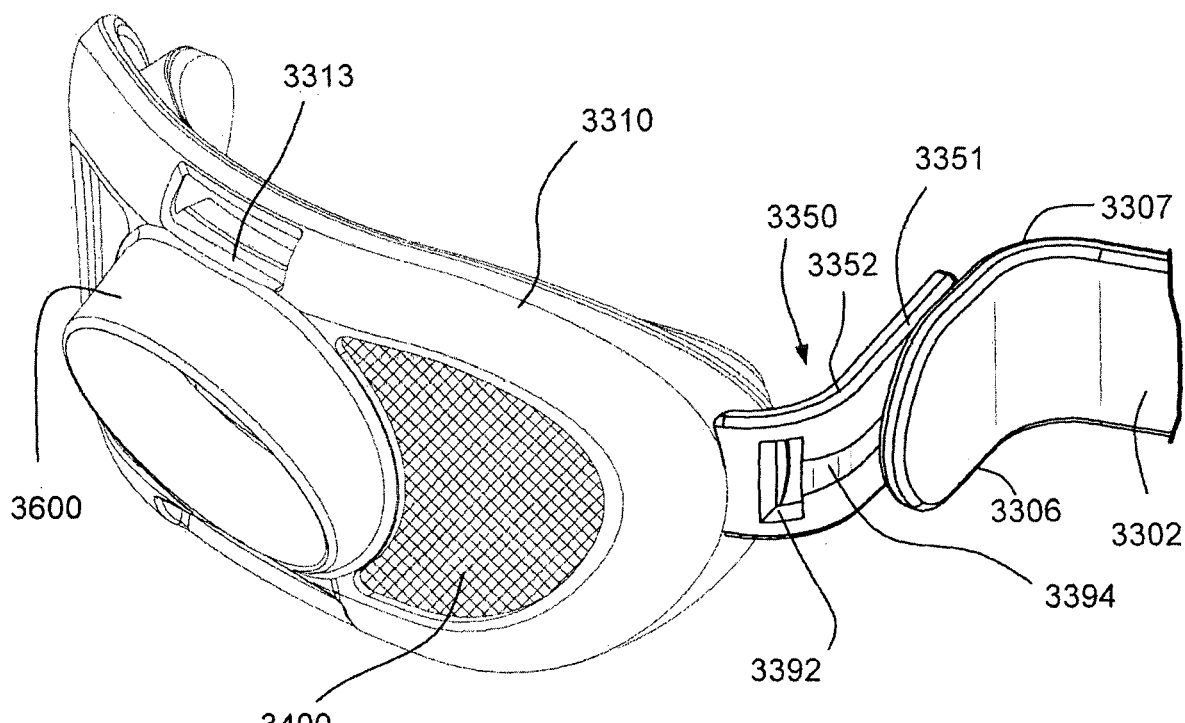

FIG. 250B shows a perspective view of a detachable rigidiser arm attached to a frame for a patient interface according to an example of the present technology.

Figure 250C:
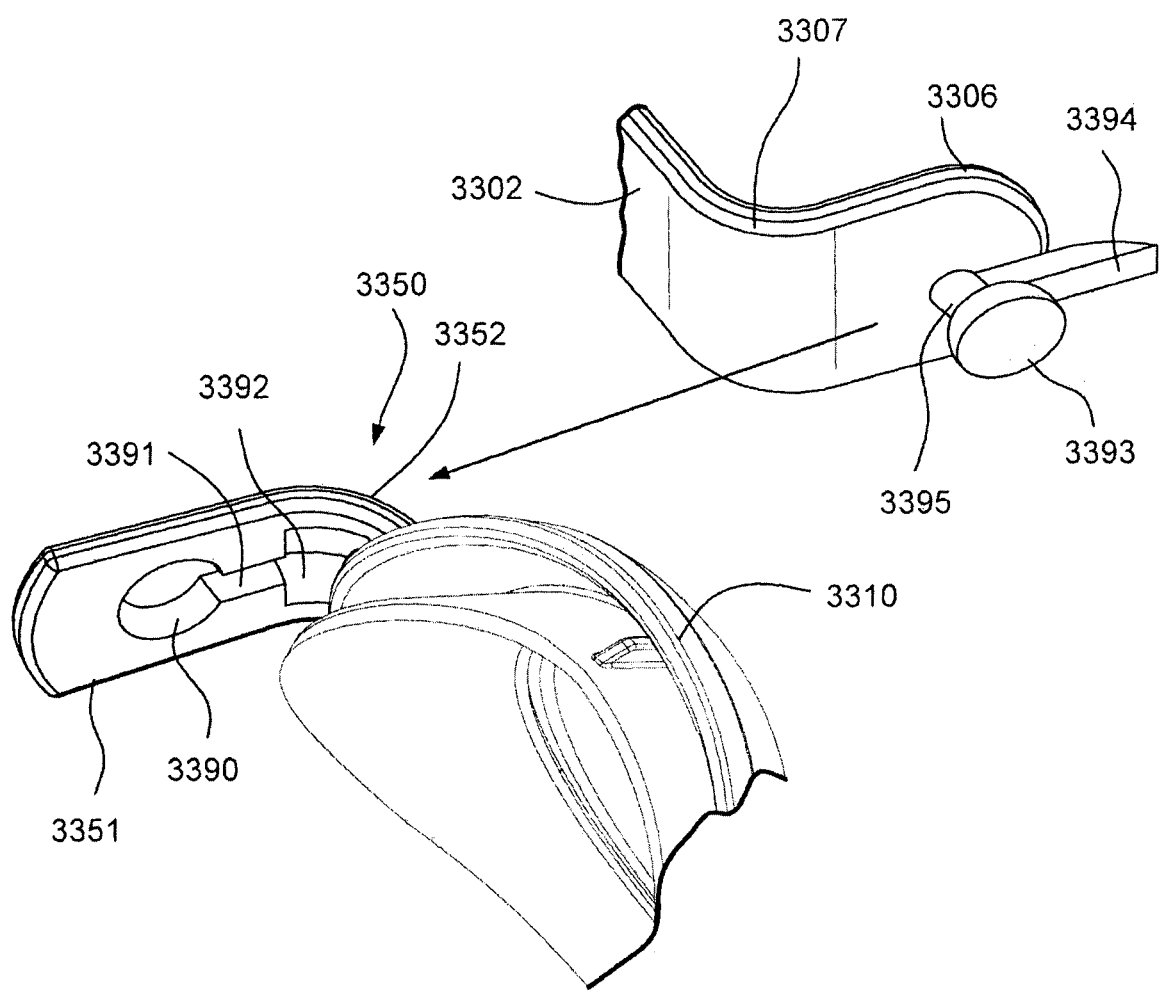

FIG. 250C shows a rear perspective view of a frame for a patient interface and a detachable rigidiser arm according to an example of the present technology.

Figure 251A:
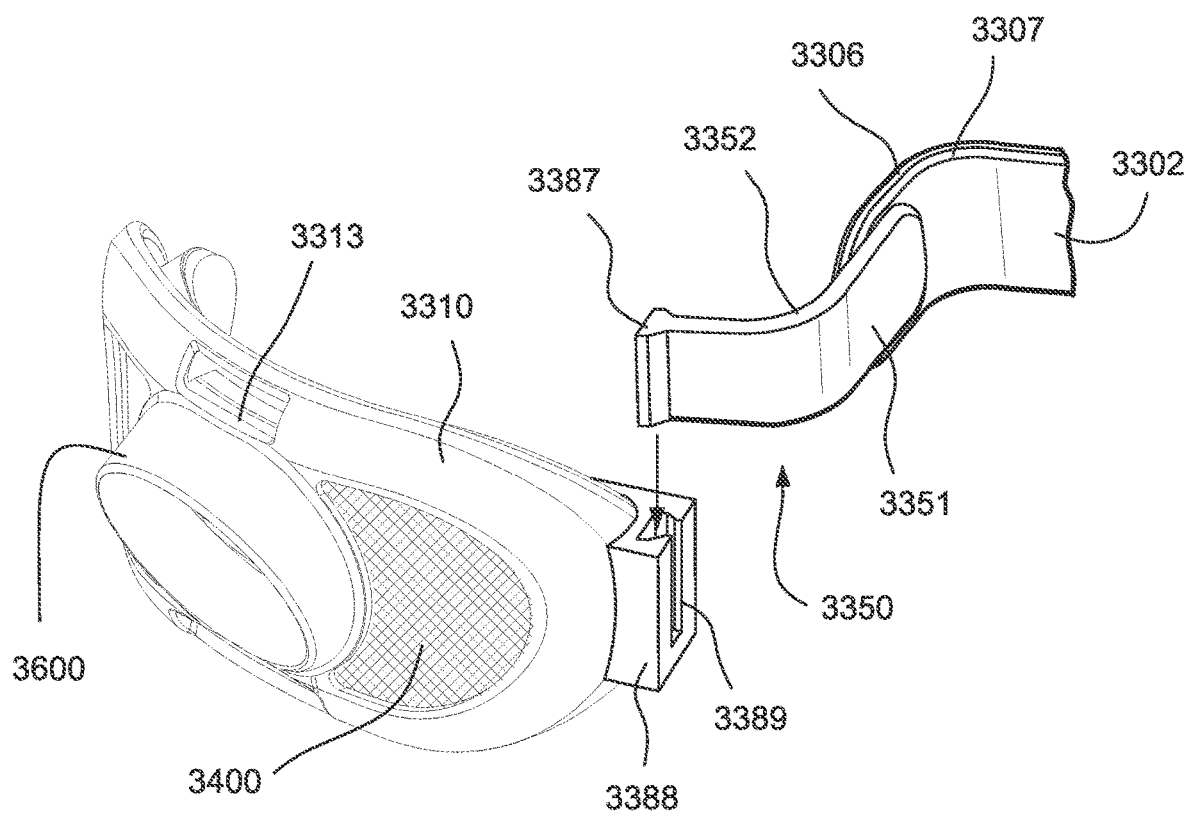

FIG. 251A shows a perspective view of a frame for a patient interface and a detachable rigidiser arm according to an example of the present technology.

Figure 251B:
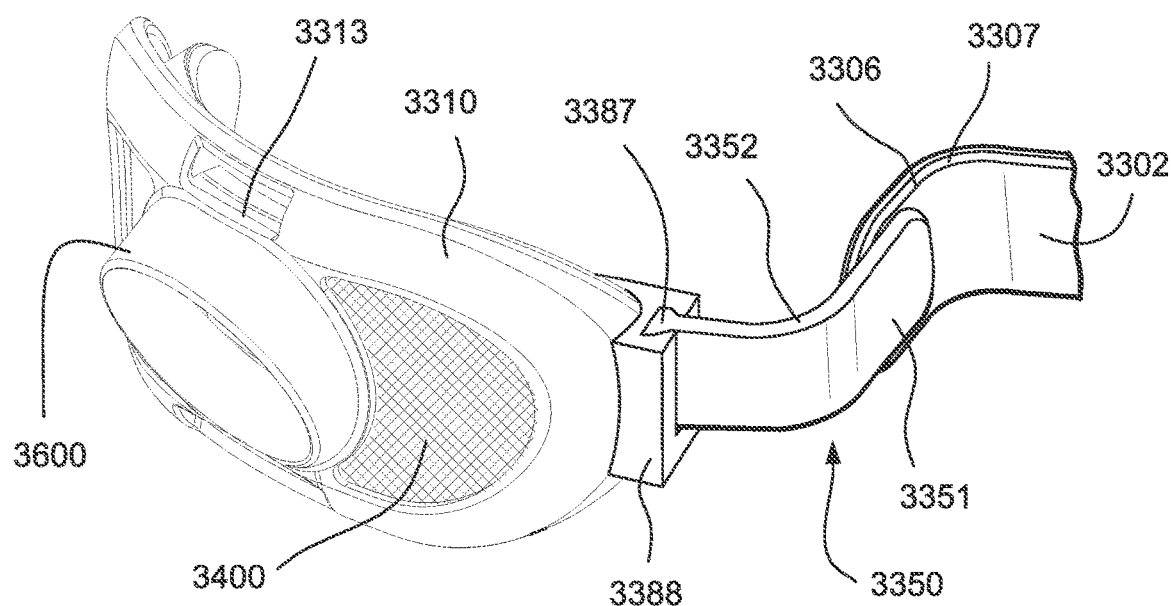

FIG. 251B shows a perspective view of a detachable rigidiser arm attached to a frame for a patient interface according to an example of the present technology.

Figure 252A:
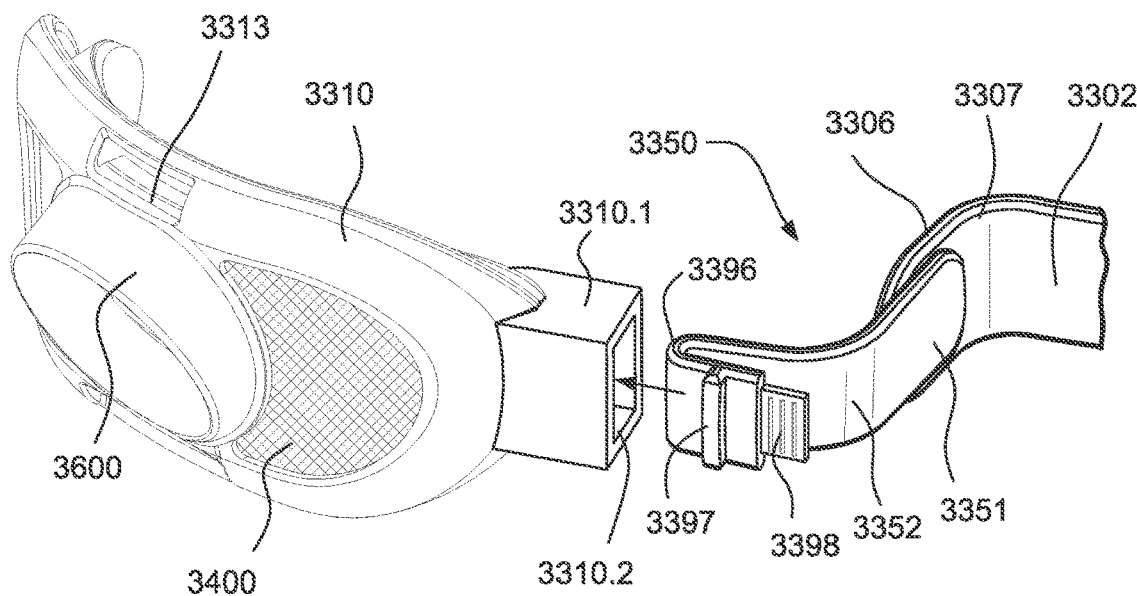

FIG. 252A shows a perspective view of a frame for a patient interface and a detachable rigidiser arm according to an example of the present technology.

Figure 252B:
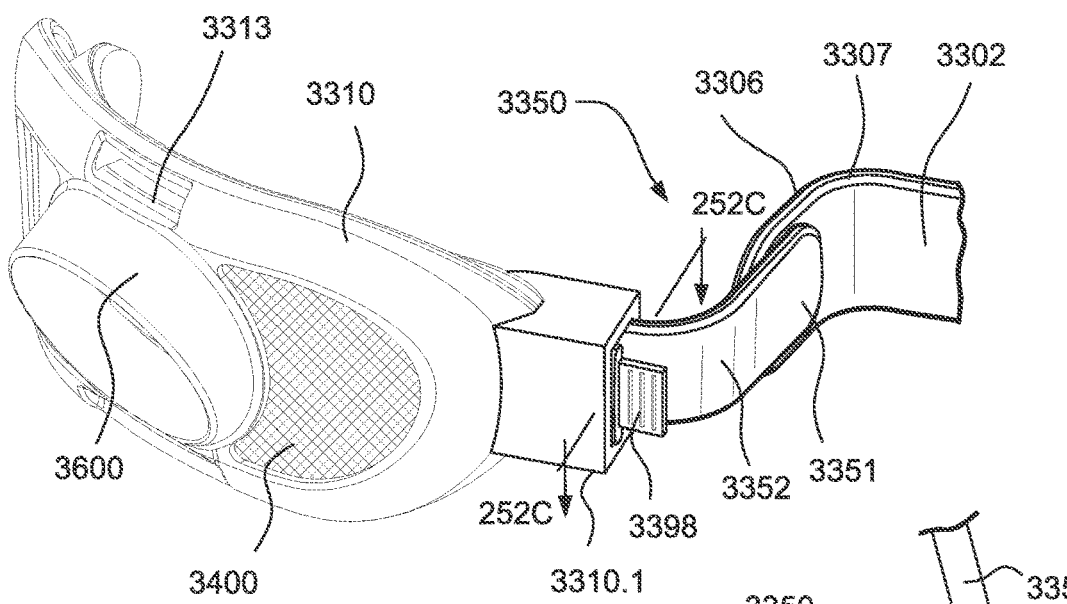

FIG. 252B shows a perspective view of a detachable rigidiser arm attached to a frame for a patient interface according to an example of the present technology.

Figure 252C:
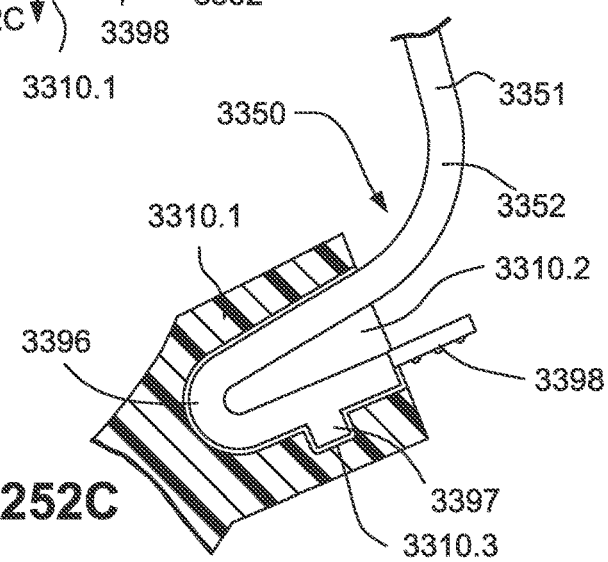

FIG. 252C shows a cross-sectional view of detachable rigidiser arm attached to a frame for a patient interface according to an example of the present technology taken through line 252C-252C in FIG. 252B.

Figure 253A:
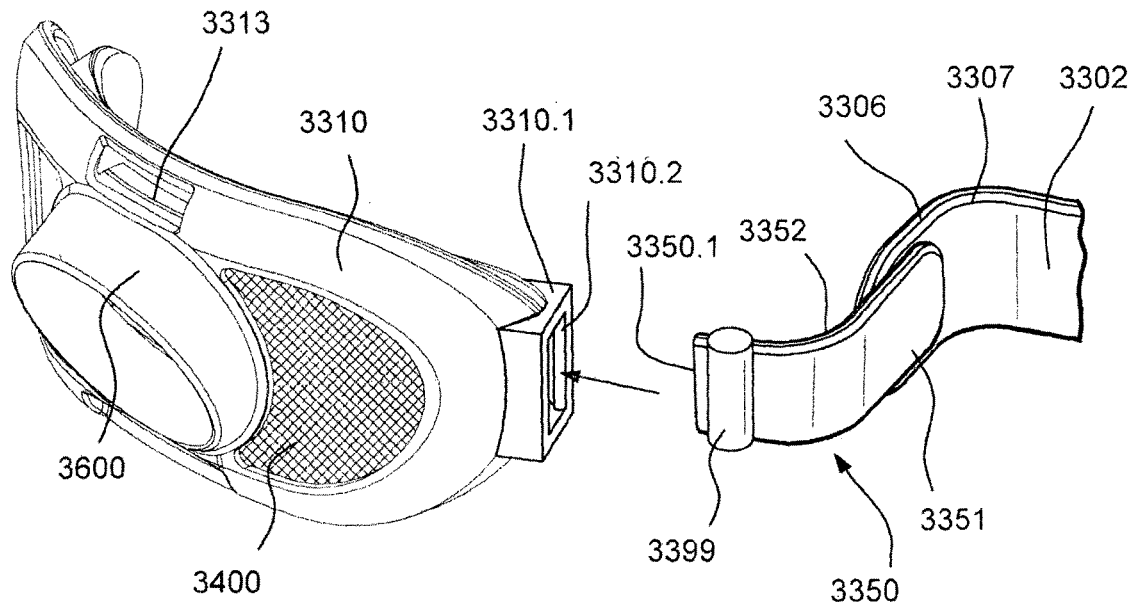

FIG. 253A shows a perspective view of a frame for a patient interface and a detachable rigidiser arm according to an example of the present technology.

Figure 253B:
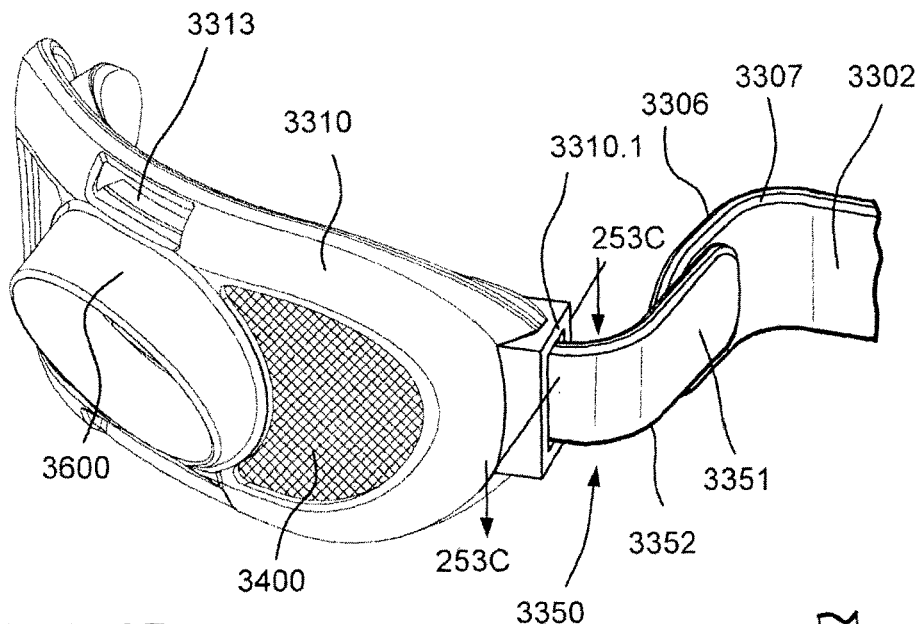

FIG. 253B shows a perspective view of a detachable rigidiser arm attached to a frame for a patient interface according to an example of the present technology.

Figure 253C:
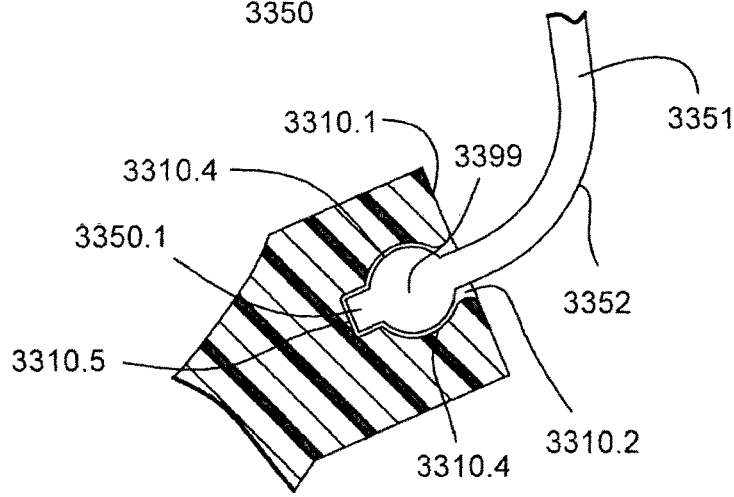

FIG. 253C shows a cross-sectional view of detachable rigidiser arm attached to a frame for a patient interface according to an example of the present technology taken through line 253C-253C in FIG. 253B.

Figure 254A:
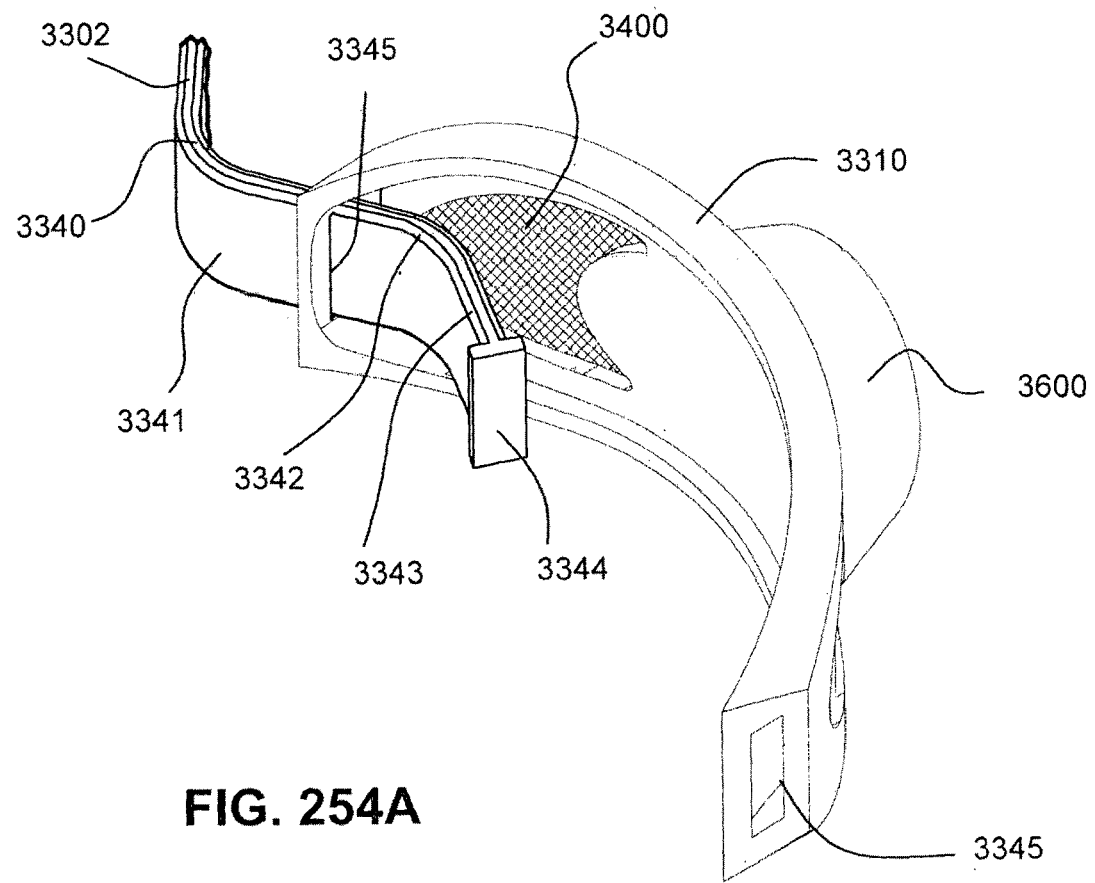

FIG. 254A shows a perspective view of a frame for a patient interface and a detachable rigidiser arm according to an example of the present technology.

Figure 254B:
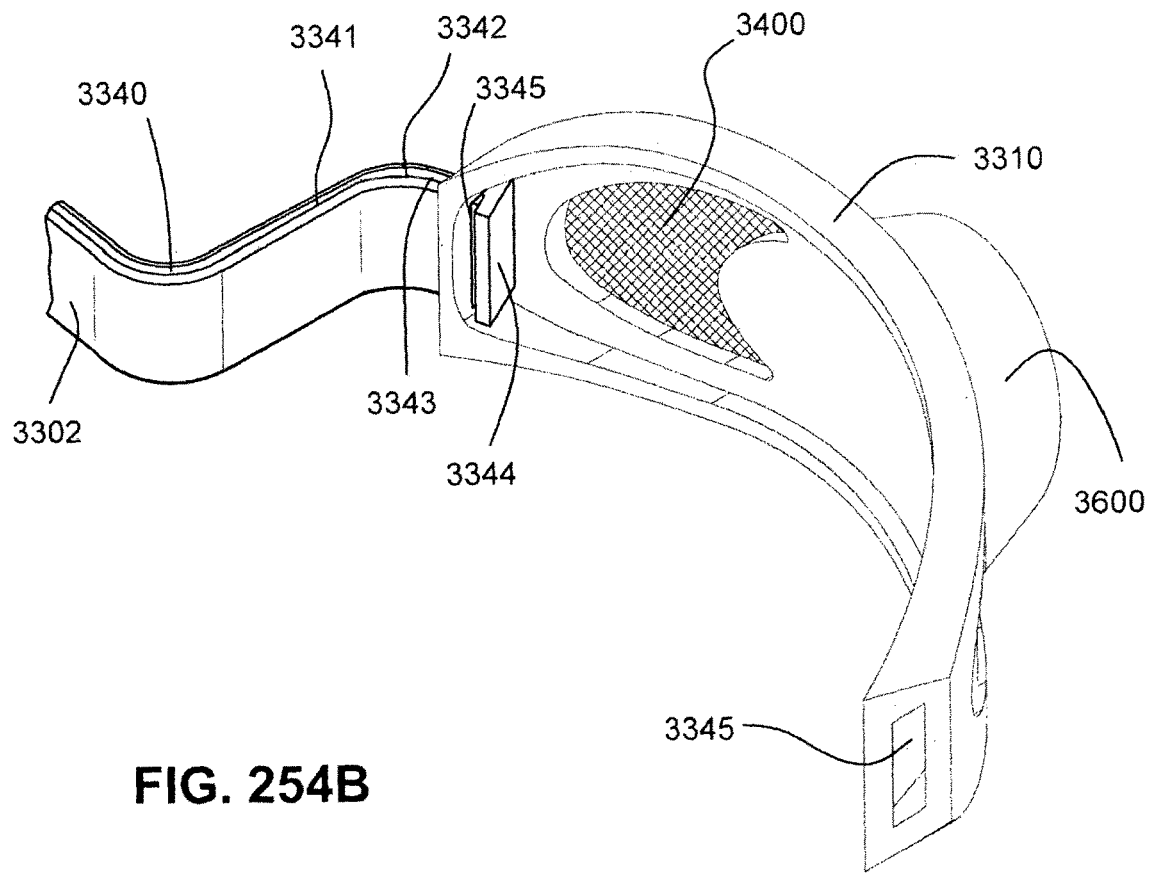

FIG. 254B shows a perspective view of a detachable rigidiser arm attached to a frame for a patient interface according to an example of the present technology.

Figure 255A:
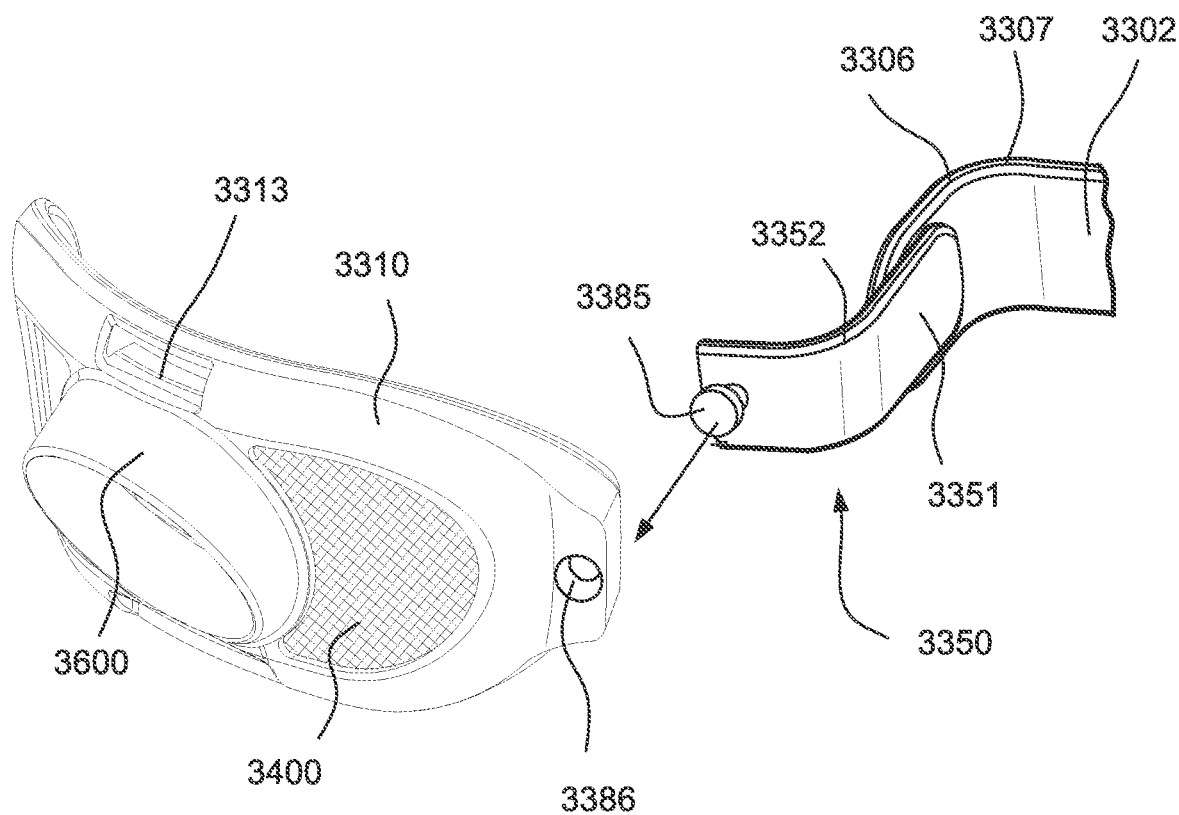

FIG. 255A shows a perspective view of a frame for a patient interface and a detachable rigidiser arm according to an example of the present technology.

Figure 255B:
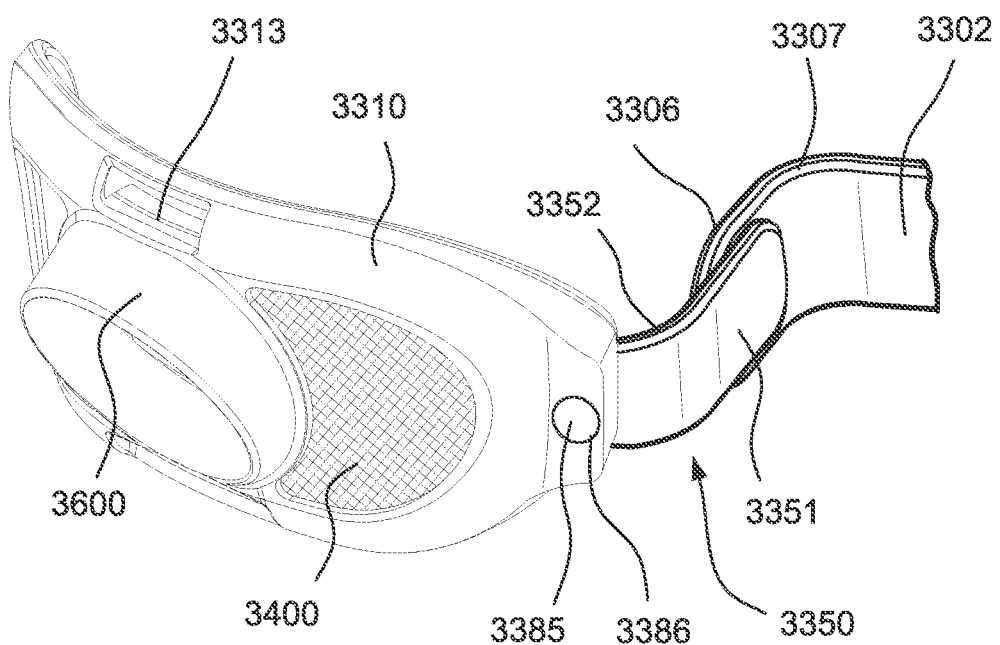

FIG. 255B shows a perspective view of a detachable rigidiser arm attached to a frame for a patient interface according to an example of the present technology.

Figure 256A:
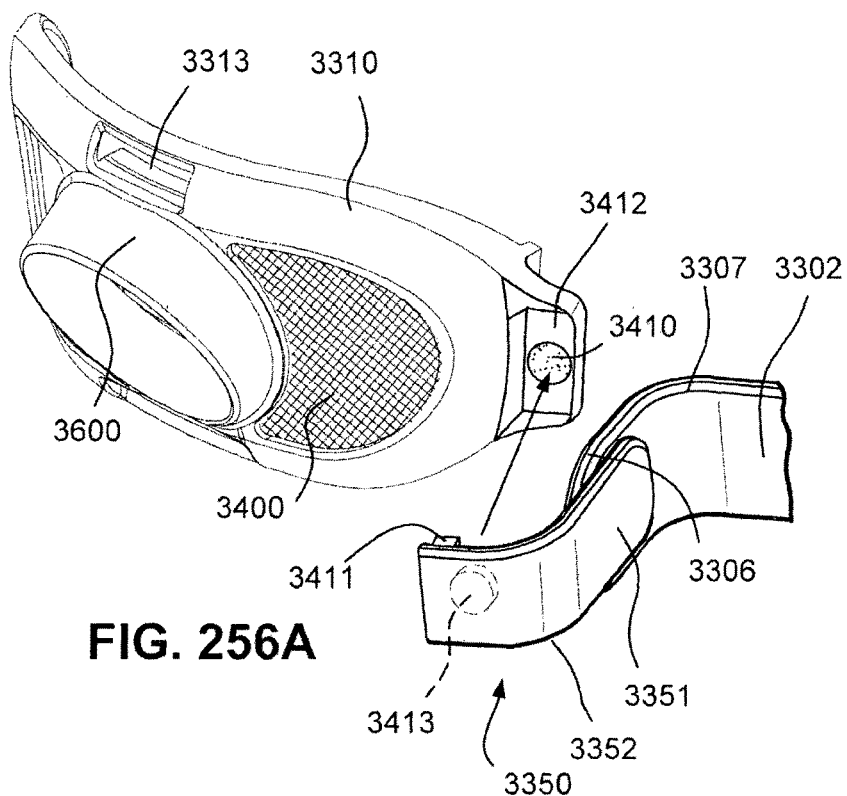

FIG. 256A shows a perspective view of a frame for a patient interface and a detachable rigidiser arm according to an example of the present technology.

Figure 256B:
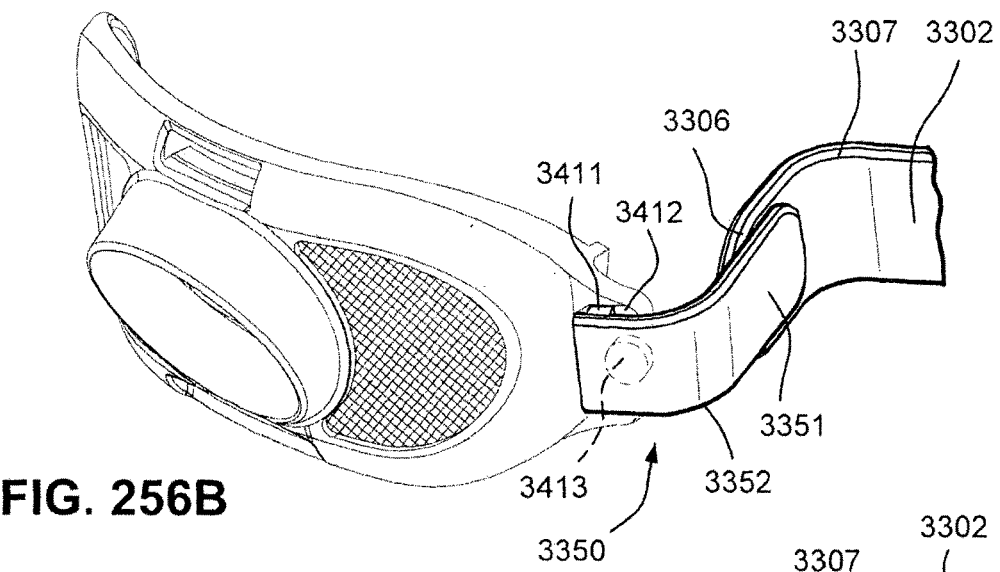

FIG. 256B shows a perspective view of a detachable rigidiser arm attached to a frame for a patient interface according to an example of the present technology.

Figure 256C:
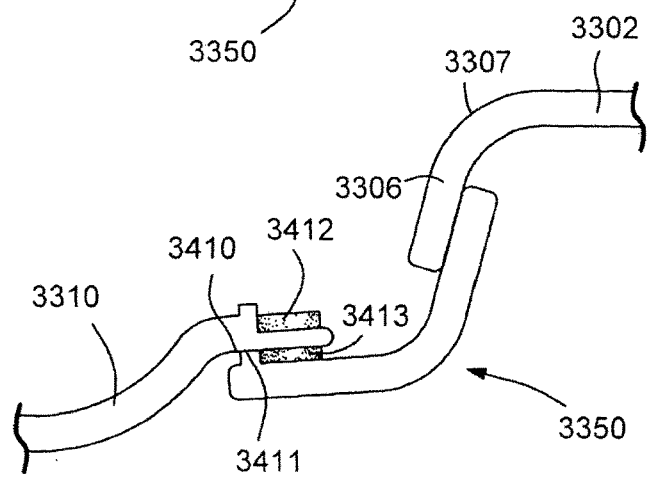

FIG. 256C shows a detailed top view of a detachable rigidiser arm attached to a frame for a patient interface according to an example of the present technology.

Figure 257A:
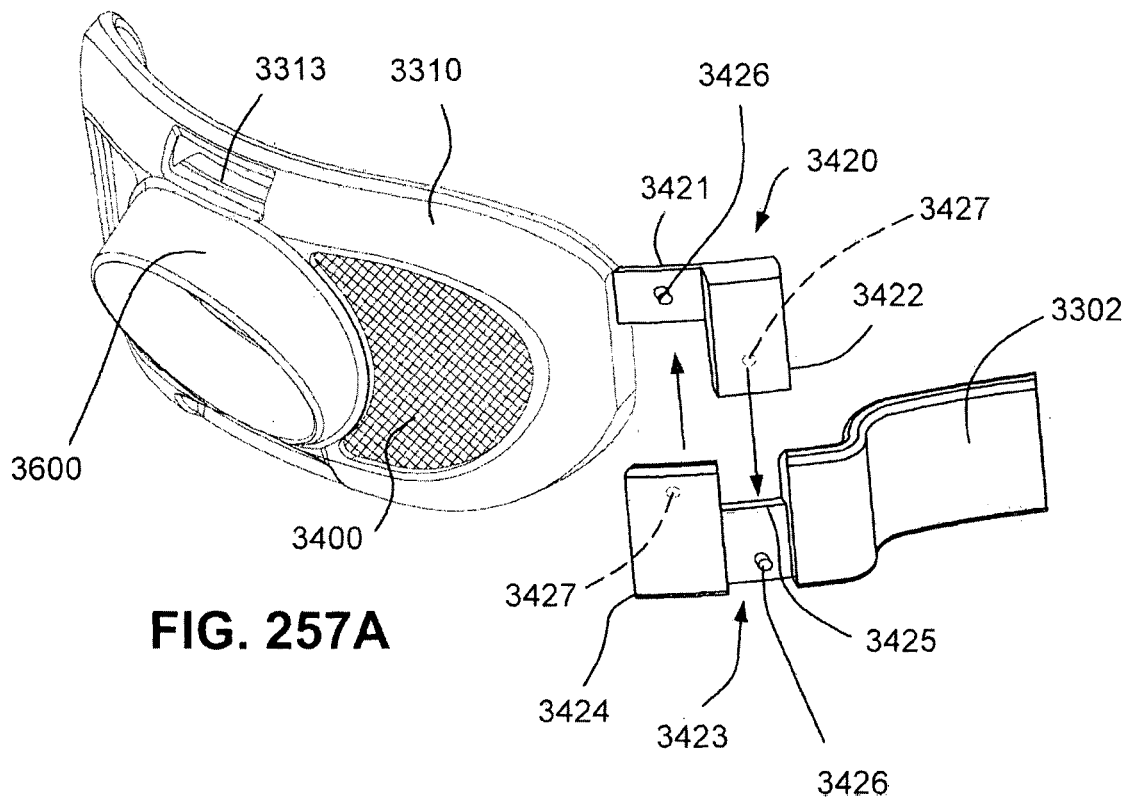

FIG. 257A shows a perspective view of a frame for a patient interface and a detachable rigidiser arm according to an example of the present technology.

Figure 257B:
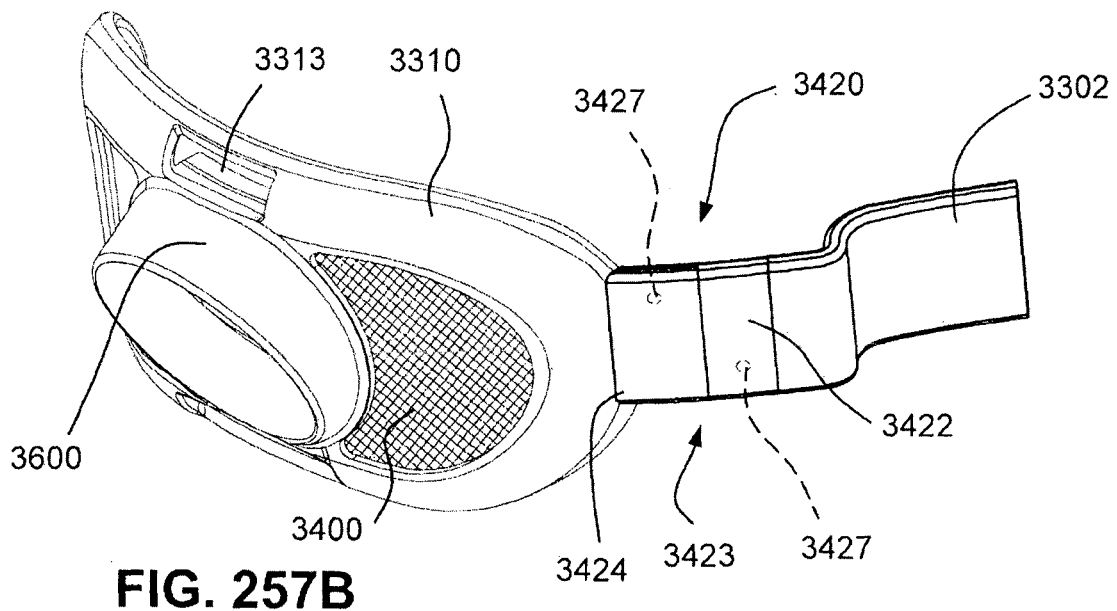

FIG. 257B shows a perspective view of a detachable rigidiser arm attached to a frame for a patient interface according to an example of the present technology.

Figure 258A:
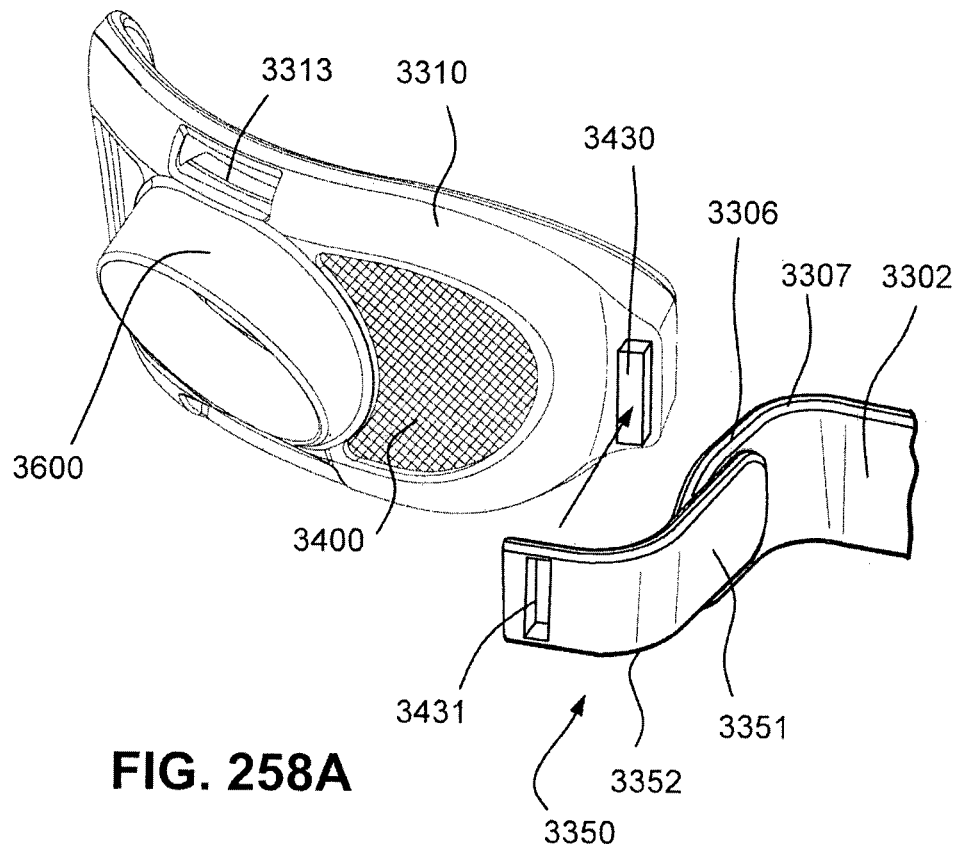

FIG. 258A shows a perspective view of a frame for a patient interface and a detachable rigidiser arm according to an example of the present technology.

Figure 258B:
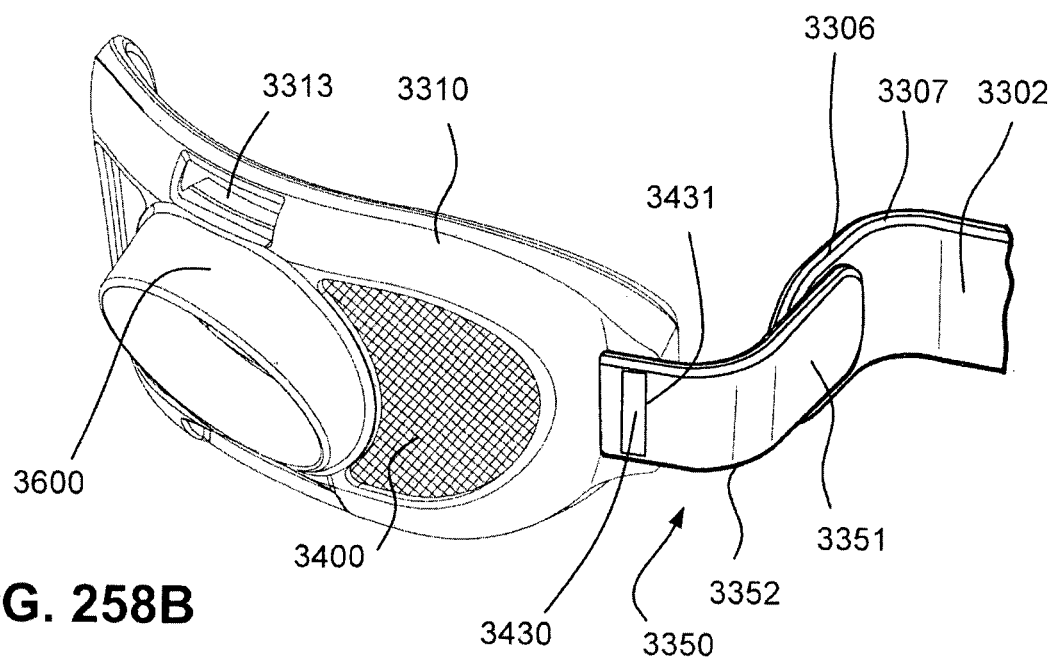

FIG. 258B shows a perspective view of a detachable rigidiser arm attached to a frame for a patient interface according to an example of the present technology.

Figure 259A:
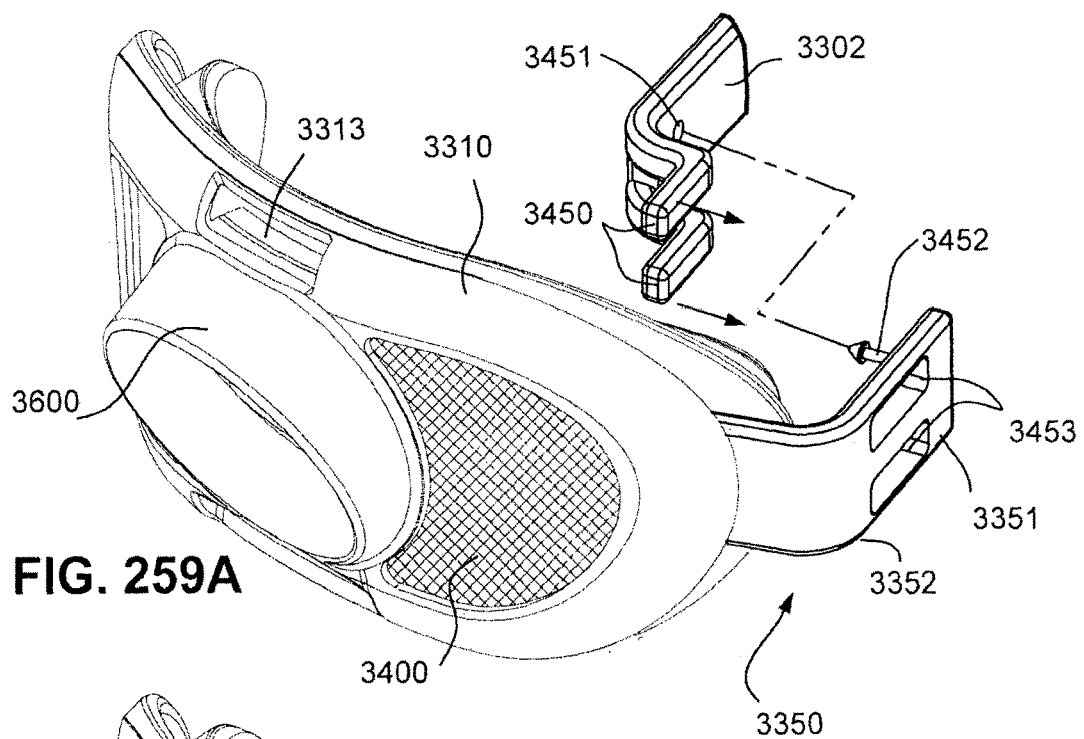

FIG. 259A shows a perspective view of a frame for a patient interface and a detachable rigidiser arm according to an example of the present technology.

Figure 259B:
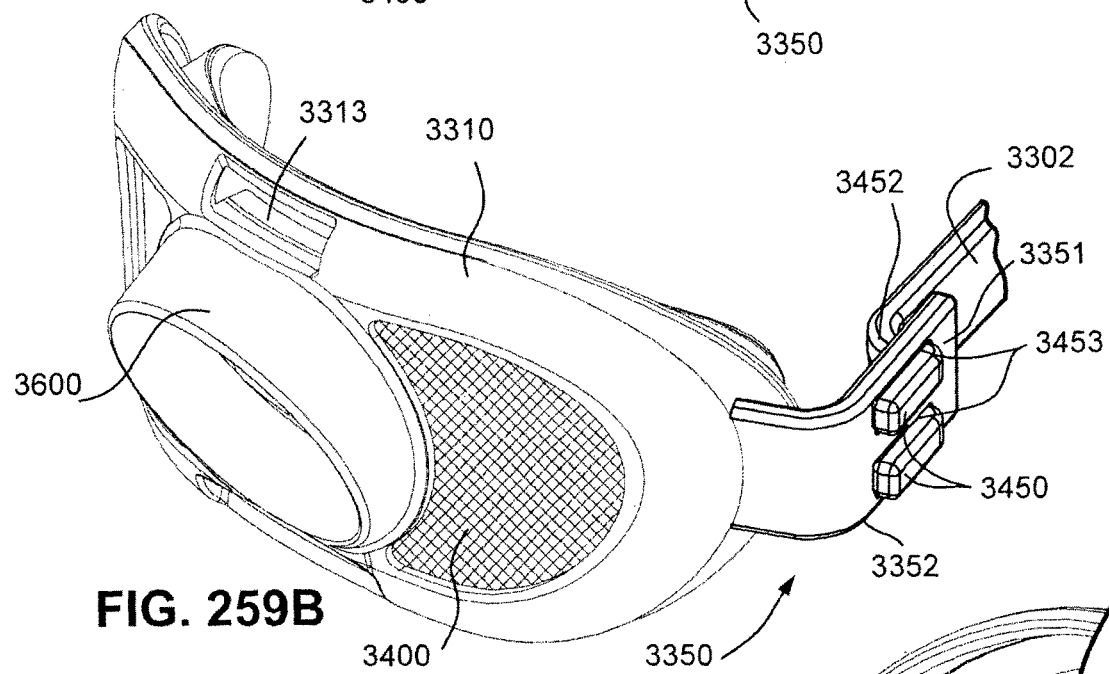

FIG. 259B shows a perspective view of a detachable rigidiser arm attached to a frame for a patient interface according to an example of the present technology.

Figure 259C:
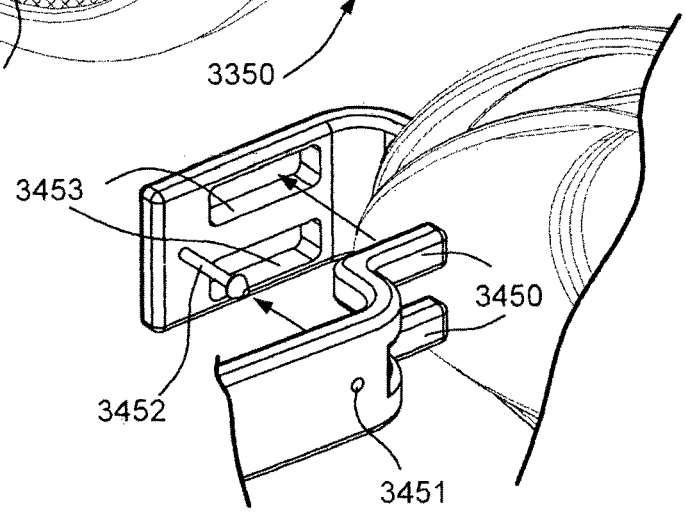

FIG. 259C shows a detailed rear perspective view of a frame for a patient interface and a detachable rigidiser arm according to an example of the present technology.

Figure 260A:
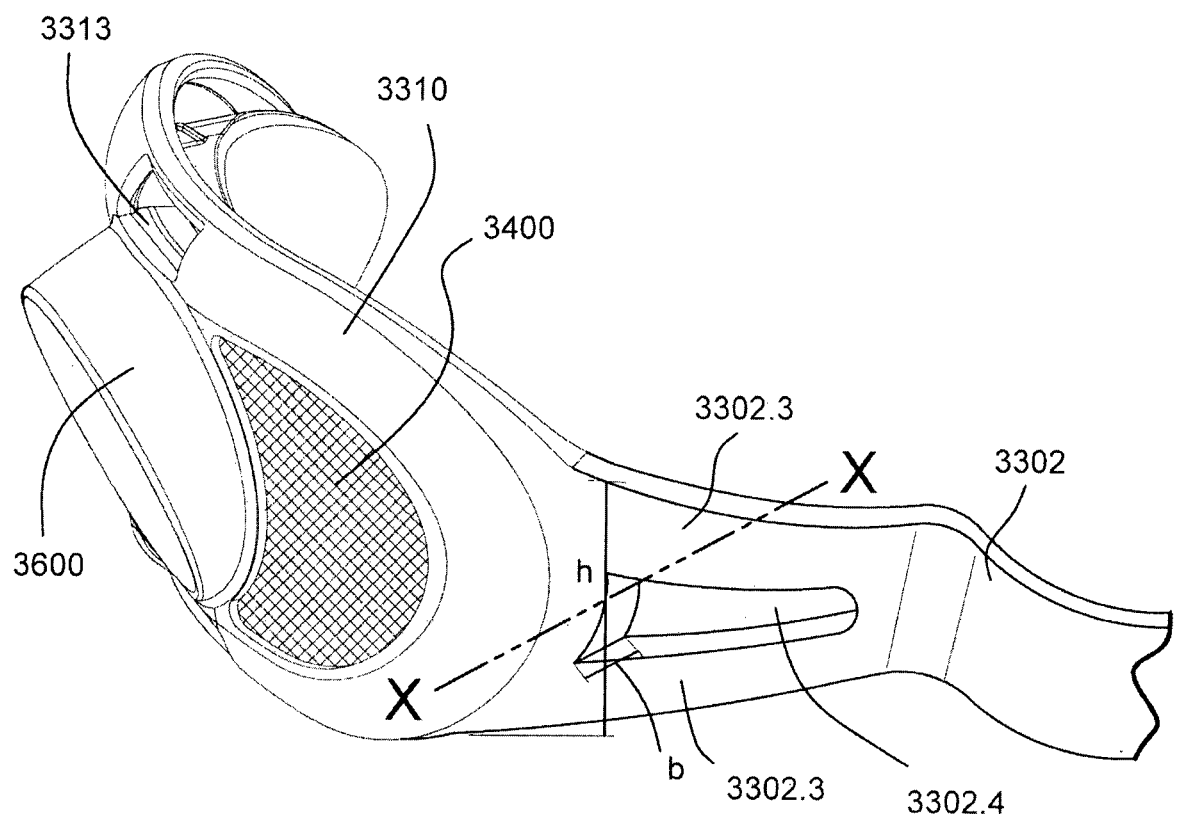

FIG. 260A shows a perspective view of a frame for a patient interface and a rigidiser arm according to an example of the present technology.

Figure 260B:
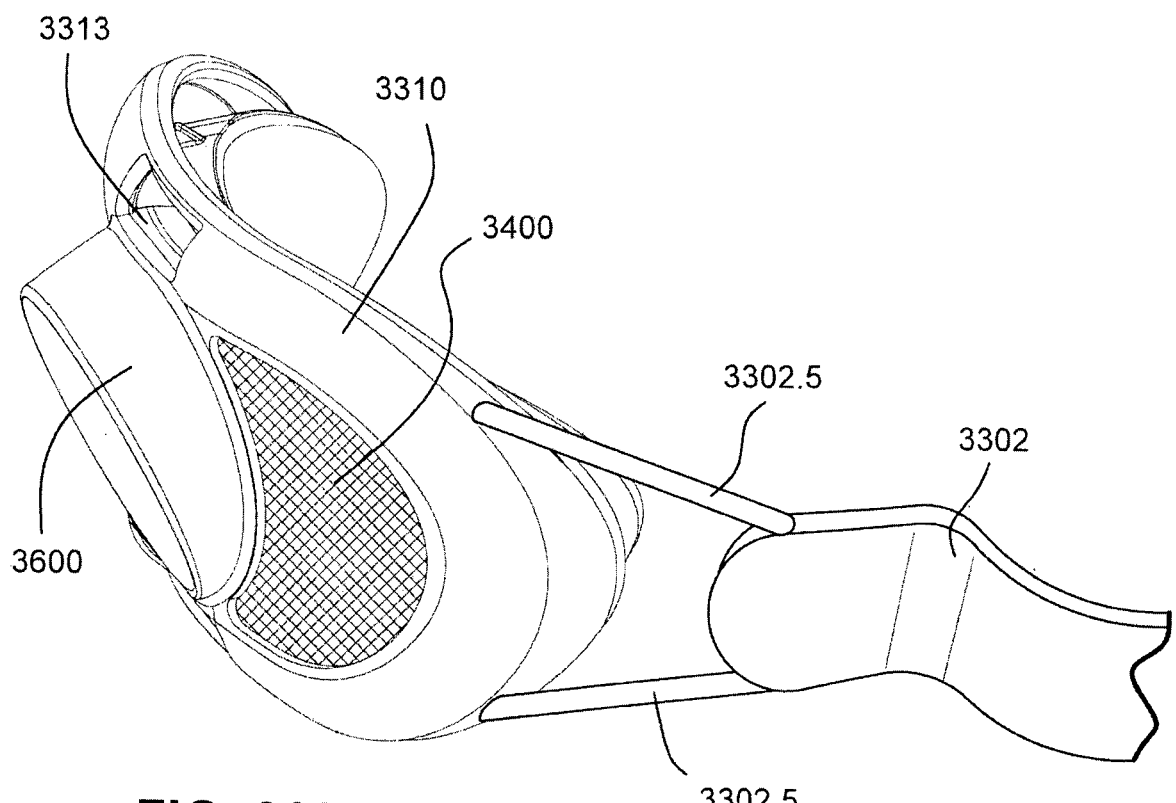

FIG. 260B shows a perspective view of a frame for a patient interface and a rigidiser arm according to an example of the present technology.

Figure 261A:
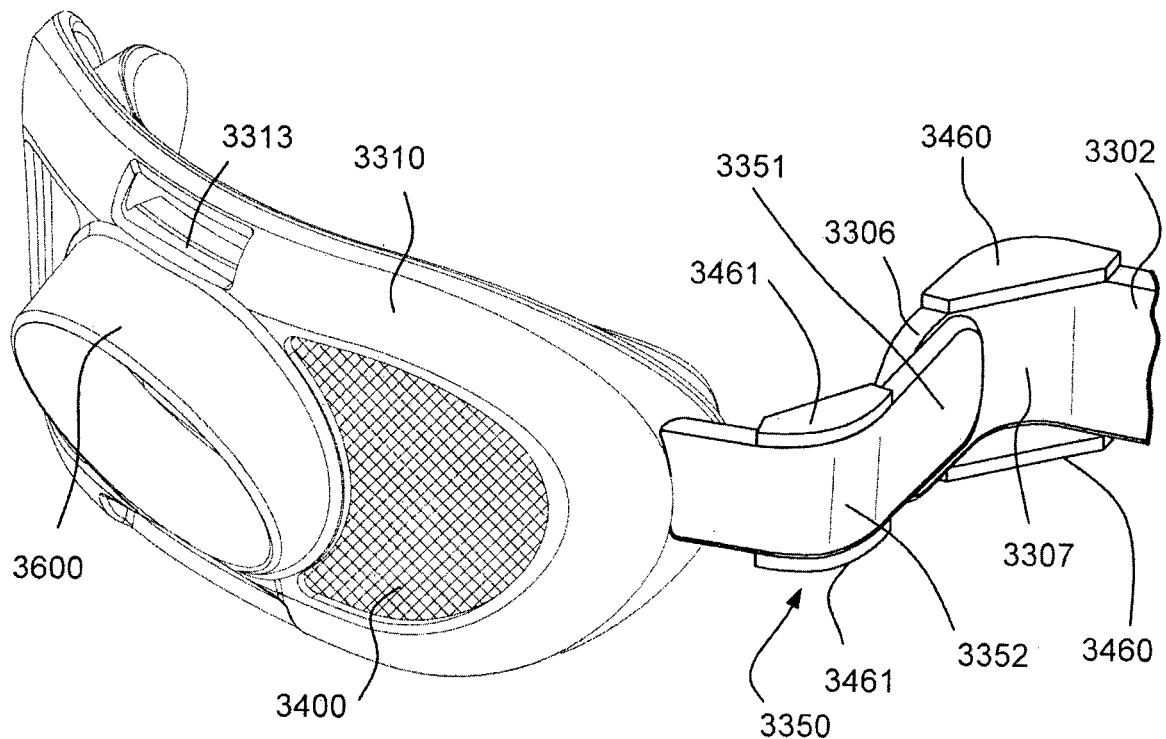

FIG. 261A shows a perspective view of a frame for a patient interface and a rigidiser arm according to an example of the present technology.

Figure 261B:
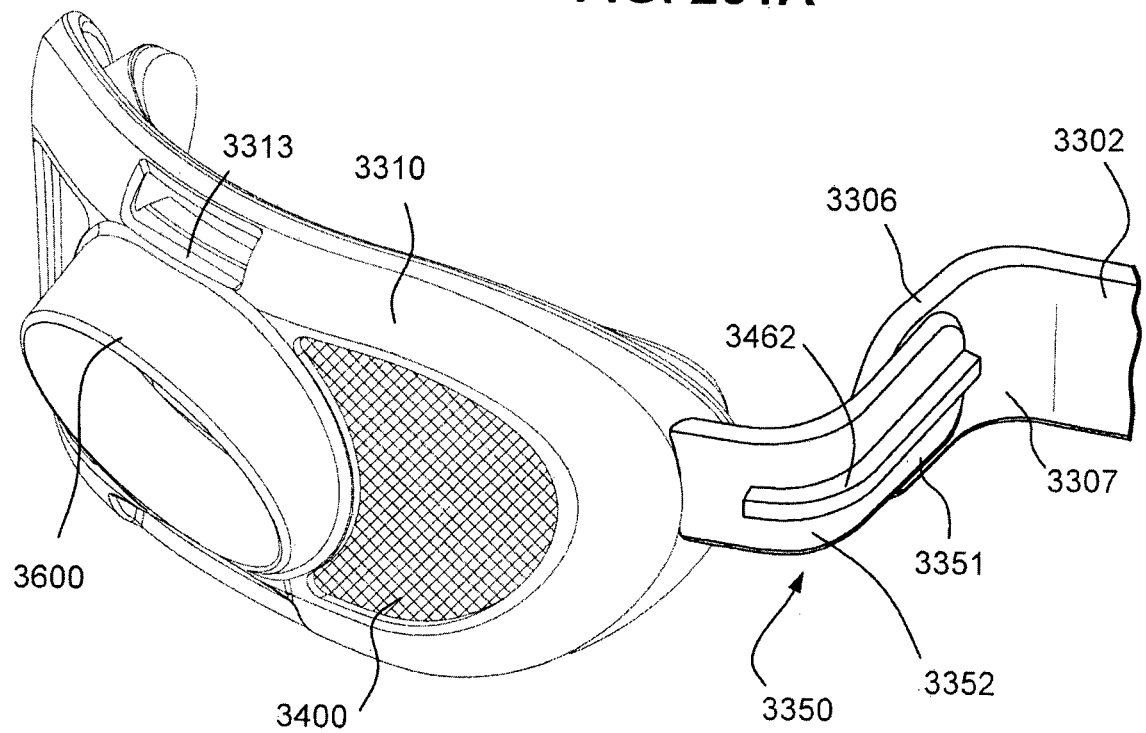

FIG. 261B shows a perspective view of a frame for a patient interface and a rigidiser arm according to an example of the present technology.

Figure 262A:
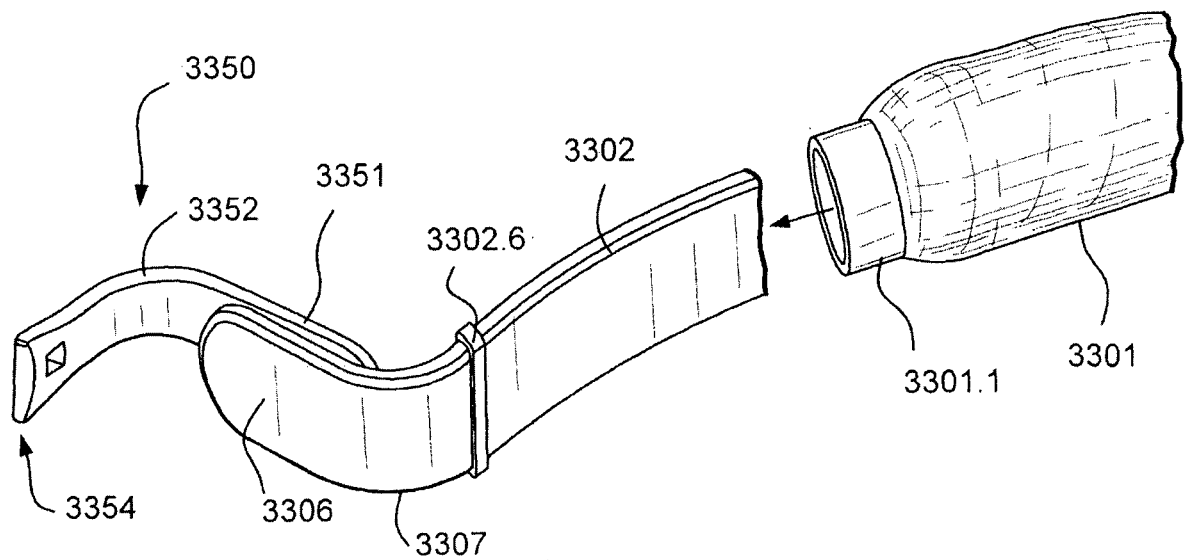

FIG. 262A shows a perspective view of a strap for a positioning and stabilising structure and a rigidiser arm for a patient interface system according to an example of the present technology.

Figure 262B:
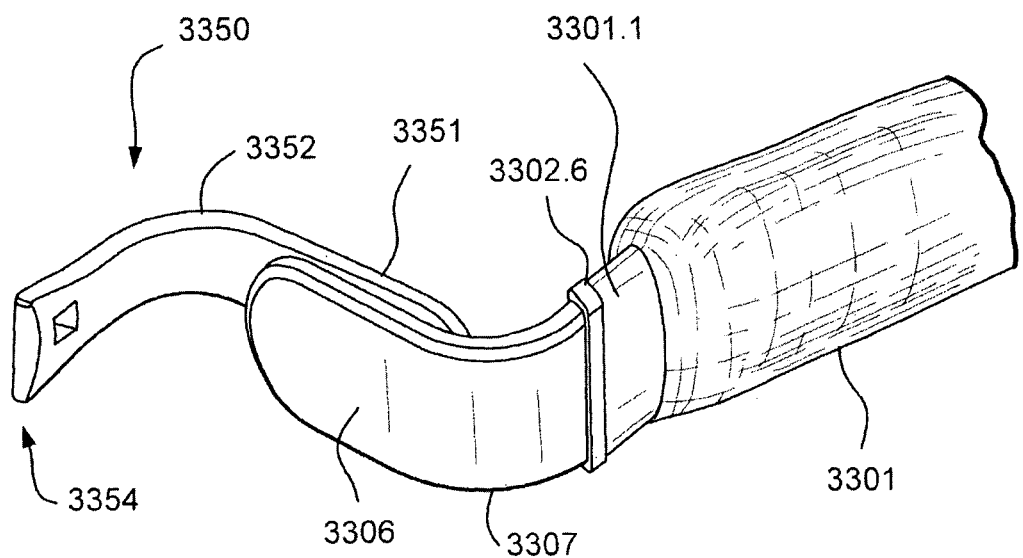

FIG. 262B shows a perspective view of a strap for a positioning and stabilising structure attached to a rigidiser arm for a patient interface system according to an example of the present technology.

Figure 263:
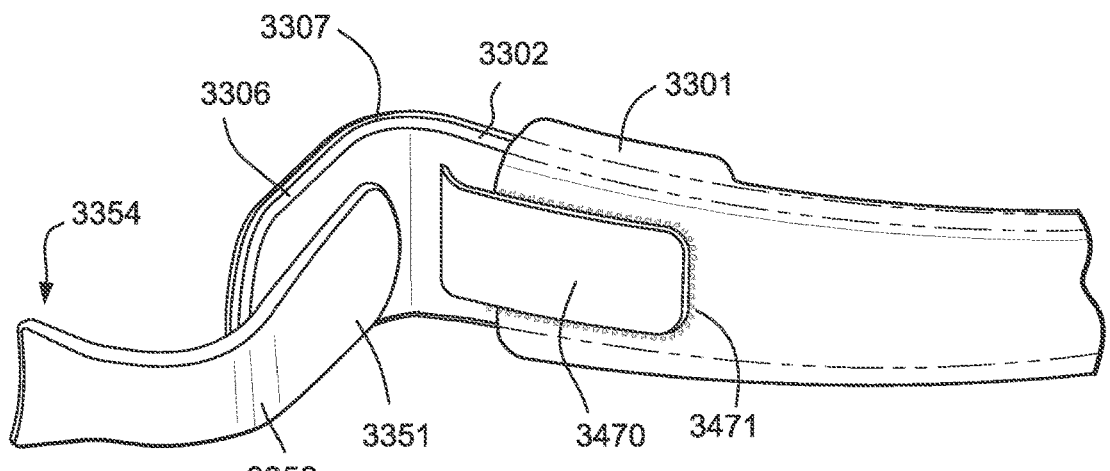

FIG. 263 shows a perspective view of a strap for a positioning and stabilising structure attached to a rigidiser arm for a patient interface system according to an example of the present technology.

Figure 264A:
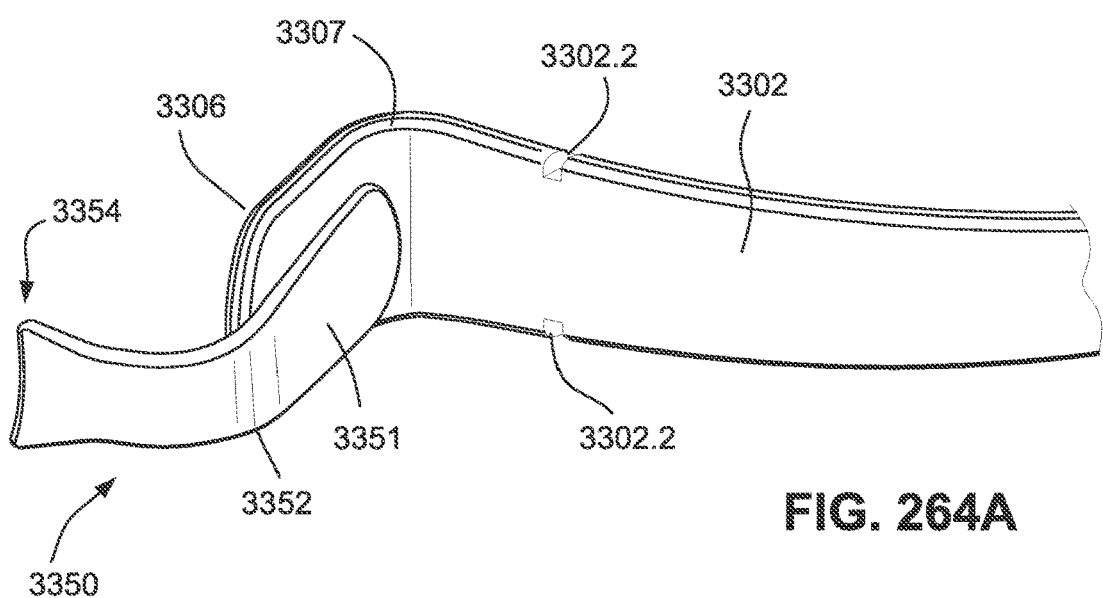

FIG. 264A shows a perspective view of a rigidiser arm for a patient interface system according to an example of the present technology.

Figure 264B:
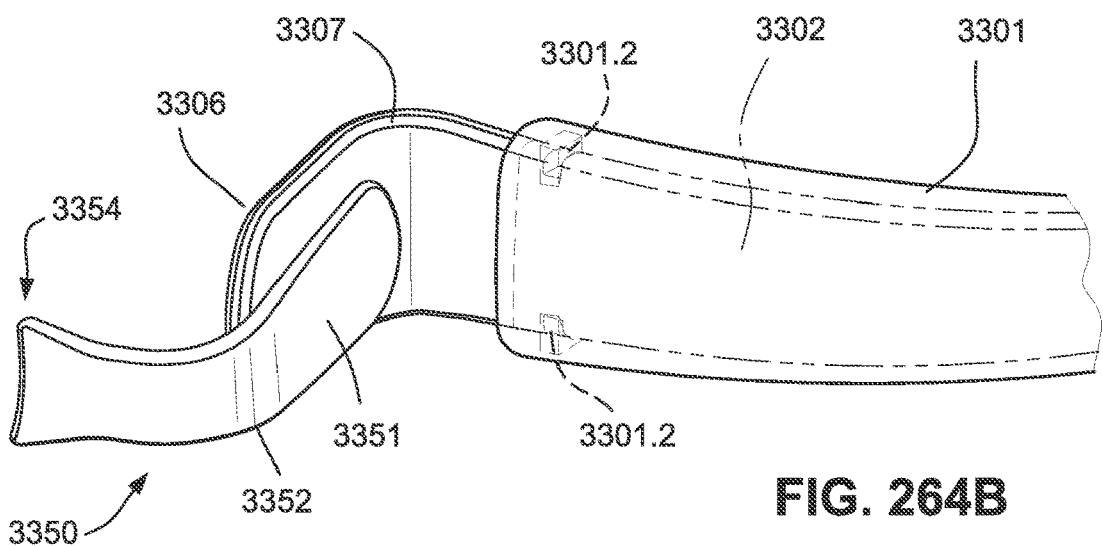

FIG. 264B shows a perspective view of a strap for a positioning and stabilising structure attached to a rigidiser arm for a patient interface system according to an example of the present technology.

Figure 265:
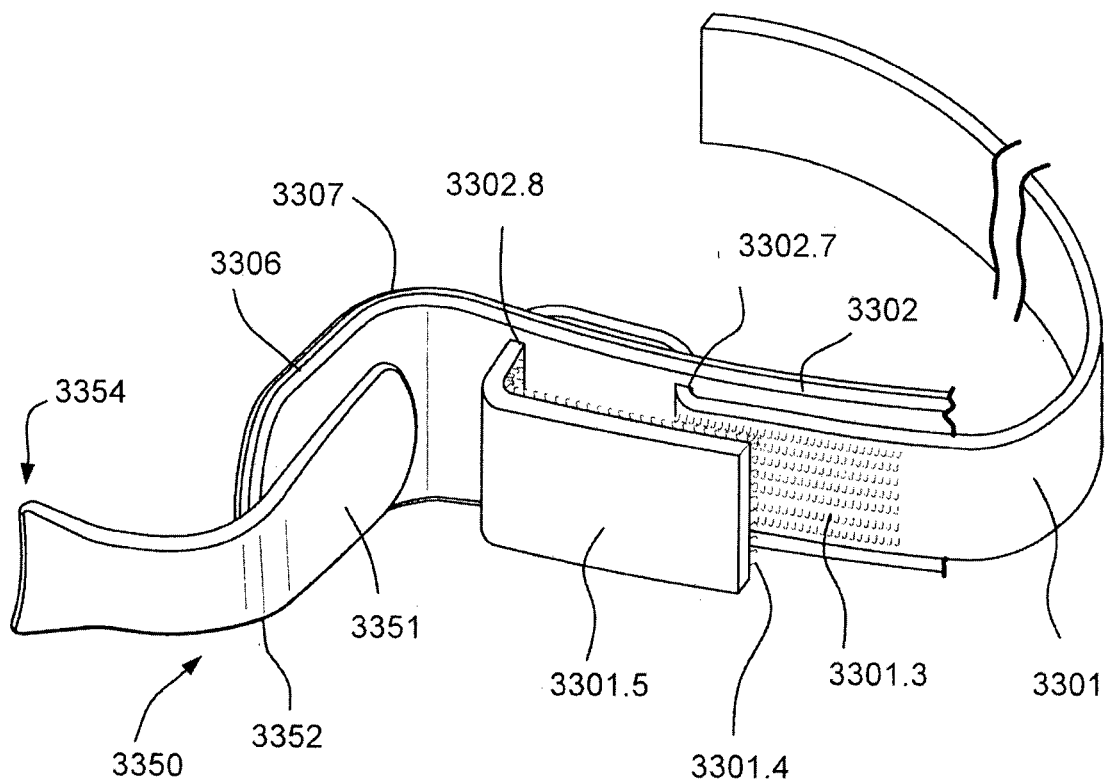

FIG. 265 shows a perspective view of a strap for a positioning and stabilising structure attached to a rigidiser arm for a patient interface system according to an example of the present technology.

Figure 266:
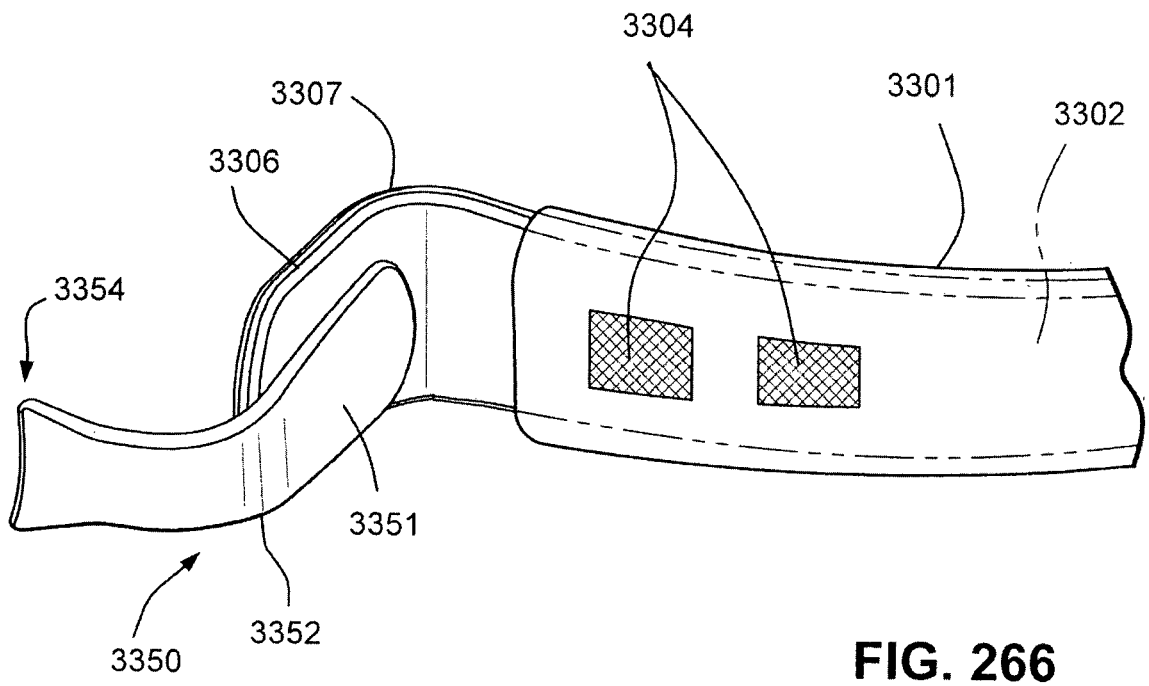

FIG. 266 shows a perspective view of a strap for a positioning and stabilising structure attached to a rigidiser arm for a patient interface system according to an example of the present technology.

Figure 267:
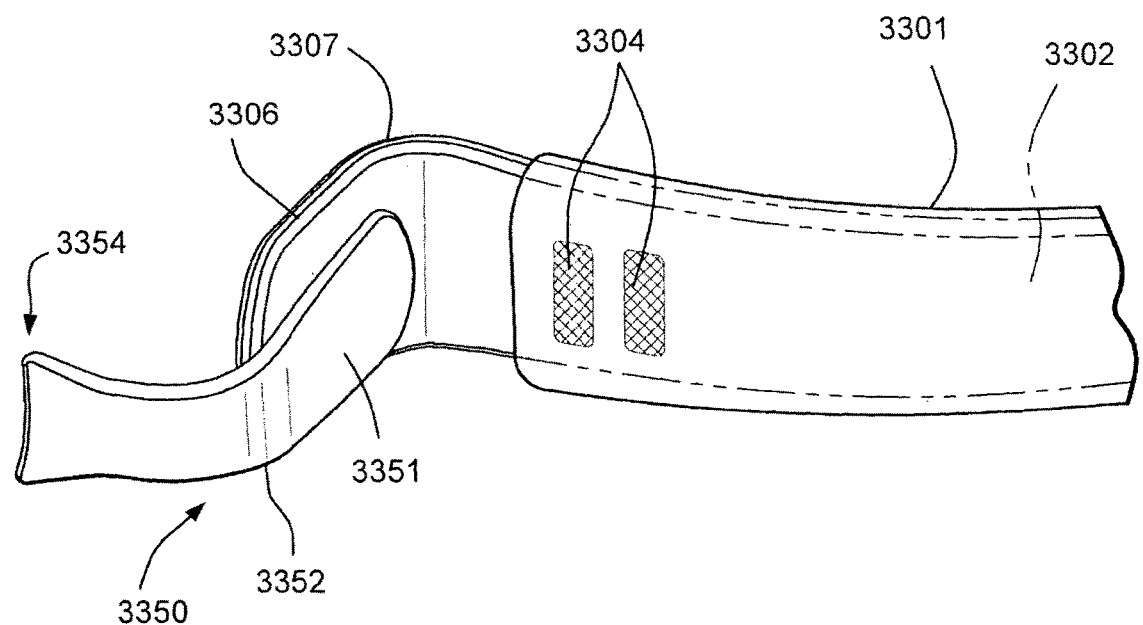

FIG. 267 shows a perspective view of a strap for a positioning and stabilising structure attached to a rigidiser arm for a patient interface system according to an example of the present technology.

Figure 268:
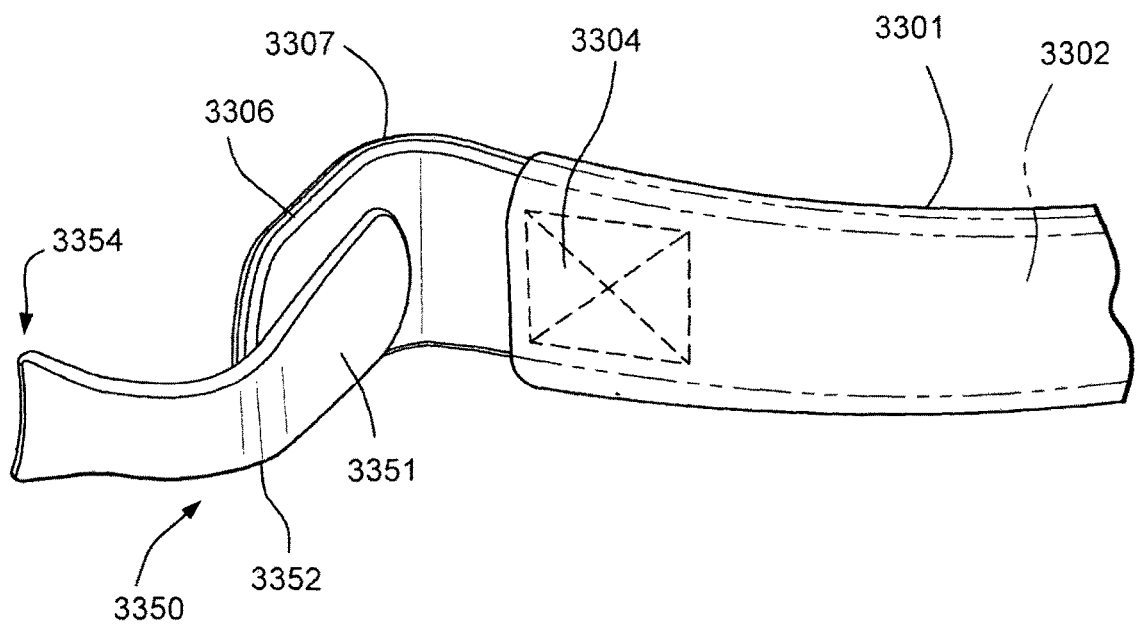

FIG. 268 shows a perspective view of a strap for a positioning and stabilising structure attached to a rigidiser arm for a patient interface system according to an example of the present technology.

Figure 269:
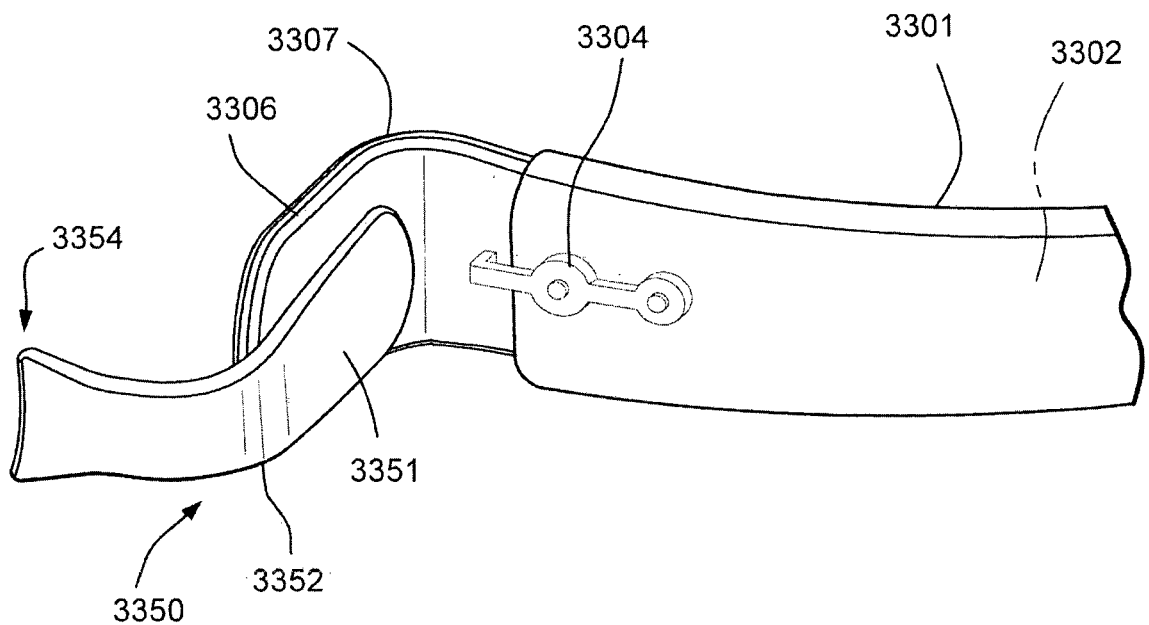

FIG. 269 shows a perspective view of a strap for a positioning and stabilising structure attached to a rigidiser arm for a patient interface system according to an example of the present technology.

Figure 270:
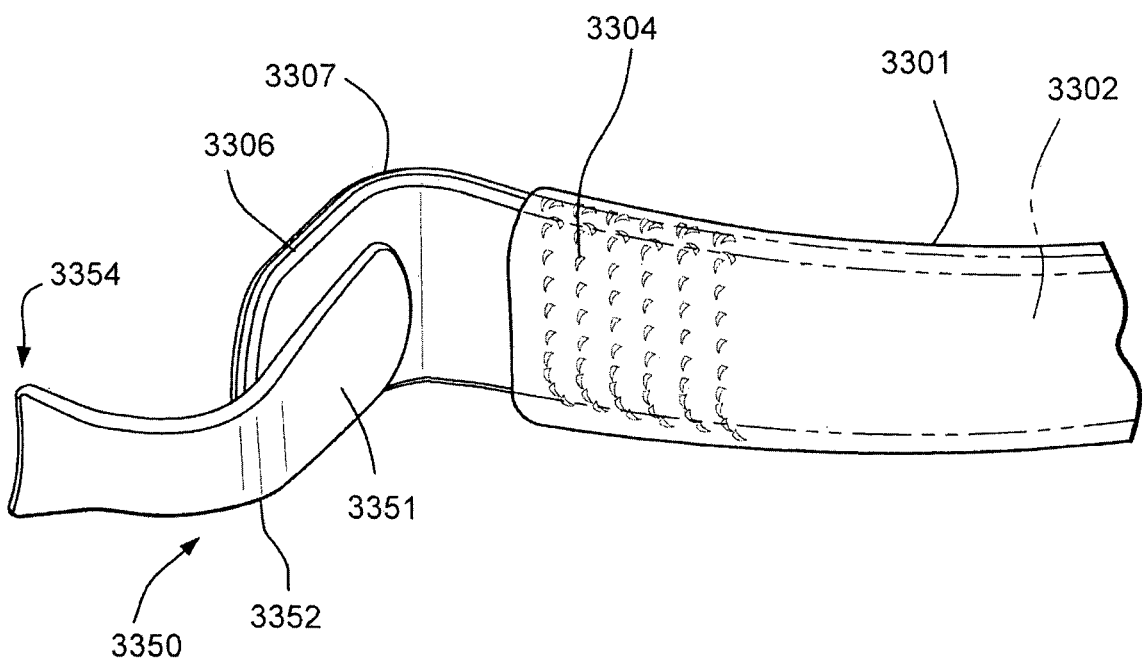

FIG. 270 shows a perspective view of a strap for a positioning and stabilising structure attached to a rigidiser arm for a patient interface system according to an example of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

Figure 1A:
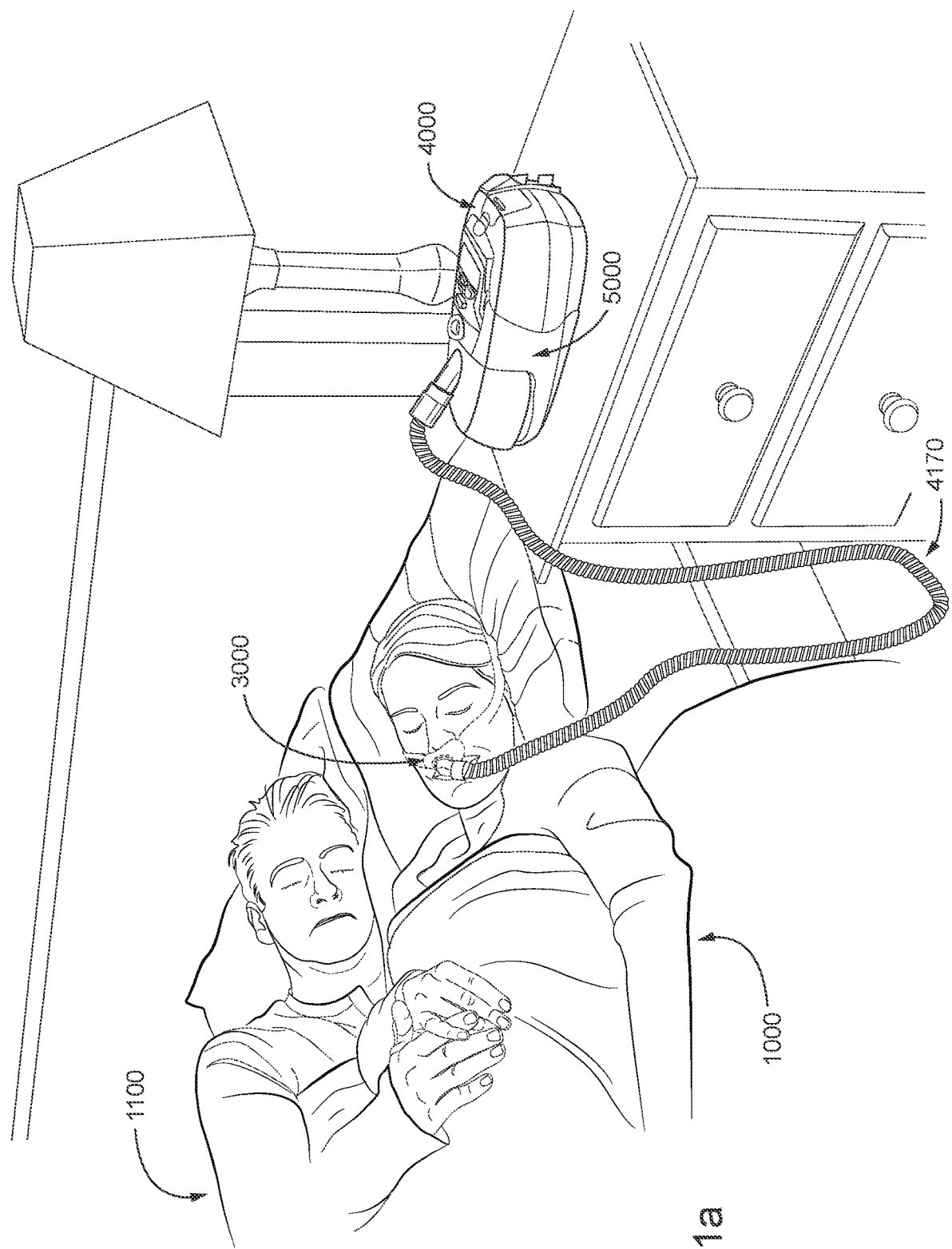
FIG. 1a shows a system in accordance with the present technology. A patient 1000 wearing a patient interface 3000, receives a supply of air at positive pressure from a PAP device 4000. Air from the PAP device 4000 is humidified in a humidifier 5000, and passes along an air circuit 4170 to the patient 1000.

In one form, the present technology comprises apparatus for treating a respiratory disorder. The apparatus may comprise a flow generator or blower for supplying pressurised respiratory gas, such as air, to the patient 1000 via an air circuit 4170 leading to a patient interface 3000, as shown in FIG. 1a.

Therapy

In one form, the present technology comprises a method for treating a respiratory disorder comprising the step of applying positive pressure to the entrance of the airways of a patient 1000.

Nasal CPAP for OSA

In one form, the present technology comprises a method of treating Obstructive Sleep Apnea in a patient by applying nasal continuous positive airway pressure to the patient.

Patient Interface 3000

Referring to FIG. 166, a non-invasive patient interface 3000 in accordance with one aspect of the present technology comprises the following functional aspects: a seal-forming structure 3100 (see, e.g., FIG. 4), a plenum chamber 3200, a positioning and stabilising structure 3300 and a connection port 3600 for connection to a short tube 4180 of the air circuit 4170. In some forms a functional aspect may be provided by one or more physical components. In some forms, one physical component may provide one or more functional aspects. In use the seal-forming structure 3100 is arranged to surround an entrance to the airways of the patient 1000 so as to facilitate the supply of air at positive pressure to the airways.

Seal-Forming Structure 3100

In one form of the present technology, the seal-forming structure 3100 provides a sealing-forming surface, and may additionally provide a cushioning function.

A seal-forming structure 3100 in accordance with the present technology may be constructed from a soft, flexible, resilient material such as silicone. The seal-forming structure 3100 may form part of a sealed path for air from a PAP device to be delivered to the nares of the patient.

Referring to FIG. 9, in one form of the present technology, the seal-forming structure 3100 may comprise a sealing flange 3110 and a support flange 3120. The sealing flange 3110 may comprise a relatively thin member with a thickness of less than about 1 mm, for example about 0.25 mm to about 0.45 mm. The support flange 3120 may be relatively thicker than the sealing flange 3110. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face, e.g., the patient's nares. The plenum chamber 3200 is made from a floppy material such as silicone.

Nasal Pillows

In one form of the present technology, the seal-forming structure 3100 of the non-invasive patient interface 3000 comprises a pair of nasal puffs, or a pair of nasal pillows 3130, each nasal puff or nasal pillow being constructed and arranged to form a seal with a respective nares of the nose of a patient, e.g. by forming a seal against a peripheral region of the nares of the patient.

Nasal pillows 3130 (FIG. 9) in accordance with an aspect of the present technology include: a frusto-cone 3140, at least a portion of which forms a seal on an underside of the patient's nose e.g. a frusto-cone portion; a stalk 3150, an upper flexible region 3142 on the underside of the frusto-cone 3140 and connecting the frusto-cone to the stalk 3150. In addition, the structure to which the nasal pillow 3130 of the present technology is connected includes a lower flexible region 3152 adjacent the base of the stalk 3150. Upper flexible region 3142 and lower flexible region 3152 can act in concert to facilitate a universal joint structure that is accommodating of relative movement—both displacement and angular—of the frusto-cone 3140 and the structure to which the nasal pillow 3130 is connected. In one example, the frusto-cone 3140 may be co-axial with stalk 3150 to which it is connected. In another example, the frusto-cone 3140 and the stalk 3150 may not be co-axial (e.g., offset). The nasal pillows 3130 may be dimensioned and/or shaped such that they extend out laterally beyond the walls of the plenum chamber 3200, discussed below.

In one form of the present technology, each stalk 3150 may comprise a variable stiffness so as to prevent the nasal pillows 3130 from rocking forward during use due to compression and/or bending of the stalk 3150. For example, the side of the stalk 3150 that is distal from the face of the patient in use may be stiffer than the region of the stalk 3150 proximal to the face of the patient. In other words, different material stiffness on opposing sides of the stalk 3150 presents more resistance if compression or bending of the stalk 3150 is not in a predetermined direction. This enables even compression of the pillows 3130 onto nares by preventing the pillows 3130 from rocking forward. Such an arrangement may be helpful in resisting buckling of the stalk 3150 that results in the nasal pillows 3130 rocking forward. The variable stiffness may also be used to provide a weak point about which rocking is facilitated such that the stalks 3150 buckle in a desired direction. In other words, even compression of the nasal pillows 3130 may be achieved. This arrangement may also allow the sealing force to be localized at the top of the nasal pillows 3130. Additionally, this arrangement may also allow any deflection of the nasal pillows 3130 to be cantered thereon. The nasal pillows 3130 may also be formed to compress against the plenum chamber 3200 when urged against the face of the patient and because the nasal pillows 3130 may be laterally wider than the plenum chamber, no portion of the plenum chamber 3200 extends beyond the pillows 3130. In another example, when compressed, the nasal pillows 3130 may be shaped and/or dimensioned so that their periphery is generally flush with the periphery of the plenum chamber 3200. In a further example of the technology, the stalks 3150 may be thinnest at the base of the frusto-cone 3140.

In an example, to engage the pillows 3130 with the entrance to the patient's airways, the pillows 3130 are placed at the entry to the nares. As the positioning and stabilising structure 3300 is adjusted, tension begins to pull the pillows 3130 into the nares. Continued insertion of the pillows 3130 into the nares causes the stalk 3150 to collapse via trampoline 3131 moving the base of pillows 3130 towards the upper surface of the plenum chamber 3200. The stalks 3150 of the nasal pillows 3130 may be connected to the plenum chamber 3200 and comprise thinned or reduced thickness, portions. The thinned portions allow the pillows 3130 to easily spring, or trampoline, and therefore adjust to suit the alar angle of the patient 1000 more readily. The trampoline 3131 may be angled away from the bottom of the pillows 3130 or a septum and/or upper lip of the patient 1000. This improves the comfort and stability of the patient interface device 3000.

It is also envisioned that a variety of sizes of nasal pillows 3130 may be used with plenum chambers having a commonly sized connection region and plenum connection region. This has the advantage of allowing the patient to be fitted with a plenum chamber 3200 and pillows 3130 sized to best fit that patient's particular anatomy, e.g., size and orientation of the nares.

In one form of the present technology the seal-forming structure 3100 forms a seal at least in part on a columella region of a patient's nose.

Nasal Cradle

While a small portion of a nasal pillow 3130 may enter a patient's nares in use, an alternative form of seal-forming structure 3100 is substantially external of the nose in use. In one form of the present technology, shown in FIG. 34, the seal-forming structure 3100 of the patient interface 3000 is constructed and arranged to form a seal against the patient's airways that surrounds both nares without being entering the nares. The seal-forming structure 3100 may serve both nares with a single orifice, e.g. a nasal cradle. In FIG. 34, the seal-forming structure 3100 according to the depicted example includes a nasal flange 3101 disposed about its periphery. This view also indicates the attachment of the plenum chamber 3200 and seal-forming structure 3100 to the frame 3310.

Nasal Cushion for Nasal Cradle

FIGS. 223 to 232 show several views of an exemplary patient interface system 3000 having a seal-forming structure 3100 in the form of a nasal cradle cushion. FIGS. 233a to 233h show several views of an exemplary patient interface system 3000 having a seal-forming structure 3100 in the form of a nasal cradle cushion donned on a patient 1000. The seal-forming structure 3100 may seal around the lower portion of the nose of the patient, particularly around the ala and tip of the nose. This seal-forming structure 3100 may define, at least in part, a gas chamber 3104, which will be discussed in greater detail below. During therapy, breathable gas may be provided to the patient from the patient interface 3000 to the nose through the gas chamber 3104. It should be understood that when the patient interface 3000 is donned on a patient, the seal-forming structure 3100 may, at least partially, along with the face of the patient, define the gas chamber 3104 through which breathable gas may be provided to the patient at positive pressure. For example, that the seal-forming structure 3100 in the form of a nasal cradle may seal below the nasal bridge (e.g., the transitional region between the bone and the cartilage of the nose), on or below the nose tip, the sides of the nose and/or the upper lip of the patient. According to another example of the present technology, the seal-forming structure 3100 in the form of a nasal cradle cushion may be structured to seal around an inferior periphery of the nose. In other words, seal may be formed with the lower surfaces of the patient's nose. It should also be understood that a nasal cradle cushion is different from nasal pillows because the nasal cradle cushion may serve both nares with a single orifice and may be structured so as not to enter the nostrils of the patient. The seal-forming structure 3100 may be a single wall cushion or the seal-forming structure 3100 may be dual wall cushion, e.g., the seal-forming structure may include an undercushion. Alternatively, the undercushion may be omitted and a rolled edge may be used around the opening of the seal-forming structure 3100 to form a secure pneumatic seal around the patient's nose.

A protruding end 3114 can be seen on either side of the seal-forming structure 3100. When donned on the patient 1000 each protruding end 3114 may be shaped to extend from the patient interface 3000 so as to seal within the gap between the respective alae and nasolabial sulci of the patient. FIG. 2c, which depicts superficial features of the face, indicates the location of the alae and the nasolabial sulci. The protruding ends 3144 may partially inflate and/or deform to seal in this area. A concave lower portion 3212 of the seal-forming structure 3100 inferior to the opening to the gas chamber 3104 may seal against the upper lip according to an example of the technology. The concave lower portion 3212 may be curved to substantially conform to a portion of the upper lip of the patient to form a seal in that region. The shape of the concave lower portion 3212 can be seen in FIG. 245c, for example, where the seal-forming structure 3100 curves inwardly from the protruding ends 3114. Since the upper lip of most patients is convex, the concave lower portion 3212 may easily conform to this region of the patient's face to form an effective seal. The posterior portion of the seal-forming structure 3100 inferior to the opening to the gas chamber 3104 that may seal against the upper lip of the patient may also be shaped and dimensioned not to cover the patient's nares when in use so as to ensure an uninterrupted pathway for the flow of pressurized gas into the patient's airways. According to another example of the present technology, the seal-forming structure 3100 may be softened, e.g., by reducing material thickness, at the posterior and inferior region of the seal-forming structure that seals against the patient's upper lip.

FIGS. 233a to 233h show how the exemplary patient interface 3000 may seal against a patient 1000, particularly the nose. It should be understood that the seal-forming structure 3100 may be concave in shape to cradle the nose of the patient. A recessed portion 3116 may receive the tip of the patient's nose and the protruding end 3114 may seal in the region of the ala and nasolabial sulcus. The protruding ends 3114 may seal against the patient's face and nose at the region where the alae join to the face of the patient proximal to the nasolabial sulcus. (See FIGS. 2c, 2d, and 2f) In most patients, this region is concave in shape and, thus, the protruding ends 3114 are intended to extend into and seal within this region. A protruding end support section 3208 may support the nasal cushion 3112 in the region of the protruding end 3114 to aid in maintaining the seal in this region, and may function like an undercushion. In an alternative example, the seal-forming structure 3100 may include rolled edge around the perimeter of the opening to the gas chamber 3104, rather than including the protruding end support section 3208. In a further alternative example, the seal-forming structure 3100 may not provided with a rolled edge or the protruding end support sections 3208.

FIGS. 223 to 232 also show that the recessed portion 3116 may be included on the seal-forming structure 3100. This recessed portion 3116 may comprise an inwardly shaped section that extends into the nasal gas chamber 3104 to receive the tip of the nose of the patient when donned by the patient. The recessed portion 3116 may provide enhanced sealing around and under the tip of the nose of the patient during therapy by allowing the shape of the seal-forming structure 3100 to better conform to the patient's nose. The seal-forming structure 3100 may also include an overhang near the recessed portion 3116 at the opening to the seal-forming structure that allows the seal-forming structure to better conform to and seal around the tip of the patient's nose.

The seal-forming structure 3100 may surround a portion of the nose, specifically the nose tip, of the patient 1000. The gas chamber 3104 may be formed by the seal-forming structure 3100 and the face of the patient.

The patient interface 3000, according to an example of the present technology, has a surface area footprint on the face which is less obtrusive than a conventional nasal face mask by a significant percentage. For some patients, it may also feel less claustrophobic. Also, the specific areas of reduced obstruction is important because these areas are found to have significant beneficial psychological impact on a bed partner when looking at the mask because it looks less medical and "opens up" the face. From the patient's perspective, the exemplary patient interface 3000 is not in or significantly reduced from their field of vision because the seal-forming structure 3100 seals below the bridge of the nose. This allows the patient to wear spectacles when reading a book or watching television after donning the patient interface 3000 before they fall asleep. By sealing below the nose bridge, irritation may be avoided in an area that has thin skin and pressure sensitive and high chance of skin breakdown due to blood flow constriction. Another advantage may be that anthropometric variations between patients above the nose bridge do not need to be considered and focus for the mask fit range can be directed towards anthropometric variations around the upper lip area. Also, unlike some other full face masks, the patient interface 3000 may not require a forehead support which may be required for providing pressure point relief. This may also avoid the problem of the forehead support being a source of pressure point and skin break down. This type of seal-forming structure 3100 may also be advantageous in that provides an alternative for respiratory therapy patients that do not find nasal pillows comfortable.

Anatomically, FIGS. 2h and 2i may be referenced for an indication as to the location of the transitional region between the nasal bone and the cartilage that may be understood to define the bridge of the nose. Thus, the exemplary seal-forming structure 3100 may seal about the periphery of the nose of the patient in contact with the softer tissues of the nose, e.g., fatty tissue and cartilage. By forming a seal with the nose on these softer tissues it may be possible to avoid irritation of the skin of the patient that would otherwise occur were the seal to be formed around/over the harder nasal structures, i.e., bone. In other words, patient discomfort may be minimised by sealing below the bridge of the nose. Also, locating the seal of the seal-forming structure 3100 around this region of the nose may allow for an effective seal to be formed because the nasal tissues and the seal-forming structure 3100 may conform to one another to form the seal. The seal-forming structure 3100 may conform to the nose predominantly.

A sealing feature described above is the location of the protruding end 3114 against the face of the patient 1000. Specifically, the protruding end 3114 may be an extended portion of the seal-forming structure 3100 that seals in the region between the nasolabial sulcus and ala. These anatomical features may be seen in FIG. 2c. Depending on the individual facial structure of the patient, this region may represent a recessed portion such that an extension from the seal-forming structure 3100 may be necessary to form an adequate seal about the nose of the patient. The protruding ends 3114 may advantageously serve this function.

Another sealing feature of the exemplary patient interface 3000 is the recessed portion 3116 for the seal-forming structure 3100 to receive the tip of the nose of the patient 1000 when donned by the patient. Specifically, at the region where the recessed portion 3116 is located the tip of the nose of the patient 1000 can be seen in dashed lines, as shown in FIGS. 233a to 233h. The seal-forming structure 3100 may be shaped to seal against the perimeter of the nose at its underside. In other words, the seal formed by the seal-forming structure 3100 against the nose may be characterized as against an inferior and peripheral portion of the nose. Thus, it may be understood that the sealing surface of the seal-forming structure 3100, as a whole, may be concave or form a pocket to receive the nose and it may further include the recessed portion 3116 to receive the tip of the nose.

The seal-forming structure 3100 may seal against the nose of the patient 1000 at the tip. The gas chamber 3104 may be defined, at least in part, by the seal-forming structure 3100, the plenum chamber 3200, and the patient's nose to provide a sealed path for breathable gas to enter the patient's airways via the nares.

In an example, the seal-forming structure 3100 in accordance with the present technology is constructed from a soft, flexible, resilient material such as silicone. In another example of the present technology, the seal-forming structure 3100, e.g., the seal-forming structure 3100 and its overhang 3206 may be formed from foam. The seal-forming structure 3100 may, according to further examples of the present technology, be formed from other materials including foam, gel, and/or low durometer silicone.

FIGS. 245a, 245d, and 245g-k, show examples of the protruding end support sections 3208. The protruding end support sections 3208 may be associated with respective protruding ends 3114 of the seal-forming structure 3100. The protruding end support sections 3208 may also be understood to extend into the gas chamber 3104 defined, at least in part, by the seal-forming structure 3100 and the plenum chamber 3200. Such a configuration may allow the protruding end support section 3208 to provide sufficient support for the protruding end 3114 to seal against the patient's face.

Protruding end support sections 3208 can be seen on either side of the seal-forming structure 3100. The protruding end support section 3208 may be positioned under the protruding end 3114 of the seal-forming structure 3100. The protruding end support section 3208 may be included to support the protruding end 3114 of the seal-forming structure 3100.

The protruding ends 3114 may be included at each side of the seal-forming structure 3100, as shown in FIGS. 234a to 239. The gas chamber 3104 and the opening thereto can also be seen. The opening to the nasal gas chamber 3104 may generally have a rectangular, lozenge or trapezoidal shape that may be curved at its respective minor sides 3104.2 and major sides 3104.1, 3104.3, as shown in FIGS. 237a to 237d. When placed against the nose of the patient the curved minor sides 3104.2 of the opening may be proximal to the respective alae of the nose. Also in this example, the distal major side 3104.1 of the opening, may be distal to the upper lip of the patient and near the tip of the nose, while the proximal major side 3104.3, may be proximal to the upper lip of the patient. The recessed portion 3116, shaped to receive the tip of the nose, is also shown.

FIGS. 234a to 234c show that the seal-forming structure 3100 may curve slightly upward as it approaches the distal major side 3104.1 of the opening to the gas chamber 3104 from the recessed portion 3116. The front upper portion of the seal-forming structure 3100 that is near the recessed portion 3116 includes a slight dip or concave region at its center such that the seal-forming structure 3100 is higher at its sides than in the middle. This view also shows the outline of a nose in dashed lines to indicate how the nose of the patient may be located relative to the seal-forming structure 3100. The peak 3118 in the seal-forming structure 3100 is tasked with sealing the front of the nares. The peak may sit further back, but may transition more gradually for creating the balloon effect to seal against the nares. The distal side 3104.1 may flick up from the seal-forming structure 3100 and may improve seal at the nose tip by making contact with the nose and may cause a compressive, pneumatic seal by cradling the nose. The recessed portion 3116 that is shaped to receive the tip of the nose is also shown.

FIGS. 235a to 235c also show the protruding ends 3114 at either side of the seal-forming structure 3100. The profile of the seal-forming structure 3100 may slope downwardly as it approaches the distal side 3104.1 opening to the gas chamber 3104 from the recessed portion 3116. This example of the seal-forming structure 3100 lacks the dip in the front region near the recessed portion. In other words, this example shows that the seal-forming structure 3100 may be more circular/rounder, relative to the example shown in FIGS. 234a to 234c in the region from the recessed portion 3116 to the distal side 3104.1 of the opening to the gas chamber 3104.

FIGS. 236a to 236c show that the shape of the opening to the gas chamber 3104 may be more balloon like and rounder than the examples shown in FIGS. 234a to 234c and FIGS. 235a to 235c. The seal-forming structure 3100 may have straight sidewalls, in contrast with sidewalls that curve smoothly from the upper surface of the seal-forming structure 3100. The straight sidewalls may have a defined top edge and may increase stability and strength of the seal-forming structure 3100.

In another example, the seal-forming structure 3100 may lack the dip in the front region near the recessed portion 3116. The straight sidewalls of the exemplary nasal cushion 3112 may also be included.

Furthermore, it should also be understood that the exemplary seal-forming structures 3100 are shown in substantially undeformed states in FIGS. 234a-c, 235a-c, and 236a-c. Some drawings may indicate a small amount of deformation due to conformation with the shape of the nose shown in dashed lines. Thus, the seal-forming structures 3100 may have a concave shape as shown when not deformed.

It should also be understood that the seal-forming structure 3100 may have a cross-section of variable thickness, as shown in FIGS. 238a to 238c. Thus, the region of the seal-forming structure 3100 proximate to the opening to the gas chamber 3104 may be thinner than the region where the seal-forming structure 3100 attaches to the plenum chamber 3200. Advantageously, this may afford more comfort for the patient by providing a thinner and, thus, more compliant region of cushion material at the area where a large amount of contact is made with the patient's nose.

The region 3112.1 may be proximal to the opening to the gas chamber 3104 and the region 3112.3 may be proximal to the connection to the plenum chamber 3200. The region 3112.2 may be the most elevated region around the upper periphery of the nasal cushion 3112.

A smoothly variable thickness for the seal-forming structure 3100 from region 3112.1 to region 3112.3 is provided. Also, the thickness x may be less than the thickness z. The region 3112.2 may abruptly become thicker than the regions 3112.1 and 3112.3. Also, the thickness x may be less than the thickness z and the thickness y may be greater than x and z. The region 3112.2 may abruptly become thicker than the regions 3112.1 and 3112.3. Also, the thickness z may be less than the thickness x and the thickness y may be greater than x and z.

FIG. 239 shows another exemplary seal-forming structure 3100 according to the present technology, the opening to the gas chamber 3104 and the protruding end 3114 are indicated to allow for understanding of the orientation of the seal-forming structure 3100. Regions of various thicknesses are hatched differently to better indicate where the thickness of the seal-forming structure 3100 may vary. Region 3113 may be the thinnest to allow for ready conformation to the tip of the nose. Region 3113, according to an example of the present technology, may have a thickness of about 0.35 mm. Region 3115 may be thicker to provide more support for the seal-forming structure 3100. Region 3115, according to an example of the present technology, may have a thickness of about 0.5 mm. Region 3117 may be thicker than the other regions to provide maximum support, resistance to deformation, and ensure an effective seal at the ala of the patient. Region 3117, according to an example of the present technology, may have a thickness of about 1 mm.

The bottom corners of the seal-forming structure 3100 may be stiffer relative to other areas of the seal-forming structure 3100 to prevent or minimise deformation at the bottom corners. Having a higher level of stiffness at the bottom corners of the seal-forming structure 3100 leads to a lower likelihood of seal disruption at these locations of the seal-forming structure 3100, especially when tube torque is experienced.

FIGS. 245a-k depict further examples of the present technology. In these views the seal-forming structure 3100, plenum chamber 3200, and the retaining structure 3242 are shown disconnected from the frame 3310 (not shown in these views). These views show the protruding end support section 3208 that extends inward from the seal-forming structure 3100 and the plenum chamber 3200 to support the protruding ends 3114 when engaged with the nose of the patient. The protruding end support sections 3208 may be in the form of a hollow protrusion that extends into the interior of the patient interface 3000. As can be seen in FIG. 245d, the protruding end support section 3208 may be seen as a pocket formed in the side of the seal-forming structure 3100 and the plenum chamber 3200. The protruding end support sections 3208 may be formed integrally with the seal-forming structure 3100 and the plenum chamber 3200. In an alternative example, the protruding end support sections 3208 may not be hollow, but rather may be a solid extension formed integrally with the seal-forming structure 3100 and the plenum chamber 3200.

It is also envisioned that the protruding end support sections 3208 may include additional supporting structures comprised of a material more rigid than the seal-forming structure 3100 and the plenum chamber 3200. It should be understood that, according to one example of the present technology, that the sides of the protruding end support sections 3208 may spaced from the seal-forming structure 3100 and the plenum chamber 3200 when the patient interface 3000 is not sealingly engaged with the patient's nose. When the patient dons the patient interface 3000, the seal-forming structure 3100 and the plenum chamber 3200 may be deformed and the protruding ends 3114 may be urged against the protruding end support sections, which in turn prevent the protruding ends from collapsing and support the protruding ends against the patient. For example, the protruding end support sections 3208 may support respective protruding ends 3114 as the protruding ends are deformed due to sealing engagement with the patient's face at the junction between the alae and the face.

Additionally, the protruding end support sections 3208 may have a profile such that the cross-sectional area of the protruding end support sections decreases as the protruding end support sections extend into the gas chamber 3104. The end of the protruding end support section 3208 that extends into the gas chamber 3104 may also be flat as shown in FIGS. 245g and 245i-k or, alternatively, the protruding end support section may come to a point. The walls that define the protruding end support sections 3208 may also increase or decrease in thickness toward the gas chamber 3104. It is also envisioned that the protruding end support sections 3208 may have a profile that is curved. For example, the protruding end support sections 3208 may have a profile that is curved to substantially follow the profile of their respective protruding ends 3114, while not directly contacting the protruding ends when the seal-forming structure 3100 is in a relaxed state. As can be seen in FIGS. 245g and 245i-k, for example, the protruding end support sections 3208 may have a profile that is generally curved away from the respective protruding ends 3114 and toward the retaining structure 3242.

FIGS. 245f-h show that the seal-forming structure 3100 may include thickened sections 3204. These thickened sections 3204 may provide additional support for the seal-forming structure 3100 when it is in sealing engagement with the nose and the face of the patient. The thickened sections 3204 may be located on opposite sides of the seal-forming structure 3100 in a position such that they are proximal to the patient's nasolabial sulcus when the seal-forming structure engages the patient's face. The thickened sections 3204 may also help to seal around the alae of the patient's nose by preventing collapse of the seal-forming structure 3100 due to sealing forces. The thickened sections 3204 may be formed integrally with the seal-forming structure 3100. Also, the thickened sections 3204 may be located on the seal-forming structure 3100 such that when the seal-forming structure engages the patient's nose and face the thickened sections 3204 may be, at least partially, urged against respective protruding end support sections 3208. The thickened sections 3204 may have a constant thickness throughout that is greater than the thickness of the remainder of the seal-forming structure 3100. Alternatively, the thickened sections 3204 may have a thickness that is variable across its area.

FIGS. 245a, 245c-f, 245h, 245i, and 245k also show that the seal-forming structure 3100 may include an overhang 3206 to seal against the nose tip of the patient. The overhang 3206 may have a reduced thickness relative to the remainder of the seal-forming structure 3100 and the overhang may be positioned and structured to form a seal around the anterior portion of the patient's nose, e.g., the tip of the nose. The overhang 3206 may extend a substantial distance, for example, the overhang can be seen in the side view of FIG. 245d.

FIGS. 245a, 245b, 245d-f, 245h, 245i, and 245k show examples of the seal-forming structure 3100 that may include a compliant region 3122. The compliant region 3122 may be relatively soft, flexible, and/or compliant relative to other portions of the seal-forming structure 3100. The compliant region's 3122 relative flexibility may be advantageous in that it may help to relieve discomfort to the patient in the regions of the tip of the nose and the septum. The compliant region 3122 may be relatively thin as compared to other portions of the seal-forming structure 3100 and, as such, may function like a mechanical spring to maintain an effective seal at the tip of the nose by wrapping against and/or contacting the tip of the nose. The compliant region 3122 may be located on the seal-forming structure 3100 at the upper apex where the seal-forming structure transitions to the plenum chamber 3200, as can be seen in FIG. 245d for example. The compliant region 3122 may be located on the seal-forming structure 3100 above the recessed portion. The compliant region 3122 may also blend into the recessed portion 3116. The compliant region 3122 may also be located substantially centrally on the seal-forming structure in horizontal direction, as can be seen in FIG. 245e for example. The seal-forming structure 3100 may have a thickness at the compliant region 3122 that is about 0.35 mm according to an example of the present technology and may be one of the thinnest regions of the seal-forming structure.

The views in FIGS. 245a-k also show the retaining structure 3242 with notches 3295 and tongue portion 3211. Additionally, these views show the sealing lip 3250.

Also, the seal-forming structure 3100 may include visual indicators that are pad printed thereon to indicate to the patient the proper insertion depth of the nose. For example, the visual indicators may include an outline of a nose to show the patient where their nose should align relative to the seal-forming structure 3100. Such visual indicators may indicate to the patient where to place the nose in the seal-forming structure 3100 so that they do not insert it too deep into the seal-forming structure, thereby resulting in a suboptimal seal.

Plenum Chamber 3200

Plenum chamber 3200 in accordance with an aspect of one form of the present technology functions to allow air flow between the two nares and the supply of air from PAP device 4000 via a short tube 4180. The short tube 4180 is typically part of the air circuit 4170 that connects to the frame 3310 via a connection port 3600 and a longer tube (additional gas delivery tube) 4178 connected to the PAP device 4000. In this way the plenum chamber 3200 may function alternatively as an inlet manifold during an inhalatory portion of a breathing cycle, and/or an exhaust manifold during an exhalatory portion of a breathing cycle.

Plenum chamber 3200 may be constructed from an elastomeric material.

Plenum chamber 3200, in accordance with another aspect of one form of the present technology, provides a cushioning function between the seal-forming structure 3100 and the positioning and stabilising structure 3300.

Whilst in one form of the plenum chamber 3200, the inlet/outlet manifold and cushioning functions are performed by the same physical component, in an alternative form of the present technology, they are formed by two or more components.

The seal-forming structure 3100 and the plenum chamber 3200 may be formed, e.g. moulded, as a single and unitary component.

Plenum chamber 3200 comprises an anterior wall 3210 and a posterior wall 3220.

Posterior wall 3220 comprises posterior surface 3222 (see FIG. 8). In one form of the present technology, the seal-forming structure 3100 is constructed and arranged relative to the posterior wall 3220 so that in use, the posterior surface 3222 is spaced from a patient's septum and/or upper lip, as can be seen in FIGS. 18 and 19. In one form, e.g. when the seal-forming structure 3100 includes nasal pillows 3130, this is achieved by arranging the posterior wall 3220 so that the posterior surface 3222 is anterior to a most posterior portion 3130.1 of the nasal pillow 3130, as shown in FIG. 8 by the posterior surface 3222. This arrangement may also focus the sealing force on the nares of the patient 1000 because the septum and/or upper lip is relieved of contact with the patient interface 3000.

The plenum chamber 3200 also comprises a flexing region 3230 (FIG. 9), which forms a connection with seal-forming structure 3100. The flexing region 3230 may be a distinct region from the anterior wall 3210 and/or the posterior wall 3220. Alternatively some or all of the respective anterior wall 3210 and posterior wall 3220 may form part of flexing region 3230. In one form of the present technology where the seal-forming structure 3100 comprises respective left and right nasal pillows 3130, there is a corresponding respective left flexing region 3232 and right flexing region 3234 (FIG. 4). Flexing regions 3230, 3232, and 3234 are constructed and arranged to bend and/or flex in response to a force encountered in use of the patient interface 3000, e.g., a tube drag force, or a movement of the patient's head, e.g., pushing the patient interface 3000 against a bed pillow. Flexing region 3230, left flexing region 3232, and/or right flexing region 3234 may be constructed from a silicone rubber, e.g., with a Type A indentation hardness in the range of about 35 to about 45. However, a wider range is possible if the thickness of the walls 3210, 3220 are adjusted accordingly to obtain a similar level of force.

Another aspect of the present technology that may be seen in FIGS. 4, 7, 8, 10 and 11, that the plenum chamber 3200 has a saddle or decoupling region 3236. As can be seen in FIG. 4, the flexing region 3230 may comprise the decoupling region 3236, which may be located between the left flexing region 3232 and the right flexing region 3234. The decoupling region 3236 may be concave in shape and may span from the anterior wall 3210 to the posterior wall 3220. By forming the plenum chamber 3200 with the decoupling region 3236 as described, it may be possible to decouple the left flexing region 3232 from the right flexing region 3234 such that movement in one of the flexing regions does not substantially affect the other flexing region. In other words, deformation and/or buckling of the left flexing region 3232 may not cause a disruption to the right flexing region 3234 and vice versa. Advantageously, this may allow the nasal pillow 3130 associated with the undisturbed flexing region to remain in position on the patient's corresponding naris in spite of a disruption to the other flexing region. The decoupling region 3236, by being recessed between the stalks 3150, may avoid contact with the septum. Also, the decoupling region 3236 may be the thinnest region of the plenum chamber 3200 to allow for the desired amount of flexibility in this region. Alternatively, the decoupling region 3236 may be the thickest region of the plenum chamber 3200. By providing the saddle region 3236 with a deep curvature, septum and/or upper lip contact may be minimised or avoided to improve patient comfort. The saddle region 3236 may be U or V shaped and has a nasolabial angle at its peak of about 70° to about 120°. The saddle region 3236 may be about 0.5 mm to about 2.5 mm in depth for clearance around the patient's septum.

Posterior wall 3220 may be arranged, in use of patient interface 3000, adjacent the superior or upper lip of the patient, as in FIGS. 18 and 19.

In one form, the plenum chamber 3200 may further comprise a sealing lip 3250 (FIG. 6). Sealing lip 3250 may be constructed from a flexible resilient material, e.g. silicone rubber with a type A hardness in a range of about 30 to about 50, forming a relatively soft component. Sealing lip 3250 may be located on or formed as part of an interior surface or interior periphery of plenum chamber 3200, or an entire interior peripheral region of plenum chamber 3200, as shown in FIGS. 5, 6 and 8. However, it is also envisioned that the sealing lip 3250 may be disposed about an exterior surface or exterior periphery of the plenum chamber 3200, or an entire exterior peripheral region of plenum chamber 3200. Sealing lip 3250 may form a pneumatic seal between plenum chamber 3200 and frame 3310, as will be described in greater detail below. Sealing lip 3250 and plenum chamber 3200 may also comprise one piece. Other patient interface devices form the pneumatic seal between the plenum chamber and frame using a compression seal to compress the plenum chamber made from a resiliently deformable material such as silicone to engage the plenum chamber to the frame and create the pneumatic seal at the same time. In contrast, one example of the present technology, forms a pneumatic seal when the plenum chamber 3200 is initially secured to the frame 3310 by interference from the sealing lip 3250 deflecting against the frame 3310. When pressure within the plenum chamber 3200 is increased above atmospheric pressure for treating breathing disorders, the pneumatic seal is strengthened and increases the sealing force as the sealing lip 3250 is urged with greater force against the frame 3310. The air pressure within the cushion/plenum chamber of these other patient interface devices does not influence the sealing force between the cushion and the frame. Also, these other patient interface devices have a cushion with side walls for engagement with the frame and sealing lips that are floppy because they readily conform to finger pressure, are not rigid, and are able to be stretched or bent elastically with little effort. In particular, due to the size and aspect ratio of a nasal cushion being relatively large, this contributes to the floppiness of the cushion. The side walls for frame engagement are so floppy that opposing sides of the cushion are able to be pinched together and brought into contact with each other with very little finger force. This ease of deformation of the side walls for frame engagement may be the primary source of difficulty for patients with arthritic hands to quickly connect the cushion to the frame in these other patient interfaces. It should also be understood that by forming the plenum chamber 3200 features discussed above with sufficient stiffness it may be possible to improve the stability of the seal made by the seal-forming structure. Furthermore, it may be possible to vary the thickness of the plenum chamber 3200 such that it becomes thinner from a plenum connection region 3240 to the seal-forming structure 3100. In one example of the present technology, the plenum chamber 3200 may be about 2-3 mm thick near or at the plenum connection region 3240, 1 mm thick at a point between the plenum connection region 3240 and the seal-forming structure 3100, and 0.75 mm thick near or at the seal-forming structure 3100. Forming the plenum chamber 3200 with these features may be accomplished by injection molding manufacturing. This gradual reduction in thickness of the plenum chamber 3200 enables greater deformability of silicone material closer to the stalks 3150 and patient's nose to enhance comfort and reduce the likelihood of seal disruption.

Some nasal pillow patient interfaces have an assembled order of (i), plenum chamber, (ii) headgear connection, and (iii) seal-forming structure. In contrast, one example of the patient interface 3000 of the present technology has an assembled order of (i) headgear connection, (ii) plenum chamber, and (iii) seal-forming structure. This difference in arrangement means that headgear tension does not cause deformation of the plenum chamber 3200 and the seal-forming structure 3100 which may lead to disruption of sealing forces.

Frame 3310

Frame 3310 functions as a central hub, as shown in FIGS. 4, 10, 75, 76 and 166, to which the short tube 4180, plenum chamber 3200 and positioning and stabilising structure 3300 are connected, either in a removable fashion or a more permanent fashion.

FIGS. 31 to 33 also show various views of the frame 3310 connected to the positioning and stabilising structure 3300, having straps 3301, via a flexible joint 3305. These views show the frame 3310 without the plenum chamber 3200 and the seal-forming structure 3100. The connection port 3600 and the vent 3400, both described in greater detail below, may be disposed on the frame 3310.

In one example of the technology, the frame 3310 may be formed from polypropylene.

In another example of the technology, the frame 3310 may be made in one size but the plenum chamber 3200 and seal-forming structure 3100 may be made in multiple sizes that are attachable to the single frame by commonly sized connections features as described herein.

In an example of the technology the frame 3310 may be molded without any undercuts such that it may be molded and then removed from the mold tool without flexing.

Connection Between Plenum Chamber and Frame

In one form of the present technology, plenum chamber 3200 is removably attachable to frame 3310, e.g., to facilitate cleaning, or to change for a differently sized seal-forming structure 3100. This may permit the plenum chamber 3200 to be washed and cleaned more often than the frame 3310 and short tube 4180. Also, it may permit the plenum chamber 3200 to be washed and cleaned separately from the strap 3301. In an alternative form, plenum chamber 3200 is not readily removable from frame 3310.

Plenum chamber 3200 may comprise the plenum connection region 3240 (FIG. 6). A retaining structure 3242 of the plenum connection region 3240 has a shape and/or configuration that is complementary to a shape and/or configuration of a corresponding frame connection region 3312 (FIG. 10). The retaining structure 3242 of the plenum chamber 3200 is more rigid than the other parts of the plenum chamber 3200, and may be made from the same material as the frame 3310, for example, polypropylene or polyamide such as Rilsan®. In other examples, the plenum connection region 3240 may be made from nylon, and the frame 3310 made from polypropylene. Nylon, polyamide and polypropylene are not floppy materials and do not readily conform to finger pressure. Therefore, when they are engaged to each other, there is an audible click and a hard to hard connection. The shape of the retaining structure 3242 is depicted in FIGS. 20 to 24 in the form resembling a parabolic cylinder or hyperbolic cylinder. The retaining structure 3242 is not stretchable and inextensible in order to maintain its general shape as it engages and disengages from the frame 3310. The shape of the retaining structure 3242 allows a slight degree of flexing but not to the extent that opposite sides of the retaining structure 3242 are able to touch each other if pinched together with finger pressure. In other words, the opposite sides of the retaining structure 3242 can only be brought into contact together with significant pinching force intended by the patient 1000 which would not occur under normal therapy circumstances. In the illustrated example, the top and bottom edges of the retaining structure 3242 are able to be pinched closer together/more easily together than the side edges of the retaining structure 3242 using the same amount of pinching force. As can be seen in FIG. 18, the curvature of the frame 3310 and retaining structure 3242 is intended to follow the natural curvature of patient's upper lip and may avoid concentration of contact pressure on any specific point of the patient's upper lip such that contact pressure from headgear tension is evenly spread over the patient's upper lip. This may minimise or eliminate skin breakdown caused by prolonged concentrated contact pressure. Another advantage for the curvature is that less material is required for the plenum chamber 3200 compared to a flat frame. A flat frame would result in more material for the plenum chamber 3200 at the side edges in order for the plenum chamber 3200 to conform to the patient's upper lip. Less material leads to an overall weight reduction for the patient interface 3000. The curvature also minimises any protrusion of the patient interface 3000 in the anterior direction from the patient's face which improves the unobtrusiveness of the patient interface 3000. Also, the retaining structure 3242 may be glued (e.g. using an adhesive) onto the plenum chamber 3200, according to an example of the technology, after molding. In another example, an integral chemical bond (molecular adhesion) may be utilized between the retaining structure 3242 and the plenum chamber 3200.

In an example of the technology, the retaining structure 3242 may be molded without any undercuts such that it may be molded and then removed from the mold tool without flexing. The retaining structure 3242 has a continuous peripheral edge on an anterior side that contacts the frame 3310. This continuous peripheral edge is exposed so that it makes contact with the frame 3310 for engagement in a hard to hard manner. This is in contrast to a majority soft to hard connection where in some prior masks there is an anterior lip portion of the seal-forming structure that covers and overlaps the majority of a detachable rigid retaining structure. The anterior lip portion is made from LSR and wraps over the retaining structure to hold it together. However, in such prior masks, it is difficult and cumbersome to wrap the anterior lip portion over a detachable clip and possible for the clip to be misplaced which would then result in the inability of connecting the seal-forming structure to the frame.

One purpose of the retaining structure 3242 is to align the plenum chamber 3200 when engaging with the frame 3310 because the shape of the retaining structure 3242 of the plenum chamber 3200 is retained (possibly at varied depths) in a space defined between the frame connection region 3312 and interfering portion 3314 of the frame 3310 (FIG. 29).

Another purpose of the retaining structure 3242 is to retain the plenum chamber 3200 to the frame 3310 by preventing relative lateral and vertical relative movement between these two parts. Plenum connection region 3240 may comprise at least one retention feature 3244, and there may be at least one complementary frame connection region 3312. Plenum connection region 3240 may comprise one or more retention features 3244 (FIG. 10). In addition to preventing relative lateral and vertical movement between the plenum chamber 3200 and the frame 3310, another purpose of the retention features 3244 is to prevent relative longitudinal movement between these two parts. The remaining portion of plenum chamber 3200 may comprise a more flexible material than the retaining structure 3242 and plenum connection region 3240.

In one form, plenum connection region 3240 is constructed from a rigid or semi-rigid material, e.g. high durometer silicone or TPE, plastic, nylon, a temperature resistant material, polypropylene, and/or polycarbonate. Plenum connection region 3240 may be constructed from a different material to other portions of plenum chamber 3200. For example plenum connection region 3240 may be a separate component that is permanently connected, integrally bonded or mechanically interlocked with connection portion 3202 (FIG. 10) of the plenum chamber 3200. Turning to FIG. 6, the connection portion 3202 of the plenum chamber 3200 may has substantially the same thickness as the retaining structure 3242 of the plenum connection region 3240. Plenum connection region 3240 may include a tongue portion 3211 constructed and arranged to be matingly received by a channel portion 3211.1, e.g., a channel portion of a frame 3310. In this way, the channel portion 3211.1 may form a mating feature for the tongue portion 3211, and vice versa. Also, the tongue portion 3211 and the channel portion 3211.1 may be dimensioned to maximize the sealing surface area in this region.

Attachment and Removal of Plenum Chamber from Frame

The plenum chamber 3200 may be fixedly attached to the frame 3310, but it also may be removably attached to the frame 3310. FIG. 12 shows the plenum chamber 3200 in a connected position relative to the frame 3310. Plenum connection region 3240 includes in this example only two retention features 3244, which are positioned on opposite sides of the connection region 3240, e.g., on the posterior and anterior sides. FIGS. 12 and 13 shows a cross-section that passes through both barbs 3246, while FIG. 17 shows another cross-section where the barbs 3246 are not present, forming e.g. a channel or groove 3211.1. The resilient barbs 3246 are a type of snap-in compression-fit member to provide a high retention force (to prevent accidental disengagement) and also enable relatively easy intentional removal. In FIG. 17, the plenum connection region 3240 and the frame 3310 simply fit together in a tongue and groove like manner. The frame 3310 and retaining structure 3242 may be shaped so that the tongue portion 3211 and the channel portion 3211.1 engage before the retention features 3244 engage with the frame. This may help align the retention features 3244 for connection.

Each retention feature 3244 may take the form of a barb 3246 (FIGS. 6 and 13) having a leading surface 3246.1 and a trailing surface 3246.2. The leading surface. 3246.1 is adapted to engage a lead-in surface 3312.1 of the frame connection region 3312 of the frame 3310, as the plenum chamber 3200 and the frame 3310 are moved into engagement with one another. As the retention feature 3244 is pushed into position it deforms. Also, upper and lower regions of the frame connection region 3312 and interfering portion 3314 of the frame 3310 may also slightly deform. Also, the retaining structure 3242 may also slightly deform especially near the retention feature 3244 (for example, see broken line in FIGS. 27 and 28). Turning to FIGS. 195 to 198, deformation of the frame connection region 3312 and interfering portion 3314 of the frame 3310 is controlled in terms of the amount of deformation permitted and also the areas of where deformation is to occur through the use of ribs 3294. In one example of the present technology, there are six ribs 3294 spaced around and against the interfering portion 3314. The spacing and position of the ribs 3294 limit the area of deformation of the interfering portion 3314 to only the area proximal to the retention features 3244. The ribs 3294 may also abut and deform against the inner surface of the plenum connection region 3240 to provide a firmer engagement between the plenum connection region 3240 and the frame connection region 3312 at these contact points when the plenum chamber 3200 is engaged with the frame 3310. Turning to FIGS. 199 to 202, the plenum connection region 3240 of the plenum chamber 3200 has notches 3295 to correspond with the ribs 3294. The notches 3295 are chamfers to minimise the friction of the plenum connection region 3240 against the ribs 3294 during assembly of the plenum chamber 3200 with the frame 3310. Once the barb 3246 is pushed in a sufficient amount, it snaps outwards in a radial sense such that the barb 3246 assumes a retained position shown in FIG. 13. The snapping action results in an audible sound to the user such as a re-assuring click sound, providing feedback to the user or patient that a proper connection has been established. In the retained position, the trailing surface 3246.2 of the barb 3246 engages with a retaining surface 3312.2 of the frame connection region 3312, as shown in FIG. 13. This reassuring click sound may also be facilitated, in one example of the technology, by forming the plenum connection region 3240 of sufficient stiffness, that stiffness being greatest near the plenum connection region 3240. This stiffness may be accomplished by overmolding manufacturing.

As can be seen in FIG. 13, the surfaces of the barb 3246 and the frame connection region 3312 are angled in certain manners to facilitate sliding connection between the plenum chamber 3200 and the frame 3310. For example, as stated above, the leading surface 3246.1 and the lead-in surface 3312.1 may be formed with angles corresponding to one another such that these to surfaces may slidingly engage with one another with relative ease. Similarly, the trailing surface 3246.2 and the retaining surface 3312.2 may be angled relative to one another to help retain the frame 3310 and the plenum chamber 3200 once connected. The angles between the trailing surface 3246.2 and the retaining surface 3312.2 are selected such that a pulling force applied, e.g., generally along the axis of the nasal pillows 3130, is sufficient to cause the barb 3246 to flex inwardly to thereby release the plenum chamber 3200 from the frame 3310. This pulling force does not require the patient 1000 to first deflect the barbs 3246 radially inwards, e.g., by squeezing the plenum chamber 3200 in an anterior-posterior direction. Rather, due to the angles involved, the radial deflection of the barbs 3246 occurs solely as a result of the axial pulling force applied. In one example of the present technology, the plenum connection region 3240 is deflected and disassembly of the plenum chamber 3200 from the frame 3310 is performed by pinching the plenum chamber 3200 and pulling the plenum chamber 3200 away from the frame 3310.

As can be seen in FIG. 13, the plenum chamber 3200 is attached to the frame 3310 via the plenum connection region 3240 and the retention feature 3244 is engaged with the frame connection region 3312 by the barb 3246. Also shown in this view, the retaining surface 3312.2 of the frame connection region 3312 and the trailing surface 3246.2 of the barb 3246 are engaged and flush with one another. For the patient to detach the plenum chamber 3200 from the frame 3310 the patient must pull the plenum chamber 3200 with respect to the frame 3310 with sufficient force to overcome the resistance of the retaining surface 3312.2 against the trailing surface 3246.2. In one example of the present technology, pinching the plenum chamber 3200 reduces the axial pulling force required to detach the plenum chamber 3200 from the frame 3310. This resistance can be "tuned" or selectively adjusted to a desired level by varying the angle at which these surfaces 3312.2, 3246.2 engage with one another. The closer to perpendicular these surfaces 3312.2, 3246.2 are with respect to the direction of the force applied by the patient 1000 to detach the plenum chamber 3200 from the frame 3310, the greater the force required to cause the detachment. This angle is shown as β in FIG. 14, where the trailing surface 3246.2 is angled with respect to a nominal vertical axis 3246.4 (corresponding to axial pull direction of plenum chamber 3200 to the frame 3310). As β is increased, the force required to detach the plenum chamber 3200 from the frame 3310 rises. Furthermore, as β increases the detachment will feel more abrupt to the patient 1000. In one example, an angle β of approximately 75 degrees has been found to generate a comfortable feel of detachment for the patient. In further examples, β may vary from 30 to 110 degrees or from 40 to 90 degrees or from 65 to 85 degrees to generate an ideal level of resistance to detachment. This has been selected to minimise the likelihood of accidental detachment, and to only permit intentional detachment by the patient 1000.

Angle α, the angle between the nominal vertical axis 3246.4 and the leading surface 3246.1, can likewise be "tuned" or selectively adjusted to require a specific level of force when the patient 1000 attaches the plenum chamber 3200 to the frame 3310. As angle α is increased, the force required to engage the retention feature 3244 with the frame connection region 3312 increases and the feeling of attachment for the patient engaging these components 3244, 3312 becomes more abrupt. In other words, as the leading surface 3246.1 of the retention feature 3244 slides along the lead-in surface 3312.1 of the frame connection region 3312 the user may experience a smoother feel of engagement as angle α decreases. In one example, an angle α of approximately 30 degrees has been found to generate a comfortable feel of attachment for the patient 1000. In further examples, angle α may vary from 50 to 70 degrees or from 15 to 60 degrees to generate an ideal level of resistance to attachment.

Furthermore, since the feel and force of engagement and disengagement of the plenum chamber 3200 and frame connection region 3312 can be tuned or selectively adjusted independently of one another, angles α and β may be chosen to cause the patient to feel a level of resistance to attachment that is different from the level of resistance of detachment. In one example of the technology, angles α and β may be chosen such that angle β is greater than angle α, such that the patient feels less resistance to attachment of the plenum chamber 3200 and frame 3310 than resistance to detachment. In other words, it may feel harder for the patient to disconnect the plenum chamber 3200 from the frame 3310 than to connect them.

As can be seen in FIG. 4, one example of the technology includes a pair of retention features 3244, 3245. Also shown in this view, the exemplary retention features 3244, 3245 are differently sized. Particularly, this view shows that the retention feature 3245 disposed on an anterior portion of the plenum connection region 3240 is narrower than the retention feature 3244 disposed on the posterior portion of the plenum connection region 3240. By sizing the retention features 3244 differently, the patient 1000 is only able to attach the plenum chamber 3200 to the frame 3310 in one orientation. Such an arrangement is shown in FIG. 10. This avoids patient frustration during attachment, minimises damage to the patient interface 3000 that may arise from incorrect attachment, ensures the seal-forming structure 3100 is in the correct orientation to provide a proper seal against the patient's airways and provide comfort by reducing or avoiding contact with a septum and/or an upper lip of the patient 1000.

In FIG. 10 two frame connection regions 3312, 3313 are shown in engagement with corresponding retention features 3244, 3245. The example depicted here shows that the narrower anterior retention feature 3245 is sized to correspond to the narrower anterior frame connection region 3313. Also, the wider posterior retention feature 3244 is engaged with the correspondingly sized posterior frame connection region 3312. An arrangement such as this, where one retention feature is uniquely dimensioned to engage with a corresponding uniquely dimensioned frame connection region, has the advantage that the patient will only be able to attach the plenum chamber 3200 to the frame 3310 in one orientation. By limiting the orientations of attachment, the patient 1000 is prevented from assembling the patient interface 3000 improperly and receiving suboptimal therapy due to an improperly assembled patient interface 3000. The arrangement described with respect to this particular example of the technology is advantageous to the patient 1000 that may have difficulty seeing how to correctly engage the components due to vision problems or the patient 1000 who may be assembling the patient interface 3000 in a dark room, e.g., the bedroom before sleep, because the patient 1000 will only be able to completely assemble the patient interface 3000 if the components are properly aligned.

As described above, the angles of the leading surface 3246.1 and the trailing surface 3246.2 on the barb 3246 are important to providing an optimum amount of resistance to assembly and disassembly of the patient interface 3000. Also described above is the benefit of sizing respective retention features 3244, 3245 and frame connection regions 3312, 3313 correspondingly such that a proper orientation of the components is ensured upon assembly Properly dimensioning the retention features 3244, 3245 and the frame connection regions 3312, 3313 may help to guide the plenum chamber 3200 onto the frame 3310. In other words, the frame connection regions 3312, 3313 and the retention features 3244, 3245 may be dimensioned in close conformity to one another such that the perimeter of the frame connection regions and the perimeter of the retention features 3244 to aid in directing and aligning the retention feature 3244 into the frame connection region 3312. This may be beneficial to a patient with limited dexterity due to a disease (e.g., arthritis) or a patient assembling the patient interface 3000 where visibility is diminished whether in a dark bedroom prior to sleep or due to limited vision. Also, by dimensioning the retention features 3244, 3245 and the frame connection regions 3312, 3313 in close conformity to one another this serve to ensure that the seal between the plenum chamber 3200 and the frame 3310 is maintained by facilitating a secure connection between these two components. Additionally, close conformity between the retention features 3244, 3245 and the frame connection regions 3312, 3313 may serve to facilitate equal alignment of the plenum chamber 3200 on the frame 3310. In one example of the present technology a difference of 0.3 mm to 2 mm may be incorporated between the retention features 3244, 3245 and the frame connection regions 3312, 3313.

It should also be understood that connection between the frame 3310 and the plenum chamber 3200 described above and below may be used with other types of masks. Such features may be applicable to nasal or full-face masks as well. Masks that seal under the bridge of the nose, such as compact nasal masks or compact full-face masks, may also incorporate the connection features described herein. Furthermore, masks that lack a forehead support may also include these connection features. It is also envisioned that examples of the present technology that include masks that seal below the tip of the nose, such as those with nasal pillows 3130 or a nasal cradle/nasal flange 3101, may also use these connection features.

Plenum Chamber and Frame Attachment and Removal Sequence

FIGS. 25 to 29 show a sequence of cross-sectional views of the connection portion 3202 of the plenum chamber 3200 and the frame connection region 3312 of the frame 3310. These sequential views show the process of attachment of the plenum chamber 3200 to the frame 3310. While these views show only the attachment of one retention feature 3244 to one frame connection region 3312, it should be understood that there may be more than one retention feature 3244 and more than one frame connection region 3312, as can be seen in FIG. 10 and discussed above. Therefore, during the attachment sequence of the plenum chamber 3200 and the frame 3310 there may be more than one instance of the depicted attachment sequence taking place to accomplish complete attachment of the plenum chamber 3200 and the frame 3312.

FIG. 25 shows a cross-sectional view of the connection portion 3202 of the plenum chamber 3200 and the frame connection region 3312 of the frame 3310 where the connection portion 3202 and the frame connection region 3312 are near one another but not in contact. The arrow indicates that the connection portion 3202 and the frame connection region 3312 are being brought together. It should be understood that for these views additional portions of the plenum chamber 3200 and the frame 3310 have not been included in the interest of simplicity. Thus, it should also be understood that frame connection region 3312 and interfering portion 3314 of the frame connection region 3312 are both part of the frame 3310 as can be seen, for example, in FIG. 13. Moreover, it should be understood then that the frame connection portion 3312 and the interfering portion 3314 of the frame connection portion 3312 will move relative to one another through the attachment sequence. Returning to FIG. 25, this view shows that the sealing lip 3250 is not deformed and the retention feature 3244 is not deformed as neither of these components 3250, 3244 are in contact with the frame 3310.

FIG. 26 shows the barb 3246 of the retention feature 3244 beginning to make contact with the frame connection region 3312 of the frame 3310. Specifically, this view shows the leading surface 3246.1 of the barb 3246 in contact with the lead-in surface 3312.1 of the frame connection region 3312. In this view, the retention feature 3244 and the frame connection region 3312 are only just coming into contact with one another such that the retention feature 3244 is not deflected. Also, the sealing lip 3250 has not been deflected because it is not yet in contact with the interfering portion 3314 of the frame connection region 3312. As described above, the angle α of the leading surface 3246.1 will begin to affect the resistance the user will feel to engagement of the plenum chamber 3200 and the frame connection region 3312 because the leading surface 3246.1 will begin to engage in frictional contact with the lead-in surface 3312.1.

FIG. 27 shows the plenum chamber 3200 and the frame 3310 further along in the attachment sequence such that the retention feature 3244 is deflected by contact with the frame connection region 3312. As can be seen in this view, the frame connection region 3312 and the interfering portion 3314 of the frame connection region 3312 are nearer to the connection portion 3202. Also shown in this view, the leading surface 3246.1 of the barb 3246 is in contact with a portion of the lead-in surface 3312.1 that is closer to the retaining surface 3312.2. In other words, the barb 3246 can be seen having moved closer to attachment with the frame connection region 3312 and having moved relative to the position shown in FIG. 26. As described earlier, the connection portion 3202 and the plenum connection region 3240 of the plenum chamber 3200 may also be deflected from a pinching force generated by the patient 1000. FIG. 27 also indicates that the retention feature 3244 has been deflected by contact with the frame connection region 3312 and the dashed lines show the outline of the retention feature 3244 in an undeformed state. FIG. 27 also shows that the sealing lip 3250 is not yet in contact with the interfering portion 3314 of the frame connection region 3312, and, therefore, the sealing lip 3250 is not deformed. Although, not shown in this view it should also be understood that the frame connection region 3312 may deflect away from the retention feature 3244 due to the force of these parts 3312, 3244 being forced together.

In FIG. 28 the plenum chamber 3200 and the frame 3310 are nearly attached and the retention feature 3244 is nearly completely engaged with the frame connection region 3312. In this view the retention feature 3244 is still deformed but the barb 3246 is in contact with a different portion of the frame connection region 3312. Specifically, the trailing surface 3246.2 of the barb 3246 is now in contact with the retaining surface 3312.2 of the frame connection region 3312. Also, due to the fact that the angle at which the trailing surface 3246.2 and the retaining surface 3312.2 contact one another, the retention feature 3244 and the frame connection region 3312 may be urged into engagement by the inherent tendency of the deflected retention feature 3244 to return to its undeformed state, in effect drawing these parts together after a certain insertion distance is reached. FIG. 28 also shows the outline of the retention feature 3244 in an undeformed state with dashed lines. Also in this view it can be seen that the sealing lip 3250 is in contact with the interfering portion 3314 of the frame connection region 3312. At this point in the attachment sequence a seal may begin to be formed by the contact of the sealing lip 3250 and the interfering portion 3314 of the frame connection region 3312. The sealing lip 3250 may also be slightly deflected by contact against the interfering portion 3314 of the frame connection region 3312.

FIG. 29 shows the plenum chamber 3200 and the frame 3310 fully attached by engagement of the barb 3246 of the retention feature 3244 with the frame connection region 3312. In this view the retaining surface 3312.2 may be relatively flush against the trailing surface 3246.2. The retention feature 3244 may also no longer be deflected by contact with the frame connection region 3312. The retention feature's 3244 return to an undeformed state from its deflected or deformed state, as shown in FIG. 28, may generate an audible click as the barb 3246 and the retention feature 3244 move to the position shown in FIG. 29 from the position shown in FIG. 28. This re-assuring audible click may be advantageous in that it provides the patient 1000 with feedback that the plenum chamber 3200 and the frame 3310 are fully engaged. By providing the patient 1000 with this feedback upon completion of engagement the patient 1000 may be able to use the patient interface 3000 with confidence that the plenum chamber 3200 and the frame 3310 are securely attached and will not separate while the patient 1000 is asleep and receiving therapy.

Furthermore, a desired level of sealing contact may be achieved when the plenum chamber 3200 and the frame 3310 are attached as shown in FIG. 29. The sealing lip 3250 can be seen deflected against the interfering portion 3314 of the frame connection region 3312. By being deflected as shown, the sealing lip 3250 may be urging itself against the interfering portion 3314 of the frame connection region 3312 with sufficient force due to the tendency of the sealing lip 3250 to return to its undeformed state such that a desired seal is generated between these components. Furthermore, as air pressure within the plenum chamber 3200 increases when therapy is applied, the sealing lip 3250 is forced to deflect towards the portion 3314 of the frame connection region 3312 thereby increasing the sealing force in this area. Even though a compression seal is formed between the retaining structure 3242 and frame connection region 3312 when the plenum chamber 3200 is engaged with the frame 3310, a pressure-activated seal also is formed between sealing lip 3250 and the portion 3314 of the frame connection region 3312 on engagement which strengthens as air pressure within increases. It may be possible in certain examples that the compression seal is not air tight resulting in undesired leakage.

Also, if a very large amount of compression of components is required to form the compression seal, this may hinder easy attachment and detachment of the plenum chamber 3200 to the frame 3310 possibly requiring more than a single hand to perform the operation or a significant amount of effort. Therefore, in one example of the present technology, the compression seal functions predominantly for the purpose of retention rather than of seal, and the pressure-activated seal functions predominantly for the purpose of creating and maintaining an air tight seal. It should be understood that such a sealing effect may be occurring about the periphery of the junction between the plenum chamber 3200 and the frame 3310. For example, FIG. 17 shows the sealing lip 3250 in a similarly deflected state against the frame connection region 3312 at a region separate from the retention features 3244. Moreover, it can be seen in FIG. 5, for example, that the sealing lip 3250 extends around the perimeter of the plenum chamber 3200. By extending the sealing lip 3250 inwardly around the perimeter of the junction between the plenum chamber 3200 and the frame 3310 the desired level of sealing can be achieved throughout this region, thereby preventing undesired leakage of pressurized gas.

Additionally, it should be understood that the sealing lip 3250 may be pressing against the interfering portion 3314 of the frame connection 3312 with a force that is urging these parts to separate. However, the friction force due to structural engagement of the trailing surface 3246.2 of the barb 3246 with the retaining surface 3312.2 of the frame connection region 3312 should be sufficient to resist the force of the sealing lip's 3250 tendency to return to an undeformed state and separate the plenum chamber 3200 from the frame 3310.

As for removal of the plenum chamber 3200 and the frame 3310, it should be understood that this process is substantially the reverse order of the process described above. In other words, the user may separate the plenum chamber 3200 from the frame 3310 by pulling these components in opposite directions and the view of FIG. 29 may be the beginning of the separation process and FIG. 25 may represent the view wherein the plenum chamber 3200 and the frame 3310 are fully separated. Pinching of the plenum chamber 3200 proximal to the plenum connection region 3240 or pinching the plenum connection region 3240 and pulling away from the frame 3310 may assist in removal of the plenum chamber 3200 from the frame 3310. It is also envisaged that the patient 1000 may pinch the plenum chamber 3200 for the purpose of gripping it, at any location, for example, the nasal pillows 3130 or stalks 3150 and simply pull it away from the frame 3310. A twisting motion while pulling may also assist in disengaging the plenum chamber 3200 from the frame 3310.

Hard-to-Hard Connection

The plenum connection region 3240 and the frame 3310 may be assembled and attached as shown in FIGS. 25 to 29. As stated above, the plenum connection region 3240 and/or retaining structure 3242 may be comprised of a semi-rigid material, e.g., high durometer silicone (a higher durometer than plenum chamber 3200)/TPE, plastic, nylon, polypropylene, polyamide and/or polycarbonate. The plenum connection region 3240 can be constructed in the form of a continuous ring or oval, two C-shaped clips, one C-shaped clip, or a single continuous piece but only surrounding a part of the plenum chamber 3200. The clip may function as a spring clip and be in the form of a C-section or double C-section. The spring force of the spring clip may be provided by resiliency of the plenum connection region 3240 being stretched against the frame connection regions 3312, 3313 or interfering portion 3314 of the frame 3310. In another example, a clip form may be not be necessary and only the retention features 3242, 3244 are permanently and directly connected to the plenum chamber 3200 without a plenum connection region 3240 and/or retaining structure 3242 for engagement with the connection regions 3312, 3313. It is also envisioned that one example of the present technology may also include the frame 3310 being comprised of the same or a similar semi-rigid material as the plenum connection region 3240. By manufacturing the frame 3310 and the plenum connection region 3240 of semi-rigid material, a "hard-to-hard" connection or bonding interface may be created. This "hard-to-hard" connection, in conjunction with the structural features of the plenum connection region 3240 and the frame connection region 3312, may provide the patient 1000 with a confident feeling (e.g., by providing an audible snap fit or re-assuring click sound) of the connection between the plenum chamber 3200 and the frame 3310 when assembling the patient interface 3000. Since a secure fit between the plenum chamber 3200 and the frame 3310 is helpful to ensure that the patient 1000 receives optimal therapy through the patient interface 3000, a design that provides the patient 1000 with confidence that a secure fit has been achieved is beneficial. A hard-to-hard connection as described herein may also be beneficial in that it may add stability to the seal made by the seal-forming structure 3100. This is contrast to a hard-to-soft or a soft-to-soft connection where either or both the plenum chamber and frame are made of a floppy material which makes it difficult for arthritic hands to properly engage the plenum chamber and frame easily, especially in darkened room.

Although the retention features 3242, 3244 are described as provided on the plenum chamber 3200 and the connection regions 3312, 3313 are provided on the frame 3310, it may be possible to switch the location to the retention features on the frame and the connection regions on the plenum chamber. Also, there may be a combination of a retention feature and a connection region on one part that corresponds with a connection region and a retention feature on the other part.
Method of Making the Plenum Chamber A process to manufacture plenum chamber 3200 may comprise the step of moulding plenum connection region 3240 in a first tool, removing moulded plenum connection region 3240 from the first tool, inserting the plenum connection region 3240 into a second tool, and moulding a portion of plenum chamber 3200 comprising connection portion 3202 in the second tool. Plenum connection region 3240 may be chemically bonded and/or mechanically interlocked to connection portion 3202.

In one form, the sealing lip 3250 is constructed and arranged to interfere with the interfering portion 3314 (FIG. 13) of frame connection region 3312 when plenum chamber 3200 and frame 3310 are assembled together. In use, sealing lip 3250 is caused to resiliently flex away from a resting position (FIG. 6) when assembled with the interfering portion 3314 of frame connection region 3213, and at least in part as a result of being a resilient material, pushes against the interfering portion 3314 (FIG. 12) to resist or prevent leakage of air between sealing lip 3250 and the interfering portion 3314. Although the sealing lip 3250 has been described as provided with the plenum chamber 3200, the sealing lip may be provided on the frame 3310. Although one sealing lip has been described, it is possible two or more sealing lips may be provided, with at least one with the plenum chamber 3200 and at least one with the frame 3310.
Positioning and Stabilising Structure 3300

Note that in one form of the present technology, a number of structural features form part of a positioning and stabilising structure 3300, e.g., a headgear assembly (which may be referred to simply as headgear). In an alternative form of the present technology, one or more of those features are located on the frame 3310. For example, a flexing joint 3305 may be wholly or partly located on the headgear, or on the frame 3310. Also, the extension 3350 may perform the same function as the flexing joint 3305 except that it is integrally formed with the rigidiser arm 3302.

The seal-forming structure 3100 of the patient interface 3000 of the present technology may be held in sealing position in use by the positioning and stabilising structure 3300 (FIGS. 75, 76 and 166). In one form, the positioning and stabilising structure 3300 comprises headgear. It should be appreciated that the positioning and stabilising structure 3300 may, in one form of the technology, be referred to as headgear.

Headgear may be removably connectable to a portion of the patient interface such as the positioning and stabilising structure 3300 via a headgear connector.
Straps The positioning and stabilising structure 3300 may comprise at least one strap 3301 (see, e.g., FIG. 65) and at least one rigidiser arm 3302 (see, e.g., FIG. 67). The strap 3301 may be made of an elastic material and may have elastic properties. In other words, the strap 3301 may be elastically stretched, e.g., by a stretching force applied by the patient and, upon release of the stretching force, returns or contracts to its original length in a neutral state. The strap 3301 may be made of or comprise any elastomeric material such as elastane, TPE, silicone etc. The material of the strap 3301 may also represent a combination of any of the above materials with other materials. The strap 3301 may be a single layer or multilayer strap. The strap 3301, particularly the side strap portions 3315, 3316 in contact with the patient 1000 during use, may be woven, knitted, braided, molded, extruded or otherwise formed. The strap 3301 may comprise or may be made of a textile material such as a woven material. Such material may comprise artificial or natural fibers for, on the one hand, providing desired and beneficial surface properties such as tactile properties and skin comfort. On the other hand, the material of the strap 3301 may include elastomeric material for providing the desired elastomeric properties. The entire strap 3301, including the side strap portions 3315, 3316 and back strap portion 3317, may all be stretchable. This enables the entire length of the strap 3301 to be stretched which leads to a comfortable force displacement profile. In order for the strap 3301 to be stretched in use, the length of the strap 3301 may be less than the average small head circumference of patients. For example, the length of the strap 3301 may be less than 590 mm in one example and less than 500 mm in another example. However, straps 3301 of different lengths may be provided to patients depending on their head circumference which may be gender specific. For example, a small sized strap may be 490 mm in length and a large sized strap may be 540 mm. In some circumstances this means that the length of the strap 3301 need not be stretched by a large distance (i.e. small sized strap for a large head circumference) which would have unnecessarily high headgear tension for such patients and also a less smooth force displacement profile as the small sized strap 3301 is being stretched to longer lengths.

According to alternative examples of the present technology, the strap 3301 may be inelastic or may not be able to stretch substantially. The rigidiser arms 3302 may or may not be included. According to these alternative examples, the length of the strap 3301 of the positioning and stabilising structure 3300 may be adjustable with ladder lock clips, buckles or a hook and loop materials. The strap 3301 may be formed from a substantially inelastic material such as a plastic or a textile. The use of an inelastic strap 3301 may be beneficial in that seal stability may be more easily maintained when the seal-forming structure 3100 is a nasal cradle cushion and tube torque is experienced by the patient interface 3000.

The strap 3301 is rigidised at a certain sections, for example, from the frame 3310 up to a position proximal to the patient's cheekbone by the inserted rigidiser arms 3302. The strap 3301 may take the form of a hollow ribbon. The strap 3301 may be considered to be threaded over the rigidiser arm 3302 when it is slipped onto the rigidiser arm 3302 and secured at one end of the rigidiser arm 3302 proximal to the frame 3310.

In one example, the strap 3301 including the side strap portions 3315, 3316 and back strap portion 3317 are made by warp knitting a textile material. The strap 3301 is a 3D knitted fabric that is knit by computer control as a single unitary piece. Variation in the thread and stitching may occur at various positions along the strap 3301 to adjust the elasticity and strength and durability of the strap 3301 at certain locations. For example, at the locations of the openings, insertion points or button-holes 3303, 3304 and the bifurcation point 3324 for the back strap portions 3317*a*, 3317*b*, an additional thread may be knitted to provide reinforcement of the strap 3301 to prevent failure/breakage of the strap 3301 at these locations that subject to high stress when the strap 3301 is stretched during repeated and prolonged use. Both the knitting method (i.e. warp knitting) and the elastic textile material (e.g. elastane) of the strap 3301 contribute to the elastic recovery of the strap 3301 after washing the strap 3301 in water and dried. In other words, the elasticity of the strap 3301 can be maintained after prolonged use by periodically washing the strap 3301 and therefore its operational life is extended.

In FIGS. 65 to 73, the strap 3301 is shown as being a single continuous strap with two pocketed ends 3311, 3313 for being attached, directly or via a flexible joint 3305, to a frame 3310. However, it may be appreciated that the strap 3301 may comprise multiple individual straps which are or may be directly connected to one another, for example, stitching or ultrasonic welding. In FIG. 65, the strap 3301 and positioning and stabilising structure 3300 is shown without any adjustment or variation means. Such adjustment may be provided, however, by varying where the strap 3301 is secured to a patient interface 3000 or other connection elements more rigid than the strap 3301 such as a flexible joint 3305. Turning to FIG. 72, in addition or alternatively, adjustment could be allowed by adding a mechanism, such as slide over ladder lock clips 3305.1 on the back 3317 or side strap portions 3315, 3316 (as shown, e.g., in FIGS. 71 to 73) or by otherwise adjusting the elastic length of the strap 3301 and positioning and stabilising structure 3300, respectively. In the example shown in FIG. 65, the strap 3301 has a tube-like configuration as can be taken from the respective schematic views in FIGS. 68 to 70 indicating an oval or circular shape or respective marks 3321a-d, 3323a-e of circular or oval shape indicating the (visible) outer surface facing towards the viewer as solid and the (invisible) inner wall facing away from the viewer in dashed lines, as well as by the cross-sectional view according to FIG. 66. However, it will be appreciated that the positioning and stabilising structure 3300 may take any other shape such as flat or sheet-like shape, single, multi-layer or laminate construction. The strap 3301 may have a longitudinal axis which may be understood to be the axis substantially parallel to the paper plane, along which the strap 3301 extends (see, e.g., dashed line in FIG. 65).

The strap 3301 have may reinforced stitching to improve durability and minimise or prevent failure points. For example, the areas of the strap 3301 at the button-holes 3303, 3304 and also at the location where it bifurcates into two back strap portions 3317a, 3317b, at bifurcation points 3324, are subject to high stress when stretched. The tendency of the material is to split away from each other at a split region 3326 and therefore reinforced stitching at these areas is one way to address this concern. In an example, a central seam runs along the centre longitudinal axis of the strap 3301 and functions as reinforced stitching. Also, the distal edges of the strap 3301 and the opening at the button-holes 3303, 3304 may be ultrasonically welded to fuse any stray fibers and strengthen the strap 3301 in these regions. Advantageously, this also prevents fraying of the fibers of the strap 3301 after extended use and repeated washing. Other techniques are envisaged for reinforcing and strengthening the pocketed end 3311, distal edges and button-hole 3303, which may include additional material such as tape. The tape may include branding and logo information also.

FIGS. 123 to 125 show increasingly detailed views of the split region 3326 between the upper back strap portion 3317a and the lower back strap portion 3317b. The edges of the upper back strap portion 3317a and the lower back strap portion 3317b should be understood to not be perfectly smooth as a result of the knitting process and it should be further understood that these views show the edges with a great deal of magnification such that imperfections are visible. With the naked eye the undulations on the edges of the upper back strap portion 3317a and the lower back strap portion 3317b would not be so easily visible and are not generally discernible by the patient 1000 by touch. Additionally, stippling is used in these views to show the texture of the back strap portions 3317a, 3317b while the split region 3326 is shown blank because the split region 3326 is an absence of material.

FIGS. 126 to 131 show various detailed views of the bifurcation point 3324 that exists where the upper back strap portion 3317a and the lower back strap portion 3317b split off from a side strap portion 3315, 3316. Also visible in these views is a reinforced portion 3325 that may include additional stitching or welding at or proximal to the bifurcation point 3324. The reinforced portion 3325 may aid in preventing the side strap portions 3315, 3316 from splitting and/or tearing due to stress from the repeated separation of the upper back strap portion 3317a and the lower back strap portion 3317b. In other words, the reinforced portion 3325 may provide additional strength at a location of stress concentration near the bifurcation point 3324. Also shown in these views are the upper back strap portion 3317a and the lower back strap portion 3317b at various angles of separation θ. These views may be understood to show that the reinforced portion 3325 provides additional strength at the bifurcation point 3324 when the upper back strap portion 3317a and the lower back strap portion 3317b are spread from one another at large angles θ.

Referring to FIGS. 176 to 181, in one example of the present technology, the ends of the strap 3301 have a reinforcement portion 3327 with a material folded over the end of the strap 3301. This provides further reinforcement in this area in addition to the welded ends 3311.1, 3313.3 (see FIG. 81). The material of the reinforcement portion 3327 may be a different material to the strap 3301. The reinforcement portion 3327 may avoid or mitigate the likelihood of a patient 1000 tearing or ripping the strap 3301 along its longitudinal axis beginning from this area. The reinforcement portion 3327 helps provide a visual and tactile indication to the patient 1000 on how to slip on or remove the strap 3301 from the rigidiser arm 3302 because it may assist in identifying the location of the button-hole 3303, 3304. The corners 3328 of the reinforcement portion 3327 have been cut and are rounded so that the corners 3328 approximately match the rounded corners of the rigidiser arm 3302 at its distal free ends 3302.1 (see FIGS. 50, 52, 55, 57, 58, 60). This provides a snug fit with the rigidiser arm 3302 which is more aesthetically pleasing. The rounded corners 3328 provide a soft edge to avoid facial scratching that could occur if they were sharp corners instead.

Rigidiser Arms

FIG. 67 shows an example of a rigidiser arm 3302. As shown, the rigidiser arm 3302 may take a crescent or semi-circular shape. The rigidiser arm 3302 may have a generally elongate and flat configuration. In other words, the rigidiser arm 3302 is far longer and wider (direction from top to bottom in the paper plane) than thick (direction into the paper plane). The rigidiser arm 3302 has a three-dimensional shape which has curvature in all three axes (X, Y and Z). Although the thickness of the rigidiser arm 3302 may be substantially uniform, its height varies throughout its length. The purpose of the shape and dimension of the rigidiser arm 3302 is to conform closely to the cheeks of the patient in order to remain unobtrusive and frame the patient's face and cheeks. The ends 3319a, 3319b of rigidiser arm 3302 may be rounded and/or slightly angled relative to the remainder of the rigidiser arm 3302. While the rigidiser arm 3302 may be flat, as indicated by the paper plane in FIG. 67, it will be appreciated, that the rigidiser arm 3302 may have a desired spatial configuration also in the direction into the paper plane in FIG. 67, particularly in order to allow improved alignment with the shape of a patient's face, such as the shape of a patient's cheek or head side region (see, e.g., FIGS. 71 and 72). The rigidiser arm 3302 may have a longitudinal axis which may be understood to be the axis substantially parallel to the paper plane, along which the rigidiser arm 3302 extends (see dashed line in FIG. 67).

The rigidiser arm 3302 is more rigid than the strap 3301 and less rigid than the mask frame 3310. In particular, the rigidiser arm 3302 and/or the strap 3301 are such that in combination the rigidiser arm 3302 imparts a shape, and an increased degree of rigidity in at least one direction or in or around at least one axis, to the strap 3301. Also, the rigidiser arm 3302 guides or defines the direction or path of stretch for the strap 3301. In other words, the patient stretches the strap 3301 in a direction substantially parallel to the longitudinal axis of the rigidiser arm 3302. Stretching of the strap 3301 in other directions leads to rotation of the rigidiser arm 3302 relative to the mask frame 3310 which is undesirable. The rigidity of the rigidiser arm 3302 biases the rigidiser arm 3302 towards its natural, unrotated, untwisted and undeformed state. To some degree, this enables the positioning and stabilising structure 3300 to be self-adjusting headgear. The self-adjusting function avoids manually shortening or lengthening the material length of headgear straps and then remembering the adjusted length. This has typically been a cumbersome process because headgear straps on both sides of the face have to be shortened or lengthened one at a time. It may remove the ability for patients to over tighten the headgear when such high levels of headgear tension is not required to maintain a good sealing force. In the shown example, strap 3301 has a tube- or sleeve-like configuration. In other words, the strap 3301 is hollow in order to receive the insertion of the rigidiser arm 3302 which is slid into the strap 3301 via the button-hole 3303. In another example, the rigidiser arm 3302 may be permanently connected to the strap 3301 at least in one location, for example, at the anchor point it is overmolded or glued to form an integral chemical bond (molecular adhesion) between the rigidiser arm 3302 and the strap 3301.

Strap 3301 comprises side strap portions 3315, 3316 and a back strap portion 3317 located between the side strap portions 3315, 3316. Side strap portions 3315, 3316 are adapted to extend along the sides of a patient's head when being worn while back strap portion 3317 is adapted to extend along the back of a patient's head, as shown in FIGS. 4 to 8 and 166. Back strap portion 3317 may be comprised of two, three or more straps arranged in parallel, particularly for providing stability. Although the smaller back strap portions 3317a, 3317b have been illustrated as equal in length, it is envisaged that one back strap portion is longer than the other back strap portion. The greater the number of smaller back strap portions 3317a, 3317b for the back strap portion 3317, the greater the spring effect provided. In other words, as the number of same sized smaller back strap portions 3317a, 3317b increases when the strap 3301 is manufactured, the more tension is exerted on the side strap portions 3315, 3316 to be pulled closer to each other by the back strap portions 3317a, 3317b. In the shown example, side strap portions 3315, 3316 of strap 3301 bifurcate into two back strap portions 3317a, 3317b. In one example, each back strap portion 3317a, 3317b has half the amount of elastane material compared to each side strap portion 3315, 3316 of the strap 3301. In one example, the positioning and stabilising structure 3300 is connected to the mask frame 3310 by a removable connection between strap 3301 and the rigidiser arm 3302 via a button-hole 3303, 3304 and the rigidiser arm 3302 being permanently connected to the mask frame 3310 via mechanical interlock. In another example, a flexible joint 3305 made from TPE may permanently connect to the rigidiser arm 3302 and the mask frame 3310. The flexible joint 3305 is overmolded with the mask frame 3310 for permanent connection and the flexible joint 3305 is permanently connected to the rigidiser arm 3302 via mechanical interlock. In another example, the flexible joint 3305 may be made from the same material as the rigidiser arm 3302, for example, Hytrel®, and is integral with the rigidiser arm 3302 and the flexible joint 3305 is permanently connected to the mask frame 3310 via mechanical interlock. The strap 3301 is removably connected with the rigidiser arm 3302 via a button-hole 3303, 3304.

The engagement of the strap 3301 to the rigidiser arm 3302 may occur in one location proximal to the mask frame 3310. This type of engagement allows for a maximum range of motion i.e. stretching of the strap 3301. This engagement is removable to enable the strap 3301 to be fully detachable from the rigidiser arm 3302 and in turn, the mask frame 3310 to facilitate washing of the strap 3301. The engagement functions as an anchor point for the strap 3301 such that when the strap 3301 is stretched, the stretching force is directed outwardly away from the anchor point. Turning to FIGS. 48 to 60, the end of the strap 3301 at the anchor point is retained by at least the distal edge of the rigidiser arm 3302 and/or a protruding end 3306 extending from the rigidiser arm 3302.

It will be appreciated by the skilled person that the rigidiser arm 3302 as referred to herein may be more rigid than the strap 3301 and allows the rigidiser arm to impart a shape to the strap 3301. The rigidiser arm 3302 may be more rigid in or around at least one axis and is inextensible in contrast to the strap 3301 which can be stretched along at least one axis. In another example, the rigidiser arm 3302 is extensible/stretchable in a direction substantially parallel to its longitudinal axis. Although elastomers typically can stretch, some thermoplastic polyester elastomers do not stretch but are flexible, for example, Hytrel® 5556 manufactured by DuPont®. For example, the rigidiser arm 3302 may have a scissor linkage structure or telescopic structure which enables the rigidiser arm 3302 to move between a compressed position to a fully elongated position. An extensible rigidiser arm 3302 may allow a better fit for patients 1000 who have longer faces so that the length of the rigidiser arm 3302 can be adjusted appropriately. Alternatively, the rigidiser arm 3302 may be referred to as a yoke and/or a stiffener. A yoke may be understood to be a rigid element adapted to support the straps 3301 of the positioning and stabilising structure 3300. A rigidiser arm 3302 may be understood to be a rigid element shaping the straps 3302 of the positioning and stabilising structure 3300 when worn on the face.

Alternative Rigidiser Arms

FIGS. 223 to 232 show an exemplary patient interface system 3000 discussed above. FIGS. 233a to 233h show such an exemplary patient interface system 3000 donned on a patient. FIGS. 240-244 show further views of an exemplary patient interface system without the straps 3301 to show features of the rigidiser arms 3302 included therewith. The patient interface system 3000 shown in these views may include rigidiser arms 3302 to ensure an effective seal by the seal-forming structure 3100 against the nose of the patient. It should be understood that the seal-forming structure 3100 described above in relation to FIGS. 223 to 239 may be included in the exemplary patient interface 3000 with the rigidiser arms 3302 shown in these drawings.

The rigidiser arms 3302 may be designed to minimize twisting and it may be stiffer than the rigidiser arms 3302 described elsewhere herein. The stiffer rigidiser arms 3302 may be advantageous to include with the seal-forming structure 3100 in the form of a nasal cradle cushion because the stiffer rigidiser arms may ensure an effective seal with this type of seal-forming structure. In the examples having nasal pillows as the seal-forming structure 3100, the nasal pillows may help to locate and retain themselves against the nares by extending into the nares. In the examples where the seal-forming structure 3100 is a nasal cradle cushion such a retention function may not as easily achieved. Thus, the rigidiser arms 3302 may be provided with the patient interface system 3000 having a nasal cradle cushion as a seal-forming structure 3100 to ensure that the seal-forming structure can maintain an effective seal against the patient's nose. According to an example of the present technology, the extensions 3370, 3371 may be configured to prevent movement of the rigidiser arms 3302 in a plane parallel to the patient's sagittal plane (see FIG. 2*f*) and/or the extensions may be configured to allow the rigidiser arms to flex in a plane parallel to the patient's Frankfort horizontal (see FIG. 2*e*). In other words, the rigidiser arms 3302 may flex outwardly and inwardly relative to the patient's face more easily to accommodate various face widths, compared to vertical movement relative to the mask frame 3310. In one example, the rigidiser arms 3302 may only be permitted to flex outwardly and inwardly relative to the patient's face and unable to or highly resistive to movement in any other direction in order to increase the stability of the patient interface 3000 especially when tube torque is experienced in the sagittal plane.

According to examples shown in FIGS. 240-244, the exemplary rigidiser arms 3302 may be connected to the mask frame 3310 by a mechanical interlock facilitated by overmolding the frame 3310 over a portion of extensions 3370, 3371. The rigidiser arms 3302 may also include a joint 3374 to connect the rigidiser arms 3302 with the extensions 3370, 3371. The rigidiser arms 3302 may be formed in one piece and of one material with the joints 3374 and the extensions 3370, 3371. The material selected for the rigidiser arms of these examples may be like the material used for rigidiser arms of other examples discussed elsewhere herein. Likewise, the frame 3310 may be formed of the same material used with other examples disclosed herein. Thus, the overmolded connection may be necessary to join the extensions 3370, 3371 to the frame 3310 because the respective materials may not be able to be bonded together. The respective materials of the rigidiser arms 3302 and the frame, as well as the overmolded connection, are described in greater detail below.

The extensions 3370, 3371 may, in the example using a nasal cradle cushion as the seal-forming structure 3100, be made wider in a vertical direction than the extensions 3350 used in examples having nasal pillows. The additional bulk of the larger extensions 3370, 3371 may provide the resistance to twisting, discussed above, that may be beneficial with the use of a nasal cradle cushion. This may be the case because in either example, the same material is used for the rigidiser arms 3302, however, more material is necessary in the nasal cradle cushion example to provide the desired increase in stiffness. According to an example of the present technology, the extensions 3370, 3371 may have a width substantially equal to a width of a main body 3333 of the rigidiser arms 3302 at the widest portion of the main body in a vertical direction to achieve the desired stiffness and resistance to twisting. According to another example of the present technology, the extensions 3370, 3371 may be wider than the main body 3333 of the rigidiser arms 3302 in a vertical direction to achieve the desired stiffness and resistance to twisting. Alternatively, the extensions 3370, 3371 may be formed with reinforcing ribs, the extensions may be formed with a geometric shape more resistant to twisting, and/or the rigidiser arms 3302 may be formed from stiffer material(s).

It should also be understood that the rigidiser arms 3302 of the examples using a nasal cradle cushion for the seal-forming structure 3100 may also be fitted with the straps 3315, 3316 in similar fashion to the examples using nasal pillows, as shown in FIGS. 223 to 233*h*. This arrangement is described in greater detail elsewhere herein.

The right-side extension 3370 shown in these drawings also includes indicia 3372 that may be raised from the extension to provide the patient with a visual and tactile reference for properly orienting the patient interface 3000 when donning the patient interface for therapy.

FIGS. 246*a*-*g* show several views of an exemplary patient interface 3000. These views show the patient interface 3000 without the straps 3301 of the positioning and stabilising structure 3300 and without the short tube 4180.

FIGS. 246*e*-*g* show views of the patient interface 3000 in which the protruding end support section 3208 is visible.

The rigidiser arms 3302 may also be used as a visual indicator for the patient as to the proper insertion depth of the nose into the seal-forming structure 3100. For example, length of the rigidiser arms 3302 could be an indication of the proper position of the patient interface 3000 relative to the ears such that the seal-forming structure is optimally located against the nose, thereby forming an effective seal.

Attachment of Straps and Rigidiser Arms

The side strap portions 3315, 3316 of strap 3301 shown in FIG. 65 each include two button-holes 3303, 3304. The button-holes 3303, 3304 may be located at the outer surface of strap 3301, i.e., the surface facing away from the patient 1000 when being worn, and are adapted to receive rigidiser arm 3302 in order to insert the rigidiser arm 3302 into the interior of the tube- or sleeve-like strap 3301 or to remove it therefrom. Alternatively, the button-holes 3303, 3304 may be located at the inner surface of the strap 3301. The button-holes 3303, 3304 may be oriented and/or shaped such that the rigidiser arm 3302 may be inserted and/or removed through such button-hole 3303 in order to assemble the positioning and stabilising structure 3300 while still preventing accidental removal or separation of the rigidiser arm 3302 from the strap 3301 during use. As shown in FIG. 65, this may be achieved by providing button-holes 3303 having a slit-like configuration, e.g., similar to button-holes, which may be oriented alongside or transversely to the strap 3301. Alternatively, the button-holes 3303 may be oriented across the strap 3301 if required. In other words, the elongate extension of the button-hole 3303, 3304 may extend substantially coaxial to the longitudinal axis of both strap 3301 and rigidiser arm 3302. This allows, particularly due to the elasticity of strap 3301, an easy insertion of the rigidiser arm 3302 into the tube- or sleeve-like strap or part of strap 3301 while, at the same time, preventing its accidental removal. An end portion of the strap 3301 between the distal tip of the strap 3301 and the button-hole 3303 wraps over the edge of the rigidiser arm 3302 and functions an anchor point. This edge of the rigidiser arm 3302 or anchor point may be a catching member. This end portion of the strap 3301 may also be referred to as the pocketed end 3311. This prevents the strap 3301 from slipping off the inserted rigidiser arm 3302 when the strap 3301 is stretched and adjusted while donning or doffing the patient interface 3000.

Referring to FIGS. 185 and 186, the rigidiser arm 3302 may be inserted into the first button-hole 3303 of the strap 3301. Said another way, the strap 3301 may be slipped over the rigidiser arm 3302 via the button-hole 3303. The distal free end 3302.1 of the rigidiser arm 3302 is first inserted into the strap 3301 via the button-hole 3303. The rigidiser arm 3302 is pushed further inside the strap 3301 until most or substantially the entire rigidiser arm 3302 is inserted into the strap 3301 such that the end portion of the strap 3301 can securely anchor to the edge of the rigidiser arm 3302. Some material of the strap 3301 near the button-hole 3303 is adjusted to sit beneath the outer side 3319 of the protrusion 3309 (see FIG. 38). Once inserted in the strap 3301, the rigidiser arm 3302 may be left floating generally unrestricted inside the strap 3301, as can be seen in FIGS. 6 to 8. Most importantly, the button-hole 3303 should be above the attachment point because the end portion of the strap 3301 is caught against the protruding end 3306 of the rigidiser arm 3302 to secure the strap 3301 to the rigidiser arm 3302 and also pulls against the protruding end 3306 when the strap 3301 is stretched. Typically, the position of the attachment point between the rigidiser arm 3302 and strap 3301 is more important than the type of attachment, for example, using a button-hole 3303, 3304 in the strap 3301. Referring to FIGS. 182 to 184, the type of attachment between the rigidiser arm 3302 and strap 3301 may facilitate easy removal of the strap 3301 from the rigidiser arm 3302 to enable separate washing of the strap 3301. In other words, the washing and cleaning regime for the strap 3301 may be at different times from the mask frame 3310. The patient 1000 slightly stretches the strap 3301 around the button-hole 3303 to unfasten the strap 3301 from the rigidiser arm 3302. After the distal end of the strap 3301 is unfastened, the strap 3301 may be pulled off completely from the rigidiser arm 3302 via the button-hole 3303.

In addition or alternatively, the rigidiser arm 3302 is affixed to the strap 3301. The affixing may be effected by attaching or affixing the second end of the rigidiser arm 3302, which after the insertion is near the button-hole 3303, to the strap 3301 of the positioning and stabilising structure 3300. The fixation may be localized, as discussed in the introductory portion of the description. Here, the connection between the rigidiser arm 3302 and the strap 3301 is not distributed along the length of the strap 3301, but is localized in the area adjacent to the button-hole 3303. Alternatively, such connection may be established in the area adjacent to the button-hole 3304. The affixing may be performed by way of sewing, welding, gluing, heat staking, clamping, buttoning, snapping a cover over the end or snapping on an external part by pushing the rigidiser arm 3302 inside the strap 3301 and fixing both the strap and the rigidiser arm 3302 to an external component, such as an external clip that holds both the strap and the respective end of the rigidiser arm 3302. The strap 3301 may alternatively be chemically bonded to the rigidiser arms 3302. The clip may also be used to attach the end of the strap 3301 to a respective end of a mask frame 3310. As such, the clip may be a part of the mask frame 3310 itself.

With the present technology, while the strap 3301 is arranged to take the shape of the rigidiser arm 3302, it is still able to stretch substantially along its entire length. Thus, the rigidiser arm 3302 imparts the required shape which directs the pressure of the positioning and stabilising structure 3300 to the required portions of the face, while the elastic positioning and stabilising structure 3300 maintains its entire operational length and is able to freely stretch over the rigidiser arm 3302. Additionally, the rigidiser arms 3302 may decouple tube torque in the coronal plane. Also, in particular, the sharp bend 3307 of the rigidiser arms 3302 may serve to handle and decouple any tube torque in the sagittal plane. At the same time, the strap 3301 of the positioning and stabilising structure 3300 may cover the rigidiser arm 3302 and provides a soft feel and enhanced comfort.

The sharp bend 3307 provides stability for the patient interface 3000. If the patient 1000 is sleeping on their side, the rigidiser arm 3302 against the side of the face on the bedding is pushed inwardly. The sharp bend 3307 decouples this movement in the coronal plane to prevent disruption of the seal force. The sharp bend 3307 has a tighter turn on its upper surface (facing away from the patient's face) compared to its lower surface (facing the patient's face). The lower surface of the sharp bend 3307 has a larger radius (washed out) than the upper surface of the sharp bend 3307 which smooths it out and avoids or minimises facial marking on the patient 1000 since the contact pressure is less concentrated if there is any contact on the patient's septum and/or upper lip (from nose droop caused by tube weight or tube torque). The distance between the two sharp bends 3307 is about 50 mm Although being shown and discussed with regard to the specific examples shown in FIGS. 65 to 70, it will be appreciated that strap 3301, or each of the strap side strap portions 3315, 3316 may be provided with one button-hole 3303, 3304 only. However, two or more button-holes may be provided. Alternatively or in addition, the strap 3301 may not be tube-like or sleeve-like but may have a flat single or laminate layer configuration. Here, the rigidiser arm 3302 may be positioned relative to the strap 3301 by the provision of retaining means including one or more loops, sleeve-like portions or pockets provided at the outer surface (e.g., the surface facing away from the patient in use) of strap 3301.

In addition or alternatively, combinations of the different connection mechanisms described herein may be provided. For example, rigidiser arm 3302 may be fixed to the strap 3301 at a single point or localized area, as discussed above, adjacent, e.g. pocketed ends 3311, 3313 of strap 3301 while being held next to strap 3301 by provision of a loop or sleeve-like element provided at the outer surface of strap 3301, e.g., in the area of the marks 3321b, 3323b. In other words, the rigidiser arm 3302 may be connected to the strap 3301 by fixing it at one localized point or area only, while functioning as an additional guiding element to strap 3301. Such guiding element functionality may be provided by a loop- or sheath-like portion or passage or a pocket of the strap 3301 into which or through which rigidiser arm 3302 extends based on the shape of the strap 3301 shown in FIG. 66. The strap 3301 may be tubular, but not necessarily cylindrical. This allows the longest stretch path possible for the strap 3301. Alternatively, the rigidiser arm 3302 may be disposed unattached into one or more pockets (e.g., a single open-ended pocket of sheath of appreciable length supporting the rigidiser arm somewhere in the middle, or a pair of pockets, each supporting a respective end of the rigidiser arm), or a plurality of loops distributed along the length of the strap 3301. Such guiding element functionality, whether attached at one end or not, allows substantially free movement or floating of the rigidiser arm 3302 relative to the strap 3301. Such configuration would allow the same advantages and benefits as the configuration discussed above. Additionally, according to an example of the technology, the rigidiser arms 3302 do not stretch or flex in the same direction as the strap 3301. Rather, the rigidiser arm 3302 may stretch or flex in a plane substantially perpendicular to its longitudinal axis.

In the shown and discussed examples, rigidiser arm 3302 does not extend beyond the end(s) of strap 3301. However, according to alternative aspects, the rigidiser arm 3302 may be, e.g., fixed to strap 3301 at a point or area adjacent to the respective pocketed ends 3311, 3313 while extending beyond strap 3301. In such a configuration, rigidiser arm 3302 may impart a shape, geometry, and/or rigidity to the strap 3301 and at the same time, provide structural means such, as a flexible joint 3305, for connecting with a patient interface 3000. This allows rigidiser arm 3302 to function both as rigidiser arm 3302 as well as a connector for connecting the strap 3301 and the positioning and stabilising structure 3300, respectively, to the frame 3310, plenum chamber 3200, or seal-forming structure 3100.

FIGS. 113 to 122 shows detailed views of the connection between the pocketed ends 3311, 3313 and the rigidiser arms 3302. FIGS. 113 and 114 show the pocketed ends 3311, 3313 around respective protruding ends 3306 of the rigidiser arms 3302. The protruding ends 3306 are not visible in these views because they are covered by the pocketed ends 3311, 3313. A straight section 3351 on an extension 3350 (discussed further below) of the rigidiser arm 3302 is shown with indicia 3358 on an outer surface 3355 of the extension 3350. The indicia 3358 may be pad printed, a raised surface or an embossment to help the patient 1000 orient the device 3000 during use when in a darkened environment. The straight section 3351 of the extension 3350 may be seen extending outwardly from the button-hole 3303 of the respective pocketed end 3311, 3313. The straight section 3351 is a part of the rigidiser arm 3302, as shown in FIGS. 47 to 60, and the rigidiser arm 3302 facilitates the connection between the strap 3301 and the mask frame 3310. FIG. 114 shows a similar view to FIG. 113, however the outer surface 3355 of the straight section 3351 is without indicia. It should be understood that FIG. 113 depicts the connection between one rigidiser arm 3302 and the respective pocketed end 3311 while FIG. 114 depicts the connection between another rigidiser arm 3302 and the other respective pocketed end 3313. By placing indicia 3358 on only one outer surface 3355, the patient 1000 can use the sense of touch to determine the orientation of the device 3000 to aid in fitting in a darkened environment. FIG. 114 also shows a flange 3359 that is visible through the button-hole 3303.

FIG. 115 shows similar features to FIG. 114 but is a more detailed view to better show the relationship between the flange 3359 and the pocketed end 3313. FIG. 116 also shows similar features to FIG. 113 but is a more detailed view to better show the indicia 3358 and the button-hole 3303 in the pocketed end 3313.

FIG. 117 shows a further detailed view of FIG. 114 to better illustrate the button-hole 3303 at the pocketed end 3313. FIG. 118 shows a further detailed view of FIG. 113 to better illustrate the button-hole 3303 at the pocketed end 3313.

FIGS. 119 to 122 show similar features to those shown in FIGS. 113 to 118, however in these views the flange 3359 is pulled from the button-hole 3303 to better show its design. FIGS. 119 and 122 show the rigidiser arm 3302 that includes the indicia 3358 on the outer surface 3355 extending from the button-hole 3303 of the pocketed end 3311. FIG. 122 should be understood to show a more detailed view of FIG. 119. FIGS. 120 and 121 show the other rigidiser arm 3302 that may not include the indicia. FIG. 121 should be understood to show a more detailed view of FIG. 120.

FIGS. 262A and 262B show another example of the present technology where the strap 3301 includes an elastic tube 3301.1 to attach the strap to the rigidiser arm 3302. According to this example, the strap 3301 may include the elastic tube 3301.1 fixed to an end of the strap. FIG. 262A shows the strap 3301 and elastic tube 3301.1 detached from the rigidiser arm 3302 and a portion of the rigidiser arm is not shown for the sake of simplicity. To attach the strap 3301 to the rigidiser arm 3302, the patient slides the elastic tube 3301.1 along the length of the rigidiser arm until it reaches a raised stop 3302.6 on the rigidiser arm. Although not shown in FIGS. 262A and 262B, it should be understood that the length of the rigidiser arm 3302, up to the point of the raised stop 3302.6, is taken up inside of the strap 3301. The raised stop 3302.6 prevents the patient from pushing the strap 3301 too far along the length of the rigidiser arm 3302 and may ensure that the strap is attached to the rigidiser arm at a desired position such that the strap retains the intended stretchable length. The shape, size, and material of the elastic tube 3301.1 may be chosen such that when the elastic tube reaches the raised stop 3302.6 a sufficient retention force due to friction is produced between the elastic tube and the rigidiser arm 3302. In other words, the force of friction between the elastic tube 3301.1 and the rigidiser arm 3302 should be sufficiently high so that when the patient dons the patient interface 3000, the force of tension in the strap 3301 is less than the force of friction retaining the elastic tube on the rigidiser arm, thereby preventing the elastic tube from being pulled off of the rigidiser arm. The elastic tube 3301.1 may be made from a material that has a relatively high coefficient of static friction with the material of the rigidiser arm 3302 to ensure that the strap 3301 will be retained on the rigidiser arm. Also, the material of the elastic tube 3301.1 should be stretchable so that it can deform as it is slid down the rigidiser arm 3302 to the raised stop 3302.6.

FIG. 263 shows another example of the present technology where the rigidiser arm 3302 may be formed with a tab 3470 to retain the strap 3301 on the rigidiser arm with a hook and loop connection. The tab 3470 may be fixed to and/or formed integrally with the rigidiser arm 3302 and the tab may include hook material 3471. Accordingly, at least a portion of the outer surface of the strap 3301 may be formed from a loop material, at least on a portion of its outer surface, to engage with the tab 3470 in a hook and loop connection. To attach the strap 3301 to the rigidiser arm 3302, the patient may slide the strap along the length of the rigidiser arm and lift the tab 3470 to slide the strap thereunder and release the tab so that the loop material portion of the strap engages with the hook material 3471 on the strap. The size of the tab 3470 should be chosen so that a sufficient area of hook material 3471 engages the strap 3301 to produce a retention force that is sufficiently high to resist the tension force of the strap when donned by the patient. In this example, the entire strap 3301 may be manufactured to have loop material on its outer surface to save cost in manufacturing the strap. Accordingly, in such an example the loop material should be sufficiently soft so as to avoid irritation of the patient's skin. Also, it should be understood that the tab 3470 may include loop material rather than hook material, in which case the strap 3301 may have a portion of hook material to attach to the loop material of the tab. Additionally, it should be understood that the tab 3470 may be formed from an elastic material so that it may be pulled away from the rigidiser arm 3302 to attach the strap 3301 and then engage the strap when released with sufficient force to maintain the hook and loop connection.

FIGS. 264A and 264B show another example of the present technology where the strap 3301 may include locks 3301.2 to engage with notches 3302.2 on the rigidiser arm 3302. According to this example of the present technology, the locks 3301.2 may be positioned at the end of the strap 3301 and the strap may include elastic material at this end to urge the locks 3301.2 into engagement with the corresponding notches 3302.2 of the rigidiser arm 3302. The strap 3301 should be sufficiently elastic at its ends in this example to ensure that the locks 3301.2 are held in the corresponding notches 3302.2 of the rigidiser arm 3302 with sufficient force to resist the force of tension of the strap when the patient interface 3000 is donned by the patient. FIGS. 264A and 264B show examples of the present technology with one notch 3302.2 on the top edge of the rigidiser arm 3302 and one notch on the bottom edge of the rigidiser arm along with corresponding locks 3301.2 on the strap 3301, however, it should be understood that any number and/or position of corresponding locks and notches may be used so long as a sufficient force of retention is maintained.

FIG. 265 shows an example of the present technology where the strap 3301 includes a length of loop material 3301.3 and a piece of hook material 3301.4 at or near the end 3301.5 of the strap. The rigidiser arm 3302 according to this example of the present technology includes a first slot 3302.7 and a second slot 3302.8. To attach the strap 3301 to the rigidiser arm 3302, the strap is first threaded through the first slot 3302.7 and then looped back through the second slot 3302.8. To fix the strap 3301 to the rigidiser arm 3302, the hook material 3301.4 at the end 3301.5 of the strap is joined with the loop material 3301.3. This example of the present technology may allow for some adjustability in the stretchable length of the strap 3301 based on where the hook material 3301.4 is attached to the loop material 3301.3. Also, it should be understood that the location of the hook material 3301.4 and the loop material 3301.3 may be interchangeable.

The examples shown in FIGS. 262A to 265 include a strap 3301 that may be detached from the rigidiser arms 3302 and flipped such that either side of the strap may be used to contact the patient. This may be advantageous in that the strap 3301 may not be completely spent when the surface of one side of the strap is worn down. Rather, the patient may simply flip the strap 3301 such that the useful life of the strap may be increased.

Also, in any of the above examples where the strap 3301 of the positioning and stabilising structure 3300 is detachable, the detachable nature of the strap may be advantageous for the total lifecycle of the patient interface 3000. For example, the strap 3301 may have a shorter useful life than the frame 3310 and short tube 4180 assembly such that expiration of the strap does not necessitate replacement of the entire patient interface 3000. In other words, the strap 3301 can replaced once expired and a new strap can be used with the remainder of the patient interface 3000 that has not expired.

Permanent Attachment Alternative

FIGS. 266 to 270 show alternative examples of the present technology where the strap 3301 may be permanently attached to the rigidiser arms 3302, i.e., the strap cannot be removed from the rigidiser arms by the patient. Permanently attaching the strap 3301 to the rigidiser arms 3302 may be advantageous in that it is unnecessary for the patient to thread the strap onto the rigidiser arms and it is also not possible for the strap to come undone from the rigidiser arms.

FIG. 266 shows an example of the present technology where the strap 3301 is permanently fixed to the rigidiser arm 3302 at attachment points 3304. According to this example, the attachment points 3304 may be formed by ultrasonic welding of the strap 3301 to the rigidiser arm 3302. While two attachment points 3304 are shown on the surface of the rigidiser arm 3302 that faces away from the patient in use, it should be understood that the number, size, shape, and/or location of the attachment point(s) 3304 may be varied so long as the desired stretchable length of the strap 3301 relative to the rigidiser arm 3302 is maintained.

FIG. 267 shows an example of the present technology that is similar to the example shown in FIG. 266. However, the example shown in FIG. 267 includes attachment points 3304 formed by heat staking rather than ultrasonic welding. Also, it should be understood that the size, shape, number, and/or location of the attachment point(s) 3304 may be varied so long as the desired stretchable length of the strap 3301 relative to the rigidiser arm 3302 is maintained.

FIG. 268 shows a further example of the present technology that is similar to the example shown in FIG. 266. However, the example shown in FIG. 268 includes attachment points 3304 formed by stitching. Also, it should be understood that the size, shape, number, and/or location of the attachment point(s) 3304 may be varied so long as the desired stretchable length of the strap 3301 relative to the rigidiser arm 3302 is maintained.

FIG. 269 shows another example of the present technology where the attachment point 3304 is fixed to the rigidiser arm 3302 in a hinged arrangement and permanently fixes the strap 3301 to the rigidiser arm. For example, the attachment point 3304 may pierce the fabric of the strap 3301 to form a permanent attachment.

FIG. 270 shows another example of the present technology where the permanent attachment of the strap 3301 to the rigidiser arm 3302 uses barbs at the attachment point 3304. The barbs of the attachment point 3304 may be formed integrally with the rigidiser arm 3302 and may be oriented such that when the strap 3301 is first slid onto the rigidiser arm, the relatively soft fabric of the strap is gripped and permanently attached by the barbs. In other words, the barbs of the attachment point 3304 may be oriented to point in the opposite direction of the force of tension of the strap 3301 when the patient interface 3000 is donned by the patient.

Stretching of Straps Relative to Rigidiser Arms

As can be seen in the example shown in FIG. 68, two rigidiser arms 3302 are inserted into side strap portions 3315, 3316 of the strap 3301 of the positioning and stabilising structure 3300, the rigidiser arm 3302 is held in place by the surrounding strap 3301 while at the same time the sleeve-like configuration of strap 3301 allows at least a portion of the strap 3301 to stretch or move relative to the rigidiser arm 3302. Preferably, this stretchable portion is a substantial portion because only at the anchor point is the strap 3301 secured to the rigidiser arm 3302. In some examples, a limitation on the movement of the rigidiser arm 3302 is generally imposed when one of the ends 3319a or 3319b of the rigidiser arm 3302 moves towards and abuts against a respective pocketed end 3311 of the strap 3301, as in FIG. 69. For example, when the positioning and stabilising structure 3300 is not on the patient's head and the straps 3301 are loose, when the inserted rigidiser arm 3302 moves too far towards the back strap portions 3317a, 3317b, its end 3319b may enter the open end of one of these back strap portions 3317a, 3317b. As the width of the back strap portions 3317a, 3317b is smaller than that of the rigidiser arm 3302, the end 3319b of the rigidiser arm 3302 abuts against the respective back strap portion 3317a, 3317b, which restricts its further movement in this direction.

The attachment of the strap 3301 to the rigidiser arm 3302 described in the preceding section may also affect the size of head that the positioning and stabilising structure 3300 may accommodate. In other words, by providing a greater length of strap 3301 along the rigidiser arm 3302 it may be possible to increase the total stretchable length of the positioning and stabilising structure 3300 such that even larger circumference heads may be accommodated without needing to increase the stretchability of the strap 3301. Furthermore, it may be possible to vary, along the length of the rigidiser arm 3302, where the strap 3301 is connected. This would allow for an even greater range of head sizes and circumferences to be accommodated without the need to alter the stretchability of the strap 3301.

The length of the strap 3301 is from about 400 mm to 700 mm. The length of the strap 3301 may be about 490 mm. The strap 3301 may provide a comfortable level of headgear tension for most head sizes. There may be two lengths or sizes of straps which are gender specific, the one for the male population being longer than the female version. Preferably, there may be two sizes/lengths of the strap 3301 for each gender. A comfortable level of headgear tension is from about 2 to about 5 Newtons. A comfortable level of headgear tension is from about 2.2 Newtons to about 4.7 Newtons. When the strap 3301 is stretched from 490 mm to 526 mm for a small circumference head of a patient 1000, the headgear tension as measured using an Instron machine is 2 Newtons. When the strap 3301 is stretched from 490 mm to 662 mm for a large circumference head of a patient, the headgear tension as measured using an Instron machine is 4.4 Newtons. For the measurement, the button-holes 3303, 3304 of the strap 3301 are attached onto clamping fixtures. A tensile testing machine with a 100 Newtons load cell is used. The strap 3301 is extended and held at predetermined extension points (e.g. 90.5 mm, 73 mm and 108 mm) for one minute, and the force value (in Newtons) is recorded for each extension point. Such measurement does not consider any friction of the material of the strap 3301 against the patient's face or hair.

The length of a split region 3326 defined between the two back strap portions 3317a, 3317b is from about 180 mm to about 220 mm. The length of the split region 3326 may be 200 mm. If the length of the split region 3326 is not long enough, the two back strap portions 3317a, 3317b will be unable to cup the back of the patient's head and therefore unable to maintain their position during therapy and the headgear tension will not remain set to the patient's preference. If the length of the split region 3326 is too long, the two back strap portions 3317a, 3317b will separate in front of the user's ears and be uncomfortable as they pass over the ears rather than above/around it and also it reduces the maximum angle range for the two back strap portions 3317a, 3317b with respect to each other.

In the neutral and unstretched condition of the strap 3301, the two back strap portions 3317a, 3317b have an angle θ from each other at about 0° to about 10°. After donning the patient interface 3000, the two back strap portions 3317a, 3317b may be split from each other such that the angle θ may be up to about 180°. This allows a maximum angular range of 180° which in turn gives a large range for the reduction of headgear tension through incrementally spreading apart the two back strap portion 3317a, 3317b. The angular range may be narrowed to a default angle of 10° to a maximum angle of 120°. The patient may use one or both hands to move the two back strap portion 3317a, 3317b now under tension on the back of their head, apart or together. By moving the two back strap portion 3317a, 3317b further apart from each other, the split region 3326 enlarges, leading to a reduction in headgear tension from the unsplit range of 2.5 to 5 Newtons. The headgear tension may be reduced from about 30% to about 50% according to one example, or to about 40% in another example, as measured by a load cell. In other words, for a small circumference head of a patient, the headgear tension may be reduced from 2 Newtons to 1.2 Newtons by enlarging the separation between the two back strap portions 3317a, 3317b. For a large circumference head of a patient, the headgear tension may be reduced from 4.4 Newtons to 2.64 Newtons by enlarging the separation between the two back strap portions 3317a, 3317b.

The rigidiser arm 3302 may thus be allowed to move generally unrestrictedly along the length of the strap 3301, attached to the strap 3301, or may be adjacent one of its ends.

The discussed configurations allow, as shown in FIG. 70, the strap 3301, and thus, the positioning and stabilising structure 3300 to stretch and expand in length. Such elongation is not limited to those portions of the strap 3301 that are not in contact with or parallel to the rigidiser arm 3302 but also, elongation, particularly elastic elongation of the strap 3301, is achieved in the area of rigidiser arm 3302. This can easily be derived from comparison of the length of the rigidiser arm 3302 in FIGS. 68 and 70 (which remains the same although the strap 3301 is stretched) with marks 3321a-d, 3323a-e visualizing the length of the strap 3301 with regard to the length of the rigidiser arm 3302. It is easily derivable by comparison of FIGS. 68 and 70 that the rigidiser arms 3302 extend along marks 3321a to 3321c and 3323a to 3323d, respectively in FIG. 68 in the un-stretched state. Contrary thereto, in the stretched state according to FIG. 70, rigidiser arms 3302 extend along marks 3321a to 3321b and 3323a to 3323c, only. Therefrom, it becomes clear that strap 3301 is stretched also in and along the area where rigidiser arms 3302 are contained in strap 3301. The rigidiser arms 3302 remain un-stretched however during stretching of the strap 3301.

As will be appreciated, positioning and stabilising structure 3300 may comprise one or more rigidiser arms 3302. While the above discussion concentrates on the relationship of a rigidiser arm 3302 with a strap 3301, it is to be noted that the example shown in FIGS. 68 to 70 comprises two rigidiser arms 3302, one being provided in each respective side strap portion 3315, 3316 of strap 3301. The above comments, although eventually referring to one rigidiser arm 3302, thus equally apply to two or more rigidiser arms 3302 connected to a mask frame 3310.

One possibly advantageous attribute of allowing the strap 3301 to stretch relative to the rigidiser arm 3302 as heretofore described may be that the patient interface 3000, along with the positioning and stabilising structure 3300, may be donned and doffed by the patient 1000 without the need to disconnect any straps or other connection features. This may be helpful to a patient 1000 that is using the device 3000 in a dark bedroom prior to or following sleep, in that the patient does not need to be able to see to connect or disconnect various components to attach or remove the patient interface 3000. Rather, the patient 1000 may only need to simply pull on or off the patient interface 3000 and positioning and stabilising structure 3300, and in the case of donning it may also be necessary to position the seal-forming structure 3100. However, this may all be accomplished by feel, sight being unnecessary.

It may however remain advantageous to allow disconnection of the plenum chamber 3200 or seal-forming structure 3100 from the positioning and stabilising structure 3300. For example, to clean the plenum chamber 3200 or seal-forming structure 3100 it may be desirable to wash it while not getting the positioning and stabilising structure 3300 wet. This may be facilitated by allowing these components to disconnect for such a purpose.

Rigidiser Arms and Mask Frame

FIGS. 47 to 60 show rigidiser arms 3302 and a mask frame 3310 according to a further example of the present technology.

FIGS. 47 to 49 and 54 show cross-sectional views of a rigidiser arm 3302 and a mask frame 3310 and the connection therebetween, according to an example of the present technology. Near a sharp bend 3307 of the rigidiser arm 3302 an extension 3350 is connected by a joint 3356. Also near the sharp bend 3307 is a protruding end 3306 of the rigidiser arm 3302 that may retain a pocketed end of a side strap portion 3316 of the positioning and stabilising structure 3300. In these views the mask frame 3310 can be seen formed around a hook 3353 and an enclosable section 3354 of the extension 3350. An opening 3335 may also be formed in the mask frame 3310 near where the mask frame 3310 surrounds the enclosable section 3354. The opening 3335 may be formed as a result of the overmolding process by which the mask frame 3310 is formed and secured around the enclosable section 3354 of the rigidiser arm 3302. The rigidiser arm 3302 according to this example may be formed from Hytrel® and the mask frame 3310 may be formed from polypropylene (PP). Hytrel® is desirable for forming the rigidiser arms 3302 because this material is resistant to creep. Since these materials cannot be integrally bonded the mask frame 3310 may be overmolded to the rigidiser arm 3302 in this example to form a secure connection. It should also be noted that in this example the extension 3350 and the rigidiser arm 3302 may be molded as one piece. The mask frame 3310 may be connected to the rigidiser arms 3302 at respective extensions 3350 located opposite distal free ends 3302.1. The extension 3350 may comprise a straight section 3351 joined to a bend 3352 joined to a hook 3353. The hook 3353 and a portion of the bend 3352 may form the enclosable section 3354.

It should be understood that the joint 3356 that connects extension 3350 to the rigidiser arm 3302 may provide a targeted point of flexibility and the joint may be shaped and formed to allow flexing in a desired direction and degree. Thus, once the patient interface 3000 is donned and the rigidiser arms 3302 are stressed by tension from straps of the positioning and stabilising structure 3300 the rigidiser arms 3302 may flex at the joints 3356 to allow them to retain a face framing shape while helping to retain the mask frame 3310 in a desired position relative to the patient's face.

FIGS. 50 and 51 show perspective and detailed perspective views, respectively, of rigidiser arms 3302 connected to a mask frame 3310, according to an example of the present technology. FIG. 51 further shows the enclosable section 3354 in dashed lines and overmolded by the mask frame 3310 to secure the mask frame to the end of the rigidiser arm 3302. The opening 3335 can be seen, as in FIGS. 47 to 49, forming a passage completely through the mask frame 3310 and the hook 3353 of the rigidiser arm 3302.

FIGS. 52 and 53 show top and detailed top views, respectively, of a mask frame 3310 connected to rigidiser arms 3302, according to an example of the present technology. In FIG. 52 the dimension L indicates the length of the rigidiser arm 3302 in the direction shown. Preferably, the nominal length L of a rigidiser arm 3302 is 114 mm. These views show particularly well how the joint 3356 may connect the extension 3350 to the rigidiser arm 3302 between the protruding end 3306 and the sharp bend 3307.

FIGS. 55 to 57 show side, front, and perspective views, respectively, of rigidiser arms 3302 and a mask frame 3310, according to an example of the present technology. In FIG. 55, the dimension H indicates the height of the rigidiser arm 3302 in the direction shown. Preferably, the nominal height H of a rigidiser arm 3302 is 33 mm. The rigidiser arm 3302 and the extension 3350 may be formed as one piece and then connected to the mask frame 3310 by overmolding the mask frame 3310 to the enclosable section 3354 of the extension 3350 of the rigidiser arm 3302. The extension 3350 accommodates nose droop by bending in a pivoting manner or vertical rotates relative to the rigidiser arm 3302. Since the extension 3350 has a smaller height, has less material than the remainder of the rigidiser arm 3302 and is decoupled from the remainder of the rigidiser arm 3302 by the sharp bend 3307, bending of the extension 3350 is localised and occurs before the remainder of the rigidiser arm 3302 starts to bend. This reduces the likelihood of disruption of sealing forces.

FIGS. 58 and 59 show partially exploded and detailed partially exploded views, respectively, of rigidiser arms 3302 and a mask frame 3310, according to an example of the present technology. The hook 3353 and the enclosable section 3354 of the extension 3350 can be seen separated from the mask frame 3310. The shape of the hook 3353 and the enclosable section 3354 may be seen in these views and it should be understood that these portions are formed to ensure a stronger mechanical interlock with the mask frame 3310 when the mask frame 3310 is overmolded. Specifically, these views show that the enclosable section 3354 may be formed with flared ends at the hook 3353 to provide surfaces for retention to the mask frame 3310. In another example of the technology, the enclosable section 3354 may include an opening for restraining the rigidiser arm 3302 within the mold tool(s) during overmolding of the mask frame 3310. A mold tool may be inserted through this opening to stabilize the rigidiser arm 3302 as the mask frame 3310 is overmolded around the rigidiser. This may be advantageous because the pressures of overmolding may cause the rigidiser arm 3302 to shift during the molding process such that a less than ideal mechanical interlock with the mask frame 3310 would be formed.

FIG. 60 shows a perspective view of a rigidiser arm 3302 according to an example of the present technology. It shows the rigidiser arm 3302 prior to permanent connection with the mask frame 3310. As discussed immediately above, the rigidiser arm 3302 may include a hook 3353 and an enclosable section 3354 to allow for connection to the mask frame 3310 via mechanical interlock. This permanently connects the rigidiser arm 3302 to the frame 3310. By having the rigidiser arm 3302 and the frame 3310 permanently connected together, it means that there are less detachable parts and reduced likelihood of losing a part during assembly/disassembly of the patient interface 3000 when cleaning.

Increasing Stability Between the Frame and Rigidiser Arms

According to certain examples of the present technology, it may be desirable to join the frame 3310 and the rigidiser arms 3302 in a manner than enhances the stability of the patient interface 3000.

FIG. 260A shows an example of the present technology wherein the rigidiser arm 3302 is molded to the frame 3310. The frame 3310 and the rigidiser arm 3302 may be formed in one piece. This example does not include the extension 3350 provided in other examples to provide the desired amount of flexural strength at the juncture between the frame 3310 and the rigidiser arm 3302. Rather, extension arms 3302.3 are molded to join the rigidiser arm 3302 to the frame 3310. As part of the molding process, a void 3302.4 may be formed between the extension arms 3302.3 to remove unnecessary material. It should be understood that by spreading the upper and lower extension arms 3302.3 apart further, the moment of inertia where the extension arms join to the frame may be increased about the axis X-X shown in FIG. 260A. The formula for the moment of inertia of this joint about X-X may be simplified to $$I = \frac{bh^3}{12}.$$

Thus, an increase in h, i.e., the space between the upper and lower extension arms 3302.1, would yield a significant increase in the moment of inertia, I, about X-X relative to increasing b, i.e., the thickness of the extension arms. Moreover, by optimizing the geometry of the rigidiser arm the rigidiser arms 3302 and/or the extension arms 3302.1 may be made thinner.

FIG. 260B shows another example of the present technology where the rigidiser arm 3302 may be joined to the frame 3310 by rods 3302.5. The rods 3302.5 may be metal or another similar material having comparable stiffness. Additionally, the rigidiser arms 3302 of this example may be formed from a relatively rigid material such as Nylon.

FIG. 261A shows another example of the present technology wherein it may be desirable to increase the stability of the rigidiser arms 3302 and extensions 3350. A pair of rigidiser arm ribs 3460 may be provided to the rigidiser arm 3302 at the sharp bend 3307 to increase rigidity. A pair of extension ribs 3461 may be provided at the bend 3352 of the extension to increase rigidity. The sharp bend 3307 and the bend 3352 may be susceptible to undesirable deflection when the patient interface 3000 is donned by the patient. Thus, these ribs may prevent excessive bending of the rigidiser arm 3302 and/or the extension 3350.

FIG. 261B shows another example of the present technology where it may be desirable to increase the stability of the extension 3350. In this example, a longitudinal rib 3462 is provided along a portion of the extension 3350 in a longitudinal direction. The longitudinal rib 3462 may extend through the bend 3352 to the straight section 3351. The longitudinal rib 3462 may increase the rigidity of the extension 3350 to prevent excessive bending.

Positioning and Stabilising Structure on a Patient

FIGS. 71 to 73 show an example of the present technology. Here, the positioning and stabilising structure 3300 comprises a strap 3301 with side strap portions 3315, 3316 and a back strap portion 3317 comprising two back strap portions 3317a, 3317b running in parallel along the back of a patient's head. The positioning and stabilising structure 3300 comprises two rigidiser arms (not shown), each contained in a respective side strap portion 3315, 3316 of the sleeve- or tube-like strap 3301. Rigidiser arms 3302 impart a predetermined shape or desired shape and/or rigidity to the strap 3301, and thus, the positioning and stabilising structure 3300. For example, the side strap portions 3315, 3316 of the strap 3301 have a certain curvature for following a desired contour around a patient's face (see curvature at reference numeral 3323 in FIGS. 52, 54, 58, and 60), which is achieved by the provision of respectively shaped rigidiser arm 3302. In the example shown, the positioning and stabilising structure 3300 is connected to the frame 3310, plenum chamber 3200 or seal-forming structure 3100 for providing breathable gas such as air, eventually pressurized breathable gas, to a patient's airways. In the shown example, such breathable gas is provided via the hose or tube 4180 connected to patient interface 3000. The tube 4180 may be connected at its other end (not shown) to a source of breathable gas, such as a blower or ventilator for providing pressurized breathable gas. The patient interface 3000 may comprise a frame portion or frame 3310 for imparting structural integrity to the patient interface 3000 and/or for connecting to the positioning and stabilising structure 3300. The positioning and stabilising structure 3300 may be connected to the frame 3310, plenum chamber 3200 or seal-forming structure 3100 via a separate connector means (not shown) provided on strap 3301 and/or rigidiser arm 3302.

FIGS. 74 to 77 show similar features to those shown in FIGS. 71 to 73, however the examples shown in FIGS. 74 to 76 and 77 depict a different connection between the positioning and stabilising structure 3300 and the mask frame 3310. At each end of the side strap portions 3315, 3316 there is a pocketed end 3311, 3313 as shown in FIGS. 65 and 81. These pocketed ends 3311, 3313 are retained on the rigidiser arms 3302 (not visible in these views because they are within the side strap portions 3315, 3316) by the protruding end 3306 of respective rigidiser arms shown, for example, in FIGS. 47 to 60. Although not visible in FIGS. 74 to 77, it should be understood that, in this example, end welds 3311.1, 3313 depicted in FIG. 81 serve to close the pocketed ends 3311, 3313 so that they may be retained against the protruding ends 3306. The rigidiser arms 3302 are then permanently and mechanically secured to the mask frame 3310 by overmolding, for example, as described with reference to FIGS. 47 to 60.

Attachment of Rigidiser Arms to Patient Interface

According to further examples of the present technology, the rigidiser arms 3302 may be detachable. By making the rigidiser arms detachable from the patient interface 3000 the rigidiser arms 3302 may be subject to less distortion during transport and storage. When the rigidiser arms 3302 are detachable, the patient interface 3000 may be packed more compactly and in a manner that adequately supports each individual component. Also, by making the rigidiser arms 3302 separable it is possible to separate them for cleaning. It should be understood that in some examples the extensions 3350 may be detached from the frame 3310. In other examples the rigidiser arms 3302 may be detached from the extensions 3350, in which case the extensions may be permanently attached to the frame 3310. A further advantage of detachable rigidiser arms 3302 may be that the attachment mechanism can be designed to produce an audible click that is a reassuring indication to the patient that the components have been effectively secured. Such an audible click may be facilitated by a hard-to-hard connection between the rigidiser arms 3302 and the frame 3310, for example. A hard-to-hard connection may be beneficial for patients that struggle with fine motor skills because it may allow them to more easily assembly the patient interface 3000 and be confident that they have done so. Also, detachable rigidiser arms 3302 may be beneficial for the patient in that he or she may customize the patient interface 3000 because of the interchangeability of parts. For example, the patient interface 3000 may be sold with a number of rigidiser arm 3302 sets that have different curve profiles, shapes, lengths, and/or stiffnesses, from which the patient may choose the most suitable set based on facial geometry and comfort. This in turn may provide a better fit and greater comfort, which may improve patient compliance. Also, the rigidiser arm 3302 sets may be provided in different colors such that the patient is provided with a variety of options aesthetically.

FIGS. 248A and 248B show an example of a rigidiser arm 3302 detached from and attached to a patient interface 3000 at the extension 3350. On the protruding end 3306 of the rigidiser arm 3302, a projection 3380 may be provided with locking wings 3381 and supported by a shaft (not shown). On the straight section 3351 of the extension 3350, an opening 3382 with notches 3383 may be provided. Stops 3384 may also be provided on the straight section 3351 of the extension 3350. The opening 3382 and notches 3383 may be sized and shaped correspondingly to the projection 3380 and the wings 3381. To assemble the rigidiser arm 3302 to the extension 3350, the projection 3380 and the wings 3381 are extended through the corresponding opening 3382 and notches 3383 and then rotated until the wings abut against their respective stops 3384. Accordingly, the length of the shaft should be sized to be slightly larger than the width of the straight section 3351 of the extension 3350 to minimize play between the rigidiser arm 3302 and the extension 3350 once attached. It should be understood that the rigidiser arm 3302 may be secured by rotation in only one direction. This may be accomplished by positioning the stops 3384 on respective sides of the opening 3382 so that, as shown for example in FIG. 248B, the rigidiser arm 3302 is secured by clockwise rotation. Also, it should be understood that to prevent misassembly of the rigidiser arms 3302, i.e., where the right side rigidiser arm may be attached to the left side extension and vice versa, the corresponding projection-wing and opening-notch sets may be differently sized. Thus, the patient would only be able to securely attach the right side rigidiser arm 3302 to the right side extension 3350 and the left side rigidiser arm to the left side extension.

FIGS. 249A and 249B show another example of the present technology where the rigidiser arms 3302 may be detachable. In this example, the extension 3350 may be provided with a pair of pins 3385 extending therefrom. The pins 3385 may each comprise a head on a shaft, the shaft being fixed to the extension 3350. The head of each pin 3385 may be larger in diameter than the shaft of each pin to allow for attachment to sockets 3386 formed in the protruding end 3306 of the rigidiser arm 3302. The sockets 3386 may include slits to allow for deflection of the material of the protruding end 3306 so that the heads of the pins 3385 can pass through the respective sockets. Accordingly, the length of the shafts of the pins 3385 should be sized to be slightly larger than the width of the protruding end 3306 to minimize play once the rigidiser arm 3302 is attached. Also, the pins 3385 and corresponding sockets 3386 may be spaced or sized differently to prevent misassembly of the rigidiser arms 3302. For example, the spacing and/or positioning of the pins 3385 and corresponding sockets 3386 of the right side rigidiser arm 3302 and extension 3350 may be different from the left side so that the patient cannot attach the left side rigidiser arm to the right side extension and vice versa. In another example, the pins 3385 and sockets 3386 of the left side rigidiser arm 3302 and extension 3350 may be sized differently from the pins and sockets of the right side rigidiser arm and extension so that the patient cannot attach the left side rigidiser arm to the right side extension and vice versa.

FIGS. 250A to 250C show another example of a rigidiser arm 3302 that is detachable according to the present technology. In this example, the rigidiser arm 3302 includes a projection 3393 with an arm 3394 to secure the rigidiser arm to the extension 3350. The arm 3394 and the projection 3393 may extend from a shaft 3395 on the rigidiser arm 3302 and the arm, the projection, and the shaft may be formed in one piece with the rigidiser arm 3302. Accordingly, the extension 3350 is provided with a slot 3392 through which the arm 3394 and the projection 3393 are passed during attachment. The extension 3350 is also formed with a shaft receiver 3390 and an arm receiver 3391 to respectively receive the shaft 3395 and the arm 3394. To attach the rigidiser arm 3302 to the extension 3350, the shaft 3395, the projection 3393, and the arm 3394 are passed through the slot 3392 and the shaft and the projection are pulled into engagement with the shaft receiver 3390 and the arm receiver 3391, respectively. The arm receiver 3391 may be narrower than the shaft 3395 and the arm 3394 to ensure that when the arm is engaged in the arm receiver a secure friction-fit results. To detach the rigidiser arm 3302 from the extension 3350, the patient would slide the rigidiser arm 3302 in the opposite direction of attachment. It should also be understood that the diameter of the projection 3393 may be greater than the diameter of shaft receiver 3390 to prevent disassembly. To prevent misassembly, the arm 3394 and the projection 3393 of the right side rigidiser arm 3302 may be sized and/or shaped to only fit in the arm receiver 3391 and shaft receiver 3390 of the right side extension 3350 and the arm and the projection of the left side rigidiser arm may be sized and/or shaped to only fit in the arm receiver and shaft receiver of the left side extension.

FIGS. 251A and 251B show another example of a rigidiser arm 3302 that may be detachable. According to this example, the extension 3350 may be formed in one piece with the rigidiser arm 3302. The extension 3350 may include a flared end 3387 that attaches to a receiver 3388 on the frame 3310. The flared end 3387 may be slid into a slot 3389 in the receiver 3388 to attach the extension 3350 and the rigidiser arm 3302 and the engagement may comprise a press-fit. The receiver 3388 may be a separate component from the frame 3310 that is attached thereto, or the receiver may be formed integrally with the frame. The right side flared end 3387 and slot 3389 may be sized and/or shaped differently from the left side flared end and slot to prevent misassembly.

FIGS. 252A to 252C show another example of a rigidiser arm 3302 that may be detachable. According to this example, the extension 3350 may be formed in one piece with the rigidiser arm 3302. The extension 3350 may be formed to provide a snap-fit engagement with a receiver 3310.1. The receiver 3310.1 may be a separate component from the frame 3310 that is attached thereto, or the receiver may be formed integrally with the frame. The receiver 3310.1 may include a pocket 3310.2 and a recess 3310.3 to receive the extension 3350 for attachment of the rigidiser arm 3302. The extension 3350 includes a bend 3396 that facilitates the snap-fit engagement. The extension 3350 may be made from an elastic material and sized such that when the extension is placed into the receiver 3310.1, the extension is compressed by reduction of the angle of the bend 3396. This compression of the extension 3350 forces a protrusion 3397 into the recess 3310.3 when the bend 3396 is forced into the pocket 3310.2. A tab 3398 may also be provided to facilitate disengagement. The patient may press the tab 3398 and compress the bend 3396 further to release the protrusion 3397 from the recess 3310.3 to detach the rigidiser arm 3302. Also, the right side extension 3350 and the corresponding receiver 3310.1 may be sized and/or shaped differently from the left side extension and corresponding receiver to prevent misassembly.

FIGS. 253A to 253C show another example of a rigidiser arm 3302 that may be detachable. According to this example, the extension 3350 may be formed in one piece with the rigidiser arm 3302. The extension 3350 may be formed to provide a snap-fit engagement with a receiver 3310.1. In this example, the extension 3350 may be held by the receiver 3310.1 with a friction fit. The receiver 3310.1 may be a separate component from the frame 3310 that is attached thereto, or the receiver may be formed integrally with the frame. In this example, a column 3399 may be provided near an end 3350.1 of the extension 3350. To attach the extension 3350, the column 3399 is inserted into the pocket 3310.2 of the receiver 3310.1. The column 3399 may be circular in cross-sectional profile to engage with complementarily shaped indentations 3310.4 of the pocket 3310.2. Cross-sectional profiles of the column 3399 other than circular are envisioned as well, such as square, rectangular, triangular, oval, etc. As these respective surfaces may be curved in this example, an end receiver 3310.5 may also be provided in the pocket 3310.2 to receive the end 3350.1 of the extension 3350. The engagement of the end 3350.1 of the extension 3350 with the end receiver 3310.5 may prevent undesirable rotation of the extension 3350 and the rigidiser arm 3302 about the longitudinal axis of the column 3399. Accordingly, this may ensure that the only motion of the rigidiser arm 3302 is due to deflection resulting from the deformable nature of the rigidiser arm 3302 and the extension 3350, and not because of play in the engagement between the extension and the receiver 3310.1. Accordingly, the right side extension 3350 and corresponding receiver 3310.1 may be sized and/or shaped differently from the left side extension and receiver to prevent misassembly.

FIGS. 254A and 254B show another example of a rigidiser arm 3302 that may be detachable. This example may not include an extension 3350 formed with the rigidiser arm 3302. Rather, the rigidiser arm 3302 may be formed with a first bend 3340, a first straight section 3341, a second bend 3342, a second straight section 3343, and a locking end 3344 formed at the end of the second straight section 3343. At each side of the frame 3310, a slot 3345 may be provided through which each rigidiser arm 3302 may be threaded for attachment to the frame. Each slot 3345 may be sized and shaped to allow the respective rigidiser arm 3302 to pass therethrough but each slot may also be smaller than the respective locking end 3344 to prevent the rigidiser arms from being pulled through. To prevent misassembly, the right side rigidiser arm 3302 and corresponding slot 3345 may be shaped and/or sized differently from the left side rigidiser arm and slot. It should also be understood that the portions of the rigidiser arm 3302 referred to above as the first straight section 3341 and the second straight section 3343 need not be straight and these sections may instead be curved as necessary to provide the desired shape/profile. Additionally, the rigidiser arm 3302 may have other curves and/or bends as desired, so long as the rigidiser arm can be threaded through the slot.

FIGS. 255A and 255B show another example of a rigidiser arm 3302 that may be detachable. According to this example, the extension 3350 may be formed in one piece with the rigidiser arm 3302. This example includes a pin 3385 with a head supported on the extension 3350 by a shaft. The head of the pin 3385 may be larger in diameter than the shaft. A socket 3386 may be formed integrally on each side of the frame 3310 for a snap-fit engagement with the respective pin 3385. To prevent misassembly, the pin 3385 of the right side rigidiser arm 3302 and the corresponding socket 3386 may be sized and/or shaped differently from the pin and socket of the left side.

FIGS. 256A to 256C show another example of a rigidiser arm 3302 that may be detachable. According to this example, the extension 3350 may be formed in one piece with the rigidiser arm 3302. A receiver 3410 and a first magnet 3412 may be provided to the frame 3310. A second magnet 3413 may be provided to the extension 3350 to secure the rigidiser arm 3302 to the frame 3310. Accordingly, the respective poles of the first magnet 3412 and the second magnet 3413 may be oriented so that the first magnet and the second magnet are attracted to one another. A post 3411 may also be provided to extension 3350 proximal to the second magnet 3413 to engage with the receiver 3410 and ensure that the extension is properly positioned in the receiver. It should also be understood that the right side post 3411 and receiver 3410 may be shaped and/or sized differently from the left side post and receiver to prevent misassembly. To prevent misassembly, the poles of the right side first magnet 3412 and second magnet 3413 may be oriented opposite to the poles of the left side first magnet and second magnet such that magnetic attraction only occurs when the respective right and left side magnets are engaged and should the patient try to place the left side rigidiser arm 3302 into the right side receiver 3410, or vice versa, magnetic repulsion will prevent engagement.

FIGS. 257A and 257B another example of a rigidiser arm 3302 that may be detachable. The frame 3310 may include a first L-shaped section 3420 on each side and a second L-shaped section 3423 may be formed on each rigidiser arm 3302. To attach the frame 3310 to the rigidiser arm 3302, the first L-shaped section 3420 is brought into engagement with the second L-shaped section 3423 by moving the L-shaped sections toward one another in opposite vertical directions. The first L-shaped section 3420 and the second L-shaped section 3423 are then rotated against one another and secured in position. A second overlapping portion 3424 may engage with a first recessed portion 3421 and a first overlapping portion 3422 may engage with a second recessed portion 3425. A peg 3426 may be provided to the first recessed portion 3421 and the second recessed portion 3425. To secure the first L-shaped section 3420 and the second L-shaped section 3423, each peg 3426 may engage with a hole 3427 provided to the first overlapping portion 3422 and the second overlapping portion 3424. The holes 3427 in these examples are shown in dashed lines to indicate that they do not extend completely through the first overlapping portion 3422 and the second overlapping portion 3424, but it should be understood that according to an alternative example that the holes could extend the completely through. It should also be understood that the engagement between the respective pegs 3426 and holes 3427 may include a press- or friction-fit to ensure a secure connection. In a further alternative example, the pegs 3426 may comprise a barb at the end of a shaft and each corresponding hole 3427 may extend completely through the first overlapping portion 3422 and the second overlapping portion 3424 such that when engaged the barb of each peg locks into the respective hole. Also, it should be understood that the pegs 3426 could be provided to the first overlapping portion 3422 and the second overlapping portion 3424 and the holes 3427 could be provided to the first recessed portion 3421 and the second recessed portion 3425 in an alternative example.

FIGS. 258A and 258B show another example of a rigidiser arm 3302 that may be detachable. According to this example, the extension 3350 may be formed in one piece with the rigidiser arm 3302. A boss 3430 may be formed on each side of the frame 3310 and a cavity 3431 may be formed at the end of each extension 3350 to receive the boss. The boss 3430 and cavity 3431 may be shaped and sized to form a secure friction-fit. It should also be understood that the boss 3430 may be formed on the extension 3350 and the cavity 3431 may be provided on the frame 3310 in an alternative example. Additionally, to prevent misassembly the boss 3430 and the cavity 3431 of the right side may be shaped and/or sized differently from the boss and the cavity of the left side.

FIGS. 259A to 259C show another example of a rigidiser arm 3302 that may be detachable. A post 3452 and a pair of slots 3453 may be provided to the extension 3350. The rigidiser arm 3302 may be provided with a hole 3451 to receive the post 3452 and a pair of prongs 3450 may be provided to the rigidiser arm 3302 to engage with respective slots 3453. To attach the rigidiser arm 3302 to the extension 3350, the prongs 3450 are first passed through corresponding slots 3453 on the extension and then the post 3452 engages with the hole 3451 to prevent separation of the rigidiser arm from the extension. The bent shape of the prongs 3450 may help secure them when passed through the openings 3453. Also, the post 3452 may include a head enlarged relative to a shaft of the post to ensure that the post securely engages with the hole 3451. It should be understood that in other examples that the post 3452 and the slots 3453 need not be provided to the extension 3350 and the hole 3451 and the prongs 3450 need not be provided to the rigidiser arm 3302, so long as the complementary components are positioned such that the prongs engage the slots and the post engages the hole. Also, more than one post 3452 and more than one hole 3451 may be provided so long as a complementary number is provided. Additionally, more or less than two corresponding prongs 3450 and slots 3453 may also be provided so long as a complementary number is provided. Furthermore, it should be understood that to prevent misassembly the number of prongs 3450 and slots 3453 and the number of posts 3452 and holes 3451 may be different as between the left and right side extensions 3350 and rigidiser arms 3302. Alternatively, the size and/or shape of the prongs 3450 and slots 3453 and the posts 3452 and holes 3451 may be varied as between the left and right side extensions 3350 and rigidiser arms 3302 to prevent misassembly.

Split Back Straps of Positioning and Stabilising Structure

According to one aspect, the structure of strap 3301 and positioning and stabilising structure 3300 is of advantage. In particular, the provision of two elastic straps or back strap portions 3317a, 3317b at the back allows the head to be cupped and the tension vector(s) to be adjusted by suitably positioning them, e.g. by spreading. The provision of two back strap portions 3317a, 3317b also allows better support and stability, as well as increased flexibility in avoiding specifically sensitive regions of the back of the head. The back strap portions 3317a, 3317b are intended to cup the head at the calvaria to maintain position and engagement. In one example, depending on the particular head shape of a patient and the amount of splitting of the back strap portions 3317a, 3317b, the upper back strap portion 3317a is to be located proximal to the parietal bone and the lower back strap portion 3317b is to be located proximal to the occipital bone or superior fibers of the trapezius muscle (i.e. near the nape of the neck or nucha). The lower back strap portion 3317b may be configured to engage the head of the patient at a position on or lower than the external occipital protuberance. In contrast to headgear of prior masks which require material length adjustment (shortening or lengthening), the tension provided by the positioning and stabilising structure 3300 is adjustable simply by opening or closing the relative angle between the two back strap portions 3317a, 3317b. To reduce headgear tension, the two back strap portions 3317a, 3317b are separated further apart on the back of the head when the patient interface 3000 is worn. To increase headgear tension, the two back strap portions 3317a, 3317b are brought closer together. This manner of adjustment is advantageous over notched straps which only permit preset incremental adjustment of headgear tension, Velcro™ (unbroken loop fabric) straps which require several attempts at fastening and unfastening until the desired headgear tension is obtained, or looping a strap through a buckle that is easier to increase than decrease headgear tension because of the motion of pulling the strap through the buckle for tightening. Also, patients 1000 are afraid to get the headgear tension wrong or to change the headgear tension.

The two smaller straps or back strap portions 3317a, 3317b at the back of the head may be equal in length and not adjustable except through the elasticity of the material or through increasing both in tightness equally by shortening the total length at the side strap portions 3315, 3316 of the positioning and stabilising structure 3300. For example, a sliding mechanism (not shown) may be provided that allows the straps 3301 to be overlapped to a different extent, thus changing the overall length of the positioning and stabilising structure 3300. Non-independently adjustable strap lengths allow the two back strap portions 3317a, 3317b to naturally center themselves on the crown of the head. The two back strap portions 3317a, 3317b may be symmetrical or asymmetrical. In other words, the upper back strap portion 3317a may naturally settle at the top of the head, while the lower back strap portion 3317b may naturally settle at the back of the head near or below the occipital lobe. This may reduce the possibility of manually over tightening one strap to compensate for the other being too loose resulting in a misfit of the positioning and stabilising structure 3300. This, again, might not only lead to discomfort but also negatively influence therapy compliance. The aggregated width of both back strap portions 3317a, 3317b may be substantially equal to the width of a side strap portion 3315. This is aesthetically pleasing as well as providing a visual indicator to the patient to adjust the back strap portions 3317a, 3317b when donning the patient interface 3000. Although two back strap portions 3317a, 3317b have been described, more are possible which may provide differing degrees of adjustment of headgear tension. When the strap 3301 is in the neutral state and unstretched, the two back strap portions 3317a, 3317b are partially separated such that a gap exists between them for inviting or indicating to the patient to adjust the back strap portions 3317a, 3317b when donning the patient interface 3000. This improves the intuitiveness for adjusting headgear tension, and visually indicates how the headgear tension may be adjusted that is sometimes lacking in prior masks.

As indicated above, two or more joints could be provided creating the positioning and stabilising structure 3300 from three, four or more separate straps rather than the strap 3301 being one continuous piece. This might complicate the assembly, but may simplify the manufacturing process. Joints may be placed at the bifurcation point 3324 between the side strap portions 3315, 3316 and two back strap portions 3317a, 3317b or centered at the back. The joints may be sewn, welded, glued, or over molded and could incorporate a high friction material to help reduce movement on the head. High friction materials may include pad printing, silicone printing to increase relative surface friction between the straps 3301, 3317a, 3317b and the patient's skin or hair in order to maintain position of the straps 3301, 3317a, 3317b on the patient's head. The high friction materials may be present only on the patient contacting surface of the back strap portions 3317a, 3317b since the rigidiser arms 3302 may perform some or most of the function of maintaining position of the side strap portions 3315, 3316 relative to the patient's face.

High friction materials may also be added to the inside surface of the back and side strap portions 3315, 3316, 3317a, 3317b, to reduce the straps from slipping against the patient's face or hair. For the arms or side strap portions 3315, 3316 this would help the positioning and stabilising structure 3300 stay on the cheeks and at the back strap portion 3317 it could stop the positioning and stabilising structure 3300 from sliding across the back of the head. Such material may be printed, cast or molded onto the surface or incorporated into joints, sewing or welding processes as mentioned above. Another way to reduce strap slippage is to have elastic yarns protruding from the textile material.

Instead of being inserted from the button-holes 3303, 3304 located close to the mask frame 3310, as shown in FIG. 65, the rigidiser arm 3302 could optionally be inserted from an opening 3308 located proximal to the bifurcation point 3324 where the positioning and stabilising structure 3300 bifurcates. Once the rigidiser arm 3302 is inserted, the elasticity of the material could be used to hook back the rigidiser arm 3302 inside the opening of one of the small back strap portions 3317a, 3317b (upper or lower). This may prevent the rigidiser arm 3302 from moving, thus securing it in place. Otherwise the button-holes 3303, 3304 could be sewn, molded or otherwise closed permanently in order to trap the rigidiser arm 3302 inside the strap 3301.

The split region 3326 at the back may include two, three or more straps for stability. A positioning and stabilising structure 3300 similar to the described, may be used with full face (covering the nose and mouth) or nasal masks also. Other positioning and stabilising structures of prior masks that may have two or more straps at the back (which may be the same width as the side straps) where the lower back strap typically engages against the head of the patient at a position on or lower than the external occipital protuberance. Such back straps are not stretchable or elastic, but may be length adjustable, and the back straps may be biased to return to a default angle to avoid crinkling and twisting at the convergence point with a single side strap. For example, the default angle may be 45° for the split between two back straps in order to cup and engage the patient's head, and the pivoting of the back straps relative to each other are for donning and doffing the patient interface to fix the patient interface into a position to provide tension to a seal-forming structure against the patient's face. The two back straps are biased to return to the 45° angle and therefore only serve the function of cupping the back of the patient's head for stability of the patient interface and cannot maintain any angle that deviates from the 45° angle.

With the use of the present technology, the provision and use of rigidiser arms 3302 may affect the stretchable length of the strap 3301. This may allow the positioning and stabilising structure 3300 to fit a large range of head sizes. This may effectively be a "one size fits most" positioning and stabilising structure 3300, which means that the out of the bag positioning and stabilising structure 3300 is more likely to fit a patient even if the patient has not previously tried or used the positioning and stabilising structure 3300. The present technology may provide a positioning and stabilising structure 3300 that allows easy donning and doffing of the patient interface 3000. In particular, this may mean that, unlike some other positioning and stabilising structures, the tension settings do not have to change and/or are not lost when the mask 3000 is doffed. The rigidiser arms 3302 may define a desired shape that ensures that there is clearance around the eyes and ears for comfort and visibility. The textile of the strap 3301 may allow the skin to breathe and sweat naturally without silicone, foam or plastics creating and retaining surface heat and condensate from perspiration.

The provision of two elastic straps 3317a, 3317b at the back of the strap 3301 may allow the patient's head to be cupped and the distribution of the applied force to be adjusted by spreading them and independently changing their position. The two smaller back strap portions 3317a, 3317b at the back of the head may be equal in length and not adjustable except through the elasticity of the material or through increasing both in tightness equally by shortening the total length at the straps of the positioning and stabilising structure 3300.

Flexible Joint 3305

FIGS. 19, 71 to 73, 75, 76 and 166 also show the connection of the positioning and stabilising structure 3300 to the frame 3310 associated with the plenum chamber 3200. Particularly, the joint 3305 at the rigidiser arm 3302 and the frame 3310 may be flexible and/or elastically deformable. Thus, when donned by the patient 1000, the seal-forming structure 3100 may be able to accommodate a variety of nasolabial angles (e.g., as shown in FIG. 2e). It should be understood, therefore, that the flexibility of this joint 3305 may allow the frame 3310, plenum chamber 3200, and other associated components to move about a number of axes relative to the rigidiser arms 3302. In one form of the present technology, the frame 3310 and the plenum chamber 3200 may be rotatable via the flexible joint 3305 about an axis defined between respective ends of the rigidiser arms 3302. By such an arrangement, the seal-forming structure 3100 may be able to be angled against the inferior region of the patient's 1000 nose over a wide range of possible nasolabial angles.

As can be seen in FIGS. 18, 19, 75, 76 and 166, the seal-forming structure 3100 is retained against the underside of the nose of the patient 1000, one example, against the patient's airways such as the nares. Proper location of the seal forming structure 3100 is a significant factor in achieving an effective seal of the frusto-cone 3140 against the patient's nares such that the leaking of pressurized gas is minimized with minimal retention forces. As the frusto-cone 3140 may extend axially from the stalk 3150 of the seal forming structure 3100, it may be advantageous to allow a degree of flexibility in the orientation of the patient interface 3000 with respect to the patient's nose to achieve an optimal seal. Such flexibility may be advantageous because patients may have a variety of nasolabial angles (see FIG. 2e) that may need to be accommodated by a common patient interface. This flexibility may be accomplished in an exemplary patient interface 3000 by providing a flexible joint 3305. In an example of the present technology, the flexible joint 3305 may be positioned between the frame 3310 and the rigidiser arm 3302. In such an exemplary arrangement, the frame 3310 may be comprised of a material that facilitates flexing at the flexible joint 3305 with rigidiser arm 3302 of the positioning and stabilising structure 3300. In an alternative arrangement, it may be the rigidiser arm 3302 that may flex via the extension 3350 to allow proper location of the seal-forming structure 3100 against the underside of the patient's nose. Additionally, it is also envisioned that flexing may occur partially at both parts. In any of the envisioned arrangements the desired result is that the patient interface 3000 may be able to rotate with respect to the underside of the patient's nose such that various nasolabial angles may be accommodated. This flexibility provided by the flexible joint 3305 allows the trampoline 3131 to be more effective in providing a comfortable force against the patient's nares or nose. Without the flexible joint 3305, the trampoline 3131 would be less effective at accommodating a variety of alar angles and maintaining stability since the stalks 3150 and plenum chamber 3200 would already be in a partially or fully collapsed state when the tension from the positioning and stabilising structure 3300 holds the seal-forming structure 3100 in sealing position against the patient's airways.

This flexible joint 3305 may be provided by forming the frame 3310 and/or the rigidiser arms 3302 from a material having a modulus of elasticity sufficient to allow flexibility in the joint 3305, while maintaining sufficient stiffness to ensure an effective seal. Additionally or alternatively, the frame 3310 and/or the rigidiser arms 3302 may be shaped structurally to allow for flexibility in this region. In other words, the frame 3310 and/or the rigidiser arms 3302 may be shaped to allow the requisite amount of flexibility in the region of the joint 3305. This may be accomplished by removing portions of these structures such that their stiffness is reduced to allow flexing.

A further possible advantage of this aspect of the technology may be that it reduces the bending moment associated with the rigidiser arms 3302 and the frame 3310. As shown in FIGS. 19, 71 to 73 and 75, the rigidiser arms 3302 may be shaped to conform to the contours of the patient's face. Also, when the seal-forming structure 3100 engages with the patient's nares, they may cause displacement of the frame 3310 due to the relatively limited amount of flexibility between the seal-forming structure 3100, the plenum chamber 3200, and the frame 3310, which are held against the nose by the positioning and stabilising structure 3300. By providing a flexible joint 3305 between the frame 3310 and the rigidiser arms 3302, the bending moment associated with these structures when the patient interface 3000 is donned by the patient may be reduced because some of the associated forces may be dissipated into the flexing of the joint. This may be advantageous because the patient interface 3000 would then be subjected to less force during use to reduce wear and tear. Also, by dissipating these forces into the bending of the flexible joint 3305, bending of the rigidiser arms 3302 and/or the frame 3310 may be reduced. This may be advantageous because if the rigidiser arms 3302 are shaped to conform to the face of the patient, then bending them may reduce the conformity, resulting in discomfort to the patient. The same may be true for bending of the frame 3310 and bending of the frame 3310 may also cause the seal-forming structure 3100 to be displaced from the patient's nose.

It should also be understood that in the arrangement discussed above, it may be advantageous to stiffen the rigidiser arms 3302. By forming the rigidiser arms 3302 from a material that is sufficiently stiff and/or shaping the rigidiser arms 3302 such that they are sufficiently stiff, it may be possible to ensure that the flexible joint 3305 does not allow the seal-forming structure 3100 to displace from the patient's nose. In other words, a proper fit and effective seal may be accomplished by sufficiently stiff rigidiser arms 3302 that maintain the desired degree of conformity to the patient's face while allowing sufficient displacement of the seal-forming structure 3100 such that it can engage the patient's nose and provide an effective seal. The rigidiser arms 3302 may be formed from Hytrel® with a flexural modulus of 180 MPa at 23° C. and a tensile modulus of 180 MPa (26). It should also be understood that in one aspect of the technology, the patient interface 3000 may be structured such that elastic deformation takes place only at the seal-forming structure 3100 and at the flexible joint 3305 between the frame 3310 and the rigidiser arms 3302.

In the example of the present technology described without a flexible joint 3305, the extension 3350 of the rigidiser arm 3302 performs a similar function to the flexible joint 3305 as described above.

Tension Vectors of Positioning and Stabilising Structure

As mentioned above, the exemplary positioning and stabilising structure 3300 may advantageously locate the headgear tension vectors with respect to the patient's head such that the compression vectors associated with the seal-forming structure 3100 are properly aligned with the nose or nares of the patient. As shown in FIGS. 72, 73, 75 and 76, a vector V is depicted to indicate an exemplary direction and magnitude of a force that urges the seal-forming structure 3100 against the nose of the patient 1000 in use. By attaching the exemplary positioning and stabilising structure 3300 operatively to the seal-forming structure 3100, the tension of the positioning and stabilising structure 3300 when worn by the patient 1000 may be sufficient to urge the patient interface 3000 against the nose or nares of the patient 1000 with a force having the direction and magnitude of the vector V. The concept of the vectors may be explained as follows. To properly and/or effectively form a seal about the nares of the patient 1000, when using nasal pillows 3130 as depicted in this example of the technology, the seal-forming structure 3100 should be urged against the patient's nares in a direction substantially coaxial to the longitudinal axes of respective stalks 3150 of the seal-forming structure 3100. The magnitude of the force must also be sufficient to allow the seal-forming structure 3100 to seal around the nares, but not so great as to cause discomfort or deformation of the relatively soft seal-forming structure 3100. Therefore, a force of the magnitude and direction depicted as the vector V must be provided to the seal-forming structure 3100. However, it is not ideal to have straps 3301 draped across the eyes and along the sides of the patient's nose or across the ears. This may be uncomfortable and disruptive to the patient 1000. Two point force and vector control allows the strap 3301 to gently stabilise the mask 3000 and pull the nasal pillows 3130 into place and form a pneumatic seal with the patient's airways.

To overcome this problem of needing to provide sealing forces of a requisite direction and magnitude while displacing them from certain regions of the patient's face, the rigidiser arms 3302 and/or frame 3310 described above may be provided. The rigidiser arms 3302 and/or frame 3310 may act as an intermediary for transferring tension forces from the positioning and stabilising structure 3300 to the seal-forming structure 3100, while allowing the straps 3301 to be directed away from the patient's eyes. In other words, the positioning and stabilising structure 3300, by virtue of being in tension, may generate a force at one end of a respective rigidiser arm 3302 and/or frame 3310, which being sufficiently stiff, transmits this force having an equivalent direction and magnitude to its opposite end where the seal-forming structure 3100 is located. Thus, the seal-forming structure 3100 may be urged against the patient's nose to form an effective seal. Said another way, the rigidiser arms 3302 and/or the frame 3310 serve to structurally decouple the positioning and stabilising structure 3300 from the seal-forming structure 3100 while continuing to maintain sealing forces of an adequate direction and magnitude.

As described above, the straps 3301 of the positioning and stabilising structure 3300 may surround the rigidiser arms 3302 in certain examples. To facilitate the force decoupling described in the preceding paragraphs while maintaining this sheath-like arrangement of the straps 3301 and rigidiser arms 3302, the rigidiser arms 3302 may comprise a smooth surface along at least a portion thereof. By providing a smooth surface along the rigidiser arms 3302, the straps 3301 of the positioning and stabilising structure 3300 may extend and/or compress along the rigidiser arms 3302 in a relatively free and/or low friction fashion. In other words, the straps 3301 float over the rigidiser arms 3302 except at the pocketed ends 3311 where it is secured to the rigidiser arms 3302. Moreover, by reducing friction of the positioning and stabilising structure 3300 along the rigidiser arms 3302, extraneous and undesired forces may be avoided, which may in turn result in a loss or disruption of the pneumatic seal of the seal-forming structure 3100 and/or an uncomfortable fit.

Some positioning and stabilising structures of prior masks that have a multi-layered laminated strap where there are layers made from different materials providing different degrees of flexibility permanently laminated to each other. Other positioning and stabilising structures of prior masks use stitching or adhesives to permanently connect the multi-layered strap together. In contrast, the positioning and stabilising structure 3300 of the present technology has a strap 3301 that is releasably engageable with the rigidiser arm 3302. This permits separate washing of the strap 3301 from the rigidiser arm 3302 and frame 3310. The releasable engagement is provided in a small area localised region (the edge of the rigidiser arm 3302 proximal to the frame 3310) using a pocketed end 3311 of the strap 3301 which permits stretch of substantially the entire length of the strap 3301 from the point of connection with the frame 3310. Other positioning and stabilising structures of prior masks may use an adjustment buckle or Velcro™ to adjust the length of one or more headgear straps (usually by shortening the length) in order to adjust the headgear tension of the patient interface 3000 on the patient's face. In contrast, the positioning and stabilising structure 3300 of the present technology does not require length adjustment to adjust the headgear tension and is particularly beneficial for patients with arthritic hands who may lack fine motor skill to be able to properly an adjustment buckle or Velcro™ for headgear tension adjustment, especially in a darkened room.

Manufacturing the Strap

A positioning and stabilising structure 3300 is manufactured to shape (e.g., formed in one piece to shape otherwise known as "fully-fashioning" without the need to cut away any substantial amounts of material) thereby producing little or no waste material. Alternatively, the positioning and stabilising structure 3300 may be divided into segments that are each manufactured to shape separately (e.g., by knitting) and then attached to one another. FIG. 132 demonstrates a single, unitary seamless structure having at least two regions (e.g. the crown portion or rear portion 210 and straps 220), wherein the at least two regions extend from a junction (the junction being the connection between the straps 220 and the rear portion 210), where the straps 220 extend at a different angular orientation to the rear portion 210. The rear portion 210 and straps 220 are formed in a continuous process (i.e. the material that makes up the component and the shape of the component are formed in a single step)—this is different to a process where a sheet of material is made and then cut to shape (this would not be considered a single step). FIG. 132 also shows that the straps 220 branch out or extend at a different angle or direction to the rear portion 210, without requiring seams or additional formation steps.

A knitted component such as a positioning and stabilising structure 3300 is defined as being formed of "unitary knit construction" when constructed as a one-piece knit element that is substantially free of additional stitching or bonding processes.

As shown in FIG. 133, the straps 220 may be formed (e.g., by warp knitting, circular knitting or 3D braiding) as a continuous piece that is subsequently cut as this procedure may further increase manufacturing efficiency.

Knitting various positioning and stabilising structure sections in a continuous manner may be advantageous as there are no or very few additional manufacturing steps that would be required to sew, fuse, adhere or otherwise attach adjoining sections. As a result, the manufacturing process may have reduced steps, the amount of material waste is reduced, there would be virtually no seams in the positioning and stabilising structure 3300 between the adjoining sections, and the positioning and stabilising structure 3300 made of a fabric without distinctive joins or seams may be more comfortable for patients.

Techniques

A number of techniques can be used in accordance with the present technology to manufacture a positioning and stabilising structure 3300 to shape with little or no waste material. The technique may produce a positioning and stabilising structure that is a single, unitary, seamless structure. Techniques that may produce a single unitary seamless structure include mechanical manipulation of yarn including interlooping (such as knitting), interweaving and/or intertwining (including braiding, knotting and crocheting). An alternative technique of 3D printing may also create a positioning and stabilising structure having a unitary, seamless structure.

A manufacturing technique in accordance with the present technology may have one or more of the following features: (1) produces little or no waste; (2) produces a positioning and stabilising structure that is comfortable for the patient; (3) produces a positioning and stabilising structure that is conformable; (4) produces a positioning and stabilising structure that is breathable; (5) produces a positioning and stabilising structure that may minimize facial marking; and/or 6) produces a positioning and stabilising structure that is lightweight.

Interlooping—Knitting

In accordance with an example of the present technology, a positioning and stabilising structure 3300 may be formed by interlooping such as knitting (e.g., threading yarn or thread to form a knitted fabric). The positioning and stabilising structure 3300 may be formed by flat knitting or circular knitting, however other forms of knitting may also be possible. Flat knitting and circular knitting may be advantageous as they are able to create a positioning and stabilising structure 3300 with a unitary, seamless structure. Flat or circular knitting machines may be utilized to create a weft knit or a warp knit. A variety of knitting processes including circular knitting and warp- or weft-flat knitting, may be utilized to manufacture the positioning and stabilising structure component or components. Flat knitting may have some advantages, including but not limited to (1) the ability to locate floating yarns within, for example, a positioning and stabilising structure strap, in order to provide extra cushioning or bulk, and/or (2) the ability to include extra loops of yarns on either the upper or lower surface of the positioning and stabilising structure strap, thus creating the effect of a soft terry cloth material, for example, or creating an unbroken loop fabric for engagement with a hook tape fastener, and/or (3) the ability to knit a 3D dimensional spacer fabric construction adjacent to double-faced knit construction within a single unified positioning and stabilising structure construction.

The positioning and stabilising structure 3300 may be formed primarily from multiple yarns that are mechanically manipulated through an interlooping process to produce a single unitary structure having various sections with different physical properties.

FIG. 134 illustrates the wale of a weft knit fabric 64, or the direction that the loops of one thread join to a loop of another thread. The course 85, or the direction of the loops from a single thread is shown in FIG. 135. FIGS. 136 and 137 illustrate a basic closed loop warp knit 90. FIG. 138 illustrates an example of a warp knit tricot jersey fabric structure in which a yarn is knitted in a vertical direction in a zig-zag manner, capturing other warp yarns, with the wale running somewhat parallel to the course.

Referring to FIGS. 136 to 139, a warp knit 90, 90-1 comprises the wales and courses running parallel to one another, while in a weft knit 100 the wales run perpendicular to the course. The positioning and stabilising structure 3300 of the present technology may be formed by either warp knit or weft knit. A warp knit, for example tricot, raschel or locknit, is typically more resistant to runs, easy to machine, and may utilize multiple yarns (allowing for the use of multiple colors or yarn types). A weft knit 100 can be formed with a single yarn; however, use of multiple yarns is also possible. The positioning and stabilising structure 3300 of the present technology may be constructed of a warp knit or a weft knit.

Knitted fabrics may have different stretchability characteristics compared to woven fabrics. Knitted fabrics are typically more flexible than woven fabrics, which may only stretch in one direction (depending on the yarn they are made from), and therefore may provide a more comfortable fit for the patient. Knitted textiles may be constructed in such a way that the fabric has a two-way stretch—i.e. a first yarn oriented in a first direction has a lower flexibility than a yarn oriented in a second direction. This arrangement may be desirable along the straps of the positioning and stabilising structure 3300 such that the straps can stretch along their length but not across their width, or vice versa. Alternatively, the knitted textile may have a four-way stretch i.e. yarn in a first direction and a second direction and both are flexible such that application to a strap would allow stretch in both lengthwise and crosswise directions.

The example of FIG. 142 shows a strap 1200 having a grain or course 1250, and illustrates how the direction of the grain or course affects stretch. The knitted fabric will tend to stretch more readily in the direction of the course. Therefore, the positioning and stabilising structure 3300 may be designed to stretch in certain directions and be more resistant to stretch in other directions. For example, the strap 1200 will tend to stretch in its width direction A (from the patient's face to the back of the head) and may have limited stretch along the length of the strap. This configuration may increase stability of the positioning and stabilising structure 3300 in the lengthwise direction while increasing fit range. The strap 1200 may be configured to stretch in certain directions and be resistant to stretch in other directions in order to better enable the strap 1200 to hold a mask assembly on a patient's face in a manner that enhances the seal with the patient's face.

Referring to FIGS. 140 and 141, a knitted strap 1105 includes a top portion 1102, a rear portion 1104, and a lower portion 1106. The lower portion 1106 may bifurcate or branch out at a junction to form the top portion 1102 and the rear portion 1104. The angular orientation of the top portion 1102 may be different compared to the rear portion 1104 e.g. the top portion 1102 may extend at about 30-110 degrees, or about 90 degrees or perpendicular to the rear portion 1104. The direction of the knit, or the grain or course 1150 of the knit, may be altered to adjust the shape or stretch of the fabric in certain areas. For example, the grain or course 1150 may be configured to curve the strap at a cheek region to avoid obstructing the patient's eyes. Further, as shown in FIG. 141, the grain or course 1150 may curve, as shown by the arrows B, to a split thereby forming the top portion 1102 and the rear portion 1104. Such configurations of the top portion 1102 and the rear portion 1104 may stabilize the straps in position on the patient's head and thus better enable the knitted strap 1105 to hold a mask assembly on a patient's face in a manner that enhances the seal with the patient's face.

The knitted strap 1105 may support a patient interface 3000 (e.g., a nasal mask) on the patient's face. A connector 1120 may be used to attach the strap 1105 to the patient interface 3000, and an air circuit 4170 may deliver breathable gas to the patient's airways via the patient interface 3000. In the illustrated example, the patient interface 3000 is positioned under the patient's nose and seals against the external surfaces of the patient's nose.

The positioning and stabilising structure 3300 of the present technology may further comprise a pocket, tunnel, layers and/or ribs. Such positioning and stabilising structures 3300 may be formed in one piece by circular or flat knitting. The pockets or tunnels may be reinforced with materials having a higher stiffness or rigidity than the knitted textile, thereby rigidising the positioning and stabilising structure 3300. Rigidising the positioning and stabilising structure 3300 may better stabilize the mask in position on the user's face. Materials used for rigidising the positioning and stabilising structure 3300 may include plastics such as nylon, polypropylene, polycarbonate, or higher stiffness textiles such as braided ropes. The rigidising of the positioning and stabilising structure 3300 may be positioned at bony regions of the patient's head, for example the cheeks, occiput or crown. The reinforcing structure may be inserted during the knitting process, for example, a stiffer or flatter yarn or a rigid polymer element may be inserted into the knit construction, during or after the knitting process. The strands or rigid components would function to withstand tension and bear the stresses e.g., due to tightening of the positioning and stabilising structure straps for therapy, or to stabilise the mask better, or would assist to act as coupling or fastening agents to attach the positioning and stabilising structure piece(s) to the mask interface.

Alternatively, the pockets or tunnels may be cushioned to add comfort. For example, pockets or tunnels may be filled with foam, gel, floating yarn, looped yarn or other cushioning material.

The positioning and stabilising structure 3300 may be formed by flat knitting or circular knitting, wherein the positioning and stabilising structure 3300 has selvedges. That is, the positioning and stabilising structure 3300 may be formed to have a finished configuration such that the ends of the yarns used to construct the positioning and stabilising structure 3300 are substantially absent from the edges of the positioning and stabilising structure components. An advantage of fashioning the positioning and stabilising structure components to the finished shape is that the yarns are not being cut, and are thus less likely to unravel and may require fewer finishing steps. By forming finished edges, the integrity of the positioning and stabilising structure 3300 is maintained or even strengthened and fewer or no post-processing steps are required to either (1) prevent unravelling of the positioning and stabilising structure component and/or (2) create an edge that is distinct yet soft (such as in ultrasonically cutting and sealing a 'soft edge' on a fabric-foam-fabric laminate material) and/or (3) enhance the aesthetic and durability characteristics of the positioning and stabilising structure 3300.

The positioning and stabilising structure 3300 of the present technology may be formed by a regular or irregular pique knit. A pique knit will orient a first yarn on the right side (non-patient contacting side that is visible once the positioning and stabilising structure 3300 is donned) and a second yarn on the wrong side (the patient contacting side that is not visible once the positioning and stabilising structure 3300 is donned). That is, the yarn exposed on the right side may be different to the yarn exposed on the wrong side. For example, the yarn on the right side may have a pleasant visual appearance and the yarn on the wrong side may have a nice hand feel for contacting the patient's skin. Alternatively, or in addition, the yarn on the right side may have a first moisture wicking property and the wrong side may have a second moisture wicking property. For example, the yarn on the right side may have a high percentage of microfiber having a first moisture wicking property and the wrong side may have a high percentage of non-microfiber having a second moisture wicking property.

The positioning and stabilising structure 3300 may be formed as a unitary knit structure which may also be uniform in material and properties, for simplicity, but it may be formed as a unitary structure including various sections that have different physical properties, joined in a seamless manner. The various sections may exhibit, for example but not limited to, different degrees of strength, abrasion resistance, wear resistance, flexibility, enhanced durability, higher or lower moisture absorption (moisture absorbability), moisture-wicking ability, water affinity, breathability or air-permeability, liquid permeability, stretch or stretch-resistance, compressibility, cushioning ability, support, stiffness, recovery, fit, and form. The various sections may be constructed to exhibit variations in directional stretch, such as four-way stretch, or bi-directional stretch, a tailored level of stretch resistance, or no stretch. This may be achieved by, for example but not limited to, selecting a particular yarn or knit construction type.

The positioning and stabilising structure 3300 as a unified seamless structure may be formed in one piece with uniform characteristics, or from two or more sections with varying characteristics. The two or more positioning and stabilising structure sections may differ by way of using two or more different yarns of different twist, denier, fibre composition, etc., thus imparting different physical properties to the positioning and stabilising structure 3300. The two or more positioning and stabilising structure sections may differ by way of using two or more various knit stitch types, thus imparting unique physical properties to the two sections.

Whereas one region may incorporate, for example, elastane or PBT (Polybutylene terephthalate polyester) to enhance stretch, the other region may incorporate, for example, nylon or polyester to enhance durability. Similarly, while one region of the positioning and stabilising structure 3300 may incorporate yarn with one denier, the other region may include a yarn with a greater or reduced denier, crimp or texture, in order to customize the cushioning, thickness or bulk.

The two or more sections within a positioning and stabilising structure construction may be connected by using tuck stitches or other knit stitches that, for example, join a first section to a second section in a seamless manner. This would be achieved by knitting the first section, then knitting the tuck stitches between the first knitted section and a second knitted section, then knitting the second section. The tuck stitches are utilized to seamlessly connect sections between wales, especially when using a narrow-tube circular knitting machine.

The positioning and stabilising structure piece may be finished without a seam. If it is made with an un-dyed yarn, this may be achieved by finishing the knitting process with a yarn that contains water-soluble fibres. The water-soluble fibers permit the fabric to shrink in the dyeing process and provide a neatly-finished edge, eliminating the need to create an additional seam on the edge.

In order to enhance manufacturing efficiency, knitting machines may also be utilized to form a series of joined positioning and stabilising structure components, such as straps or crown components. That is, the knitting machines may form a single component that includes a plurality of positioning and stabilising structure pieces. Each of the positioning and stabilising structure segments may have substantially identical shapes and sizes. Alternatively, each of the positioning and stabilising structure pieces may even have different shapes and sizes, which may be programmed in sequence. Moreover, a knit release area (which may consist of, for example but not limited to, dissolvable yarns, loosely knitted yarns, finer denier yarns or easy-to-tear placeholder yarns) may be knitted into the series of positioning and stabilising structure components in order to allow the various positioning and stabilising structure parts, for example, straps, to be separated without the need for cutting operations.

Variable Thread Count

In another example, the thread count may vary across the fabric to enhance comfort, fit and/or performance. For example, the thread count may be higher in regions requiring greater stiffness (e.g., cheek region, occiput). In regions (e.g., along the straps) where a lower stiffness is desired, however, the thread count may be lower thereby permitting the material to flex more easily.

The thread count, and therefore the stiffness, may be determined by the type of yarn, the type of stitch (e.g., a criss-cross stitch may be stiff), and the distance between stitches.

Yarn

Yarn may be utilized to create the positioning and stabilising structure 3300 of the present technology. The yarn may be synthetic, and may be twisted or textured, and could be made from, but not limited to nylon, polyester, acrylic, rayon, or polypropylene. The yarn could be a conventional staple yarn, a microfiber yarn, or combination of both. The yarn may incorporate an elastane fiber or filament to provide stretch and recovery properties, such as fibers bearing the LYCRA trademark from the DuPont Company. The yarn may be made of synthetic materials, or natural fibres such as cotton, wool or bamboo, or natural filament such as silk.

The yarns used to construct any component of the positioning and stabilising structure may be formed of a monofilament or a plurality of single filaments, that is, a multifilament yarn.

The yarn may include separate filaments that are each formed of different materials. The yarn may also include filaments that are each formed of two or more different materials, such as bicomponent yarn with filaments having a sheath-core configuration or two halves formed of different materials. Different degrees of twist or crimping, as well as different deniers, may affect the properties of the positioning and stabilising structure 3300.

The materials utilized to construct the positioning and stabilising structure components 2900 may be made recyclable or biodegradable, for example, the yarns may include recyclable or biodegradable fibers or filaments.

Areas of the positioning and stabilising structure 3300 subject to greater wear (for example but not limited to areas or regions coming into contact with a patient's pillow), such as an area of positioning and stabilising structure 3300 located at the back of the head or nape of the neck, may possibly be more densely fabricated and may thus be a heavier weight and less extensible. Conversely, this area may be subject to the greatest amount of moisture accumulation through sweat, and therefore may need to be made of a thin, yet strong, net-like construction with a custom aperture pattern. In this case, the abrasion-resistance may need to be inherent in the yarn properties only.

3D Printing

In another example, positioning and stabilising structure 3300 may be manufactured to shape using a 3D printer. As shown in FIG. 143, a 3D printer may be used to print a plurality of connected links 2802 thereby forming a flexible 3D printed textile 2804. Referring to FIG. 144, a positioning and stabilising structure piece 2900 may be formed to include a rigidiser arm 3302. The rigidiser arm 3302 includes holes 2922 through which the links of the textile 2804 may pass as the textile 2804 is printed to integrate the textile 2804 and the rigidiser arm 3302. The rigidiser arm 3302 could be made from any suitable material (e.g., a polymer such as Nylon 12 or a sintered solid from a metal powder, or any other material able to be used as an additive manufacture process). As the additive manufacture ("3D Printing" process technologies improve, it is envisioned that the material selection will become broader for the purposes of 3D printing textiles, with the optional inclusion of a rigid component such as the rigidiser arm 3302. Structure could be inherent in material or by virtue of shape, form or structure.

Further, as shown in FIG. 145, a 3D printed strap 2924 may be integrated into holes 2912(1), 2914(1) of male and female clips 2912, 2914.

Fashioning and Finishing the Strap

FIGS. 79 and 80 show views of the strap 3301 at an intermediate step of production. The exemplary strap 3301 shown is a raw length of strap that has not been cut to length from the knitted material produced, in examples, by the methods and processes described above. For example, a pair of button-holes 3303 can be seen at the left-most end of the strap 3301, however, once finished only hole will be at that end because the raw strap will have been cut between those holes to produce the strap shown in FIG. 81. Also, the knitting process that forms the raw length of strap 3301 shown in FIG. 79 forms multiple split regions 3326 along the length of the strap. However, the finished strap 3301 shown in FIG. 81 only includes one split region 3326. Again, this is because during finishing the strap 3301 will be cut between the right-most button-hole 3303 shown in FIG. 79 to separate the raw length of strap 3301 shown there into multiple straps.

According to one example of the technology, the strap 3301 may be formed using a warp labelling machine with multiple bars to form chains in the fabric. According to another example, the strap 3301 may be formed by a Comez machine with six bars for joining the two side strap portions 3315, 3316 and the two back strap portions 3317a, 3317b in the center. By adding more bars to the Comez machine more directions of knitting may be accommodated. The knitting process may also include forming the strap 3301 with a different weave at the bifurcation point 3324. The material of the strap 3301 may include a 1740 count. The order of pattern types for knitting a strap 3301 may be as follows: normal, then button-hole, then normal, then split, then normal, then button-hole, and then normal. A subsequent strap 3301 would then be knitted with this same order again going forward for each strap 3301 produced.

In one example of the present technology, the thread used for knitting the strap 3301 may be double helically wound.

To add further strength at potential failure points, the strap 3301 may be formed with extra stitching at these points. Potential failure points may include the button-holes 3303, 3304 and the bifurcation points 3324. Also, additional threads may be knitted along the middle of the strap 3301 for additional reinforcement.

FIG. 80 shows a cross-sectional view of the side strap portion 3316 of FIG. 79 taken through line 80-80. A bifurcation point 3324 can be seen to indicate the split region 3326 of the side strap portion 3316 and the division between the upper back strap portion 3317a and the lower back strap portion 3317b.

FIG. 79 also indicates dimensions $L_1$-$L_6$ for the various features of the strap 3301. $L_1$ indicates a distance between a button-hole 3303 of one strap 3301 and a button-hole 3303 of an adjacent strap. In one example of the technology $L_1$ may be about 515 mm. $L_2$ indicates a distance between button-holes 3303 of the same strap 3301 and this value may, according to one example, be about 500 mm. $L_3$ indicates the length of the split region 3326 which may be about 200 mm in one example of the technology. $L_4$ may indicate the distance between adjacent button-holes 3303 of adjacent straps 3301 and may be about 15 mm in one example. $L_5$ may indicate the width of a button-hole 3303 and may be about 5 mm in one example. $L_6$ may indicate the width of the strap 3301 and may be about 15 mm in one example.

FIGS. 81 to 83 show views of a finished strap 3301 according to an example of the present technology. As can be seen in FIG. 81 there is only one split region 3326 and only one button-hole 3303 at each end of the strap 3301. Therefore, it should be understood that this strap 3301 has been cut and finished from the strap 3301 shown in FIG. 79, according to an example of the technology. Also, shown in FIG. 81 is a strap logo 3357 that may be formed on the strap 3301 in the form of a corporate logo or other artwork, for example. The strap logo 3357 may be formed by pad printing or ultrasonic welding. If the strap logo 3357 is formed by ultrasonic welding this may help to splay the back strap portions 3317a, 3317b at the bifurcation points 3324 to encourage spreading the back strap portions 3317a, 3317b by the patient 1000 to ensure ideal fitment and strap tension.

FIG. 81 also shows end welds 3311.1, 3313.1. As described above, the side strap portion 3316 may be knitted into a hollow or tube-like shape. Thus, the ends will be open if not closed by welding, for example, which prevents tearing along open ends. The end welds 3311.1, 3313.1 may be formed by ultrasonic welding to seal loose fibers of the strap 3301. While ultrasonic welding may reduce the stretchability of the fabric that comprises the strap 3301 it may serve to reduce fraying at the ends and to add strength at high stress points. Since the end welds 3311.1, 3313.1 are proximal to the respective pocketed ends 3311, 3313 the end welds provide strength for the strap 3301 to be retained to the rigidiser arms 3302 at their respective protruding ends 3306. It should be understood that the pocketed ends 3311, 3313 and their respective end welds 3311.1, 3313.1, according to one example of the technology, are the primary portion of the strap 3301 for retention and/or anchoring to the rigidiser arms 3302. The strap 3301 may lose elasticity after prolonged use but it should be understood that by washing and drying the strap 3301 at least some or all of this elasticity may be recovered.

The StretchWise™ headgear provided by Fisher & Paykel™ for the Pilairo™ mask has a rigid detachable pivotal connection between rigid plastic hooked ends of the headgear strap and rigid plastic vertical bars located on the mask frame. In contrast, the strap 3301 of one example of the present technology does not have a rigid detachable connection between the strap 3301 and the mask frame 3310 which avoids problems such as creep and breakage of hooked ends after repeated engagement and disengagement of rigid components. A significant amount of force is required to materially deform the rigid hooked ends of the StretchWise™ headgear to engage and disengage it from the rigid bars. In contrast, the rigidiser arms 3302 of the present technology are inserted into button-holes 3303 of the strap 3301 and retained in a pocketed end of the strap 3301 without such a significant force because no plastic deformation of either the rigidiser arm 3302 or the strap 3301 is required to connect or disconnect the strap 3301 to and from the mask frame 3310. Another deficiency of the StretchWise™ headgear is that elasticity of the headgear strap does not recover to substantially the original level of elasticity after washing the headgear strap. In other words, the StretchWise™ headgear will become looser over time.

FIG. 82, similar to FIG. 80, shows a cross-sectional view of the strap 3301 taken through line 83-83 of FIG. 81. The bifurcation point 3324 can be seen that indicates the initiation of the split region 3326. Also, the strap logo 3357 can be seen raised from the side strap portion 3316 in this view.

FIG. 83 shows a detailed view of the strap 3301 and particularly shows the strap logo 3357. Also, the bifurcation point 3324 can be seen at the beginning of the split region 3326.

FIG. 81 also shows additional dimensions that describe features of the exemplary strap 3301. $L_7$ may indicate the distance between the finished end of the strap 3301 at the end weld 3311.1, 3313.1 and may be about 5 mm in one example. $L_8$ may indicate the width of the end welds 3311.1, 3313.1 and may be about 1 mm in one example.

Donning the Patient Interface and Positioning and Stabilising Structure

An exemplary patient interface 3000 and positioning and stabilising structure 3300 may be donned in a simple yet adjustable manner according to various examples of the present technology. As will be described in greater detail below, FIGS. 84 to 112 depict various sequences of a wearer (i.e., a patient) 1000 donning and adjusting the patient interface 3000 and positioning and stabilising structure 3300.

Figure 84:
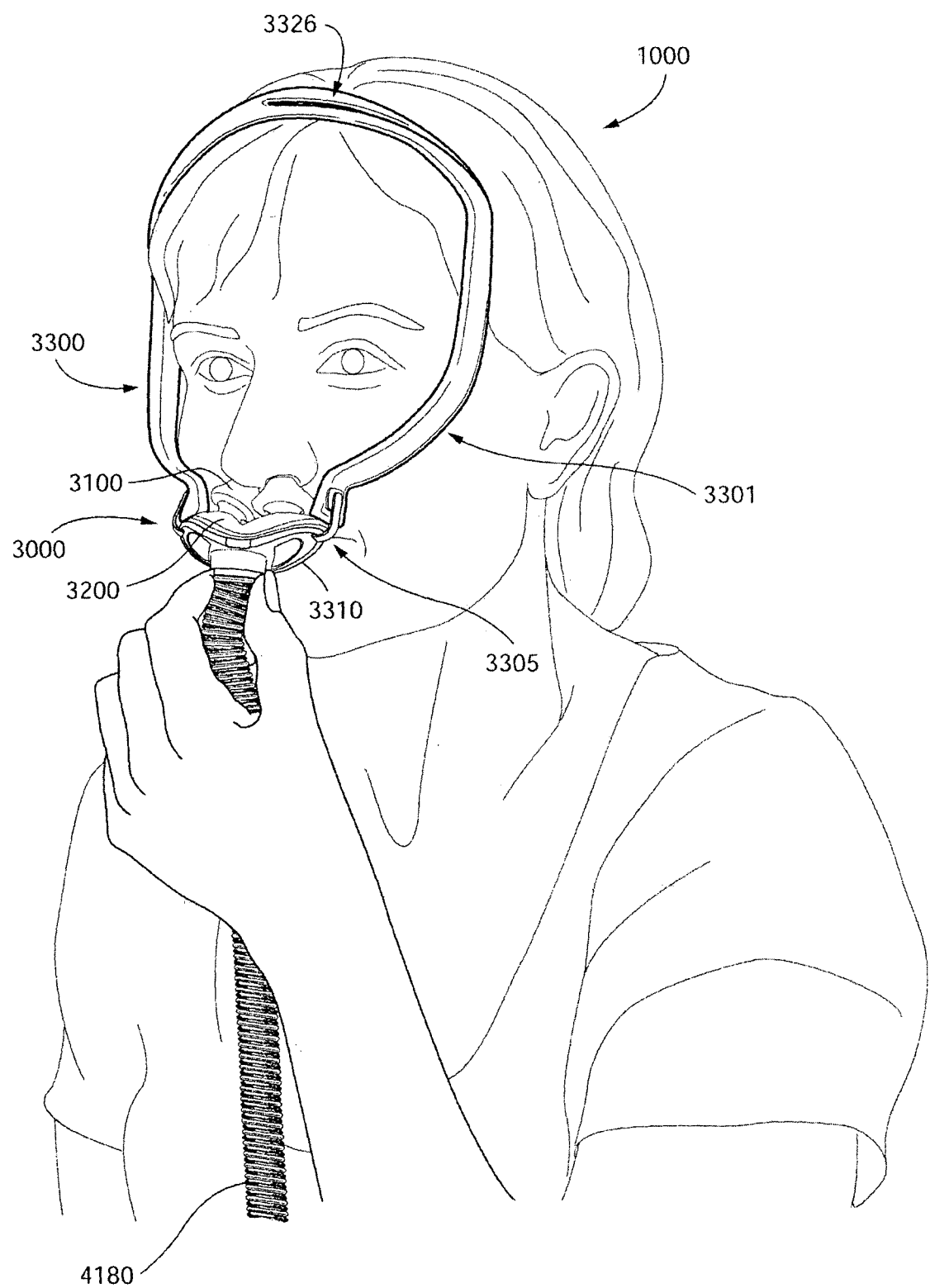
Figure 85:
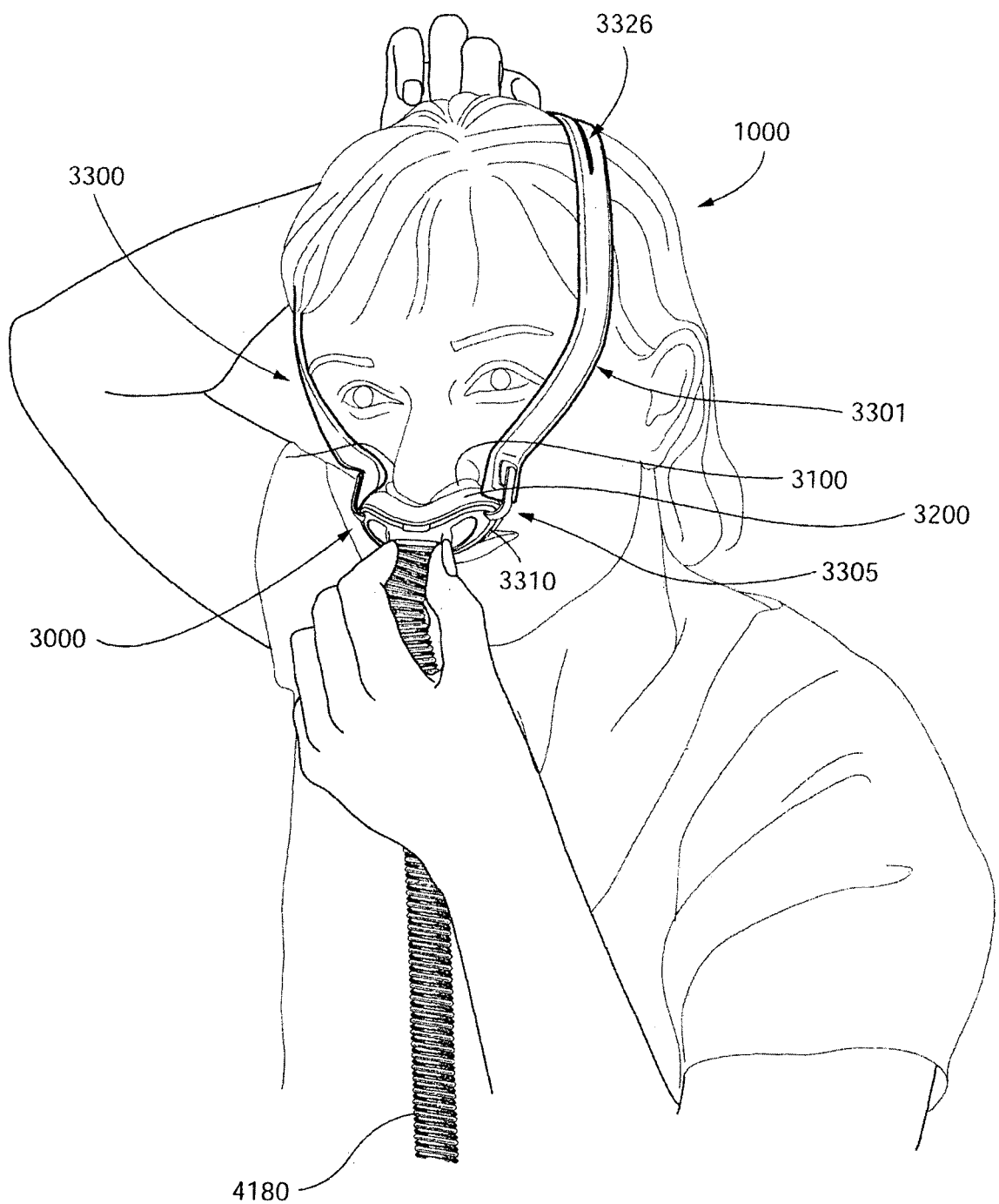
Figure 86:
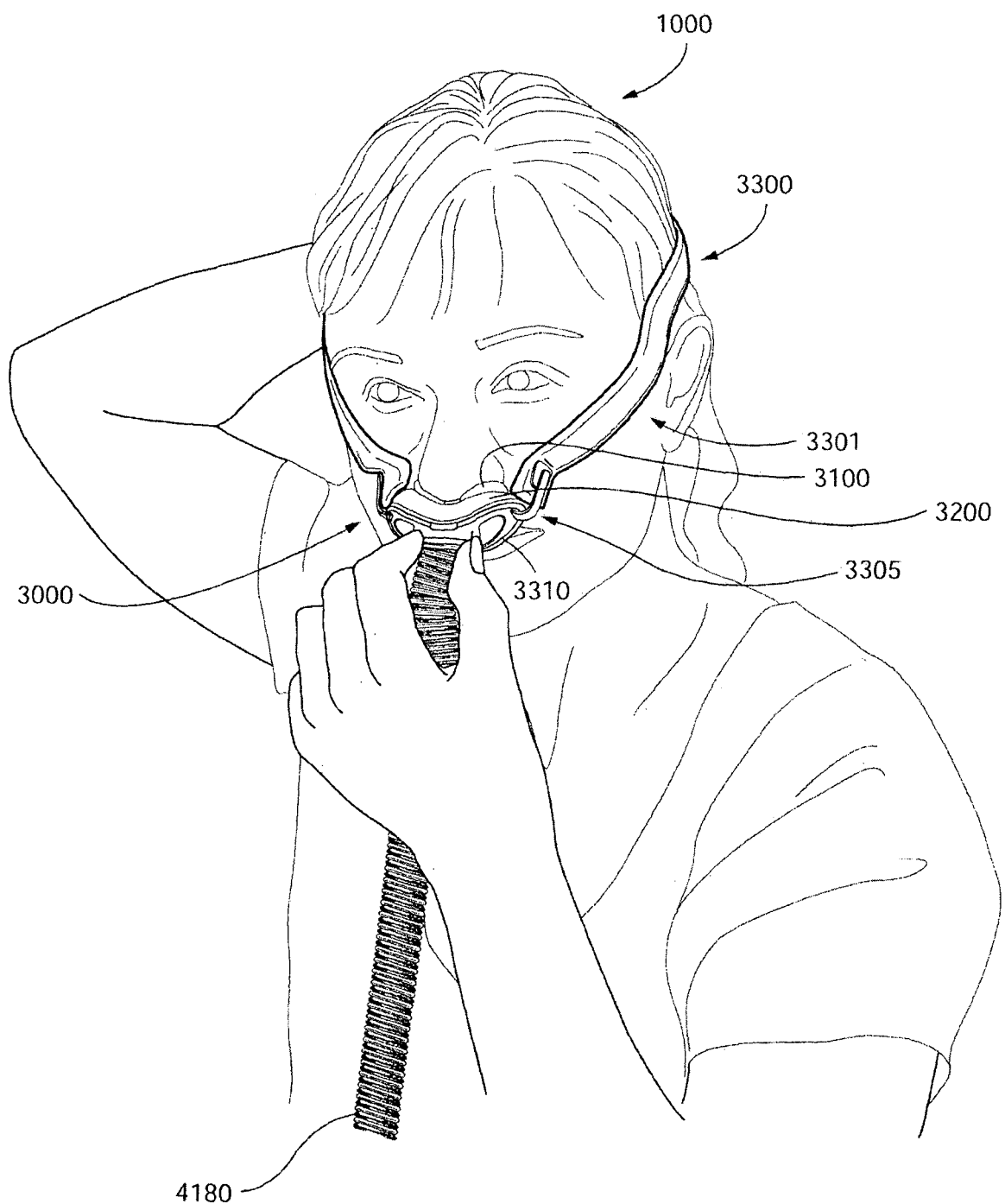
Figure 87:
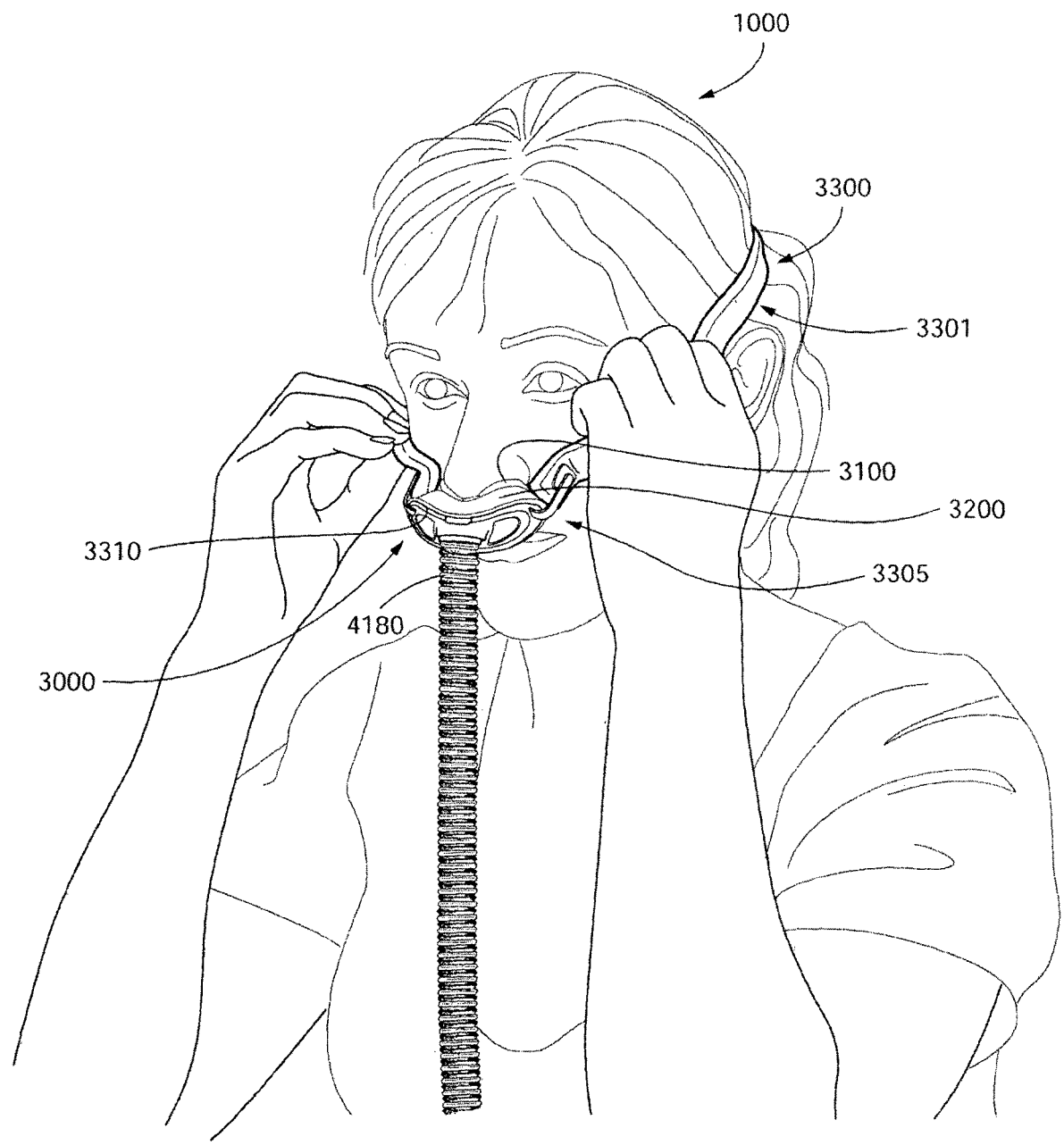
Figure 88:
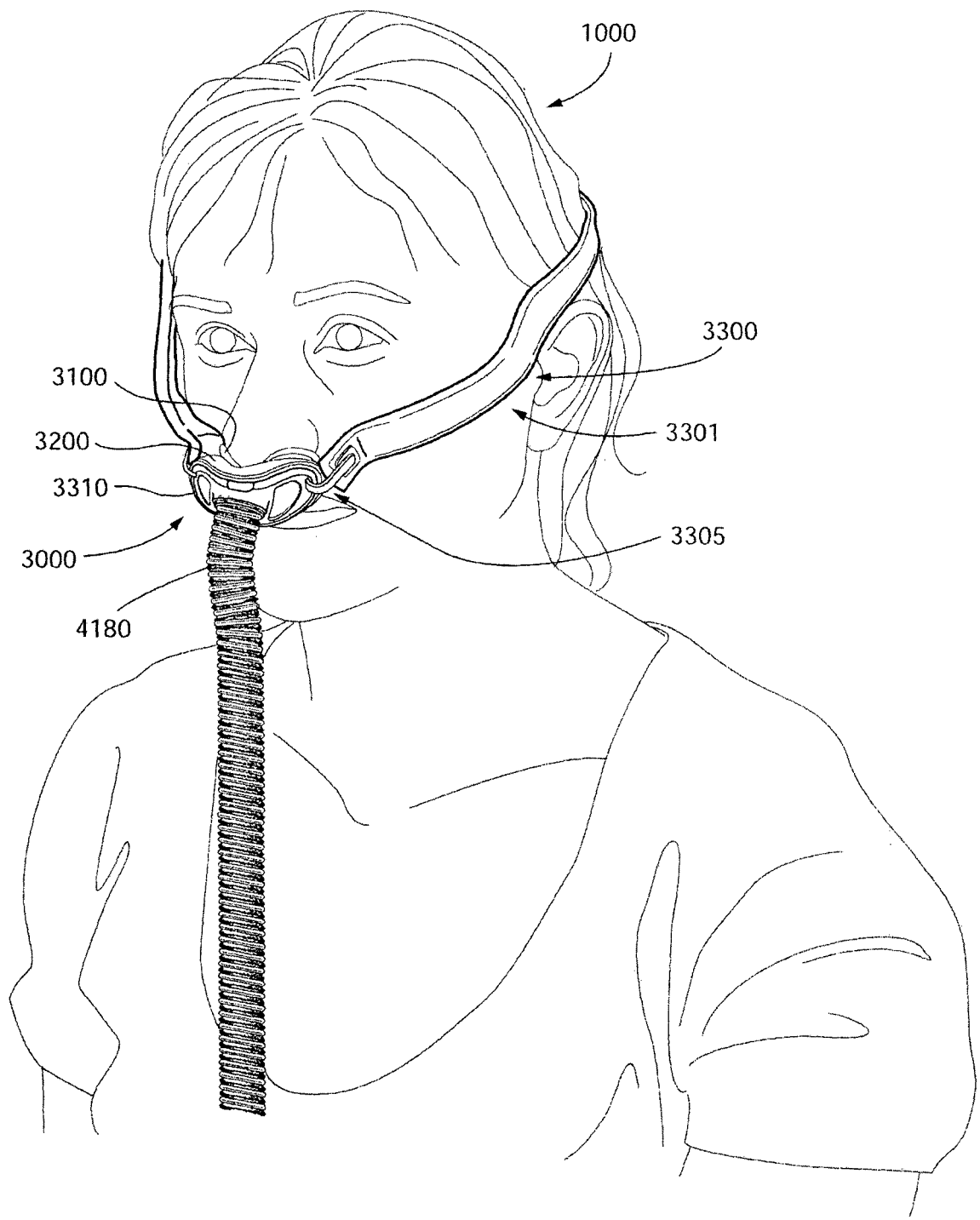

FIGS. 84 to 88 show a series of perspective views of a patient 1000 donning the patient interface 3000 and positioning and stabilising structure 3300. In FIG. 84 the patient 1000 begins donning the patient interface 3000 and positioning and stabilising structure 3300 by holding the patient interface 3000 and placing the seal-forming structure 3100 against the nose. FIG. 85 then shows the patient 1000 beginning to don the positioning and stabilising structure 3300. The patient 1000 pulls the strap 3301 near the split region 3326 with one hand while holding the patient interface 3000 with the other hand to stretch the strap 3301 over the head. FIG. 86 then shows the patient 1000 pulling the strap 3301, while still holding the split region 3326 with one hand and the patient interface 3000 with the other, further towards the back of the head. At the completion of this step the strap 3301 should be located at the back of the head near the crown and near or above the occipital lobe so that proper tension sealing force is placed on the positioning and stabilising structure 3300 to hold the patient interface 3000 against the patient's 1000 nose. FIG. 87 then shows the patient 1000 adjusting the positioning and stabilising structure 3300 to locate the rigidiser arms (not visible in these views) under the cheek bones and to adjust the fit of the seal-forming structure 3100 against the nose to ensure a complete seal. By locating the rigidiser arms 3302 under the cheek bones the positioning and stabilising structure 3300 may be prevented from riding up on the face of the patient 1000 and into the patient's line of sight. FIG. 88 then shows the patient 1000 with the patient interface 3000 and positioning and stabilising structure 3300 donned and prepared for therapy.

Figure 89:
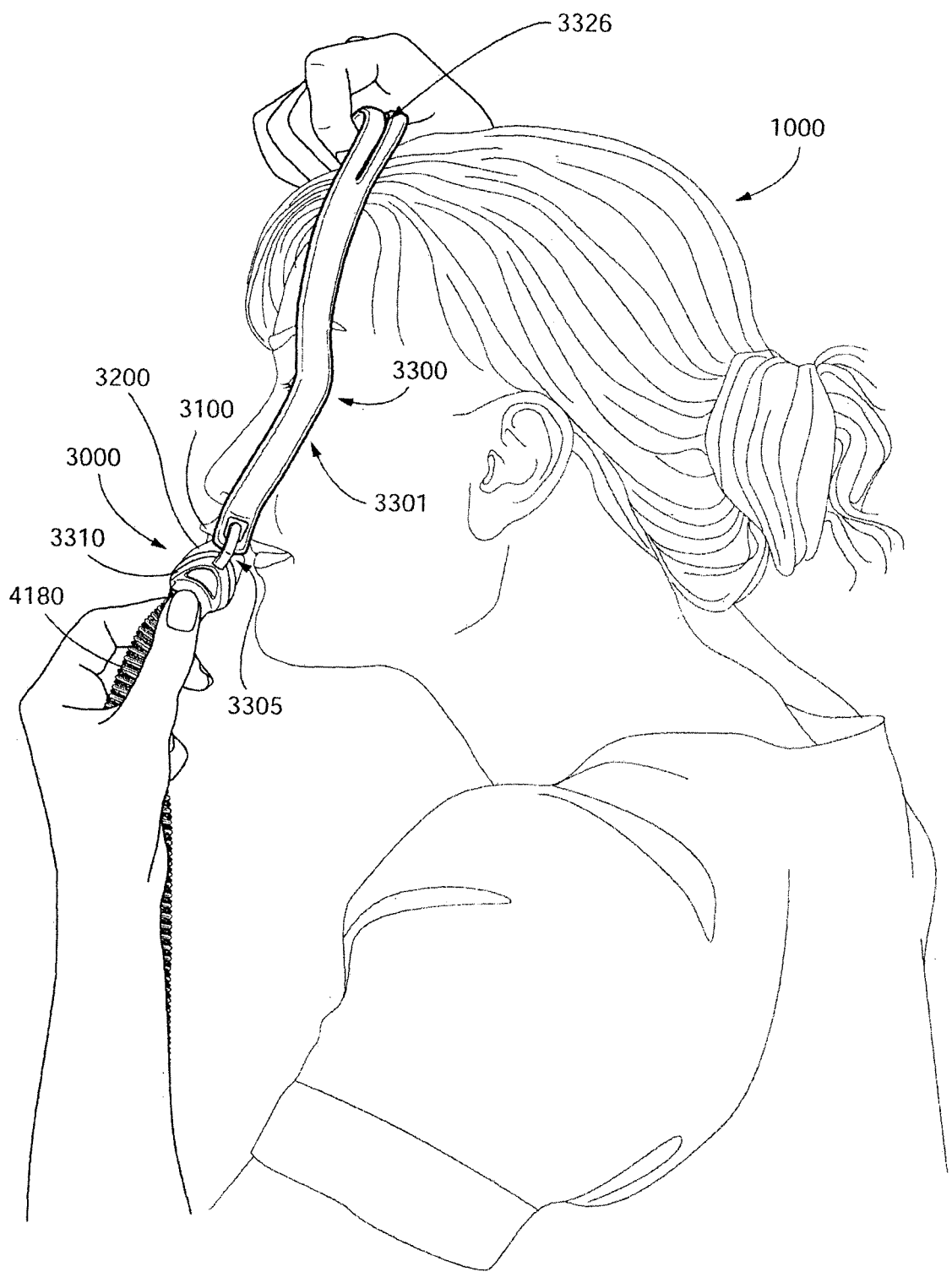
Figure 90:
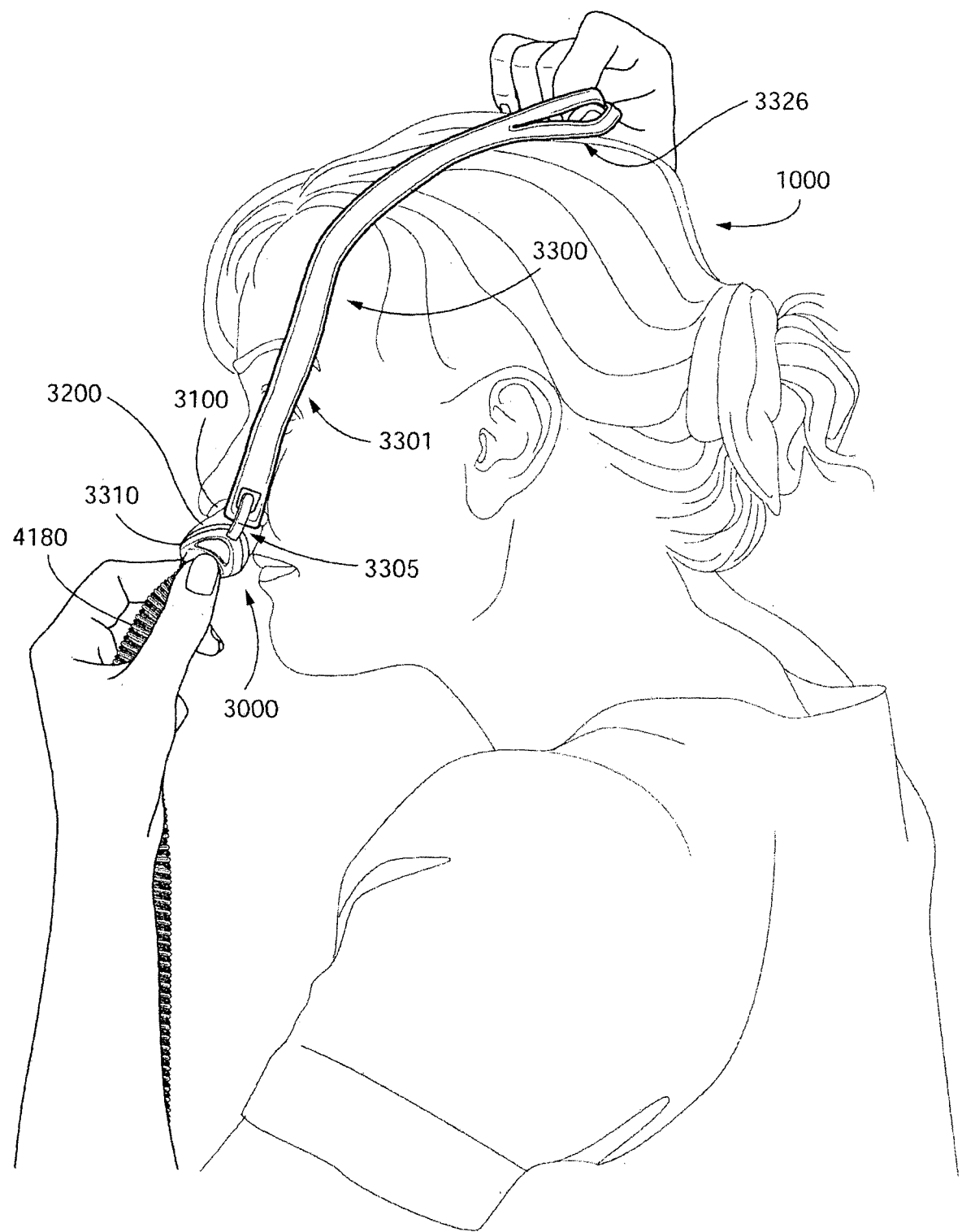
Figure 91:
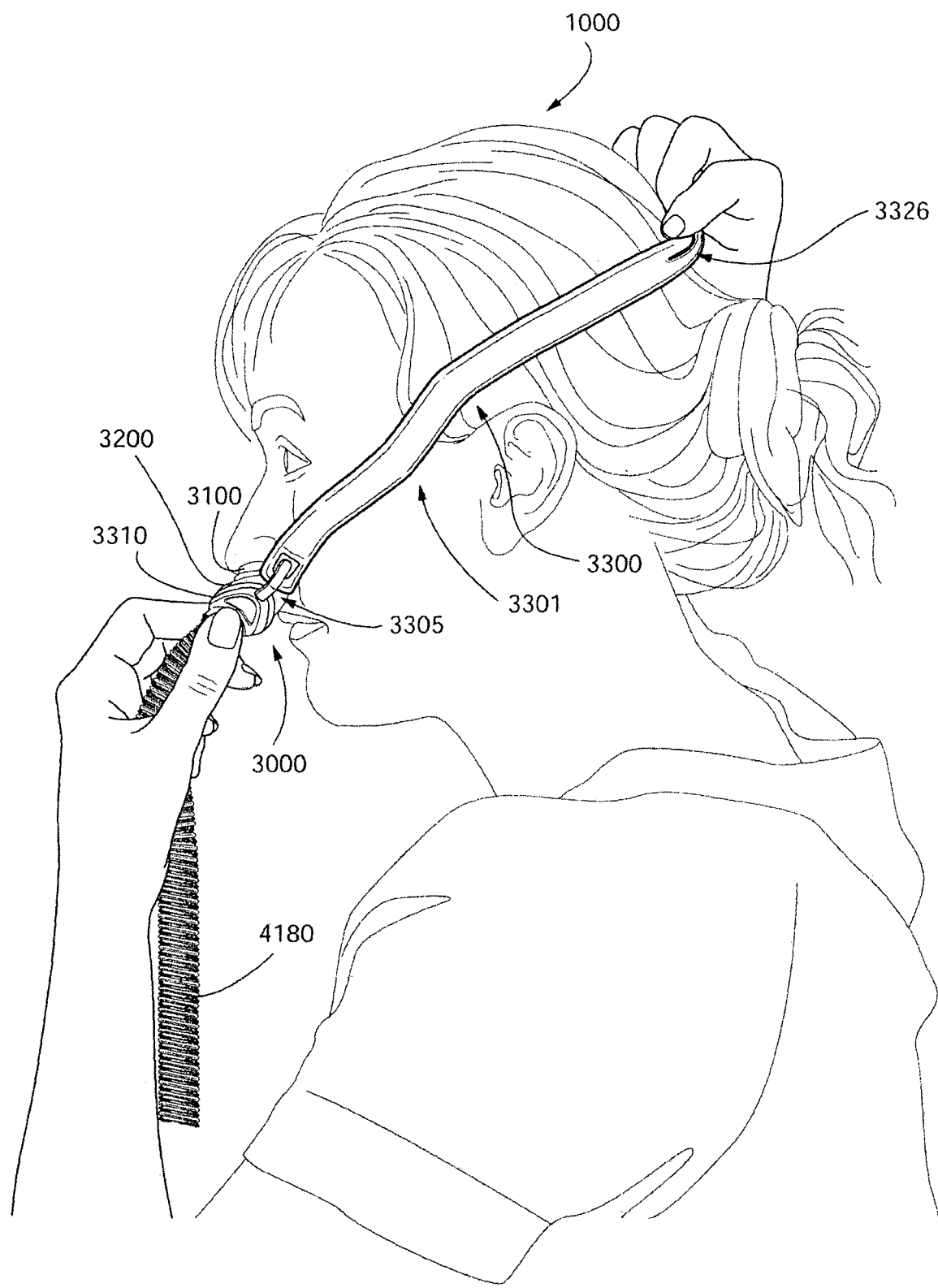
Figure 92:
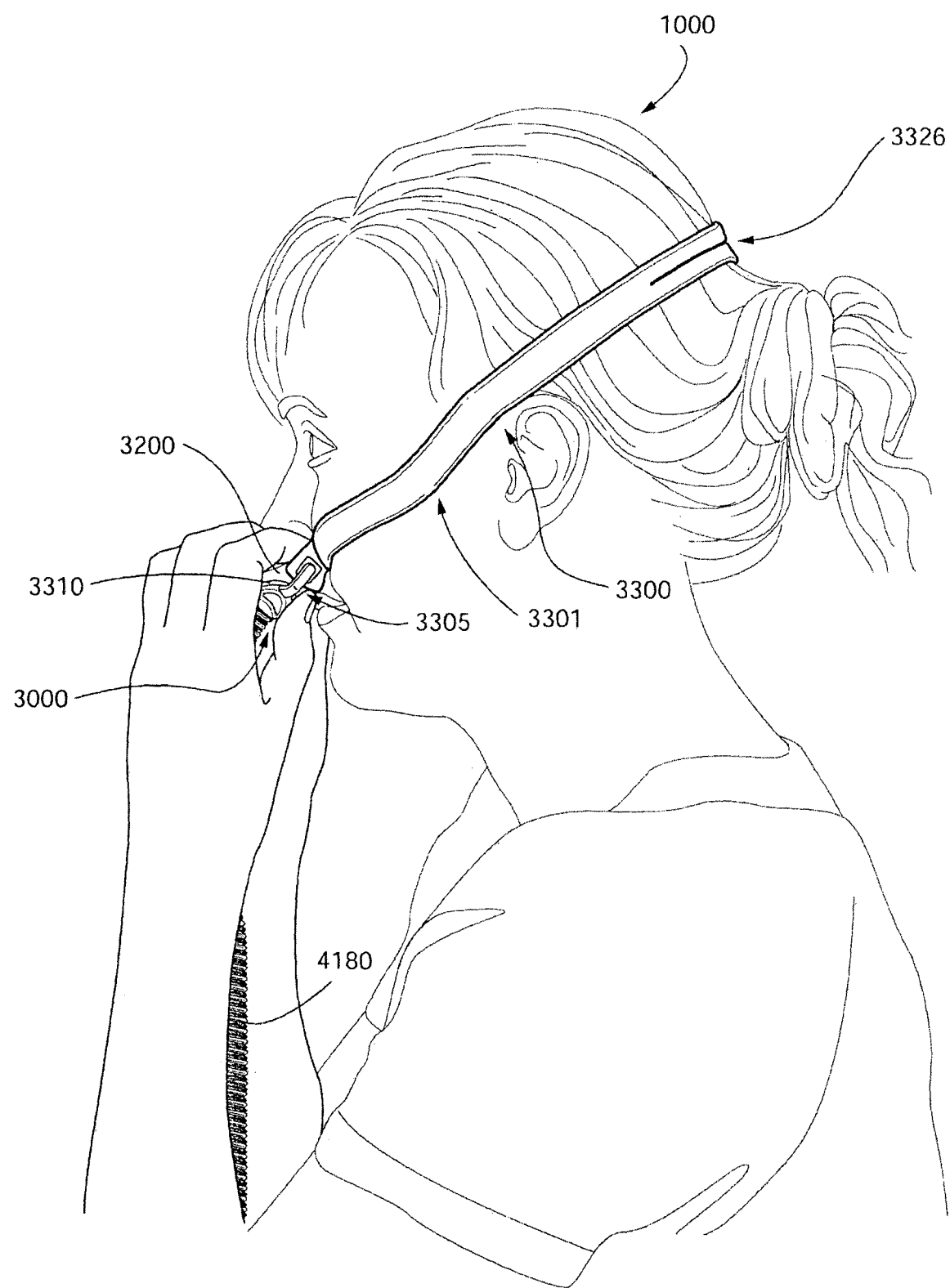
Figure 93:
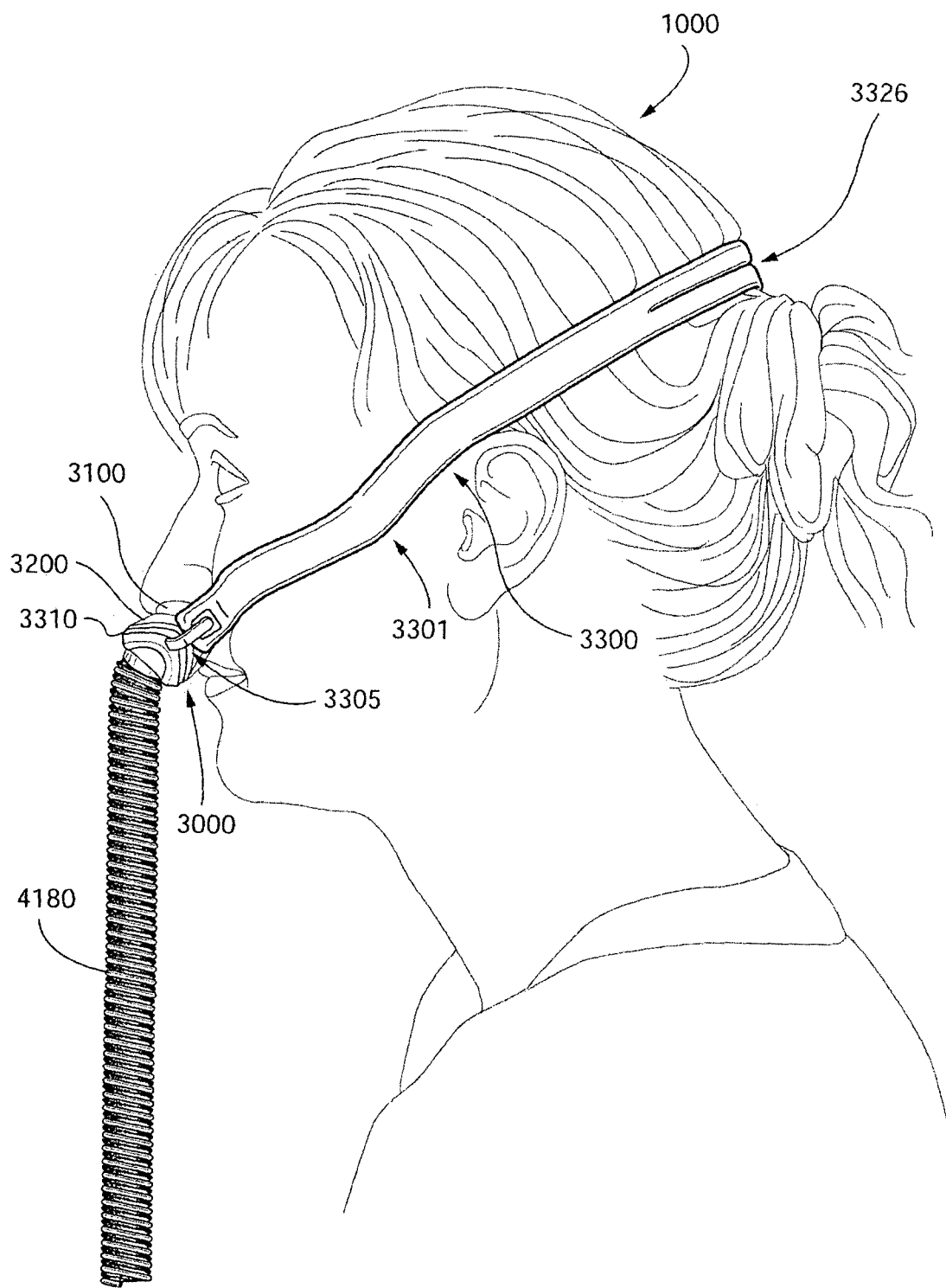

FIGS. 89 to 93 show a series of side views of a patient 1000 donning the patient interface 3000 and positioning and stabilising structure 3300. FIG. 89 shows the patient 1000 holding the patient interface 3000 in one hand and raising it toward the nose while holding the strap 3301 of the positioning and stabilising structure 3300 in the other hand. At this point the strap 3301 may not be significantly stretched. FIG. 90 shows the patient 1000 locating the patient interface 3000 against the nose, particularly the seal-forming structure 3100, with one hand and pulling the strap 3301 of the positioning and stabilising structure 3300 to stretch it over the head with the other hand. A separation at the split region 3326 can be seen as well due to the pulling of the strap 3301. FIG. 91 shows the patient 1000 still holding the seal-forming structure 3100 and the patient interface 3000 against the nares while pulling the strap 3301 of the positioning and stabilising structure 3300 further toward the back of the head. At this point, the initial step of donning the patient interface 3000 and positioning and stabilising structure 3300 should be nearly complete such that the strap 3301 is located against the back of the patient's 1000 head. FIG. 92 then shows the patient 1000 adjusting the seal-forming structure 3100 and the patient interface 3000 against the nose to ensure a proper seal and proper location of the rigidiser arms 3302 relative to the cheek bones. FIG. 93 then shows the patient 1000 with the patient interface 3000 and positioning and stabilising structure 3300 donned and prepared for therapy.

Figure 94:
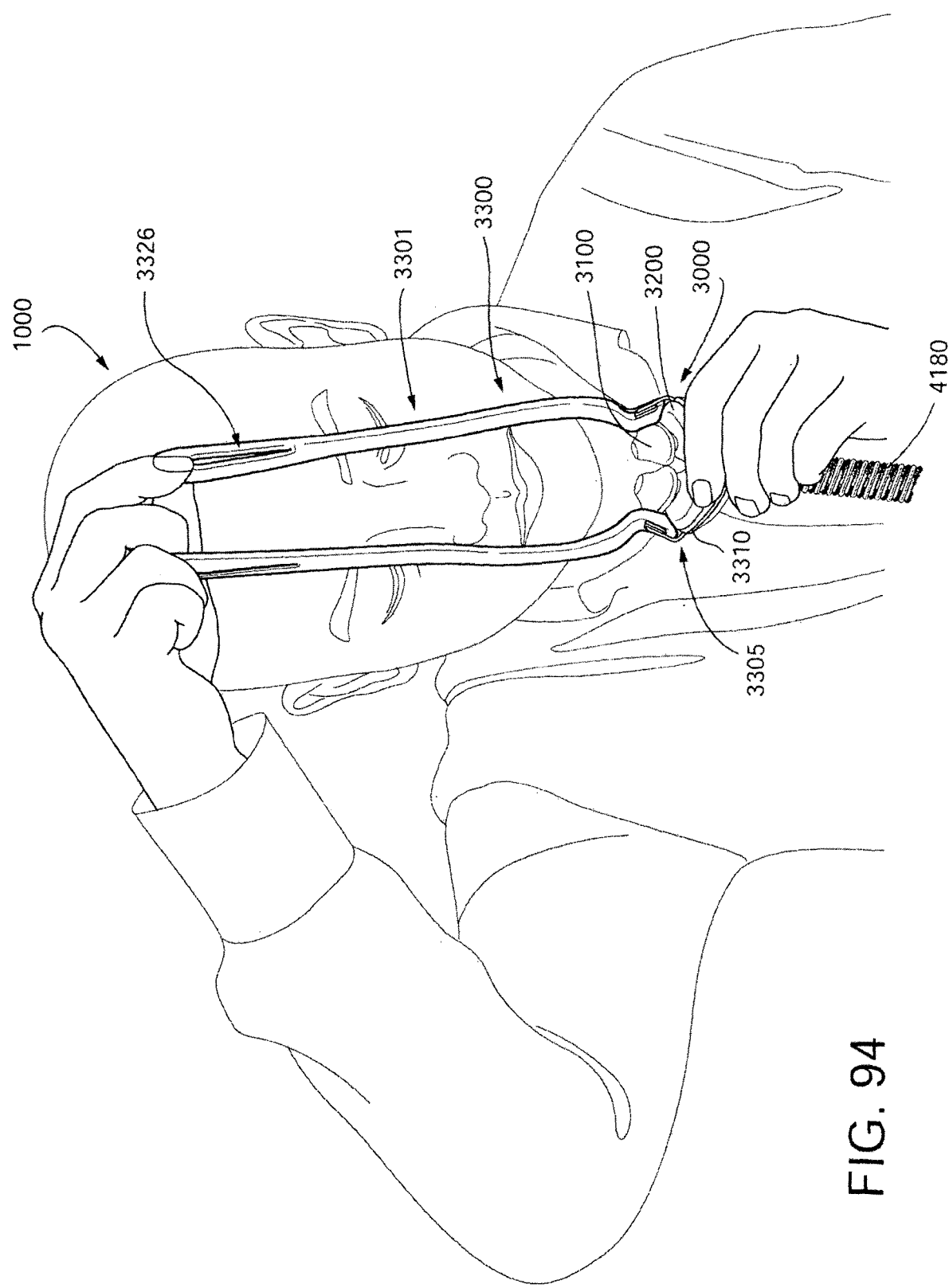
Figure 95:
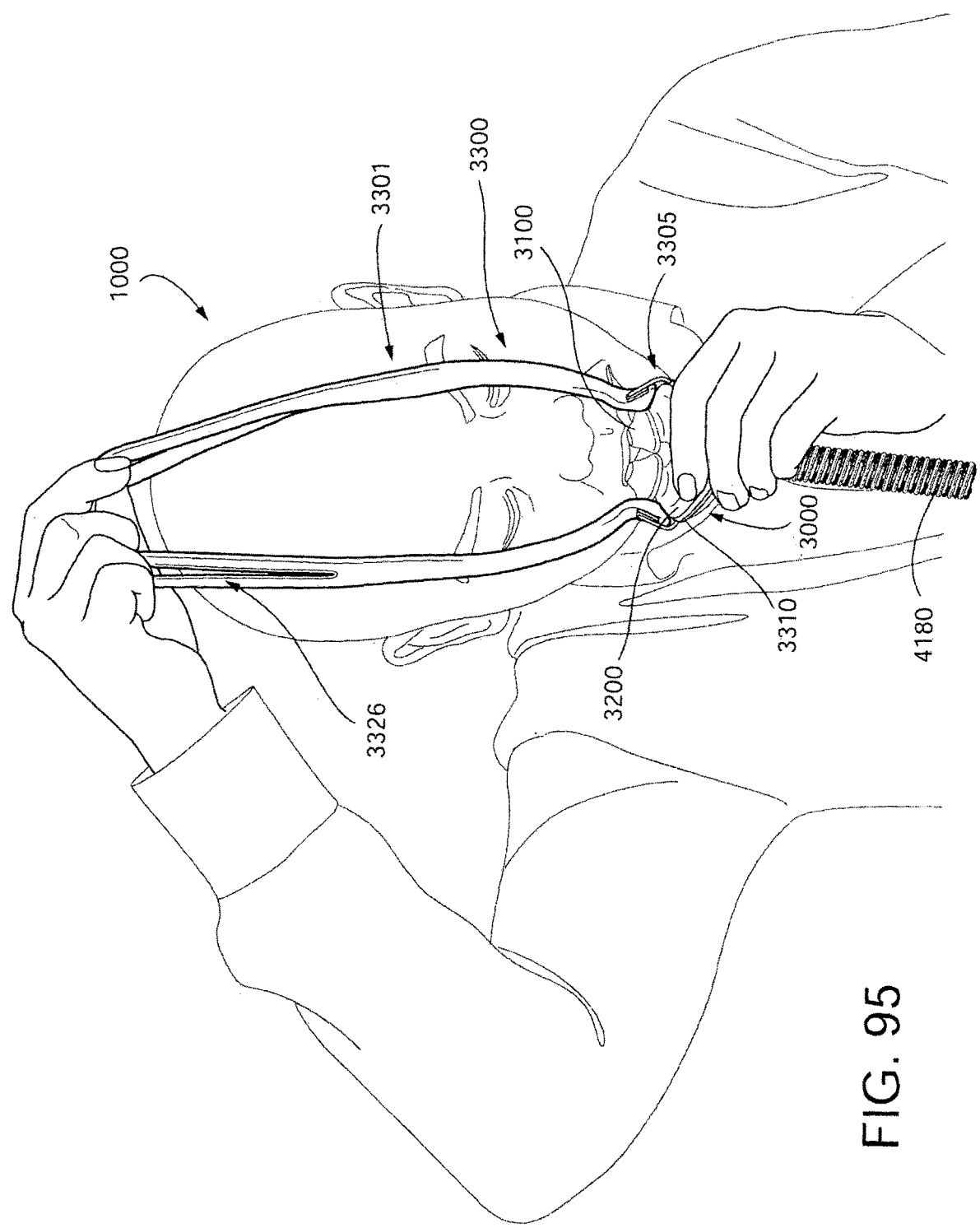
Figure 96:
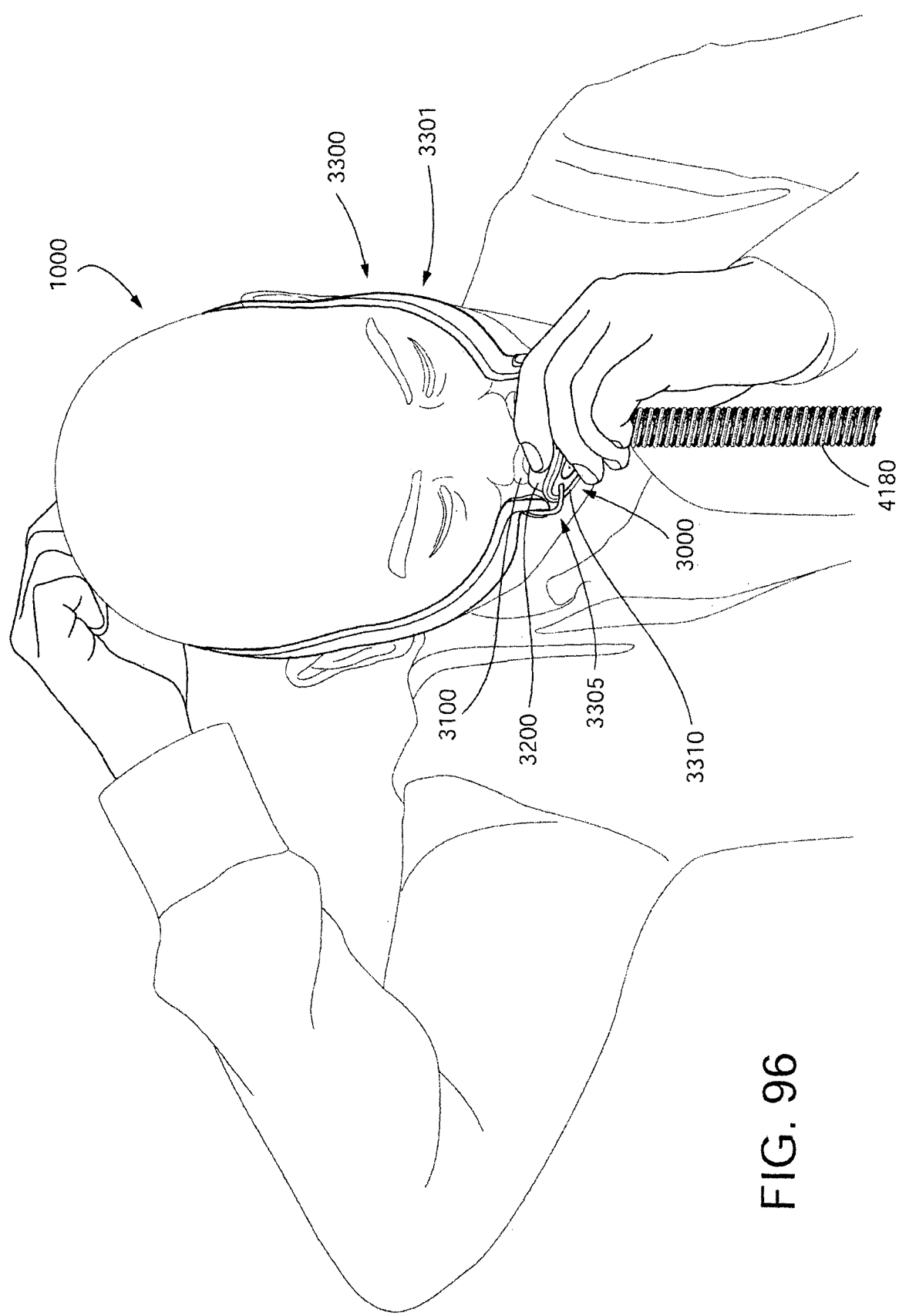
Figure 97:
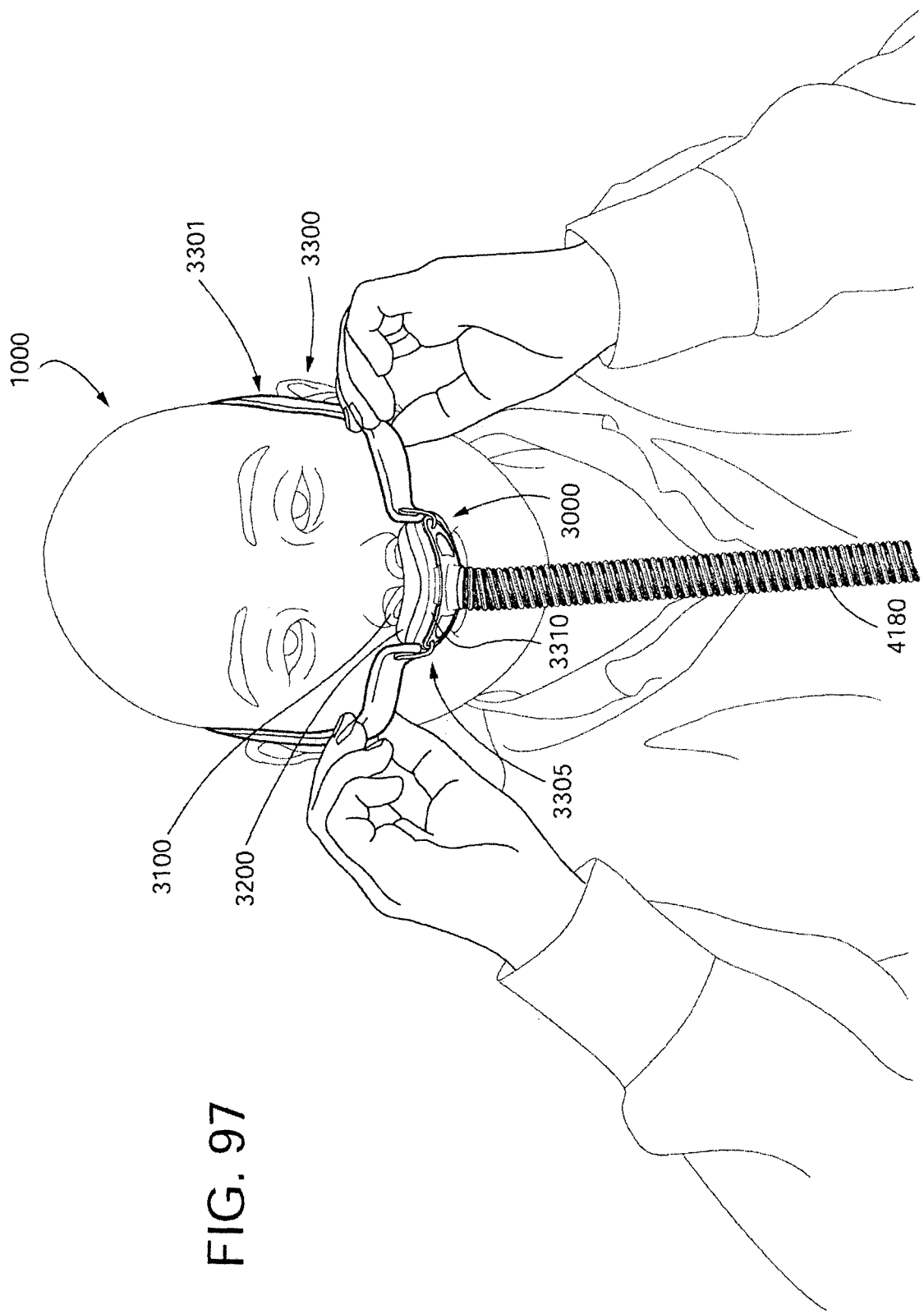
Figure 98:
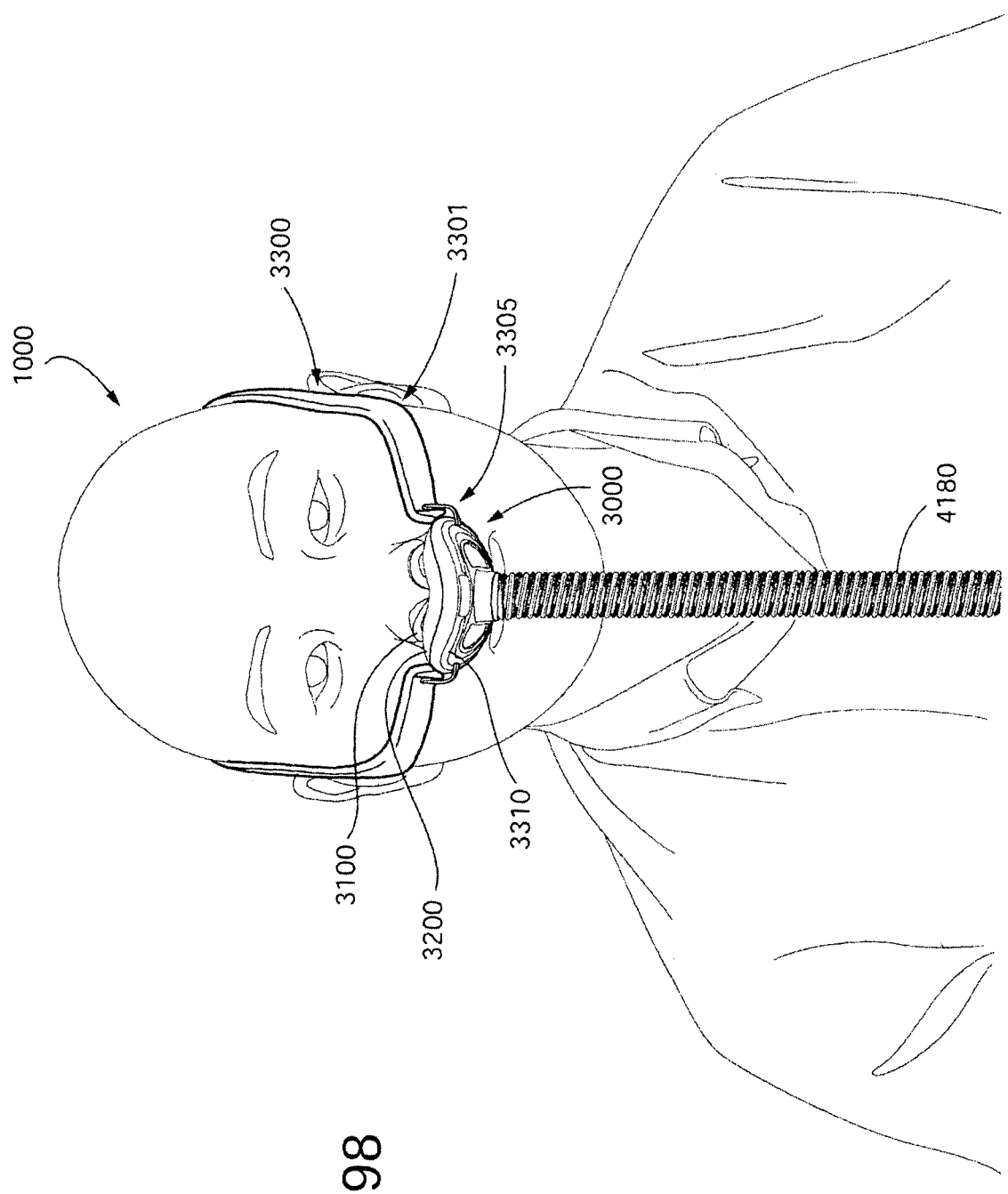

FIGS. 94 to 98 show a series of front views of a patient 1000 donning the patient interface 3000 and positioning and stabilising structure 3300. FIG. 94 shows the patient 1000 beginning to don the patient interface 3000 and positioning and stabilising structure 3300. Holding the patient interface 3000 with one hand and the strap 3301 of the positioning and stabilising structure 3300 with the other hand, the patient 1000 raises the patient interface and positioning and stabilising structure toward the face. FIG. 95 shows the patient 1000 with the positioning and stabilising structure 3300 in one hand and the strap 3301 slightly stretched. FIG. 95 also shows the patient interface 3000 held in the other hand and near the nose for placing the seal-forming structure 3100 against the nose. FIG. 96 shows the patient 1000 having stretched and pulled the strap 3301 of the positioning and stabilising structure 3300 over the head and locating the strap 3301 against the back of the head while holding the seal-forming structure 3100 and the patient interface 3000 against the nose. FIG. 97 shows the patient 1000 then adjusting the positioning and stabilising structure 3300 and the patient interface 3000 by locating the rigidiser arms 3302 in a comfortable position to seat under the cheek bones so that the positioning and stabilising structure 3300 does not ride up into the patient's line of sight and a seal can be maintained against the nares with the seal-forming structure 3100. FIG. 98 then shows the patient 1000 with the patient interface 3000 and positioning and stabilising structure 3300 donned and prepared for therapy.

Figure 99:
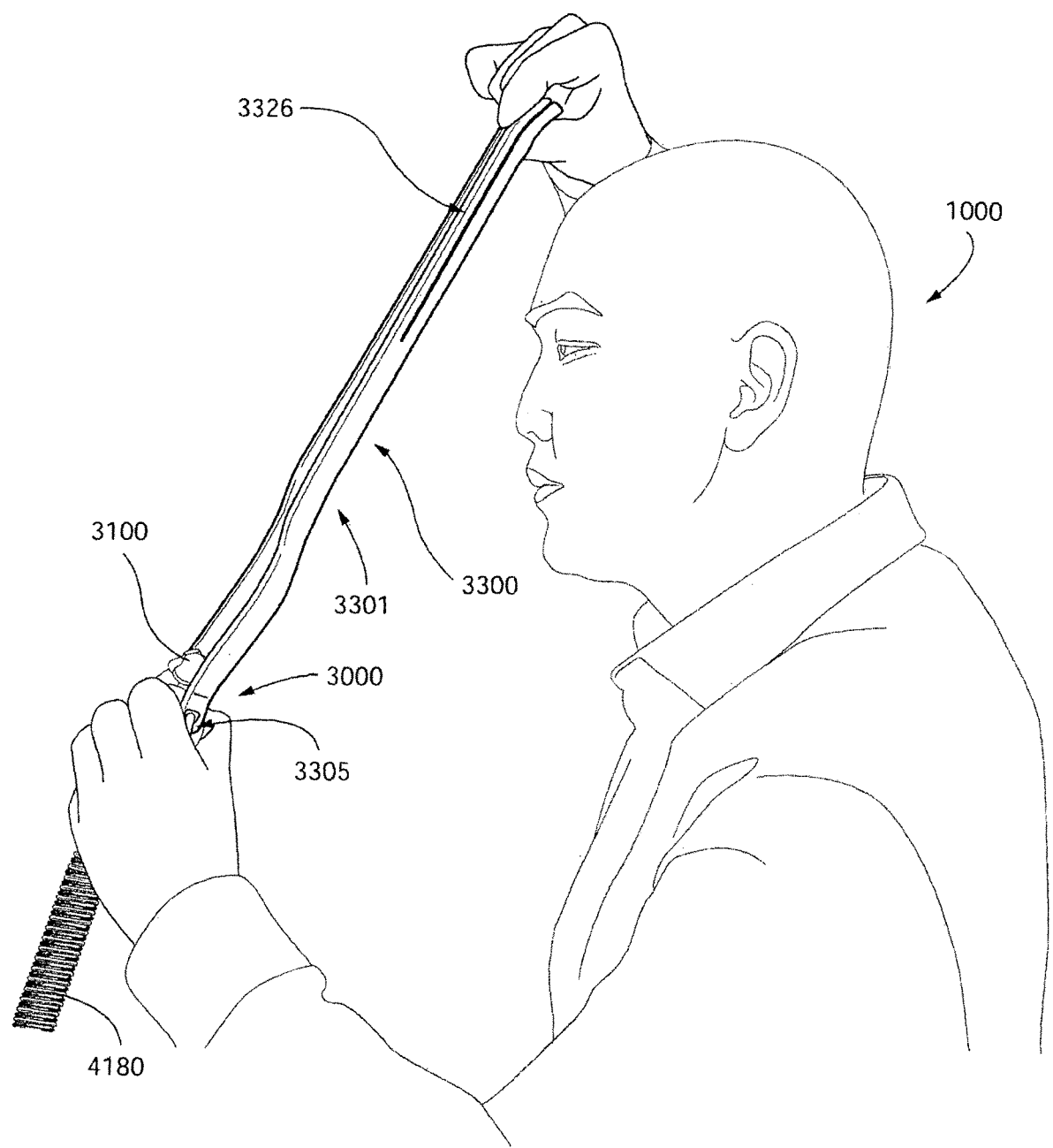
Figure 100:
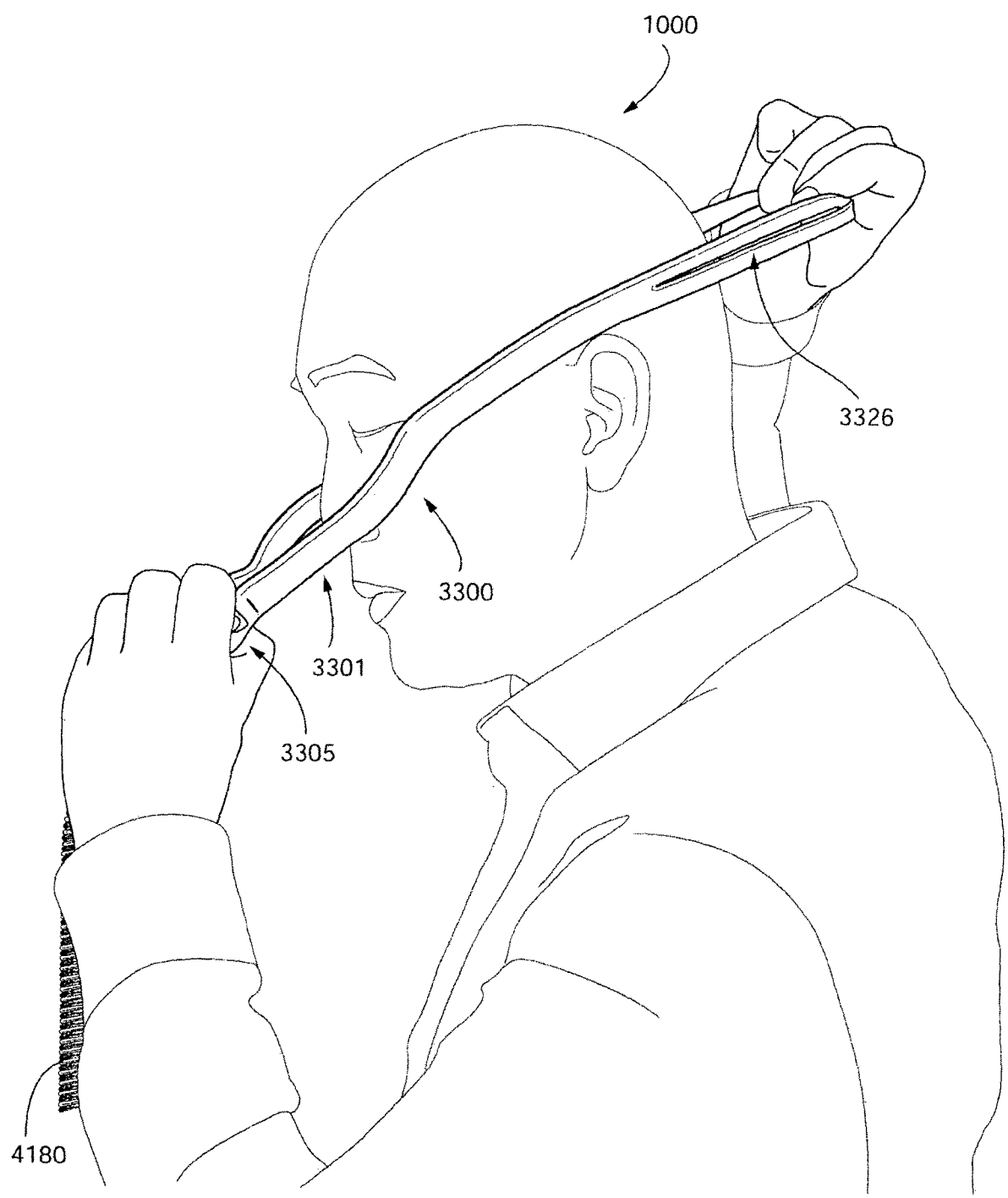
Figure 101:
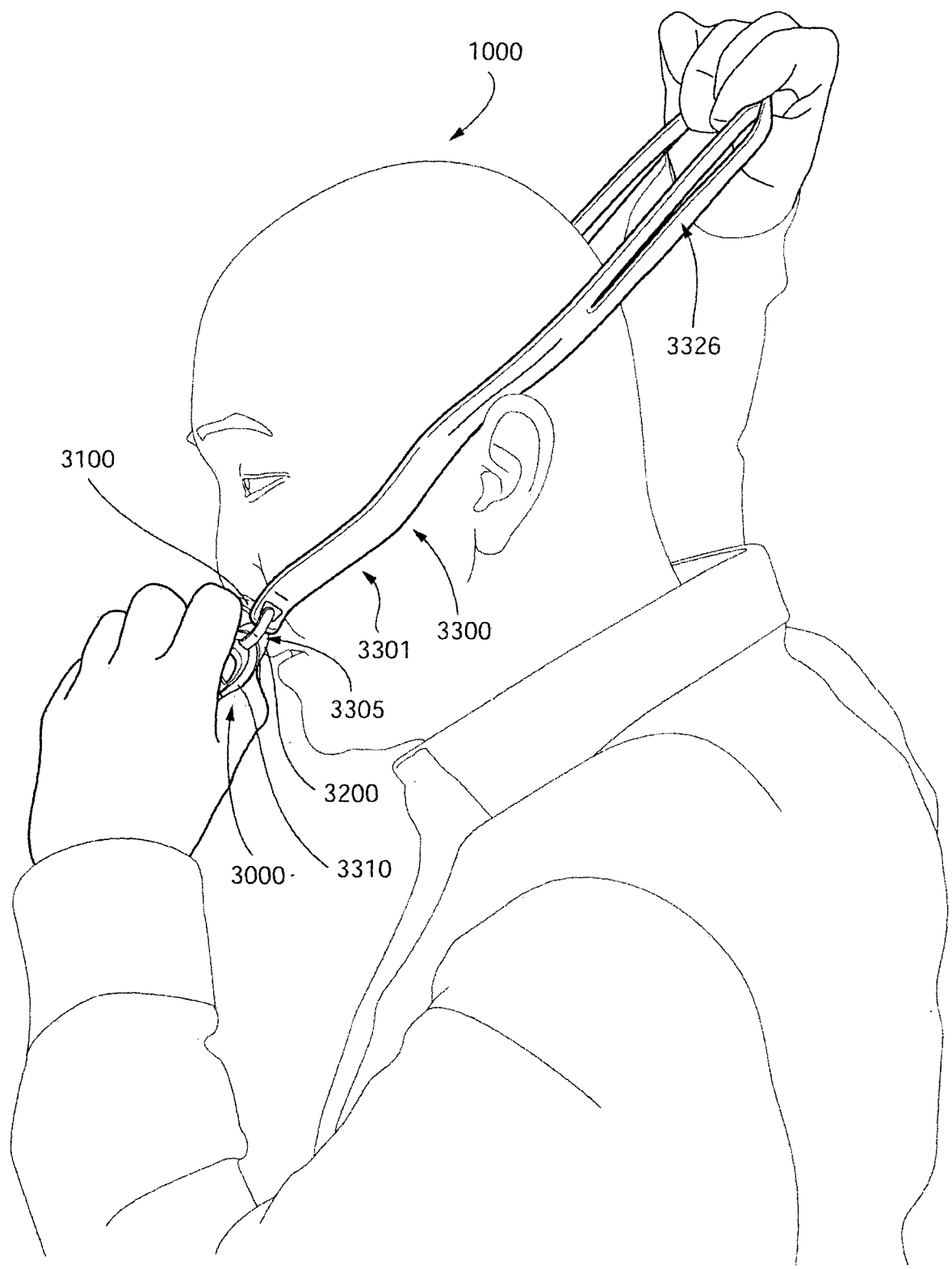
Figure 102:
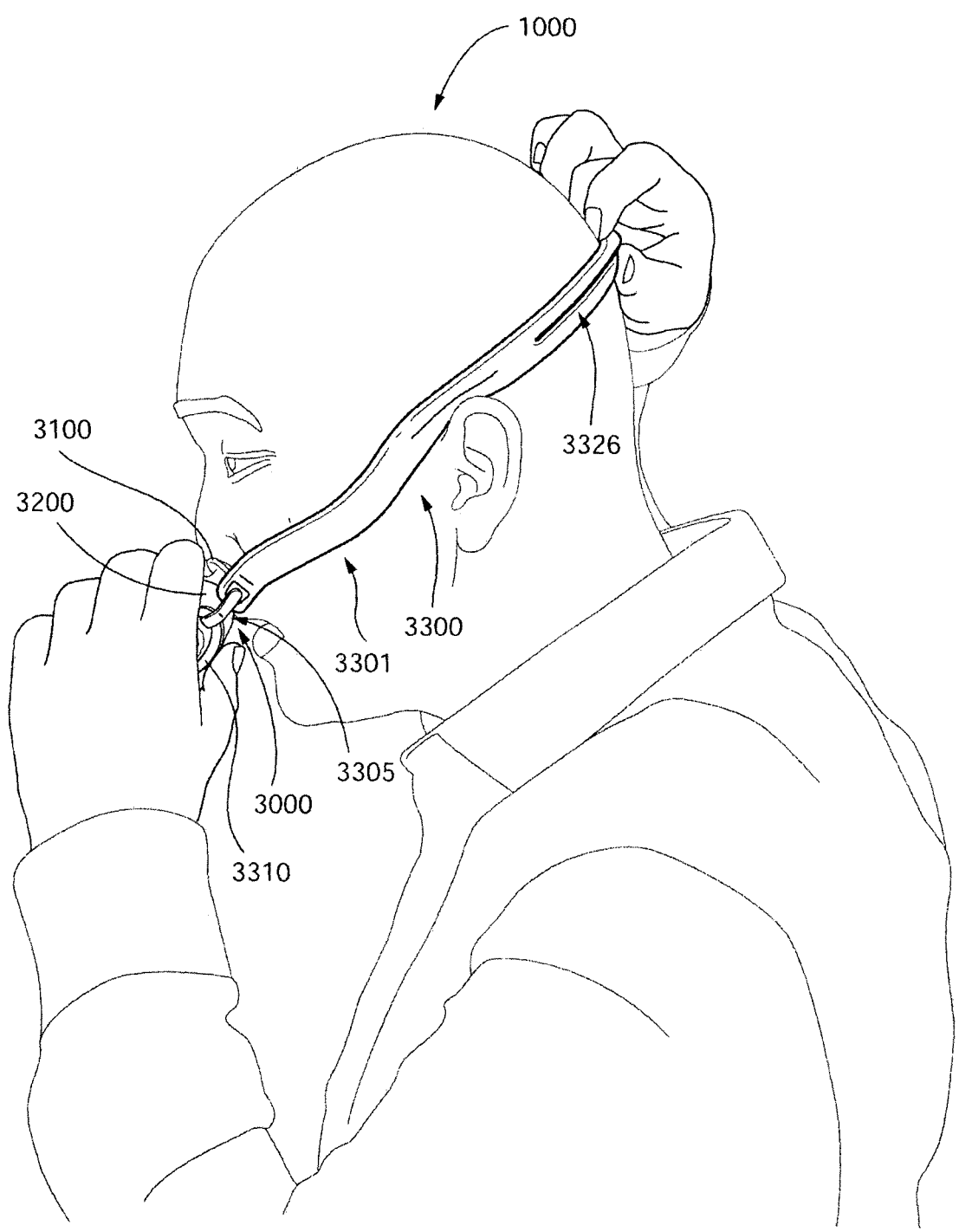
Figure 103:
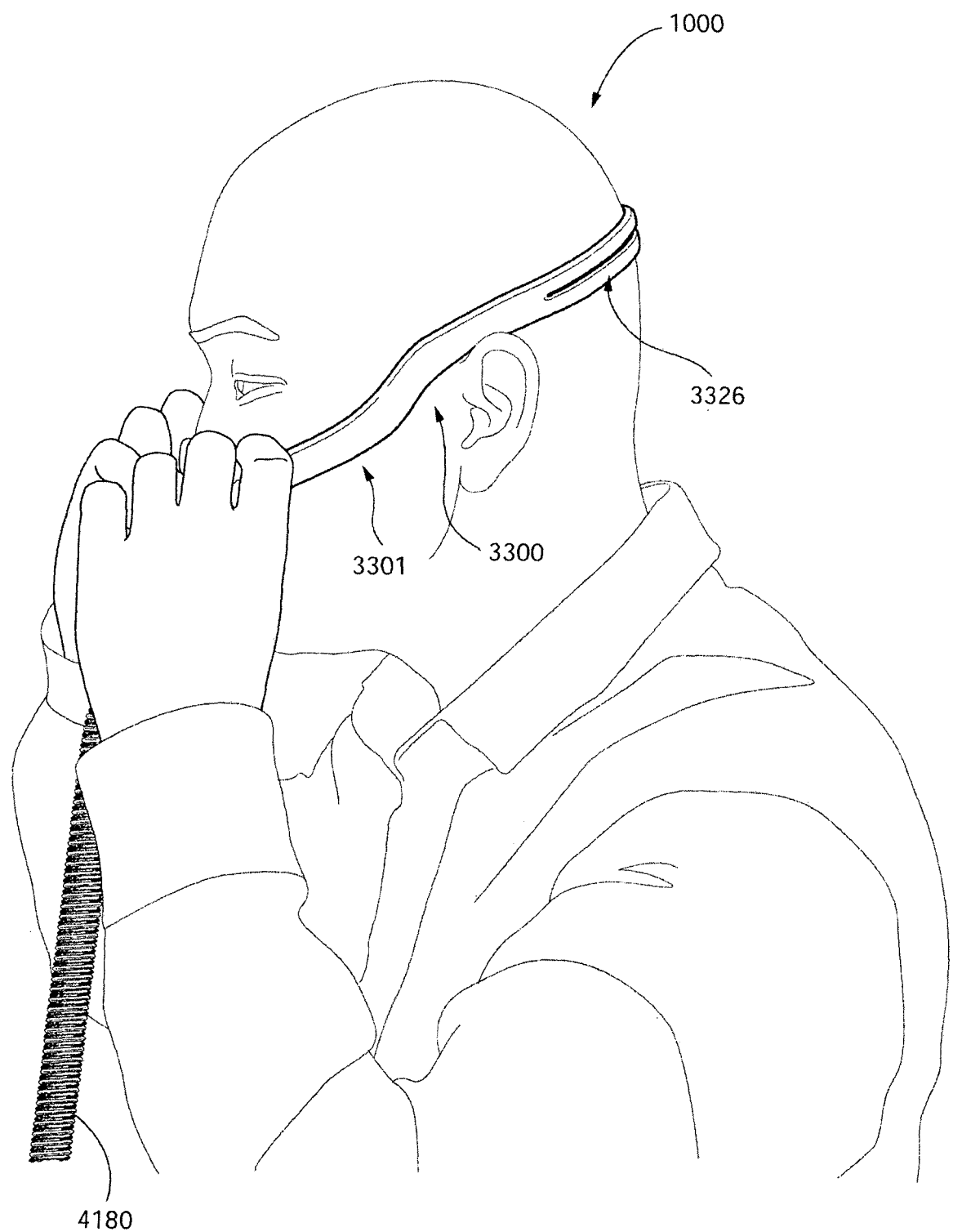
Figure 104:
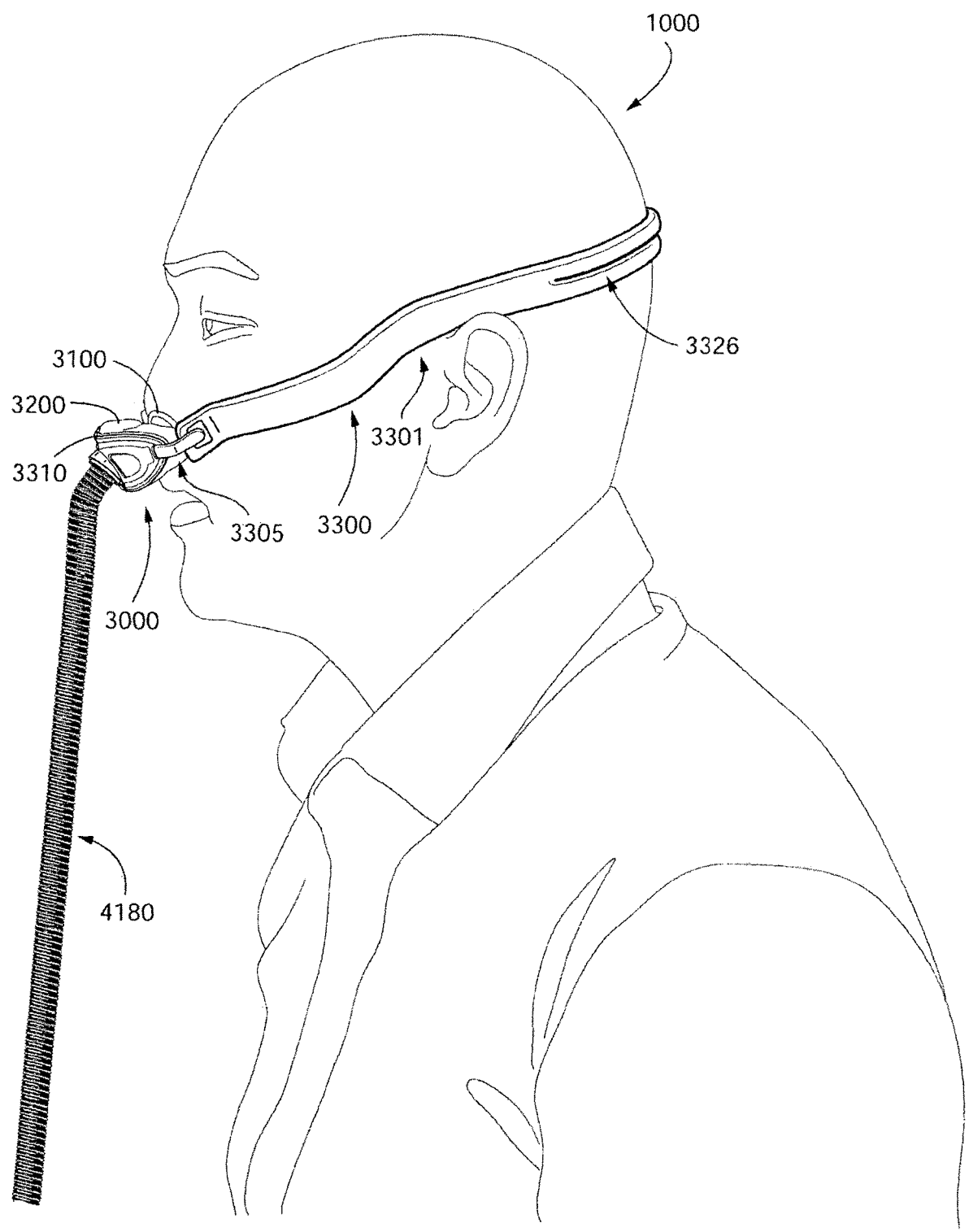

FIGS. 99 to 104 show a series of perspective views of a patient 1000 donning the patient interface 3000 and positioning and stabilising structure 3300. FIG. 99 shows the patient 1000 beginning to don the patient interface 3000 and positioning and stabilising structure 3300 by stretching the strap 3301 while holding the strap 3301 with one hand and the patient interface 3000 with the other hand. FIG. 100 then shows the patient 1000 placing the patient interface 3000 and positioning and stabilising structure 3300 on the head by raising the patient interface 3000 toward the face and pulling the strap 3301 over the back of the head. FIG. 101 then shows the patient 1000 placing the seal-forming structure 3100 against the nares with one hand while holding the strap 3301 in a stretched state near the back of the head. FIG. 102 then shows the patient 1000 locating the strap 3301 at the back of the head by beginning to release its tension sealing force. The patient 1000, in FIG. 102, is still holding the patient interface 3000 against the nose to ensure that a proper seal is retained as tension sealing force is released from the strap 3301. FIG. 103 shows the patient 1000 adjusting the patient interface 3000 against the nares to ensure a proper fit and seal as well as to locate the rigidiser arms under the cheek bones. FIG. 104 then shows the patient 1000 with the patient interface 3000 and positioning and stabilising structure 3300 donned and prepared for therapy.

FIGS. 105 to 107 show perspective views of the patient 1000 adjusting the patient interface 3000 against the nares to ensure a proper seal by the seal-forming structure 3100. From FIG. 105 to FIG. 107 the patient 1000 can be seen tilting the patient interface 3000 progressively further downward and against the nose to complete the seal against the nose with the seal-forming structure 3100. These views show the patient 1000 adjusting the patient interface 3000 with one hand, although it should be understood that the patient interface 3000 could be located and adjusted with two hands.

Figure 108:
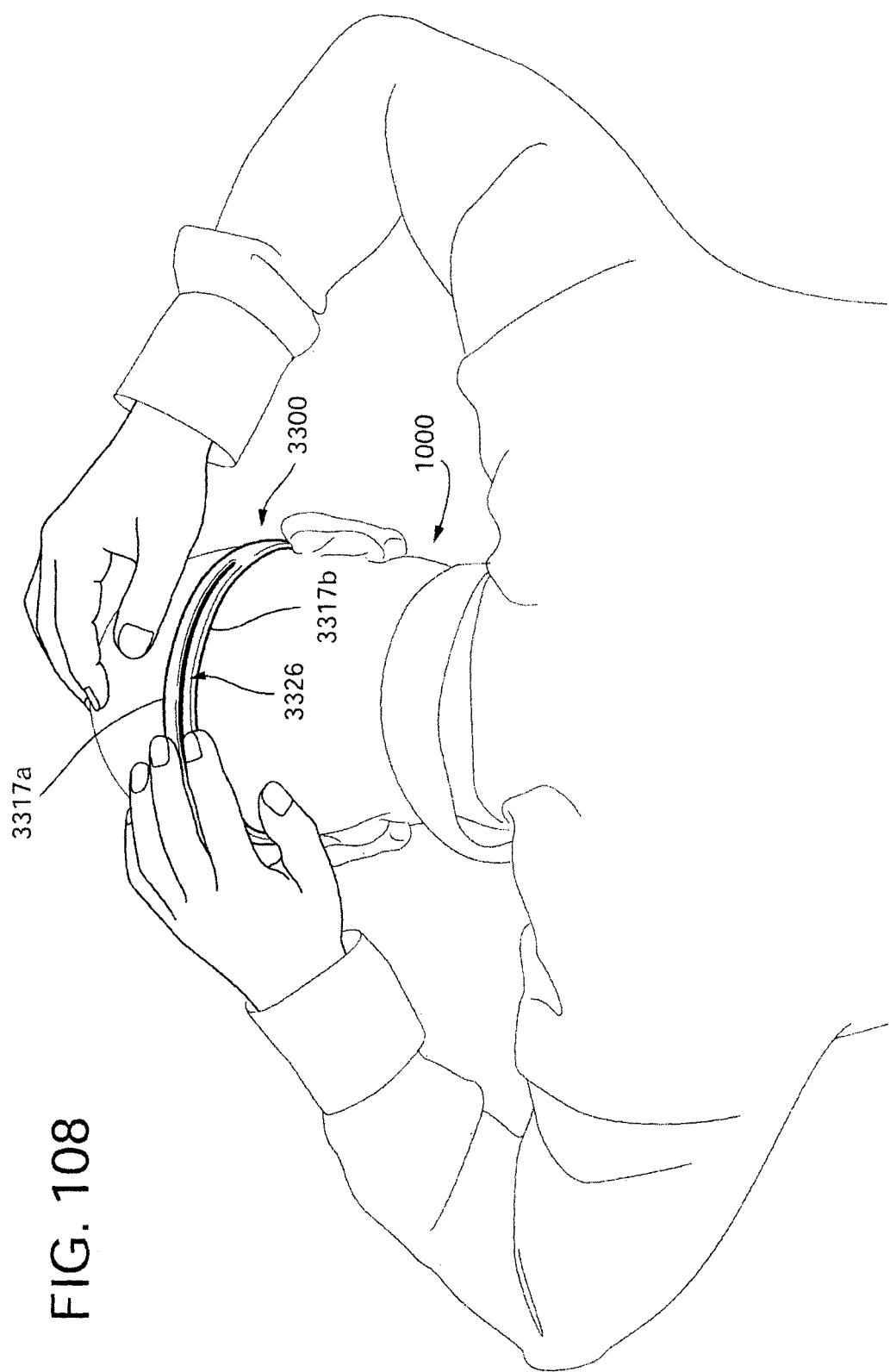
Figure 109:
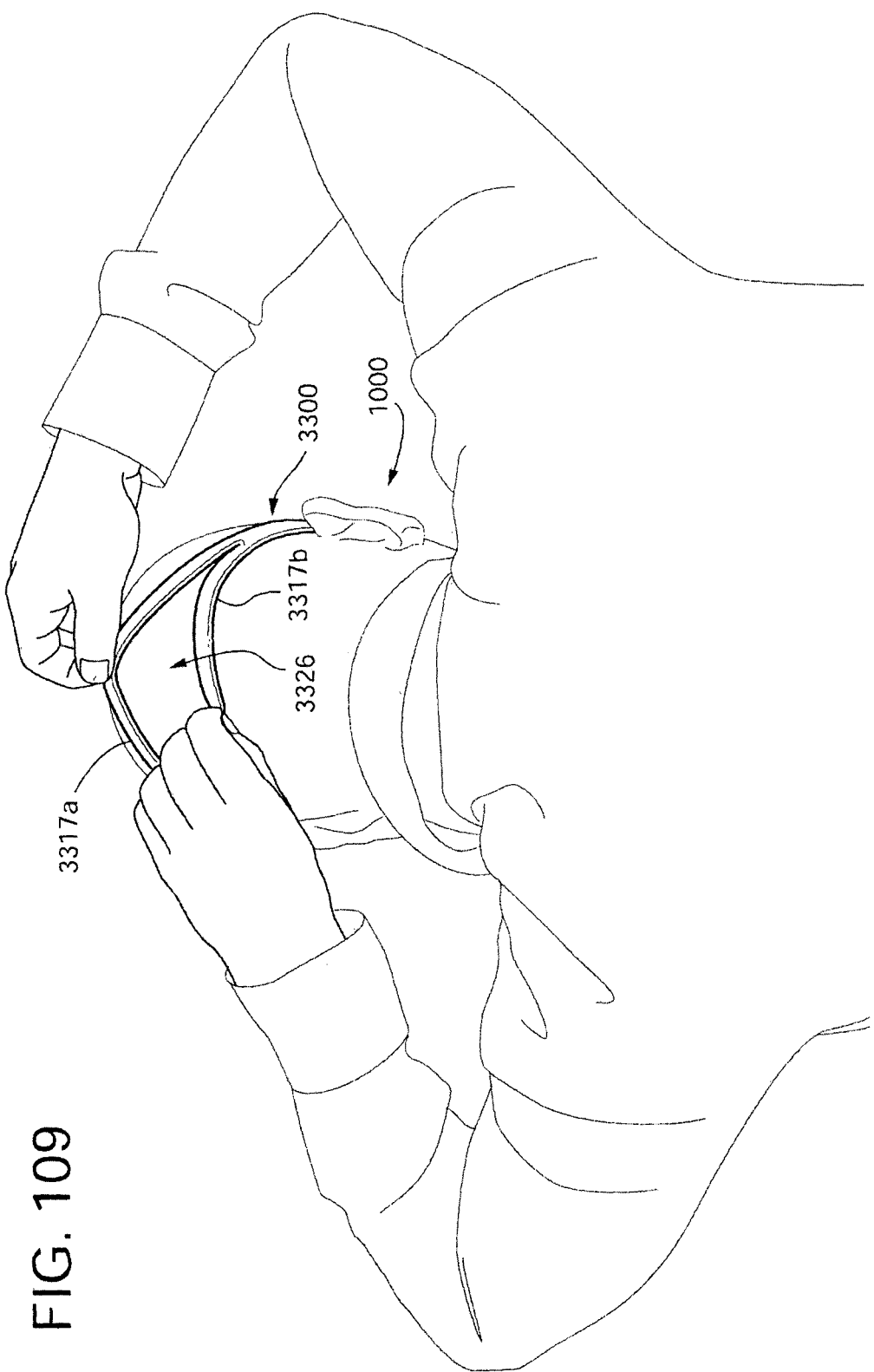
Figure 110:
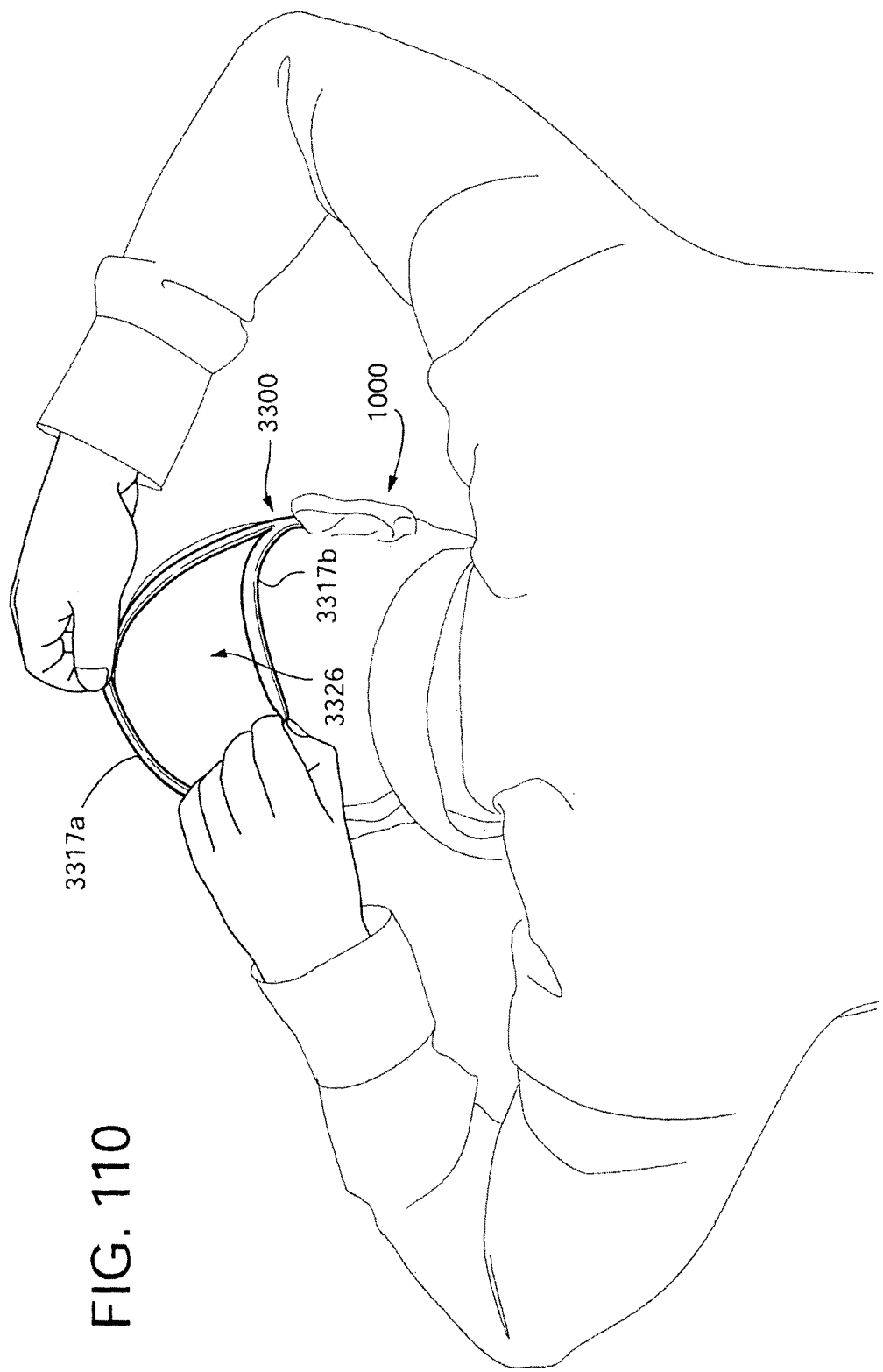
Figure 111:
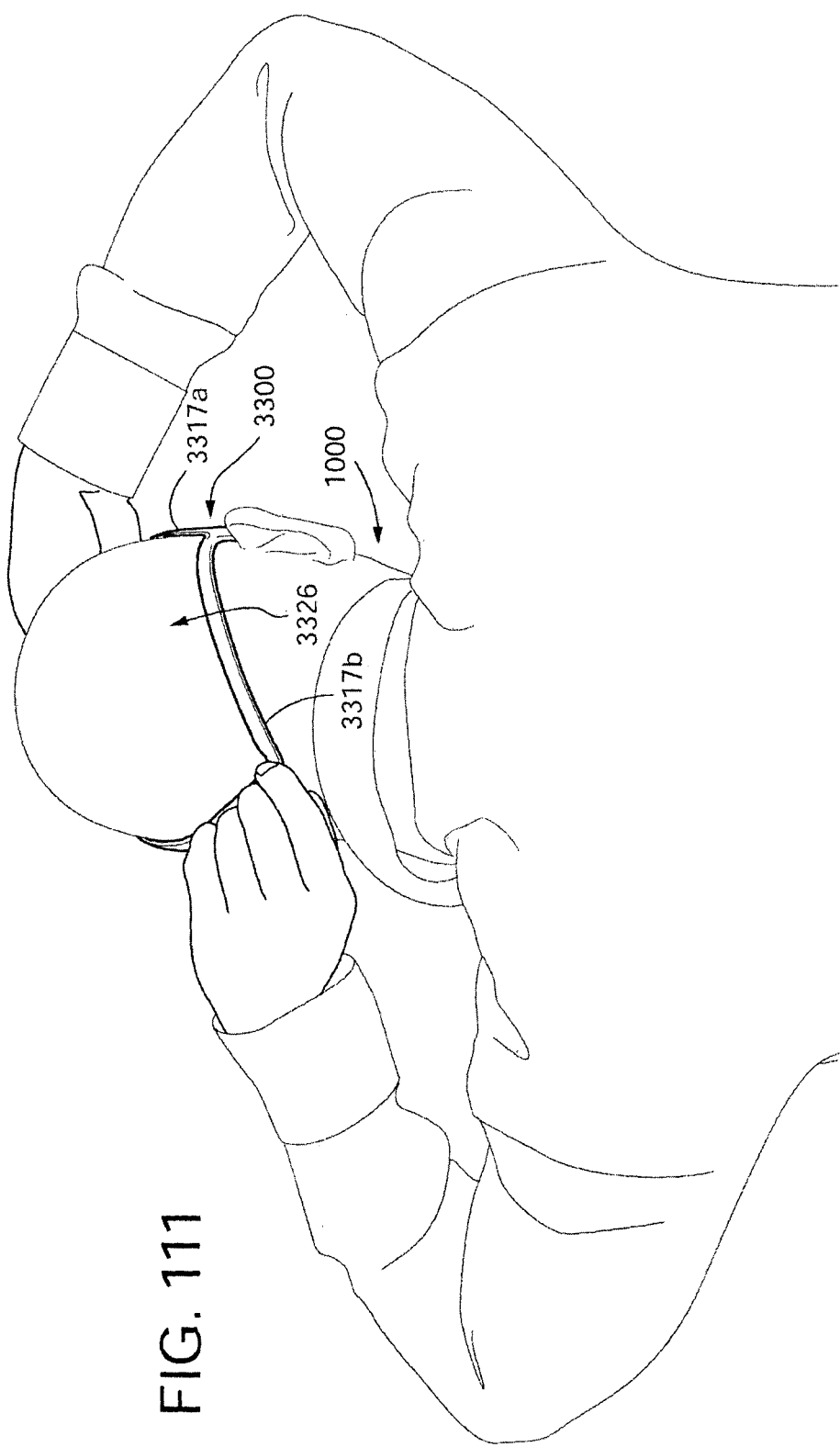
Figure 112:
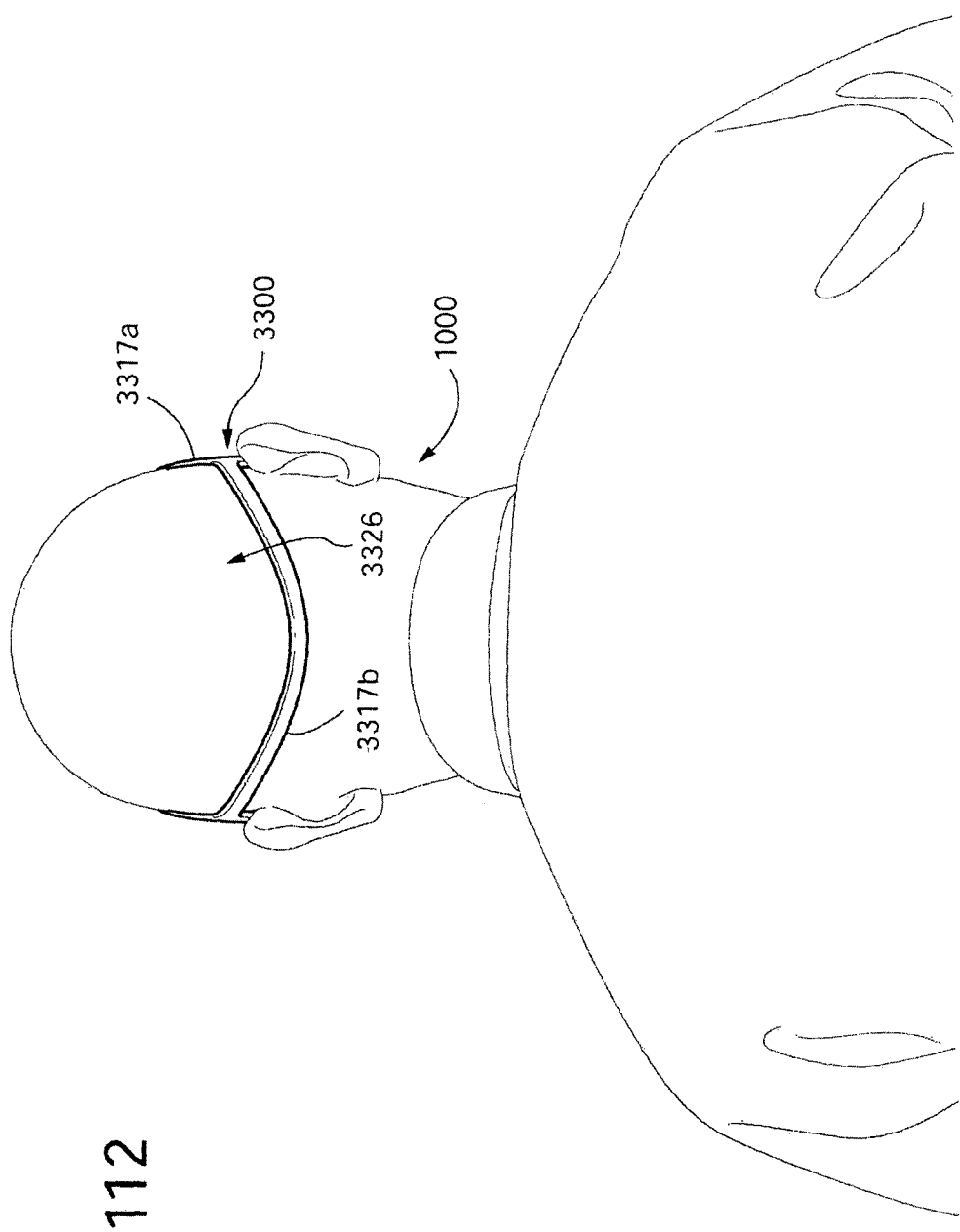

FIGS. 108 to 112 show a series of rear views of a patient 1000 adjusting the positioning and stabilising structure 3300 against the back of the head. FIG. 108 shows the positioning and stabilising structure 3300 resting against back of the head. The strap 3301 will have its largest amount of tension sealing force in this position. FIG. 109 then shows the patient 1000 grasping the upper back strap portion 3317a with one hand and the lower back strap portion 3317b with the other hand and pulling these back strap portions 3317a, 3317b apart at the split region 3326. It should be understood that by pulling these back strap portions 3317a, 3317b apart that the tension sealing force in positioning and stabilising structure 3300 is decreasing from the position shown in FIG. 108 because the back strap portions 3317a, 3317b are becoming nearer to the patient interface 3000, which is resting in a constant position against the nares. By moving the back strap portions 3317a, 3317b closer to the patient interface 3000, the stretched length of the strap 3301 is decreased thus decreasing its tension sealing force. FIG. 110 is similar to FIG. 109, however in this view the patient 1000 has pulled the upper back strap portion 3317a and the lower back strap portion 3317b further apart. It should be understood that the tension sealing force in the positioning and stabilising structure 3300 has decreased further due to the spreading of the back strap portions 3317a, 3317b. FIG. 111 shows a further view of the patient 1000 spreading the upper back strap portion 3317a and the lower back strap portion 3317b apart. Tension sealing force will be decreased again from the position shown in FIG. 110. Also, at this point the patient 1000 has nearly completed adjustment of the positioning and stabilising structure 3300 to the desired level of tension sealing force. The upper back strap portion 3317a may be located near the top of the head and the lower back strap portion 3317b may be located near or below the occipital lobe. FIG. 112 then shows the patient 1000 with the positioning and stabilising structure 3300 fully adjusted to a desired level of tension sealing force. Again, the upper back strap portion 3317a may be located near the top of the head and the lower back strap portion 3317b may be located near or below the occipital lobe. Furthermore, it should also be understood that as the tension sealing force in the positioning and stabilising structure 3300 decreases as the upper back strap portion 3317a and the lower back strap portion 3317b are pulled apart, θ increases accordingly. Although not indicated in these views θ may be about 0° in FIG. 108 and it increases through the adjustment sequence. If θ has increased to a maximum of about 180° in FIG. 112, then the tension sealing force in positioning and stabilising structure 3300 may be about 40% of the tension sealing force in FIG. 108. In another example of the present technology, it may be possible to maintain angle θ at a predetermined value at the initial point of bifurcation of the upper back strap portion 3317a and lower back strap portion 3317b, for example, if the rigidiser arm 3302 extends to the bifurcation point 3324 and splits into upper and lower arms both extending slightly into the back strap portions 3317a, 3317b. This may encourage the patient 1000 to split the back strap portions 3317a, 3317b to adjust headgear tension. Also, it reinforces the bifurcation point 3324, for example, using an external seam tape or a plastic clip on the Y-shaped section where a side strap portion 3315, 3316 converges with the back strap portions 3317a, 3317b. Such a plastic clip may provide a branding opportunity by pad printing branding and logo information on it.

In one form of the present technology, the positioning and stabilising structure 3300 has two points of connection with the frame 3310 and hence there are two rigidiser arms 3302 and a single hollow strap 3301 with split region 3326. One problem with this type of patient interface 3000 is that the split region 3326 may ride up or down depending on which back strap portion 3317a, 3317b has more pull. In order to this problem, the split region 3326 that contacts the back of the patient's head has an even distribution in pull in either direction (top to bottom). Therefore the problem of riding up or down is alleviated.

The positioning and stabilising structure 3300 may comprise at least one strap 3301 (see, e.g., FIG. 166) and at least one rigid element or rigidiser arm 3302 (see, e.g., FIG. 19). The strap may be made of an elastic material and may have elastic properties. In other words, the strap 3301 may be elastically stretched, e.g., by a stretching force and, upon release of the stretching force, returns or contracts to its original length. The strap 3301 may be made of or comprise any elastomeric material such as elastane, TPE, silicone etc. The strap material may also represent a combination of any of the above materials with other materials. The strap 3301 may be a single layer or multilayer strap. The sides of the strap 3301, particularly the sides for contacting the patient during use, may be woven, knitted, braided, molded, extruded or otherwise formed. This may be achieved by the strap 3301 being made of or comprising a layer of a material exhibiting the respective properties. The strap 3301 may comprise or is made of a textile material such as a woven material. Such material may comprise artificial or natural fibers for, on the one hand providing desired and beneficial surface properties such as tactile properties. On the other hand, the strap material may include elastomeric material for providing the desired elastomeric properties.

In the FIGS. 65 to 145, the strap 3301 is shown as being one individual strap for being attached, directly or via the frame 3310, to a seal-forming structure 3100. However, it may be appreciated that the strap 3301 may comprise multiple individual straps which are or may be connected to one another. Adjustment may be provided, however, by varying where the strap is secured to a patient interface or other rigid elements such as a connector. In addition or alternatively, adjustment could be allowed by adding a mechanism, such as slide over ladder lock clips on the back or side straps (as shown, e.g., in FIGS. 75, 76 and 166) or by otherwise adjusting the elastic length of the strap 3301 and positioning and stabilising structure 3300, respectively.

Rigidiser Arm 3302

As can be seen in FIGS. 19 and 166, an example of the present technology may comprise stiffened headgear to retain the patient interface 3000 on the patient 1000. As shown in the drawings depicting this example, the positioning and stabilising structure 3300 may contain at least one rigidiser arm 3302.

In the present example of the technology, the seal-forming structure 3100 of the patient interface 3000 is retained in a desired position on the underside of the nose of the patient 1000 by the support of rigidiser arms 3302. The positioning and stabilising structure 3300 may locate the patient interface 3000 such that it does not contact the patient 1000 except at the seal-forming structure 3100.

In certain prior art examples the patient interface may be designed to at least partially rest against the upper lip of the patient and in doing so the face of the patient's upper lip provides a measure of support to retain the patient interface in a desired location, as described in U.S. Pat. No. 7,900,635. In the present example, however, it is desired that the patient interface 3000 not rest against the upper lip of the patient 1000, as can be seen in FIGS. 18 and 19. Particularly, FIG. 19 shows the posterior wall 3220 of the plenum chamber 3200 is shown separated from the septum and/or upper lip of the patient 1000 by a gap or spacing S. This arrangement has the advantage of preventing irritation or injury to the patient 1000 at the septum and/or upper lip by contact and friction with the posterior wall 3220 of the plenum chamber 3200 during extended periods of wear. Avoidance of concentrated pressure on certain locations of the septum and/or the upper lip can prevent skin breakdown and sores from forming.

The arrangement of this particular example, wherein the patient's septum and/or upper lip is separated from the posterior wall 3220 of the plenum chamber 3200 is accomplished by rigidiser arm 3302, as can be seen in FIGS. 19 and 166. As shown in FIG. 19, the rigidiser arm 3302 of the positioning and stabilising structure 3300 may be supported against the cheek of the patient 1000, approximately above the nasolabial sulcus (see FIG. 2c). The rigidiser arm 3302 of the positioning and stabilising structure 3300 may be formed with a predetermined curve at the curved profile 3323 to approximate the curve of the patient's corresponding cheek region until the patient's cheekbone. The rigidiser arm 3302 may extend across a substantial portion of the cheek region from the point of connection with the frame 3310 until the distal free end 3302.1 of the rigidiser arm 3302. The distance between the point of connection with the frame 3310 until the distal free end 3302.1 of the rigidiser arm 3301 is about 120 mm. Rigidiser arm 3302 may extend at an angle, e.g., approximately a right angle, away from the patient's face and substantially parallel to the nasal ala. In other words, an inner surface of the main section 3333 of the rigidiser arm 3302, in particular, the curved profile 3323 contacts and extends across a substantial portion of the patient's cheek region. This contact results in the locating and locking the patient interface 3000 on the patient's face at semi-fixed position. This contact minimises any vertical movement of the rigidiser arms 3302 relative to the patient's face. Also, at least a region of the curved profile 3323 proximal to the sharp bend 3307 is intended to maintain contact with the patient's cheekbone or cheek. When the patient 1000 lies with one side of their face against a bed pillow, the force exerted against the rigidiser arm 3302 and/or some of the extension 3350 or flexible joint 3305 on the bed pillow is minimised or prevented from transmitting to the other rigidiser arm because the sharp bend 3307 and extension 3350 of that rigidiser arm 3302 largely absorb such a force before affecting the seal with the patient's airways. In other words, lateral force acting upon the positioning and stabilising structure 3300 is at least partially decoupled because the region of the curved profile 3323 is in contact with the patient's cheek and there is some absorption of this force by the extension 3350 or flexible joint 3305.

Rigidiser arm 3302 may also provide a supported decoupling of the patient interface 3000, such that the patient interface 3000 may be located in a desirable position at the underside of the patient's nose with the tension forces of positioning and stabilising structure 3300 retaining the patient interface 3000 in position not causing undesirable contact of the patient interface 3000 against the septum and/or upper lip. Furthermore, the rigidiser arm 3302 may be dimensioned such that the posterior wall 3220 is distance from the patient's septum and/or upper lip by spacing S. Additionally, the tension of the positioning and stabilising structure 3300 is transmitted primarily to the patient's cheeks across the width and breadth of rigidiser arm 3302 and not against inwardly towards the face of the patient 1000 against the nose. This exemplary arrangement is advantageous because using the tissue of the cheeks, a relatively large region of the face, to dissipate retention forces may afford the patient greater comfort, as opposed to using the patient's nose and/or upper lip, which may be more sensitive due to its cartilaginous nature. This exemplary arrangement also allows the seal-forming structure 3100 to be retained with an amount of force sufficient to create a seal against the patient's airways at the underside of the patient's nose, while not allowing the retention force to rise to the level of causing discomfort to the patient 1000.

It may be desirable to avoid contact between the rigidiser arms 3302 and the plenum chamber 3200. Thus, the plenum chamber 3200 may be made sufficiently wide so as to avoid contact with the rigidiser arms 3302.

Stretching of Headgear Strap Relative to Rigidiser Arm

In the example shown in FIG. 166, two rigidiser arms 3302 are inserted into right and left side strap portions 3315, 3316 of the strap 3301 of the positioning and stabilising structure 3300, the rigidiser arm 3302 is held in place by the surrounding strap 3301 while at the same time a sleeve-like configuration of strap 3301 allows at least a portion of the strap to stretch or move relative to the rigidiser. The rigidiser arm 3302 cannot be seen in this view as it is contained within the strap 3301.

The attachment of the strap 3301 to the rigidiser arm 3302 described in the preceding section may also effect the size of head that the positioning and stabilising structure 3300 may accommodate. In other words, by providing a greater length of strap 3301 along the rigidiser arm 3302 it may be possible to increase the total stretchable length of the positioning and stabilising structure 3300 such that even larger heads may be accommodated without needing to increase the stretchability of the strap. Furthermore, it may be possible to vary, along the length of the rigidiser 3302, where the strap 3301 is connected. This would allow for an even greater range of head sizes to be accommodated without The rigidiser arm 3302 may thus be allowed to move generally unrestrictedly along the length of the sleeve, attached to the sleeve 3301, or may be adjacent to one of its ends.

Split Back Straps of Positioning and Stabilising Structure

According to one aspect, the structure of strap 3301 and positioning and stabilising structure 3300 is of advantage. In particular, as FIG. 166 depicts, the provision of two elastic straps or strap portions 3317*a*, 3317*b* at the back allows the head to be cupped and the tension vector(s) to be adjusted by suitably positioning them, e.g. by spreading. The provision of two back strap portions 3317*a* and 3317*b* also allows better support and stability, as well as increased flexibility in avoiding specifically sensitive regions of the back of the head.

The two smaller straps or strap portions 3317*a*, 3317*b* at the back of the head may be equal in length and not adjustable except through the elasticity of the material or through increasing both in tightness equally by shortening the total length at the arms of the positioning and stabilising structure. For example, a sliding mechanism (not shown) may be provided that allows the straps to be overlapped to a different extent, thus changing the overall length of the positioning and stabilising structure 3300.

As indicated above, two or more joints could be provided creating the positioning and stabilising structure 3300 from three, four or more separate straps rather than strap 3301 being one continuous piece. This might complicate the assembly, but may simplify the manufacturing process. Joints may be placed at the bifurcation or Y-junction between the side strap portions 3315, 3316 and two back strap portions 3317*a*, 3317*b* or cantered at the back. The joints may be sewn, welded, glued, or over molded and could incorporate a high friction material to help reduce movement on the head.

In one example of the present technology, one or more threads of the strap 3301 may consist of an adhesive or glue. After the strap 3301 is manufactured with this thread, heat is applied to the strap 3301 causing the adhesive or glue thread to melt to reinforce the strap 3301 in areas at or proximal to the adhesive or glue thread.

High friction materials may also be added to the inside surface of the back and side strap portions 3315, 3316, 3317*a*, 3317*b*, to reduce the straps slipping. For the arms or side strap portions 3315, 3316 this would help the positioning and stabilising structure 3300 stay on the cheeks and at the back strap portion 3317 it could stop the positioning and stabilising structure 3300 from sliding across the back of the head. Such material may be printed, cast or molded onto the surface or incorporated into joints, sewing or welding processes as mentioned above.

The split region 3326 at the back of the patient's head may include two, three or more straps 3317*a*, 3317*b* for stability. A positioning and stabilising structure 3300 similar to the described, may be used with full face (one or more seals for the nose and mouth) or nasal masks also.

It is possible that the maximum distance permitted between the back strap portions 3317*a*, 3317*b* may be limited or constrained to prevent the back strap portions 3317*a*, 3317*b* being split apart completely or split beyond a predetermined distance. A joining strap across the split region 3326 or netting across the split region 3326 may be connected to the back strap portions 3317*a*, 3317*b* to limit their ability to split apart beyond a predetermined distance.

The Connection Between a Mask Frame and a Rigidiser Arm

According to examples of the present technology to be described in greater detail below in reference to FIGS. 35 to 64, the patient interface 1000 may include a mask frame 3310 and a rigidiser arm 3302. As will become apparent from the following description the rigidiser arm 3302 may function to direct the vector of tension generated by a strap 3301 or straps of the positioning and stabilising structure 3300 in a desired direction so as to ensure effective sealing of the seal-forming structure 3100 against the patient's airways, while directing straps 3301 of the positioning and stabilising structure 3300 away from the patient's eyes and line of sight. Thus, it should also be understood that the rigidiser arm 3302 and the mask frame 3310 must be formed and connected to facilitate an effective direction of the sealing force. It may be advantageous to allow the rigidiser arm 3302 to flex relative to the mask frame 3310 to accommodate the various shapes and sizes of patients' faces and heads. To improve patient comfort, the direction and degree of flexing between the rigidiser arm 3302 and the mask frame 3310 may be specifically controlled. A flexible joint 3305 may accomplish this or the rigidiser arm 3302 may be directly connected to the mask frame 3310.

A Flexible Joint to Connect a Rigidiser Arm and a Mask Frame

Referring to FIGS. 35 to 38, a patient interface 3000 is provided generally comprising a mask frame 3310, a rigidiser arm 3302 and a flexible joint 3305. A retaining structure 3242 may be removably detachable with the mask frame 3310. The retaining structure 3242 may hold a seal-forming structure 3100 on the mask frame 3310. The rigidiser arm 3302 may be made from a thermoset or thermoplastic. For example, Hytrel® 5556 manufactured by DuPont™ is a thermoplastic polyester elastomer which exhibits excellent creep resistance and may be used as the material for the rigidiser arm 3302. The rigidiser arm 3302 may be part of a positioning and stabilising structure 3300 to locate and retain the mask frame 3310 in position on a patient's face for delivery of respiratory therapy. In one example, the positioning and stabilising structure 3300 has two rigidiser arms 3302 at its distal ends. Each rigidiser arm 3302 may be permanently connected to opposite sides of the mask frame 3310.

An elastic fabric strap 3301 may be slipped over each rigidiser arm 3302 to form the positioning and stabilising structure 3300 as disclosed, for example, in U.S. Provisional Application No. 61/676,456, filed Jul. 27, 2012, which is incorporated by reference herein in its entirety. The elastic fabric strap 3301 may extend around the head of the patient 1000 and may be bifurcated to provide self-adjustment. The rigidiser arm 3302 may also include a protruding end 3306 that retains a pocketed end of the elastic fabric strap 3301. In an example, the rigidiser arm 3302 is inserted through a button-hole proximal to the pocketed end and into the hollow elastic fabric strap 3301. When the elastic fabric strap 3301 is stretched as the patient interface 3000 is donned, the direction of stretch and headgear tension vector of the elastic fabric strap 3301 is guided by the shape and profile of the rigidiser arm 3302. The protruding end 3306 is a fixed anchor at the base of the rigidiser arm 3302 proximal to the mask frame 3310 and provides the starting point for the stretch of the elastic fabric strap 3301. The protruding end 3306 permits the elastic fabric strap 3301 to be connected and disconnected from the rigidiser arm 3302 to facilitate washing of the elastic fabric strap 3301 separately from the mask frame 3310 and rigidiser arms 3302. The rigidiser arm 3302 also frames the face by keeping the elastic fabric strap 3301 away from the eyes and over the ears which leads to the patient interface 3000 being perceived as unobtrusive by the patient. The rigidiser arm 3302 may be generally a planar arm of a predetermined thickness. The thickness of the rigidiser arm 3302 may vary along its length and may be about 1 mm at a distal free end 3302.1 and gradually increases in thickness to 1.5 mm along the curved profile 3323 until the distal portion of the rigidiser arm 3302 proximal to the point of connection with the flexible joint 3305. Since the distal free end 3302.1 has less material relative to the other areas of the rigidiser arm 3302 there is a tendency for any flexing of the rigidiser arm 3302 to occur on or proximal to the distal free end 3302.1 first before other areas of the rigidiser arm 3302 start to flex. The order of flexing is intended to improve comfort because the distal free end 3302.1 is close to the patient's ears, cheekbones and temples which can be a particularly sensitive region of the face and conformity and less resistance to bending and deformation may be required. A sharp bend 3307 may be provided at a distal portion of the rigidiser arm 3302 proximal to the point of connection with the flexible joint 3305. The sharp bend 3307 may be at an angle of substantially 90 degrees or less. The sharp bend 3307 may also provide increased rigidity to fix the rigidiser arm 3302 in position relative to the mask frame 3310. The sharp bend 3307 may prevent or minimise stretching in a longitudinal direction. Also, the sharp bend 3307 may accommodate compression of the rigidiser arm 3302. If a force is applied to the side of a rigidiser arm 3302 in the coronal plane, the majority of the flexing may occur at or proximal to the sharp bend 3307.

The flexible joint 3305 may be provided between the rigidiser arm 3302 and the mask frame 3310. The flexible joint 3305 may be made from thermoplastic elastomer (TPE) which provides high elastic properties. For example, a Dynaflex™ TPE compound or Medalist® MD-115 may be used. The mask frame 3310 may be made from polypropylene (PP) material. PP is a thermoplastic polymer with good resistance to fatigue. An advantage of the flexible joint 3305 may be that it enables the rigidiser arm 3302 and the mask frame 3310 to be permanently connected to each other. Hytrel® and PP cannot be integrally bonded to each other by forming covalent or hydrogen bonds. Integrally bonded includes chemically bonded but without the use of an added adhesive substance. In an example, the rigidiser arm 3302 is provided with a protrusion 3309 that extends outwardly from the distal portion of the rigidiser arm 3302. Turning to FIG. 38, the inner side 3318 of the protrusion 3309 is the surface of the rigidiser arm 3302 that the protrusion 3309 extends from. An outer exposed side 3319 of the protrusion 3309 is opposite the inner side 3318 (see FIG. 38). The protrusion 3309 may have a void 3320 in a central region of the protrusion 3309. The void 3320 may extend substantially vertically through the protrusion 3309 from a top side 3321 to a bottom side 3322 of the protrusion 3309, and may be enclosed around its perimeter by the protrusion 3309. The outer side 3319 may be a substantially planar surface that extends beyond the protrusion 3309. When viewed from above, the protrusion 3309 may have a generally T-shaped cross section with the void 3320 visible in the central region. The protrusion 3309 may also serve to retain the elastic fabric strap alternatively or in addition to the protruding end 3306.

Another advantage of the flexible joint 3305 may be that it is relatively more flexible than the rigidiser arm 3302. This flexibility may be provided by the combination of the TPE material and also the structural features of the flexible joint 3305. Structurally, the flexible joint 3305 may have a predetermined thickness to enable a predetermined degree of flexing, and also the amount of curvature of the flexible joint 3305 may be selected to contribute to the degree of flexing. The flexible joint 3305 may be able to flex radially on its longitudinal axis relative to the mask frame 3310 but may be resistant to flexing in other directions. This flexibility may provide a self-adjustment function to the patient interface 3000 and may compensate for deviations to facial contours, nose dips or sleeping positions. This flexing may accommodate the anthropometric range of most patients. Greater flexibility may be required at this location compared to the flexibility within the rigidiser arm 3302 itself. Also, since flexing is restricted to a certain direction, stability of the mask frame 3310 may be improved and the position of the mask frame 3310 may be substantially maintained relative to the nose and mouth if the elastic fabric of the positioning and stabilising structure 3300 requires adjustment.

The flexible joint 3305 may be overmolded to the mask frame 3310. PP and TPE can be integrally bonded to each other. In other words, a fusion bond or chemical bond (molecular adhesion) between the flexible joint 3305 and the mask frame 3310 is possible. This may form a permanent connection between the flexible joint 3305 and mask frame 3310. The flexible joint 3305 may be overmolded to the protrusion 3309 of the rigidiser arm 3302. TPE and Hytrel® cannot be integrally bonded to each other. However, during overmolding in accordance with an example of the present technology, the TPE material for the flexible joint 3305 flows into the void 3320 of the protrusion 3309 and around the protrusion 3309. TPE material surrounds the front and rear sides and the top and bottom sides 3321, 3322 of the protrusion 3309. Consequently, a mechanical interlock may be provided to form a permanent connection between the flexible joint 3305 and the rigidiser arm 3302. The outer side 3319 of the protrusion 3309 may be flush with the outer surface of the flexible joint 3305. This is visually aesthetically pleasing.

Referring to FIGS. 42 to 46, in another example, at the distal end of the rigidiser arm 3302 may be an extension 3350. The extension 3350 may project from the outer surface of the rigidiser arm 3302 via a stem 3361. The extension 3350 may be L-shaped when viewed from above. The extension 3350 may have a sharp bend 3307 of approximately 90 degrees which separates a first section 3363 from a second section 3364 of the extension 3350. The first section 3363 may be oriented in a plane that is parallel to the outer surface of the rigidiser arm 3302 at the distal end. The end 3363A of the first section 3363 may have curved corners. The second section 3364 may have a height and thickness that is less than the first section 3363. Therefore the top and bottom edges of the second section 3364 may be set back from the top and bottom edges of the first section 3363. The rigidiser arm 3302 may also include a protruding end 3306 that retains a pocketed end 3311 of the elastic fabric strap 3301. The stem 3361 may also serve to retain the elastic fabric strap alternatively or in addition to the protruding end 3306.

The second section 3364 may have a first protrusion 3365 and a second protrusion 3366. The protrusions 3365, 3366 may extend laterally in an outwardly direction from the rigidiser arm 3302. Adjacent to the first protrusion 3365 may be a first slot 3367 and adjacent to the second protrusion 3366 may be a second slot 3368. The slots 3367, 3368 each may provide a void through the thickness of the second section 3364 and may have approximately the same height as the protrusions 3365, 3366.

A flexible joint 3305 made from TPE may be overmolded to the second section 3364 of the extension 3350 of the rigidiser arm 3302. During overmolding, TPE material may flow through the slots 3367, 3368 and surround the protrusions 3365, 3366. The majority of the second section 3364 may be enclosed by the TPE material of the flexible joint 3305. This may provide a mechanical interlock which enables the flexible joint 3305 to be permanently connected to the rigidiser arm 3302. Since the second section 3364 may have a height and thickness that is less than the first section 3363, the TPE material overmolded to the second section 3364 may not excessively protrude beyond the first section 3363. The flexible joint 3305 may also be overmolded to the mask frame 3310 to connect the flexible joint 3305 and the rigidiser arm 3302 thereto.

Similar to the previously described example, greater relative flexibility may be provided by the flexible joint 3305 relative to the rigidiser arm 3302. Flexing in this location and the control of the direction of flexing, may accommodate the anthropometric range of most patients and maintains stability of the patient interface 3000 in use.

A Direct Connection Between a Rigidiser Arm and a Mask Frame

Referring to FIGS. 39 to 41, in another example, a flexible joint 3305 made from TPE may not be required. An extension 3350 may be used. The rigidiser arm 3302 may have a main body or main section 3333 comprising the curved profile 3323 and sharp bend 3307. The rigidiser arm 3302 may also include a protruding end 3306 that retains a pocketed end of the elastic fabric strap. Along a majority of its longitudinal axis, a curved profile 3323 may be shaped to correspond to an obtuse angle to closely follow the contour of the face of a patient. At the distal end of the rigidiser arm 3302, an extension 3350 may be provided after the sharp bend 3307. The extension 3350 may project outwardly from the rigidiser arm 3302 in the coronal plane. A recess 3329 (see FIGS. 40, 50, 57, 58) may be defined in a surface of the rigidiser arm 3302 at the point the extension 3350 projects from the rigidiser arm 3302. The height of the extension 3350 may be less than the height of the main section 3333 of the rigidiser arm 3302. This may enable greater flexibility for the extension 3350 compared to the main section 3333 of the rigidiser arm 3302 because of a relative reduction of material for the extension 3350 relative to the rigidiser arm 3302. The rigidiser arm 3302 including the extension 3350 may be made from Hytrel®. Hytrel® provides the rigidiser arm 3302 with a flexural modulus of 180 MPa at 23° C. and a tensile modulus of 180 MPa (26). The enclosable section 3354 of the extension 3350 may be overmolded by the PP material of the mask frame 3310 at the edge of the mask frame 3310. This is performed in-mold and during overmolding, the PP material of the mask frame 3310 may surround the inner, outer, top and bottom surfaces of the enclosable section 3354 to permanently connect the rigidiser arm 3302 with the mask frame 3310 via a mechanical interlock. The encapsulation of the enclosable section 3354 of the extension 3350 by the PP material of the mask frame 3310 provides a mechanical retention without an integral bond between the rigidiser arm 3302 and the mask frame 3310.

The connection between the rigidiser arm 3302 and the mask frame 3310 is a hinged connection at or proximal to bend 3352. In other words, the rigidiser arm 3302 is able to pivot relative to the mask frame 3310. The position of the pivot point as far forward as possible in line with the nasal pillows and nares of the patient 1000 to cater for varying nose droop and minimize the moment arm and tube drag caused by the air circuit 4170. The flexing and rotational movement of the rigidiser arm 3302 relative to the mask frame 3310 in the coronal plane is to accommodate various head widths without excessive force, preferably, less than 1 or 2 Newtons, required to minimise or eliminate pinching of the patient's cheeks between the two rigidiser arms 3302. The distance between the two bends 3352 is about 62 mm. This spacing between the between the two bends 3352 avoids the protruding end 3306 of the rigidiser arms 3302 and extension 3350 or flexible joint 3305 touching the patient's nose proximal to the nose tip and side of the patient's nose. These areas of the patient's face may be particularly sensitive so avoidance of contact in these areas may improve comfort.

As the patient interface 3000 is donned, the rigidiser arms 3302 may be spread outwardly to accommodate various head widths. Pivoting of the rigidiser arm 3302 relative to the mask frame 3310 will occur as well as flexing of the rigidiser arm 3302 along its longitudinal axis.

Additional Features and Examples of the Present Technology

In another example the rigidiser arm 3302 may be relatively more resiliently flexible than the mask frame 3310. The rigidiser arm 3302 may also be formed so as to be flexible only horizontally, i.e., in a plane parallel to the Frankfort horizontal and the transverse plane. Moreover, the rigidiser arm 3302 may not be flexible in a vertical direction, i.e., in a plane perpendicular to the Frankfort horizontal. In other words, the rigidiser arm 3302 is more flexible in a plane parallel to the Frankfort horizontal and the transverse plane and less flexible in any other plane (preferably, not flexible). Furthermore, material of the rigidiser arm 3302 may not be stretchable or extensible. If the rigidiser arm 3302 is stretched at its ends, the curved profile of the rigidiser arm 3302 flattens. These features alone or in combination with shape and dimension may allow the rigidiser arm 3302 to flex and/or frame the face of the patient 1000 without riding or flexing up across or down against the patient's ears. In turn, this enables the elastic fabric strap 3001 to navigate above the patient's ears proximal to the Otobasion superior.

In the example shown in FIGS. 35 to 38, indicia such as a corporate logo may be provided on the outer surface 3319 of the protrusion 3309 to conceal the location of the mechanical interlock. In the example shown in FIGS. 39 to 41, the indicia may be provided on an outer surface 3355 of the extension 3350. The indicia may visually assist the patient in determining the correct orientation of the patient interface 3000 when donning the patient interface 3000, to prevent it from being donned upside down. If the indicia are also a raised/embossed surface, this may provide tactile feedback for the patient 1000 especially if they are donning the patient interface 3000 in a darkened environment.

In a further example, an adhesive accelerator may be used after surface treatment to permanently connect the rigidiser arm 3302 to the mask frame 3310, or to permanently connect the rigidiser arm to the flexible joint 3305. In this example, a mechanical interlock is not necessary.

In another example, the rigidiser arm 3302 is made from a material that can be integrally bonded with the mask frame 3310 made from PP material. The rigidiser arm 3302 may be made from a fiber reinforced composite PP material, for example, Curv® manufactured by Propex Inc. Curv® has a similar level of resilient flexibility as Hytrel®. Curv® is provided in sheet form, and requires laser cutting into the desired shape of the rigidiser arm 3302. To obtain the desired thickness for the rigidiser arm 3302, compression or layering of sheets may be performed to adjust the thickness of the rigidiser arm 3302 in certain areas. Since Curv® is made from the same material as the mask frame 3310, an integral bond is possible when the rigidiser arm 3302 is overmolded to the mask frame 3310.

The patient interface 3000 may include a nasal cradle as disclosed, for example, in U.S. Provisional Application No. 61/823,192, filed May 14, 2013, which is incorporated herein by reference in its entirety. Nasal pillows may be releasably engageable with the mask frame 3310. After the rigidiser arms 3302 are permanently connected to the mask frame 3310, the elastic fabric strap of the positioning and stabilising structure 3300 may be slipped over the rigidiser arms 3302 and secured to the rigidiser arms 3302.

Although a T-shaped protrusion 3309 has been described, it is envisaged other shapes and forms are possible, including a mushroom shaped protrusion, to permanently connect the rigidiser arm 3302 (via a flexible joint in one example) mechanically to the mask frame 3310. Although a void 3320 has been described, it is envisaged that the protrusion 3309 may not have a void but rather recesses or slots to retain the flexible joint 3305 or mask frame 3310 to the rigidiser arm 3302.

It is envisaged that it is possible to reverse the described connection arrangement and provide the protrusion extending from the mask frame 3310 or flexible joint 3305 rather than rigidiser arm 3302. In such an example the rigidiser arm 3302 would be overmolded to the flexible joint 3305 or the mask frame 3310.

It is envisaged that the flexible joint 3305 can be permanently connected to the mask frame 3310 without an integral bond. For example, a mechanical interlock may be provided to permanently connect the flexible joint 3305 to the mask frame 3310.

Although the rigidiser arm 3302, flexible joint 3305 and mask frame 3310 have been described as permanently connected to each other, it is envisaged that some or all may releasably detachable from each other using for example, a mechanical clip (snap-fit) assembly.

The Shape of a Rigidiser Arm

FIGS. 61 to 64 show a rigidiser arm 3302 according to an example of the present technology plotted in two and three dimensions. FIGS. 61 to 63 show three two dimensional views of a rigidiser arm 3302 according to an example of the present technology plotted on a grid. FIG. 61 shows the X-Y plane, FIG. 62 shows the X-Z plane, and FIG. 63 shows the Y-Z plane. The origin is also indicated in these views for orientation purposes. Numbered coordinates are also shown in each of these and these coordinates may define the curve of the rigidiser arm 3302 in these planes.

The following chart lists the coordinates of the profile of the rigidiser arm 3302 shown in these views. It should be understood that each coordinate is numbered consistently across each of the four views.

| Point # | X | Y | Z |
|---|---|---|---|
| 1 | 26.67 | 14.25 | 12.76 |
| 2 | 22.00 | 26.87 | 24.92 |
| 3 | 27.30 | 28.57 | 26.37 |
| 4 | 37.94 | 32.84 | 30.10 |
| 5 | 46.72 | 37.84 | 34.57 |
| 6 | 59.77 | 51.55 | 45.79 |
| 7 | 65.02 | 61.69 | 52.45 |
| 8 | 68.36 | 73.68 | 56.36 |
| 9 | 69.09 | 83.53 | 55.98 |
| 10 | 69.78 | 94.70 | 54.31 |
| 11 | 69.06 | 102.83 | 54.02 |
| 12 | 68.69 | 110.47 | 55.36 |
| 13 | 72.25 | 113.84 | 51.65 |
| 14 | 73.00 | 110.04 | 49.69 |
| 15 | 73.70 | 103.72 | 48.28 |
| 16 | 73.81 | 95.03 | 48.56 |
| 17 | 73.26 | 86.38 | 49.37 |
| 18 | 71.54 | 75.71 | 48.65 |
| 19 | 67.84 | 66.29 | 44.75 |
| 20 | 60.55 | 55.68 | 36.66 |
| 21 | 52.68 | 48.30 | 29.33 |
| 22 | 43.87 | 42.88 | 23.34 |
| 23 | 33.65 | 38.87 | 18.62 |
| 24 | 27.58 | 37.35 | 16.76 |
| 25 | 21.65 | 36.15 | 15.26 |
| 26 | 26.67 | 22.22 | 2.56 |

FIG. 64 shows a further view of the rigidiser arm 3302 depicted in FIGS. 61 to 63 in three dimensions. The X, Y, and Z axes are indicated, as well as the origin, to aid in orientation.

The shape of the curve of the rigidiser arm 3302 is intended to closely follow the patient's cheek. With the elastic fabric strap 1200 covering the rigidiser arm 3302, the relative position of the rigidiser arm 3302 in contact with the patient's cheek during use is such that it does not slip on the patient's face. For example, the rigidiser arm 3302 may sit slightly below the patient's cheekbone which prevents the rigidiser arm 3302 from sliding upwards. Also, contact between most of or all the inner side surface of the rigidiser arm 3302 and the patient's face may increase friction to prevent slippage and ultimately minimise disruption of sealing forces. The shape of the curved profile 3323 of the rigidiser arm 3302 directs the positioning and stabilising structure 3300 between the eyes and ears over the majority of the anthropometric range. This orientation is advantageous because it is aesthetic and unobtrusive from the perspective of the patient 1000 and the patient's bed partner 1100. When viewed from above, the curved profile 3323 of the rigidiser arm 3302 has a larger radius than the rigidiser arm 3302 when viewed from the side.

The Flexibility of a Rigidiser Arm

As described earlier and referring to FIGS. 52 and 55, the rigidiser arm 3302 is more flexible in certain directions at certain locations along the rigidiser arm 3302. Flexural stiffness of the rigidiser arm 3302 is compared. For comparative purposes, the flexibility of the rigidiser arm 3302 is measured against rigidised headgear of some prior masks by ResMed Limited in an outwardly lateral direction in the coronal plane and in the inferior vertical direction in the sagittal plane.

| Mask name | Mask type | Newtons of force (N) required to displace upper distal tip of rigidiser arm by 5 mm | |
|---|---|---|---|
| | | Vertical Down | Laterally Outwards |
| Present Technology | nasal pillows | 0.132 | 0.0143 |
| ResMed Pixi | paediatric nasal | 1.107 | 0.0356 |
| ResMed Mirage Swift LT | nasal pillows | 1.15 | 0.0258 |
| ResMed Mirage Swift I | nasal pillows | 0.966 | 0.0647 |
| ResMed Mirage Vista | nasal | 4.35 | 0.0776 |

This comparison shows the differences in force (in Newtons) required to displace the upper distal tip of a rigidised headgear component when connected to a mask frame by a distance of 5 mm. Choosing the upper distal tip of a rigidised headgear component as the location to measure is because this location comes into contact with a sensitive facial area and certain types of flexibility provides comfort without compromising seal stability. Measuring the direction of flexibility in an outwardly lateral direction in the coronal plane (laterally outwards) is intended to measure the ability of the rigidiser arm 3302 to accommodate patients with large face widths as shown in FIG. 52 in broken line. The resilient flexibility of the rigidiser arm 3302 allows the patient interface 3000 to more precisely fit a wider range of facial shapes. For example, the same patient interface 3000 could be used on patients with a narrow angular face (the so-called crocodile shape) as those with a wider flatter face (the so-called panda shape). Measuring the direction of flexibility in the inferior vertical direction in the sagittal plane (vertical down) is intended to measure the ability of the rigidiser arm 3302 to handle tube torque exerted by the air circuit 4170 during therapy as shown in FIG. 55 in broken line. Both measurements are taken using an Instron machine with a 50N load cell.

For measuring the vertical down direction, each mask is secured to a plate and sits level with it and has the rigidised headgear component at an angle that would be normally be on a patient's face. This plate is fastened to a large circular base plate used for the Instron machine. The rigidised headgear component is held in a jig to prevent twisting and slipping and this jig is manually lowered such that it makes contact with the upper distal tip of the rigidised headgear component. The Instron machine is zeroed at this height position. Next, compression extension of 5 mm is applied at a rate of 50 mm/minute, and the measurements are recorded.

For measuring the laterally outwards direction, a spacer and a 90 degree elbow are secured to a first plate. Each mask is secured to a second plate and sits level with it and has the rigidised headgear component at an angle that would be normally be on a patient's face. A spring clamp is used to fix the second plate with the 90 degree elbow on the first plate such that the first plate is held perpendicular to the second plate. A large prong is used to locate it to the upper distal tip of the rigidised headgear component. The Instron machine is zeroed at this height position. Next, compression extension of 5 mm is applied at a rate of 50 mm/minute, and the measurements are recorded.

The measurements show that the rigidiser arm 3302 connected to the frame 3310 is more flexible in both directions by a significant factor. For accommodating large face widths, the rigidiser arm 3302 is 1.8 times more flexible than the second most flexible mask in this direction (ResMed Mirage Swift LT). For accommodating tube torque, the rigidiser arm 3302 connected to the frame 3310, the rigidiser arm 3302 is 8.39 times more flexible than the second most flexible mask in this direction (ResMed Pixi). By having a more flexible rigidiser arm 3302 when displaced in these directions provides the patient 1000 with greater comfort, less likelihood of seal disruption caused by tube torque and therefore leads to increased patient compliance with therapy in terms of frequency of use and therapy duration.

Relative flexibility of the rigidiser arm 3302 in different directions is also an important consideration. If flexibility in the vertical down direction is too high (i.e. equal to the laterally out direction), there may be seal instability. In one example, the rigidiser arm 3302 is more flexible in the laterally out direction than the vertical down direction. The rigidiser arm 3302 is 9 to 10 times more flexible in the laterally out direction than the vertical down direction. Preferably, the rigidiser arm 3302 is about 9.23 times more flexible in the laterally out direction than the vertical down direction. Tube torque may also be addressed in conjunction with other mask components such has the short tube 4180 (e.g. making it lighter weight, more slinky or more flexible) or the use of a swivel connector, ball and socket joint or gusset or pleated section. However, varied facial widths are predominantly addressed by the flexibility of the rigidiser arm 3302 and therefore the rigidiser arm 3302 needs to be more flexible in the laterally out direction compared to the vertical down direction.

Some rigidised headgear components of prior masks are more rigid than the frame. Typically, these stiff headgear components use threaded arms and bolts to manually adjust the headgear to fit the patient's head. Although a flexible frame may improve mask comfort, provide a good seal, minimise inadvertent leak and minimise the risk that headgear straps are too tight for low pressure level for therapy, some difficulty would arise if the flexible frame was needed to be releasably detachable with a seal-forming structure. Seal-forming structures are resiliently flexible so that they form a seal against the patient's airways. If both the seal-forming structure and frame are of similar flexibility (i.e. very flexible or floppy), it would be difficult for a patient 1000 to engage these two parts together, especially a patient with arthritic hands in a darkened room.

Some rigidised headgear components of prior masks are detachable from the frame. Typically this is by way of a snap-fit or clip connection between the rigidiser arm and the mask frame, both of which are rigid and stiff components. This type of hard-to-hard connection between the rigidiser arm and frame may result in less flexibility at the point of connection which means more force is required to flex at this point causing discomfort for patients with larger face widths since a pinching force may be experienced when the rigidiser arms are forced to flex outwardly. Some of these rigidiser headgear components have the hard clip at the distal end of the rigidiser arm for releasable connection with the frame. The hard clip is permanently connected to a headgear strap which may damage a washing machine tub or other laundry items when the headgear is washed in a washing machine. Also, some of these rigidised headgear components tend to require a patient interface with a wider frame which means that the headgear straps commence from the frame position at a larger distance apart from other. The wider frame may have integrally formed lateral arms which are considered part of the frame as they are made from the same material. A wider frame may be perceived by patients 1000 and their bed partners 1110 as more obtrusive and aesthetically undesirable because they cover a larger footprint on the face. In contrast, in one example of the present technology, the rigidiser arm 3302 is made from a material that is more flexible than the frame 33310 but less flexible than the strap 1200. In other words, the strap 1200 is the most flexible component of the positioning and stabilising structure 3300 as it is made from an elastic fabric. The second most flexible component of the positioning and stabilising structure 3300 is the rigidiser arm 3302 which is made from Hytrel® in one example. The most rigid or stiff component is the frame 3310 which not intended to flex, stretch or bend easily or at all because it is the seal-forming structure 3100 that is meant to form a seal with the patient's airways by resilient deformation. The differences in flexibility of individual components can control the amount of flexing at certain locations and also determine the order that certain components start to flex when a certain force is applied i.e. tube torque or accommodating a larger face width. The differences in flexibility of individual components may also decouple forces before they can begin to disrupt the seal of the seal-forming structure 3100 in a specific manner or sequence. These factors aim to address the requirements of comfort, stability and provision of a good seal at the same time for a patient interface 3000. Another advantage of the rigidiser arm 3302 is that the same sized rigidiser arm 3302 may be used for patient interfaces 3000 with different sized seal-forming structures 3100 or different sized headgear straps 3301. When a rigidiser arm 3302 is flexed inwardly, it is likely to make contact with the sides of patient's nose first before the making contact with the nasal pillows 3130 and dislodging the seal. Then inward range of movement of the rigidiser arms 3302 is limited by the patient's nose and therefore disruption of the sealing force by movement in such a direction is minimised or eliminated.

Vent 3400

In one form, the patient interface 3000 may include a vent 3400 constructed and arranged to allow for the washout of exhaled air (including exhaled carbon dioxide).

One form of vent 3400 in accordance with the present technology comprises a plurality of very small holes, in other words, a multi-hole vent. Two or more multi-hole vents may be provided on the frame 3310. They may be located on both sides of the connection port 3600 for an air circuit 4170. These holes may be the interspaces between the fibers of a textile material. Alternatively, these holes may be microholes (1 micron or less) defined in a substrate of a semi-permeable material using a laser drill operating in the ultraviolet spectral range. Laser drilled microholes may be straight-walled or tapered/trumpet shaped. Another way to create microholes is by using a chemical etchant after masking off areas of the substrate. There may be about 20 to about 80 holes or about 32 to about 42 holes or about 36 to about 38 holes. In one example, if this form of vent 3400 is insert molded, the direction of the holes through the thickness of the vent 3400 may be modified to be skewed rather than perpendicular. This may avoid exhaled air (including exhaled carbon dioxide) blowing directly into the face of a bed partner 1100 if the patient 1000 is facing him or her. In one example, the final number of holes may be determined by blanking off some holes from an original larger number of holes. For example, there may 40 holes and 2 holes are occluded (by filling) so that the final number of holes is 38 holes. The ability to selectively occlude holes both in terms of the quantity and the position of the holes to be occluded provide increased control over the air flow rate and the air diffusion pattern.

Referring to FIGS. 146 to 152, the patient interface 3000 is a nasal pillows mask and preferably two vents 3400 are located in the plenum chamber 3200 of a mask frame 3310 or specifically located in a cushion clip (that may be preassembled with a cushion) of a mask frame 3310. A connection port 3600 or short tube 4180 is located between the two vents 3400. Referring to FIGS. 153 and 154, a method for manufacturing a patient interface 3000 for the treatment of respiratory disorders is provided. A porous textile is received (51) for processing. The method comprises cutting (57) a vent portion 72, 73 from the textile. The textile is formed by interlacing fibers to form an interlaced structure defining tortuous air paths for air to pass therethrough. The textile has a predetermined amount of porosity. The vent portion is held (59) in a mold. The held vent is permanently connected (60) to a mask frame 3310. The vent portion and mask frame 3310 may both be made from a plastic material. This forms a vent 3400 for the patient interface 3000 to washout exhaled air (including exhaled carbon dioxide).

Any type of cutting tool 67 may be used to cut the vent portion 72, 73 from the textile 65, for example, a laser or mechanical cutter. More than one vent portion can be cut from the textile 65 at the same time, and preferably two vent portions are cut to form two vents at the same time. If two are cut from roughly the same region of the textile 65, the airflow rate and material properties of the two vent portions may sometimes be substantially similar. This assists in determining and locating defective material that has been supplied and also reduces the amount of calibration for equipment to adjust the airflow rate if required. In another example, where heat staking by a staking punch 68 is required, rather than cutting the vent portion 72, 73 before heat staking, the vent portion 72, 73 can be cut from the textile 65 after heat staking. In such a scenario, the first cutting by the cutter 67 can be eliminated.

In one example of the present technology, the material of the interlaced fibers is a thermoset or thermoplastic which may include polyester, nylon, polyethylene and preferably polypropylene. In a specific example, the textile 65 may be SEFAR material Tetex Mono 05-1010-K 080 woven polypropylene material. A thermoset may also be used. The textile is typically provided in the form of a roll or ribbon 65 before the cutting step. The weave of the textile 65 is preferably a satin weave. However, other weaves are envisaged including plain weave, plain reverse Dutch weave and twill weave. The textile 65 may also be knitted (e.g. warp knitted) instead of woven. The voids or holes defined by the knit/weave of fibers through the textile 65 do not necessarily have a uniform dimension since there is some variation between the positioning, spacing and compression of the fibers in the weave of the textile. The voids are preferably not straight through holes but rather define a tortuous air flow path between adjacent fibers through the thickness of the textile 65. A tortuous air flow path may have different pressure regions (higher or lower) along the air path. A tortuous air flow path significantly diffuses the air flow and thereby reduces noise. If the voids were straight through holes, then the fibers of the textile 65 may be arranged in the form of a mesh grid or a matrix. Advantageously, the air flow exiting from the vent 3400 is non-linear, avoids laminar flow and a wide plume with turbulent flow is generated.

The patient interface 3000 includes nasal mask, full-face mask or nasal pillows. The mask frame 3310 of the patient interface 3000 has at least one vent 3400, preferably, two vents 3400. If there are two vents 3400, a left vent is positioned on the left side of the anterior surface of the mask frame 3310 and a right vent is positioned on the right side of the anterior surface of the mask frame 3310. The left and right vents 3400 are separated by an aperture or connection port 3600 for receiving a short tube 4180 operatively connected to a PAP device 4000. Alternatively, a single continuous vent 3400 positioned in the center of the mask frame 3310 is possible and the short tube 4180 is connected to a side of the mask frame 3310. The single continuous vent 3400 may have a superficial surface area equivalent to the combined superficial surface area of two vents 3400.

In an example where two or more vents 3400 are provided to the mask frame 3310, the total or average airflow rate through all the vents 3400 is used to obtain the desired airflow rate by selecting vent portions with different airflow rates. For example, a first vent portion with a low airflow rate may be used with a second vent portion with a high airflow rate. The two vent portions combined may then provide an average airflow rate that is the desired airflow rate.

The vent portion is cut or removed from the textile by laser cutting, ultrasonic cutting or mechanical cutting or heat cutting (using a hot anvil). Laser, ultrasonic and heat cutting because they cut and fuse the peripheral edge of the vent 3400 to eliminate stray fibers with loose ends at the peripheral edge of the vent 3400. A laser cutter 69 can be used for laser cutting. Laser, ultrasonic and heat cutting also assists with subsequent overmolding because it flattens the peripheral edge of the vent and makes it easier to overmold compared to an uneven edge. Consequently, trapped air bubbles are avoided at the bonding location between the vent 3400 and mask frame 3310, resulting in the mask frame 3310 with the integrated vent 3400 being highly visually appealing and structurally reliable.

The permanent connection can be obtained by molecular adhesion using overmolding, co-injection molding or two shot (2K) injection molding. This produces an integral bond and is strengthened when the materials of the vent portion with the mask frame 3310 interact by forming covalent bonds or hydrogen bonds. Some molds allow previously molded parts to be reinserted to allow a new plastic layer to form around the first part. This is referred to as overmolding. The overmolding process involves the use of two materials to form one cohesive component. There are two types of overmolding: insert and "two-shot (2K)".

Two-shot or multi-shot molds are designed to "overmold" within a single molding cycle and must be processed on specialized injection molding machines with two or more injection units. This process is actually an injection molding process performed twice. A high level of molecular adhesion is obtained. The method for manufacturing a patient interface 3000 as described may be performed by overmolding the vent portion of textile to the mask frame 3310. The vent portion is held in a mold 70 and a molding machine 71 overmolds the vent portion to the mask frame 3310. Since the textile 65 and mask frame 3310 are preferably made from the same plastic material, overmolding performs a fusion of material between the vent portion of textile and mask frame 3310 which is structurally strong and a permanent bond. In the final assembled patient interface 3000, it is virtually undetectable by the unaided human eye that the vent 3400 and mask frame 3310 are two distinct parts.

The vent 3400 has a maximum cross-sectional width of about 16 mm to about 21 mm, preferably, 18.2 to 18.6 mm, and a maximum cross-sectional height of about 19 mm to about 25 mm, preferably, 21.6 mm to 22 mm, and a thickness of about 0.36 mm to about 0.495 mm, preferably, 0.40 to 0.45 mm. Therefore the superficial area of two vents 3400 is about 800 mm$^2$. The superficial area of the porous region of the vent 3400 may be about 201.6 mm$^2$ to about 278.6 mm$^2$, preferably, 240 mm$^2$. Therefore, for two vents 3400 the superficial area of the porous region is about 480 mm$^2$ to 500 mm$^2$. The anterior side of the mask frame 3310 has a superficial area of about 1800 mm$^2$. The superficial area of the vents 3400 comprises at least 35% of the superficial area of the anterior side of the mask frame 3310. Preferably, the two vents 3400 comprise 40% to 60% of the anterior side of the mask frame 3310. Preferably, the two vents 3400 comprise 45% to 55% of the anterior side of the mask frame 3310. More preferably, the two vents 3400 comprise about 50% of the anterior side of the mask frame 3310. The interlaced fibers of the vent 3400 provide a semi-rigid woven structure which it to form a significant area of the anterior surface of the mask frame 3310. The vent 3400 has sufficient rigidity that is able to support its own weight under gravity and does not fold over itself when there is tube torque, and is not floppy. Some prior masks with a vent made of loose fabric cannot maintain their shape, geometry and profile during breathing cycles of the patient (inhalation and exhalation) and therefore the vent will fold over itself during therapy. When such a prior vent folds over itself, the porous region of the vent is reduced by a percentage in a random manner because the folded over sections may partially or fully occlude the vent at these folded over sections. This leads to insufficient washout of exhaled air (including exhaled carbon dioxide). In contrast, the vent 3400 of the present technology does not fold over itself and therefore can ensure that the porous region of the vent 3400 maintains a substantially constant rate of washout for the exhaled air during breathing cycles of the patient 1000 leading to proper washout of exhaled air (including exhaled carbon dioxide) during therapy.

In one example, the airflow rate of the vent portion of the textile 65 is first measured (52) by an airflow meter 66. A determination (53) is made on whether there is a difference between the measured airflow rate and a desired airflow rate. If the airflow rate through the vent portion exceeds (56) a predetermined range, the amount of porosity of the vent portion is selectively reduced (54). The desired predetermined range is about 42 to about 59 liters per minute at 20 cm H$_2$O pressure, preferably, about 47 to about 55 liters per minute at 20 cm H$_2$O pressure. For example, the airflow rate through the SEFAR material Tetex Mono 05-1010-K 080 woven polypropylene material may be about 37 to about 64 liters at 20 cm H$_2$O pressure, preferably, about 42 to about 58 liters at 20 cm H$_2$O pressure. The variance over the length of the textile may be sinusoidal over the length of the textile ribbon. Different areas of the textile when first received from a textile manufacturer may exhibit different air flow rates due to the manufacturing process but not limited to calendering without even heat and force distribution. After the porosity of the vent portion has been reduced, the airflow rate is measured (55) again for verification to confirm it is now within the predetermined range. The average diameter of the opening of the voids is preferably less than 0.1 mm, and preferably provide a total open area (porous region) of approximately 1% to 10% of the superficial area of the vent 3400. For example, the total open area (porous region) may be 22 mm$^2$ where the superficial area of the vent is 240 mm$^2$.

If the desired air flow rate exists in the textile 65, optionally, the holes in a peripheral edge region of a desired vent portion are occluded (56A). The peripheral edge region of the vent portion is overmolded to the mask frame 3310. Since the holes that existed at the peripheral edge region have been occluded, the airflow rate of the vent portion should not significantly differ after overmolding.

In some examples, the airflow rate may be measured (58) after the vent portion is cut from the textile, and also the vents may be measured (61) after being overmolded to the mask frame. This enables the airflow rate to be known and determined to be within the desired predetermined range after certain manufacturing steps. This may prevent wastage so that the part may be discarded as soon as it is known that it is not within the desired predetermined range.

The porosity of the vent portion can be reduced by several ways, including: heat staking, plastic deformation by compression, ultrasonic welding, applying a sealant (e.g. hot melt adhesive) and applying a thin film. Preferably, heat staking by a staking punch 68 is used to reduce porosity due to increased precision, greater certainty of occlusion of holes in the textile, manufacturing speed, good visual appeal after heat staking, and no additional material is required. Some material shrinkage occurs when heating a plastic material which is accounted for by having excess material surrounding the specific physical dimension for the shape of the vent. The porosity of the vent portion is reduced by partially occluding or by fully occluding holes in the vent portion. The staking punch 68 may use several heat weld heads of various sizes to perform the heat staking. The size of the heat weld head is selected depending on the airflow rate of the vent where a larger size is used if the airflow rate is very high.

The order of the cutting and porosity reduction steps may be interchanged. In other words, the porosity reduction may be performed first on the textile 65 and then the vent portion is cut from the textile 65. In such a scenario, the cutting by the cutter 67 can be eliminated.

Any area or region of the vent portion may be selected to reduce porosity. Preferably, the porosity of a substantially continuous peripheral edge region of the vent portion is reduced. This provides good visual appeal because this is adjacent to or at the location where the vent portion is overmolded to the mask frame. Any visual differences between the peripheral edge region and the rest of the vent portion may be less noticeable to the human eye at this location since it may appear to be a defined edge of the mask frame 3310 for receiving the vent 3400. Alternatively, the area for porosity reduction may be in the form of a character/letter or logo in a central region 79 of the vent 3400 to enhance visual impact and improve brand awareness. It may also be used as a replacement indicator for the patient 1000 to replace the vent 3400 after a certain period of use.

After reducing the porosity of a region of the vent portion, the airflow rate of the vent portion is again measured by the airflow meter 66 to confirm that the airflow rate is now within the desired predetermined range of about 47 to 53 liters per minute at 20 cm $H_2O$ pressure. If the airflow rate is not within the desired predetermined range, then the vent portion may undergo heat staking again or the vent portion is discarded. This minimizes wastage by avoiding having to discard a mask frame with an overmolded defective vent, when only the defective vent portion can be discarded. In a further example for nasal pillows, it also avoids discarding a mask frame which has an air delivery tube overmolded to it.

FIGS. 156 and 158 show a section of a textile 65 before heat staking. Loose ends 81 of vertically oriented fibers 80 (warp) along the top edge of the textile 65 are visible. The opening of the voids 83 are defined between the vertically oriented fibers 80 and the horizontally oriented fibers 82 (weft). Some voids 83 are considered more porous than other voids because they have a larger opening and therefore permit greater airflow through it and increased exhaled air washout.

FIGS. 157 and 159 show a section of textile 65 after heat staking. The voids 83 that previously existed before heat staking have been occluded to reduce or prevent airflow through it. FIG. 157 is a graphical depiction for illustrative purposes only, however, a microscope photograph is likely to show that discrete fibers of the textile after heat staking are visually undetectable due to material deformation and melting of the fibers caused by the heat and compression of the heat staking process. The sectional side view depicted in FIG. 159 illustrates that the discrete fibers of the textile 65 after heat staking are visually undetectable due to material deformation and melting of the fibers caused by the heat and compression of the heat staking process. Therefore this region of the vent portion after heat staking becomes substantially air impermeable, in order to selectively adjust the overall airflow rate of the entire vent portion.

Turning to FIG. 155, a section of textile 65 has two vent portions 72, 73 that have been heat staked intended for left side and right side vents. A notional left side vent portion 84 is also depicted showing the outline of the vent portion prior to heat staking. The vent portions 72, 73 are in the shape of a semi-circle or are D-shaped. Each vent portion 72, 73 substantially conform to the shape of a vent aperture in the mask frame 3310. The vent portions 73, 73 are initially made slightly larger than the vent aperture to assist with overmolding and also to take into account plastic shrinkage that is expected due heat from the later steps of heat staking and overmolding. Preferably, the peripheral edge of each vent portion 72, 73 is continuously curved or arcuate with no straight lines. Two corners 74, 75 with an acute angle are the distal ends of a longer side 76 of the vent portion. The longer side 76 has a length of about 19 mm to about 24 mm, preferably, in the range of 21.6 mm to 22 mm. Opposite the longer side 76 is a third corner 77 of the vent portion with an obtuse angle. A substantially continuous peripheral edge region 78 of the vent portion is heat staked to reduce porosity of the textile material 65 in this region. The peripheral edge region 78 may have location alignment features/pins. The width for the peripheral edge region 78 to be heat staked is selected based on the amount of porosity to be reduced in order to obtain the desired air flow rate overall through the vent. A central region 79 located within the peripheral edge region 78 has no heat staking applied to it, and the porosity remains as per the original textile 65.

Sound caused by exhaled air (including exhaled carbon dioxide) passing through the vent 3400 is minimised because of greater air diffusion as it passes through the textile/interlaced fibers, in particular, for nasal pillows when a patient 1000 exhales out of their nose and the exhaled air (including exhaled carbon dioxide) flows out through the vent 3400. Diffusion of the exhaled air (including exhaled carbon dioxide) avoids direct or focused airflow to a bed partner 1100 or the patient 1000 depending on vent orientation and sleeping position. Referring to FIGS. 167 to 175, in one example of the present technology, the vent 3400 is significantly more diffused than the multi-hole vent of a SWIFT FX™ nasal pillows mask by ResMed Limited. Turning to FIG. 175, at close distances to the vent at about 100 mm, the air speed of exhaled air (including exhaled carbon dioxide) from the vent 3400 of the present technology is about 5 times less than the SWIFT FX™ nasal pillows mask. In other words, the patient 1000 and their bed partner 1100 are less likely to feel the exhaled air (including exhaled carbon dioxide) from the vent 3400 compared to the multi-hole vent. This improves comfort for the patient 1000 and their bed partner 1100. The average air velocity has a non-linear curve and was measured using a directional hot wire anemometer in a closed room. Air velocity is a major factor on whether exhaled air (including exhaled carbon dioxide) passing through the vent 3400 may be felt by a person. Other factors which may affect what is felt by a person that were not measured in FIGS. 167 to 175 include ambient room temperature, people's hair follicle density and people's skin sensitivity. At greater distances from the vent, the air speed of exhaled air (including exhaled carbon dioxide) from both vents will approach zero and be indistinguishable from the surrounding ambient conditions. However, the air speed of exhaled air (including exhaled carbon dioxide) from the vent 3400 of the present technology will reach this limit of zero at a closer distance to the vent 3400 than the multi-hole vent. Although a specific multi-hole vent that has been used in the SWIFT FX™ nasal pillows mask was compared, it is envisaged that the vent 3400 of the present technology is superior in terms of noise level and air diffusion compared to most multi-hole vents.

Another method for manufacturing a vent 3400 for washout of exhaled air (including exhaled carbon dioxide) from a patient interface 3000 is also provided. A vent portion is cut from a semi-permeable material having a thickness less than 0.45 mm and a predetermined amount of porosity to diffuse airflow. Cutting occurs if the semi-permeable material is provided in the form of a larger sheet, ribbon or roll, particularly with a large width. The vent portion is molecularly adhered to a mask frame 3310 of a patient interface to form the vent 3400. The predetermined amount of porosity is such that an airflow rate of approximately 47 to 53 liters per minute at 20 cm $H_2O$ pressure of respiratory gas from the patient interface 3000 is obtained. Also, the predetermined amount of porosity is such that an A-weighted sound power level is less than or equal to 25 dbA, with uncertainty 3 dbA and an A-weighted sound pressure at a distance of 1 meter is less than or equal to 17 dbA with uncertainty 3 dbA are generated. Preferably the A-weighted sound power level dbA (uncertainty) is about 22.1 (3) dbA and the A-weighted sound pressure dbA (uncertainty) is about 14.1 (3) dbA measured using ISO 17510-2:2007, 10 cmH2O pressure at 1 m. In other words, the vent 3400 of the present technology is quieter than the multi-hole vents of prior masks as described in the table of noise of prior masks described under the heading of Description of the Related Art. The patient 1000 and their bed partner 1100 are less likely to hear sound caused by exhaled air (including exhaled carbon dioxide) passing through the vent 3400 compared to a multi-hole vent. Heat staking or other previously described techniques of occluding the holes may also be used to specifically adjust the airflow rate of the vent portion until the desired airflow rate is achieved, if necessary.

The vent portion 72 is held in a mold 70 to enable the vent portion 72 to be overmolded to the mask frame 3310 in a molding machine 71. The semi-permeable material may be textile or non-textile so long as the thickness is less than about 0.45 mm. A thin vent is one feature that enables a compact and unobtrusive patient interface 3000 to be provided. Also, a thin vent molded to the mask frame 3310 has visual appeal because the fusion between these two parts appear seamless and flush and the thin vent does not have to excessively protrude inwardly or outwardly relative to the mask frame 3310. Also, a thin vent is light weight since less material is required, reducing the overall weight of the patient interface 3000. For example, the textile material 65 may weigh about 200 to 250 grams per $m^2$. The textile material 65 may weigh about 217 to about 234 grams per $m^2$. Smaller diameter fibers can produce a thinner textile material to achieve the same air flow rate, and this would produce an more light weight vent 3400.

The vent 3400 of the patient interface 3000 is simple to clean and is re-usable. A mild cleaning solution or soapy water can be used to clean the vent 3400. Hot water can also be used to flow through the vent 3400 for cleaning. The vent 3400 can be hand washed and rinsed without disassembly from the mask frame 3310 because it is permanently connected, for example, overmolded, to the mask frame 3310. Less detachable parts for the patient interface 3000 avoids the possibility of losing individual parts and also reduces cleaning time by not having to detach and re-attach many parts from one another. If the vent 3400 is formed by interlaced plastic fibers, durability of the vent 3400 is maintained even after repeated cleaning in contrast to a vent made from another less durable material, for example, a cloth textile or GORE-TEX™. In contrast to the vent 3400 of the present technology, GORE-TEX™ is a non-woven material and its voids occlude very quickly during use from atmospheric particulate matter being trapped in the voids, eventually leading to significant blockage of the vent. Blockage of the vent causes inadequate washout of exhaled air (including exhaled carbon dioxide CO2) by the patient leading to an increase in CO2 levels in the blood and ultimately hypoxia due to CO2 re-breathing. Also, the voids in GORE-TEX™ are invisible to the naked eye meaning that the patient is unable to visually determine blockage caused by mucous, dust, dirt, and grime. Washing the GORE-TEX™ material with water does not alleviate this problem because the purpose of GORE-TEX™ is to repel water. In contrast to the vent 3400 of the present technology, GORE-TEX™ is not a robust material as it is similar to paper and easily tears and subject to damage easily if attempting to clean with a brush or fingers. This is a further reason that GORE-TEX™ cannot be cleaned and re-used because it would be irreparably damaged by the cleaning process due to its paper like fragility. A sintered material such as a sintered cylindrical block for a vent suffers similar deficiencies as with GORE-TEX™ in that the fine pores of the sintered material become clogged after use and cannot be properly cleaned for re-use and visual inspection of blockage is not discernible to the naked eye. Vents made from non-plastic materials are not as easily manufactured as the vent 3400 of the present invention because they may require an additional manufacturing step or cannot be permanently connected to a mask frame using an integral bond such as overmolding. Without an integral bond between the vent and the mask frame there may a reduction in durability and reliability, and/or the visual aesthetics are less pleasing.

In one example, the vent 3400 has consistent and continual air flow through the vent 3400 to enable proper washout of exhaled air (including exhaled carbon dioxide). The vent 3400 is fast to manufacture and is fast to assemble thereby leading to low cost production compared to some prior art vent manufacturing methods. This may be attributed to its relatively simple geometric shape, low amount of processing steps to have the vent 3400 permanently attached to the mask frame 3310, and also a low amount of processing steps and types of equipment needed in the event adjustment to the airflow rate is required. Also, if the vent 3400 is a textile formed by interlaced plastic fibers, it has a fabric look which is aesthetically pleasing for patients 1000 and their bed partners 1100 compared to a multi-hole vent or a sintered block vent.

Another example is described for manufacturing the vent 3400. The plastic fibers are spun monofilaments and are woven or knitted on a narrow weaving loom into an interlaced structure. The interlaced structure may be in the form of narrow ribbons, rather than a roll with a large width. Alternatively, the plastic fibers may be multifilament which may provide tighter turns and more a tortuous path than monofilaments. This permits greater control of the permeability of the textile 65 because heat slitting is avoided. Another advantage is that the heat staking step of the earlier example described for controlling and correcting the air flow rate can be avoided or the number of heat weld heads for the staking punch 68 may be reduced. Therefore, the textile 65 of the vent 3400 may be manufactured within the desired predetermined range and heat staking is used only to blank off a peripheral edge area of the vent 3400 for the purposes of overmolding to the mask frame 3310 for permanent attachment.

It may be possible to further limit any unintended variation of the air flow rate of the vent 3400 during manufacture. In the examples described earlier, the roll or ribbon 65 may be calendered which is a finishing process where the roll or ribbon 65 is passed under rollers at high temperatures and pressures to produce a flat sheet. However, in another example, the roll or ribbon 65 may not be non-calendered first but instead is first cut into narrow ribbons having a width substantially similar to the height of the vent 3400. Each narrow ribbon is calendered to make them flat using a heated roller that has a contact surface with a width substantially similar to the width of the ribbon, to ensure that heat and pressure is applied evenly onto the ribbon. Therefore any unintended variation of the air flow rate of the vent 3400 caused by uneven calendering may be avoided.

In another example, the textile 65 may be evenly calendered with a predetermined pressure and predetermined level of heat to achieve an air flow rate within the desired predetermined range. Thus, the earlier described heat staking step for the purposes of adjusting the air flow rate by occluding voids may be avoided.

In another example, the textile 65 may omit calendering and void occlusion. The textile 65 may be knit or woven into an interlaced structure into narrow ribbons or strips. The textile 65 is then cut using the cutting/fusing techniques described earlier into the shape of the vent portions 72, 73. The vent portions 72, 73 are then permanently connected to the frame 3310 or other component in the pneumatic path of the patient interface 3000.

Although the vent 3400 has been described as being made from interlaced plastic fibers, it is envisaged that materials for the fibers apart than plastic may be used that are biocompatible, and have a similar flexural stiffness to prevent the shape, geometry, profile of the vent 3400 from changing during breathing cycles of the patient 1000. For example, thin metallic wire or yarn may be used. An additive may be sprayed to stiffen the metallic or yarn scaffold of the vent to provide a flexural stiffness to prevent the shape, geometry, profile of the vent 3400 from changing during breathing cycles of the patient 1000. The vent 3400 is described as having the form of an interlaced structure which includes woven fibers and knitted fibers.

Location of Vent 3400

In one form of the present technology, vent 3400 is located on, or formed as part of frame 3310. Specifically, in the example of the technology depicted in FIGS. 75 and 76 a pair of vents 3400 may be disposed on either side of an anterior surface of the frame 3310. In one example, the anterior surface of the mask frame 3310 is curved and therefore the vents 3400 are not facing a direction that is perpendicular to the sagittal plane but are rather facing off the perpendicular axis between the sagittal plane and the coronal plane. Positioning the vents 3400 in this manner in the mask frame 3310 directs the flow of air from the vents 3400 towards the lateral sides rather than straight centre which avoids a direct stream of air to a bed partner 1100 if the patient 1000 is directly facing him or her. An area in front of the centre of the patient interface 3000 has a lower average air velocity from the vents 3400 compared to an area along the vent axis i.e. the area along the direction perpendicular to the superficial anterior surface of the vent 3400.

Although the vent 3400 has been described as being permanently connected to the frame 3310, it is envisaged that the vent 3400 may be located somewhere else in the pneumatic region of the patient interface 3000, for example, on or proximal to the seal-forming structure 3100 or on a cuff/adaptor 4190 (see FIGS. 1b and 1c), which would allow the washout of exhaled air (including exhaled carbon dioxide). The vent 3400 may be permanently connected to the other pneumatic components in the pneumatic region of the patient interface 3000, for example, on an elbow if the patient interface 3000 has an elbow to decouple tube torque.

The pore size characterisation of the vent 3400 may be estimated using a Bubble Point test method described in American Society for Testing and Materials Standard (ASTM) Method F316. The Bubble Point test is a sensitive visual technique. The textile material 65 may have a bubble point pressure of about 60 to about 100 psig (per square inch gauge). Preferably, the bubble point pressure of the textile material 65 has a bubble point pressure of about 80 psig.

In one example of the present technology, the vent 3400 may be provided as a removable vent cap for a patient interface 3000. The vent cap has a vent frame to removably engage with a vent orifice. The vent orifice may be located in a mask frame, elbow or cushion member/plenum chamber 3200. The textile material 65 of the vent 3400 is permanently connected to the vent frame. The vent 3400 having a porous region for washout of exhaled air. The textile 65 in the form of interlaced fibers. A tortuous air path for the exhaled air is defined by spaces between the interlaced fibers. The textile is structured such that the shape, geometry and profile of the vent is substantially unchanged during breathing cycles of the patient 1000 and the porous region maintains a substantially constant rate of washout for the exhaled air.

Although the vent 3400 has been described as an interlaced structure, it may be possible for the vent 3400 to have a non-woven structure such as a fiber reinforced polymer in the form of an unsealed and porous plastic matrix. A two layered structure for the vent 3400 is possible by having a non-woven structure as a first layer bonded to a woven structure as a second layer.

Connection Port 3600

Connection port 3600 allows for connection of the patient interface 3000 to a short tube 4180 of the air circuit 4170, as shown in FIG. 166. In one example of the present technology, the short tube 4180 may be connected directly to the patient interface 3000 by the connection port 3600. The short tube 4180 may be connected to the frame 3310 at the connection port 3600 by insert molding the frame onto the short tube 4180. The connection port 3600 may be located on the patient interface 3000 and may provide either a fixed or movable connection to the gas delivery tube 4180.

The connection port 3600 may be part of the frame 3310 such that the frame is molded to include the connection port in one piece. Additionally, the connection port 3600 may be connected to the frame 3310 at a limited portion or portions of its periphery. This may result in open areas between the connection port 3600 and the frame 3310 and these open areas may include the vent(s) 3400 described herein. As shown in FIGS. 10, 15 and 18, the connection port 3600 may be formed at an angle relative to the frame 3310 to direct the tube from the mask at an angle. Also, the connection port 3600 may be angled in any direction and at any angle relative to the frame 3310. In the illustrated example, the connection port 3600 is angled downward relative to the frame 3310 to cater for a majority of patients who typically have the tube 4180 directed downwards during treatment. This minimises looping of the tube 4180 and may improve seal and stability of the patient interface 3000 during treatment. It may also be possible to form the connection port 3600 separately from the frame 3310 and connect these components such that the connection port 3600 may rotate relative to the frame 3310 using a swivel connection. In such an example, may improve reduce tube torque of the short tube 4180 disrupting sealing forces, or may improve comfort and seal if the short tube 4180 is configured in a tube-up position up over the patient's head.

FIG. 18 shows the short tube 4180 angled downwardly relative to the patient interface 3000 by virtue of its connection to the connection port 3600 which is formed at a downward angle relative to the frame 3310. This arrangement may prevent the short tube 4180 from looping out away from the patient at a great distance to avoid entanglement.

It should also be understood that the flow of gas into the patient interface 3000 may be more evenly distributed in the example of the technology where no elbow is used to connect the air circuit 4170 to the patient interface 3000. The sharp bend of an elbow may cause a large density of the flow lines on one side of the elbow. This may induce jetting where the flow is condensed and this may result in a suboptimal flow into the patient interface 3000 and, specifically, the nasal pillows 3130. It should also be understood that the vent 3400, described above, may contribute to the reduction in jetting. While the use of elbows in prior masks have been to decouple tube torque by allowing at least relative rotational movement between the air circuit 4170 and the frame 3310, one form of the present technology has a particularly floppy short tube 4180 that is capable of decoupling tube torque that conventional elbows would be responsible for.

Forehead Support

In one form of the present technology, patient interface 3000 does not include a forehead support. In one form, the patient interface 3000 provides sufficient stability that a forehead support is not required which leads to less obtrusiveness and opens up the eyes and nasal bone.

In one alternative form, the patient interface 3000 includes a forehead support.

Anti-Asphyxia

In one form of the present technology, patient interface 3000 may include an anti-asphyxia valve (AAV). In further examples of the present technology, when a full-face mask is used an AAV may be included with the decoupling structure 4190 (see FIG. 1b), the air circuit 4170 (see FIGS. 1a to 1c), or the patient interface 3000.

Ports

In one form of the present technology, patient interface 3000 may include one or more supplemental oxygen ports 4185 that allow access to the volume within the plenum chamber 3200. In one form this allows a clinician to supply supplemental oxygen. In one form this allows for the direct measurement of a property gases within the plenum chamber 3200, such as the pressure.

Decoupling Structure(s) 4190

Figure 1B:
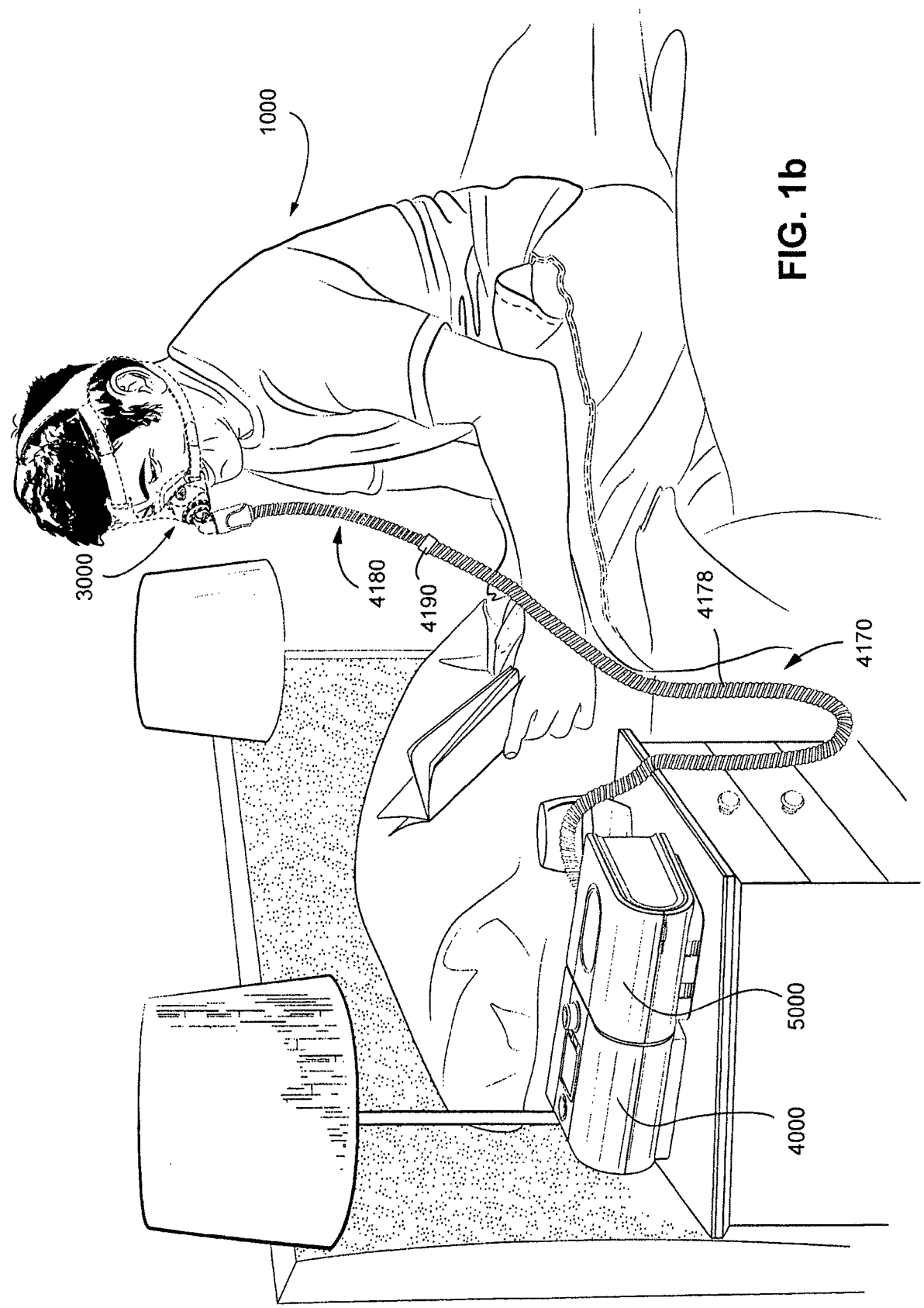
FIG. 1b shows a PAP device 4000 in use on a patient 1000 with a nasal mask.
Figure 1C:
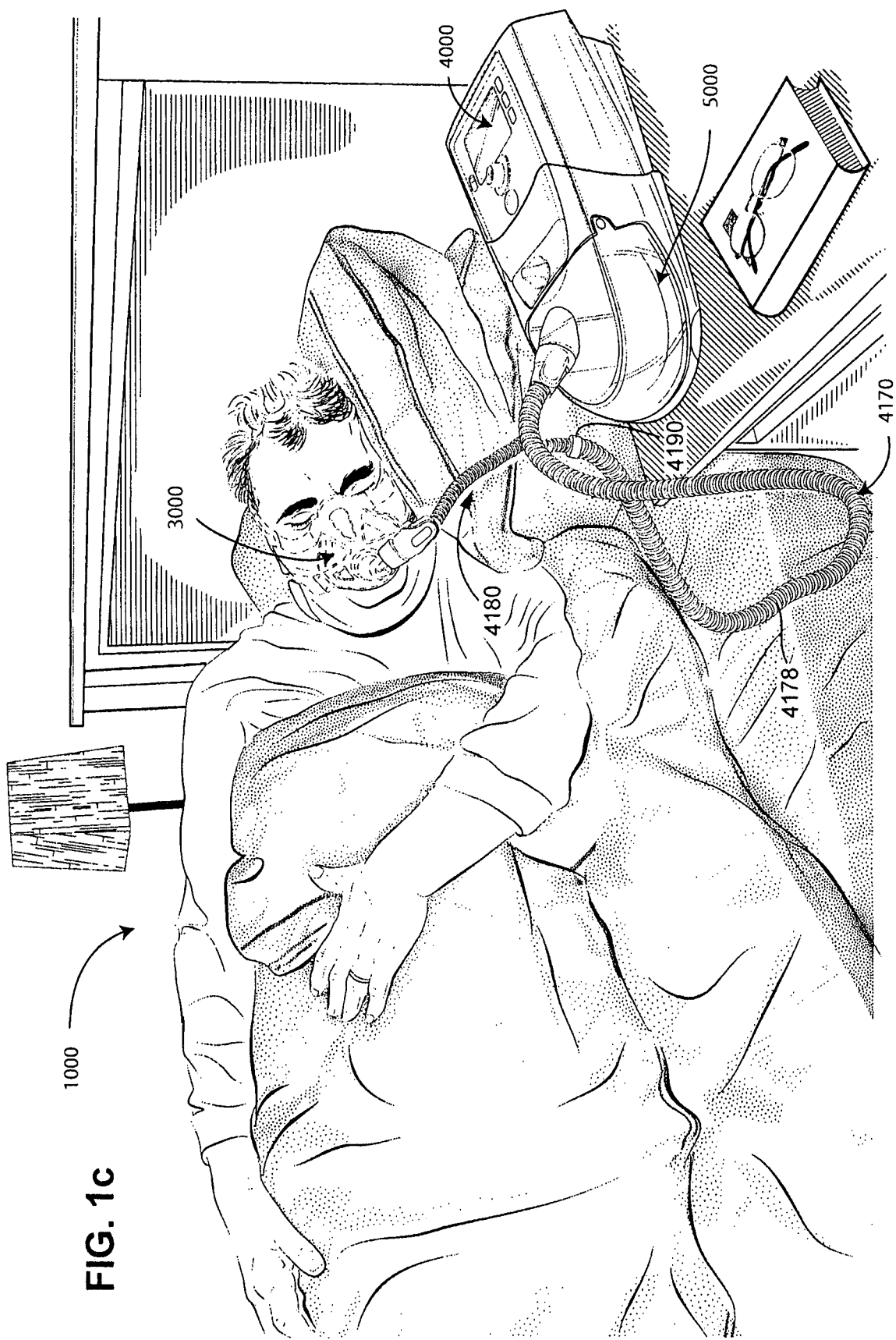
FIG. 1c shows a PAP device 4000 in use on a patient 1000 with a full-face mask.

In one form, the patient interface 3000 includes at least one decoupling structure, for example, a rotatable cuff or adapter 4190, as shown in FIGS. 1b and 1c, or a ball and socket. Referring to FIGS. 1b and 1c, decoupling of a tube-drag force is provided at least in part by short tube 4180. In this way, short tube 4180 functions at least in part as a decoupling structure 4190.

Referring to FIGS. 1b and 1c, at an end of the short tube 4180 is the rotatable cuff or adapter 4190 to facilitate connection to a third end of an additional gas delivery tube 4178 that may be different in at least one aspect from the short tube 4180. The rotatable cuff 4190 allows the short tube 4180 and the additional gas delivery tube 4178 to rotate relative to one another at respective ends. The additional gas delivery tube 4178 may incorporate similar features to the short tube 4180, but may have a larger inner diameter (e.g., 18 mm-22 mm). This additional degree of freedom provided to the tubes may help to reduce tube drag forces by alleviating twisting, and therefore kinking, of the air circuit 4170. Another end of the additional gas delivery tube 4178 may be connected to a PAP device 4000.

Short Tube 4180

In one form of the present technology, a short tube 4180 is connected to frame 3310 at the connection port, as shown in FIG. 166, and forms part of the air circuit 4170.

The short tube 4180 is a gas delivery tube in accordance with an aspect of the present technology is constructed and arranged to allow a flow of air or breathable gasses between the PAP device 4000 and the patient interface 3000.

Gas delivery tubes are subject to tube drag forces which represent the force subjected to the tube while in use as it lays on the patient and other surfaces (e.g., a bed, a nightstand, a hospital bed, a table, floor, etc.) during use. Since the short tube 4180 is connected to the patient interface 3000 to provide breathable gas to the patient 1000 these tube drag forces can affect the connection between the patient interface 3000 and the patient 1000. For example, tension and torsion tube drag forces may cause the patient interface 3000 to displace from the patient's face, thereby causing leakage of the breathable gas from the patient interface 3000. Thus, it is desirable to decrease the tube drag forces. This may be accomplished by reducing the weight of the short tube 4180, improving its flexibility (e.g., by decreasing its bend radius such that the tube 4180 can be curved more tightly), and adding at least one degree of freedom for the short tube 4180. Also, such a reduction in tube drag forces must be accomplished without significantly reducing the strength of the tube 4180 such that it may resist occluding forces, e.g., when a patient may lay his or her arm on the tube 4180 or when twisted into a kinked position.

FIGS. 160 to 162 show three side views of an exemplary short tube 4180 in three different states. FIG. 160 shows the short tube 4180 in a neutral state or normal condition. In the neutral state, the short tube 4180 is not subject to any external forces, i.e., it is not stretched or compressed. The short tube 4180 may be comprised of a web of material 4172 that is spaced between adjacent coils of a helical coil 4174. The helical coil 4174 of the short tube 4180 may have a width of WC. The web of material 4172 may span the distance between adjacent coils WF. Further, as shown in FIG. 160, the web of material 4172 may be folded such that a vertex or peak of the fold 4182 extends radially outward from between adjacent coils. It should be understood that due to the fold of the web of material 4172, the width of material comprising the web of material 4172 may be wider than the width between adjacent coils WF. Also, the web of material 4172 may be folded along a predetermined fold line 4186.

Also shown in FIG. 160, the distance between adjacent coils WF may be equal, or substantially equal, to the width of the helical coil WC when the short tube 4180 is in the neutral state. In such an arrangement, the maximum bend radius R (shown in FIG. 163) of the tube 4180 is decreased and flexibility is improved. This is because an amount of material greater than in prior art tubes must be used to span the distance between adjacent coils. For one, the distance WF being equal to the width of the coil WC results in a larger amount of material to span the distance, and because it is folded an even greater amount of material must be provided to comprise the web of material 4172. This principle is described in greater detail in relation to FIG. 163. The shape of the fold is important to the overall flexibility of the tube. A larger radius in the folds of the web produces a more flexible tube. A very sharp crease makes the tube less flexible. After multiple thermal disinfection cycles, the folds start to relax and the tube becomes less flexible. When the fold is relaxed, it is observed that the fold diameter is reduced relative to the coil diameter and hence the peaks of the folds are lowered.

Additionally, in FIG. 160 it can be seen that the fold of the web of material 4172 extends not only radially outward from the short tube 4180, but the fold of the web of material 4172 is centrally located between adjacent coils of the helical coil 4174. Furthermore, FIG. 160 also shows how the slope of the web of material 4172 may increase towards the vertex or peak of the fold 4182 from adjacent coils of the helical coil 4174. In other words, the web of material 4172 is flatter further away from the predetermined fold line 4186 and the web of material 4172 becomes steeper and pointier near the vertex or peak of the fold 4182.

Also in FIG. 160, as will be discussed in greater detail below, it can be seen that an outer portion or outer surface 4184 of the helical coil 4174 has a curved profile that is rounded over a wide angle. In other words, the helical coil 4174 may have a profile of a portion of the perimeter of an oval. By providing a rounded outer surface or profile 4184 to the helical coil 4174, a softer and smoother tactile feel may be provided to the patient 1000. Additionally, this rounded outer surface 4184 may also decrease the propensity of the short tube 4180 to snag on surfaces while in use, such as bedding, the patient's clothing, bedroom or hospital furniture, etc. As can been in FIG. 160, a coil diameter DC can be seen, which is the diameter of one of the plurality of helical coils measured perpendicularly to the longitudinal axis of the short tube 4180.

Another feature that may be seen in FIG. 160, the short tube 4180, in its neutral state, has the fold of the web of material 4172 rising radially outward from the gas delivery tube such that the vertex or peak of the fold 4182 is at substantially the same height, or the same height, as the outer surface 4184 of the helical coil 4174. The fold of the web of material 4172 also defines a fold diameter DF between opposite vertices of the fold 4182 measured perpendicularly to the longitudinal axis of the short tube 4180. Said in another way, when the short tube 4180 is in its neutral state, the diameter of the web of material 4172 spanning respective vertices of its fold 4182 across the longitudinal axis of the gas delivery tube may be equal to the diameter of the helical coil 4174 spanning respective outer surfaces 4184 across the longitudinal axis. It could also be said that if the short tube 4180 is laid out straight in a neutral state, that a single cylinder could be circumscribed flush to the vertex or peak of the fold 4182 and the outer surface 4184 of the helical coil 4174. Also, it may be said that when the short tube 4180 is in a neutral state that the fold diameter DF is equal to, or substantially equal to, the coil diameter DC.

Such an arrangement, in conjunction with the rounded outer profile 4184 of the helical coil 4174, may provide an improved tactile feel, making for a smoother and softer feel for the patient. Additionally, the short tube's 4180 decreased propensity to snag may also be enhanced by having the vertex or peak of the fold 4182 and the outer surface 4184 of the helical coil 4174 rise to the same height because there is no single surface that protrudes prominently to snag on external surfaces.

In another example of the present technology, the web of material 4172 may be folded multiple times in between adjacent coils of the helical coil 4174. This may allow for additional flexibility of the short tube 4180 along with further extensibility due to the additional amount of material that is between each adjacent coil. Also, in another example of the present technology there may be certain regions or portions along the length of the short tube 4180 where the web of material 4172 is folded between adjacent coils of the helical coil 4174 and other regions of the gas delivery tube where the web of material is not folded. Such an arrangement may allow for varying degrees of flexibility and extensibility along the length of the gas delivery tube. For example, it may be possible to provide portions of the short tube 4180 with increased or decreased stiffness at locations near the patient interface 3000 and the PAP device 4000. In one example, portions of the short tube 4180 near the patient interface 3000 and the PAP device 400 may have fewer folds per unit length of tube to increase the stiffness of the tube in these regions so as to ensure that kinking is reduced in these regions. Another reason not to fold a section of web of material 4172 could be for manufacturing reasons. For example, not having a fold on the web 4172 at the distal ends where overmolding of a cuff is to occur. This may reduce the tendency of creating a weak spot in the web 4172 where it joins the cuff as a folded web at these locations can get caught in a weak pinched state.

FIG. 161 shows another side view of the exemplary short tube 4180. In this view, the short tube 4180 is in a compressed or contracted state. In this state, the length of the short tube 4180 will be less than its length when it is in the neutral state shown in FIG. 160. For example, the short tube 4180 may be compressed to a length that is up to 50% less than in the neutral state. When the short tube 4180 is compressed to its compressed state the web of material 4172 is compressed such that its fold becomes steeper and the distance between adjacent coils WF of the helical coil 4174 decreases. In the compressed state, the distance between adjacent coils WF may decrease to less than the width of the helical coil WC. Also, the vertex or peak of the fold 4182 of the web of material 4172 may be forced further outward in the radial direction such that the vertex or peak rises above the outer surface 4184 of the helical coil 4174. In other words the web of material 4172 may become taller. This effect may be controlled by the amount of material between adjacent coils and the angle of the fold and the thickness TW of the web of material 4172. Moreover, it should also be understood that while the width of the helical coil WC may not decrease during compression of the short tube 4180, the adjacent coils of the helical coil 4174 may be forced together as is common with other springs. Also in FIG. 161, it can be seen that when the short tube 4180 is in the compressed state the angle at the vertex or peak 4182 of the fold of the web of material 4172 (i.e., the angle between each portion of the web of material on either side of the predetermined fold line) is decreased and, again, the web of material may become taller.

FIG. 162 shows an additional side view of the short tube 4180 when it is in its extended or elongated state. In this state the short tube 4180 may have a length greater than in the neutral state shown in FIG. 160. For example, the short tube 4180 may be extended up to 200% of its length when in the neutral state. Also, in this view it can be seen that the distance between adjacent coils WF of the helical coil 4174 increases and the fold of the web of material 4172 becomes flatter. Also, the distance between adjacent coils WF may increase to greater than the width of the helical coil WC. Further, in FIG. 162 it can be seen that the vertex or peak of the fold 4182 of the web of material 4172 may be forced radially inward such that the vertex or peak descends to below the height of the outer surface 4184 of the helical coil 4174. Again, this may be controlled by the amount of material between adjacent coils and the angle of the fold. Moreover, it should also be understood that while the width of the helical coil WC may not increase during extension of the short tube 4180, the adjacent coils of the helical coil 4174 may be forced apart as is common with other springs. Also in FIG. 162 it can be seen that when the short tube 4180 is in the extended state, the angle at the vertex or peak of the fold of the web of material (i.e., the angle between each portion of the web of material on either side of the predetermined fold line) is increased and, again, the web of material 4172 may become flatter.

FIG. 163 shows an exemplary short tube 4180 curved between two ends. When curved as shown in FIG. 163, the web of material 4172 between adjacent coils of the helical coil 4174 may be extended at the outer side of the curved portion 4179 and the web of material at the inner portion of the bend 4176 may be compressed. When curved such as this, the limits of the bend radius R may be better understood. In one example, when draped over a cylinder having a 13 mm diameter, the tube may have a bend radius R of 44 mm under its own weight (i.e., with no additional weight applied). The greater the amount of material that comprises the web of material 4172 the lower the possible bend radius R because, as can be seen in FIG. 163, the outer side of the curved portion 4179 can only be extended up to the maximum possible distance between adjacent coils WF. At the outer portion of the bend 4179 the short tube 4180 can only bend and extend, at that outer portion 4179, up to the width of the web of material 4172 provided between adjacent coils. Thus, if more material is provided for the web of material 4172 between adjacent coils flexibility is improved because the short tube 4180 can be flexed such that the outer portion of the bend 4179 is extended further and the maximum bend radius R is decreased.

Also, it can be seen that the distance between adjacent coils WF at the inside of the curved inner portion of the bend 4176 is decreased to the point that adjacent coils of the helical coil 4174 are nearly touching. Therefore, the bend radius R is also limited by the web of material 4172 at the inner portion of the bend 4176. As can be seen in FIG. 164, the web of material 4172 is compressed between adjacent coils of the helical coil 4174 at the inner portion of the bend 4176. Thus, the thicker the web of material 4172 the greater the maximum bend radius R because the greater the amount of material between adjacent coils, the less they are able to approach one another at the inner portion of the bend 4176.

Therefore, to optimize the bend radius R of the short tube 4180 a sufficient width of the web of material 4172 must be provided to allow the outer portion of the bend 4179 to extend to meet the desired bend radius, but also a sufficient thickness of the web of material must be provided to allow adjacent coils of the helical coil 4174 to come together at the inner portion of the bend 4176 to achieve the desired bend radius.

FIG. 164 shows a cross-sectional view of an exemplary short tube 4180 taken as shown in FIG. 163. This cross-sectional view of the short tube 4180 shows the gas delivery tube in its neutral state such that the distance between adjacent coils WF is equal to the width of the helical coil WC. The short tube 4180 may also have an internal diameter DI that is about 18 mm. The short tube 4180 may have a pitch P of between 3.2 mm to 4.7 mm, or preferably 4.5 mm to 4.7 mm. This view also shows that the helical coil 4174 may have greater thickness TC than the thickness TW of the web of material 4172. With the helical coil 4174 being thicker than the web of material 4172, the helical coil is able to provide structural strength and this gives the short tube 4180 a spring effect. Also in this view, it can be seen that the web of material 4172 may have a substantially uniform and/or continuous thickness.

FIG. 164 also shows that at least a portion of the web of material 4172 may be asymmetrical about the predetermined fold line 4186. For example, the web of material 4172 may include a humped portion 4181 adjacent to the helical coil 4174 on one side of the predetermined fold line 4186 and a slanted portion 4183 may be included on the other side adjacent to the other side of the helical coil. Also, the slope of the web of material 4172 to the vertex or peak 4182 of the fold may be steeper on the side of the slanted portion 4183 than on the side of the humped portion 4181. Due to the different steepnesses, when the short tube 4180 is in the neutral state, the width WFS between the edge of the helical coil on the side of the slanted portion 4183 and the predetermined fold line 4186 may be less than the width WFF between the edge of the helical coil on the side of the humped portion 4181 and the predetermined fold line. Thus, when extended, the web of material 4172 may be extended such WFS may increase more than WFF because a greater amount of material is comprised in that region. In other words, the short tube 4180 may be extended a certain amount in a first direction (e.g., from the slanted portion 4183 to the humped portion 4181) and a different amount in a second direction opposite the first direction (e.g., from the humped portion to the slanted portion). Such an arrangement may be advantageous where the patient interface 3000 is attached to the short tube 4180 at one end and the PAP device 4000 at the other, because the patient 1000 may move while wearing the patient interface 3000, thus necessitating a greater amount of extensibility in the direction of the patient 1000. The asymmetric profile of the tube 4180 is typically a result of how the tube 4180 was made. Alternatively though, it may also be possible for the web of material 4172 to have substantially symmetrical profile about the predetermined fold line 4186.

The width of the humped portion WH and the width of the slanted portion WS may be different as can be seen in FIG. 164. Thus, the web of material 4172 may be flexed over a greater range toward the adjacent coil across the slanted portion 4183 than across the humped portion 4181. In other words, due to the larger gap at WS a greater amount of flexibility (i.e., smaller bend radius) may exist in this particular region than at WH, which has a smaller gap. Also, because of the smaller gap at WH this portion may be compressible to a lesser extent than at WS, because the web of material 4172 is already closer to the coil 4174 at WH than at WS.

Another feature shown in FIG. 164 is that the superficial surface area (e.g., the outermost surface area of the short tube 4180) may be comprised in a greater proportion by the outer surface 4184 of the helical coil 4174 than the web of material 4172 if the helix coil 4174 generally feels better than the web 4172, particularly if the folds in the web are very sharp. This may provide a better tactile feel for the patient because, as can be seen in FIG. 164, the outer surface 4184 of the helical coil 4174 is rounded and therefore smoother than the vertex or peak of the fold 4182 of the web of material 4172.

Also it can be seen in FIG. 164 that the web of material 4172 and the helical coil 4174 may be integrally bonded so that the interior surface of the short tube 4180 is smooth and continuous. It should be understood that either adjacent sides of the web of material 4172 may be joined to one another to form the smooth and continuous interior surface or the web of material 4172 may be bonded to adjacent sides of adjacent coils of the helical coil 4174. By forming the short tube 4180 in this manner, such that the interior surface is smooth and continuous, a smoother flow of breathable gas may be provided through the gas delivery tube. Typically, the folds are formed after the overmolding of the cuffs on both ends of the short tube 4180 to prevent tape pinch.

It should also be understood that any suitable combination of materials may comprise the web of material 4172 and the helical coil 4174. The materials of each respective component 4172, 4174 may be the same or they may be different in at least one aspect. In one example of the present technology, the web of material 4172 and the helical coil 4174 may be made from a thermoplastic elastomer (TPE) or thermoplastic polyurethane (TPU). The web 4172 and coil 4174 may both be made from the same plastic material (or different blends of the same plastic material) which is advantageous to produce an integral chemical bond (molecular adhesion) between the web 4172 and the coil 4174. Material choices are constrained by a number of factors. The mechanical properties of the material for the web 4172 for allowing flexibility are a deciding factor. The ability to withstand thermal disinfection is another important factor. Not being sticky and tacky are other factors. Also, the short tube 4180 must avoid occlusion and withstand hoop stress when an external force is applied on the circumferential surface of the tube 4180 which may occur if a patient's limb lies on top of the short tube 4180. This is addressed by providing the short tube 4180 with a minimum internal diameter, and specifying the helix pitch and structural rigidity of the helical coil 4174.

The choice of materials may also affect the spring stiffness (P=kx, where P is load, k is stiffness and x is deflection) of the short tube 4180. The stiffer the spring k, the smaller the deflection under a constant load. The spring rate is the amount of weight required to deflect a spring (any spring) per measurement unit. For example, materials having different moduli of elasticity and different flexural stiffness may be used for the web of material 4172 and the helical coil 4174, respectively, to create the desired spring stiffness. Similarly, the spring stiffness may also be chosen by using a material with the same modulus of elasticity for both the web of material 4172 and helical coil 4174. Also, the pitch of the helical coil 4174, as discussed in reference to FIG. 164, may also affect the spring stiffness of the gas delivery tube 4180. In one example, the spring stiffness may be about 0.03 N/mm.

FIG. 165 shows another view of an exemplary short tube 4180 in a bent or curved state. In this view, similar to FIG. 163, the short tube 4180 is curved over a radius R. However, in this view the short tube 4180 can be seen draped over the edge of a flat, elevated surface (e.g., a table) to demonstrate how the tube 4180 might bend when subjected to tension at one end due to gravity. The weight of the portion of the short tube 4180 that hangs over the corner of the table may cause extension of the tube 4180 and bending at a region of the tube 4180 near the edge of the table. This view depicts similar bending characteristics to those shown in FIG. 163. Specifically, the web of material 4172 is extended at the outer side of the bent region 4179 and compressed at the inner portion of the bend 4176, such that WF is greater at the outside of the curve than on the inside.

FIG. 166 shows an exemplary short tube 4180 attached directly to a patient interface 3000. In prior masks, the gas delivery tube is attached to a mask through a swivelling elbow. By redirecting the gas delivery tube with a swivelling elbow at its junction with the patient interface, prior art assemblies seek to reduce tube drag forces. However, the inclusion of a swivelling elbow adds weight and parts which can, in turn, mitigate the reduction of tube drag forces. Thus, in accordance with the present technology, the short tube 4180 may be directly connected to a mask frame 3310. FIG. 166 further shows that the short tube 4180 may be angled downwardly from the connection to the mask frame 3310, which may also contribute to reducing tube drag forces. The downward angle may be facilitated in part by the connection port 3600.

Referring again to FIGS. 1b and 1c, a short tube 4180 according to the present technology can be seen connecting a patient interface 3000 at a first end. This connection may be the fixed connection described above in relation to FIG. 166. In this example, a cuff is overmolded on the first end of the tube 4180 which is then overmolded to a corresponding connection port 3600 defined in the patient interface 3000. This example is elbow-less in the sense that there is no elbow between the tube 4180 and the mask frame 3310. In other examples, it is possible for a swivel elbow to be positioned between the tube 4180 and the mask frame 3310 to enable the swivel elbow and the tube 4180 to freely rotate relative to the mask frame 3310. It should be understood that the patient interfaces 3000 shown in these views are shown in dashed lines to indicate that a variety of different patient interfaces may be connected to the short tube 4180. At a second end of the short tube 4180 is a rotatable cuff, swivel cuff or adapter 4190 to facilitate connection to a third end of an additional gas delivery tube 4178 that may be different from the short tube 4180. The rotatable cuff allows the short tube 4180 and the additional gas delivery tube 4178 to rotate relative to one another at respective ends. The additional gas delivery tube 4178 may incorporate similar features to the short tube 4180, but may have a larger inner diameter (e.g., 18 mm-22 mm). This additional degree of freedom provided to the tubes 4178, 4180 may help to reduce tube drag forces by alleviating twisting, decoupling any tube drag forces experienced, and therefore kinking, of the short tube 4180. A fourth end of the additional gas delivery tube 4178 may be connected to a PAP device 4000. A two part swivel that is snapped in is in-mold-assembled into the cuff. Alternatively, a one part swivel snapped on is possible.

Referring to FIGS. 203 to 222, the tube 4180 of the present technology is compared to prior short tubes which have a helical coil. The comparison indicates that the flexural stiffness or floppiness of the tube 4180 of the present technology is superior because it has a lower gram-force (gf) when the tube 4180 is stretched. The lower end of the tubes is held in a fixed position such that the longitudinal axis of the tubes commences from an angle that is perpendicular to the direction of force being applied to elongate the short tubes. In other words, the lower end of the short tube is held so that it is initially parallel and tangent to a horizontal surface (see FIGS. 203, 208, 213, 218). The upper end of the short tubes is held by an Instron machine directly above the held lower end of the short tube. The Instron machine stretches the short tubes by a distance of 30 mm in a series of steps from 0 to 30 mm, to 60 mm, to 90 mm and to 120 mm, in a vertically upwards direction. The Instron machine also measures the force in Newtons at each distance which may correspond to the spring stiffness of the short tube. A torque gauge and force gauge (Torque Gauge RM No. MTSD05997 and Mecmesin Force Gauge RM No, MFGX05996) are used to measure the grams-force at the fixed lower end of the short tube at each distance the short tube is elongated. Since the tubes having different weights and lengths, at the initial position, the Instron machine, torque gauge and force gauge are zeroed. By zeroing the measurement equipment in this manner, the measurements would be independent of weight and length of each tube. A 1 cm grid is also placed in the background to generally indicate the angle of the short tube at each distance. The comparison shows:

| Distance | Grams-Force | Newtons Force |
|---|---|---|
| Tube 4180 of Present Technology (FIGS. 203 to 207) | | |
| 0 | 0 | 0 |
| 30 mm | 0 | 0 |
| 60 mm | 40 | 0.2 N |
| 90 mm | 80 | 0.58 N |
| 120 mm | 140 | 2.2 N |
| ResMed ™ Swift FX ™ Nasal Pillows Mask tube (FIGS. 208 to 212) | | |
| 0 | 0 | 0 |
| 30 mm | 40 | 0.1 N |
| 60 mm | 120 | 0.32 N |
| 90 mm | 320 | 1.1 N |
| 120 mm | 580 | 3.1 N |
| Philips Respironics ™ GoLife ™ Nasal Pillows Mask tube (FIGS. 213 to 217) | | |
| 0 | 0 | 0 |
| 30 mm | 60 | 0.24 N |
| 60 mm | 160 | 0.4 N |
| 90 mm | 500 | 0.71 N |
| 120 mm | 2820 | 6.6 N |
| Philips Respironics ™ Wisp ™ Nasal Mask tube (FIGS. 218 to 222) | | |
| 0 | 0 | 0 |
| 30 mm | 20 | 0.04 N |
| 60 mm | 120 | 0.17 N |
| 90 mm | 300 | 0.73 N |
| 120 mm | 480 | 1.4 N |

The comparison above shows that the short tube 4180 of the present technology only begins to experience tube torque between 30 mm and 60 mm elongation whereas the prior tubes already experience tube torque by 30 mm elongation. At every distance measured, the prior tubes have a significantly higher grams-force indicating that they are less floppy and have a higher flexural stiffness compared to the tube 4180 of the present technology. Therefore seal disruption as a result of tube torque is less likely to occur with the tube 4180 compared to prior tubes. Also, the floppiness of the tube 4180 enables it to be directly connected to the frame 3310 without requiring a swivel elbow or a ball and socket elbow typically used to address tube torque. This eliminates an additional part which leads to overall weight reduction for the patient interface 3000. Comfort is improved because the tube 4180 is barely felt by the patient 1000 and it provides a greater freedom of movement for the patient 1000 before any tube drag acts to pull the seal-forming structure 3100 off the patient's face.

As described above, as the short tube 4180 is moved relative to the patient interface 3000, it may create tube drag forces. The tube drag forces herein may comprise forces and/or moments, however it will understood that the term tube drag forces encompasses forces and/or moments unless stated otherwise.

One of the causes of such tube drag forces may be bending of the short tube 4180. For instance, bending created in the short tube 4180 as the patient 1000 turns their body away from the PAP device 4000 may result in tube drag forces at the patient interface 3000, potentially disrupting the seal, and/or creating discomfort to the patient.

To demonstrate the effect of tube drag forces, a simplified representation of a system comprising a patient interface 3000 and a short tube 4180 may be considered. It may be assumed that in this system, the patient interface is placed on the patient 1000, and the headgear is de-coupled from the patient interface. In this case, any tube drag forces must be reacted by the patient interface 3000, wherein any moments for instance may be reacted as a force couple on the patient 1000, and/or any forces may be reacted by equal and opposite reaction forces on the patient 1000.

The resulting tube drag forces at the patient interface 3000 may be related to the structure of the short tube 4180. More specifically, as the short tube 4180 is bent, the bending stiffness of the short tube 4180 may affect the tube drag forces created at the patient interface 3000.

Typically, when a cylindrical tubular object of constant cross section is fixed at a fixed end and loaded at a free end (i.e. cantilevered), the resulting force and moment at the fixed end can be described as $$d = \frac{Pl^3}{3EI}$$

(disregarding gravity) wherein d is the deflection, P is the vertical force, l is the length of the tube, E is the elastic modulus of the material and I is the second moment of area of the cross-section. Here, the resulting reactions at the fixed end would be a vertical force of P in the opposite direction, and a moment of lP.

Applying this to a system comprising a patient interface 3000 and a short tube 4180, the reactions at the proximal end would be a vertical force of P, and a moment of lP, which may form a part of the tube drag force. The above equation may be rearranged to $$P = \frac{3dEI}{l^3}.$$

It then follows that for a given deflection d (i.e. for a given movement by the patient 1000), and tube length l, the tube drag force would be increased as EI is increased, or as EI is decreased, tube drag would be decreased.

For a circular tube of constant cross section, I may be calculated using the equation $$I = \frac{\pi(d_o^4 - d_i^4)}{64}.$$

Therefore, as an example, for a given inner diameter (di) of 15 mm, a decrease in the outer diameter (do) from 19 mm to 18 mm would decrease tube drag forces by approximately 32%. Similarly, a decrease in the elastic modulus in the material used would achieve a decrease in tube drag forces, although the relationship may be linear in this case.

Therefore, while the short tube 4180 in the present technology may not be a circular tube of constant cross section, the total bending stiffness of the short tube 4180 may be a result of geometric and material properties of various portions of the short tube 4180, such as the web of material 4172 and the helical coil 4174.

Reducing the bending stiffness of the short tube 4180 may result in weakening the structural integrity of the short tube 4180. That is, as an example, if the thickness of the web of material 4172 was changed by reducing the outer diameter of the short tube 4180, the bending stiffness and therefore tube drag forces may be reduced, however this may result in a more fragile construction of the short tube 4180 and lead to occlusion of the short tube 4180 during normal use.

Therefore an advantage of the present technology is the combination of the geometry and material of the short tube 4180 working to reduce bending stiffness while maintaining appropriate strength to avoid occlusion and be durable.

The tube 4180 is substantially silent without a sticky noise/stiction that may occur from axial compression and elongation of the tube 4180. One example to reduce or eliminate noise may be applying an additive to prevent the coils of the helical coil 4174 sticking to each other. Prior tubes for patient interfaces have been known to suffer from this type of noise which can be annoying to the patient 1000 and their bed partner 1100 when trying to sleep as it is intermittent noise. The tube 4180 is intended to be light weight to minimise tube drag forces caused by the weight of the tube 4180 under gravity. In one example of the present technology, in the neutral state, the length of the tube 4180 may be about 285 mm to 305 mm including the end cuffs and may weigh about 18.7 grams to 19.1 grams. Thus, the weight of the tube 4180 with the end cuffs may be about 62.6 g/m to 65.6 g/m. There is no air leak between the tube 4180 and the end cuffs that are overmolded to the ends of the tube 4180. One of the end cuffs may be a swivel cuff 4190 to allow 360° relative rotation between the short tube 4180 and the long tube 4178, while the other end cuff is a frame cuff that does not swivel. The swivel cuff 4190 may have a bump off which provides an external tactile circumferential edge for an index finger of the patient 1000 to disengage the tube 4180 from a tube adapter 4190 connected to a long tube 4178. The bump off may tolerate a higher force to enhance durability of the swivel end cuff 4190 and short tube 4180 after repetitive engagement and disengagement from the long tube 4178.

Although a single helical coil 4174 has been described, it is envisaged that more than helical coil may be provided for the tube 4180. Multiple helical coils for the tube 4180 enable multi-start (double start, triple start, etc), in other words, more than one thread. This may permit each helical coil to be made from a different material or have different dimensions in order to enhance floppiness of the tube 4180 for reducing tube drag forces but also to prevent or resist kinking and occlusion by having a strong structure.

Mask System

One or more of the mask components may configured and arranged together to decouple tube torque to minimise the likelihood of seal disruption. The short tube 4180 is able to decouple tube torque because of its enhanced floppiness and ability to stretch. If tube torque is greater than what the short tube 4180 can decouple, the positioning and stabilising structure 3300 also decouples tube torque. The rigidiser arms 3302 flex in the sagittal plane to decouple tube torque. Also, the cushioning function of the plenum chamber 3200 and/or seal-forming structure 3100 will decouple some amount of tube torque. Any combination of two or more of these features improves the ability to decouple tube torque. The combination of all of these features further enhances the ability to decouple a larger amount of tube torque.

One or more of the mask components may be configured and arranged together to improve comfort for the patient 1000. The short tube 4180 is light weight and the plenum chamber 3200 and seal-forming structure 3100 are also light weight therefore the headgear tension provided by the positioning and stabilising structure 3300 is not required to be uncomfortably high in order to provide a good seal. Reducing the need for an elbow to connect the short tube 4180 to the frame 3310 also reduces overall weight of the patient interface 3000 which lowers the level of headgear tension required by the positioning and stabilising structure 3300. Also, the perception by the patient 1000 when a patient interface 3000 is light weight is that it is "barely there" such that it does not feel like you are wearing a patient interface 3000 leading to less anxiety and claustrophobia. The shape and flexibility of the rigidiser arms 3302 provide comfort for the patient 1000 because they sit under the cheek bones and also direct the headgear strap 3301 around the patient's ears which may be sensitive facial regions for some patients 1000. The strap 3301 is made from a fabric textile and feels good against the patient's skin because it does not retain surface heat and condensate from perspiration compared to a plastic headgear strap. Also, the strap 3301 being made from a fabric textile is less dense than a plastic material which leads to weight and bulk reduction. The split region 3326 of the strap 3301 enables the patient 1000 to adjust headgear tension to a level they feel is comfortable for them. Any combination of two or more of these features improves comfort for the patient 1000. The combination of all of these features greatly enhances comfort for the patient 1000.

One or more of the mask components may be configured and arranged together to improve the chances of an optimal seal with the patient 1000. This may lead to better therapy compliance and an increase in average daily usage by an additional 36 minutes. An optimal seal may be obtained through a combination of improved decoupling of tube torque and also enhanced comfort for the patient 1000 as described above.

One or more of the mask components may be configured and arranged together to improve the visual appeal of the patient interface 3000 leading to better therapy compliance, especially for first time patients 1000. The patient interface 3000 has a low profile and small footprint on the patient's face because the frame 3310 is not very wide and is also curved to correspond to facial geometry. Also, the unitary strap 3301 with the split region 3326 and the smooth continuous surface of the curved profile of rigidiser arm 3323 is not obtrusive, does not appear bulky or complex and does not cover a large surface area of the patient's face. Any combination of two or more of these features improves the visual appeal of the patient interface 3000. The combination of all of these features greatly enhances the visual appeal of the patient interface 3000.

One or more of the mask components may be configured and arranged together to improve assembly and disassembly of the patient interface 3000. The patient interface 3000 provides simplicity to the patient 1000 as there are two detachable components from the frame 3310, which are the seal-forming structure 3100 and strap 3301. Less detachable components also means that the patient interface 3000 is easy to assembly and disassemble when the patient interface 3000 needs to be cleaned. The frame 3310, plenum chamber 3200/seal-forming structure 3100 and strap 3301 may be washed individually and on different schedules, for example, the plenum chamber 3200/seal-forming structure 3100 may be washed more frequently than the strap 3301. The shape and structure of the components visually and tactilely suggest to the patient 1000 how to assemble and disassemble the patient interface 3000 in an intuitive manner. For example, the mating relationship between the plenum chamber 3200 and the frame 3310 which generates an audible click sound when engagement is correct is intuitive to a patient 1000. Also, providing visual and tactile indicators on the frame 3310, plenum chamber 3200 and the positioning and stabilising structure 3300 adds a further guide for the patient 1000 to avoid incorrect assembly/disassembly or misorientation/misalignment of mask components. Some of these features are especially advantageous for patients 1000 in a darkened environment who may have arthritic hands. For example, the audible click sound may be heard, or the touch and feel of the shapes of the mask components and tactile indicators are also useful in low lighting conditions. Also, by simply stretching the strap 3301 to don or doff the patient interface 300 from the patient's face avoids complicated engagement/disengagement procedures. Any combination of two or more of these features improves the simplicity of the patient interface 3000. The combination of all of these features greatly enhances the simplicity of the patient interface 3000.

In one example of the present technology, a frame assembly includes the sub-assemblies of the frame 3310, short tube 4180, vent 3400 and rigidiser arms 3302. The sub-assemblies of the frame assembly are permanently connected to each other, for example, the frame 3310 and short tube 4180 are permanently connected to each other, the frame 3310 and rigidiser arms 3302 are permanently connected to each other, and the frame 3310 and the vent 3400 are permanently connected to each other. A cushion assembly is removably engageable with the frame assembly. The cushion assembly includes the seal-forming structure 3100, plenum chamber 3200, retaining structure 3242, and plenum connection region 3240. The strap 3301 is removably engageable with the frame assembly, in particular, with the rigidiser arms 3302.

Although a strap 3301 made from fabric has been described, it is envisaged that the strap may be made from silicone or a plastic material at least at a distal end. A silicone strap enables overmolding to the plenum chamber 3200 for a permanent connection.

Preventing Incorrect Assembly and Disassembly of Mask System

Referring to FIGS. 187 to 190, the patient interface 3000 is provided with visual indicators and tactile indicators to prevent or minimise misorientation when engaging mask components together. They also provide intuitiveness to patients 1000 when disengaging mask components from each other. In FIGS. 187 and 188, on the outer surface 3355 of the extension 3350 of the rigidiser arms 3302 there is pad printing 3290 provided. The mask name and brand logo are pad printed indicate orientation to the patient 1000 where the words are oriented the right side up. These provide a visual indication for the patient 1000. In FIG. 189, there is raised/embossed text 3291 near an upper edge the frame 3310. This provides the patient 1000 with a visual and tactile indicator of the whether the frame 3310 is oriented up or down, and especially useful in low light conditions when attaching the strap 3301 to the rigidiser arm 3302. Also, there is recessed text 3292 on the outer surface of the rigidiser arm 3302. This provides the patient 1000 with a visual and tactile indicator of the orientation of the rigidiser arm 3302 and is helpful when attaching the strap 3301 to the rigidiser arm 3302. There may be pad printing 3293 on one side of the plenum chamber 3200. The pad printing 3293 may indicate the Left pillow 3130 and Right pillow 3130 and also the size of the seal-forming structure 3100 (Small, Medium, Large). For example, when the patient 1000 sees the pad printing 3293 on the plenum chamber 3200, they would be aware that they are facing the top surface of the plenum chamber 3200. All these visual and tactile indicators assist the patient 1000 in identifying the sides and surfaces of the patient interface 3000 to avoid misorientation and improper assembly and disassembly. This may avoid inadvertent damage to the patient interface 3000 and also ease any user frustration associated with assembly and disassembly.

PAP Device 4000

A PAP device 4000 in accordance with one aspect of the present technology comprises mechanical and pneumatic components 4100, electrical components 4200 and is programmed to execute one or more algorithms 4300. The PAP device may have an external housing 4010, formed in two parts, an upper portion 4012 of the external housing 4010, and a lower portion 4014 of the external housing 4010. In alternative forms, the external housing 4010 may include one or more panel(s) 4015. The PAP device 4000 may comprise a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may comprise an inlet air filter 4112, an inlet muffler, a controllable pressure device capable of supplying air at positive pressure (e.g., a controllable blower 4142), and an outlet muffler. One or more pressure sensors and flow sensors may be included in the pneumatic path.

The pneumatic block 4020 may comprise a portion of the pneumatic path that is located within the external housing 4010.

The PAP device 4000 may have an electrical power supply 4210 and one or more input devices 4220. Electrical components 4200 may be mounted on a single Printed Circuit Board Assembly (PCBA) 4202. In an alternative form, the PAP device 4000 may include more than one PCBA 4202.

PAP Device Mechanical & Pneumatic Components 4100

Air Filter(s) 4110

A PAP device 4000 in accordance with one form of the present technology may include an air filter 4110, or a plurality of air filters 4110.

In one form, an inlet air filter 4112 is located at the beginning of the pneumatic path upstream of a controllable blower 4142. See FIG. 3c.

In one form, an outlet air filter 4114, for example an antibacterial filter, is located between an outlet of the pneumatic block 4020 and a patient interface 3000. See FIG. 3c.

Pressure Device 4140

In a form of the present technology, a pressure device for producing a flow of air at positive pressure is a controllable blower 4142. For example the blower 4142 may include a brushless DC motor with one or more impellers housed in a volute. The blower 4142 may be capable of delivering a supply of air, for example about 120 litres/minute, at a positive pressure in a range from about 4 cmH2O to about 20 cmH2O, or in other forms up to about 30 cmH2O.

Humidifier 5000

Humidifier Overview

In one form of the present technology there is provided a humidifier 5000, as shown in FIG. 3b, that may comprise a water reservoir and a heating plate.

Glossary

For the purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide (CO2) sensors, oxygen (O2) sensors, effort sensors, movement sensors, noise sensors, a plethysmograph, and cameras.

Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, g-f/cm², hectopascal. 1 $cmH_2O$ is equal to 1 g-f/cm² and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a positioning and stabilising structure. A mask frame may be a non-airtight load bearing structure in the mask. However, some forms of mask frame may also be air-tight.

Positioning and stabilising structure: Positioning and stabilising structure will be taken to mean a form of positioning and stabilizing structure designed for use on a head. Preferably the positioning and stabilising structure comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology. Furthermore, where a value or values are stated herein as being implemented as part of the technology, it is understood that such values may be approximated, unless otherwise stated, and such values may be utilized to any suitable significant digit to the extent that a practical technical implementation may permit or require it. It should be further understood that any and all stated values may be variable by up 10-20% from the value stated.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST

| | |
|---|---|
| porous textile is received | 51 |
| airflow rate is measured | 52 |
| difference determination | 53 |
| porosity selectively reduced | 54 |
| airflow rate is measured | 55 |
| airflow rate exceeds range | 56 |
| occlude vent portion | 56A |
| cutting | 57 |
| airflow rate is measured | 58 |
| vent held in mold | 59 |
| vents connected | 60 |
| vents measured | 61 |
| weft knit fabric | 64 |
| textile | 65 |
| airflow meter | 66 |
| cutting tool | 67 |
| staking punch | 68 |
| laser cutter | 69 |
| mold | 70 |
| molding machine | 71 |
| vent portion | 72 |
| vent portion | 73 |
| acute corner of vent portion | 74 |
| acute corner of vent portion | 75 |
| longer side of vent portion | 76 |
| obtuse corner of vent portion | 77 |
| peripheral edge region of vent portion | 78 |
| central region of vent portion | 79 |
| vertically oriented fibers | 80 |
| loose ends | 81 |
| horizontally oriented fibers | 82 |
| voids | 83 |
| notional left side vent portion | 84 |
| course | 85 |
| basic closed loop warp knit | 90 |
| warp knit | 90-1 |
| weft knit | 100 |
| rear portion | 210 |
| straps | 220 |
| patient | 1000 |
| bed partner | 1100 |
| top portion of knitted strap | 1102 |
| rear portion of knitted strap | 1104 |
| knitted strap | 1105 |
| lower portion of knitted strap | 1106 |
| connector | 1120 |
| course | 1150 |
| strap | 1200 |

-continued

| | |
|---|---|
| course | 1250 |
| connected links | 2802 |
| flexible 3D printed textile | 2804 |
| positioning and stabilising structure piece | 2900 |
| hole | 2912(1) |
| female clips | 2912 |
| female clips | 2914 |
| hole | 2914(1) |
| holes of rigidiser arm | 2922 |
| 3D printed strap | 2924 |
| patient interface | 3000 |
| seal-forming structure | 3100 |
| gas chamber | 3104 |
| distal major side | 3104.1 |
| minor side | 3104.2 |
| proximal major side | 3104.3 |
| nasal flange | 3101 |
| sealing flange | 3110 |
| nasal cushion | 3112 |
| region | 3112.1 |
| region | 3112.2 |
| region | 3112.3 |
| region | 3113 |
| protruding end | 3114 |
| region | 3115 |
| recessed portion | 3116 |
| region | 3117 |
| peak | 3118 |
| support flange | 3120 |
| compliant region | 3122 |
| nasal pillows | 3130 |
| most posterior portion | 3130.1 |
| frusto-cone | 3140 |
| upper flexible region | 3142 |
| stalk | 3150 |
| flexible region | 3152 |
| plenum chamber | 3200 |
| connection portion | 3202 |
| thickened section | 3204 |
| overhang | 3206 |
| protruding end support section | 3208 |
| anterior wall | 3210 |
| tongue portion | 3211 |
| channel portion | 3211.1 |
| concave lower portion | 3212 |
| posterior wall | 3220 |
| posterior surface | 3222 |
| flexing region | 3230 |
| left flexing region | 3232 |
| right flexing region | 3234 |
| decoupling region | 3236 |
| plenum connection region | 3240 |
| retaining structure | 3242 |
| wide retention feature | 3244 |
| narrow retention feature | 3245 |
| barb | 3246 |
| leading surface | 3246.1 |
| trailing surface | 3246.2 |
| additional surface | 3246.3 |
| nominal vertical axis | 3246.4 |
| sealing lip | 3250 |
| pad printing | 3290 |
| embossed text | 3291 |
| recessed text | 3292 |
| pad printing | 3293 |
| ribs | 3294 |
| notches | 3295 |
| positioning and stabilising structure | 3300 |
| strap | 3301 |
| elastic tube | 3301.1 |
| lock | 3301.2 |
| loop portion | 3301.3 |
| hook portion | 3301.4 |
| end | 3301.5 |
| rigidiser arm | 3302 |
| distal free end | 3302.1 |
| notch | 3302.2 |
| extension arm | 3302.3 |
| void | 3302.4 |

-continued

| | |
|---|---|
| rod | 3302.5 |
| raised stop | 3302.6 |
| first slot | 3302.7 |
| second slot | 3302.8 |
| button-hole | 3303 |
| attachment point | 3304 |
| flexible joint | 3305 |
| ladder lock clips | 3305.1 |
| protruding end | 3306 |
| sharp bend | 3307 |
| opening | 3308 |
| protrusion | 3309 |
| frame | 3310 |
| receiver | 3310.1 |
| pocket | 3310.2 |
| recess | 3310.3 |
| indentation | 3310.4 |
| end receiver | 3310.5 |
| pocketed end | 3311 |
| welded end | 3311.1 |
| wide frame connection region | 3312 |
| lead-in surface | 3312.1 |
| retaining surface | 3312.2 |
| narrow frame connection region | 3313 |
| welded end | 3313.1 |
| interfering portion | 3314 |
| right side strap portion | 3315 |
| left side strap portion | 3316 |
| back strap | 3317 |
| back strap portion | 3317a |
| back strap portion | 3317b |
| inner side of protrusion | 3318 |
| outer side of protrusion | 3319 |
| end of rigidiser arm | 3319a |
| end of rigidiser arm | 3319b |
| void of protrusion | 3320 |
| top side of protrusion | 3321 |
| marks | 3321a to 3321d |
| bottom side of protrusion | 3322 |
| curved profile of rigidiser arm | 3323 |
| marks | 3323a to 3323e |
| bifurcation point | 3324 |
| reinforced portion | 3325 |
| split region | 3326 |
| reinforcement portion | 3327 |
| rounded corners | 3328 |
| recess of rigidiser arm | 3329 |
| main section of rigidiser arm | 3333 |
| opening of frame | 3335 |
| first bend | 3340 |
| first straight section | 3341 |
| second bend | 3342 |
| second straight section | 3343 |
| locking end | 3344 |
| slot | 3345 |
| extension | 3350 |
| end | 3350.1 |
| straight section of extension | 3351 |
| bend of extension | 3352 |
| hook of extension | 3353 |
| enclosable section of extension | 3354 |
| outer surface of extension | 3355 |
| joint | 3356 |
| strap logo | 3357 |
| indicia | 3358 |
| flange | 3359 |
| stem | 3361 |
| first section of extension | 3363 |
| end | 3363A |
| second section of extension | 3364 |
| first protrusion of second section | 3365 |
| second protrusion of second section | 3366 |
| first slot of second section | 3367 |
| second slot of second section | 3368 |
| extension | 3370 |
| extension | 3371 |
| indicia | 3372 |
| joint | 3374 |
| projection | 3380 |
| wing | 3381 |
| opening | 3382 |
| notch | 3383 |
| stop | 3384 |
| pin | 3385 |
| socket | 3386 |
| flared end | 3387 |
| receiver | 3388 |
| slot | 3389 |
| shaft receiver | 3390 |
| arm receiver | 3391 |
| slot | 3392 |
| projection | 3393 |
| arm | 3394 |
| shaft | 3395 |
| bend | 3396 |
| protrusion | 3397 |
| tab | 3398 |
| column | 3399 |
| vent | 3400 |
| receiver | 3410 |
| first magnet | 3412 |
| post | 3411 |
| second magnet | 3413 |
| first L-shaped section | 3420 |
| first recessed portion | 3421 |
| first overlapping portion | 3422 |
| second L-shaped section | 3423 |
| second overlapping portion | 3424 |
| second recessed portion | 3425 |
| peg | 3426 |
| hole | 3427 |
| boss | 3430 |
| cavity | 3431 |
| prong | 3450 |
| hole | 3451 |
| post | 3452 |
| slot | 3453 |
| rigidiser arm rib | 3460 |
| extension rib | 3461 |
| longitudinal rib | 3462 |
| tab | 3470 |
| hook material | 3471 |
| connection port | 3600 |
| PAP device | 4000 |
| external housing | 4010 |
| upper portion of the external housing | 4012 |
| lower portion of the external housing | 4014 |
| panel | 4015 |
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| pressure device | 4140 |
| controllable blower | 4142 |
| air circuit | 4170 |
| web of material | 4172 |
| helical coil | 4174 |
| inner portion of the bend | 4176 |
| long tube | 4178 |
| outer portion of the bend | 4179 |
| short tube | 4180 |
| humped portion | 4181 |
| peak of the fold | 4182 |
| slanted portion | 4183 |
| outer surface of the helical coil | 4184 |
| supplemental oxygen port | 4185 |
| fold line | 4186 |
| rotatable adapter | 4190 |
| electrical components | 4200 |
| printed circuit assembly (PCBA) | 4202 |
| electrical power supply | 4210 |
| input device | 4220 |
| humidifier | 5000 |

PATENT LITERATURE

U.S. Pat. Nos. 7,743,767; 7,318,437; US patent publication 2009/0044808; WO publication 2000/069521; U.S. Pat. Nos. 5,724,965; 6,119,694. 6,823,869; US patent publication 2009/0044808; WO publication 2009/052560; WO publication 2005/010608; U.S. Pat. No. 4,782,832; WO publication 2002/11804; U.S. Pat. No. 6,854,465; US publication 2010/0000543; US publication 2009/0107508; WO publication 2011/121466; U.S. Pat. No. 7,562,658; EP patent 2,022,528; EP 1356841; US publication 2012/0318270; U.S. Pat. No. 8,439,038; US 2009/0078259; US publication 2009/0277525; US publication 2010/0224276; U.S. Pat. No. 6,581,594; US publication 2009/0050156; US2010/0319700; US publication 2009/0044810

The invention claimed is:

1. A patient interface configured for sealed delivery of a supply of pressurized, breathable gas at a continuously positive pressure with respect to ambient air pressure to a patient's nares, the patient interface being configured to maintain a therapeutic pressure in a range of about 4 cmH2O to about 30 cmH2O above ambient air pressure in use, throughout the patient's respiratory cycle, while the patient is sleeping, to ameliorate sleep disordered breathing, said patient interface comprising:

a frame member comprising a gas washout vent configured to allow a flow of patient exhaled CO2 to an exterior of the patient interface to minimise rebreathing of exhaled CO2 by the patient;

a cushion member configured to deliver the supply of pressurized, breathable gas to the patient's nares, the cushion member further comprising:

a seal-forming structure and a plenum chamber at least partly forming a gas chamber, the seal-forming structure being configured to seal against the patient's face around both nares at an inferior periphery of the patient's nose such that the seal-forming structure contacts the patient's face below the bridge of the nose, at lateral sides of the patient's nose, and at the patient's upper lip, the seal-forming structure being configured not to enter the patient's nares in use, and the seal-forming structure having no undercushion; and a retaining structure configured to releasably engage with the frame member to releasably secure the seal-forming structure and the plenum chamber to the frame member; and a positioning and stabilising structure configured to maintain the seal-forming structure in sealing contact with patient's face while maintaining the therapeutic pressure at the patient's nares;

wherein the seal-forming structure and the plenum chamber are made from one piece of a first material and the retaining structure is made from a second material, the first material being silicone and the second material being silicone with a higher durometer than the first material, such that the retaining structure is more rigid than the seal-forming structure and the plenum chamber; and wherein the plenum chamber further comprises a sealing lip, the sealing lip being configured such that an increase in air pressure within the gas chamber increases a sealing force of the plenum chamber against the frame member.

2. The patient interface of claim 1, wherein the plenum chamber is located between the retaining structure and the seal-forming structure.

3. The patient interface of claim 1, further comprising a frame member made from the second material.

4. The patient interface of claim 1, wherein the first material permits the seal-forming structure to readily conform to finger pressure and the second material prevents the retaining structure from readily conforming to finger pressure.

5. The patient interface of claim 1, wherein said seal-forming structure has a varied thickness adjacent the nasal opening at predetermined positions around the perimeter of the nasal opening.

6. The patient interface of claim 1, wherein a lower portion of said seal-forming structure is concave in a relaxed state to seal against the upper lip of the patient and to follow a curvature of the upper lip of the patient.

7. The patient interface of claim 1, wherein the frame member further comprises ribs and the plenum chamber further comprises notches corresponding to the ribs.

8. The patient interface of claim 1, wherein the retaining structure is permanently joined to the plenum chamber with a chemical bond between the first material and the second material.

9. The patient interface of claim 1, wherein said seal-forming structure includes a recessed portion that is configured to receive the tip of the nose of the patient, the recessed portion being located at a region of the seal-forming structure that is thinner than laterally adjacent regions of the seal-forming structure that are configured to contact the patient's ala.

10. The patient interface of claim 9, wherein said seal-forming structure comprises a compliant region located above the recessed portion, said compliant region being thin and flexible relative to the remainder of the seal-forming structure.

11. The patient interface of claim 1, wherein said seal-forming structure comprises a pair of protruding ends extending symmetrically about the nasal opening, each protruding end configured to seal against a region of the patient's face where the ala of the nose joins to the patient's face.

12. The patient interface of claim 11, wherein said seal-forming structure comprises a pair of protruding end support sections corresponding to each protruding end and structured to support each protruding end,
wherein said pair of protruding end support sections extend into the gas chamber.

13. The patient interface of claim 1, wherein the positioning and stabilising structure further comprises a pair of rigidiser arms, each joined to a corresponding lateral side of the frame member.

14. The patient interface of claim 13, wherein the positioning and stabilising structure further comprises a strap having two ends, each end removably connected to a corresponding one of the rigidiser arms.

15. A patient interface configured for sealed delivery of a supply of pressurized, breathable gas at a continuously positive pressure with respect to ambient air pressure to a patient's nares, the patient interface being configured to maintain a therapeutic pressure in a range of about 4 cmH2O to about 30 cmH2O above ambient air pressure in use, throughout the patient's respiratory cycle, while the patient is sleeping, to ameliorate sleep disordered breathing, said patient interface comprising:

a frame member comprising a gas washout vent configured to allow a flow of patient exhaled CO2 to an exterior of the patient interface to minimise rebreathing of exhaled CO2 by the patient;

a cushion member configured to deliver the supply of pressurized, breathable gas to the patient's nares, the cushion member further comprising:
  a seal-forming structure and a plenum chamber at least partly forming a gas chamber, the seal-forming structure being configured to seal against the patient's face around both nares at an inferior periphery of the patient's nose such that the seal-forming structure contacts the patient's face below the bridge of the nose, at lateral sides of the patient's nose, and at the patient's upper lip, the seal-forming structure being configured not to enter the patient's nares in use, and the seal-forming structure having no undercushion; and
  a retaining structure configured to releasably engage with the frame member to releasably secure the seal-forming structure and the plenum chamber to the frame member; and
a positioning and stabilising structure configured to maintain the seal-forming structure in sealing contact with patient's face while maintaining the therapeutic pressure at the patient's nares;
wherein the seal-forming structure and the plenum chamber are made from one piece of a first material and the retaining structure is made from a second material, the first material being silicone and the second material being silicone with a higher durometer than the first material, such that the retaining structure is more rigid than the seal-forming structure and the plenum chamber;
wherein the plenum chamber further comprises a sealing lip, the sealing lip being configured such that an increase in air pressure within the gas chamber increases a sealing force of the plenum chamber against the frame member; and
wherein a retention force between the retaining structure and the frame member is higher than a disengagement force to disengage the retaining structure from the frame member.

16. The patient interface of claim 15, wherein said seal-forming structure has a varied thickness adjacent the nasal opening at predetermined positions around the perimeter of the nasal opening.

17. The patient interface of claim 15, wherein said seal-forming structure comprises a pair of protruding ends extending symmetrically about the nasal opening, each protruding end configured to seal against a region of the patient's face where the ala of the nose joins to the patient's face.

18. The patient interface of claim 15, wherein said seal-forming structure comprises a pair of protruding end support sections corresponding to each protruding end and structured to support each protruding end,
  wherein said pair of protruding end support sections extend into the gas chamber.

19. The patient interface of claim 15, wherein a lower portion of said seal-forming structure is concave in a relaxed state to seal against the upper lip of the patient and to follow a curvature of the upper lip of the patient.

20. The patient interface of claim 15, wherein the frame member further comprises ribs and the plenum chamber further comprises notches corresponding to the ribs.

21. The patient interface of claim 15, wherein the retaining structure is permanently joined to the plenum chamber with a chemical bond between the first material and the second material.

22. The patient interface of claim 15, wherein the positioning and stabilising structure further comprises a pair of rigidiser arms, each joined to a corresponding lateral side of the frame member, and
wherein the positioning and stabilising structure further comprises a strap having two ends, each end removably connected to a corresponding one of the rigidiser arms.

23. The patient interface of claim 15, wherein said seal-forming structure includes a recessed portion that is configured to receive the tip of the nose of the patient, the recessed portion being located at a region of the seal-forming structure that is thinner than laterally adjacent regions of the seal-forming structure that are configured to contact the patient's ala.

24. The patient interface of claim 23, wherein said seal-forming structure comprises a compliant region located above the recessed portion, said compliant region being thin and flexible relative to the remainder of the seal-forming structure.

25. A patient interface configured for sealed delivery of a supply of pressurized, breathable gas at a continuously positive pressure with respect to ambient air pressure to a patient's nares, the patient interface being configured to maintain a therapeutic pressure in a range of about 4 cmH2O to about 30 cmH2O above ambient air pressure in use, throughout the patient's respiratory cycle, while the patient is sleeping, to ameliorate sleep disordered breathing, said patient interface comprising:
  a frame member comprising a gas washout vent configured to allow a flow of patient exhaled CO2 to an exterior of the patient interface to minimise rebreathing of exhaled CO2 by the patient;
  a cushion member configured to deliver the supply of pressurized, breathable gas to the patient's nares, the cushion member further comprising:
    a seal-forming structure and a plenum chamber at least partly forming a gas chamber, the seal-forming structure being configured to seal against the patient's face around both nares at an inferior periphery of the patient's nose and below the bridge of the nose, at lateral sides of the patient's nose, and at the patient's upper lip, the seal-forming structure being configured not to enter the patient's nares in use, and the seal-forming structure having no undercushion; and
    a retaining structure configured to releasably engage with the frame member to releasably secure the seal-forming structure and the plenum chamber to the frame member; and
  a positioning and stabilising structure configured to maintain the seal-forming structure in sealing contact with patient's face while maintaining the therapeutic pressure at the patient's nares;
  wherein the seal-forming structure and the plenum chamber are made from one piece of a first material and the retaining structure is made from a second material, the first material being silicone and the second material being silicone with a higher durometer than the first material, such that the retaining structure is more rigid than the seal-forming structure and the plenum chamber; and
  wherein the plenum chamber further comprises a sealing lip, the sealing lip being configured such that an increase in air pressure within the gas chamber increases a sealing force of the plenum chamber against the frame member;
  wherein said seal-forming structure includes a recessed portion that is configured to receive the tip of the nose of the patient, the recessed portion being located at a region of the seal-forming structure that is thinner than laterally adjacent regions of the seal-forming structure that are configured to contact the patient's ala, and wherein said seal-forming structure comprises a pair of protruding ends extending symmetrically about the nasal opening, each protruding end configured to seal against a region of the patient's face where the ala of the nose joins to the patient's face.

26. The patient interface of claim 25, wherein said seal-forming structure comprises a compliant region located above the recessed portion, said compliant region being thin and flexible relative to the remainder of the seal-forming structure.

27. The patient interface of claim 25, wherein said seal-forming structure has a varied thickness adjacent the nasal opening at predetermined positions around the perimeter of the nasal opening.

28. The patient interface of claim 25, wherein the seal-forming structure includes an overhang at the nasal opening of the seal-forming structure, said overhang located proximal to the recessed portion.

29. The patient interface of claim 25, wherein said seal-forming structure comprises a pair of protruding end support sections corresponding to each protruding end and structured to support each protruding end, wherein said pair of protruding end support sections extend into the gas chamber.

30. The patient interface of claim 25, wherein the frame member further comprises ribs and the plenum chamber further comprises notches corresponding to the ribs.

31. The patient interface of claim 25, wherein the retaining structure is permanently joined to the plenum chamber with a chemical bond between the first material and the second material.

32. The patient interface of claim 25, wherein the positioning and stabilising structure further comprises a pair of rigidiser arms, each joined to a corresponding lateral side of the frame member, and wherein the positioning and stabilising structure further comprises a strap having two ends, each end removably connected to a corresponding one of the rigidiser arms.

33. The patient interface of claim 25, wherein a lower portion of said seal-forming structure is concave in a relaxed state to seal against the upper lip of the patient and to follow a curvature of the upper lip of the patient.

34. The patient interface of claim 33, wherein said lower portion has a reduced material thickness relative to the rest of the seal-forming structure.

* * * * *